(12) United States Patent
Li et al.

(10) Patent No.: US 12,195,473 B2
(45) Date of Patent: Jan. 14, 2025

(54) KRAS MUTANT PROTEIN INHIBITORS

(71) Applicant: JACOBIO PHARMACEUTICALS CO., LTD, Beijing (CN)

(72) Inventors: Amin Li, Beijing (CN); Sujing Li, Beijing (CN); Peng Wang, Beijing (CN); Chaojie Dang, Beijing (CN); Dan Liu, Beijing (CN)

(73) Assignee: JACOBIO PHARMACEUTICALS CO., LTD, Beijing (CN)

( * ) Notice: Subject to any disclaimer, the term of this patent is extended or adjusted under 35 U.S.C. 154(b) by 302 days.

(21) Appl. No.: 17/562,492

(22) Filed: Dec. 27, 2021

(65) Prior Publication Data

US 2022/0213109 A1 Jul. 7, 2022

Related U.S. Application Data

(63) Continuation of application No. 17/407,418, filed on Aug. 20, 2021, now Pat. No. 11,787,811, which is a continuation of application No. 17/197,095, filed on Mar. 10, 2021, now Pat. No. 11,180,506, which is a continuation of application No. PCT/CN2020/137497, filed on Dec. 18, 2020.

(30) Foreign Application Priority Data

Dec. 19, 2019 (WO) ................ PCT/CN2019/126687
Jan. 8, 2020 (WO) ................ PCT/CN2020/070885
Jan. 22, 2020 (WO) ................ PCT/CN2020/073723
Mar. 10, 2020 (WO) ................ PCT/CN2020/078565

(51) Int. Cl.
*C07D 487/04* (2006.01)
*A61K 9/00* (2006.01)
*A61P 35/00* (2006.01)

(52) U.S. Cl.
CPC .......... *C07D 487/04* (2013.01); *A61K 9/0019* (2013.01); *A61P 35/00* (2018.01)

(58) Field of Classification Search
None
See application file for complete search history.

(56) References Cited

U.S. PATENT DOCUMENTS

| | | |
|---|---|---|
| 11,180,506 B2 | 11/2021 | Li et al. |
| 2018/0006336 A1 | 1/2018 | Odom et al. |
| 2019/0374542 A1 | 12/2019 | Allen et al. |
| 2019/0375749 A1 | 12/2019 | Chen et al. |

FOREIGN PATENT DOCUMENTS

| | | |
|---|---|---|
| CN | 110036010 | 7/2019 |
| CN | 110382482 | 10/2019 |
| CN | 113651814 | 11/2021 |
| WO | 2012080187 | 6/2012 |
| WO | 2015058084 | 4/2015 |
| WO | 2018140600 | 8/2018 |
| WO | 2018217651 | 11/2018 |
| WO | 2019099524 | 5/2019 |
| WO | 2019141250 | 7/2019 |
| WO | PCT/CN2020/137497 | 12/2020 |

OTHER PUBLICATIONS

Belf et al., Tetraheron (1967), 23, pp. 4719-4727.*
U.S. Appl. No. 17/197,095, filed Mar. 10, 2021.
U.S. Appl. No. 17/407,418, filed Aug. 20, 2021.
Liu J, Kang R, Tang D. The KRAS-G12C inhibitor: Activity and resistance. Cancer Gene Therapy. Jul. 2022;29(7):875-8. https://doi.org/10.1038/s41417-021-00383-9.
Zhu C, Guan X, Zhang X, Luan X, Song Z, Cheng X, Zhang W, Qin JJ. Targeting KRAS mutant cancers: from druggable therapy to drug resistance. Molecular Cancer. Aug. 4, 2022;21(1):159. https://doi.org/10.1186/s12943-022-01629-2.
Bian Yun-yi, Yang Xiao-dong, Zhan Cheng, Yao Guang-yu, Bi Guo-shu, Fan Hong. Progress in pharmacological strategies targeting KRAS gene mutated cancers[J]. Fudan University Journal of Medical Sciences, 2020, 47(03):439-447,455 https://doi.org/10.3969/j.issn.1672-8467.2020.03.021.
Wilson CY, Tolias P. Recent advances in cancer drug discovery targeting RAS. Drug Discovery Today. Dec. 1, 2016;21(12):1915-9.SSN 1359-6446, https://doi.org/10.1016/j.drudis.2016.08.002.
Lanman et al. Discovery of a Covalent Inhibitor of KRAS(G12C)(AMG510) for the Treatment of Solid Tumors, J. Med. Chem. 2020, 63, 1, 52-65, Publication Date: Dec. 10, 2019 https://doi.org/10.1021/acs.jmedchem.9b01180.
Banerjee S, Norman DD, Lee SC, Parrill AL, Pham TC, Baker DL, Tigyi GJ, Miller DD. Highly potent non-carboxylic acid autotaxin inhibitors reduce melanoma metastasis and chemotherapeutic resistance of breast cancer stem cells. Journal of medicinal chemistry. Feb. 23, 2017;60(4):1309-24. DOI: 10.1021/acs.jmedchem.6601270.
Olah GA, Wang Q, Sandford G, Surya Prakash GK. Synthetic methods and reactions. 181. Iodination of deactivated aromatics with N-iodosuccinimide in trifluoromethanesulfonic acid (NiS—Cf3SO3H) via in situ generated superelectrophilic iodine (1) trifluoromethanesulfonate. The Journal of Organic Chemistry. May 1993;58(11):3194-5. DOI: 10.1021/jo00063a052.

(Continued)

*Primary Examiner* — Brian J Davis

(74) *Attorney, Agent, or Firm* — Robin L. Teskin; Baker, Donelson, Bearman, Caldwell & Berkowitz PC

(57) ABSTRACT

The invention relates to a KRAS mutant protein inhibitor shown as formula (I), a composition containing the inhibitor and the use thereof.

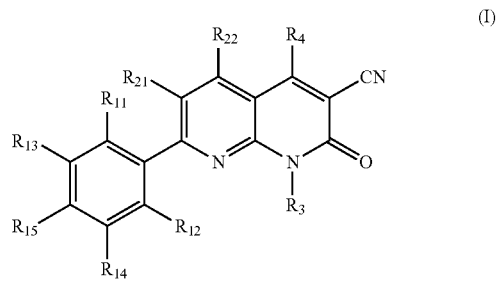

10 Claims, 5 Drawing Sheet

(56) References Cited

OTHER PUBLICATIONS

Brahamam Pujala: "Discovery of Pyrazolopyrimidine Derivatives as Novel Dual inhibitors of BTK and PI3Kdelta-Supporting Information" ACS Med. Chem. Lett, Oct. 28, 2016(Oct. 28, 2016), pp. $1-$42,XP093110587, Retrieved from the Internet: URL: htps://pubs.acs.org/doi/10.1021/acsmedchemlet.6b00356 [retrieved on Dec. 9, 2023].

Zienkiewicz J, Kaszynski P, Young VG. Fused-ring thiadiazines: preparation and crystallographic characterization of 3-9 phenyl derivative of benzo-, pyridio [2, 3-e]-, pyrazino [2, 3-e]-, and tetrafluorobenzo-[1, 2, 4] thiadiazines. The Journal of Organic Chemistry. Apr. 2, 2004;69(7):2551-61., XP093110585. ISSN:0022-3263. DO1:10.1021/10035835h.

\* cited by examiner

KRAS MUTANT PROTEIN INHIBITORS

CROSS-REFERENCE TO RELATED APPLICATIONS

This application is a continuation of U.S. application Ser. No. 17/407,418, filed Aug. 20, 2021, which is a continuation application of U.S. application Ser. No. 17/197,095, filed Mar. 10, 2021, now U.S. Pat. No. 11,180,506, which is a continuation of Int'l Appl. No. PCT/CN2020/137497, filed Dec. 18, 2020, each of which is incorporated herein by reference in its entirety.

TECHNICAL FIELD

The invention relates to a KRAS mutant protein inhibitors, a composition containing the inhibitors and the use thereof.

BACKGROUND ART

RAS represents a population of 189 amino acid monomeric globular proteins (21 kDa molecular weight) that are associated with the plasma membrane and bind to GDP or GTP, and RAS acts as a molecular switch. When the RAS contains bound GDP, it is in a stationary or closed position and is "inactive". When cells are exposed to certain growth-promoting stimuli, RAS is induced to exchange their bound GDP for GTP. In the case of binding to GTP, RAS is "opened" and is capable of interacting with other proteins (its "downstream targets") and activating the proteins. The RAS protein itself has an inherently low ability to hydrolyze GTP back to GDP, thereby turning itself into a closed state. Closing RAS requires an exogenous protein called GTPase activating protein (GAP) that interacts with RAS and greatly accelerates the conversion of GTP to GDP. Any mutation in RAS that affects its ability to interact with GAP or convert GTP back to GDP will result in prolonged protein activation, and thus conduction to the cell to inform its signaling of continued growth and division. Since these signals cause cell growth and division, over-activated RAS signaling can ultimately lead to cancer.

Structurally, the RAS protein contains a G domain responsible for the enzymatic activity of RAS, guanine nucleotide binding and hydrolysis (GTPase reaction). It also contains a C-terminal extension called the CAAX cassette, which can be post-translationally modified and responsible for targeting the protein to the membrane. The G domain contains a phosphate binding ring (P-ring). The P-loop represents a pocket of a binding nucleotide in a protein, and this is a rigid portion of a domain with conserved amino acid residues necessary for nucleotide binding and hydrolysis (glycine 12 and lysine 16). The G domain also contains a so-called switch I region (residues 30-40) and a switch II region (residues 60-76), both of which are dynamic parts of the protein, since the dynamic portion is converted between stationary and loaded states. The ability is often expressed as a "spring loaded" mechanism. The primary interaction is the hydrogen bond formed by threonine-35 and glycine-60 with the gamma-phosphate of GTP, which maintains the active conformation of the switch 1 region and the switch 2 region, respectively. After hydrolysis of GTP and release of phosphate, the two relax into an inactive GDP conformation.

The most notable members of the RAS subfamily are HRAS, KRAS and NRAS, which are primarily involved in many types of cancer. Mutation of any of the three major isoforms of the RAS gene (HRAS, NRAS or KRAS) is one of the most common events in human tumor formation. Approximately 30% of all tumors in human tumors were found to carry some mutations in the RAS gene. It is worth noting that KRAS mutations were detected in 25%-30% of tumors. In contrast, the rate of carcinogenic mutations in NRAS and HRAS family members was much lower (8% and 3%, respectively). The most common KRAS mutations were found at residues G12 and G13 in the P-loop as well as at residue Q61.

G12C is a frequently occurring KRAS gene mutation (glycine-12 is mutated to cysteine). This mutation has been found in about 13% of cancers, about 43% in lung cancer, and almost 100% in MYH-associated polyposis (familial colon cancer syndrome). However, targeting this gene with small molecules is a challenge.

Thus, despite advances in this field, there remains a need in the art for improved compounds and methods for treating cancer, such as by inhibiting KRAS, HRAS or NRAS. The present invention fulfills this need and provides other related advantages.

SUMMARY OF INVENTION

In one aspect, provided herein is A compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof:

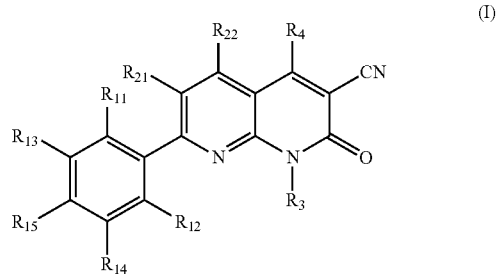

Wherein:

$R_{11}$, $R_{12}$, $R_{13}$, $R_{14}$ or $R_{15}$ is independently selected from halogen, —$C_{1-6}$alkyl, —$C_{2-6}$alkenyl, —$C_{2-6}$alkynyl, hetero$C_{2-6}$alkyl, —CN, —$OC_{1-6}$alkyl, —$SC_{1-6}$alkyl, —$NR_5R_6$, —C(=O)$R_5$, —C(=O)$OR_5$, —OC(=O)$R_5$, —C(=O)$NR_5R_6$, —$NR_5$C(=O)$R_6$, —$NR_5SO_2R_6$, —$SO_2R_5$, —S(=O)$_2NR_5R_6$, —$POR_5R_6$, —$C_{3-6}$carbocyclic, 3- 6 membered heterocyclic, —$C_{6-10}$aryl, or 5-10 membered heteroaryl, each hydrogen in $R_{11}$, $R_{12}$, $R_{13}$, $R_{14}$ or $R_{15}$ is independently optionally substituted with 1, 2, 3, 4, 5 or 6 substituent(s) selected from halogen, —$C_{1-6}$alkyl, —$C_{2-6}$alkenyl, —$C_{2-6}$alkynyl, hetero$C_{2-6}$alkyl, —CN, oxo, —$OC_{1-6}$alkyl, —$SC_{1-6}$alkyl, —$NR_5R_6$, —C(=O)$R_5$, —C(=O)$OR_5$, —OC(=O)$R_5$, —C(=O)$NR_5R_6$, —$NR_5$C(=O)$R_6$, —$NR_5SO_2R_6$, —$SO_2R_5$, —S(=O)$_2NR_5R_6$, —$POR_5R_6$, —$C_{3-6}$carbocyclic, 3-6 membered heterocyclic, —$C_{6-10}$aryl, or 5-10 membered heteroaryl; each heterocyclic or heteroaryl at each occurrence independently contains 1, 2, 3 or 4 heteroatom(s) selected from N, O, S, S=O or S(=O)$_2$;

$R_{21}$ or $R_{22}$ is independently selected from hydrogen, halogen, —$C_{1-6}$alkyl, —$C_{2-6}$alkenyl, —$C_{2-6}$alkynyl, hetero$C_{2-6}$alkyl, —CN, —$OC_{1-6}$alkyl, —$SC_{1-6}$alkyl, —$NR_5R_6$, —C(=O)$R_5$, —C(=O)$OR_5$, —OC(=O)

$R_5$, —C(=O)$NR_5R_6$, —$NR_5$C(=O)$R_6$, —$NR_5SO_2R_6$, —$SO_2R_5$, —S(=O)$_2NR_5R_6$, —$POR_5R_6$, —$C_{3-6}$carbocyclic, 3-6 membered heterocyclic, —$C_{6-10}$aryl, or 5-10 membered heteroaryl, each hydrogen in $R_{21}$ or $R_{22}$ is independently optionally substituted with 1, 2, 3, 4, 5 or 6 substituent(s) selected from halogen, —$C_{1-6}$alkyl, —$C_{2-6}$alkenyl, —$C_{2-6}$alkynyl, hetero$C_{2-6}$alkyl, —CN, oxo, —$OC_{1-6}$alkyl, —$SC_{1-6}$alkyl, —$NR_5R_5$, —C(=O)$R_5$, —C(=O)$OR_5$, —OC(=O)$R_5$, —C(=O)$NR_5R_6$, —$NR_5$C(=O)$R_6$, —S(=O)$_2NR_5R_6$, —$POR_5R_6$, —$C_{3-6}$carbocyclic, 3-6 membered heterocyclic, —$C_{6-10}$aryl, or 5-10 membered heteroaryl; each heterocyclic or heteroaryl at each occurrence independently contains 1, 2, 3 or 4 heteroatom(s) selected from N, O, S, S=O or S(=O)$_2$;

$R_3$ is selected from —$C_{1-14}$alkyl, —$C_{2-14}$alkenyl, —$C_{2-14}$alkynyl, —$C_{6-10}$aryl, 5-10 membered heteroaryl, 3-14 membered heterocyclic, —$C_{3-14}$carbocyclic,

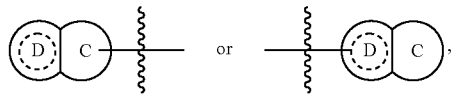

each ring C at each occurrence is independently selected from a $C_{3-14}$carbocyclic or 3-14 membered heterocyclic ring, each ring D at each occurrence is independently selected from a $C_{6-10}$aryl or 5-10 membered heteroaryl ring, each hydrogen in $R_3$ is independently optionally substituted with 1, 2, 3, 4, 5 or 6 $R_{31}$; each heterocyclic or heteroaryl at each occurrence independently contains 1, 2, 3 or 4 heteroatoms selected from N, O, S, S=O or S(=O)$_2$;

Each $R_{31}$ at each occurrence is independently selected from halogen, —$C_{1-6}$alkyl, —$C_{2-6}$alkenyl, —$C_{2-6}$alkynyl, hetero$C_{2-6}$alkyl, —CN, —$OC_{1-6}$alkyl, —$SC_{1-6}$alkyl, —$NR_5R_6$, —C(=O)$R_5$, —C(=O)$OR_5$, —OC(=O)$R_5$, —C(=O)$NR_5R_6$, —$NR_5$C(=O)$R_6$, —$NR_5SO_2R_6$, —$SO_2R_5$, —S(=O)$_2NR_5R_6$, —$POR_5R_6$, —$C_{3-6}$carbocyclic, 3-6 membered heterocyclic, —$C_{6-10}$aryl, or 5-10 membered heteroaryl, each hydrogen in $R_{31}$ is independently optionally substituted with 1, 2, 3, 4, 5 or 6 substituent(s) selected from halogen, —$C_{1-6}$alkyl, —$C_{2-6}$alkenyl, —$C_{2-6}$alkynyl, hetero$C_{2-6}$alkyl, —CN, oxo, —$OC_{1-6}$alkyl, —$SC_{1-6}$alkyl, —$NR_5R_6$, —C(=O)$R_5$, —C(=O)$OR_5$, —OC(=O)$R_5$, —C(=O)$NR_5R_6$, —$NR_5$C(=O)$R_6$, —S(=O)$_2NR_5R_6$, —$POR_5R_6$, —$C_{3-6}$carbocyclic, 3-6 membered heterocyclic, —$C_{6-10}$aryl, or 5-10 membered heteroaryl; each heterocyclic or heteroaryl at each occurrence independently contains 1, 2, 3 or 4 heteroatom(s) selected from N, O, S, S=O or S(=O)$_2$;

$R_4$ is selected from

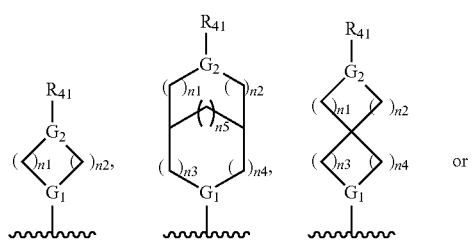

-continued

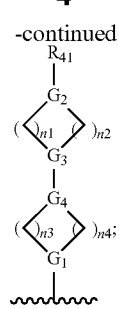

Each $G_1$, $G_2$, $G_3$ or $G_4$ at each occurrence is independently selected from N or CH;

Each n1, n2, n3, n4 or n5 at each occurrence is independently selected from 0, 1, 2, 3, 4, 5 or 6, provided that n1 and n2 is not 0 at the same time, n3 and n4 is not 0 at the same time;

Each hydrogen in

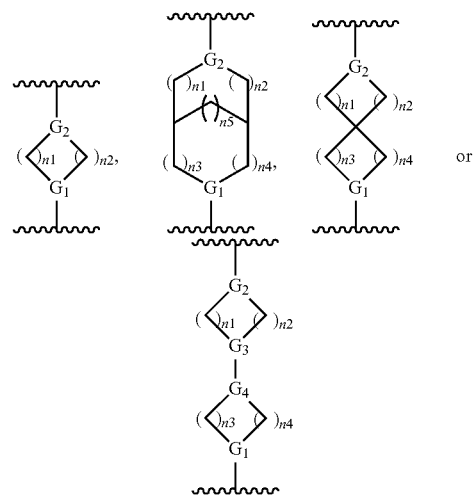

is independently optionally substituted with 1$R_{42}$, 2$R_{42}$, 3$R_{42}$, 4$R_{42}$, 5$R_{42}$ or 6$R_{42}$;

Each $R_{41}$ at each occurrence is independently selected from

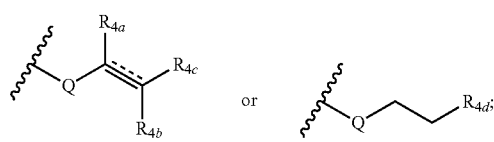

Each of Q at each occurrence is independently selected from C(=O), $NR_5$C(=O), S(=O)$_2$ or $NR_5$S(=O)$_2$;

═ in

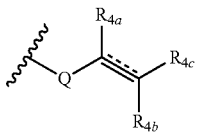

is selected from ═ or ≡;

when ═ is ═, $R_{4a}$, $R_{4b}$ or $R_{4c}$ is independently selected from hydrogen, halogen, —$C_{1-6}$alkyl, —$C_{2-6}$alkenyl, —$C_{2-6}$alkynyl, hetero$C_{2-6}$alkyl, —CN, —$OC_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl, each hydrogen in R$_{4a}$, R$_{4b}$ or R$_{4c}$ is independently optionally substituted with 1, 2, 3, 4, 5 or 6 substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; each heterocyclic or heteroaryl at each occurrence independently contains 1, 2, 3 or 4 heteroatom(s) selected from N, O, S, S=O or S(=O)$_2$; or when ≡ is =, R$_{4a}$ is selected from hydrogen, halogen, —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3- 6 membered heterocyclic, —C$_{6-10}$aryl, or 5-10 membered heteroaryl, each hydrogen in R$_{4a}$ is independently optionally substituted with 1, 2, 3, 4, 5 or 6 substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; and R$_{4b}$ and R$_{4c}$ together with the carbon which they both attach to form a C$_{3-10}$ carbocyclic ring or a 3-10 membered heterocyclic ring, each hydrogen in the C$_{3-10}$ carbocyclic ring or the 3-10 membered heterocyclic ring is optionally substituted by 1, 2, 3, 4, 5 or 6 substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; each heterocyclic or heteroaryl at each occurrence independently contains 1, 2, 3 or 4 heteroatom(s) selected from N, O, S, S=O or S(=O)$_2$; or when is ≡ is =, R$_{4a}$ and R$_{4c}$ with the carbon they respectively attach to form a C$_{3-10}$ carbocyclic ring or a 3-10 membered heterocyclic ring, each hydrogen in the C$_{3-10}$ carbocyclic ring or the 3-10 membered heterocyclic ring is optionally substituted by 1, 2, 3, 4, 5 or 6 substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; and R$_{4b}$ is selected from hydrogen, halogen, —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl, each hydrogen in R$_{4b}$ is independently optionally substituted with 1, 2, 3, 4, 5 or 6 substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; each heterocyclic or heteroaryl at each occurrence independently contains 1, 2, 3 or 4 heteroatom(s) selected from N, O, S, S=O or S(=O)$_2$;

when ≡ is =, R$_{4a}$ is absent, R$_{4b}$ is absent, R$_{4c}$ is selected from hydrogen, halogen, —C$_{1-6}$alkyl, —C$_{2-6}$alkenyl, —C$_{2-6}$alkynyl, heteroC$_{2-6}$alkyl, —CN, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl, each hydrogen in R$_{4c}$ is independently optionally substituted with 1, 2, 3, 4, 5 or 6 substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; each heterocyclic or heteroaryl at each occurrence independently contains 1, 2, 3 or 4 heteroatom(s) selected from N, O, S, S=O or S(=O)$_2$;

R$_{4d}$ is halogen;

Each R$_{42}$ at each occurrence is independently selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl, each hydrogen in R$_{42}$ is independently optionally substituted with 1, 2, 3, 4, 5 or 6 substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_6$, —NR$_5$SO$_2$R$_6$, —SO$_2$R$_5$, —S(=O)$_2$NR$_5$R$_6$, —POR$_5$R$_6$, —C$_{3-6}$carbocyclic, 3-6 membered heterocyclic, —C$_{6-10}$aryl, or 5-10 membered heteroaryl; or Two R$_{42}$ together with the atom which they both or respectively attach to form a C$_{3-6}$ carbocyclic or 3-6 membered heterocyclic ring, each hydrogen in the C$_{3-6}$ carbocyclic or 3-6 membered heterocyclic ring is independently optionally substituted with 1, 2, 3, 4, 5 or 6 substituents selected from halogen, —C$_{1-6}$alkyl, —C$_{2-6}$alkenyl, —C$_{2-6}$alkynyl, heteroC$_{2-6}$alkyl, —CN, oxo, —OC$_{1-6}$alkyl, —SC$_{1-6}$alkyl, —NR$_5$R$_6$, —C(=O)R$_5$, —C(=O)OR$_5$, —OC(=O)R$_5$, —C(=O)NR$_5$R$_6$, —NR$_5$C(=O)R$_5$, —NR$_5$SO$_2$R$_6$, —SO$_2$R$_5$, —S(=O)$_2$NR$_5$R$_6$, —PO(R$_5$)$_2$, —C$_{3-6}$carbocyclic, 3-6 membered heterocyclic, —C$_{6-10}$aryl, or 5-10 membered heteroaryl; each heterocyclic and heteroaryl at each occurrence independently contains 1, 2, 3 or 4 heteroatom(s) selected from N, O, S, S=O or S(=O)$_2$;

Each R$_5$ and R$_6$ at each occurrence is independently selected from hydrogen or —C$_{1-6}$alkyl; or R₅ and R₆ together with the atom which they both or respectively attach to form a 3-10 membered heterocyclic ring, the 3-10 membered heterocyclic ring is optionally further contains 1, 2, 3 or 4 heteroatoms selected from N, O, S, S(=O) or S(=O)₂, and each hydrogen in the 3-10 membered heterocyclic ring is independently optionally substituted with 1R₅₁, 2R₅₁, 3R₅₁, 4R₅₁, 5R₅₁ or 6R₅₁;

Each R₅₁ is selected from halogen, —C₁₋₆alkyl, —C₂₋₆alkenyl, —C₂₋₆alkynyl, heteroC₂₋₆alkyl, —CN, —OC₁₋₆alkyl, —SC₁₋₆alkyl, —NR₇R₈, —C(=O)R₇, —C(=O)OR₇, —OC(=O)R₇, —C(=O)NR₇R₈, —NR₇C(=O)R₈, —NR₇SO₂R₈, —SO₂R₇, —S(=O)₂NR₇R₈, —POR₇R₈, —C₃₋₆carbocyclic, 3-6 membered heterocyclic, —C₆₋₁₀aryl, or 5-10 membered heteroaryl, each hydrogen in R₅₁ is independently optionally substituted with 1, 2, 3, 4, 5 or 6 substituent(s) selected from halogen, —C₁₋₆alkyl, —C₂₋₆alkenyl, —C₂₋₆alkynyl, heteroC₂₋₆alkyl, —CN, oxo, —OC₁₋₆alkyl, —SC₁₋₆alkyl, —NR₇R₈, —C(=O)R₇, —C(=O)OR₇, —OC(=O)R₇, —C(=O)NR₇R₈, —NR₇C(=O)R₈, —NR₇SO₂R₈, —SO₂R₇, —S(=O)₂NR₇R₈, —POR₇R₈, —C₃₋₆carbocyclic, 3-6 membered heterocyclic, —C₆₋₁₀aryl, or 5-10 membered heteroaryl; each heterocyclic or heteroaryl at each occurrence independently contains 1, 2, 3 or 4 heteroatom(s) selected from N, O, S, S=O or S(=O)₂;

Each R₇ and R₈ at each occurrence is independently selected from hydrogen or —C₁₋₆alkyl.

In some embodiments, there is provided a compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof:

Wherein:

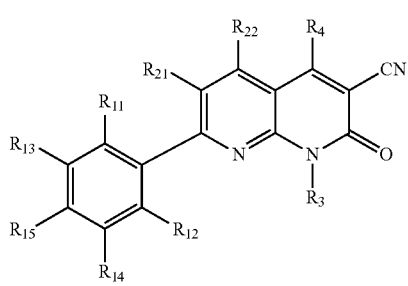

(I)

R₁₁, R₁₂, R₁₃, R₁₄ or R₁₅ is independently selected from —OH; halogen; —NR_aR_b; —C₁₋₆alkyl; —OC₁₋₆alkyl; —C₁₋₆alkylene-OH; —C₁₋₆alkylene-O—C₁₋₆alkyl; —C₁₋₆alkyl substituted with halogen, —NH₂, —CN or —OH; —O—C₁₋₆alkyl substituted with halogen, —NH₂, —CN or —OH; —O—C₁₋₆alkyl; —SO₂R_a; —CN; —C(=O)NR_aR_b; —C(=O)R_a; —OC(=O)R_a; —C(=O)OR_a; or —C₃₋₆carbocyclic;

R_a or R_b is independently selected from hydrogen or —C₁₋₆alkyl;

R₂₁ is selected from hydrogen; halogen; —C₁₋₆alkyl; —C₁₋₆alkyl substituted with halogen, —NH₂, —CN or —OH; —C₂₋₆alkenyl; or —C₃₋₆carbocyclic;

R₂₂ is selected from hydrogen; halogen; —C₁₋₆alkyl; —C₁₋₆alkyl substituted with halogen, —NH₂, —CN or —OH; —C₂₋₆alkenyl; or —C₃₋₆carbocyclic;

R₃ is selected from —C₆₋₁₀aryl or 5-10 membered heteroaryl, each of 5-10 membered heteroaryl at each occurrence independently contains 1, 2, 3 or 4 heteroatoms selected from N, O or S, each hydrogen in the —C₆₋₁₀aryl or 5-10 membered heteroaryl at each occurrence is independently optionally substituted with 1R₃₁, 2R₃₁, 3R₃₁, 4R₃₁, 5R₃₁ or 6 R₃₁;

Each R₃₁ at each occurrence is independently selected from halogen, —C₁₋₆alkyl, —CN, —OH, —O—C₁₋₆alkyl, —NH₂, —NH(C₁₋₆alkyl), —N(C₁₋₆alkyl)₂ or —C₃₋₆carbocyclic;

R₄ is

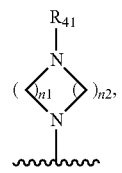

each hydrogen in the

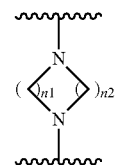

is independently optionally substituted with 1R₄₂, 2R₄₂, 3R₄₂, 4R₄₂, 5R₄₂ or 6 R₄₂;

n1 or n2 is independently selected from 1, 2, 3, 4, 5 or 6;

R₄₁ is

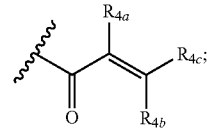

R_{4a}, R_{4b} or R_{4c} is independently selected from hydrogen, halogen, —C₁₋₆alkyl or —C₁₋₆alkylene-N(C₁₋₆alkyl)₂;

Each R₄₂ at each occurrence is independently selected from —C₁₋₆alkyl; —C₁₋₆alkylene-CN or —C₁₋₆alkyl substituted with halogen.

In some embodiments, R₁₁, R₁₂, R₁₃, R₁₄ or R₁₅ is independently selected from —OH; —F; —Cl; —Br; —NR_aR_b; —C₁₋₃alkyl; —OC₁₋₃alkyl; —C₁₋₃alkylene-OH; —C₁₋₃alkylene-O—C₁₋₃alkyl; —C₁₋₃alkyl substituted with —F or —Cl; —O—C₁₋₃alkyl substituted with —F or —Cl; —SO₂R_a; —CN; —C(=O)NR_aR_b; —C(=O)R_a; —OC(=O)R_a; —C(=O)OR_a; 3-membered carbocyclic; 4-membered carbocyclic; 5-membered carbocyclic or 6-membered carbocyclic;

R_a or R_b is independently selected from hydrogen or —C₁₋₃alkyl.

In some embodiments, R₁₁, R₁₂, R₁₃, R₁₄ or R₁₅ is independently selected from —OH, —F, —Cl, —NH₂, —NHCH₃, —N(CH₃)₂, —CH₃, —CH₂CH₃, —CH₂CH₂CH₃, —CH(CH₃)₂, —OCH₃, —OCH₂CH₃, —OCH₂CH₂CH₃, —OCH(CH₃)₂, —CH₂OH, —CH₂CH₂OH, —CH₂OCH₃, —CHF₂, —CH₂F, —CF₃, —OCH₂F, —OCHF₂, —OCF₃, —SO₂CH₃, —CN, —C(=O)NH₂, —C(=O)CH₃, —OC(=O)CH₃, —C(=O)OCH₃ or 3-membered carbocyclic.
In some embodiments, $R_{11}$, $R_{12}$, $R_{13}$, $R_{14}$ or $R_{15}$ is independently selected from —OH, —F, —Cl, —NH₂, —CH₃ or —CF₃.
In some embodiments, the
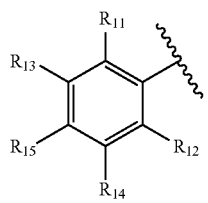
in the formula (I) is selected from:
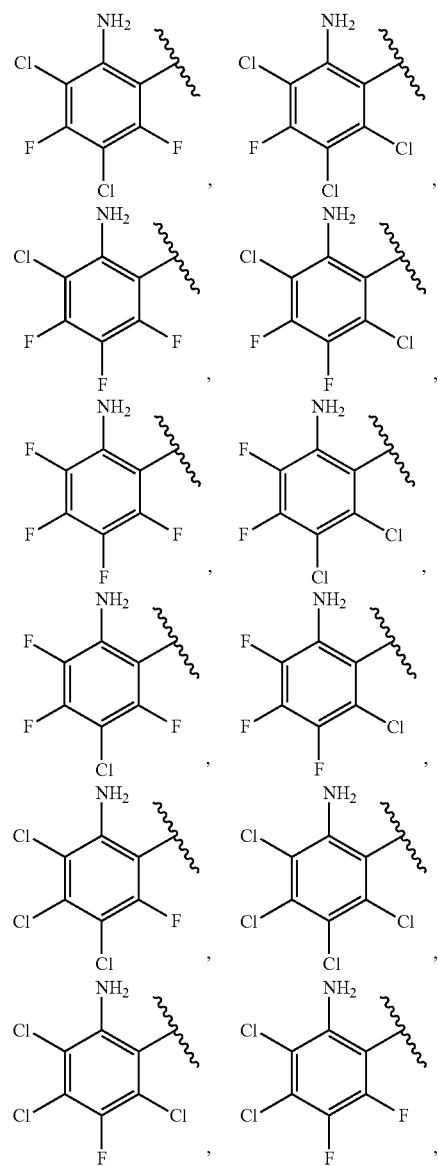
-continued
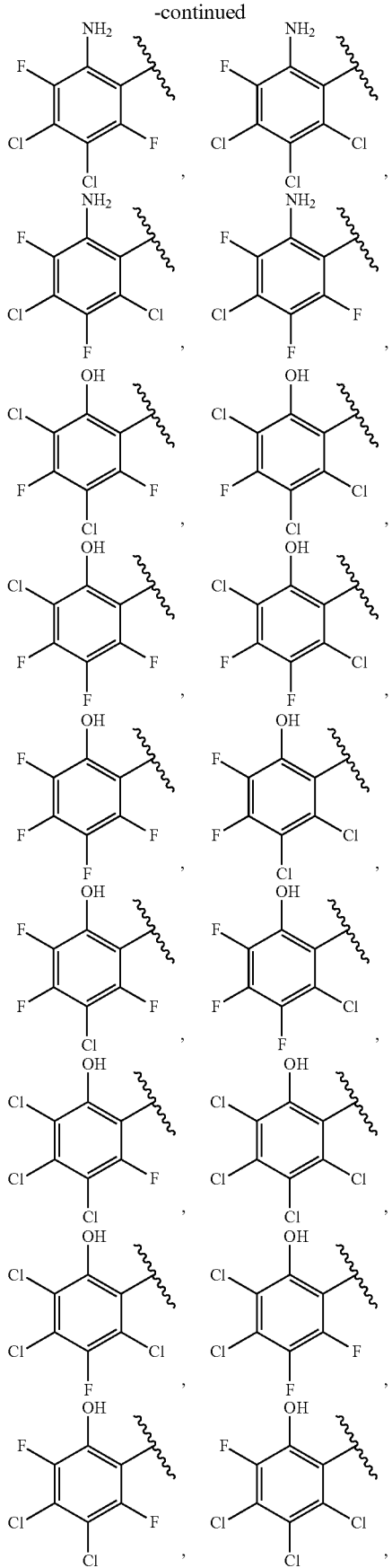

-continued
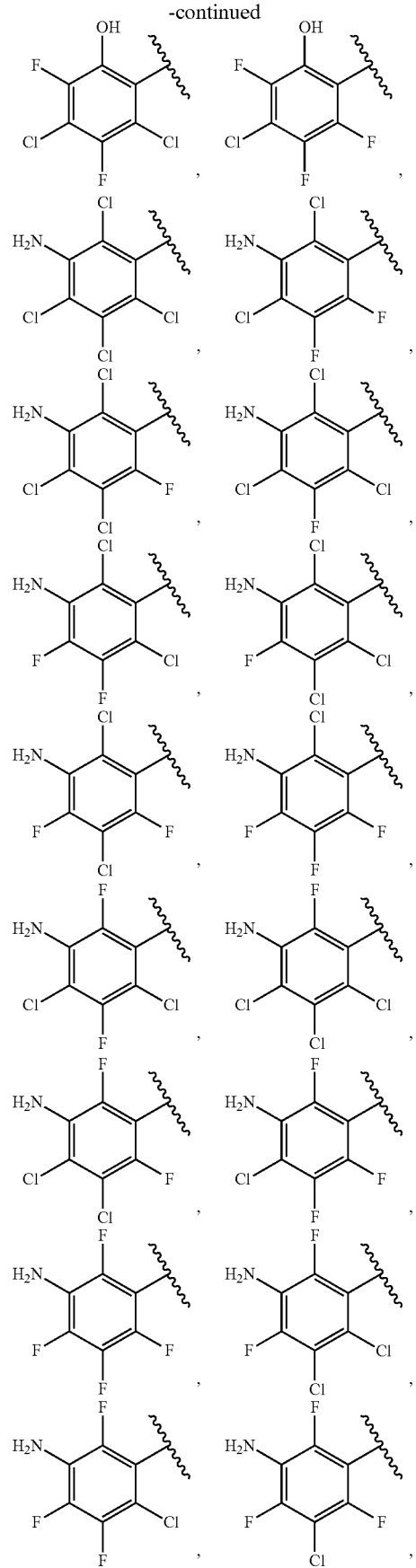
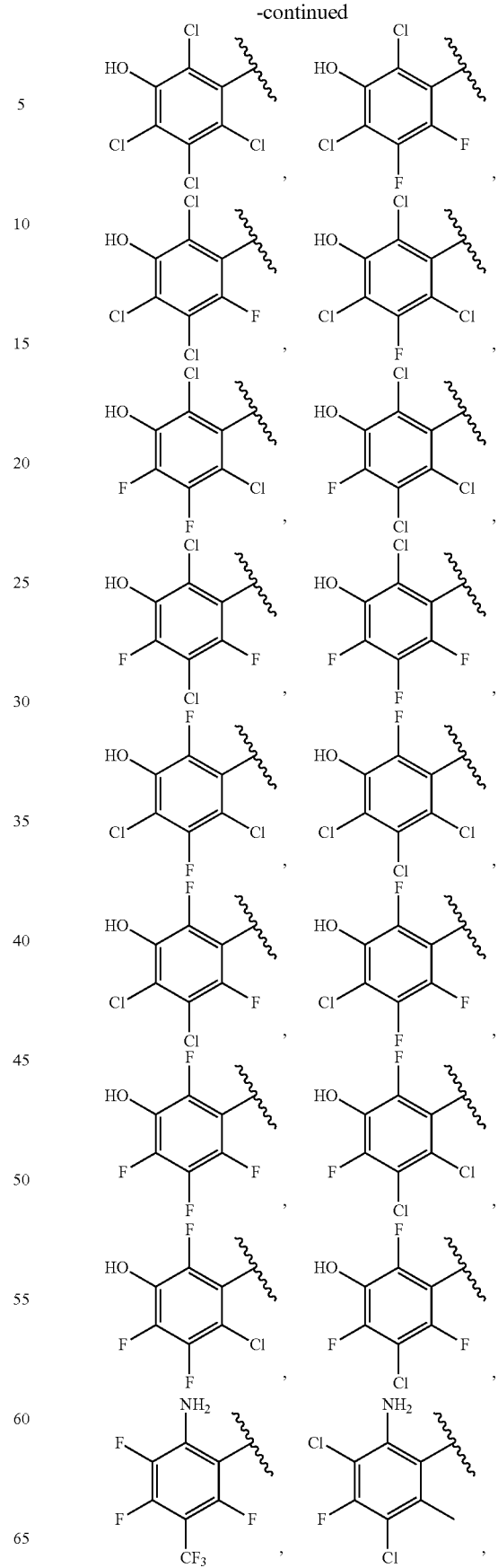

13

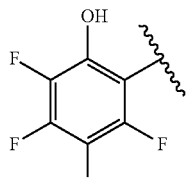, 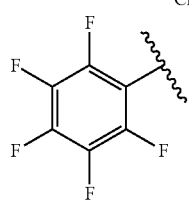 or

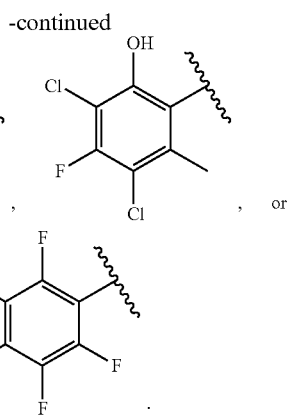

In some embodiments, $R_{21}$ is selected from hydrogen; —F; —Cl; —Br; —$C_{1-3}$alkyl; —$C_{1-3}$alkyl substituted with —F or —Cl; —$C_{2-3}$alkenyl; or —$C_{3-6}$carbocyclic.

In some embodiments, $R_{21}$ is selected from hydrogen; —F; —Cl; methyl; ethyl; propyl; isopropyl; methyl substituted with —F; ethyl substituted with —F; propyl substituted with —F; isopropyl substituted with —F; ethenyl; propenyl; 3 membered carbocyclic; 4 membered carbocyclic; 5 membered carbocyclic; or 6 membered carbocyclic.

In some embodiments, $R_{21}$ is —Cl.

In some embodiments, $R_{22}$ is selected from hydrogen; —F; —Cl; —Br; —$C_{1-3}$alkyl; —$C_{1-3}$alkyl substituted with —F or —Cl; —$C_{2-3}$alkenyl; or —$C_{3-6}$carbocyclic.

In some embodiments, $R_{22}$ is selected from hydrogen; —F; —Cl; methyl; ethyl; propyl; isopropyl; methyl substituted with —F; ethyl substituted with —F; propyl substituted with —F; isopropyl substituted with —F; ethenyl; propenyl; 3 membered carbocyclic; 4 membered carbocyclic; 5 membered carbocyclic; or 6 membered carbocyclic.

In some embodiments, $R_{22}$ is hydrogen.

In some embodiments, $R_3$ is selected from phenyl, naphthyl, 5 membered heteroaryl, 6 membered heteroaryl, 7 membered heteroaryl, 8 membered heteroaryl, 9 membered heteroaryl or 10 membered heteroaryl, each heteroaryl at each occurrence independently contains 1, 2 or 3 heteroatoms selected from N or O, each hydrogen in $R_3$ at each occurrence is independently optionally substituted with $1R_{31}$, $2R_{31}$, $3R_{31}$, $4R_{31}$ or $5R_{31}$.

In some embodiments, $R_3$ is selected from phenyl or 6 membered heteroaryl, the heteroaryl contains 1 or 2 heteroatoms selected from N, each hydrogen in the phenyl or 6 membered heteroaryl at each occurrence is independently optionally substituted by $1R_{31}$, $2R_{31}$, $3R_{31}$ or $4R_{31}$.

In some embodiments, $R_3$ is selected from

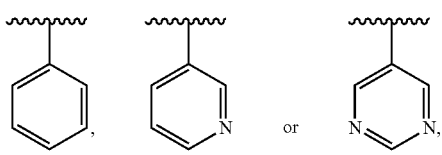 [SMILES: *c1ccccc1 ; *c1cccnc1 ; *c1cncnc1]

each hydrogen in the $R_3$ at each occurrence is independently optionally substituted by $1R_{31}$, $2R_{31}$, $3R_{31}$ or $4R_{31}$.

In some embodiments, each $R_{31}$ at each occurrence is independently selected from —F, —Cl, —Br, —$C_{1-3}$alkyl, —CN, —OH, —O—$C_{1-3}$alkyl, —NH$_2$, —NH($C_{1-3}$alkyl), —N($C_{1-3}$alkyl)$_2$ or —$C_{3-6}$carbocyclic.

14

In some embodiments, each $R_{31}$ at each occurrence is independently selected from —F, —Cl, methyl, ethyl, propyl, isopropyl, —CN, —OH, methoxy, ethoxy, propoxy, isopropoxy, —NH$_2$, —NHCH$_3$, —NHCH$_2$CH$_3$, —NH(CH$_2$CH$_2$CH$_3$), —NH(CH(CH$_3$)$_2$), —N(CH$_3$)$_2$, —N(CH$_2$CH$_3$)$_2$, —N(CH$_3$)(CH$_2$CH$_3$), 3 membered carbocyclic, 4 membered carbocyclic, 5 membered carbocyclic or 6 membered carbocyclic.

In some embodiments, each $R_{31}$ at each occurrence is independently selected from methyl or isopropyl.

In some embodiments, $R_3$ is selected from

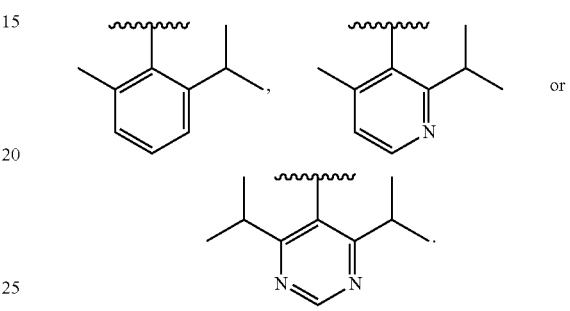

In some embodiments, $R_3$ is

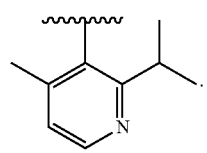 [SMILES: *c1c(C)ccnc1C(C)C]

In some embodiments, $R_4$ is

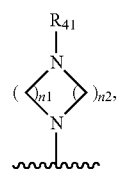

each hydrogen in the

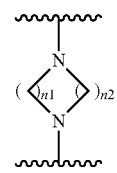

is independently optionally substituted with $1R_{42}$, $2R_{42}$, $3R_{42}$ or $4R_{42}$;

n1 is selected from 1, 2 or 3;

n2 is selected from 1, 2 or 3.

In some embodiments, $R_4$ is selected from

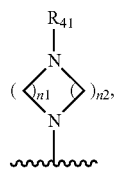

each hydrogen in the

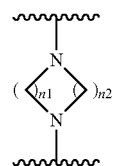

is independently optionally substituted with $1R_{42}$ or $2R_{42}$;
n1 is selected from 1 or 2;
n2 is selected from 1 or 2.
In some embodiments, $R_4$ is

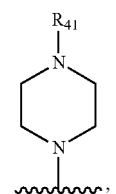

each hydrogen in the

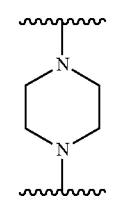

is independently optionally substituted with $1R_{42}$ or $2R_{42}$.
In some embodiments, $R_{41}$ is

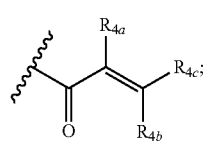

$R_{4a}$, $R_{4b}$, or $R_{4c}$ is independently selected from hydrogen, —F, —Cl, —Br, —$C_{1-3}$alkyl or —$C_{1-3}$alkylene-N($C_{1-3}$alkyl)$_2$.

In some embodiments, $R_{4a}$, $R_{4b}$ or $R_{4c}$ is independently selected from hydrogen, —F, —Cl, methyl, ethyl, propyl, isopropyl, —$CH_2$—$N(CH_3)_2$, —$CH_2$—$N(CH_2CH_3)_2$ or —$CH_2$—$N(CH_3)(CH_2CH_3)$.

In some embodiments, $R_{4a}$, $R_{4b}$ or $R_{4c}$ is independently selected from hydrogen, —F, methyl or —$CH_2$—$N(CH_3)_2$.

In some embodiments, $R_{4a}$ is selected from hydrogen or —F; $R_{4b}$ is hydrogen; $R_{4c}$ is selected from hydrogen or —$CH_2$—$N(CH_3)_2$.

In some embodiments, $R_{41}$ is selected from:

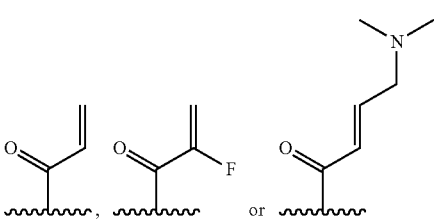

In some embodiments, $R_4$ is selected from

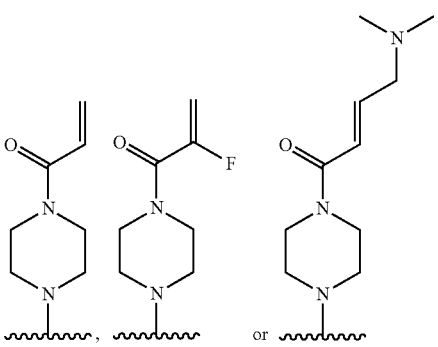

each hydrogen in the

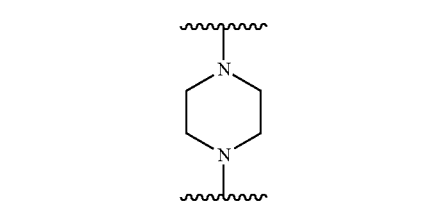 [SMILES: *N1CCN(*)CC1]

at each occurrence is independently optionally substituted with $1R_{42}$ or $2R_{42}$.

In some embodiments, each $R_{42}$ at each occurrence is independently selected from —$C_{1-3}$alkyl; —$C_{1-3}$alkylene-CN; or —$C_{1-3}$alkyl substituted with —F or —Cl.

In some embodiments, each $R_{42}$ at each occurrence is independently selected from methyl; ethyl; propyl; isopropyl; -methylene-CN; -ethylene-CN; -propylene-CN; methyl substituted with —F; ethyl substituted with —F; propyl substituted with —F; or isopropyl substituted with —F.

In some embodiments, each $R_{42}$ at each occurrence is independently selected from methyl; ethyl; -methylene-CN or methyl substituted with —F.

In some embodiments, each $R_{42}$ at each occurrence is independently selected from —$CH_3$, —$CH_2CH_3$, —$CH_2CN$, —$CHF_2$ or —$CF_3$.

In some embodiments, $R_4$ is selected from:
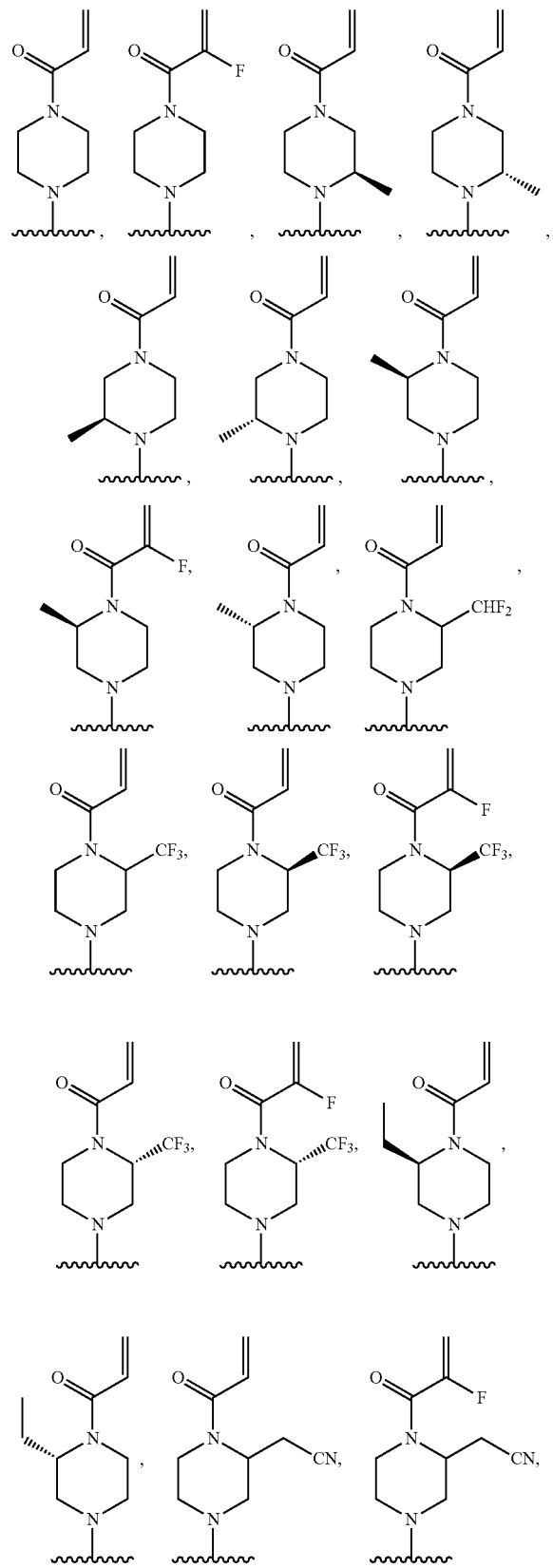
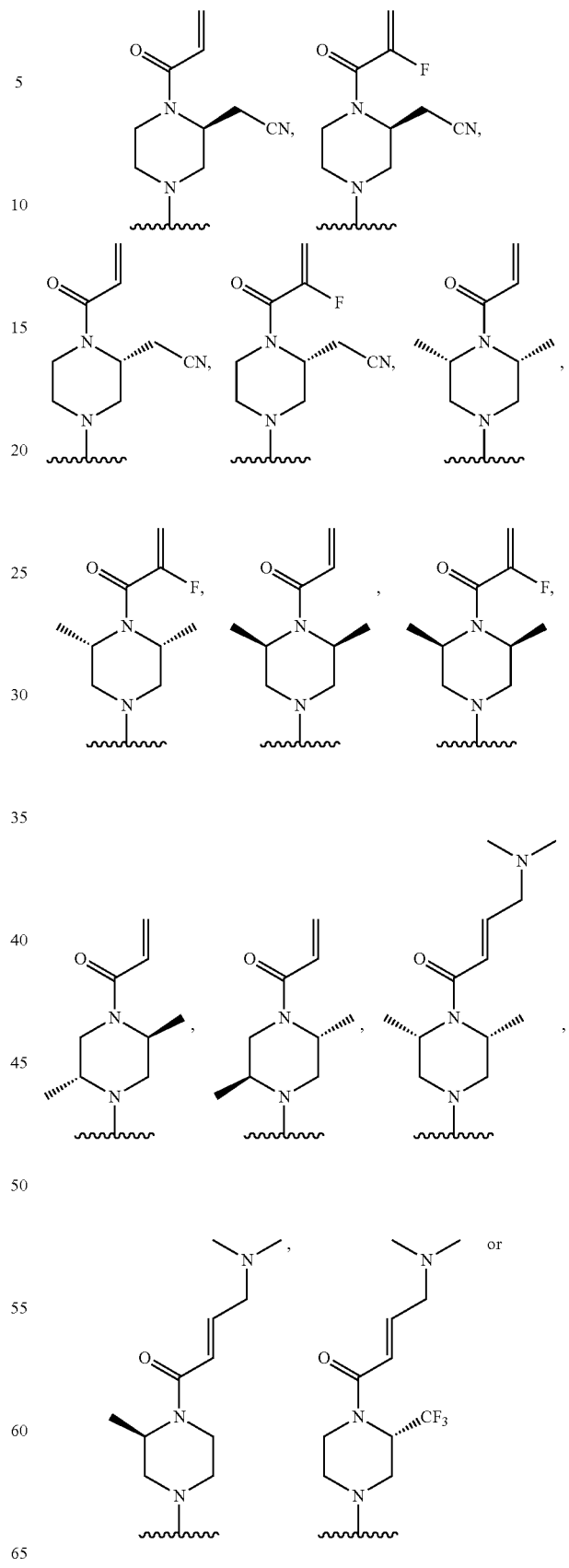

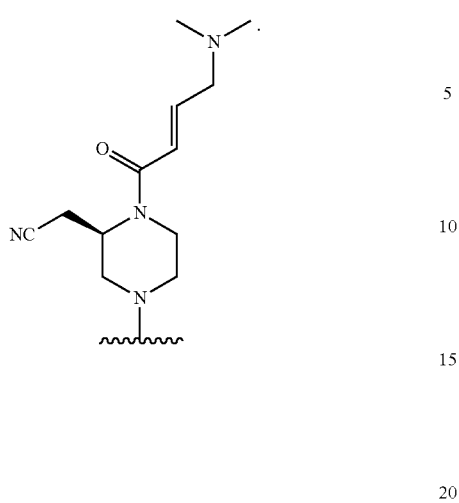
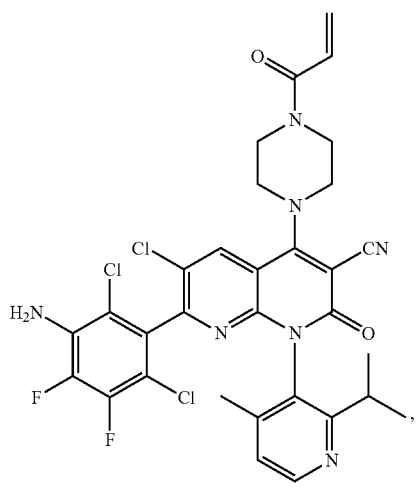
In some embodiments, R₄ is selected from:
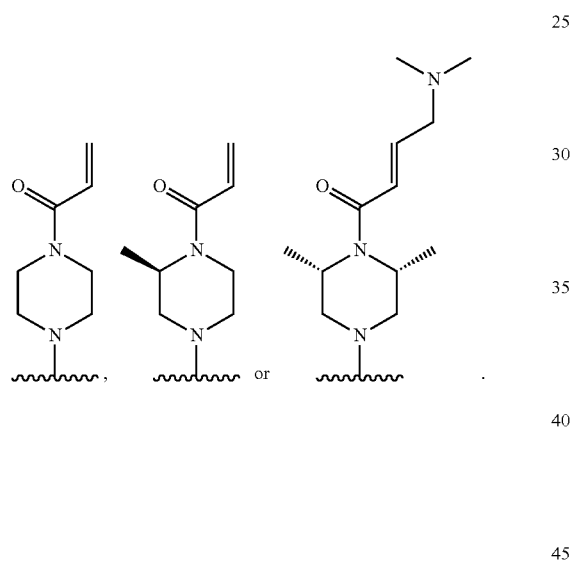
In some embodiments, the compound is selected from:
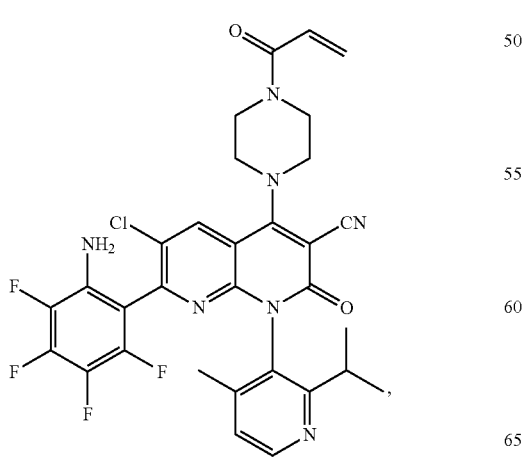
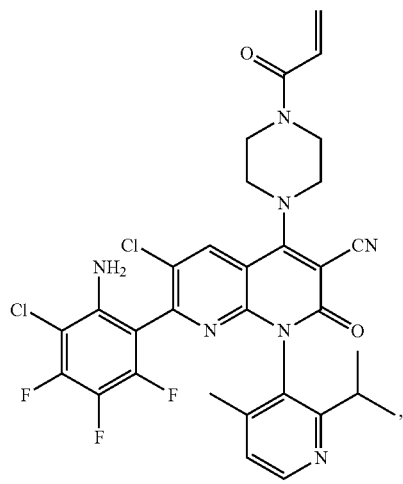
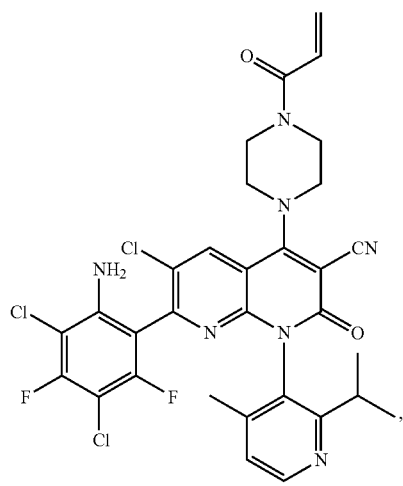

-continued
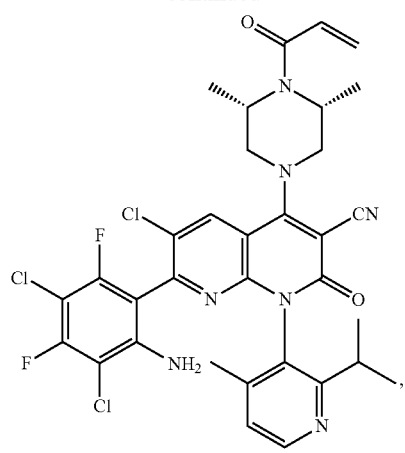
-continued
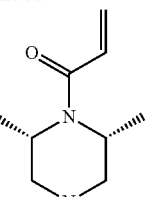
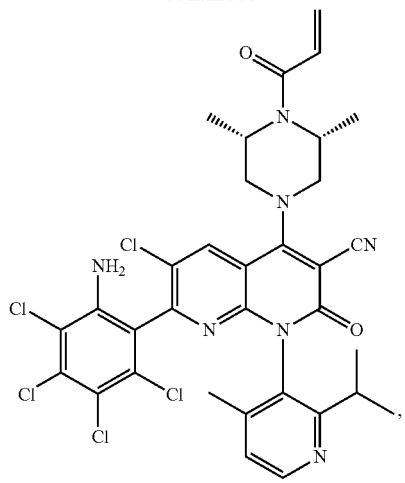
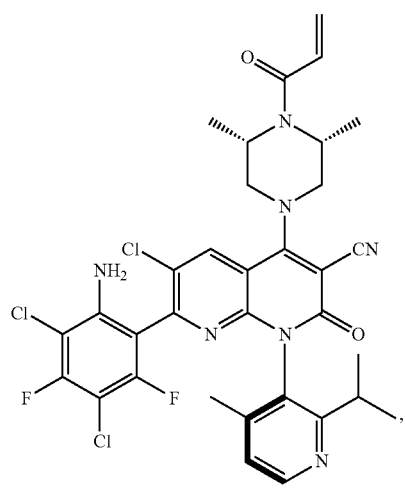
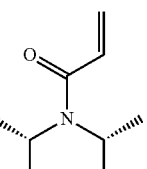
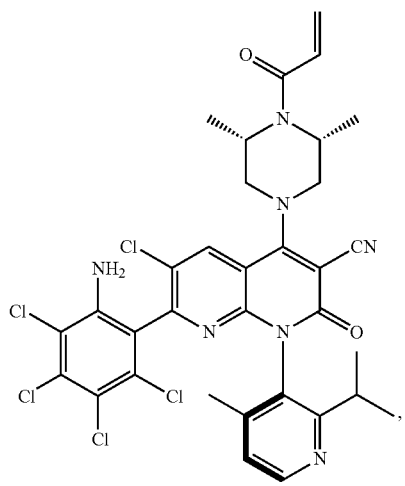
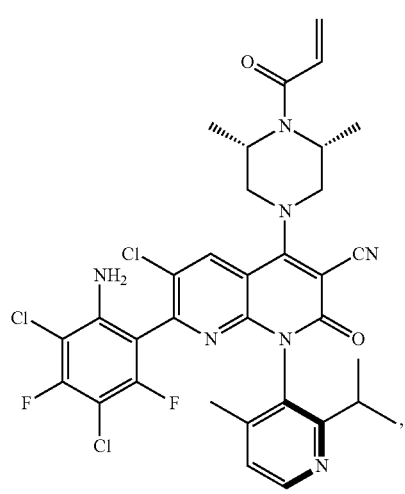
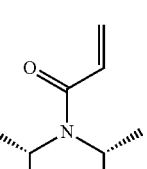
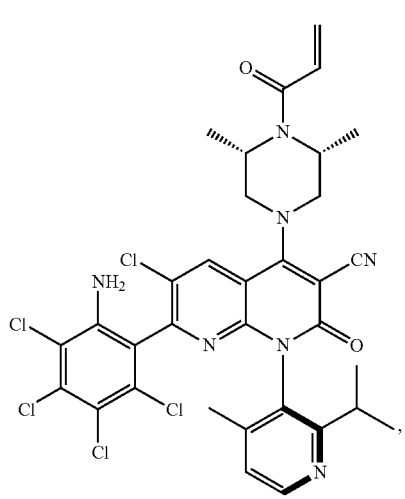

-continued
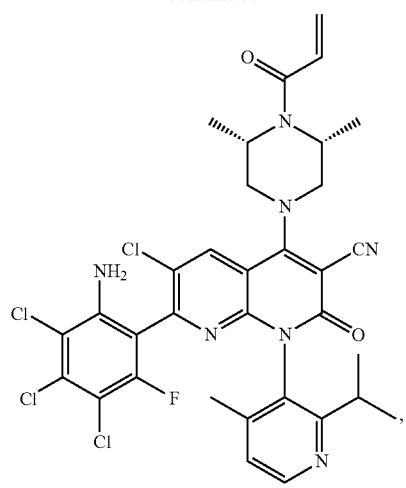
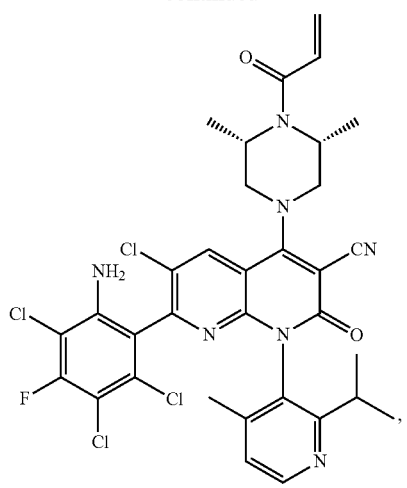
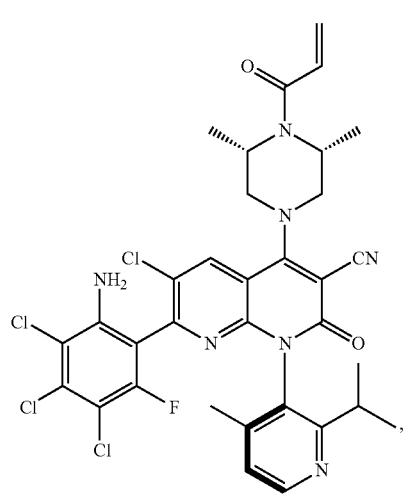
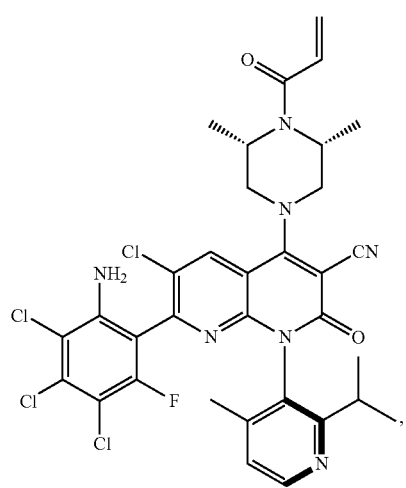

-continued
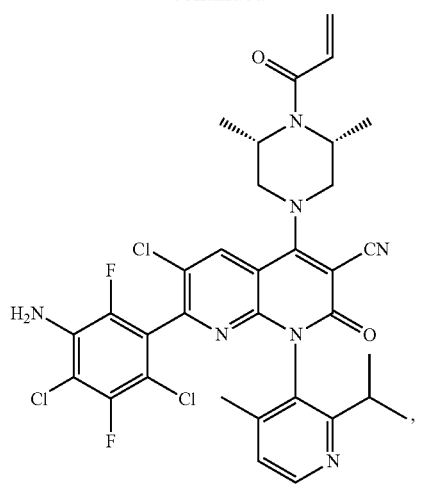
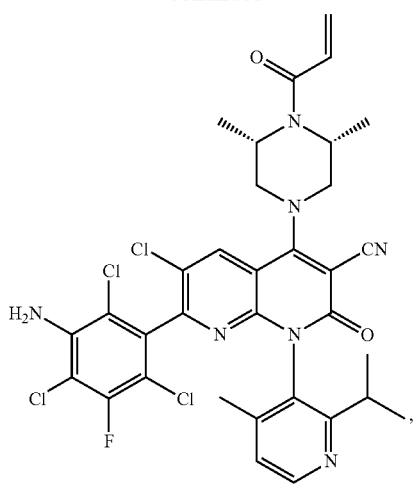
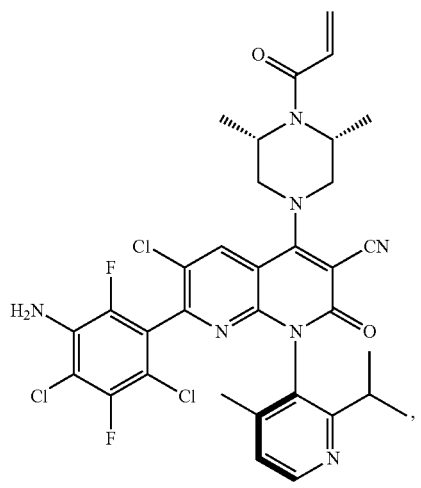
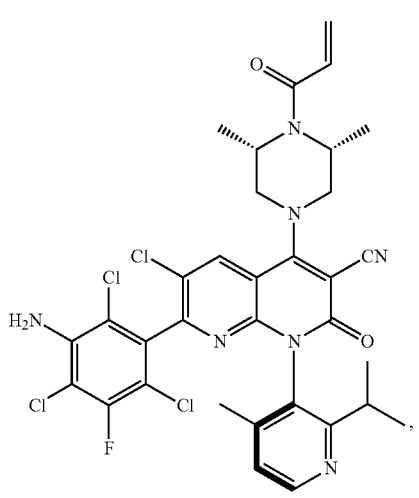
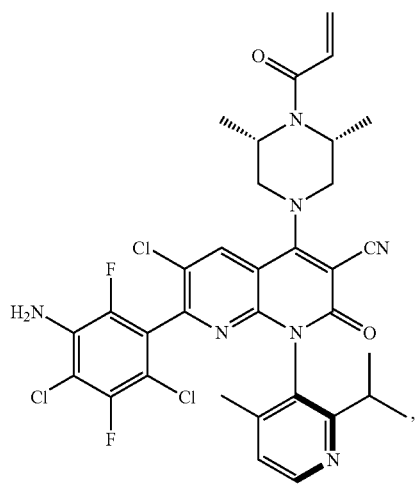
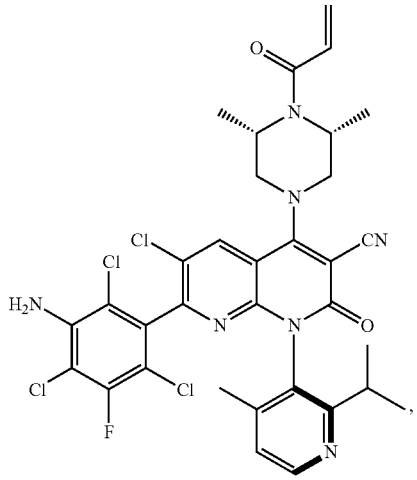

-continued
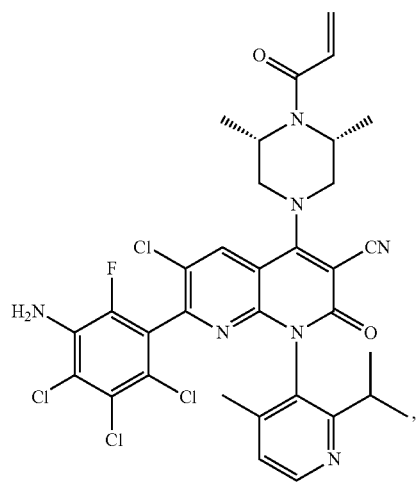
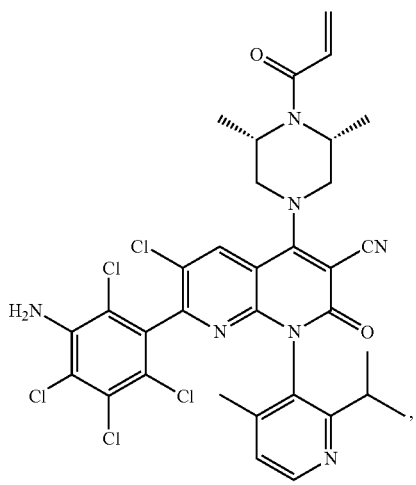
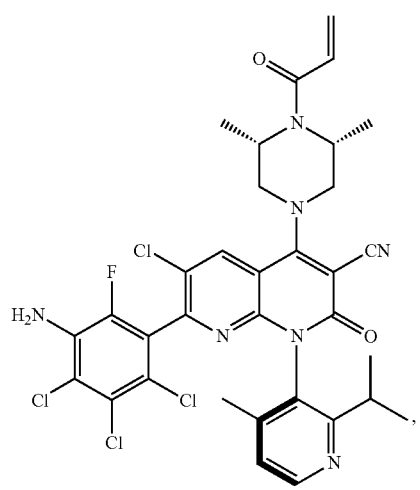
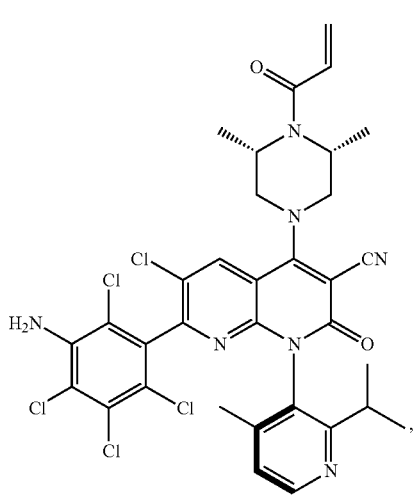
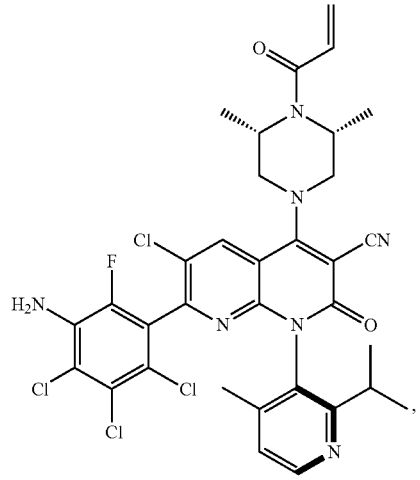
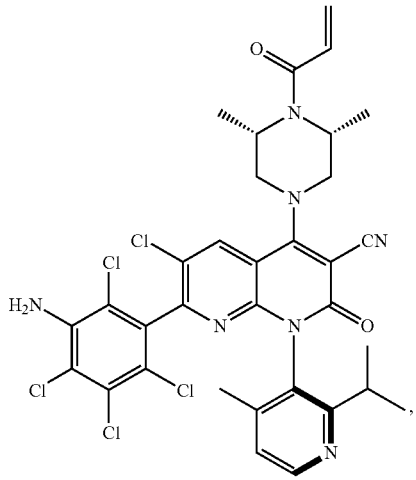

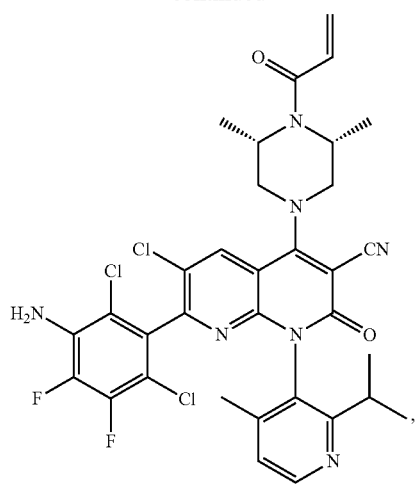
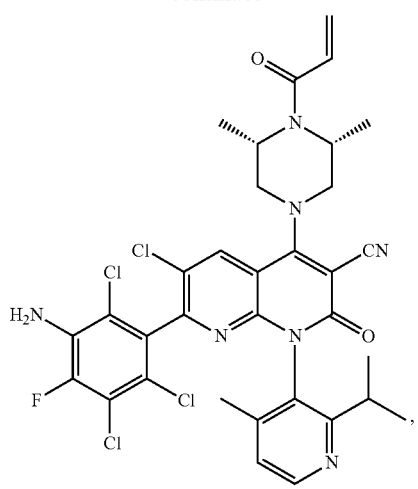
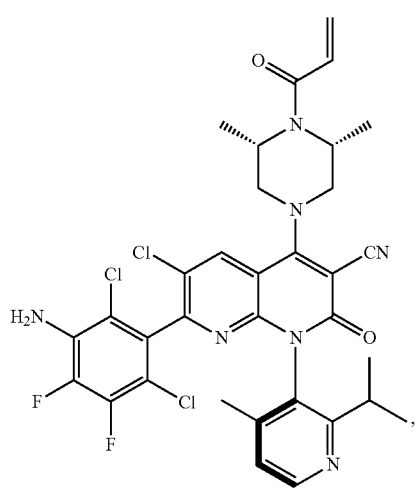
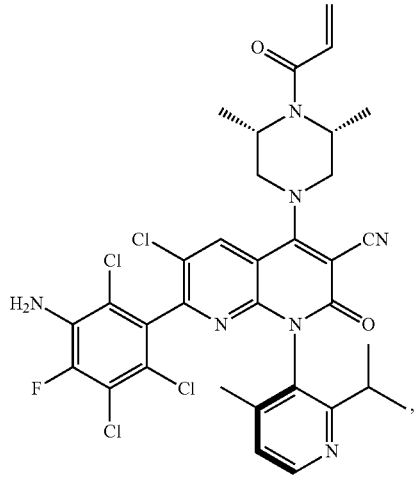

-continued
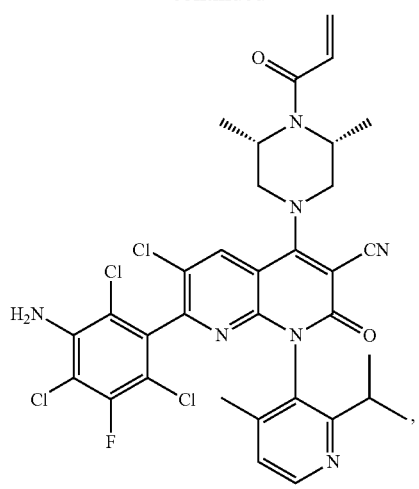
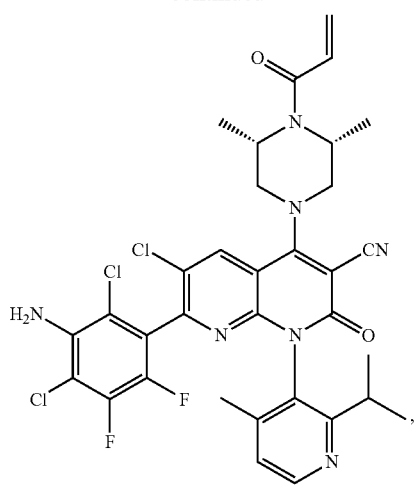
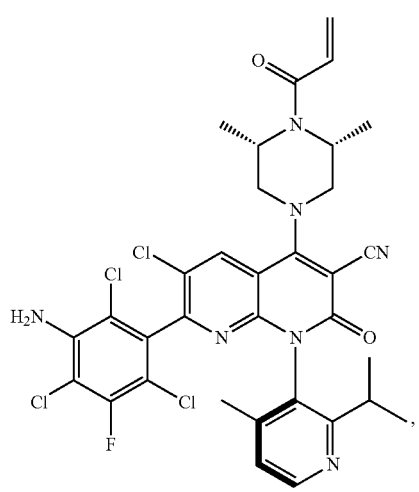
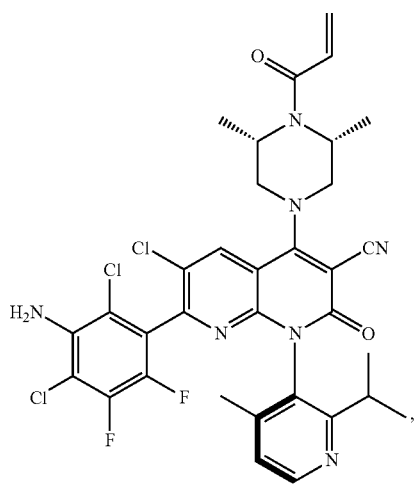

33
-continued
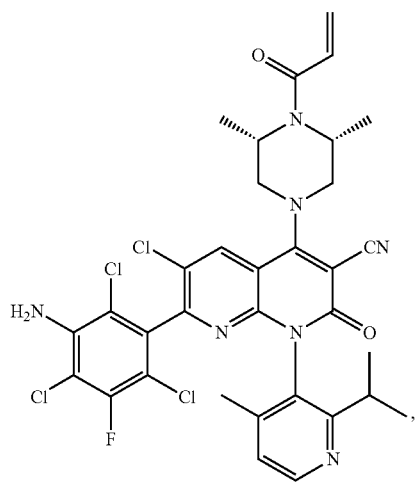
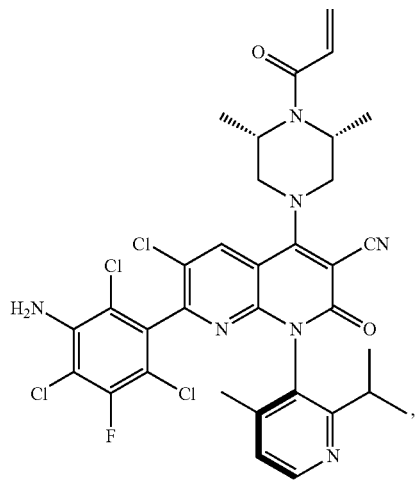
34
-continued
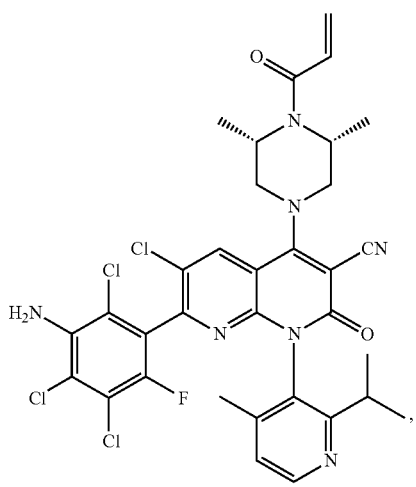
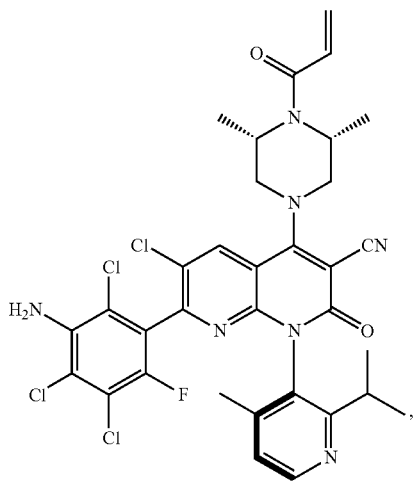

-continued
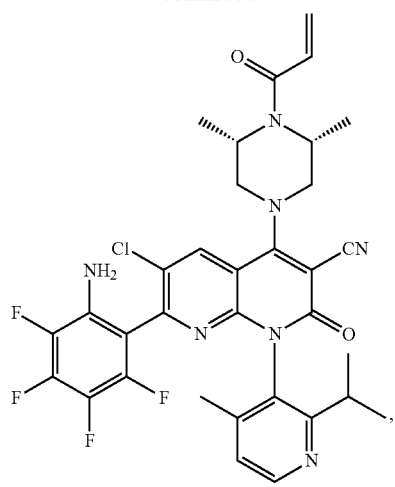
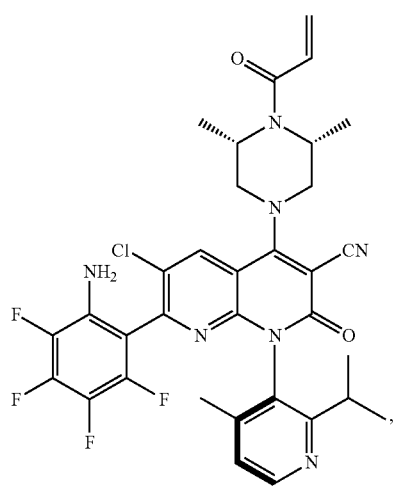
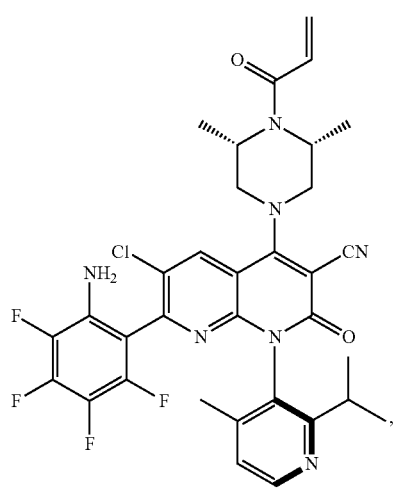
-continued
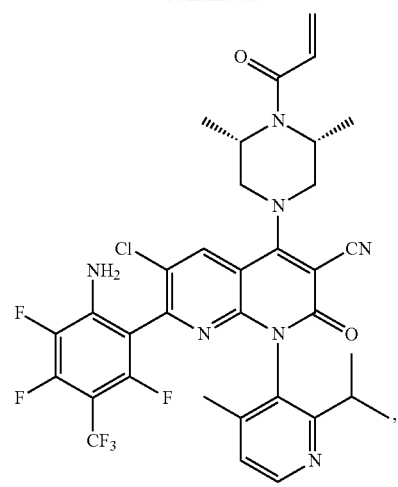
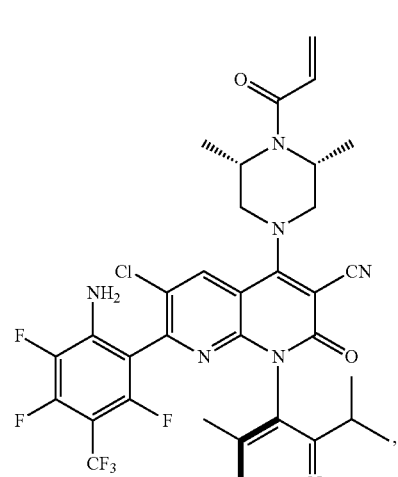
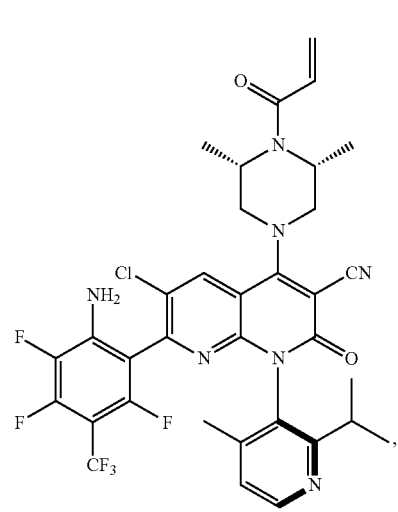

37
-continued
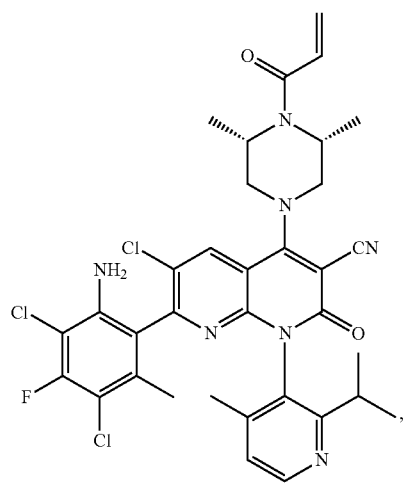
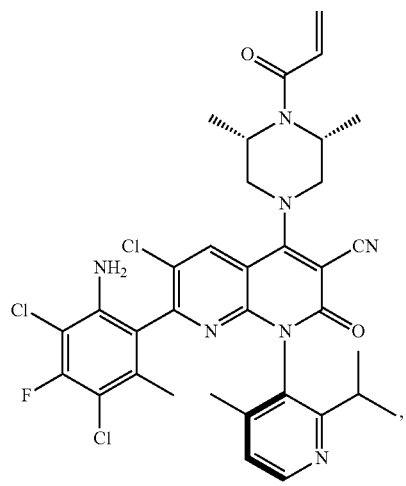
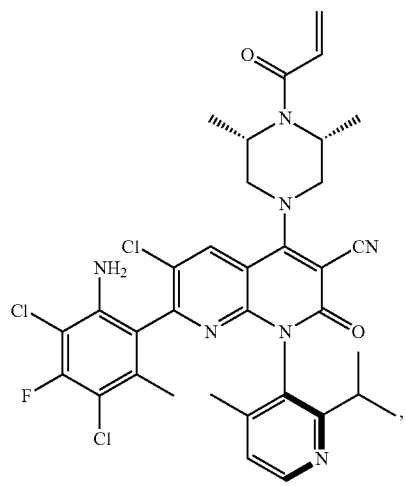
38
-continued
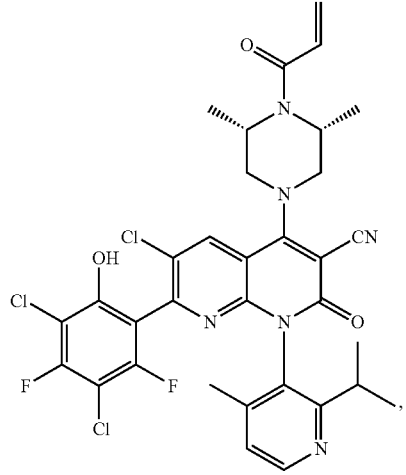
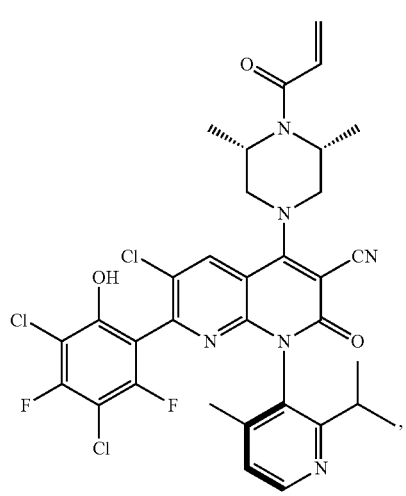

39
-continued
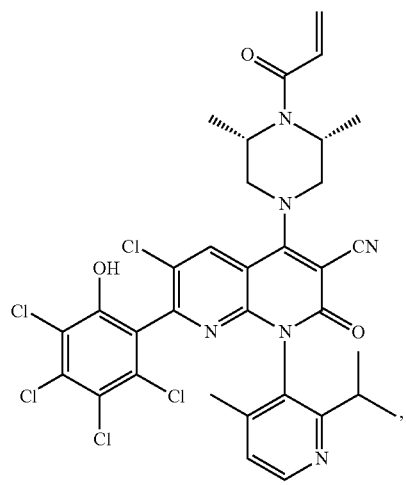
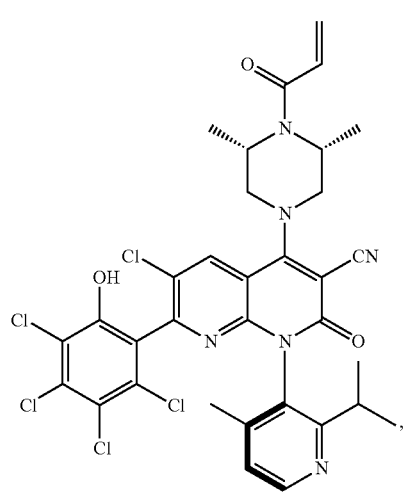
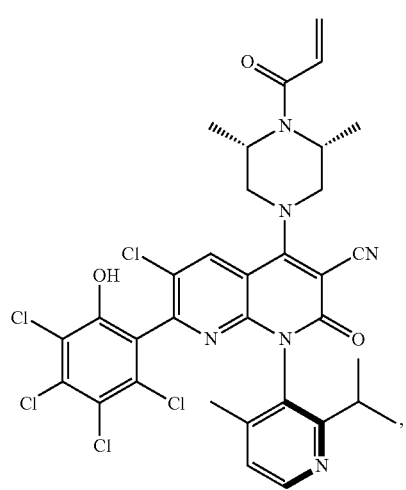
40
-continued
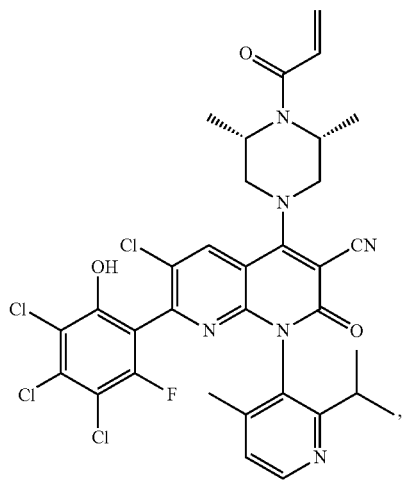
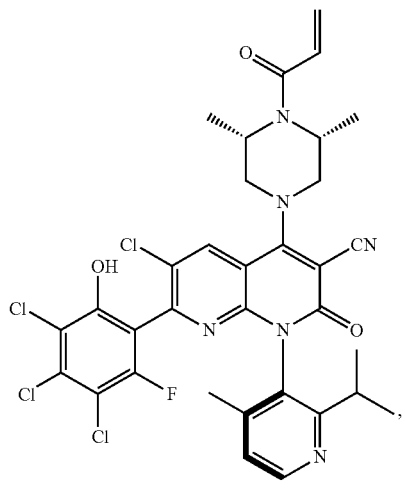

41
-continued
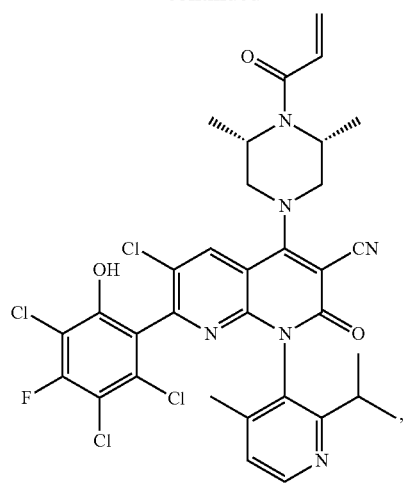
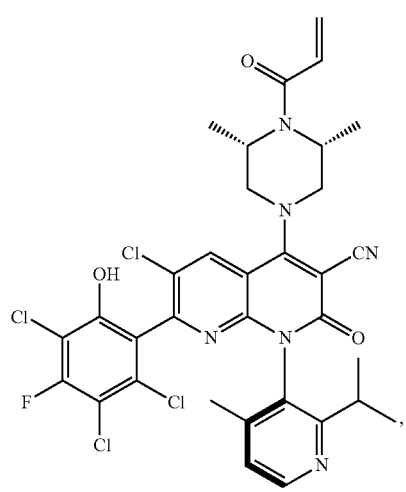
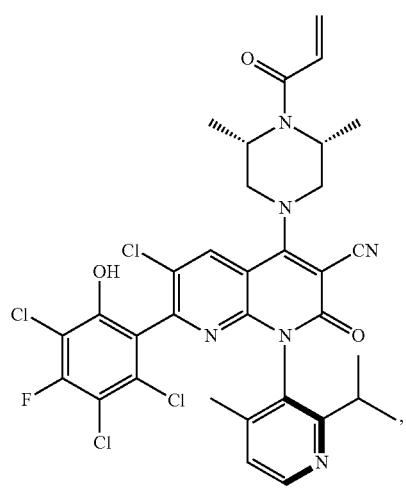
42
-continued
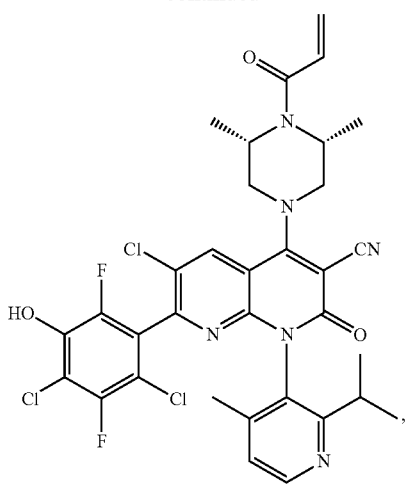
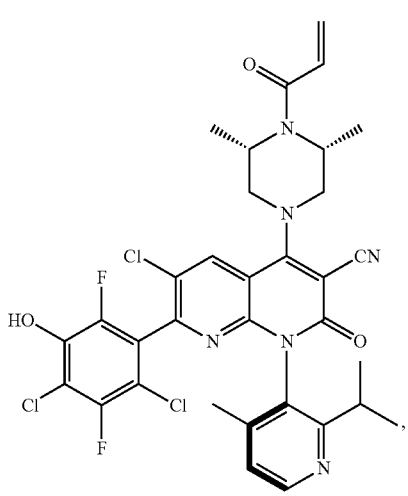
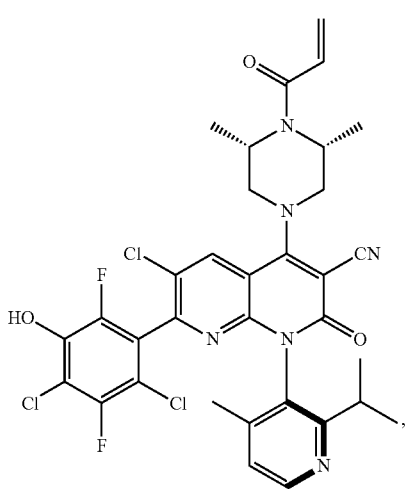

-continued
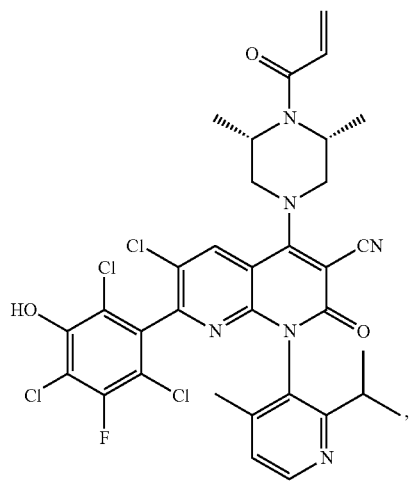
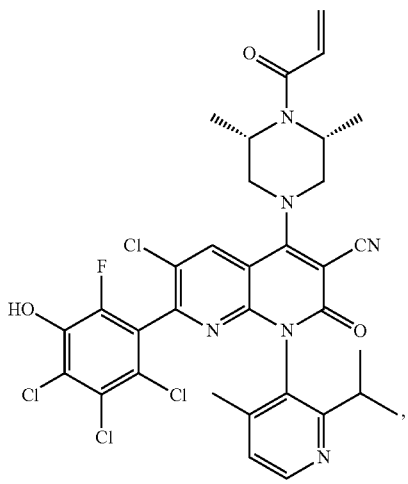
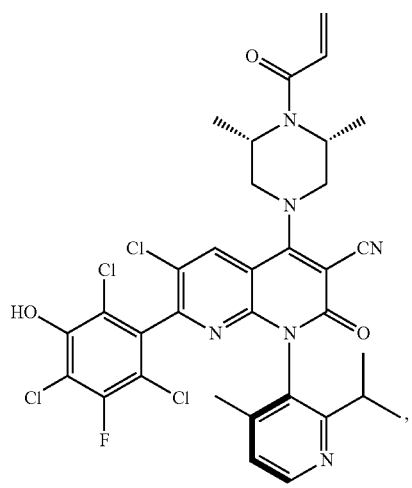
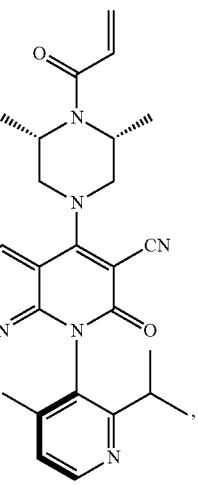
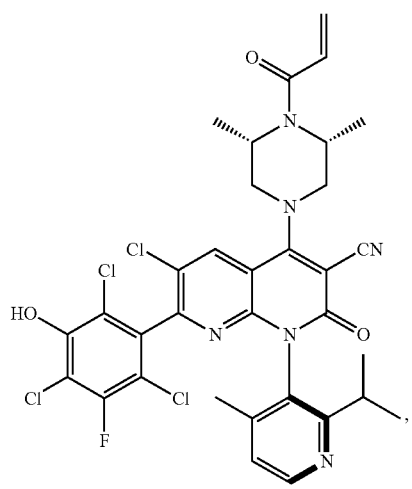
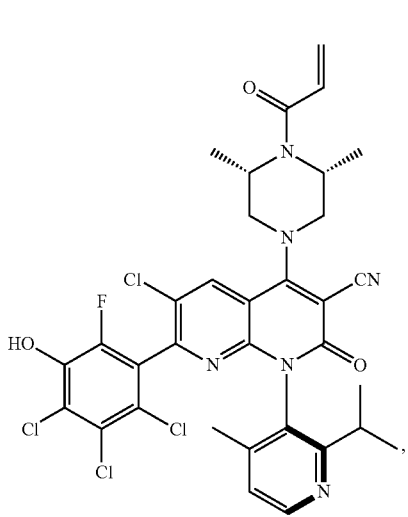

-continued
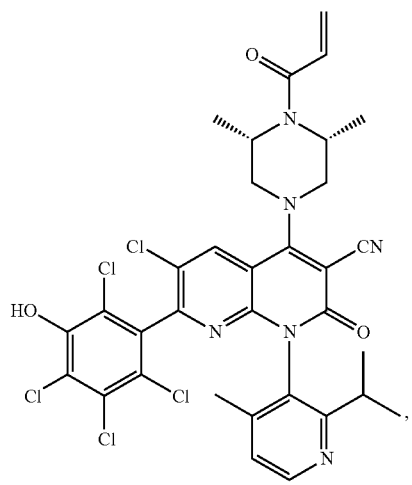
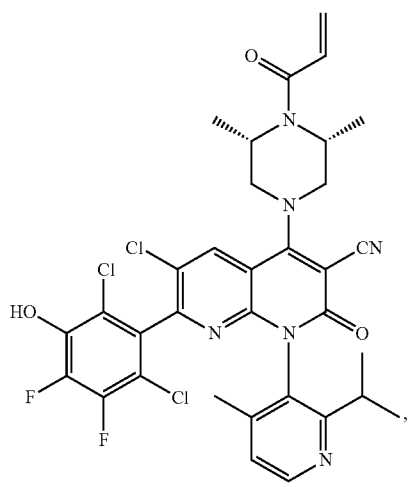
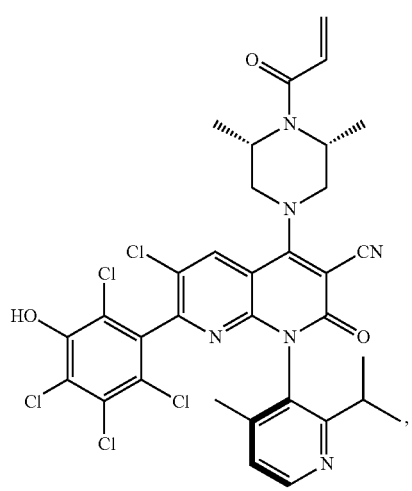
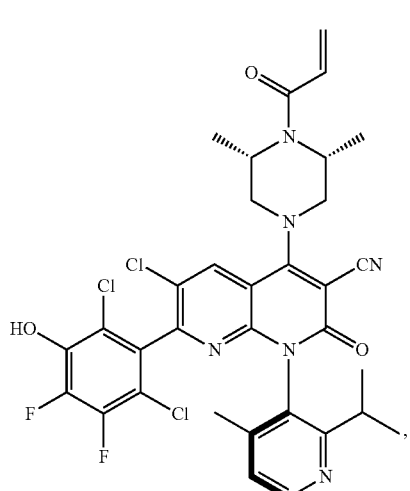
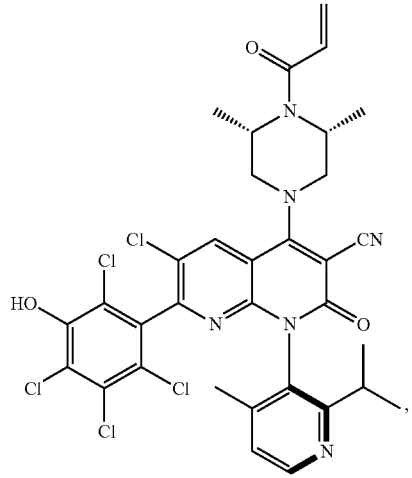
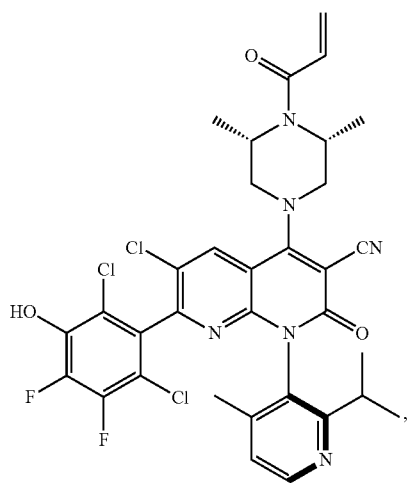

-continued
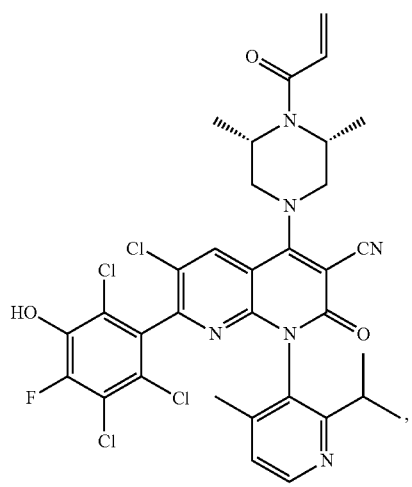
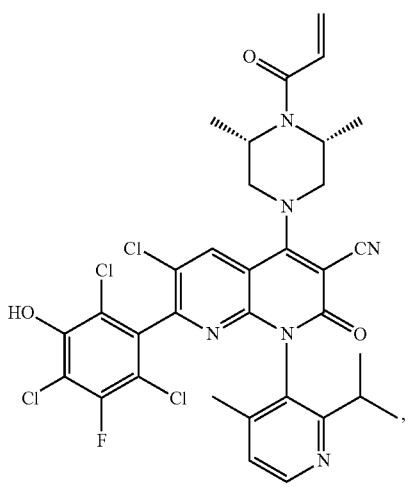
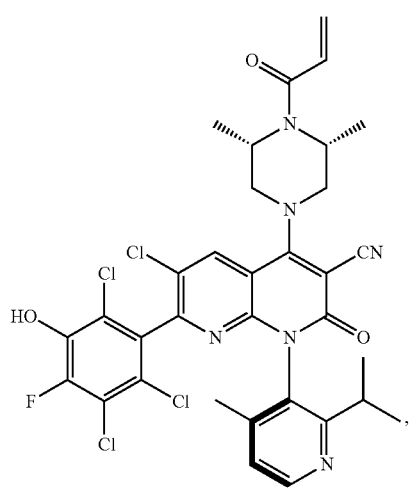
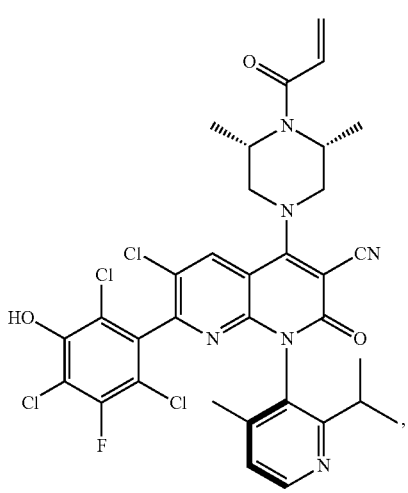
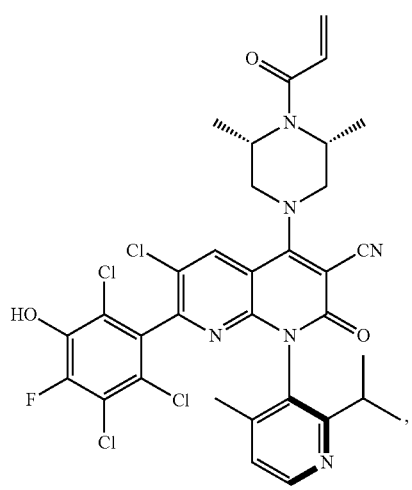
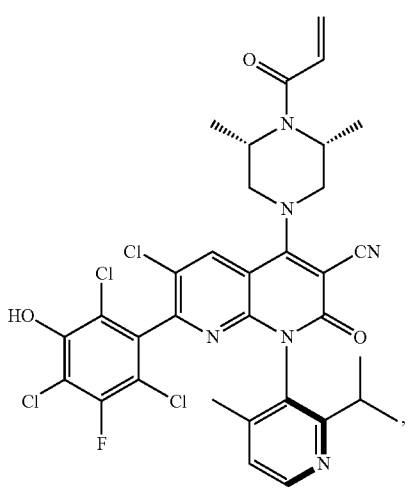

-continued
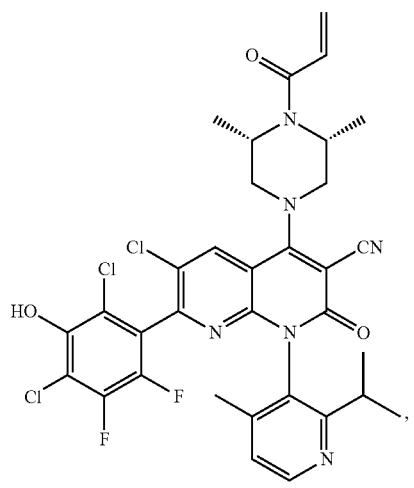
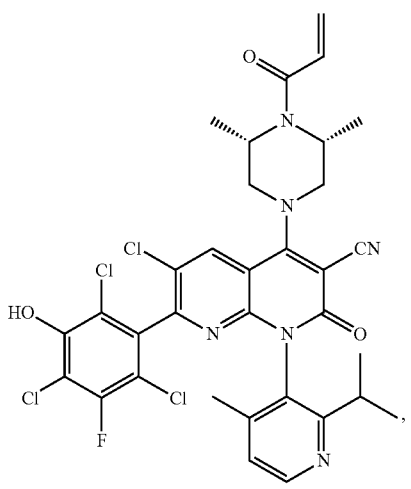
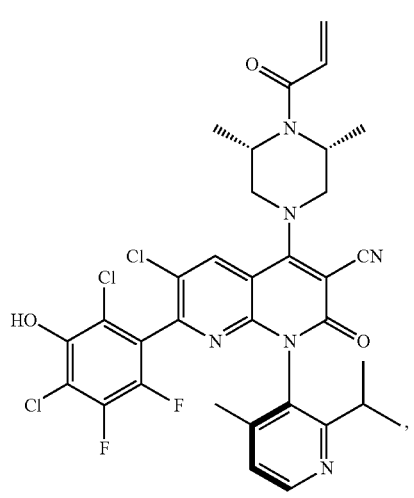
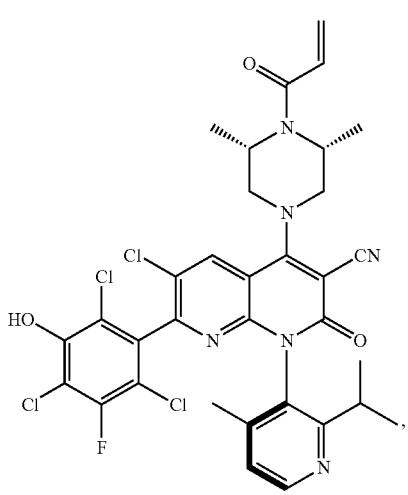

51
-continued
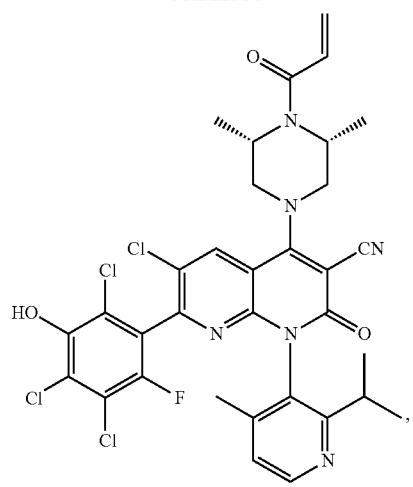
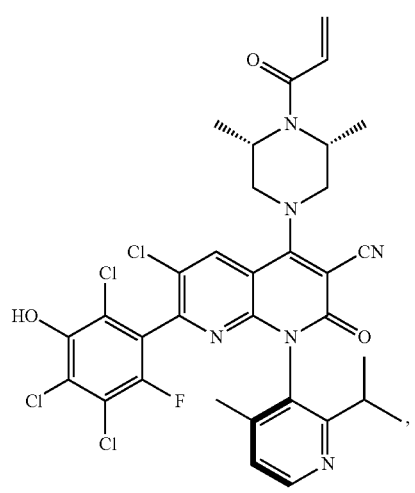
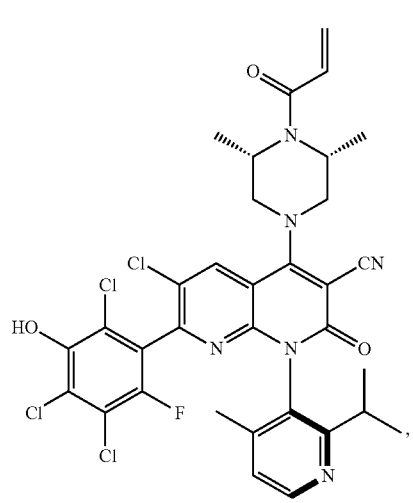
52
-continued
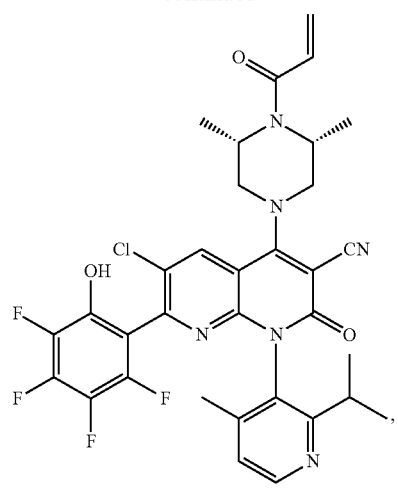
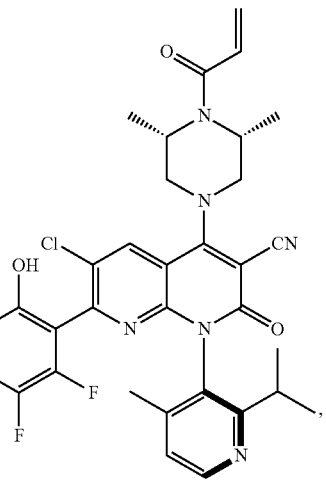

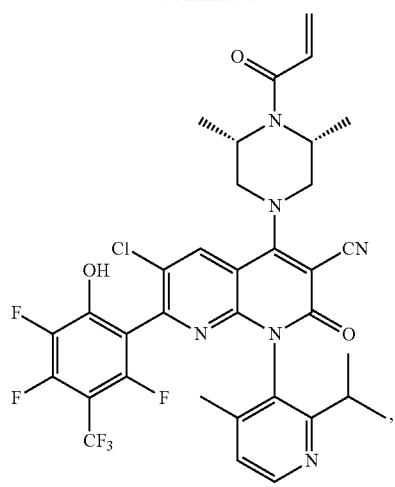
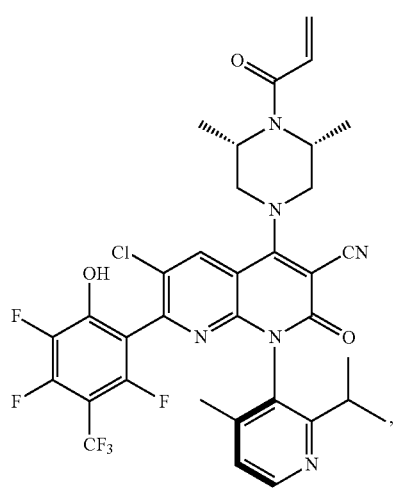
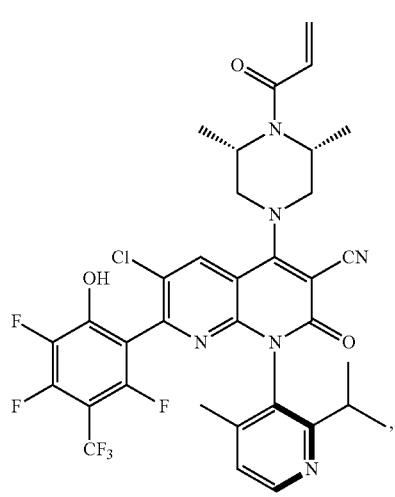
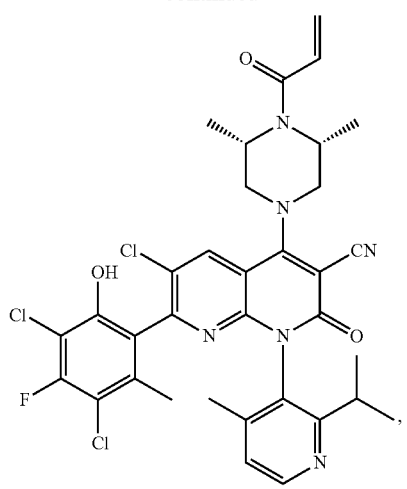
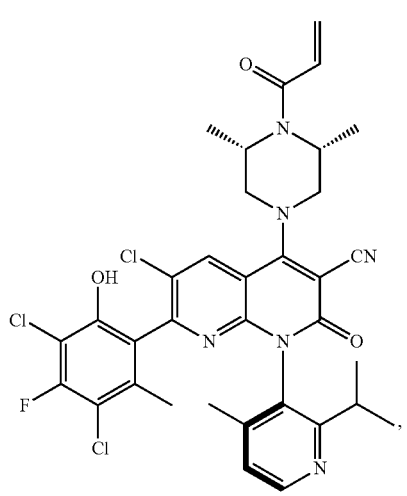
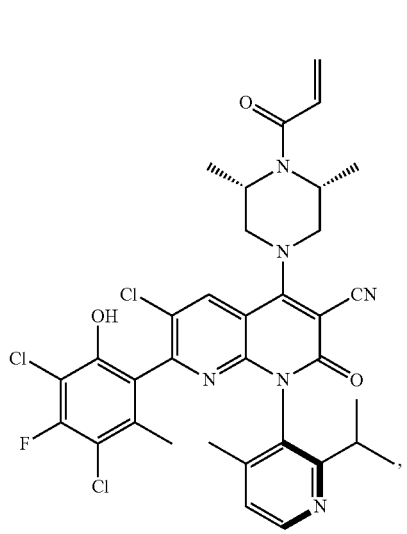

55
-continued
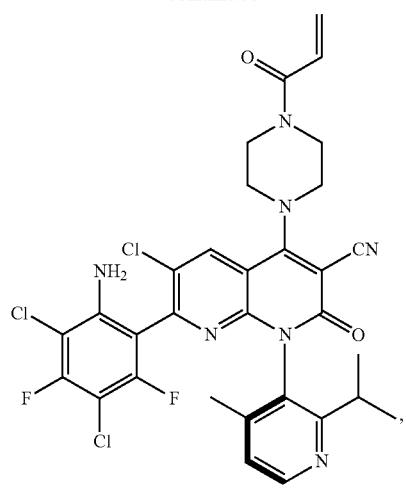
56
-continued
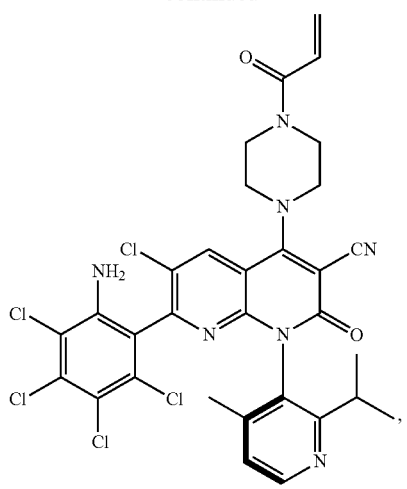
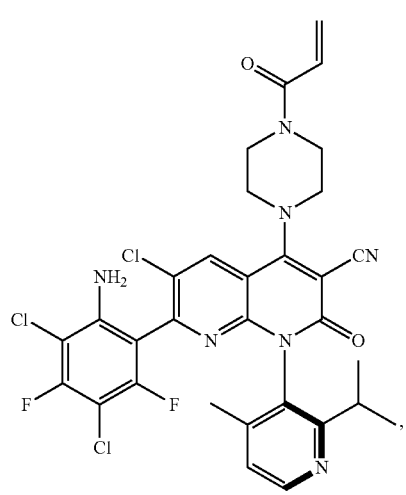
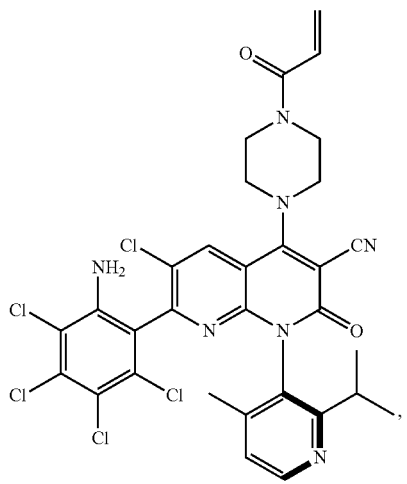

-continued
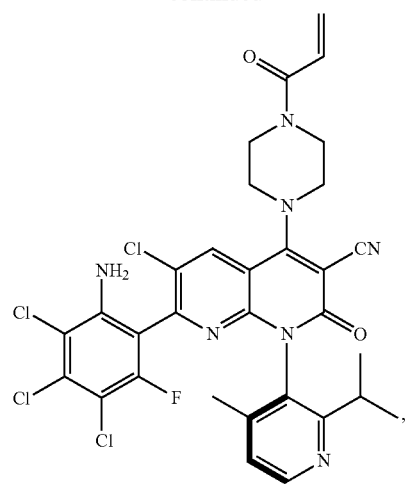
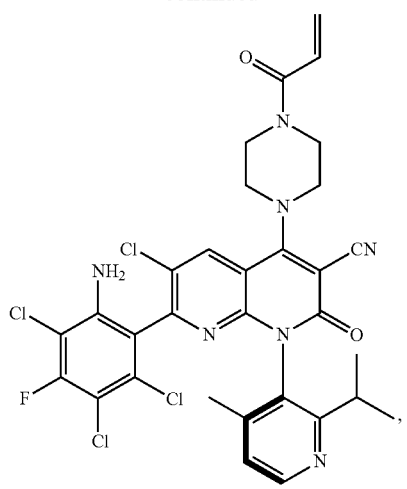
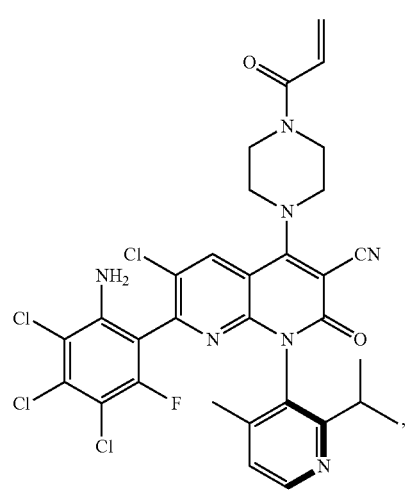
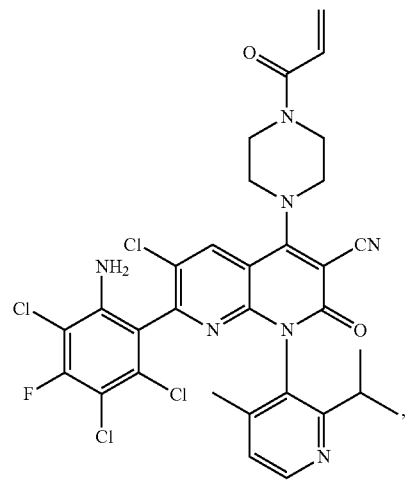

-continued
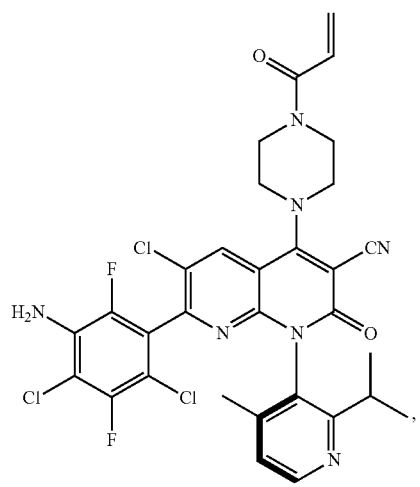
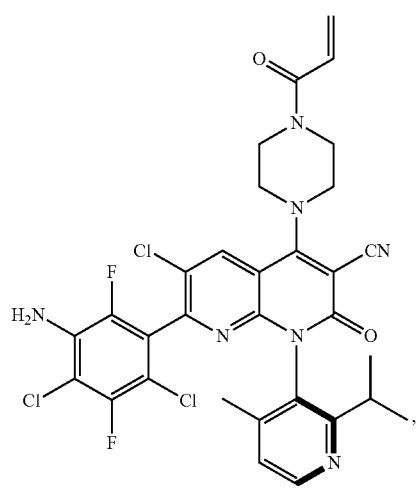
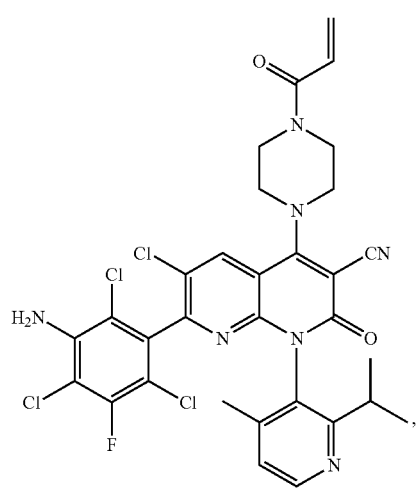
-continued
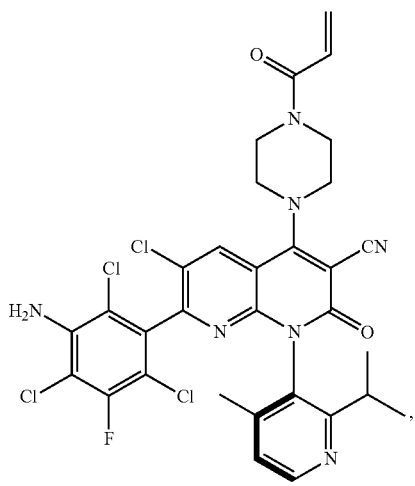
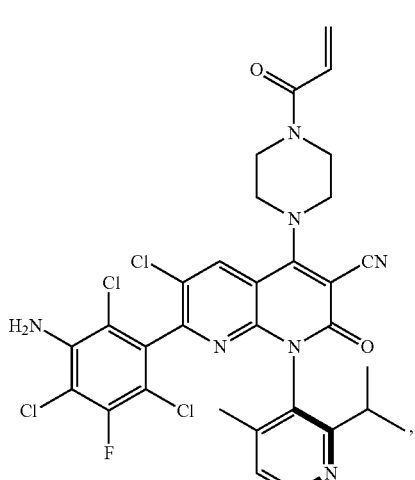
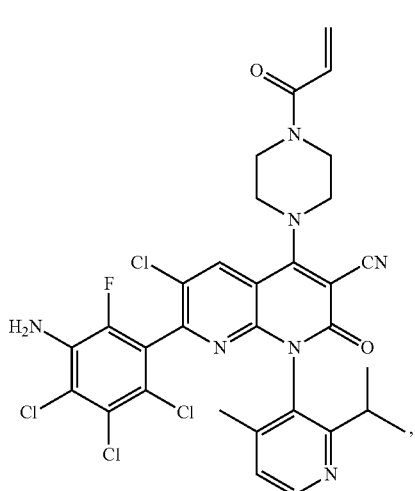

-continued
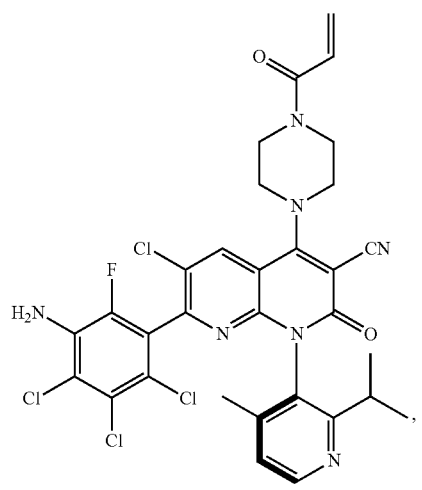
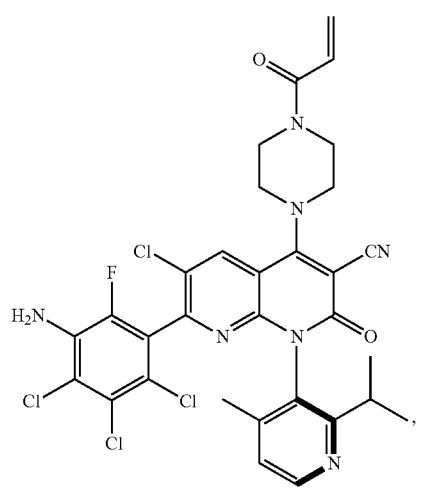
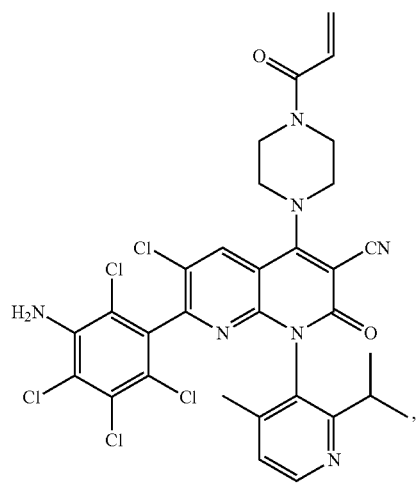
-continued
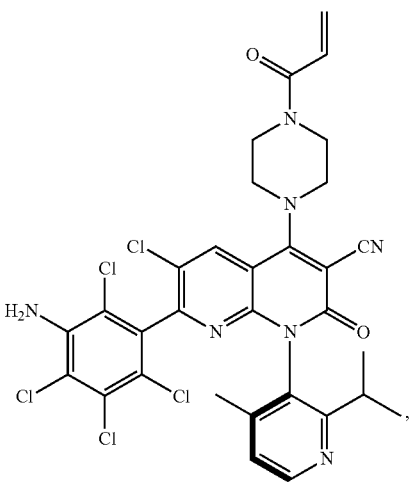
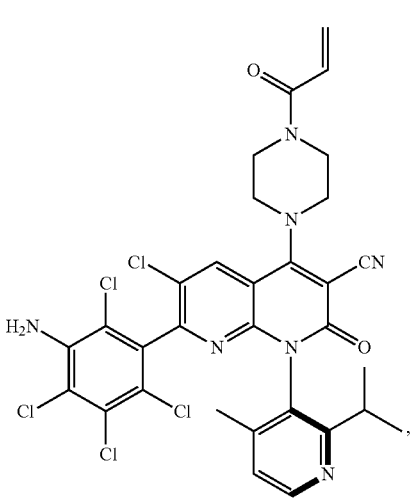
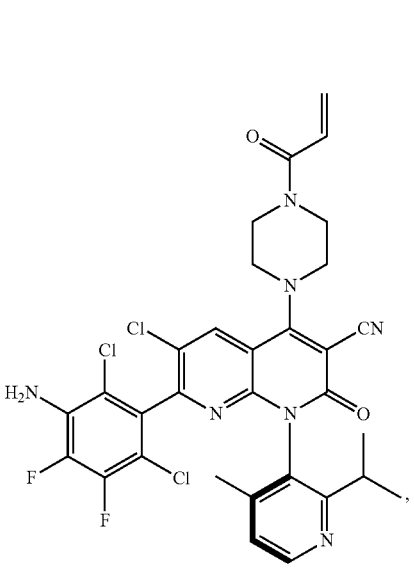

63
-continued
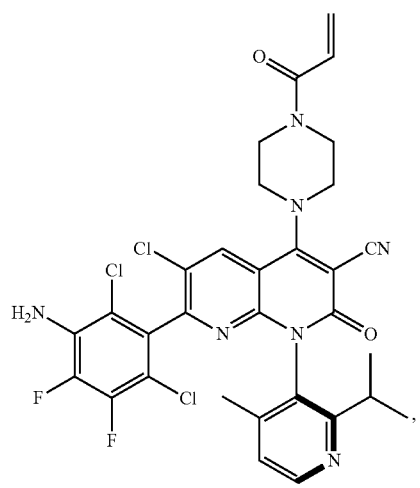
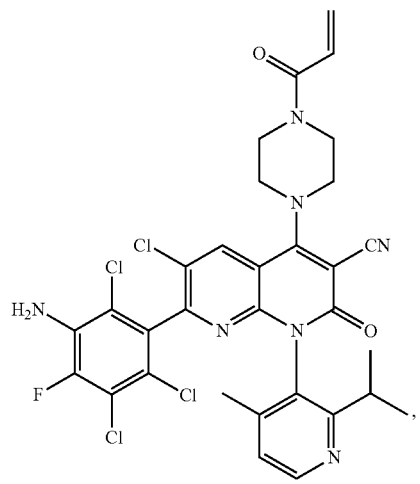
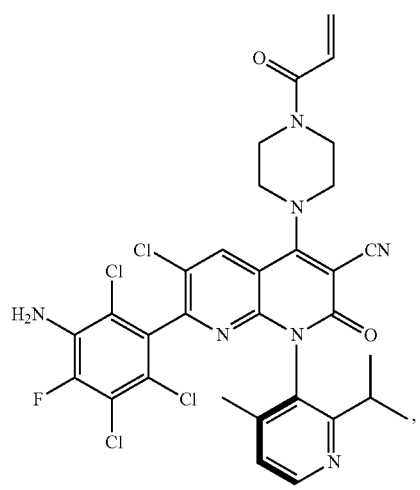
64
-continued
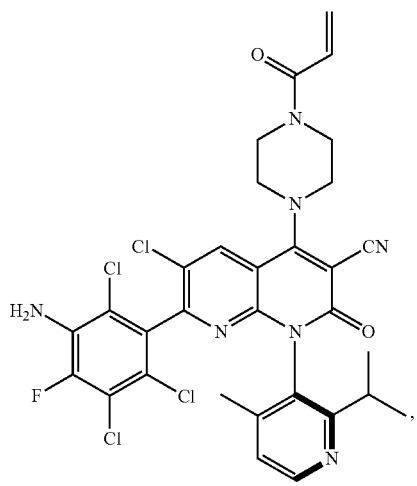
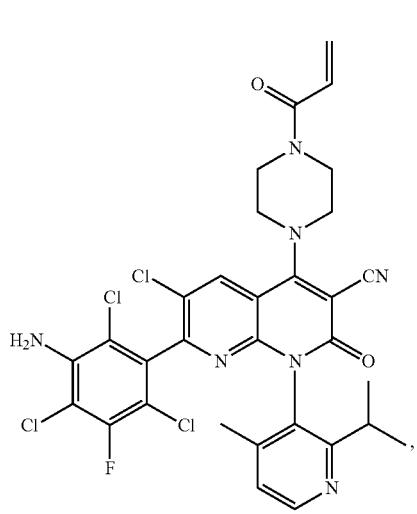
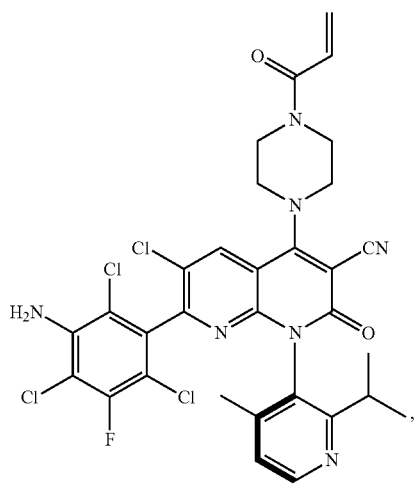

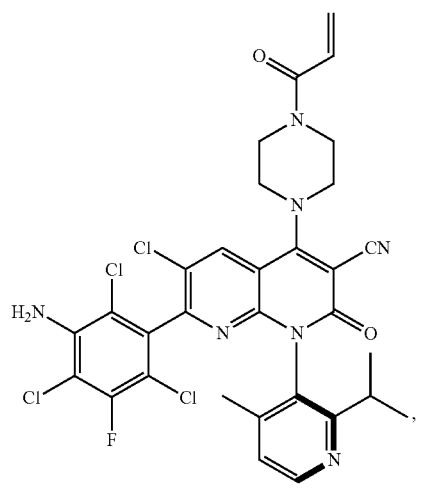
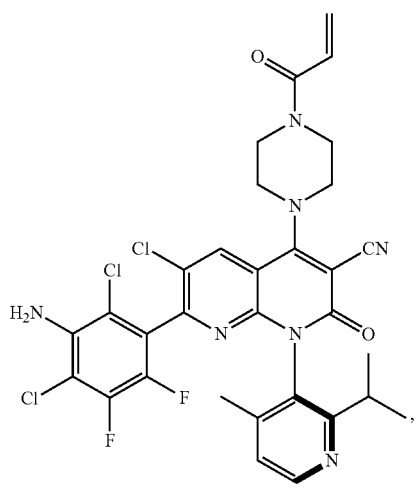
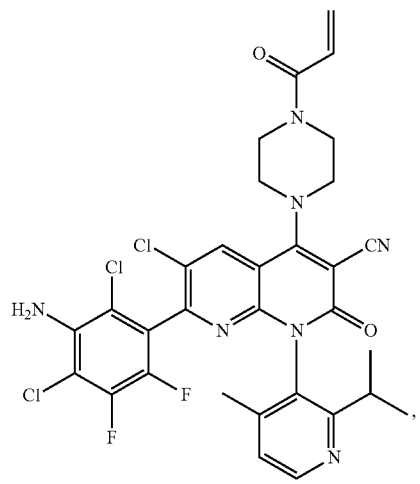
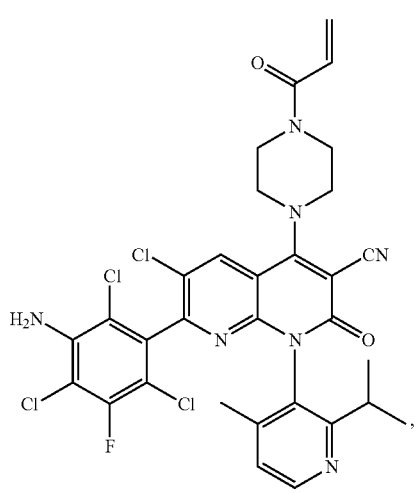
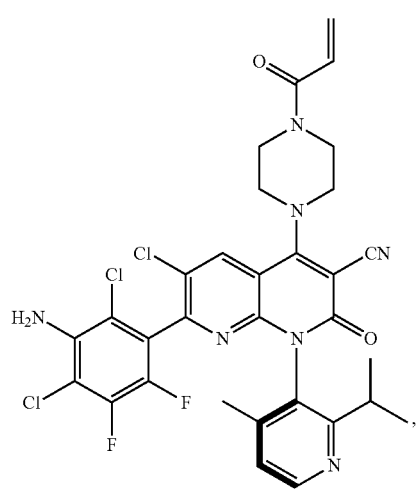
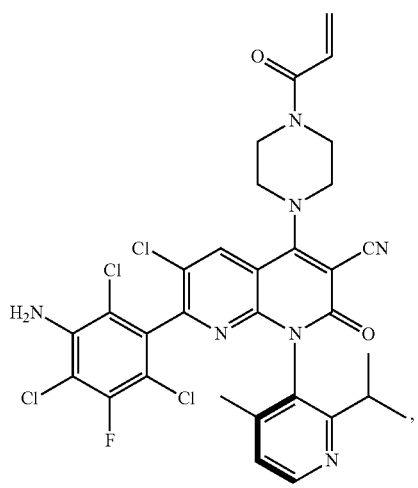

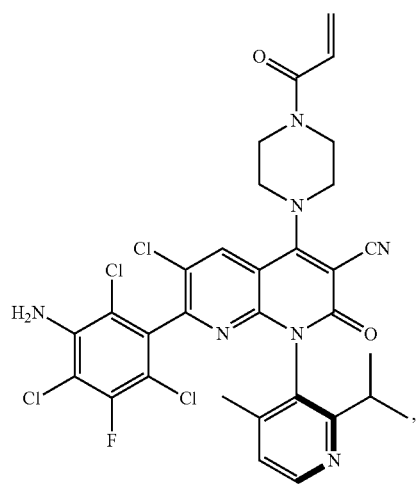
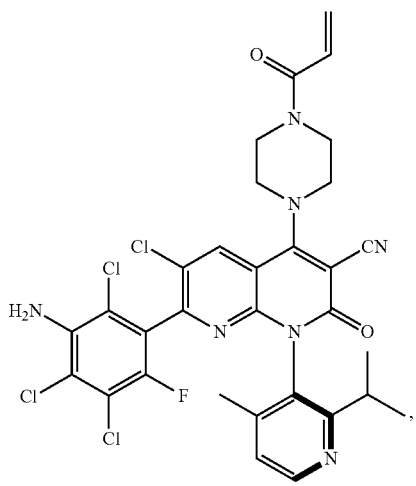
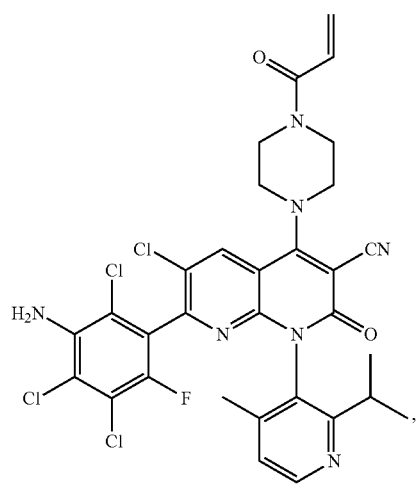
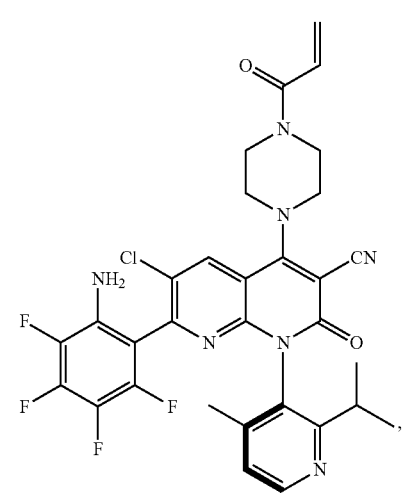
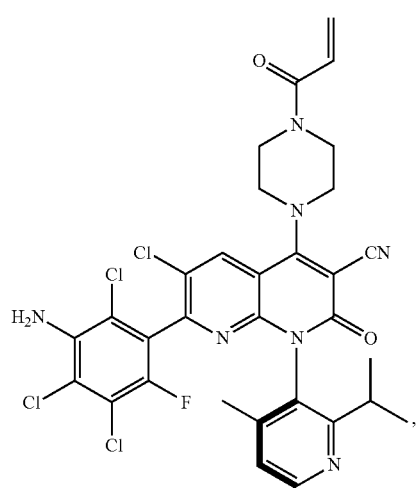

-continued
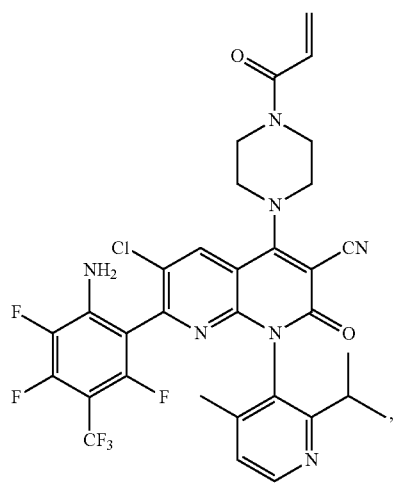
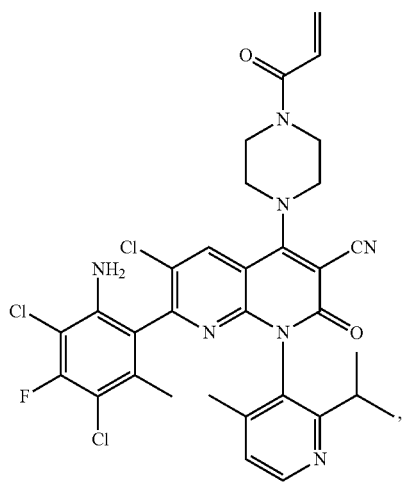
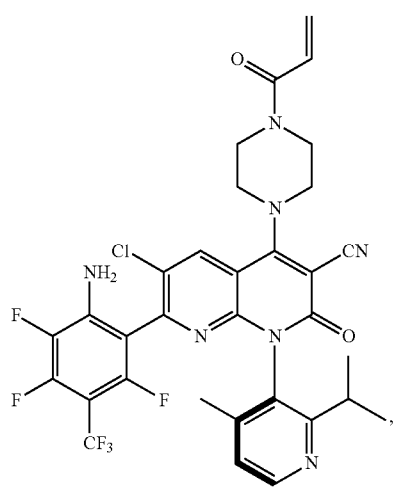
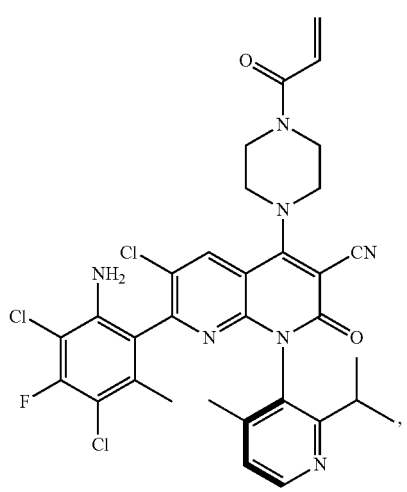
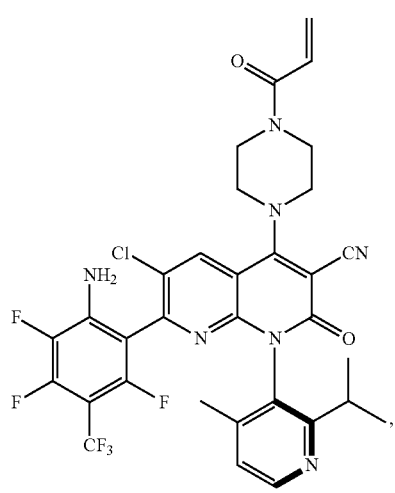

71
-continued
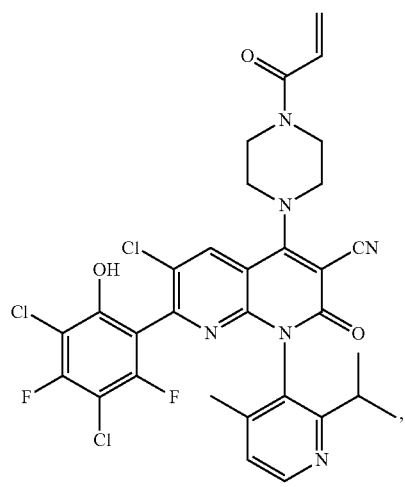
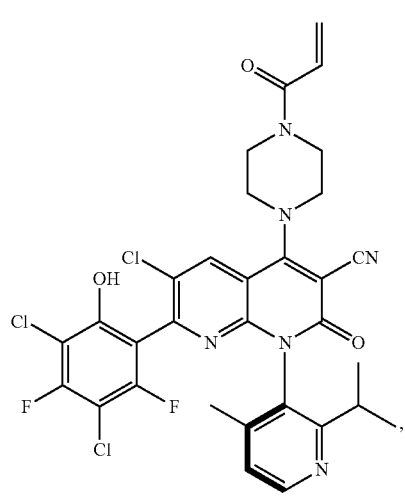
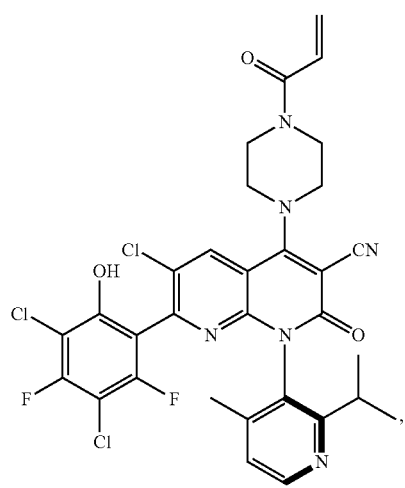
72
-continued
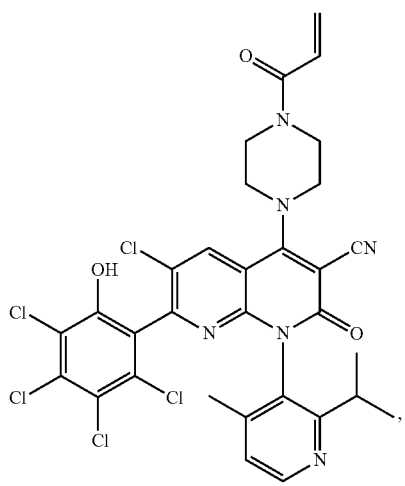
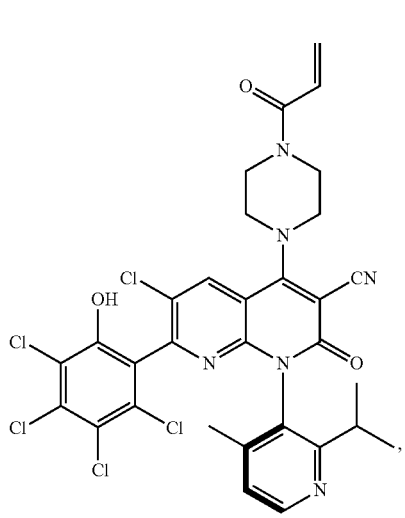

73
-continued
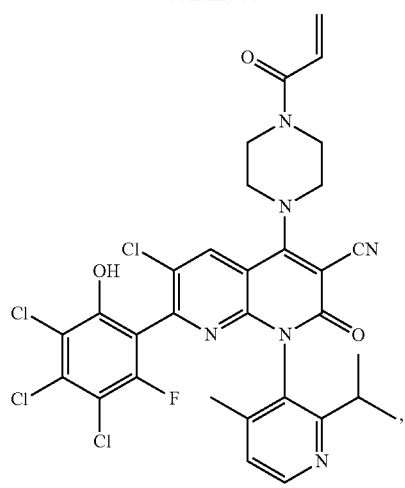
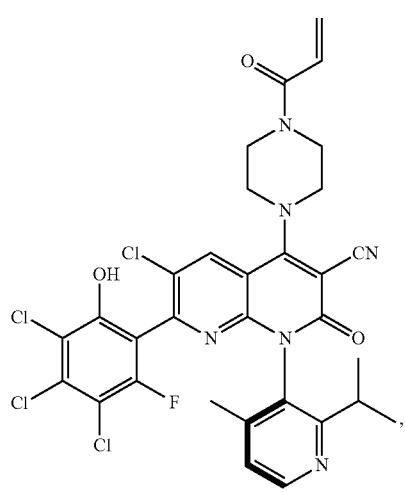
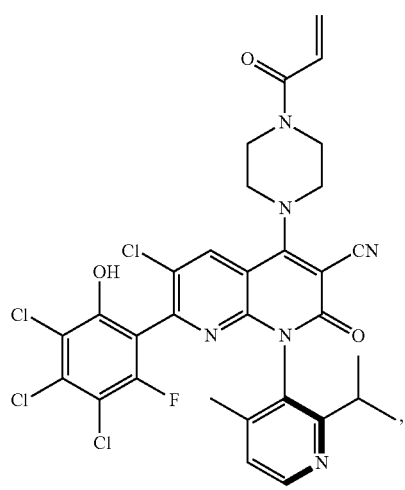
74
-continued
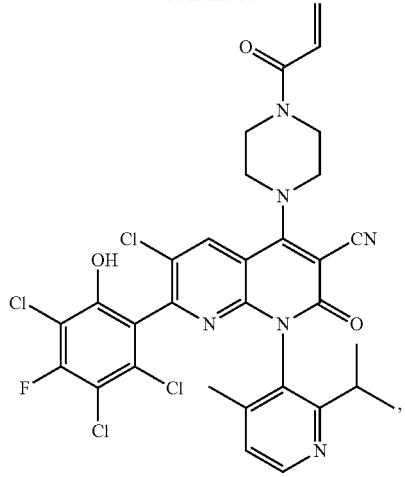
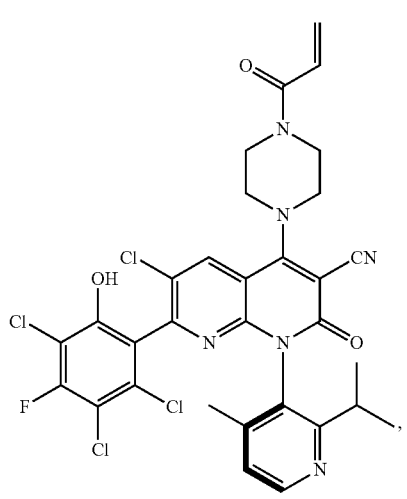
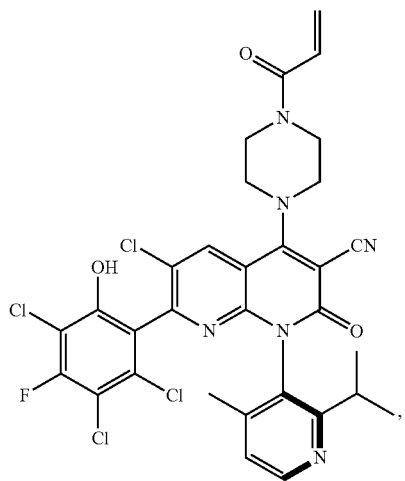

75
-continued
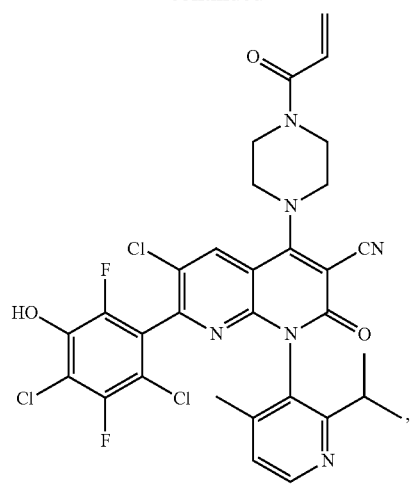
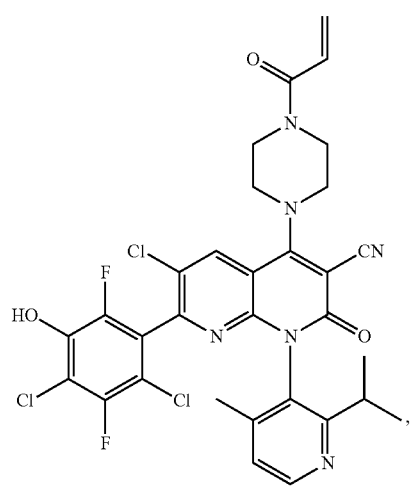
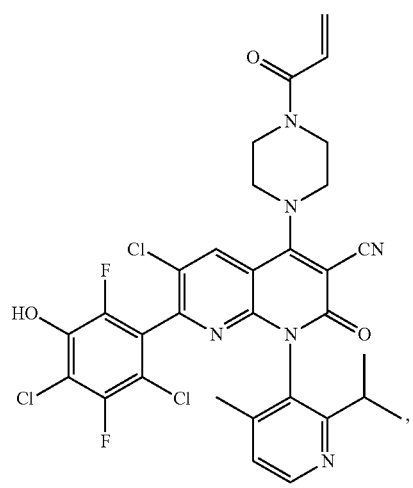
76
-continued
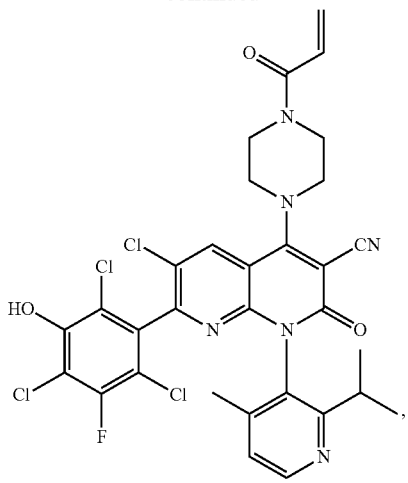
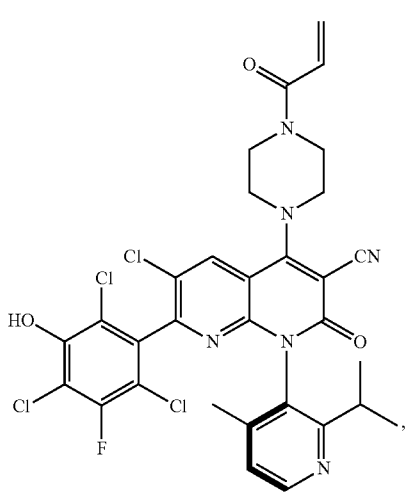

77
-continued
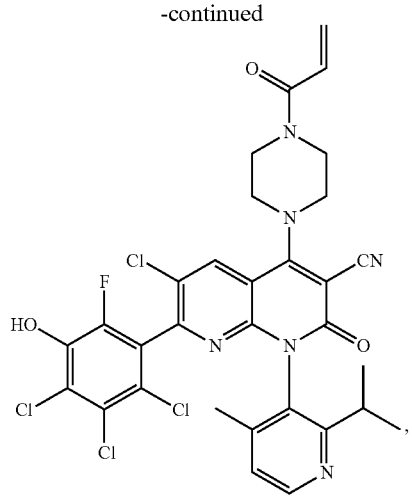
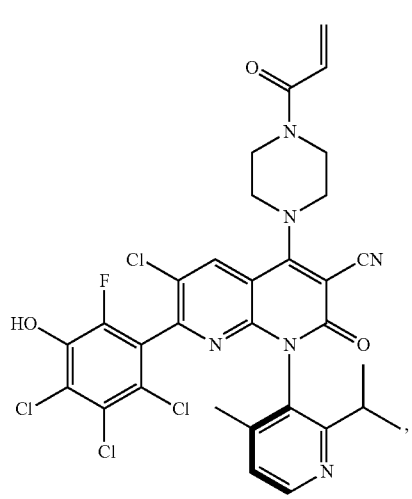
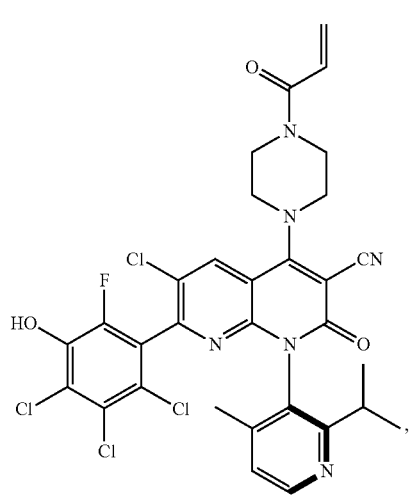
78
-continued
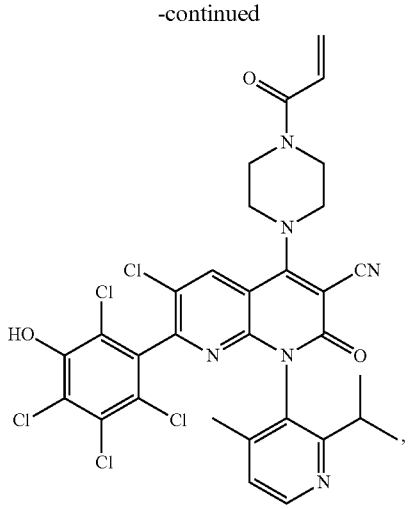
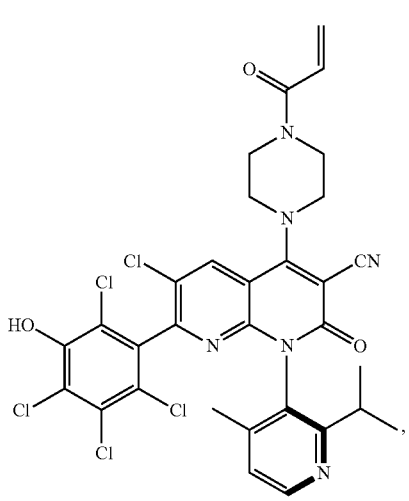

-continued
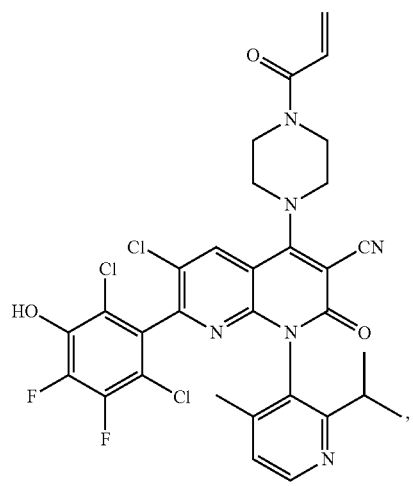
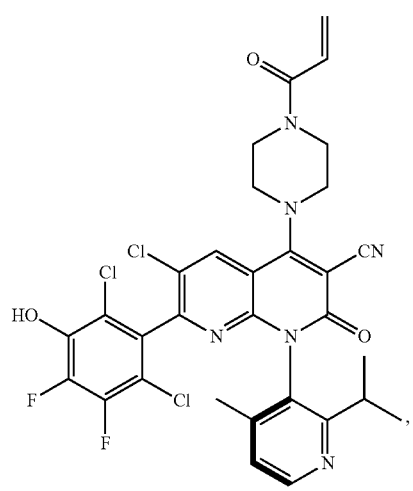
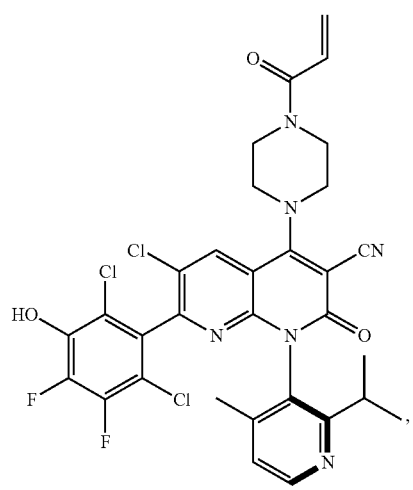
-continued
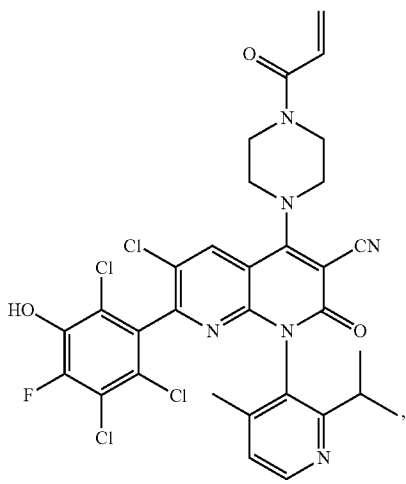
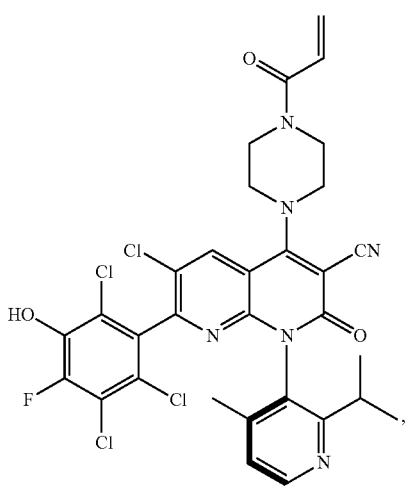
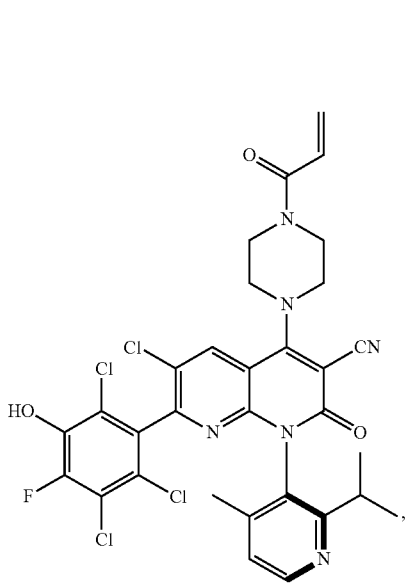

81
-continued
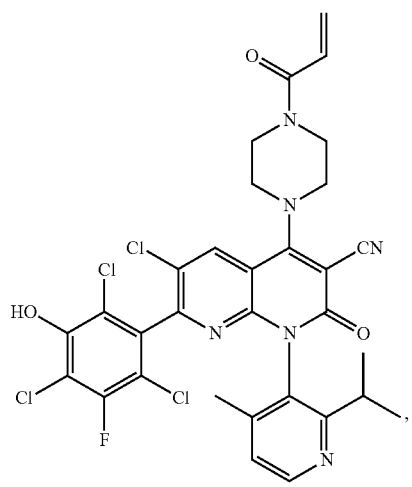
82
-continued
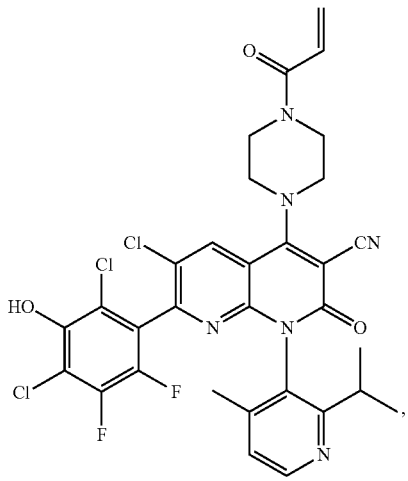
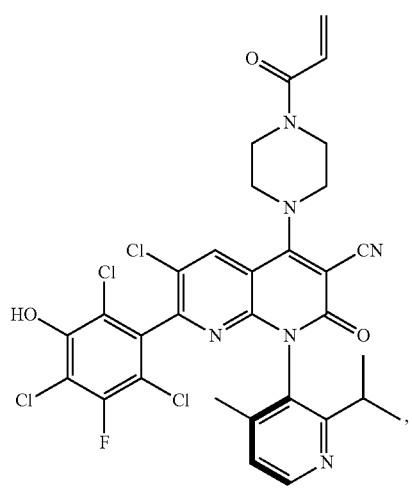
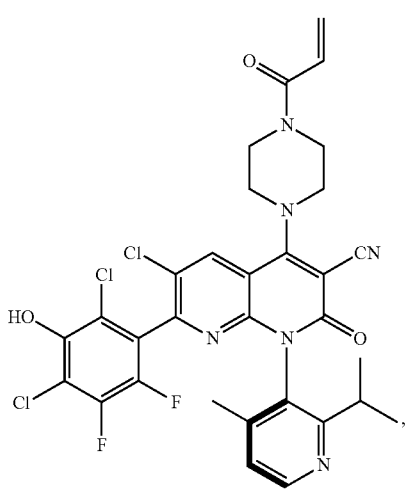
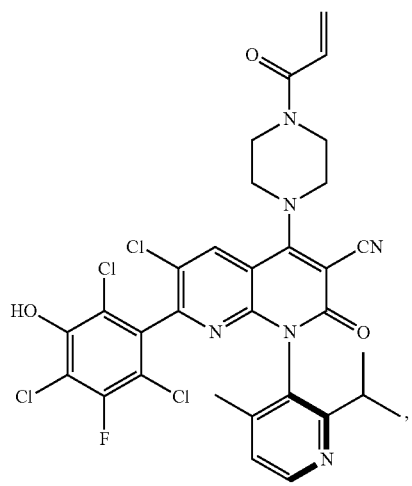
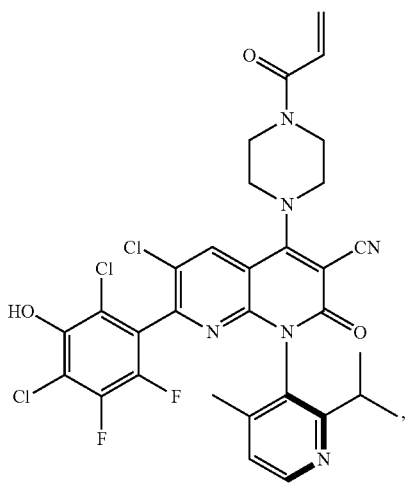

83
-continued
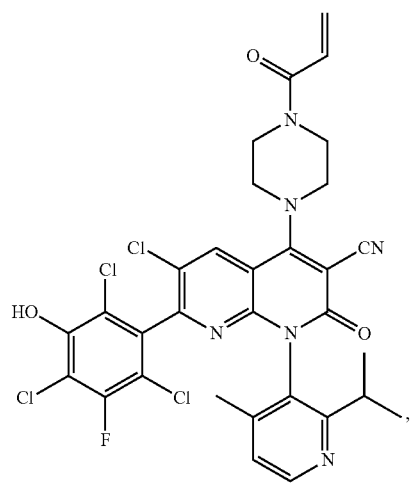
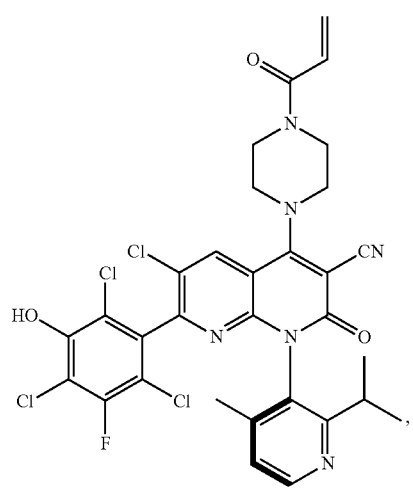
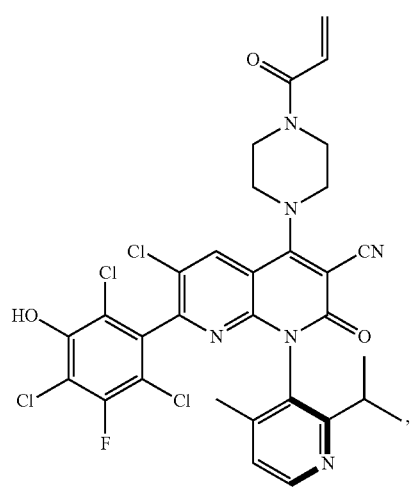
84
-continued
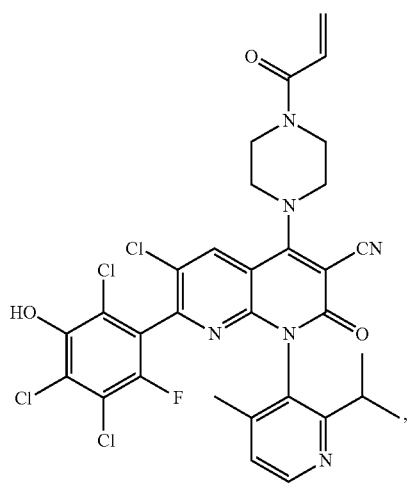
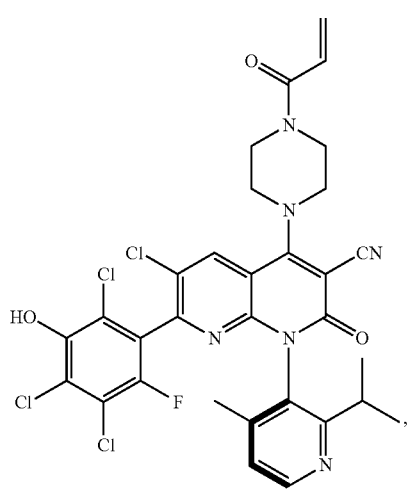
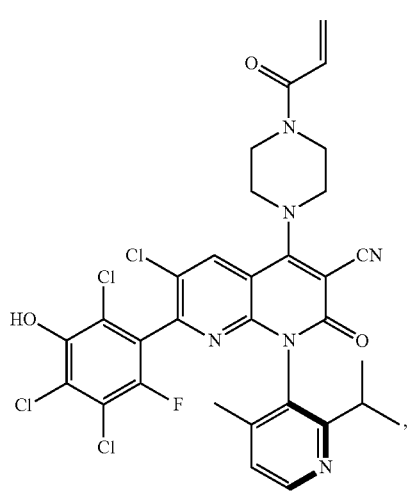

85
-continued
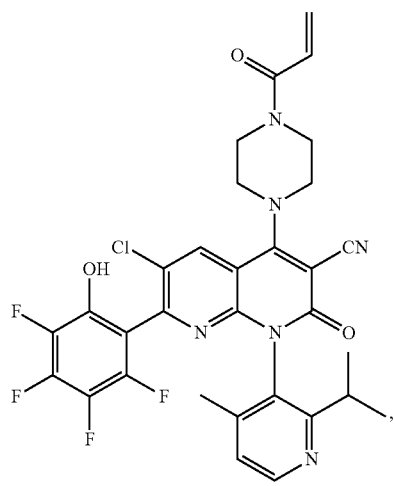
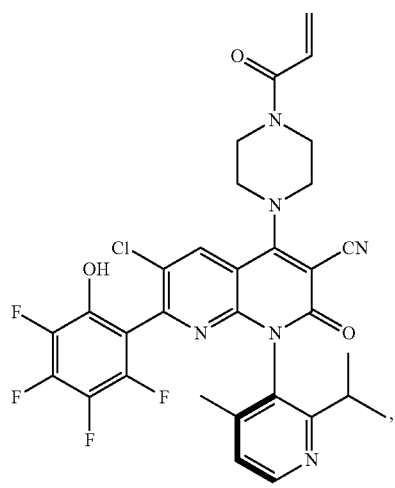
86
-continued
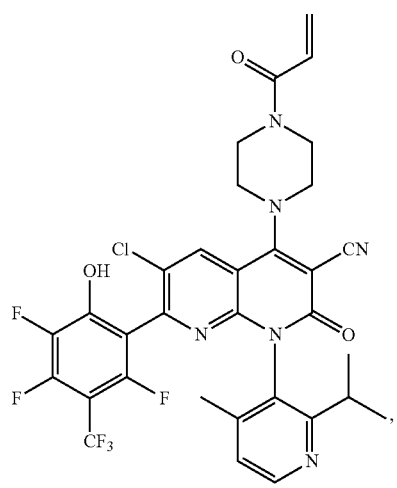 [SMILES: C=CC(=O)N1CCN(c2c(C#N)c(=O)n(-c3c(C)ccnc3C(C)C)c3nc(-c4c(N)c(F)c(F)c(F)c4F)c(Cl)cc23)CC1]
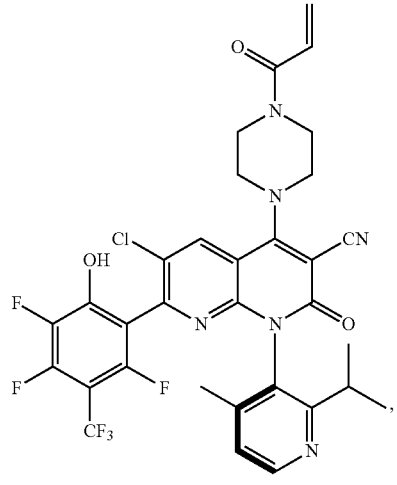

87
-continued
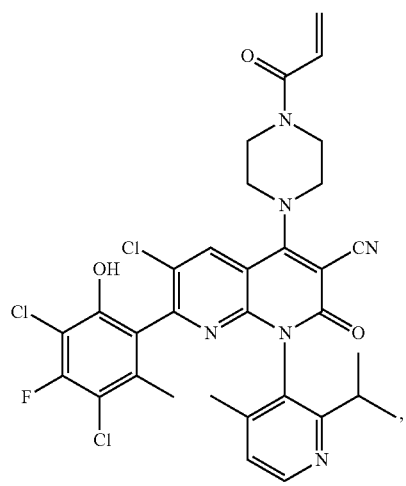
88
-continued
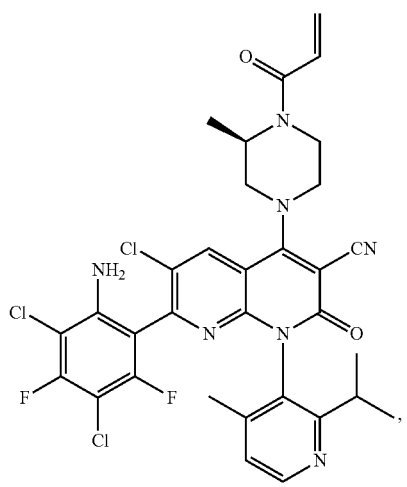
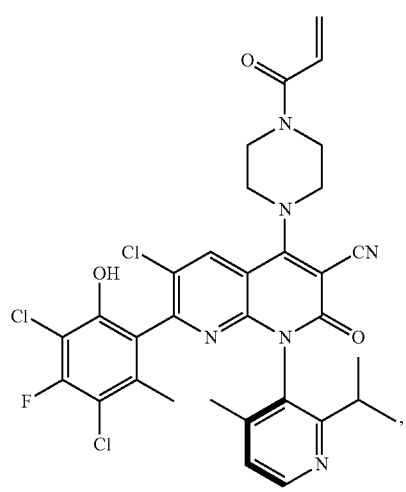
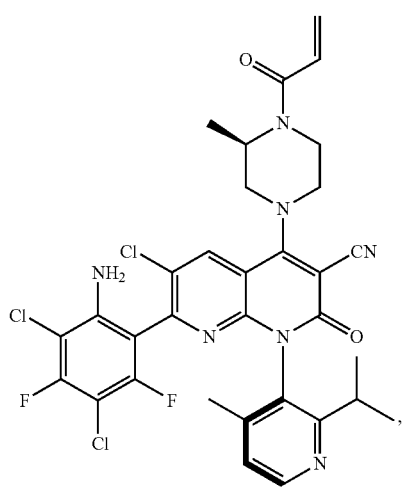
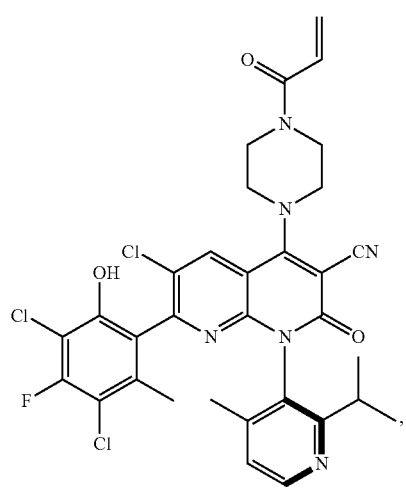
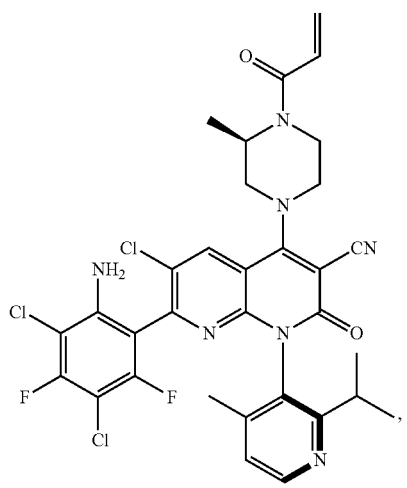

89
-continued
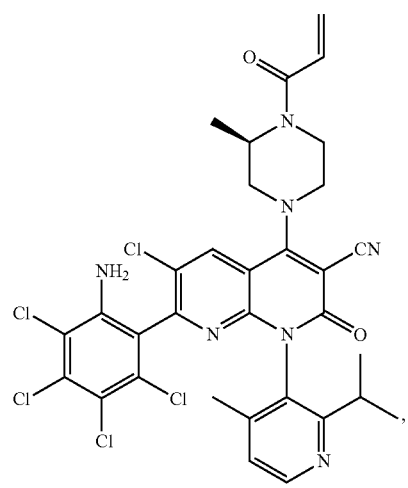
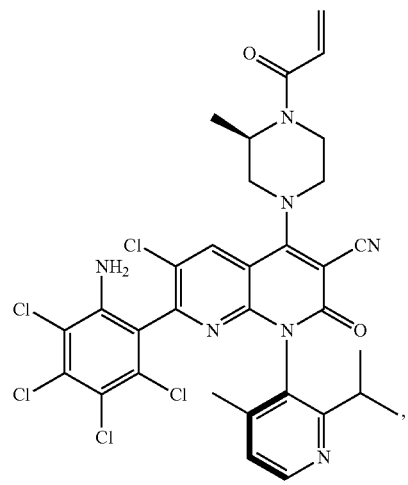
90
-continued
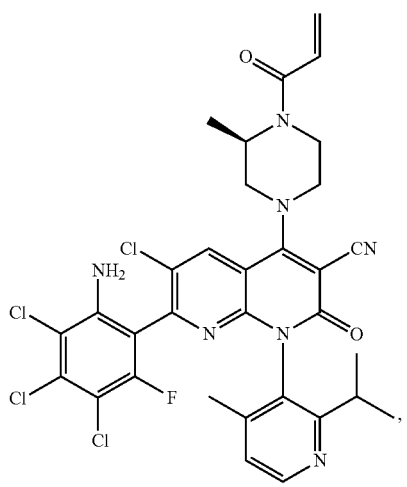
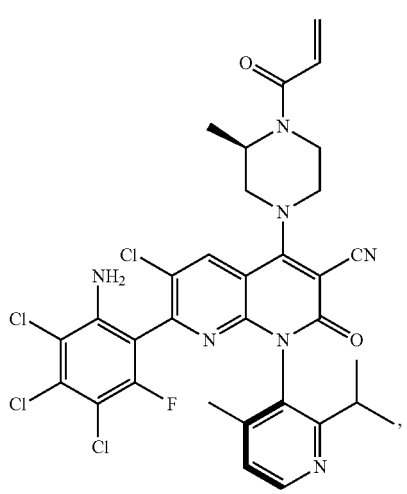

91
-continued
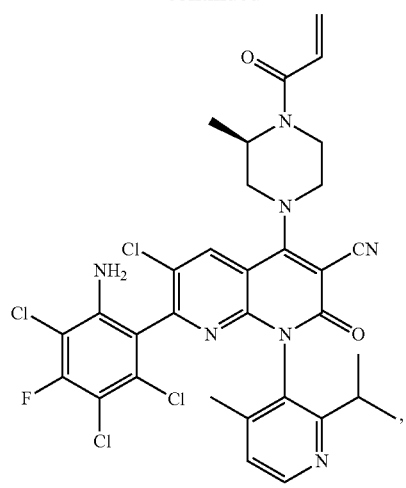
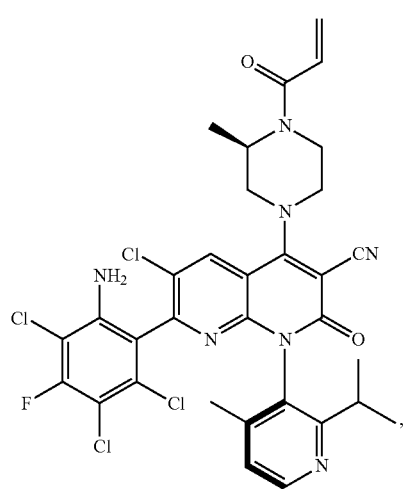
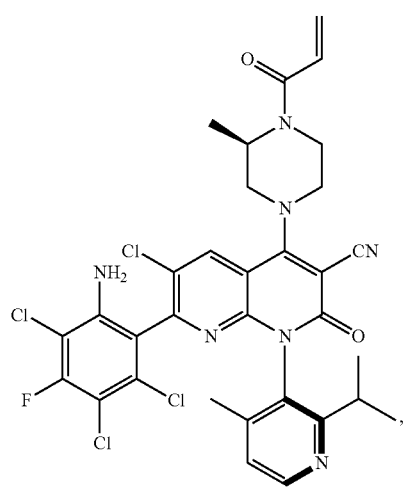
92
-continued
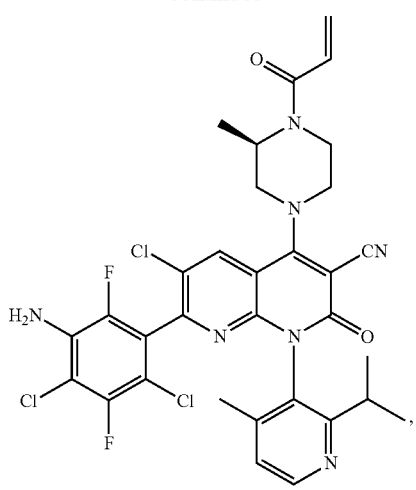

93
-continued
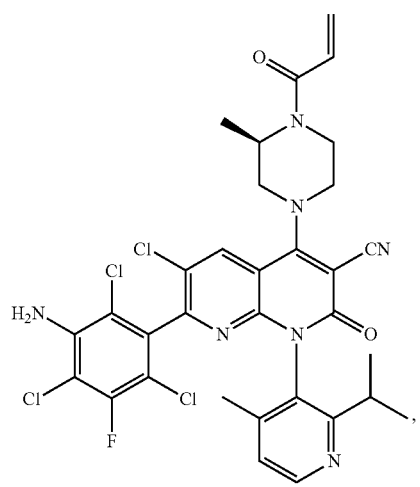
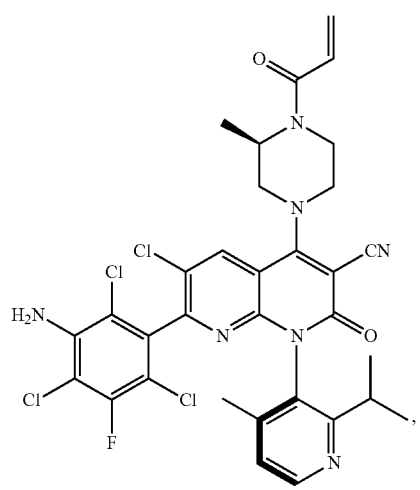
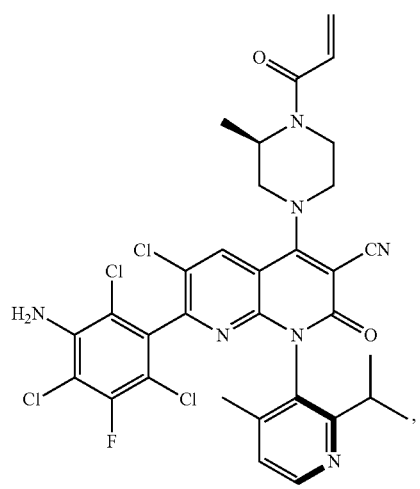
94
-continued
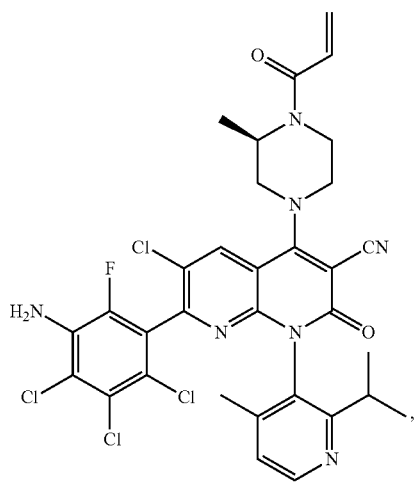
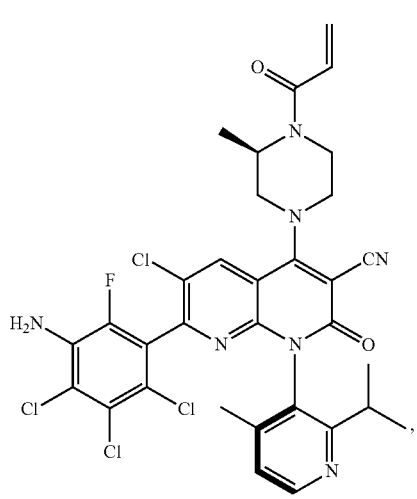
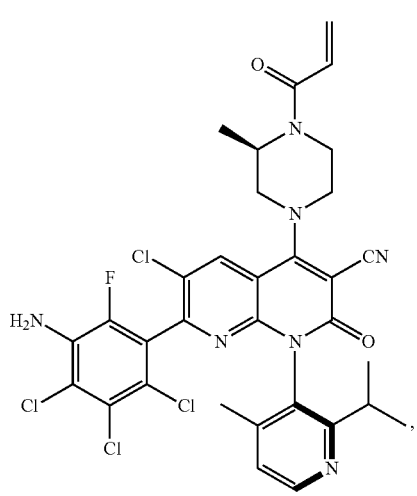

95
-continued
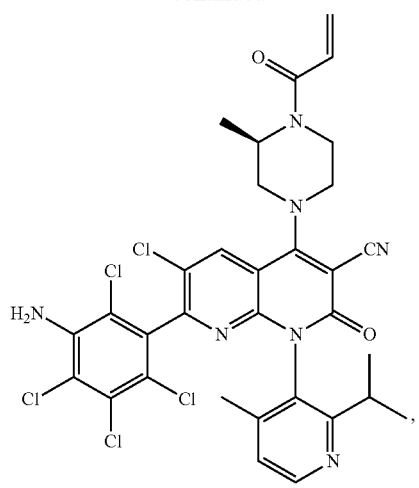
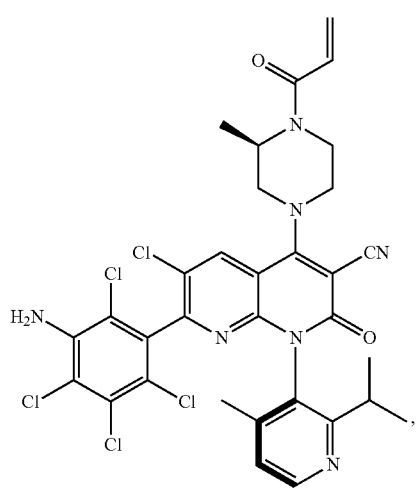
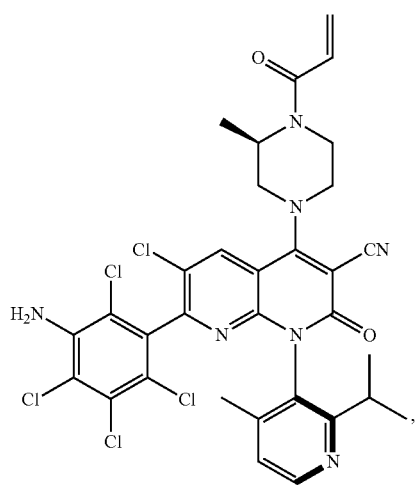
96
-continued
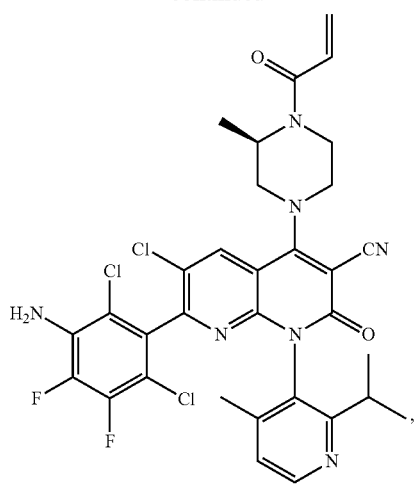
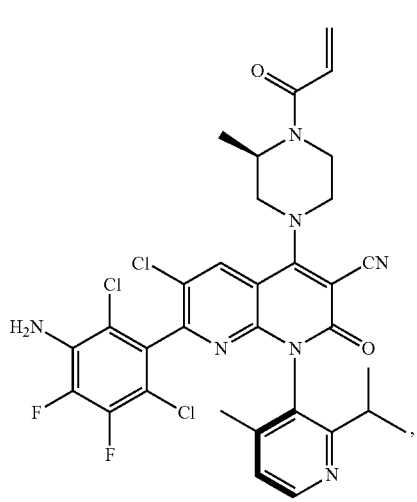
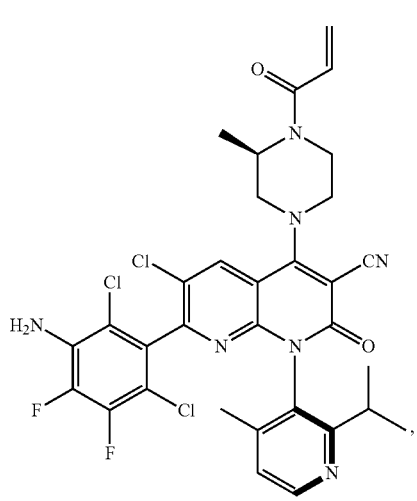

97
-continued
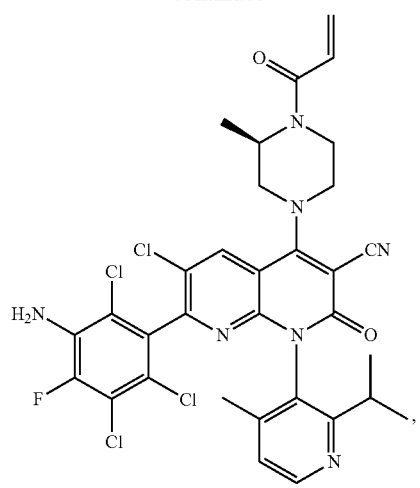
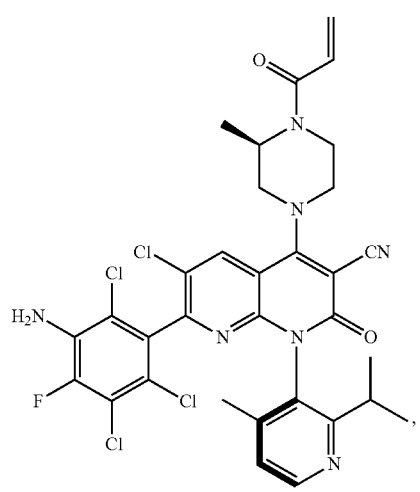
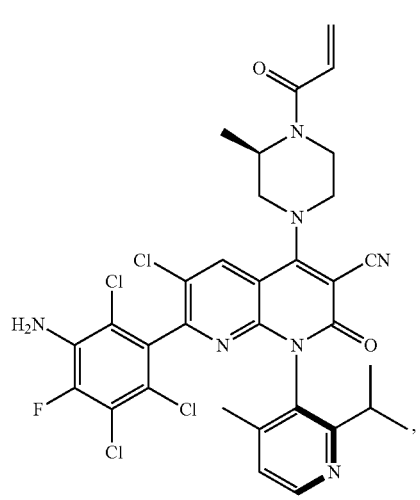
98
-continued
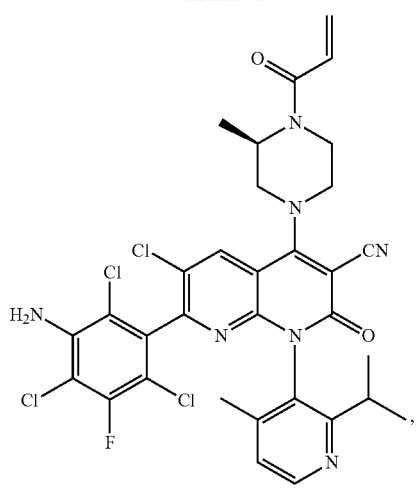
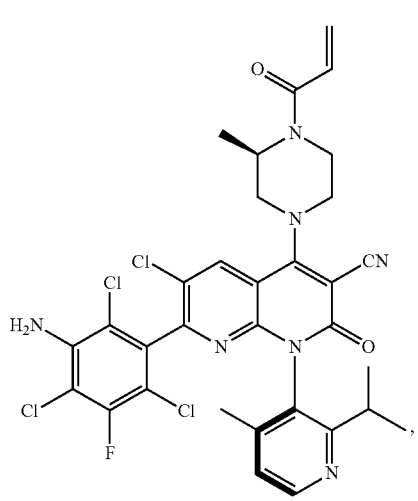
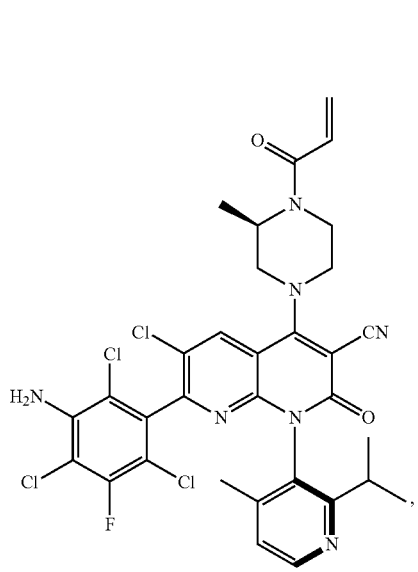

99
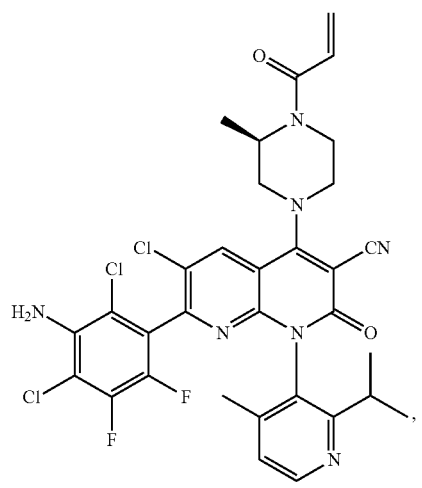
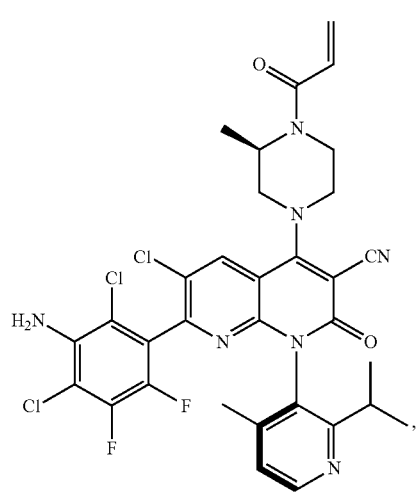
100
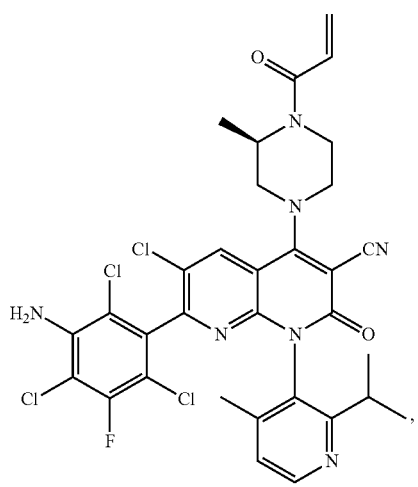
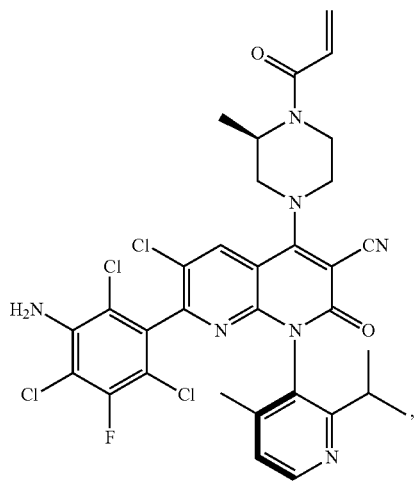

101
-continued
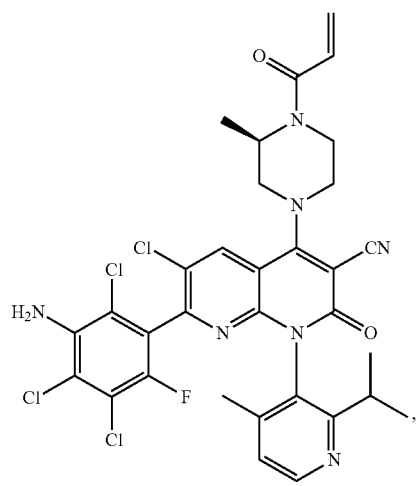
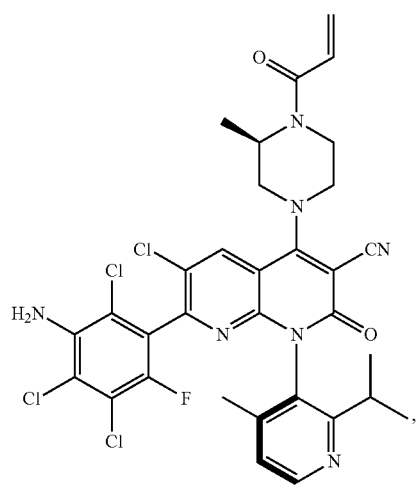
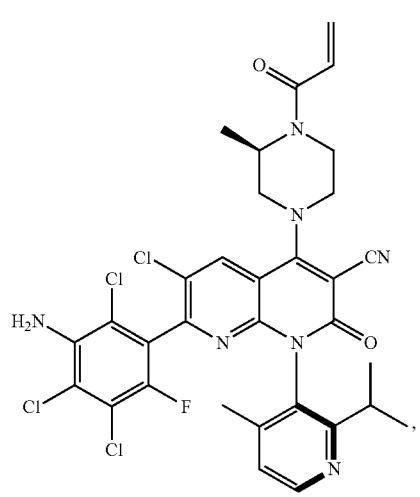
102
-continued
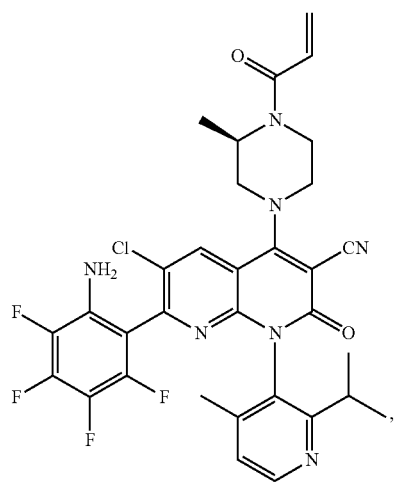
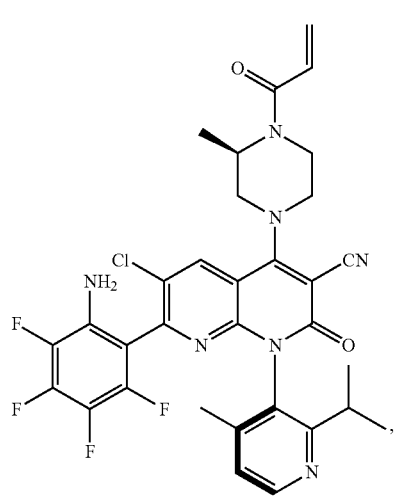
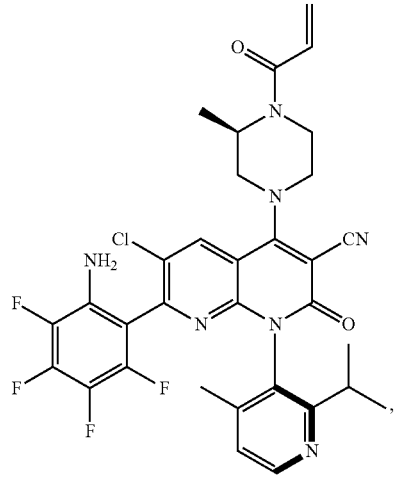

103
-continued
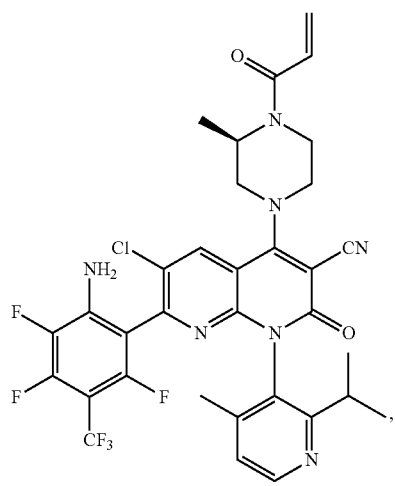
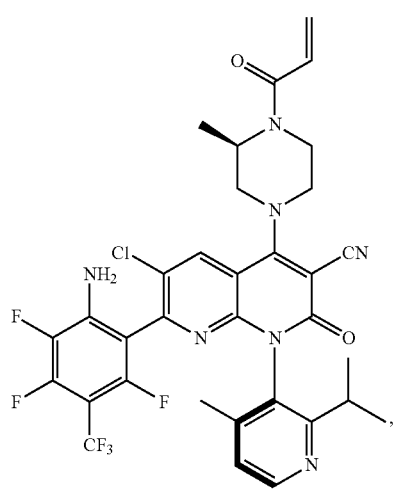
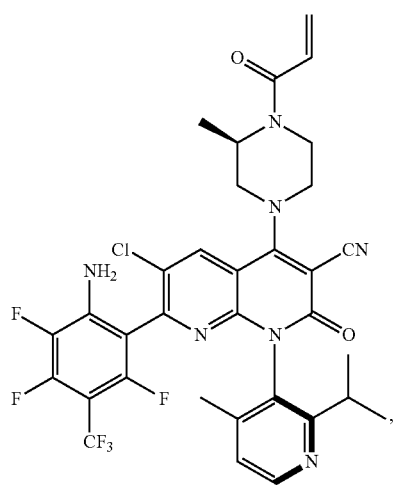
104
-continued
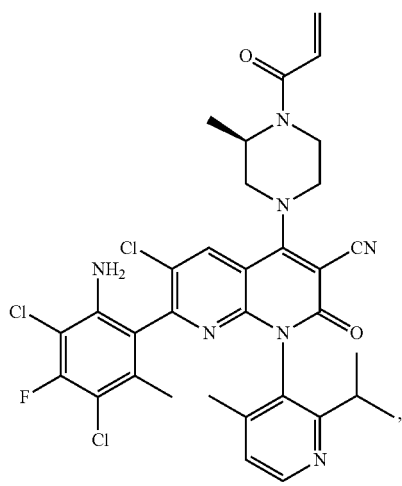
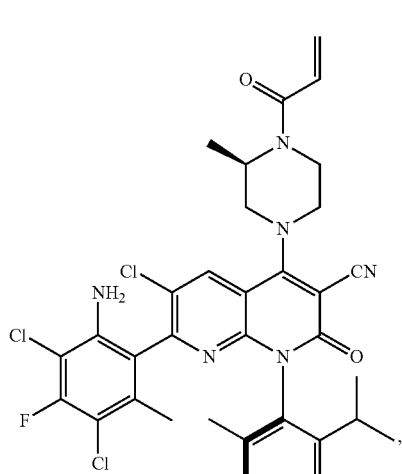
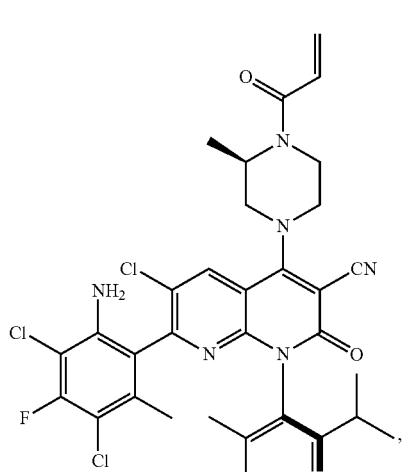

105
-continued
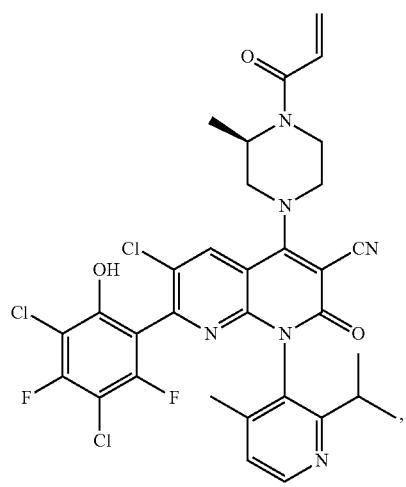
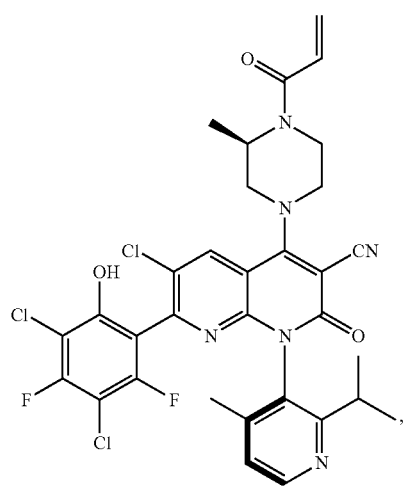
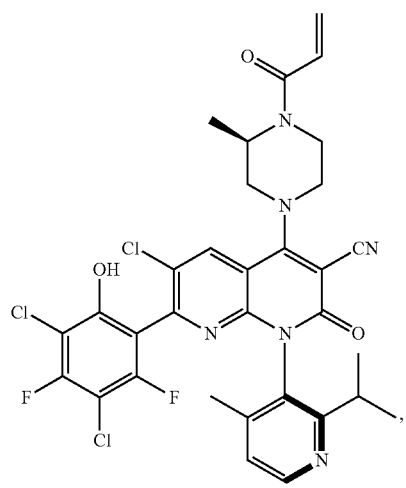
106
-continued
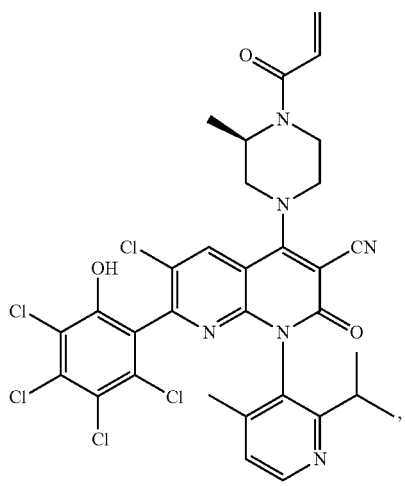
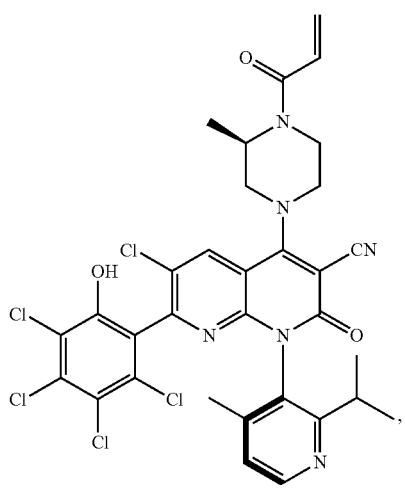
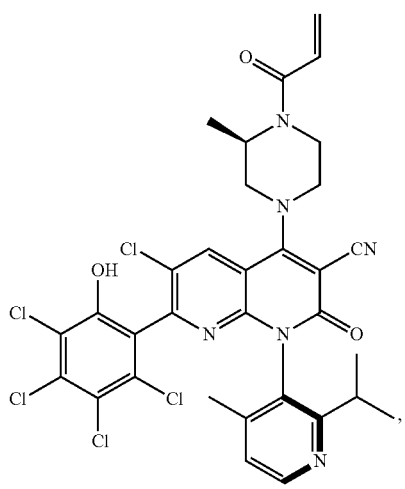

107
-continued
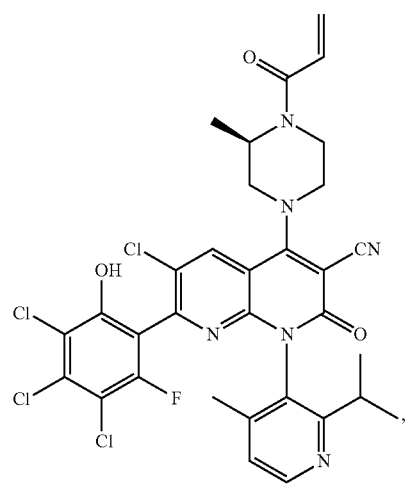
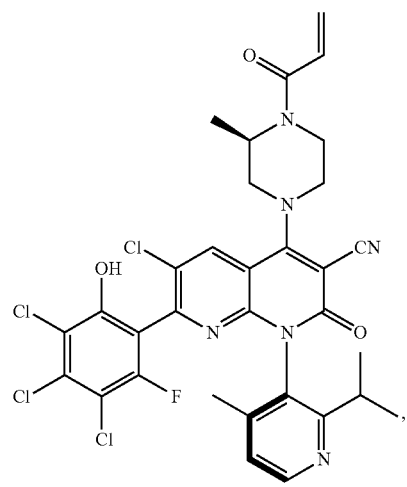
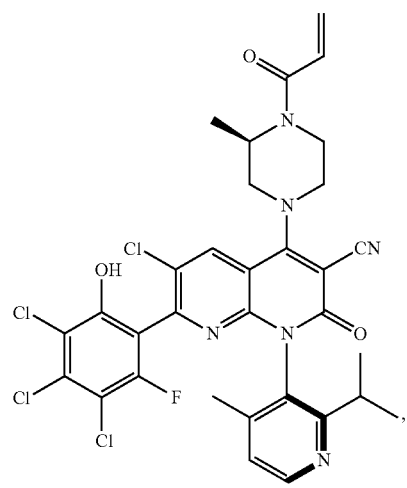
108
-continued
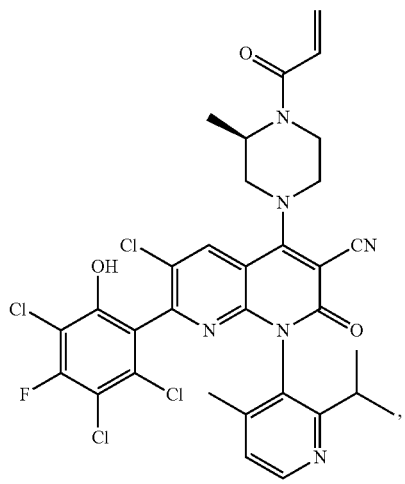
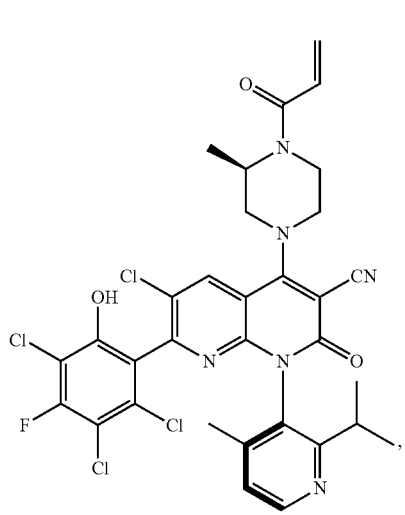
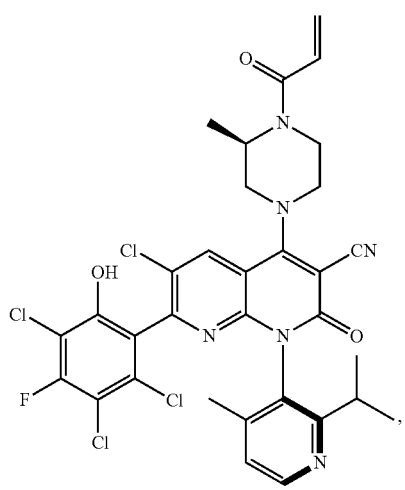

109
-continued
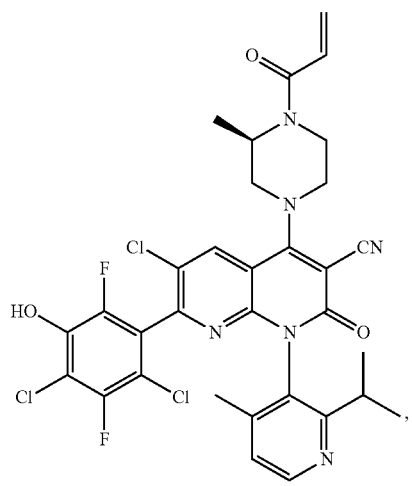
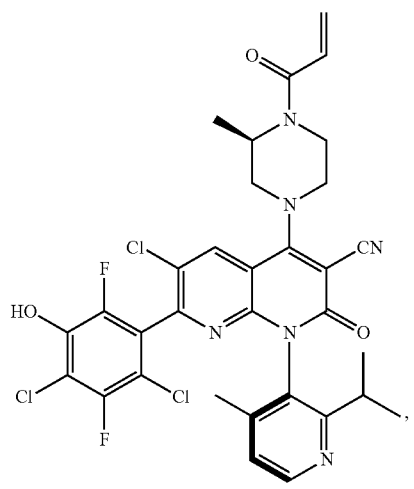
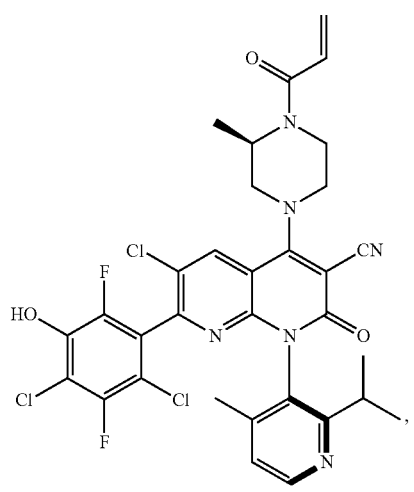
110
-continued
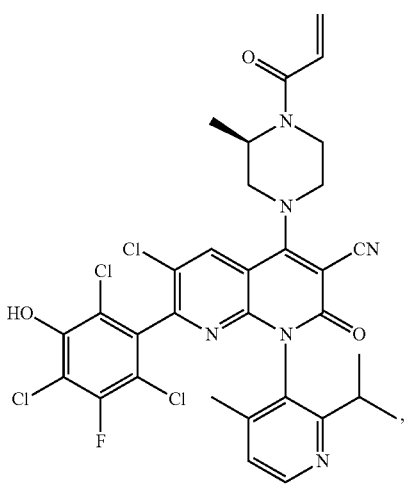
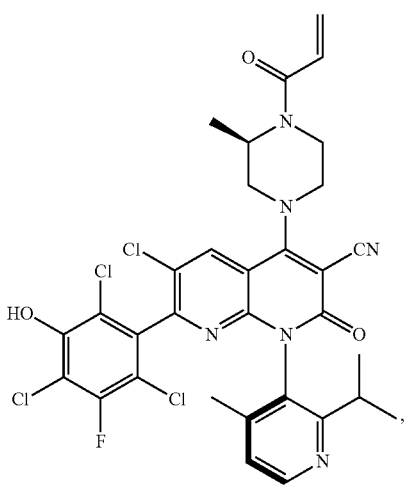
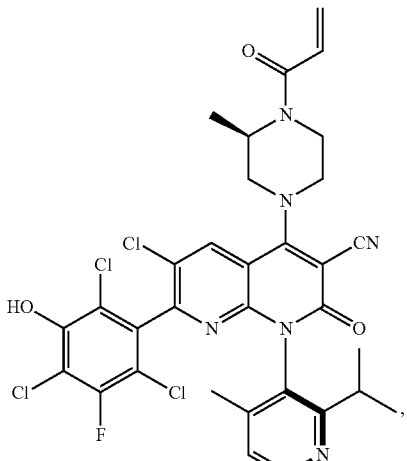

111
-continued
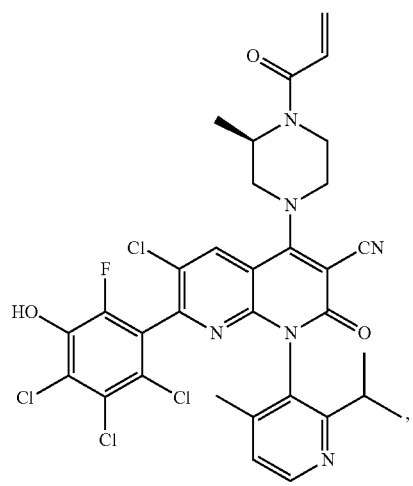
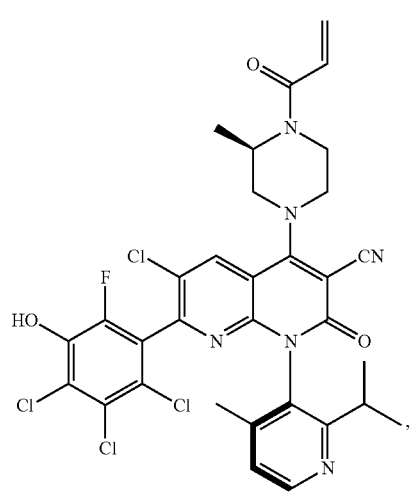
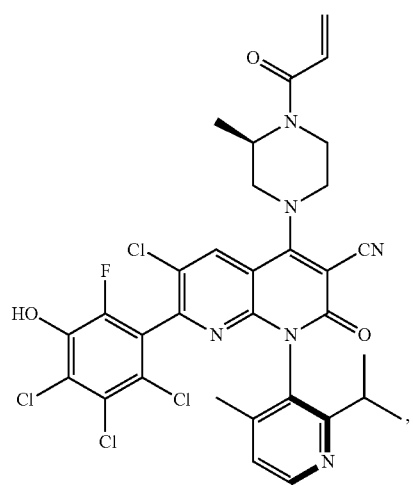
112
-continued
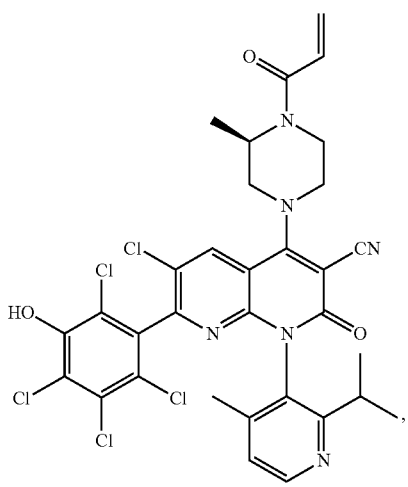
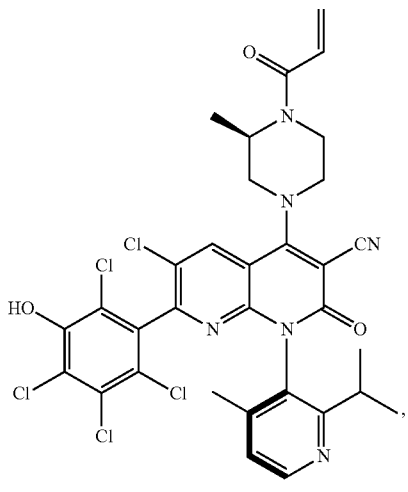

113
-continued
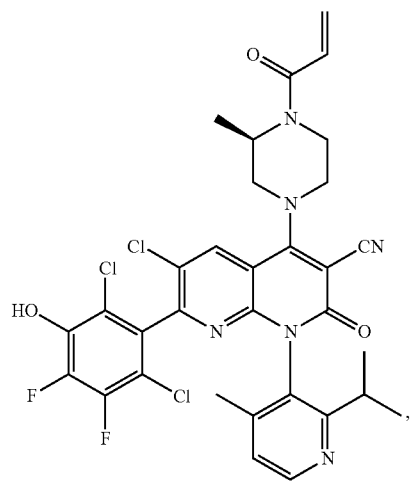
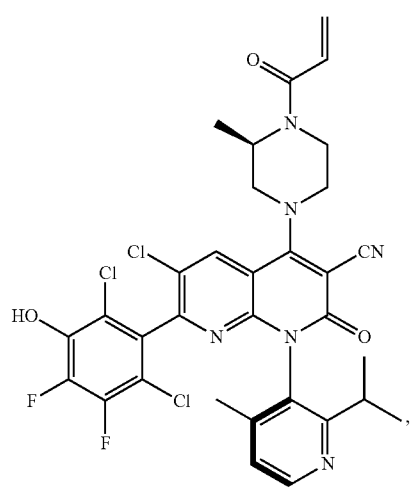
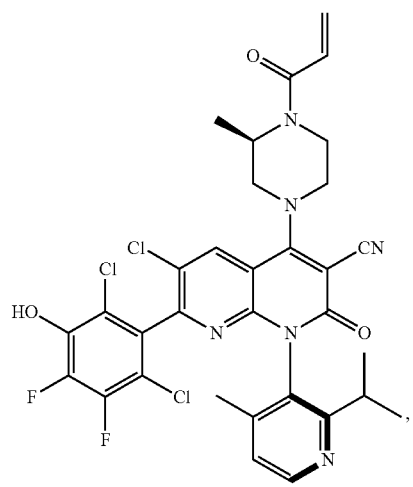
114
-continued
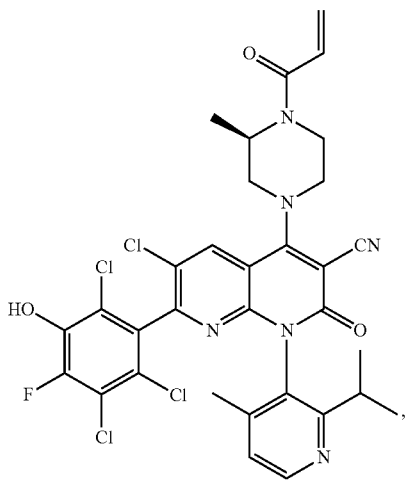
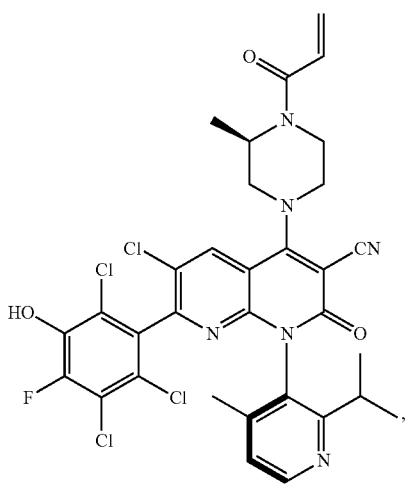
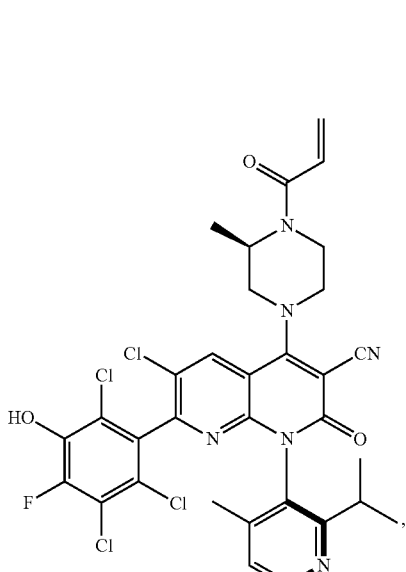

-continued
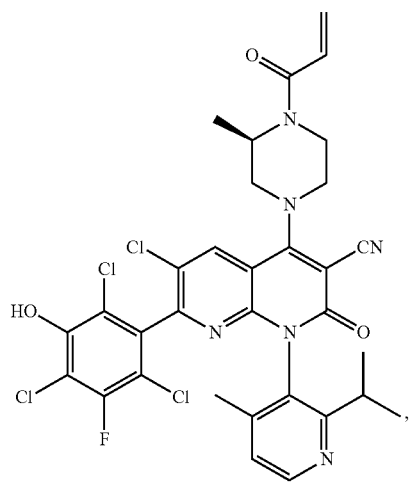
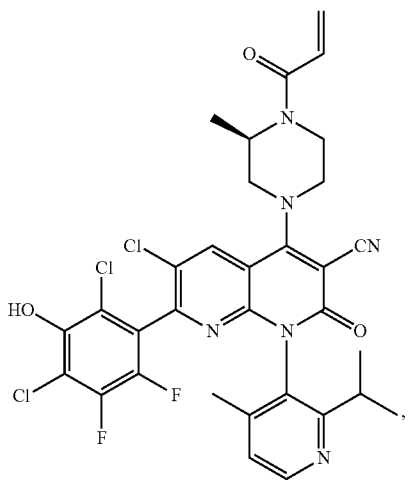
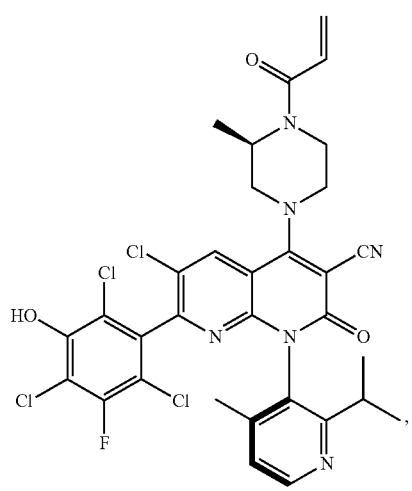
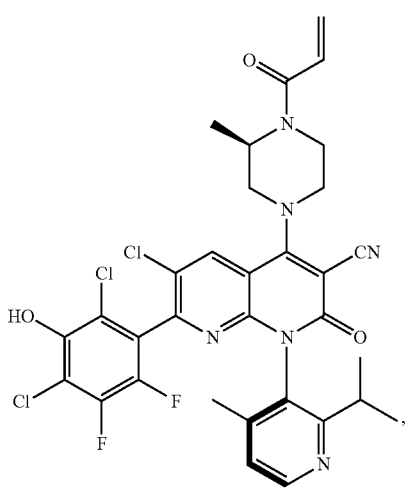
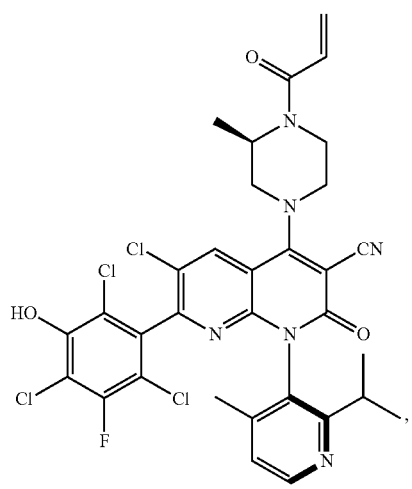
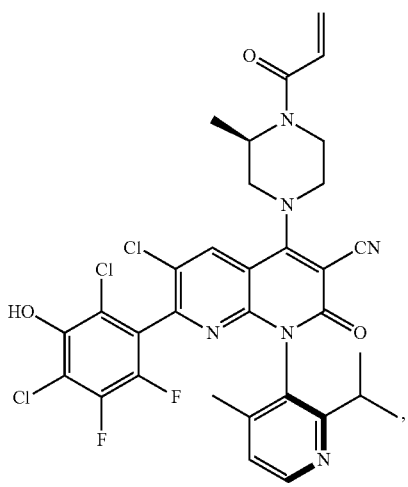

117
-continued
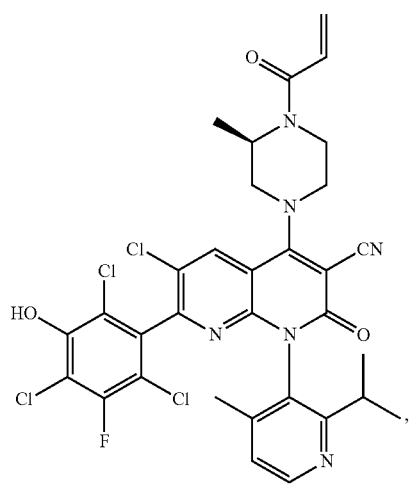
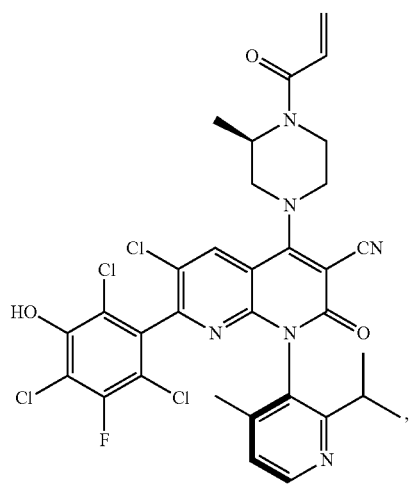
118
-continued
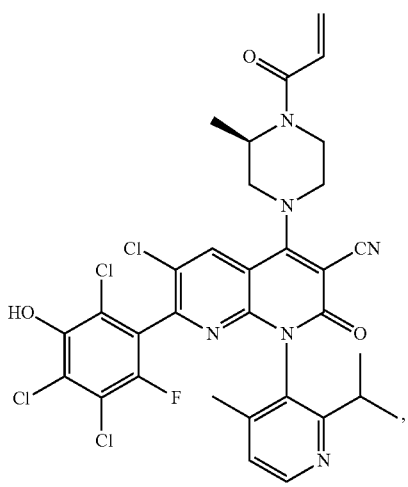
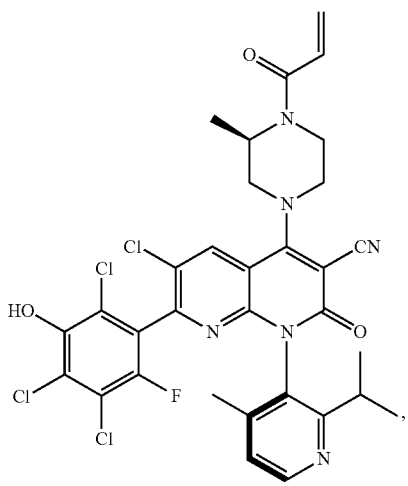

119
-continued
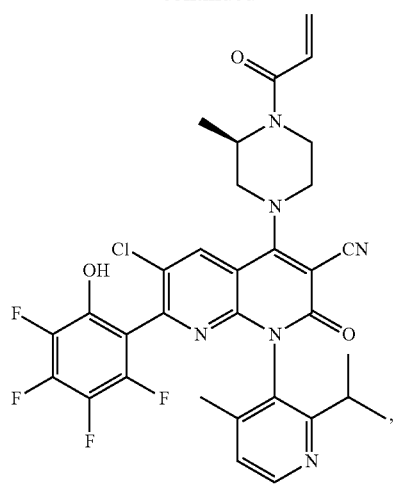
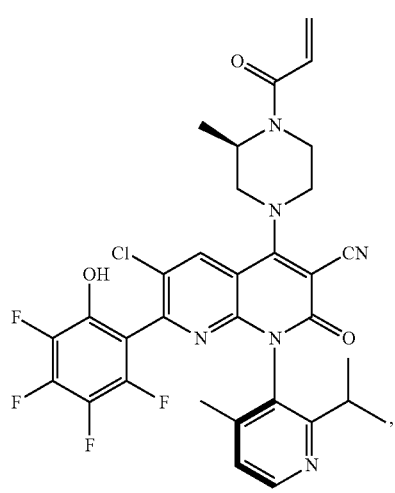
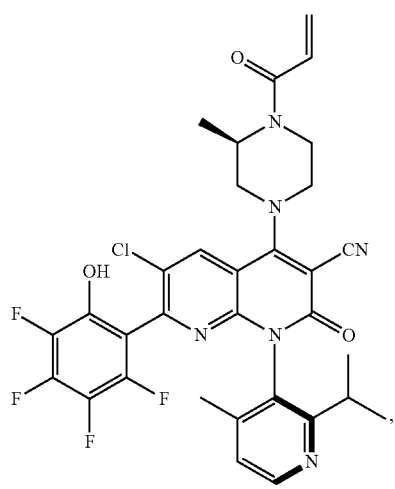
120
-continued
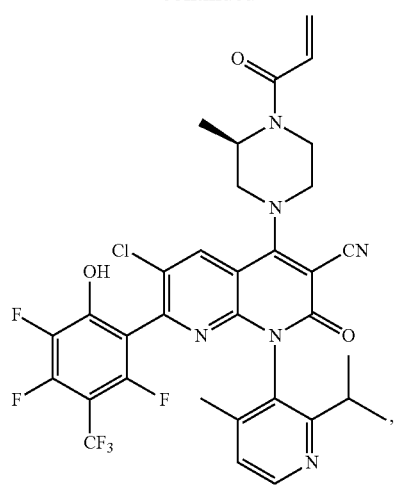
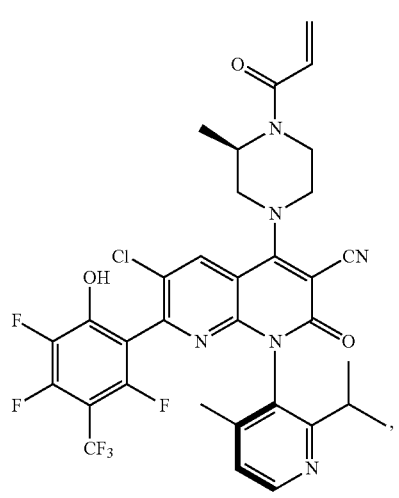
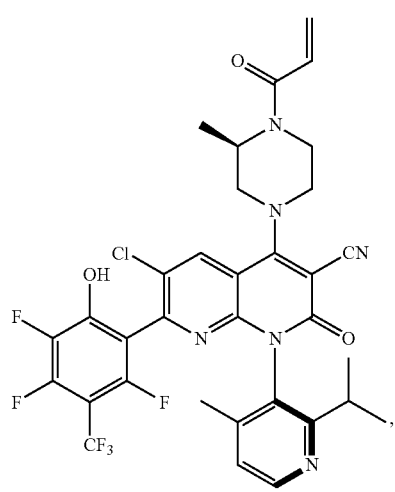

121
-continued
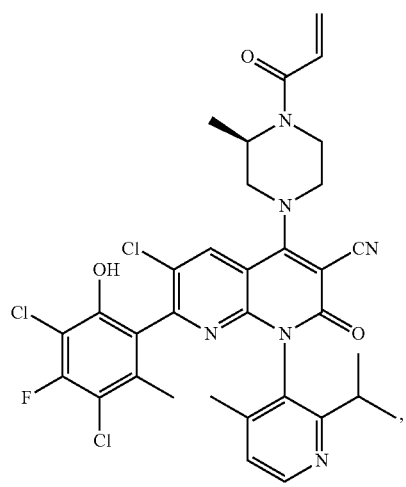
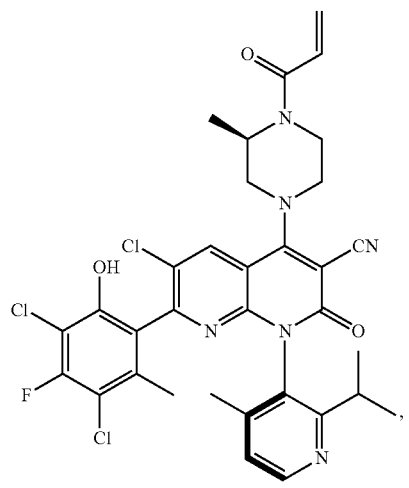
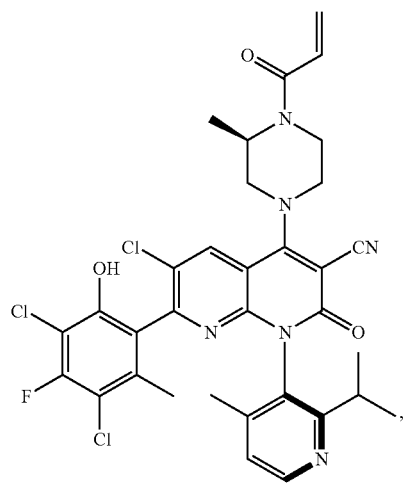
122
-continued
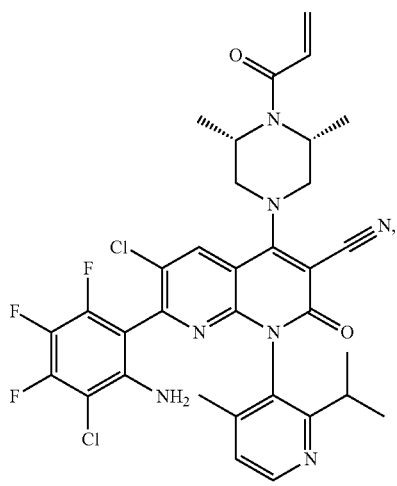
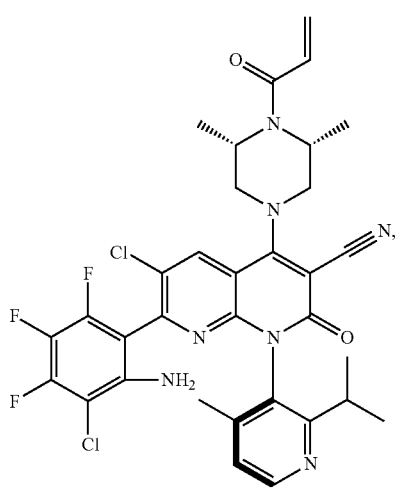
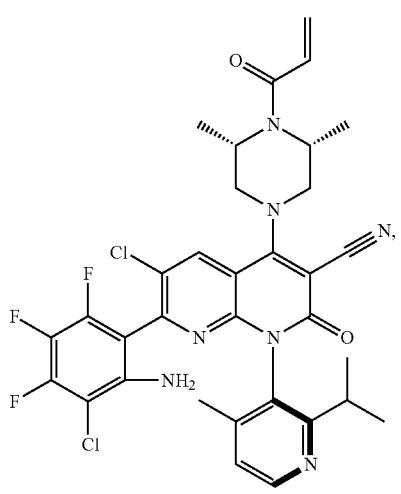

123
-continued
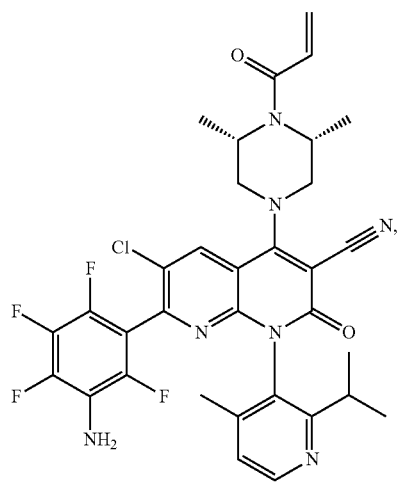
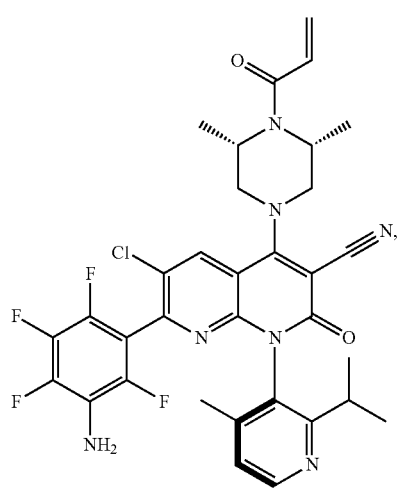
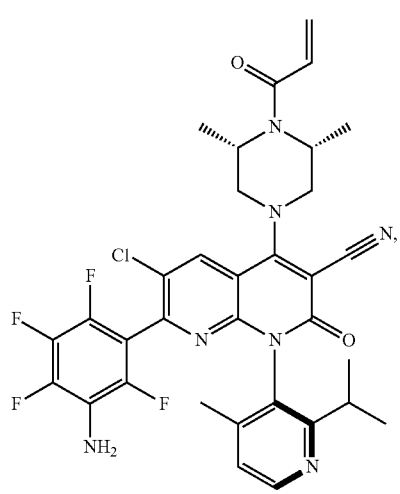
124
-continued
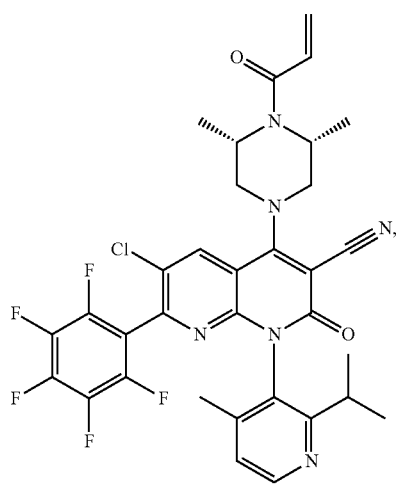
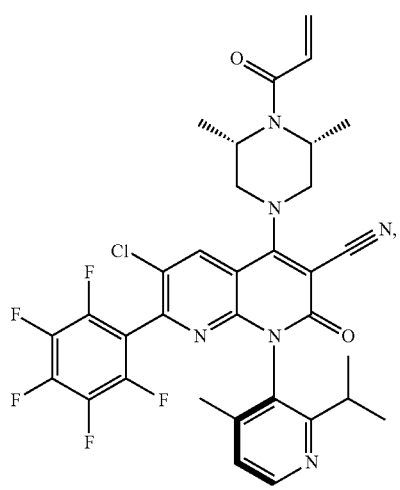
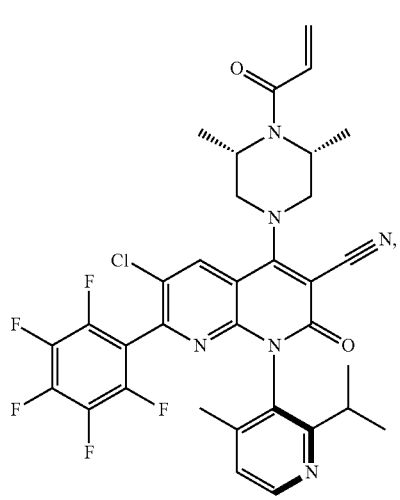

125
-continued
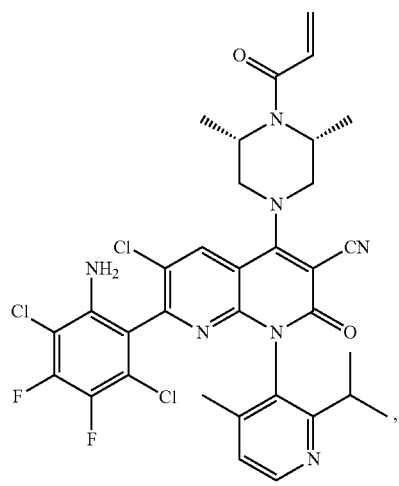
126
-continued
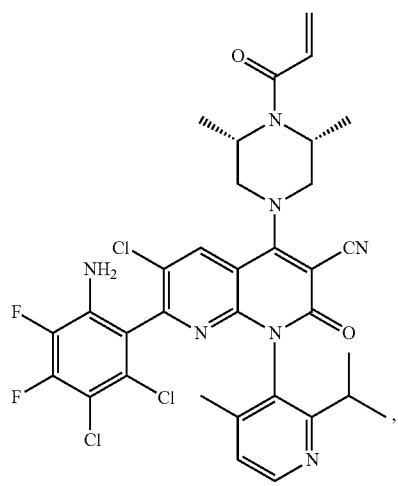
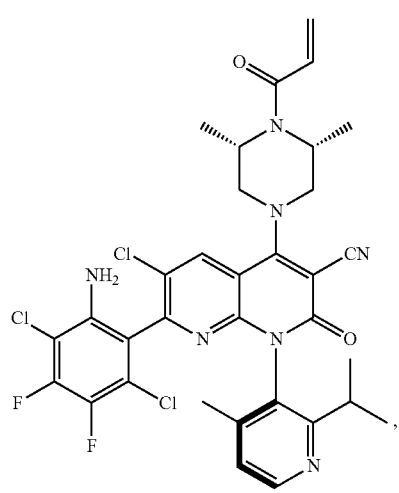
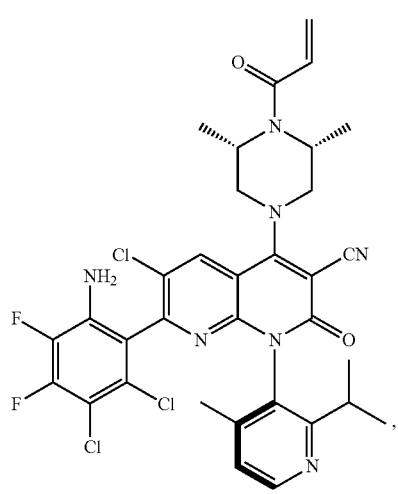
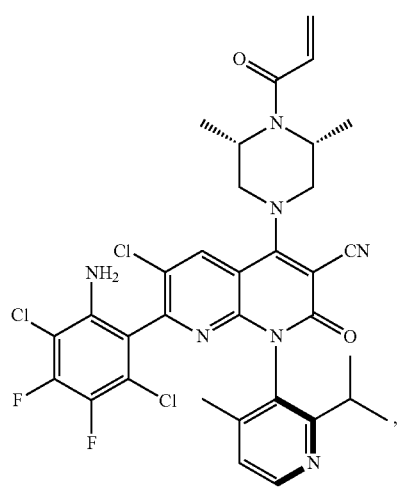
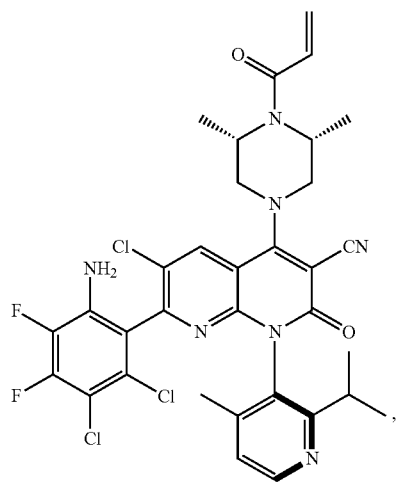

127
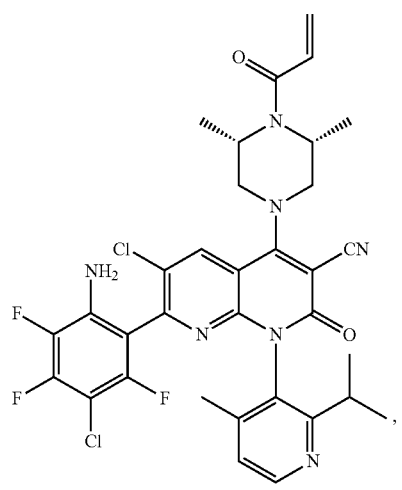
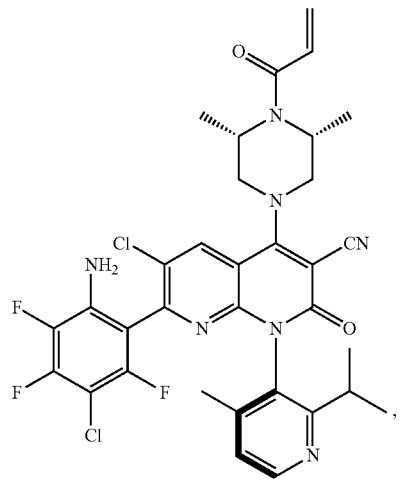
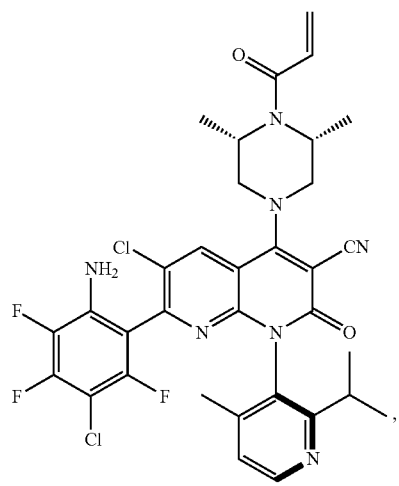
128
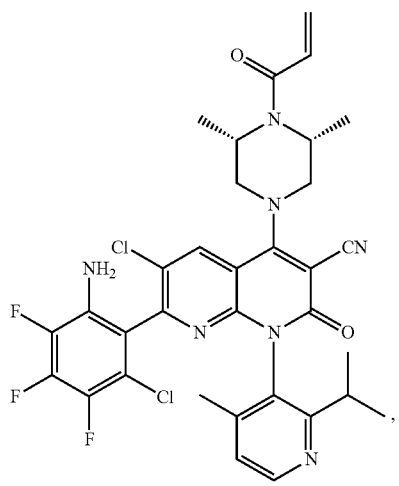
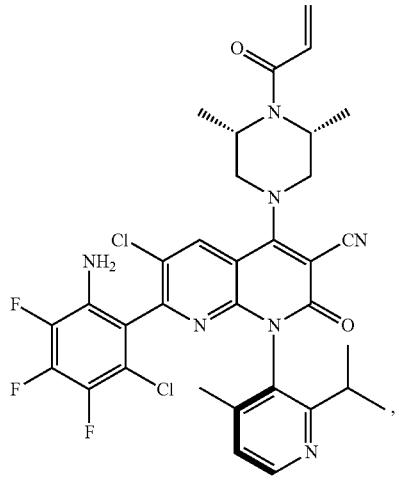
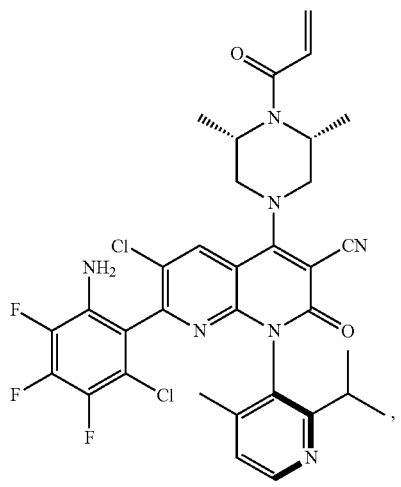

129
-continued
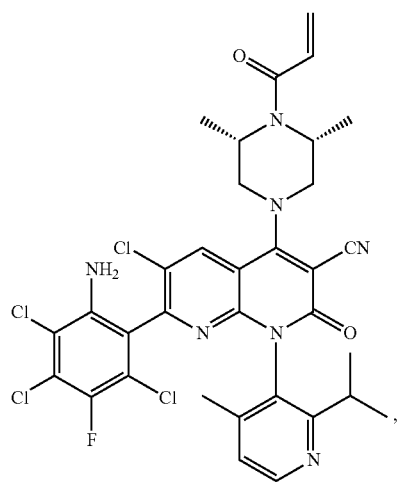
130
-continued
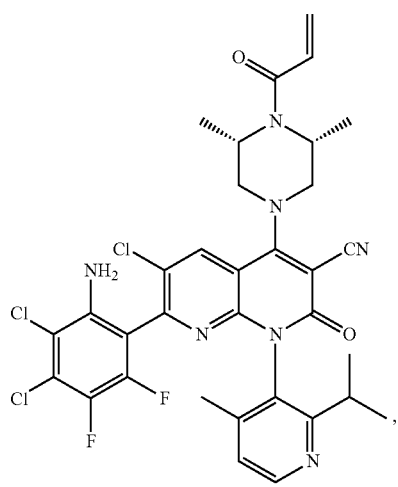
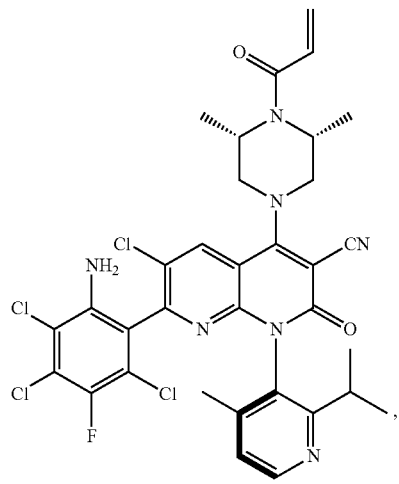
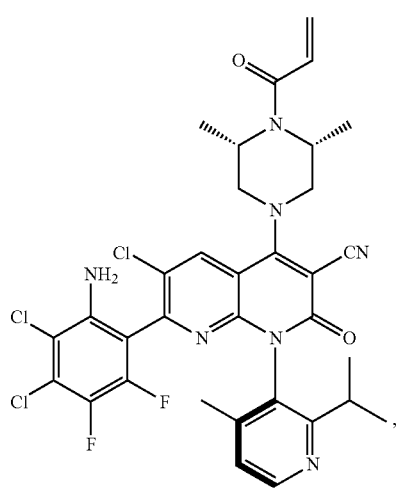
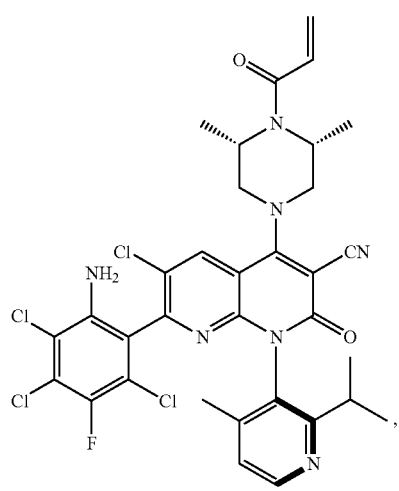
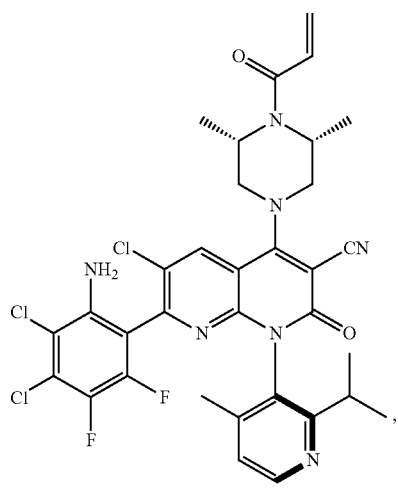

131
-continued
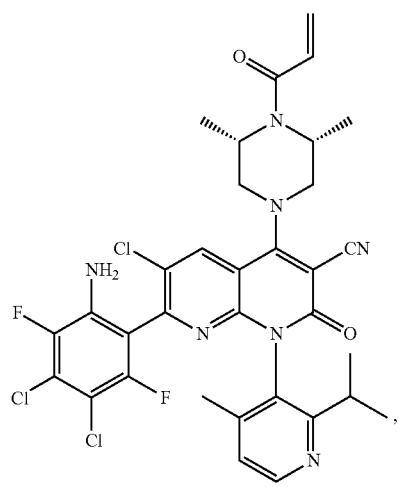
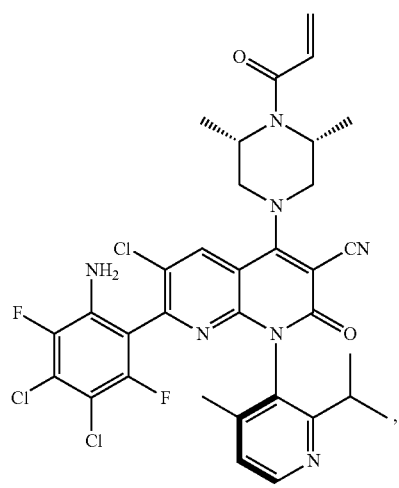
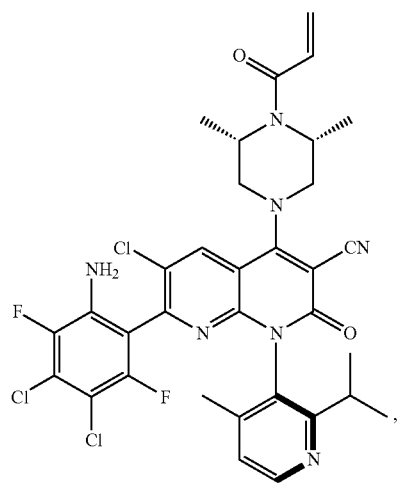
132
-continued
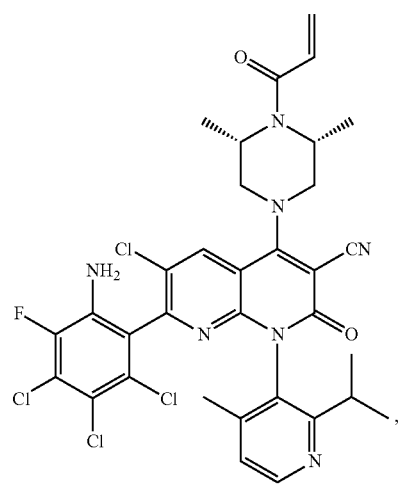
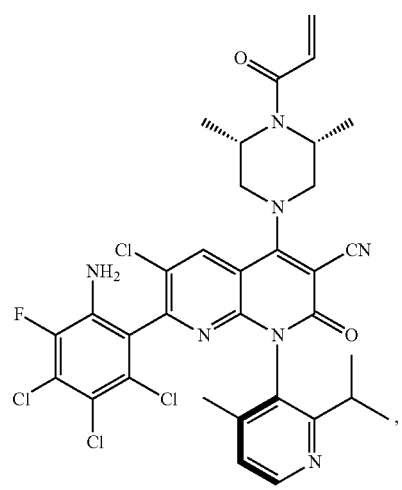
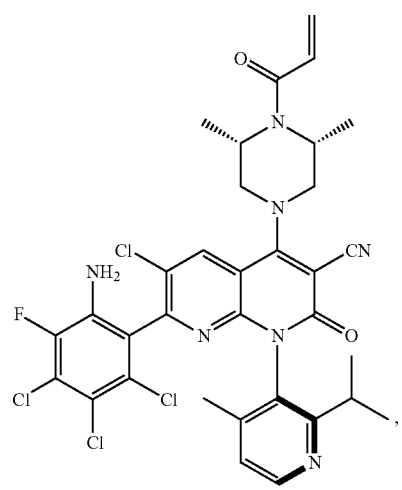

133
-continued
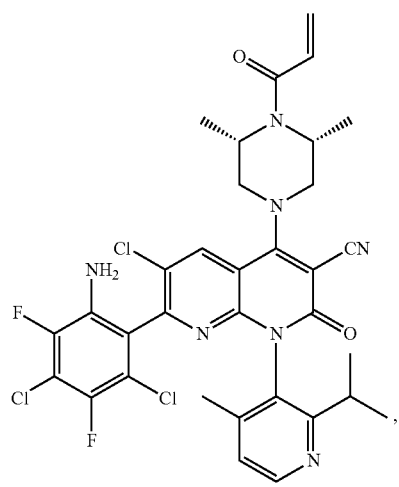
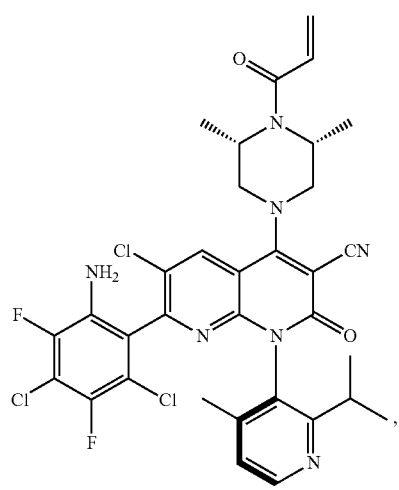
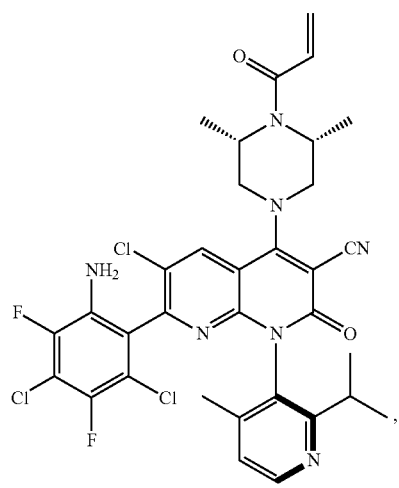
134
-continued
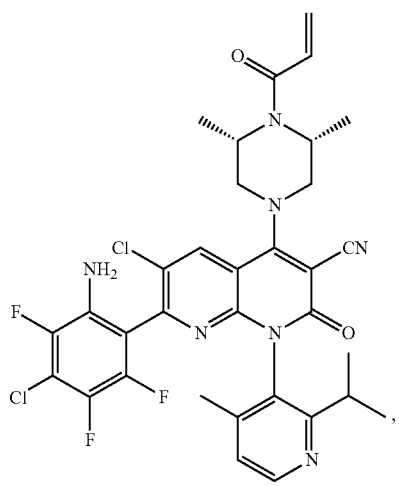
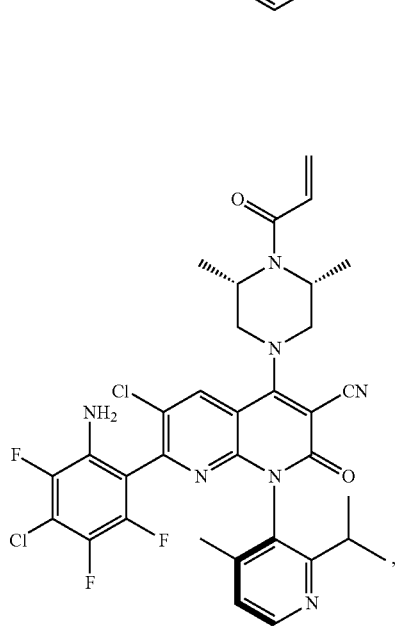
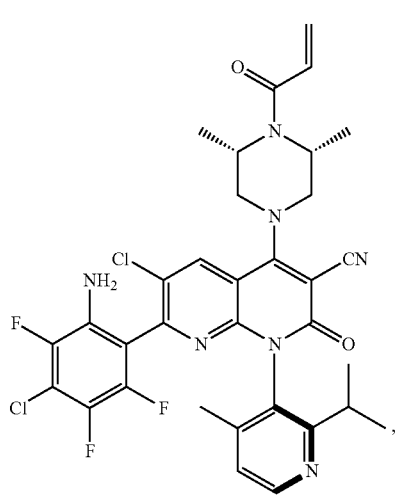

135
-continued
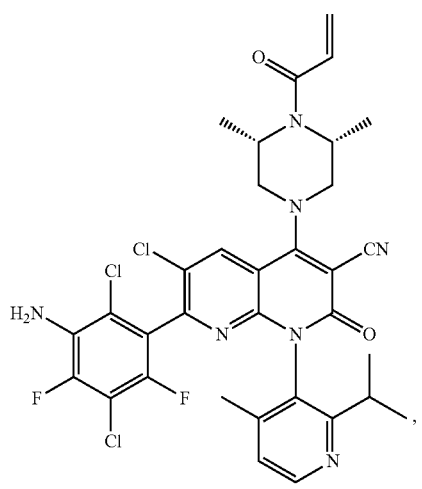
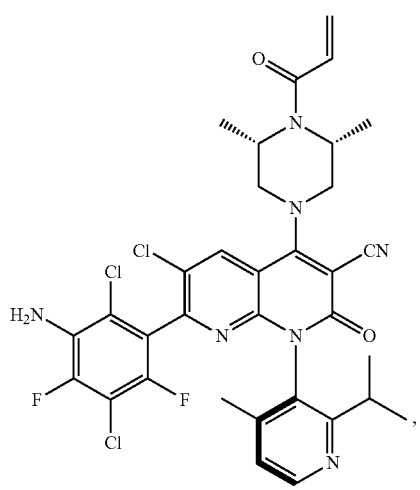
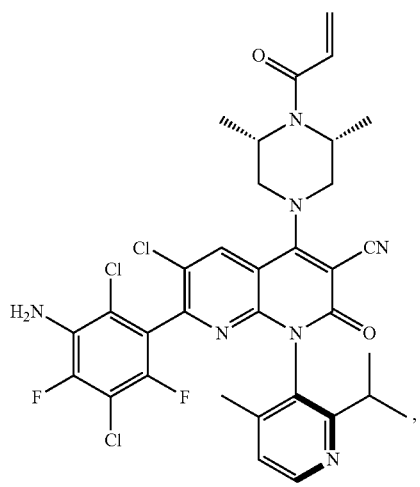
136
-continued
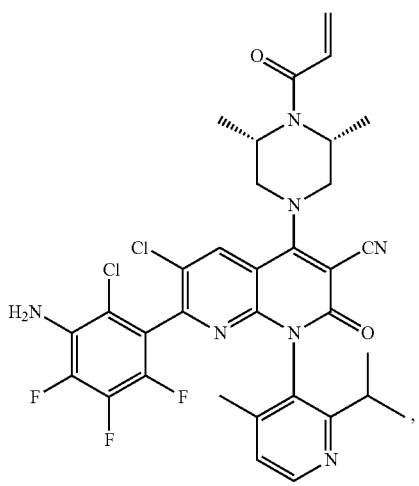
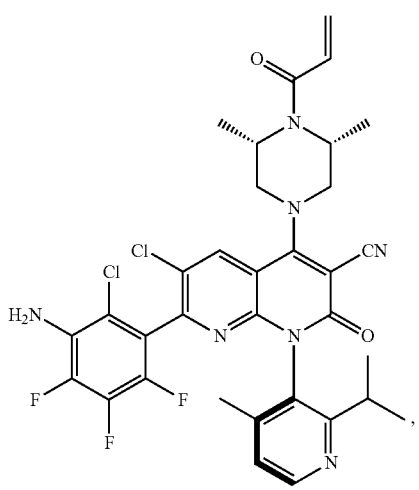
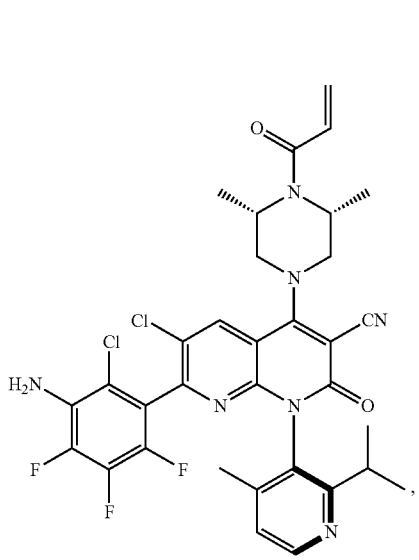

137
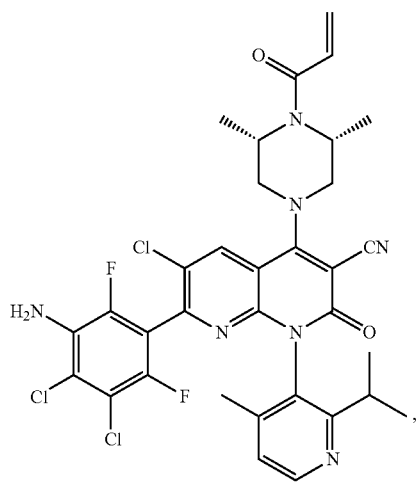
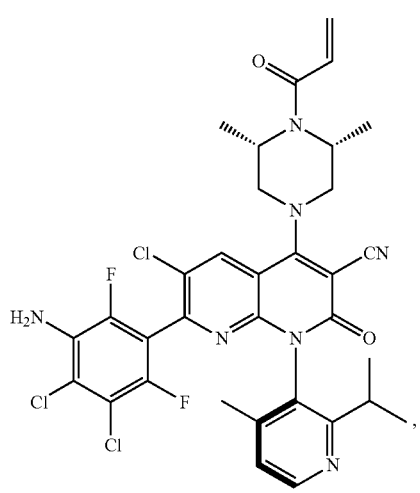
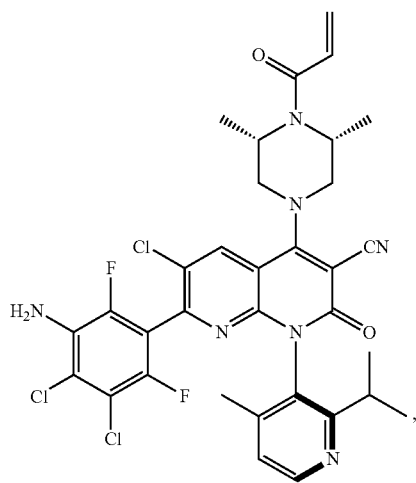
138
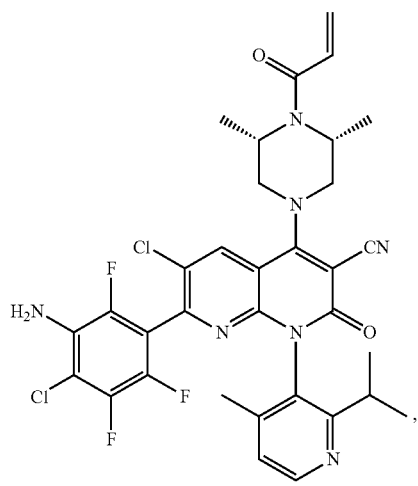
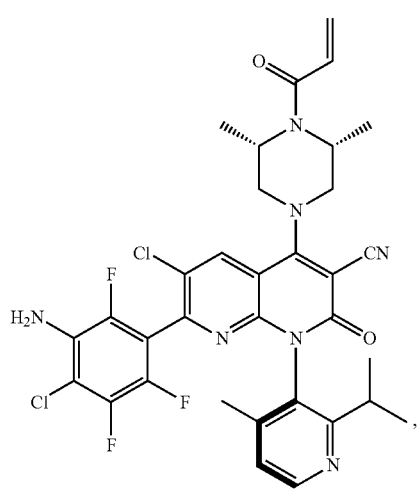
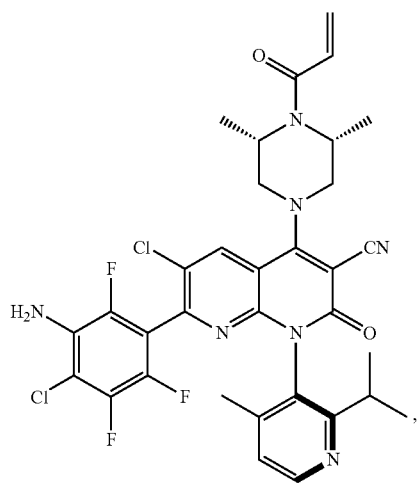

139
-continued
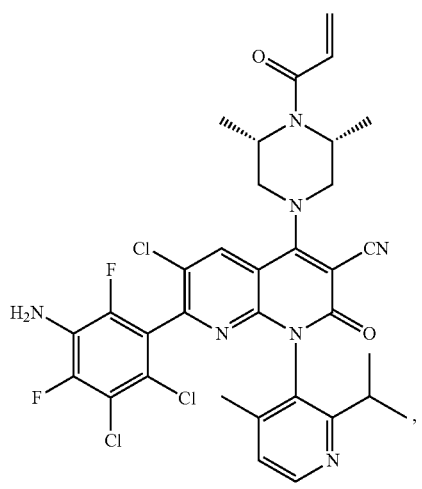
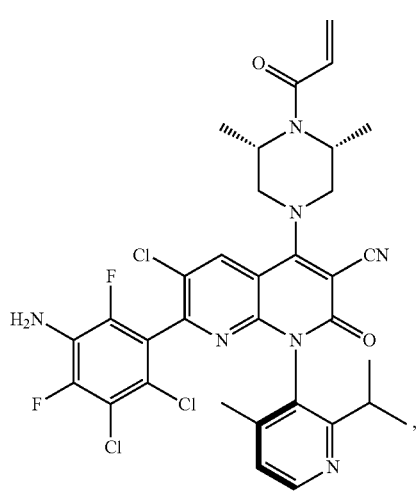
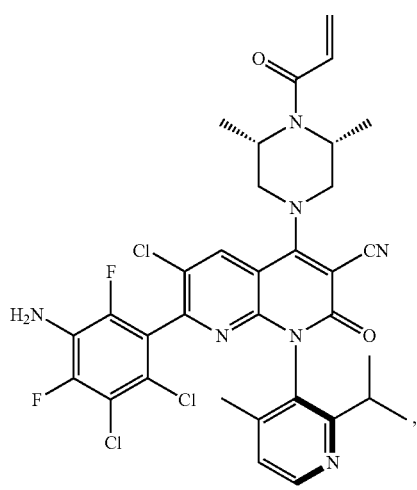
140
-continued
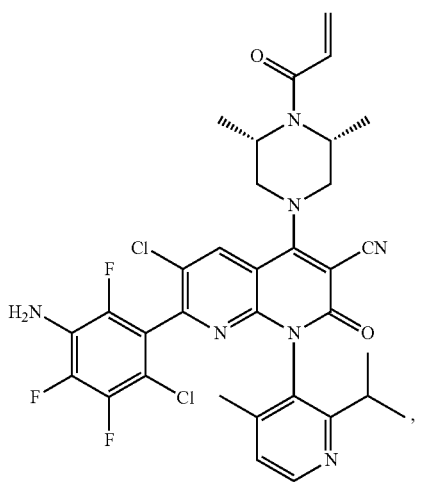
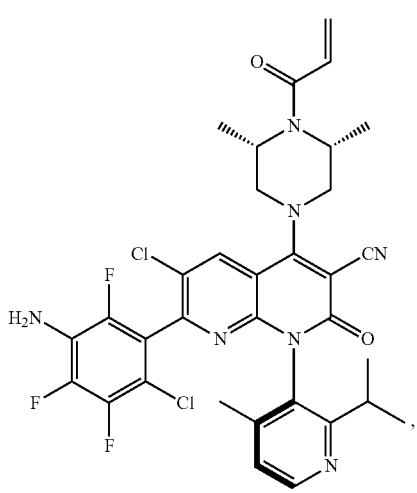
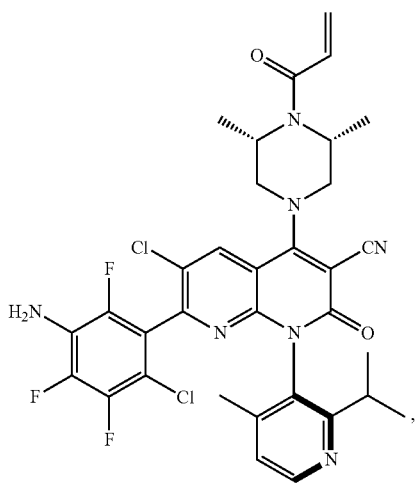

141
-continued
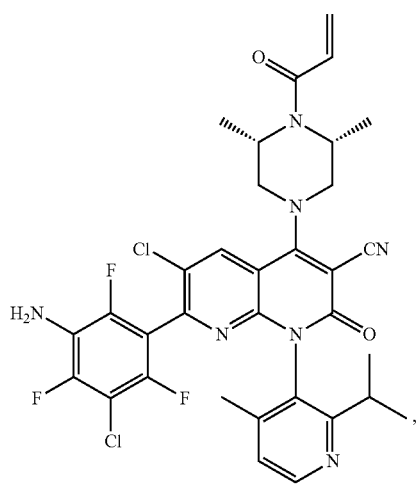
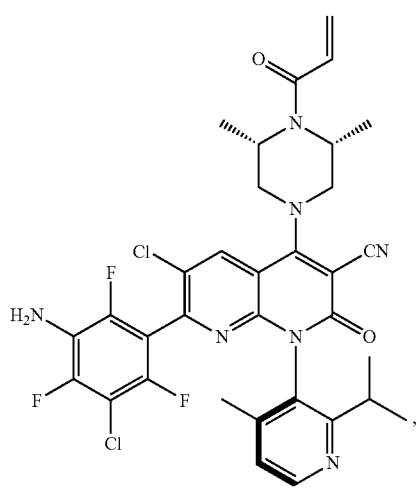
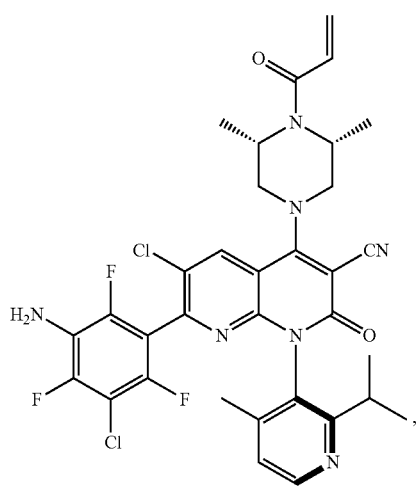
142
-continued
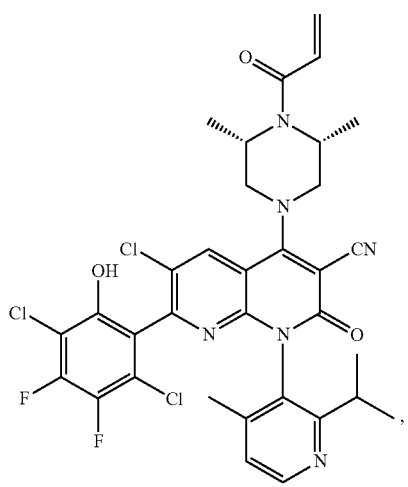
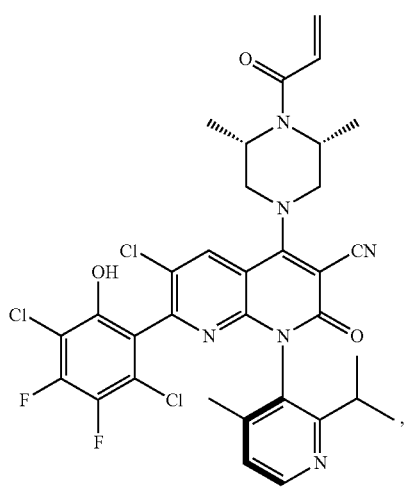
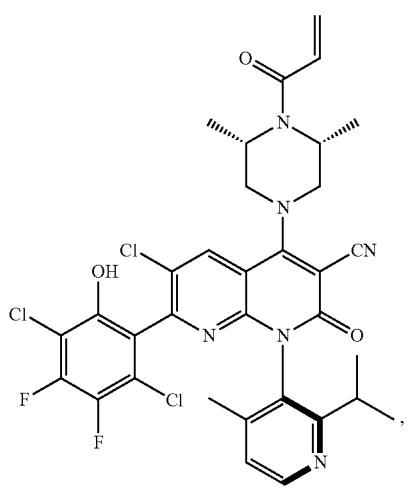

143
-continued
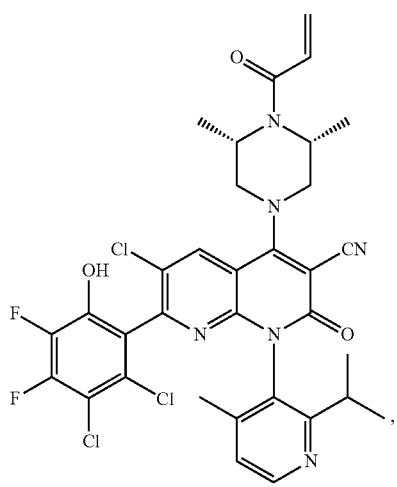
144
-continued
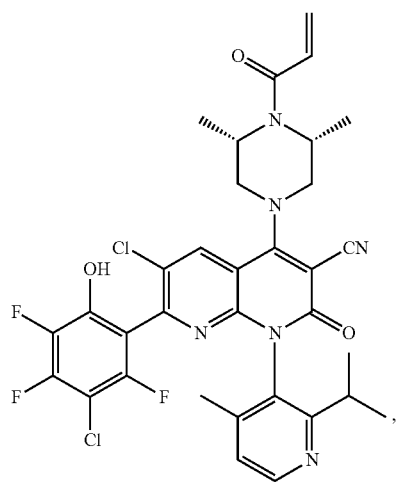
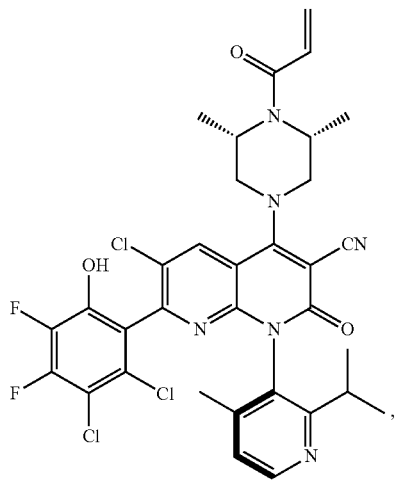
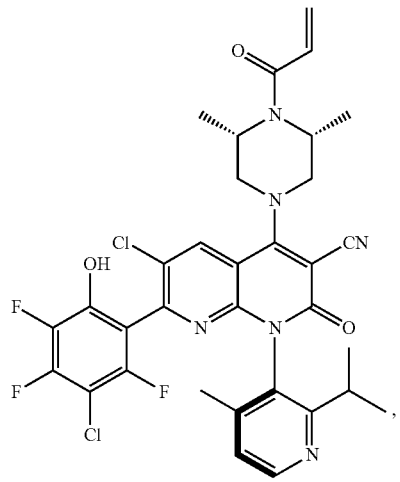
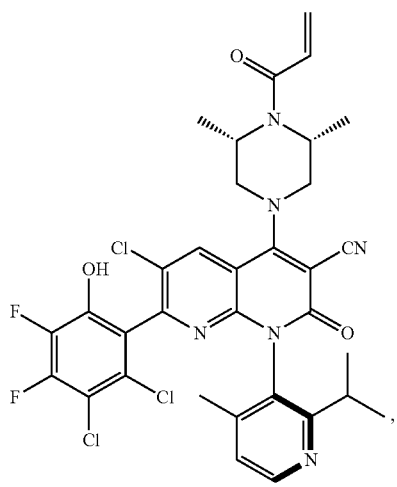
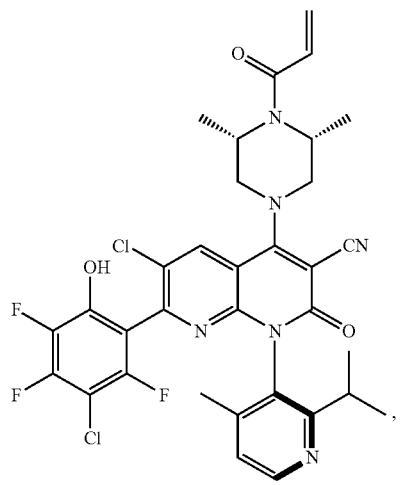

145
-continued
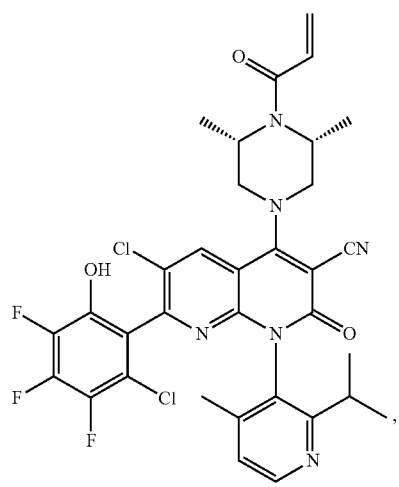
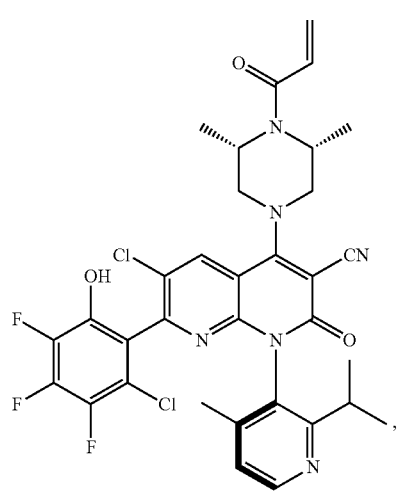
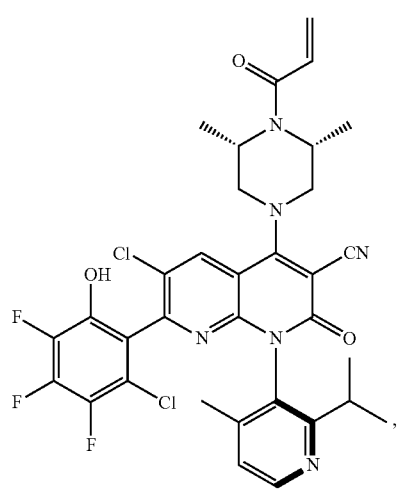
146
-continued
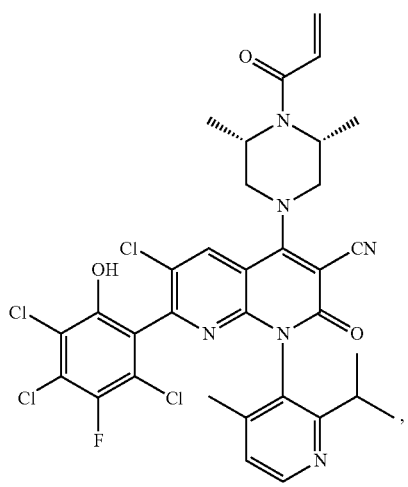
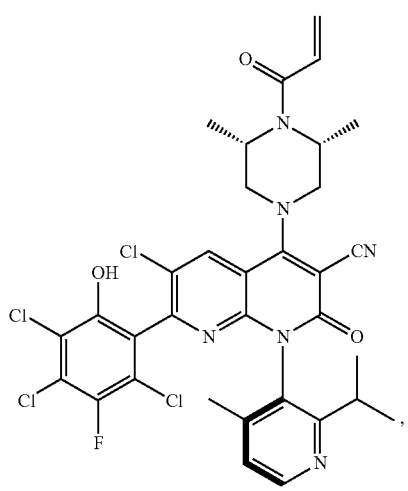
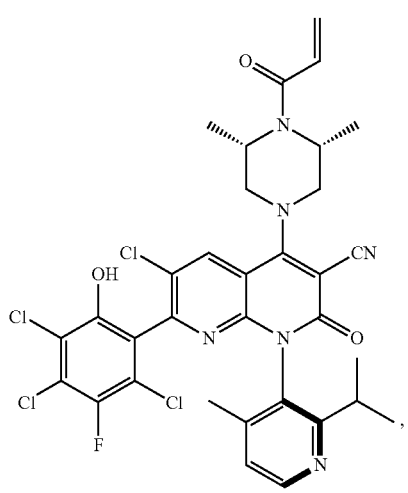

147
-continued
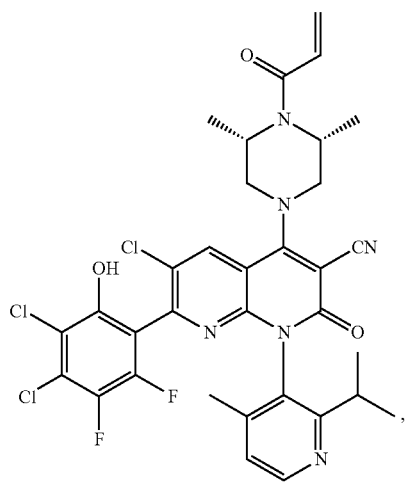
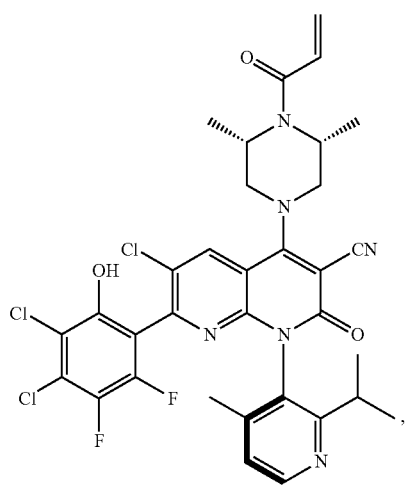
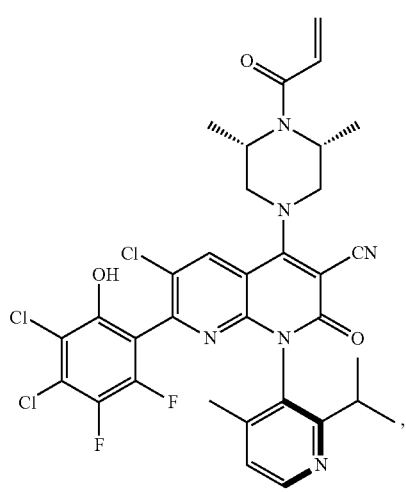
148
-continued
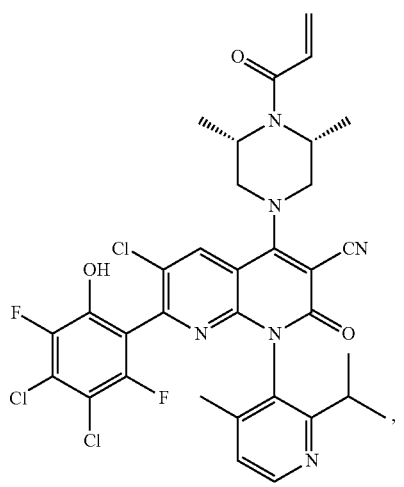
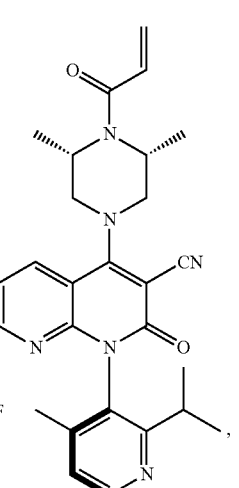
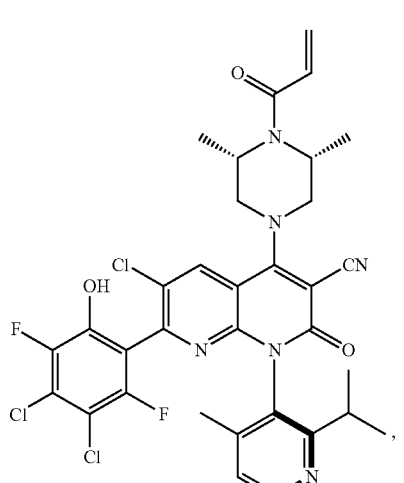

149
-continued
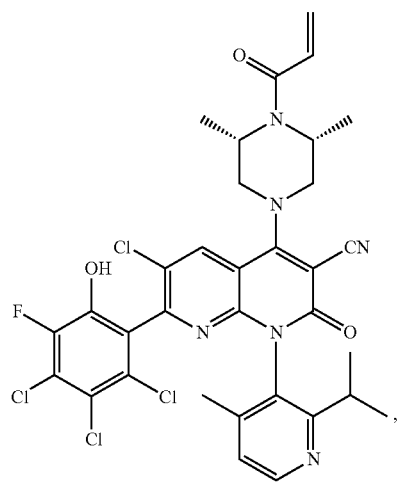
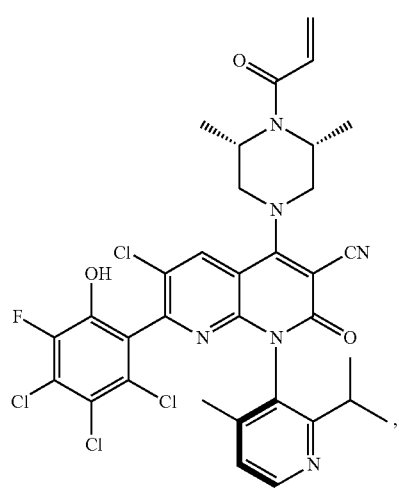
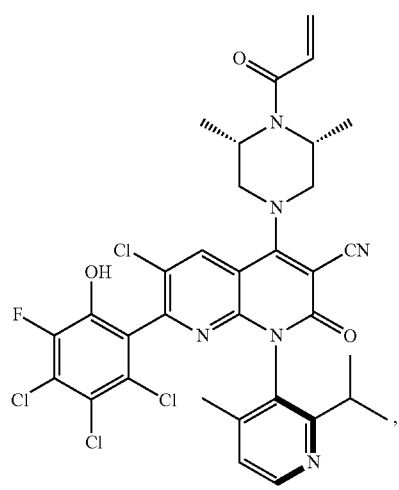
150
-continued
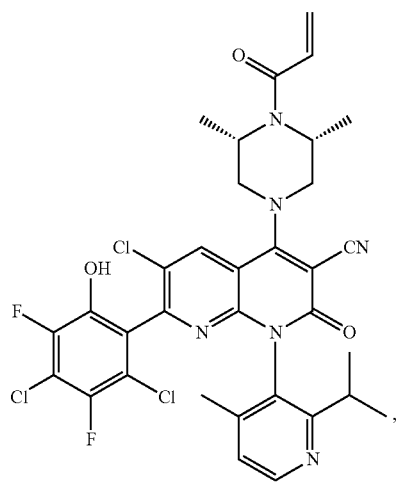
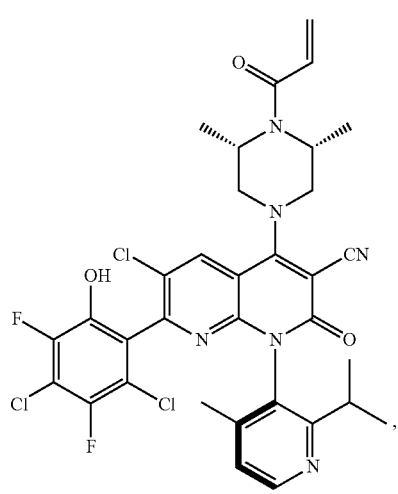
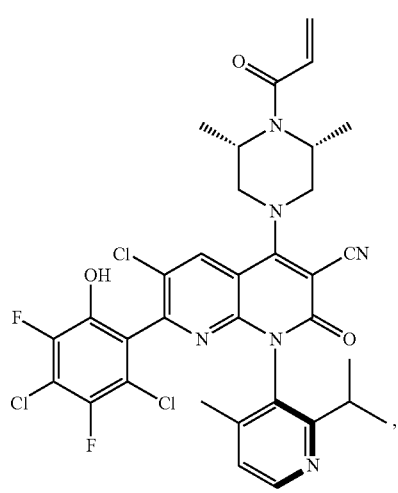

151
-continued
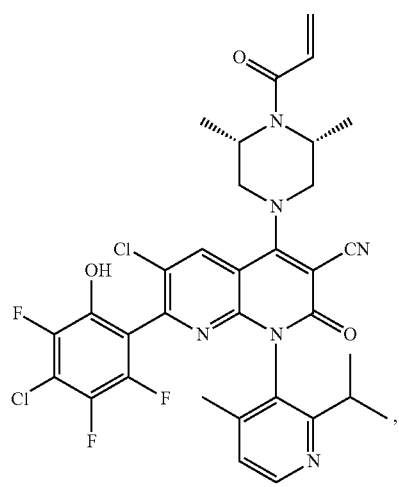
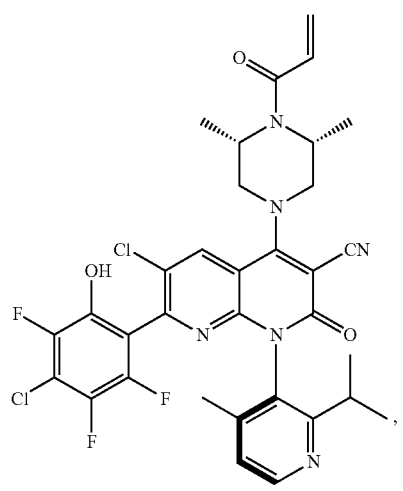
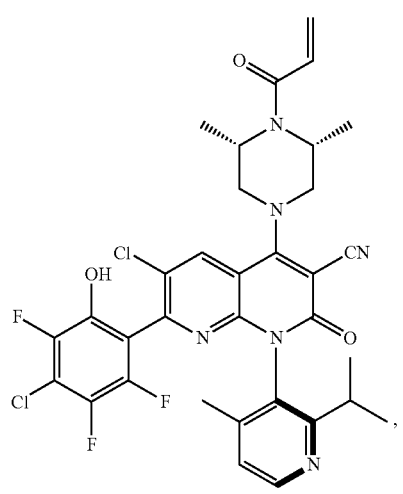
152
-continued
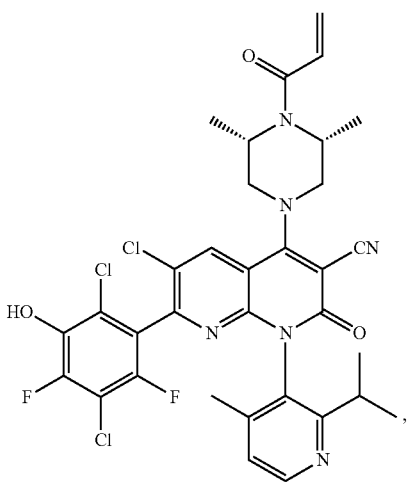
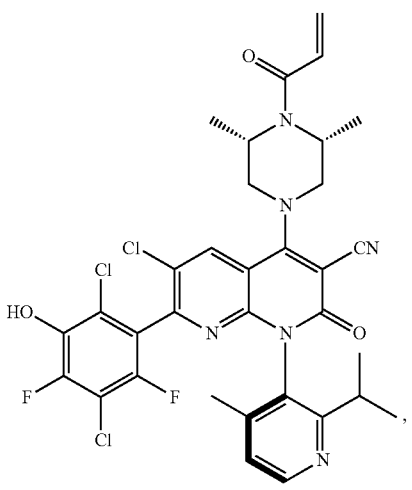
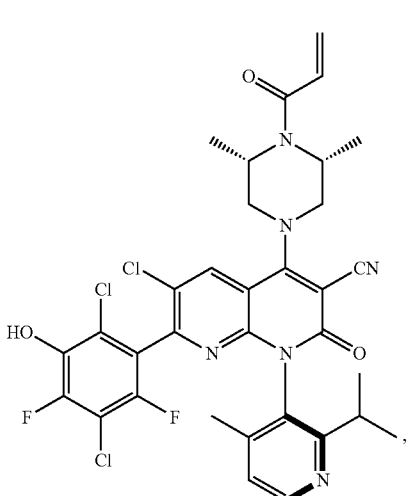

153
-continued
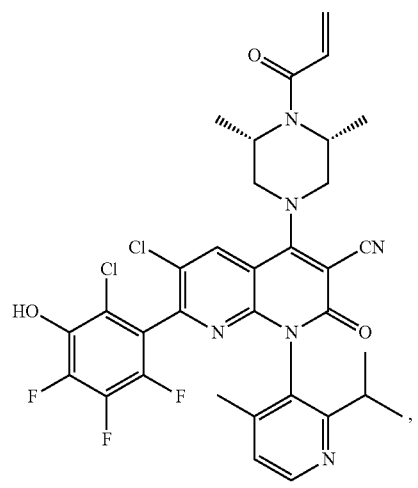
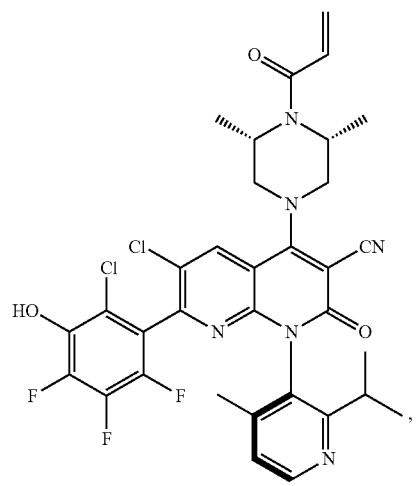
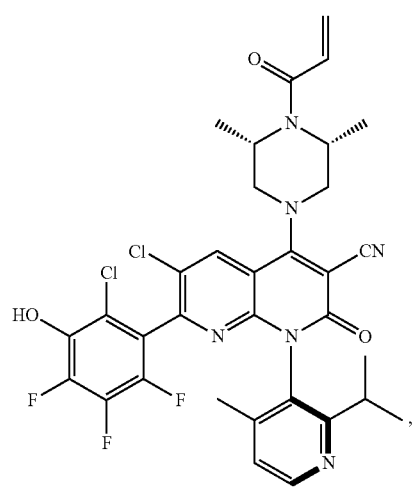
154
-continued
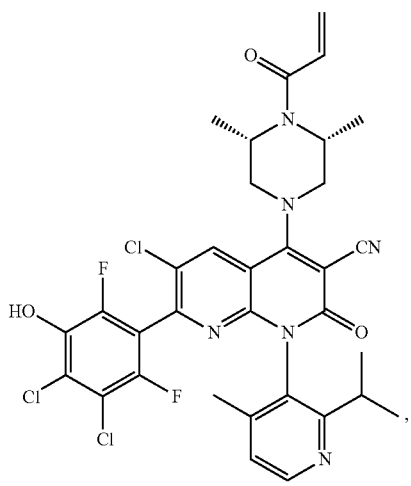
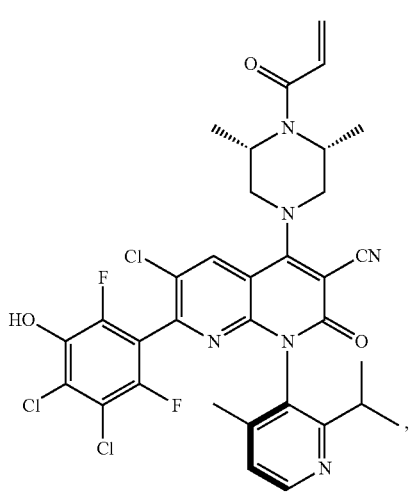
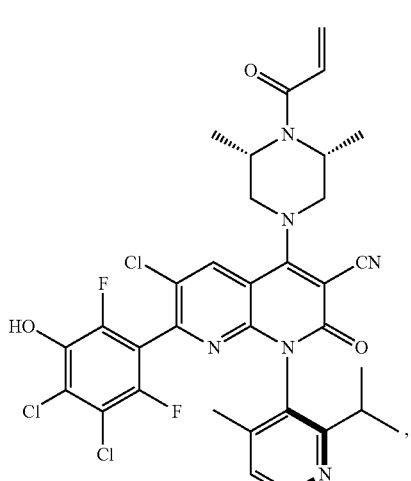

155
-continued
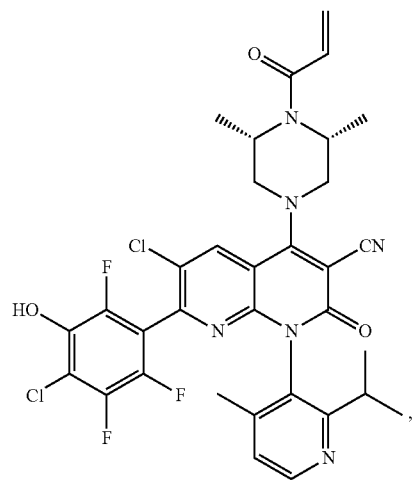
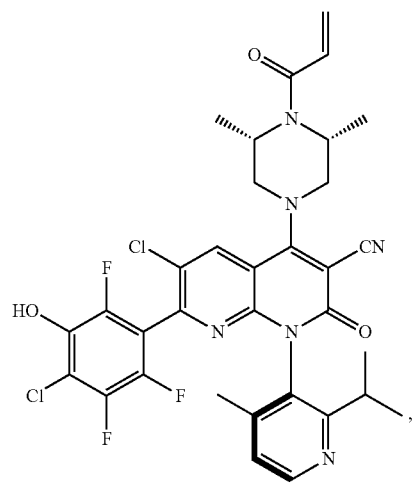
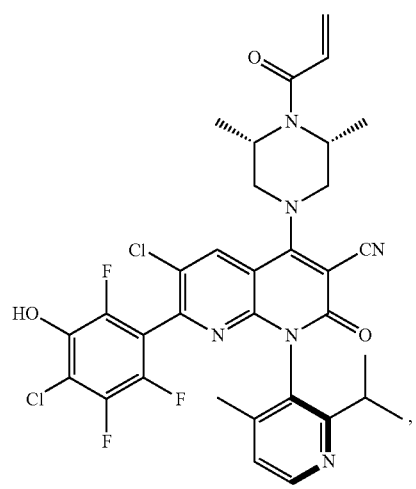
156
-continued
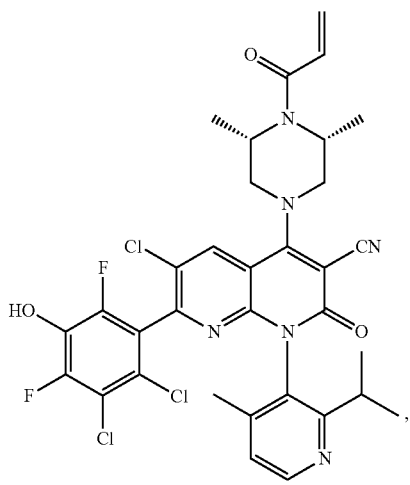
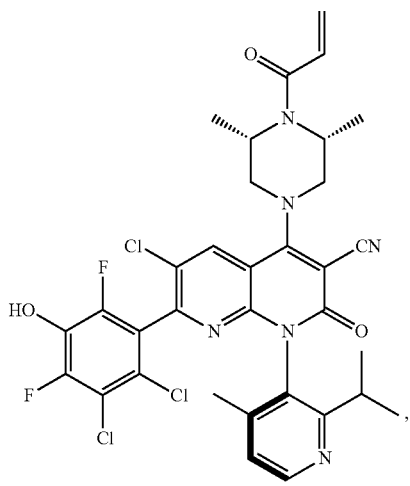
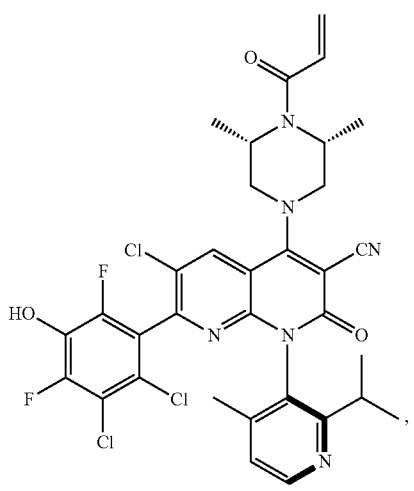

157
-continued
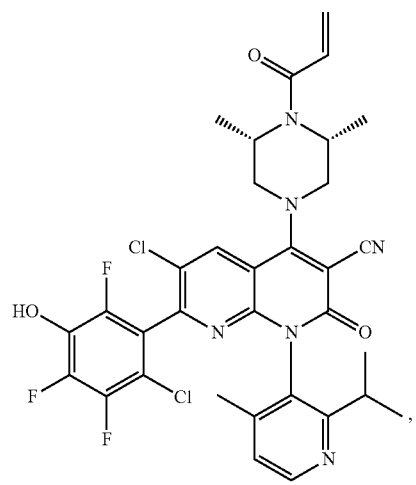
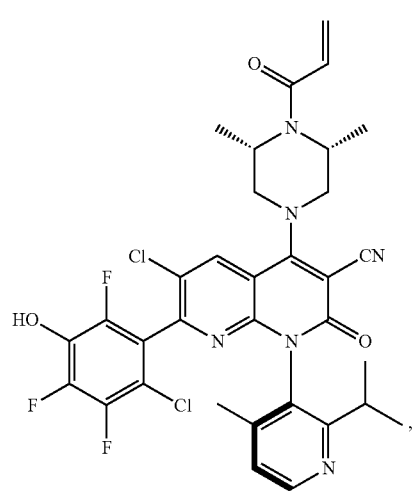
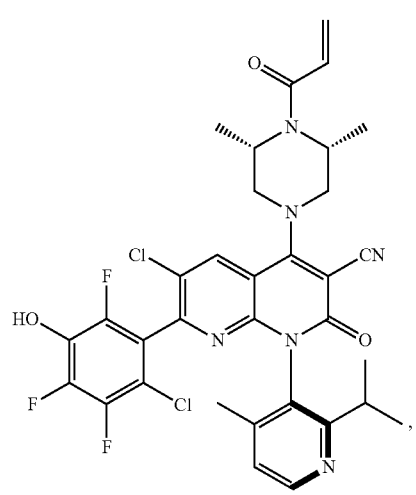
158
-continued
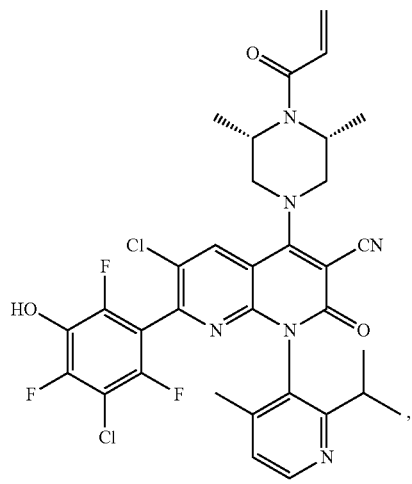
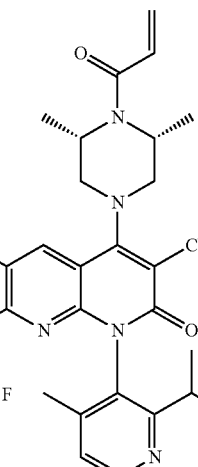
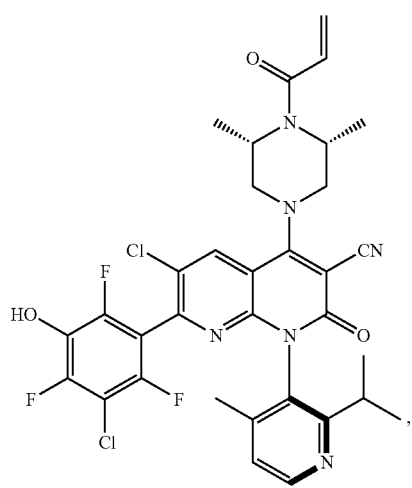

159
-continued
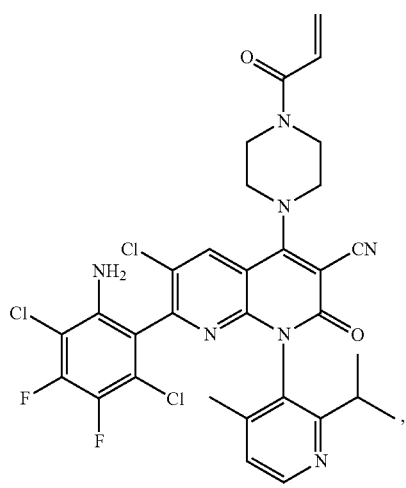
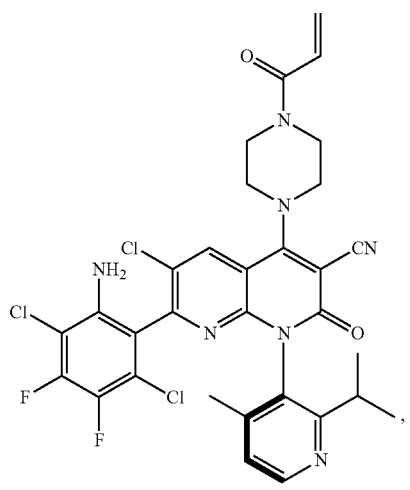
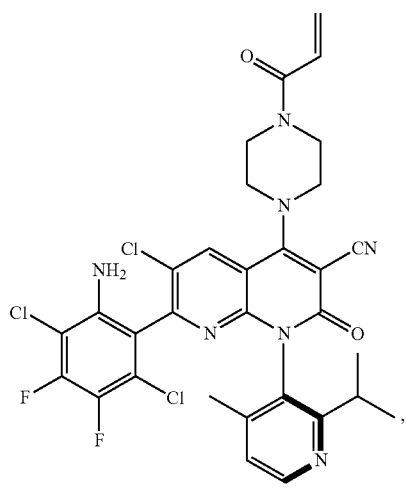
160
-continued
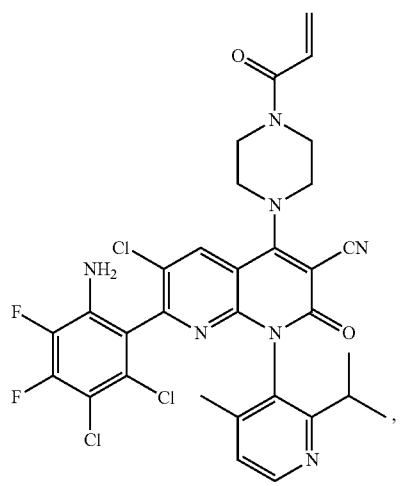
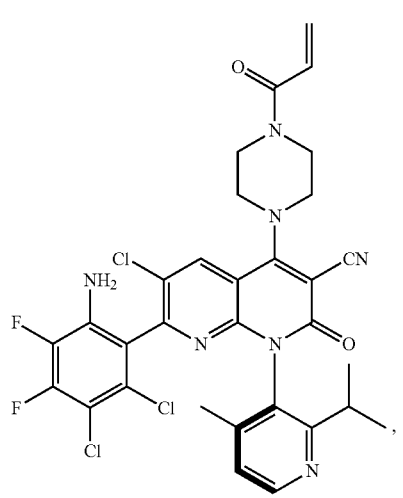
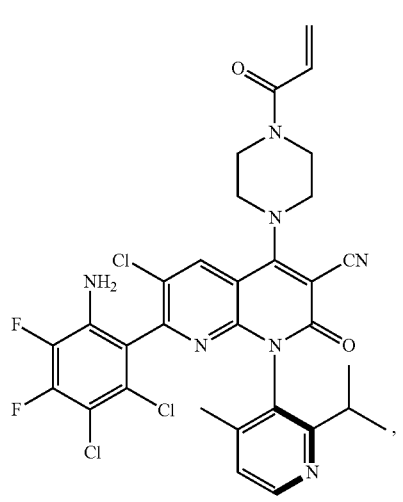

-continued
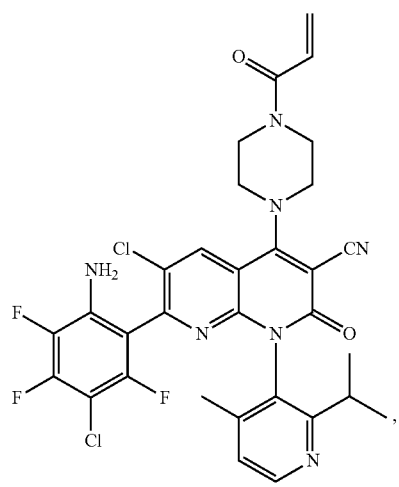
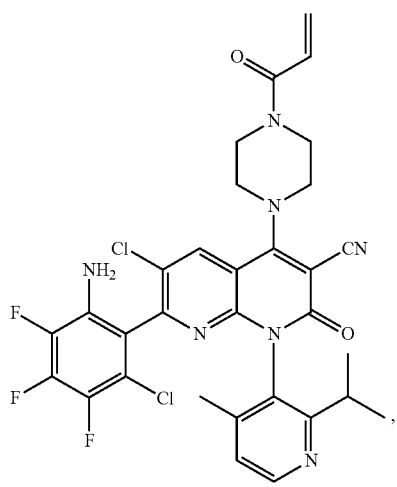
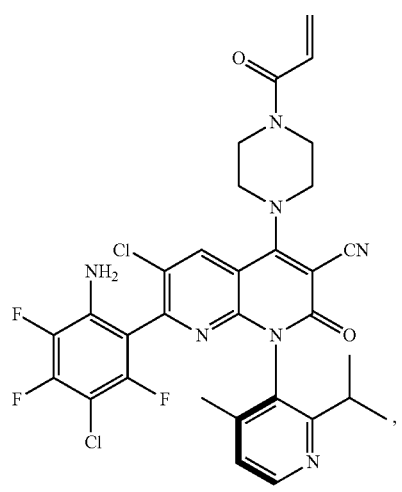
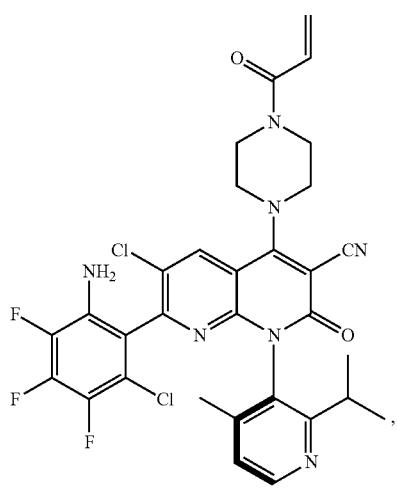
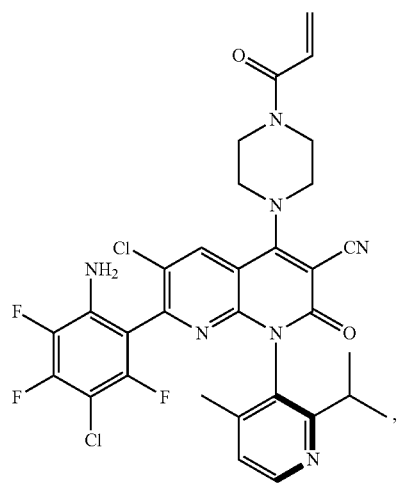
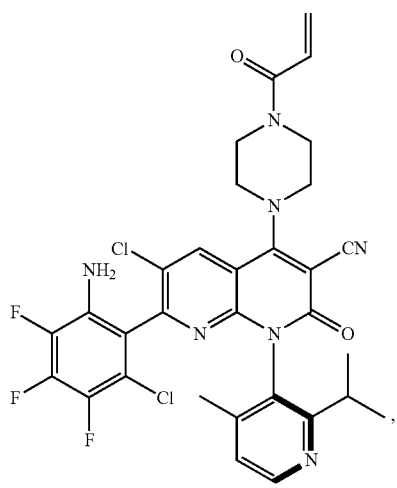

163
-continued
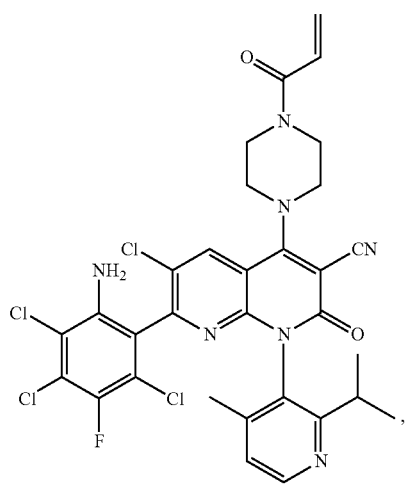
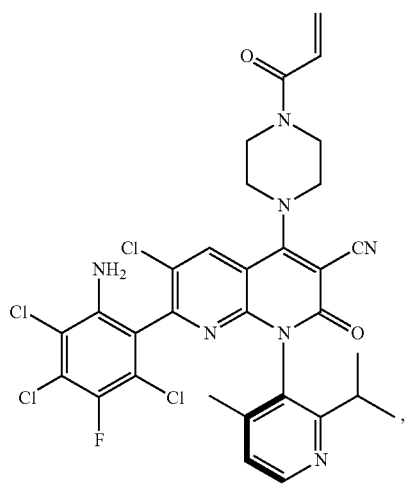
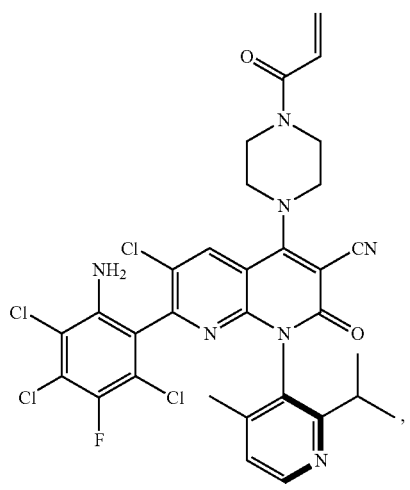
164
-continued
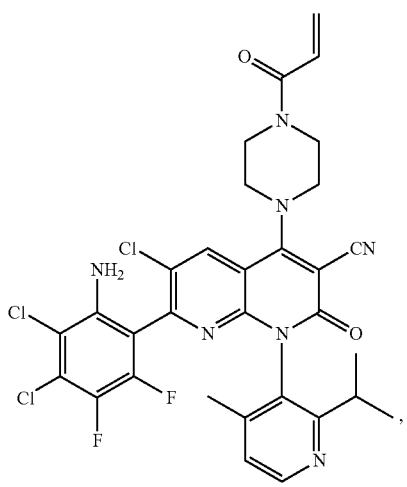
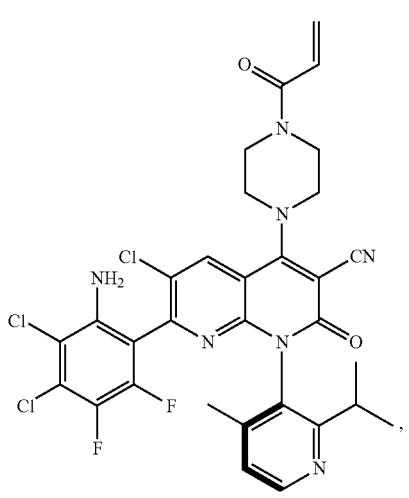
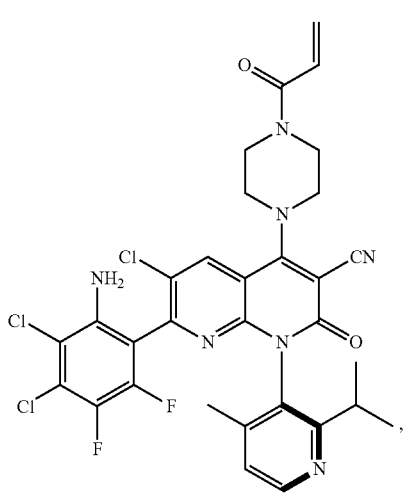

165
-continued
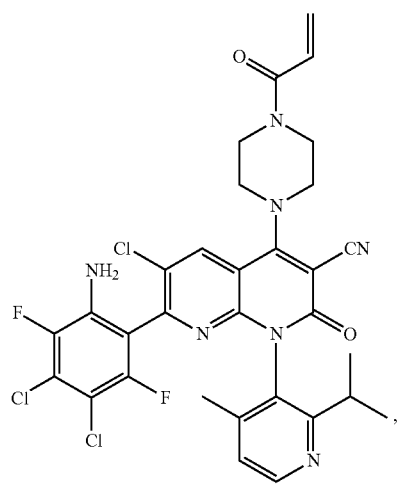
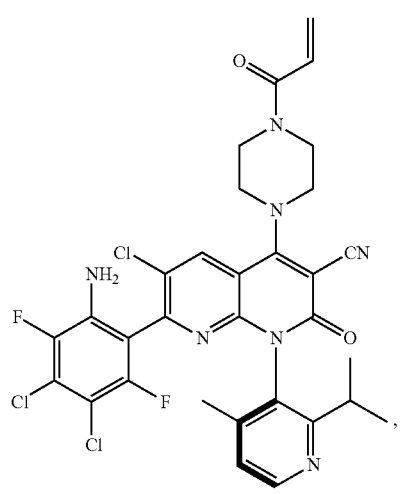
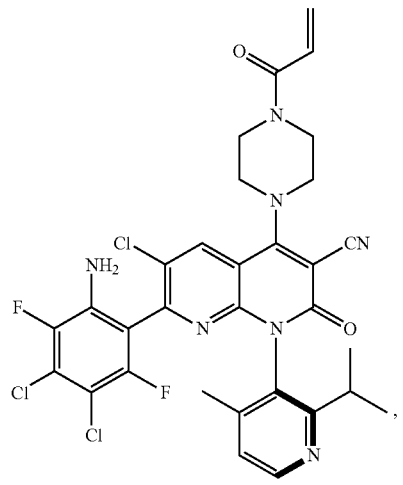
166
-continued

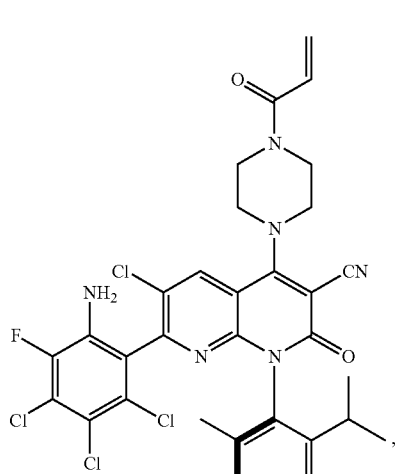
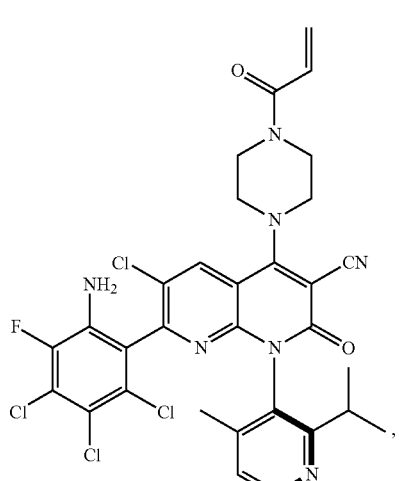

167
-continued
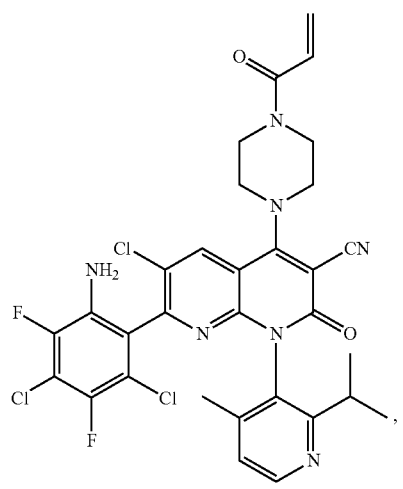
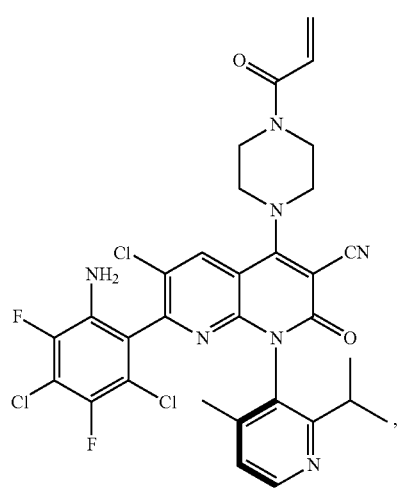
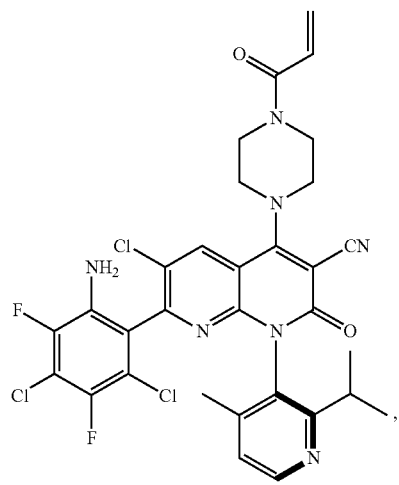
168
-continued
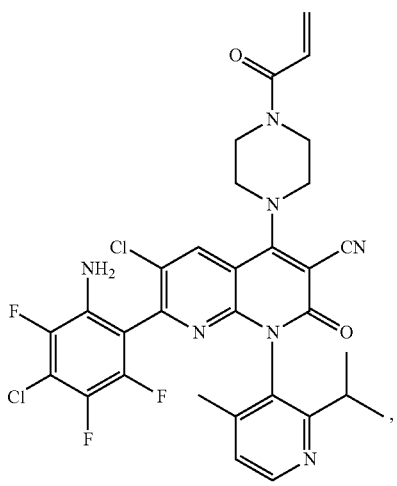
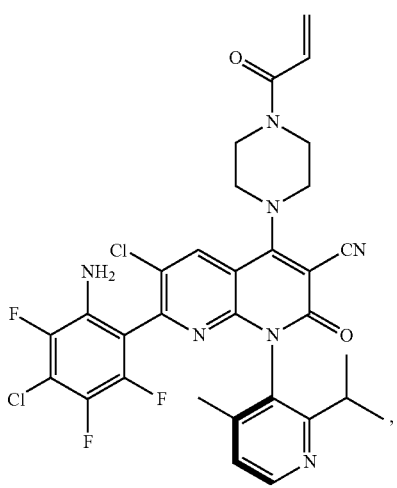
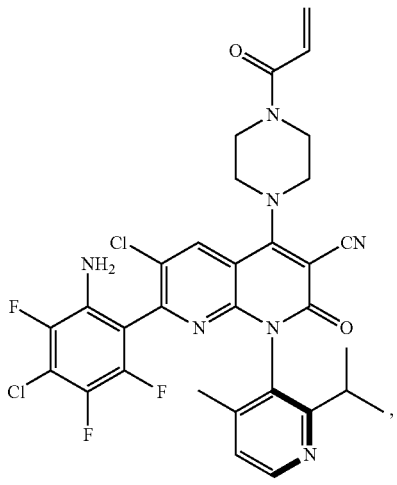

169
-continued
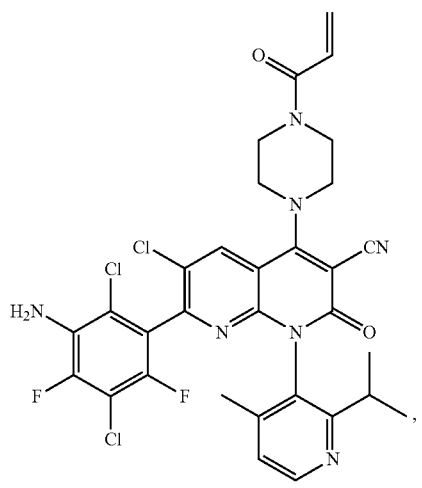
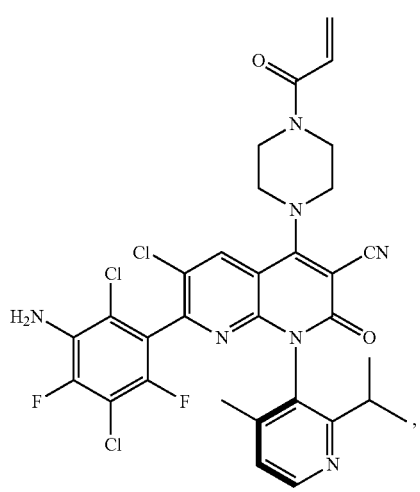
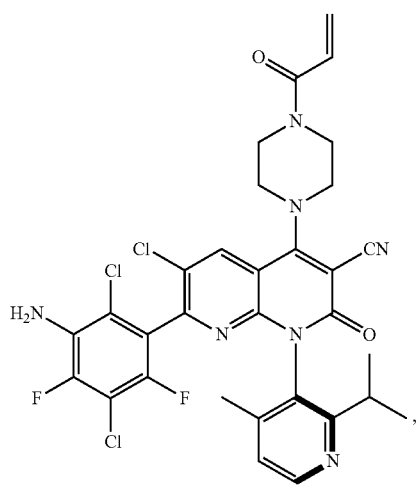
170
-continued
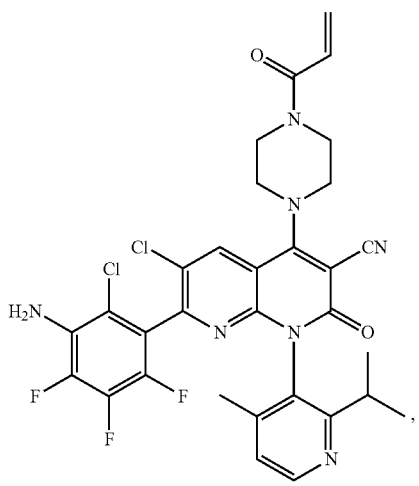
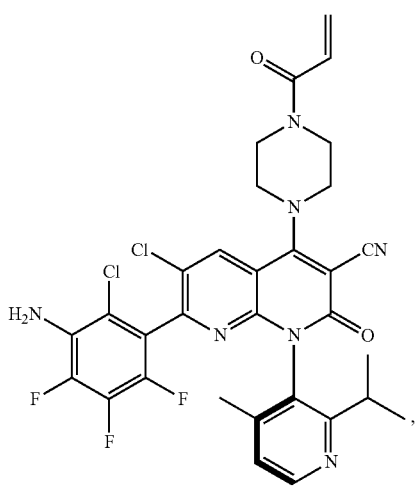
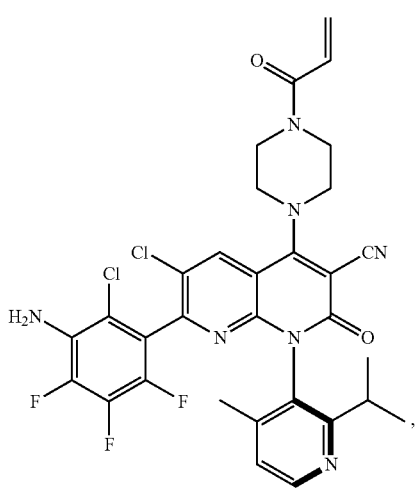

171
-continued
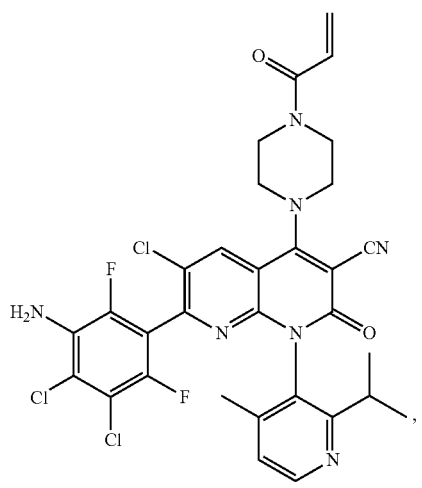
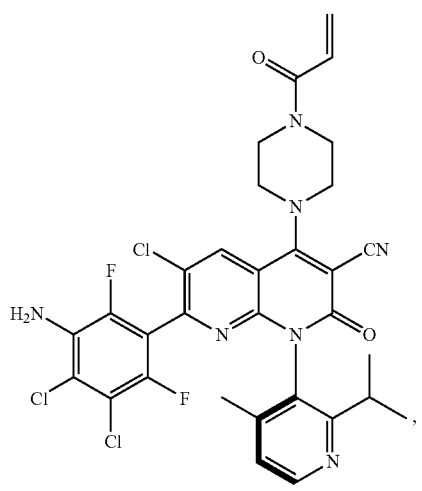
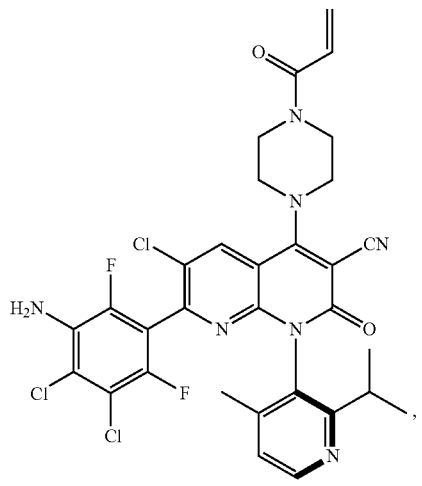
172
-continued
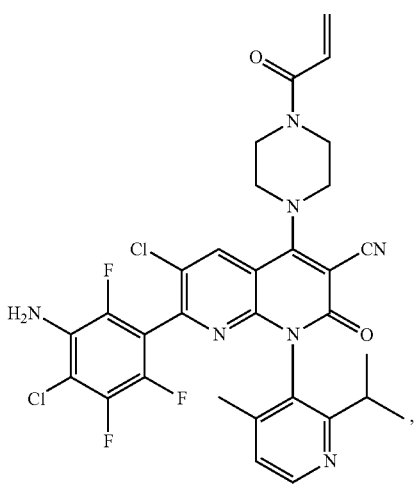
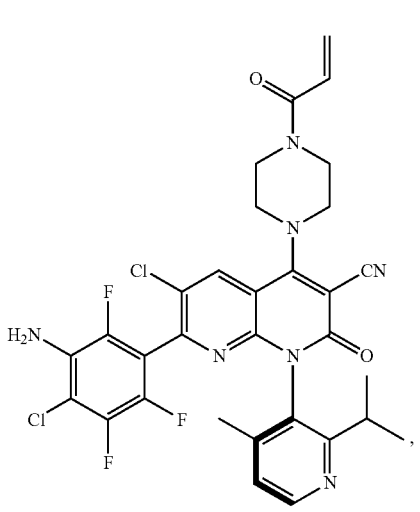
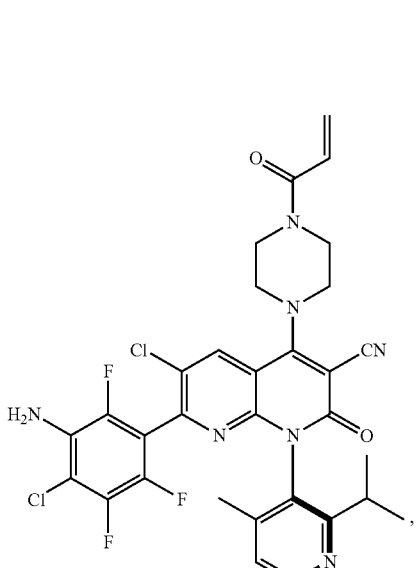

173
-continued
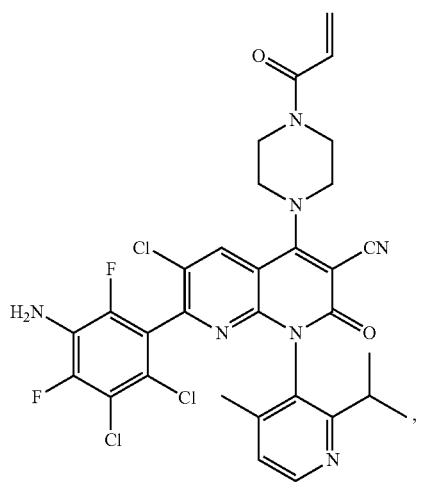
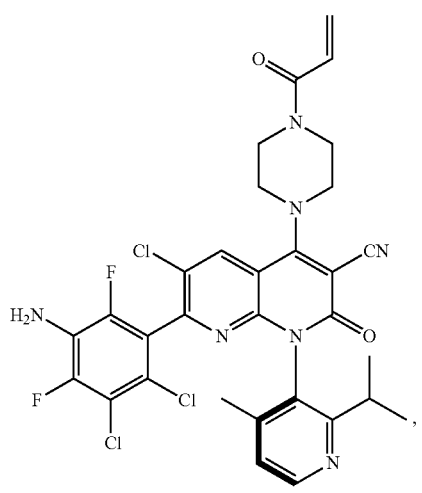
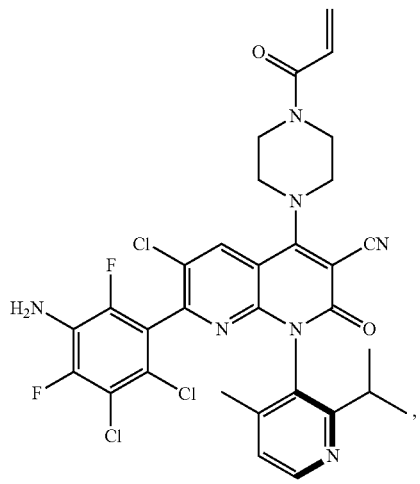
174
-continued
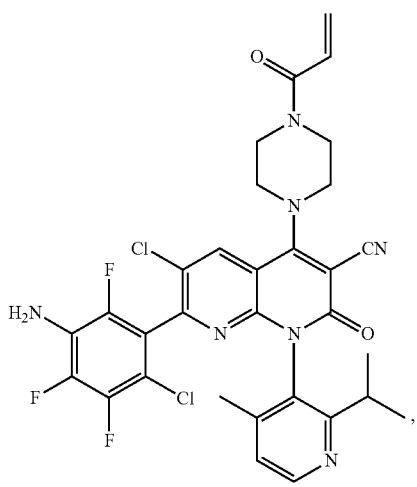
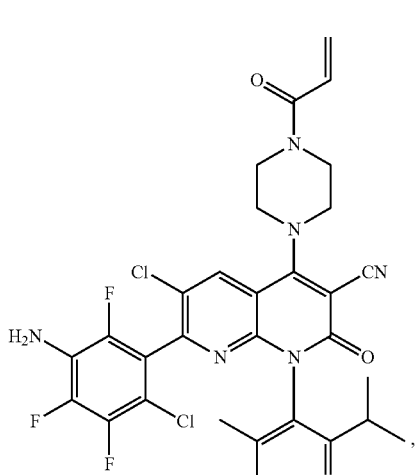
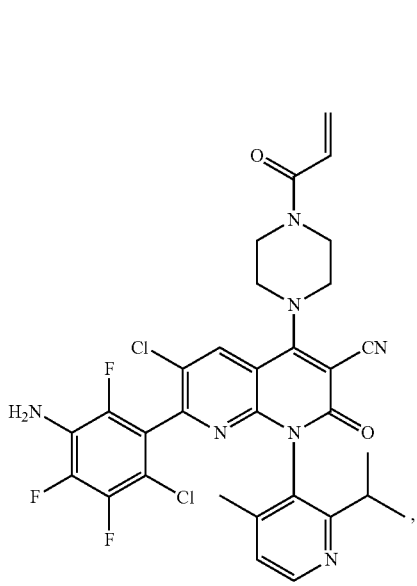

175
-continued
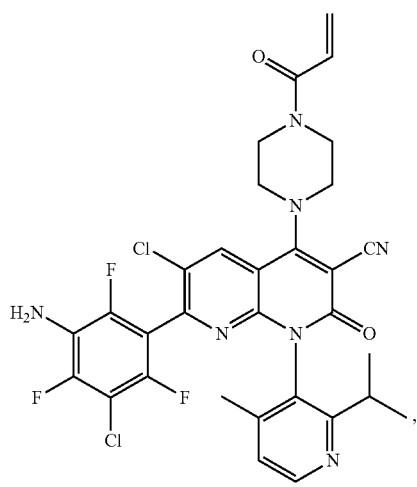
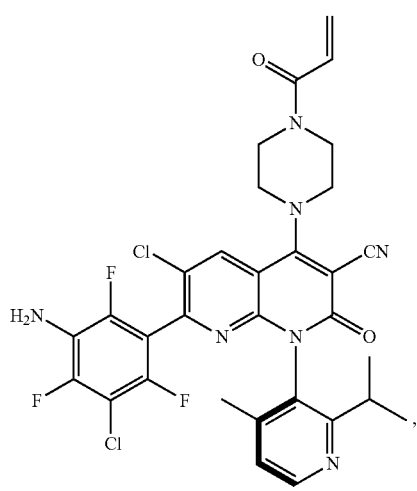
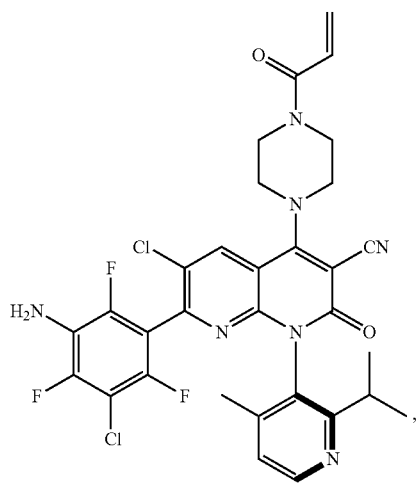
176
-continued
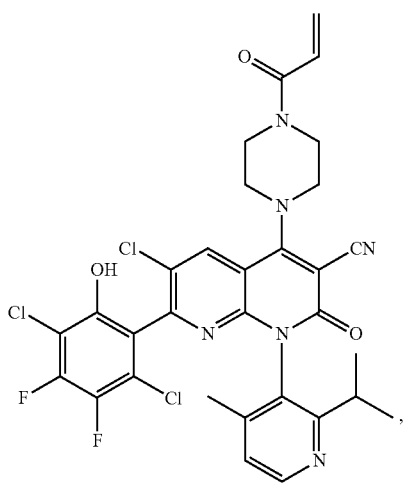
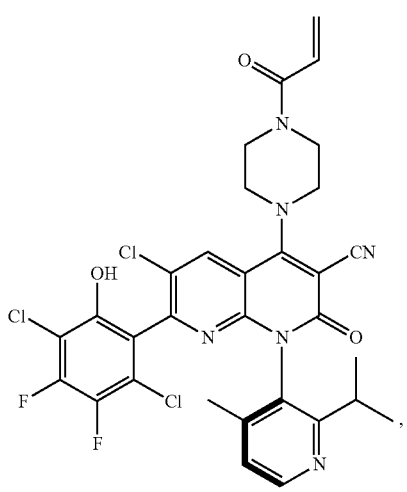
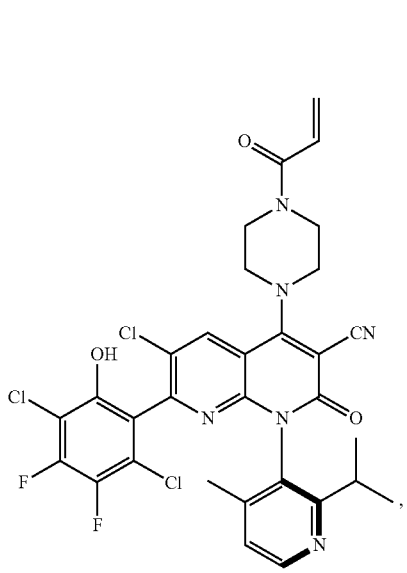

-continued
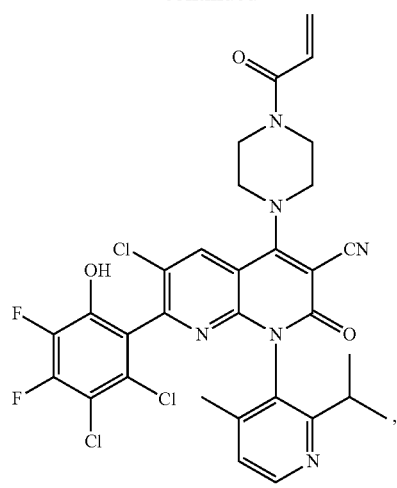
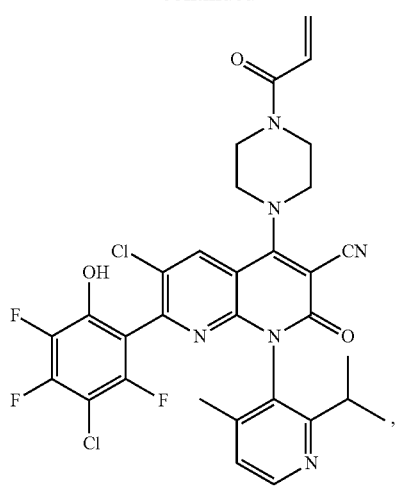
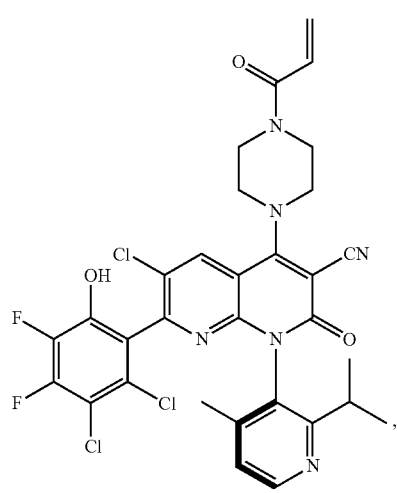
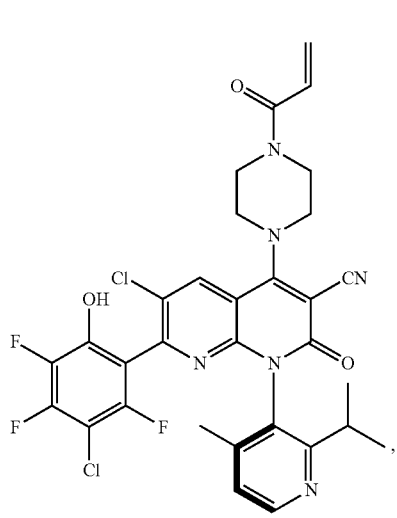
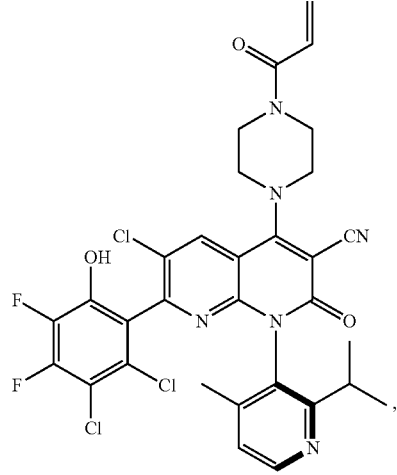
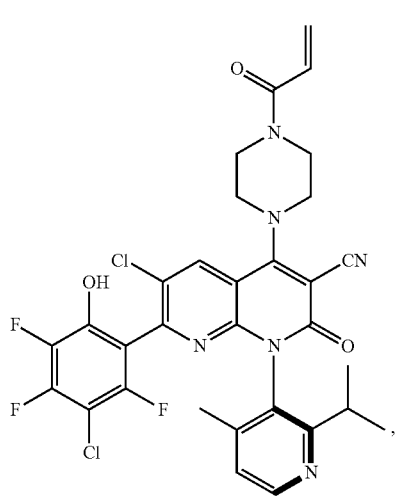

179
-continued
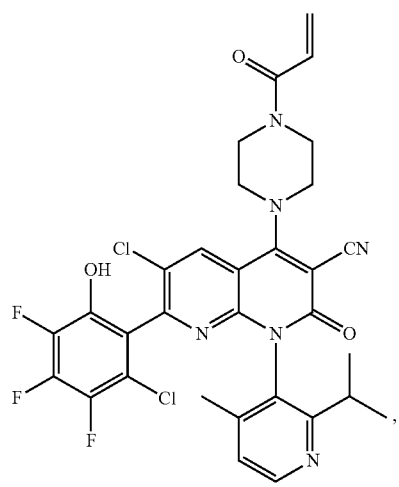
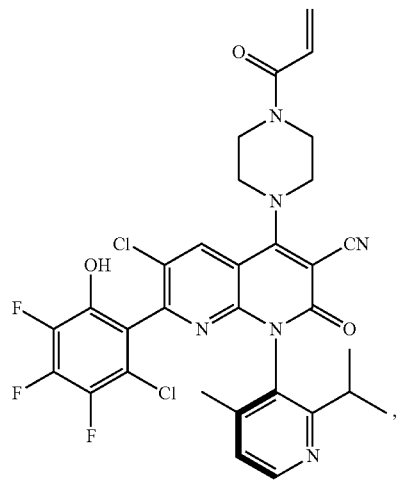
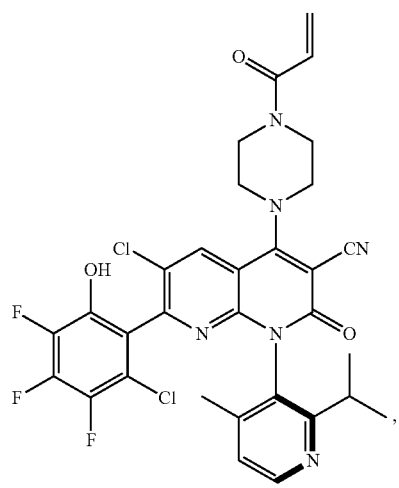
180
-continued
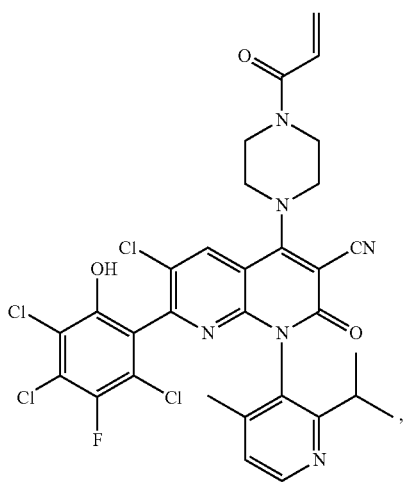
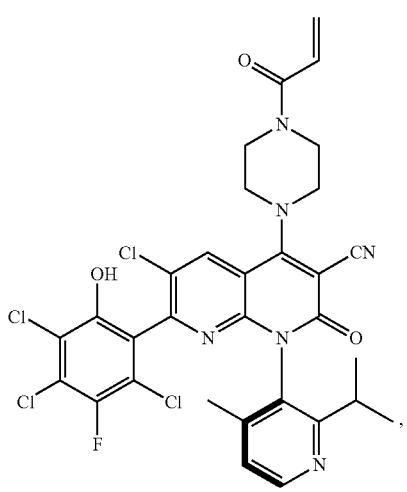
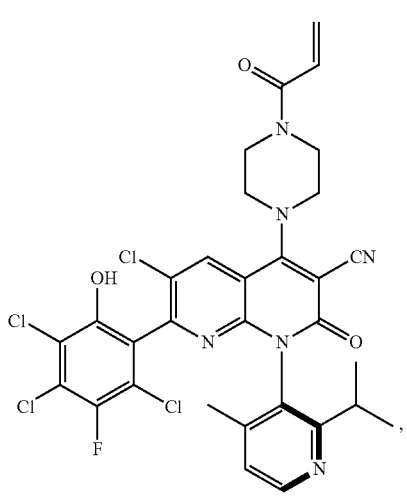

181
-continued
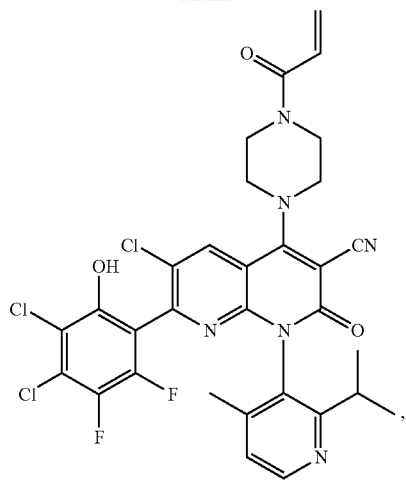
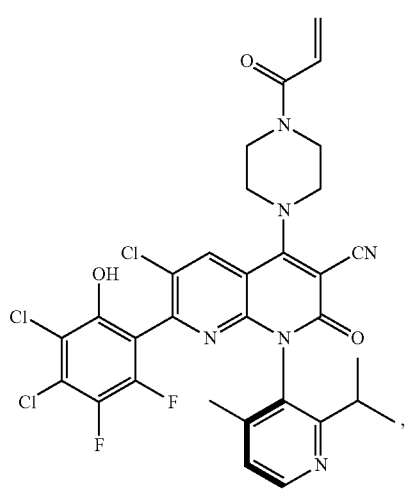
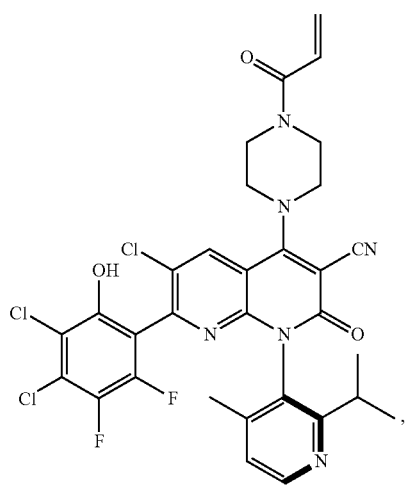
182
-continued
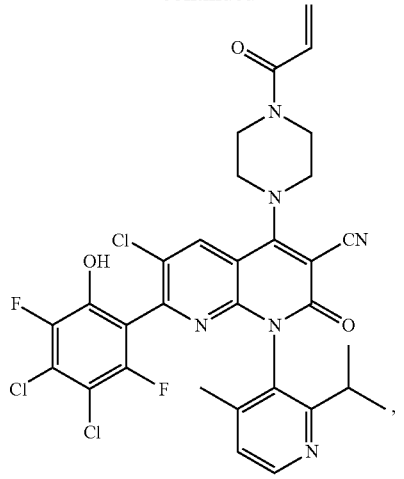
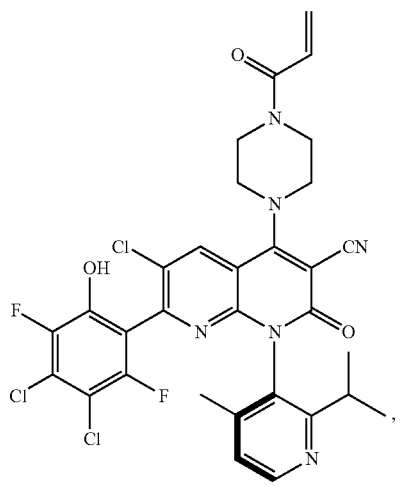
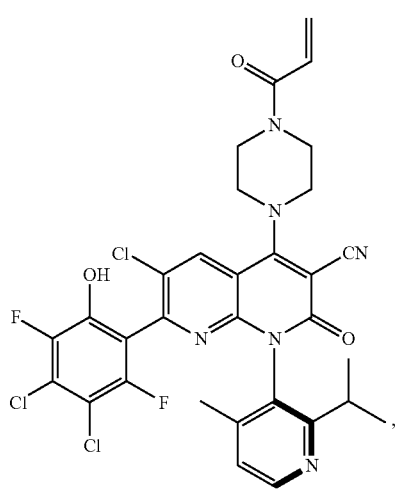

-continued
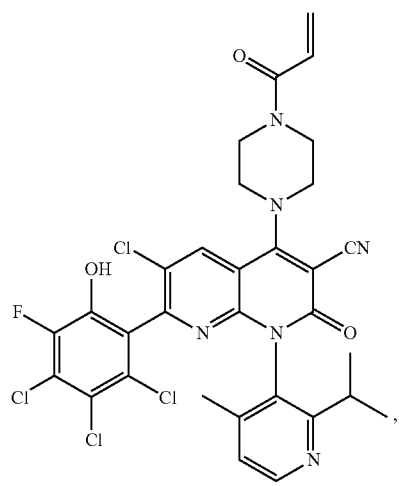
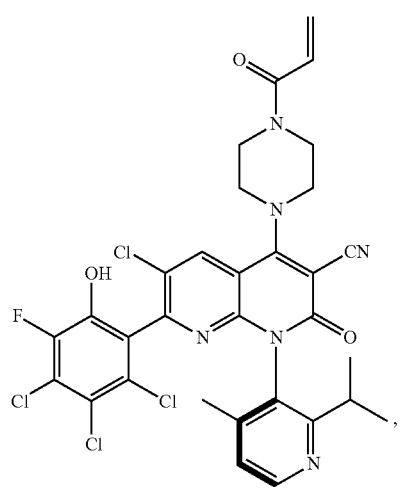
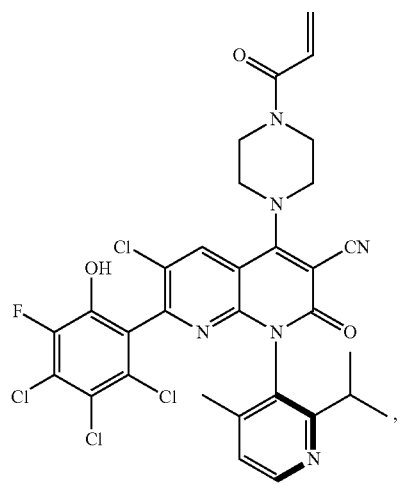
-continued
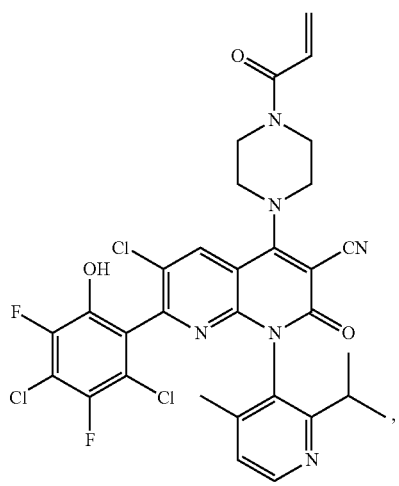
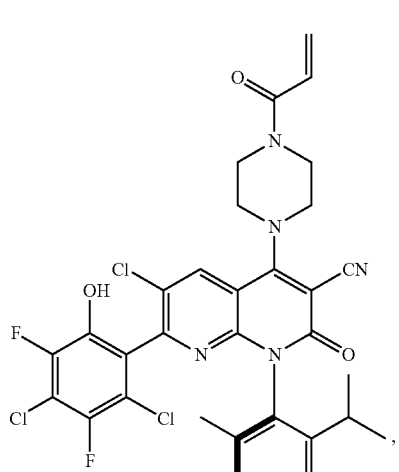
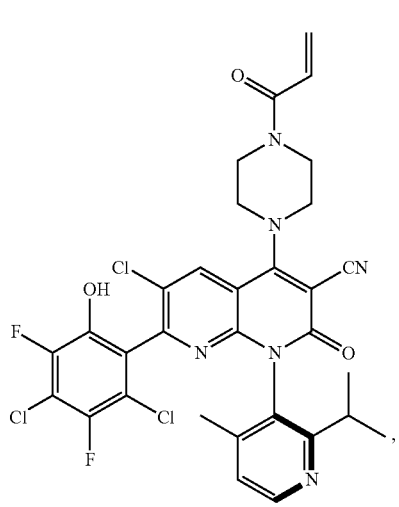

185
-continued
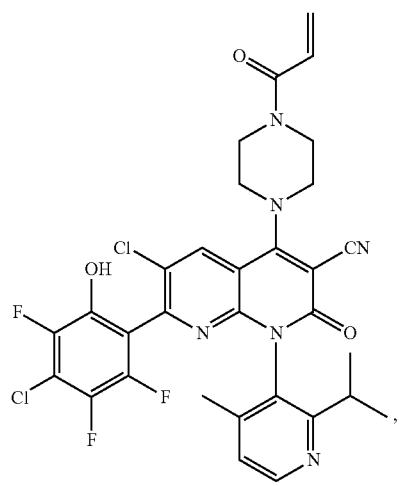
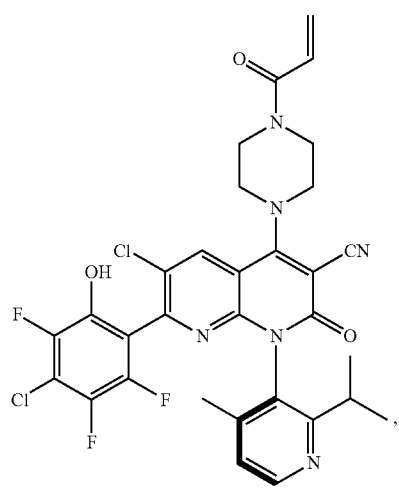
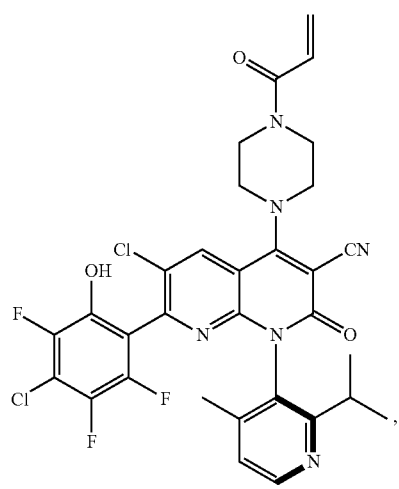
186
-continued
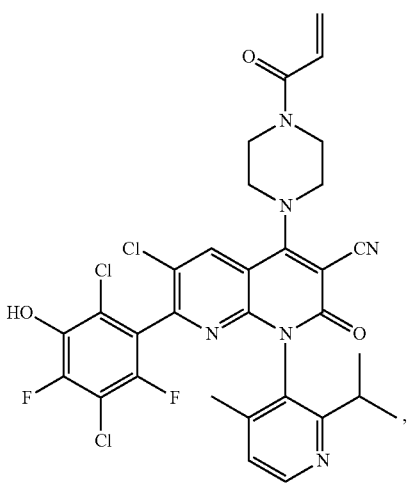
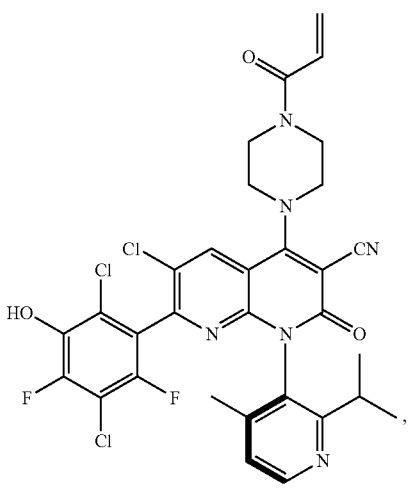
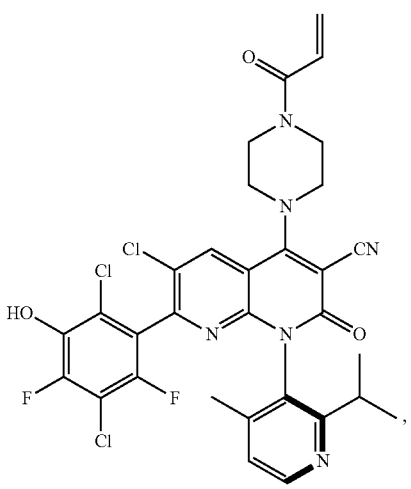

187
-continued
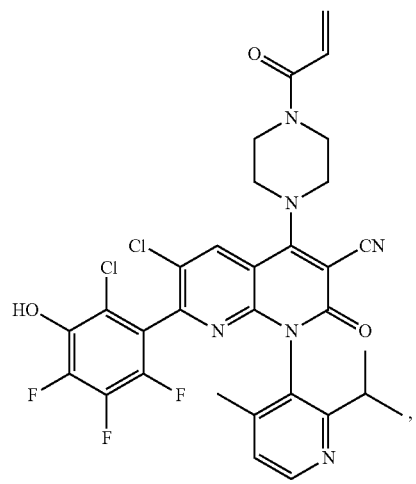
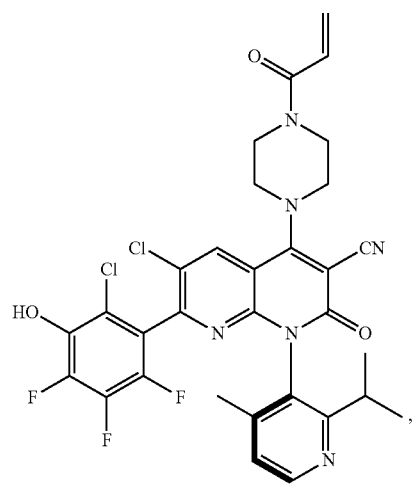
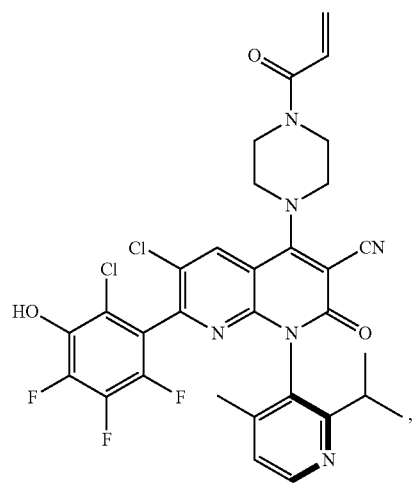
188
-continued
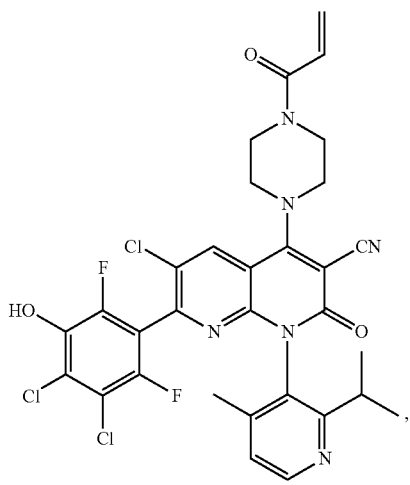
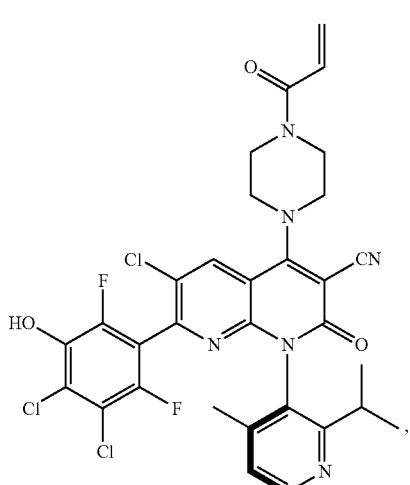
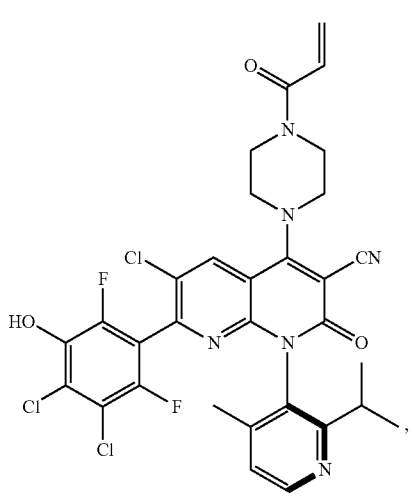

189
-continued
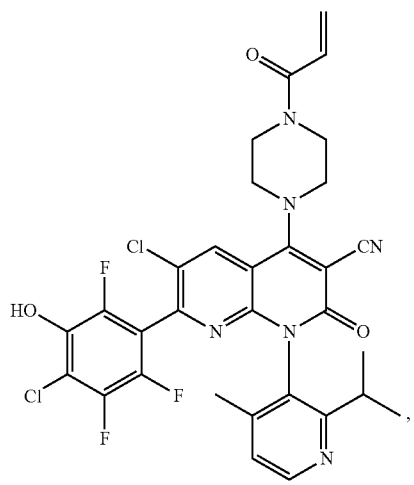
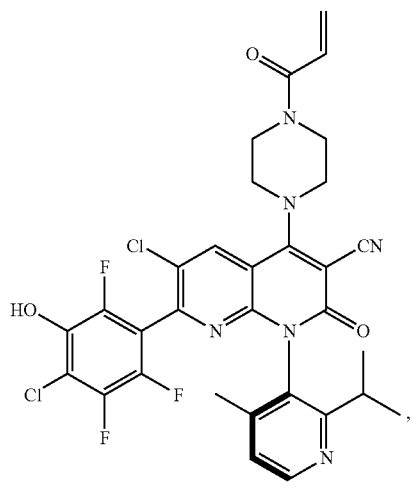
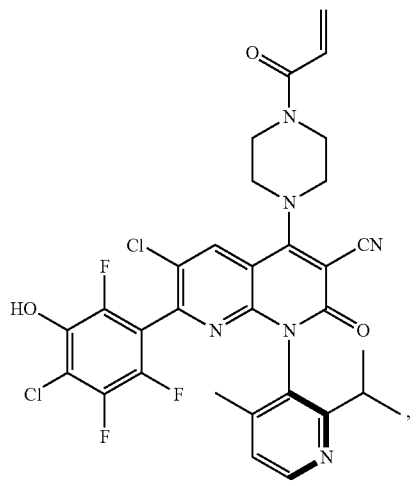
190
-continued
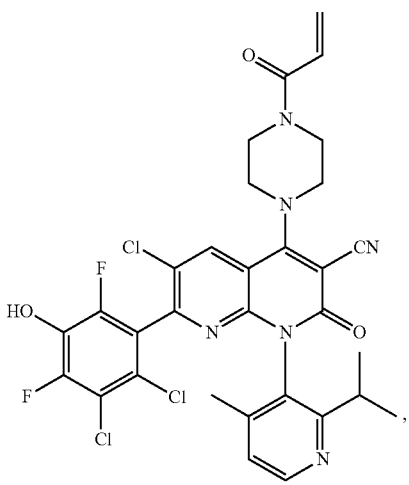
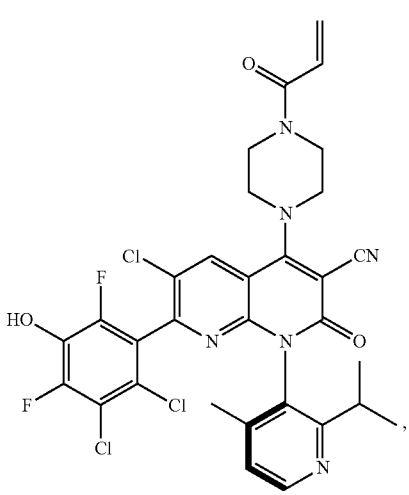
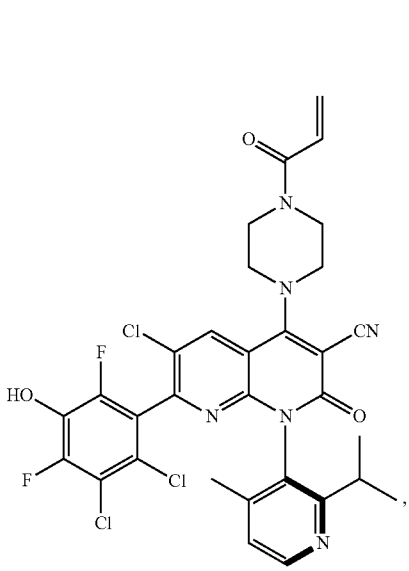

191
-continued
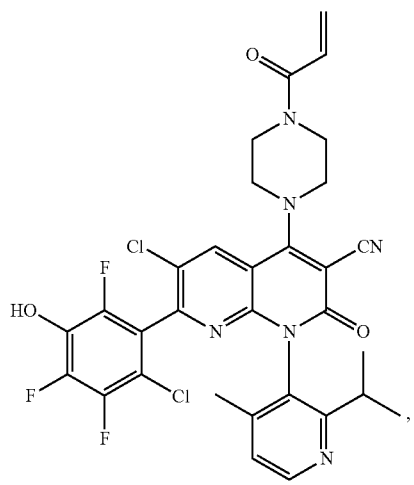
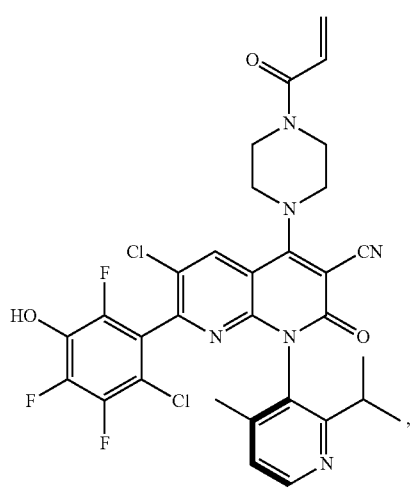
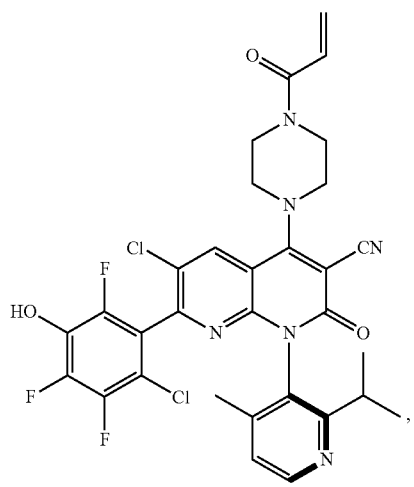
192
-continued
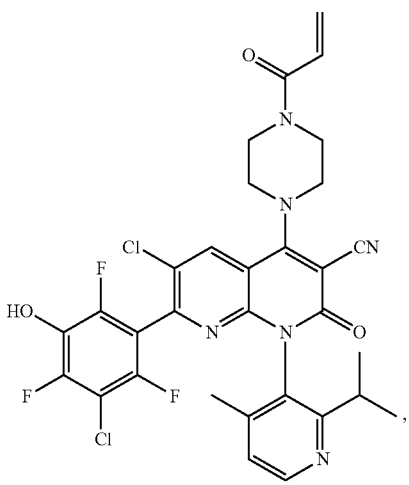
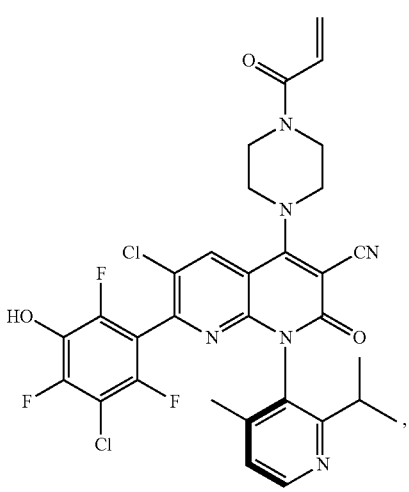
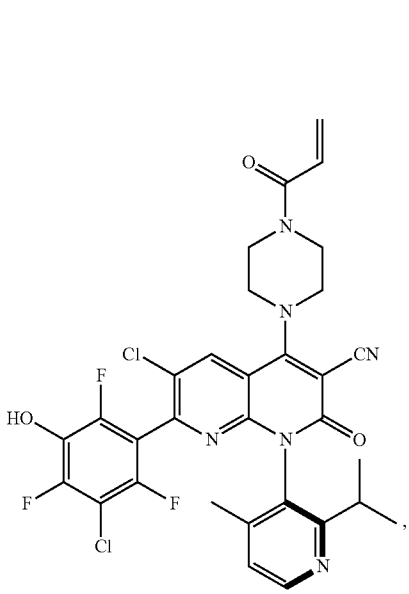

193
-continued
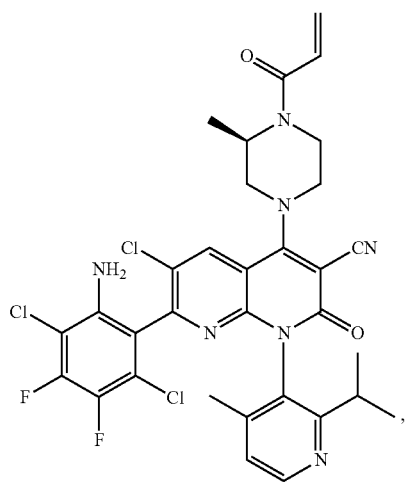
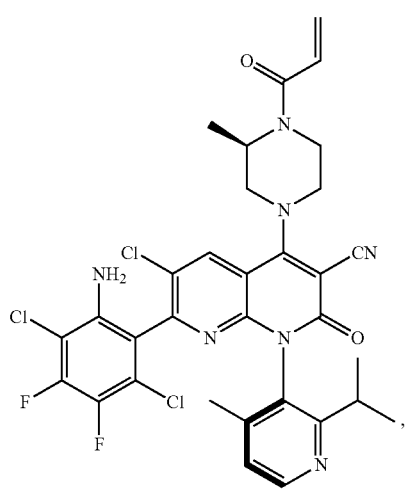
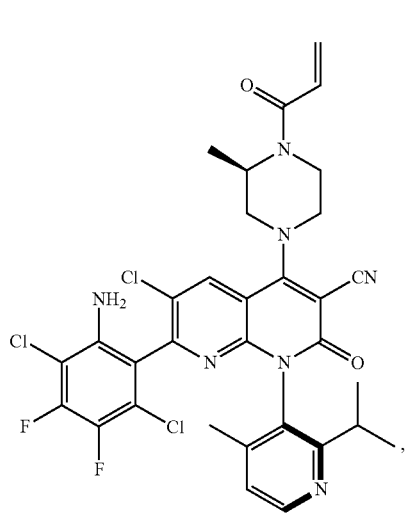
194
-continued
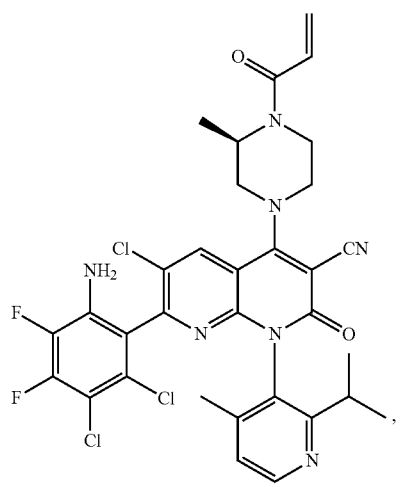
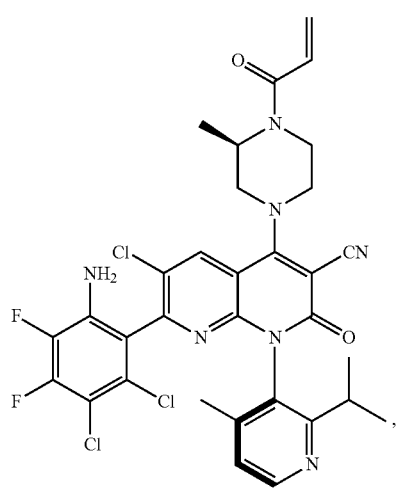
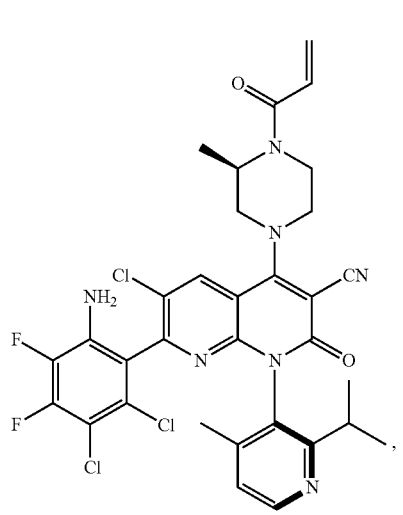

195
-continued
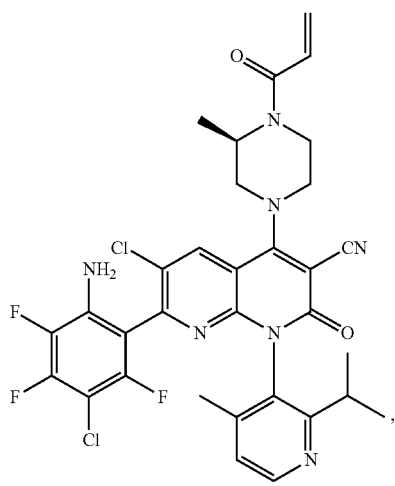
196
-continued
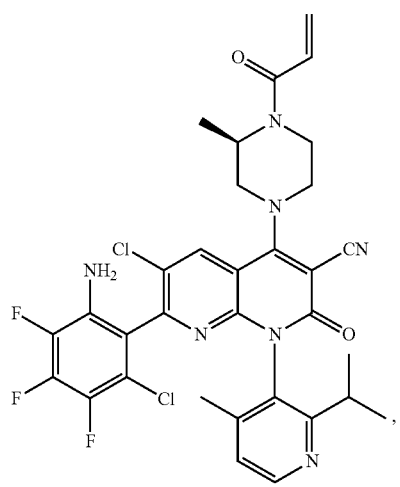
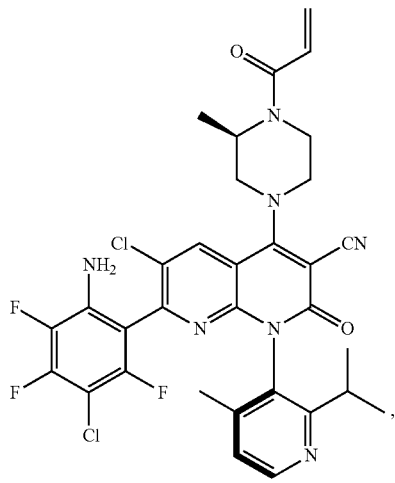
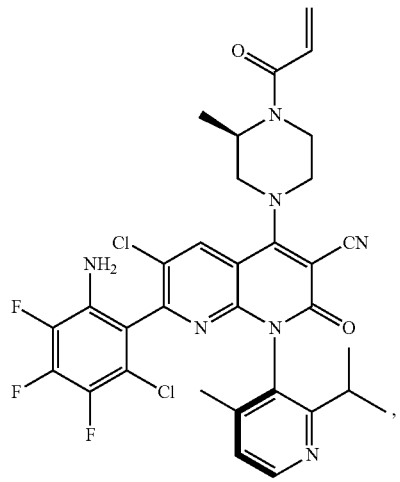
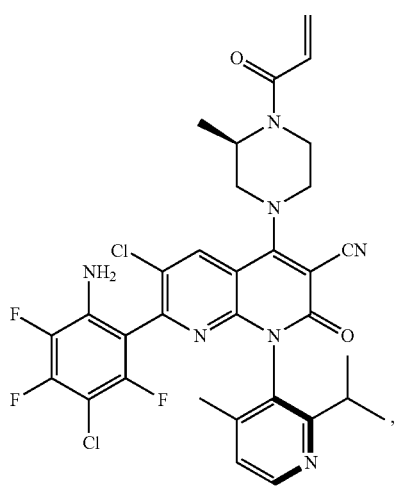
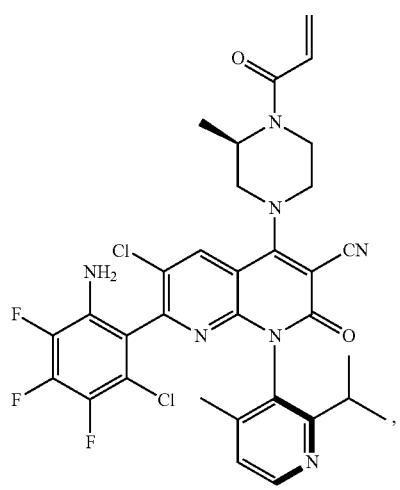

-continued
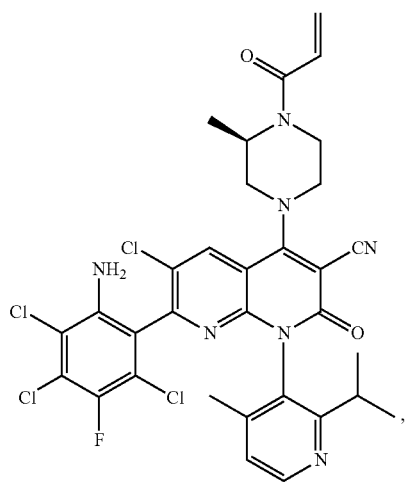
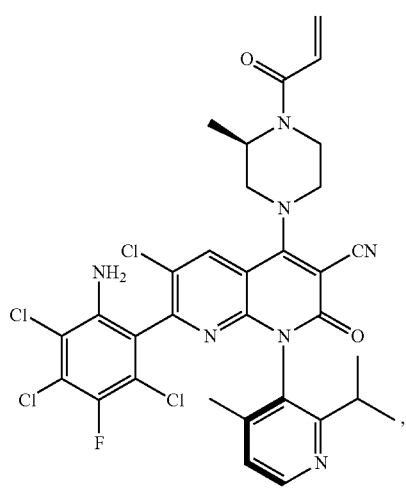
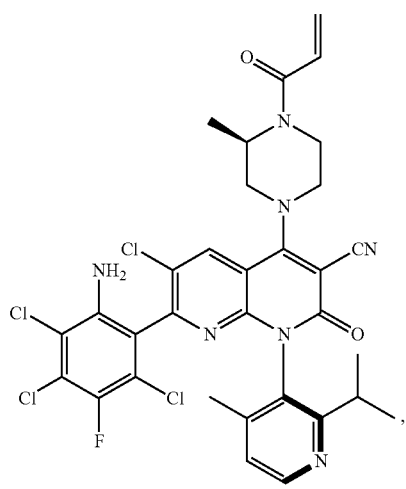
-continued
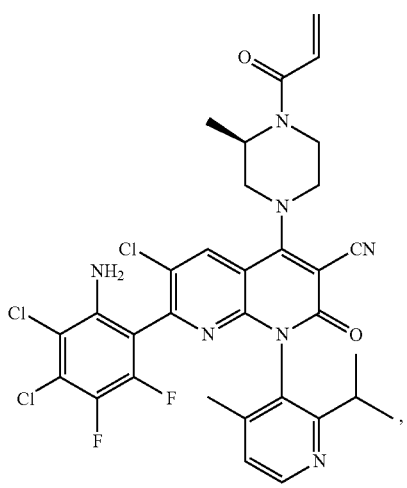
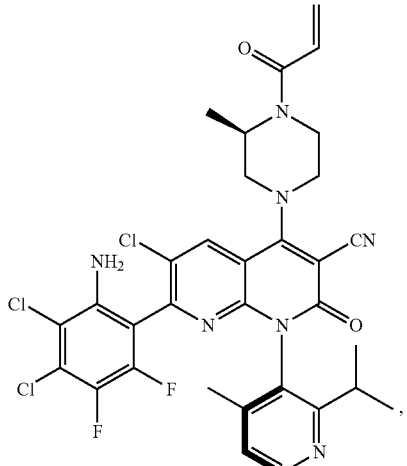
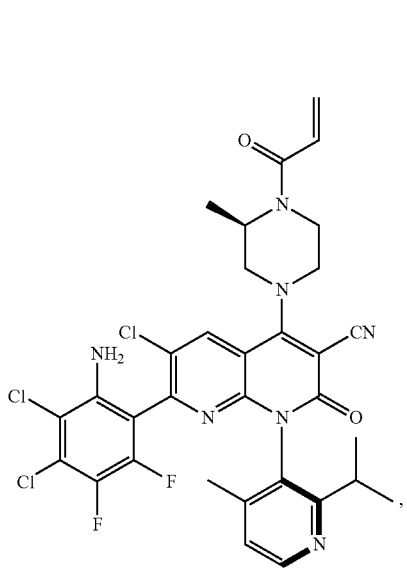

199
-continued
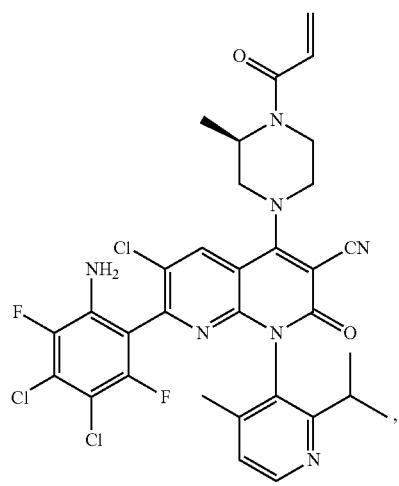
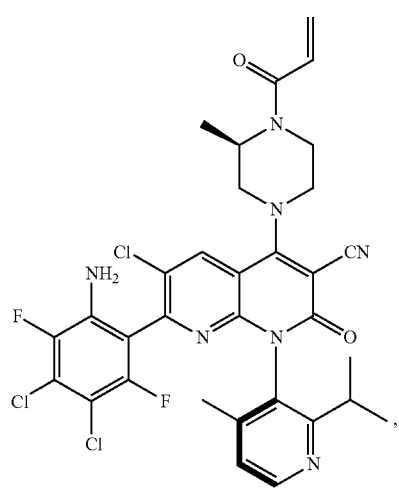
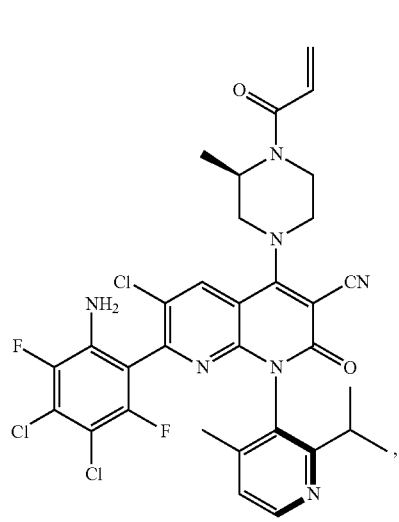
200
-continued
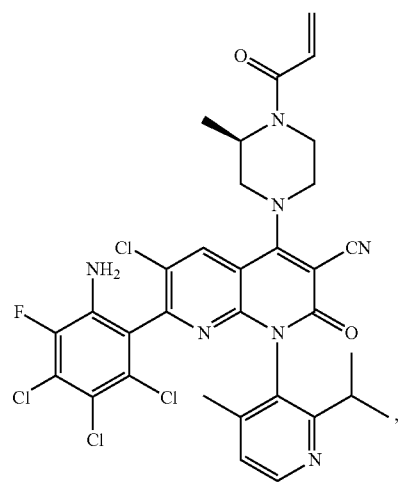
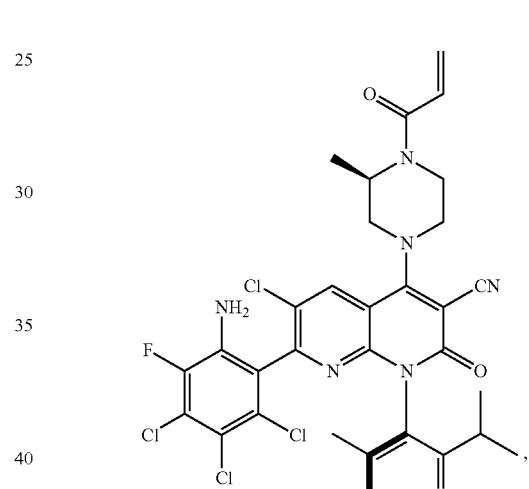
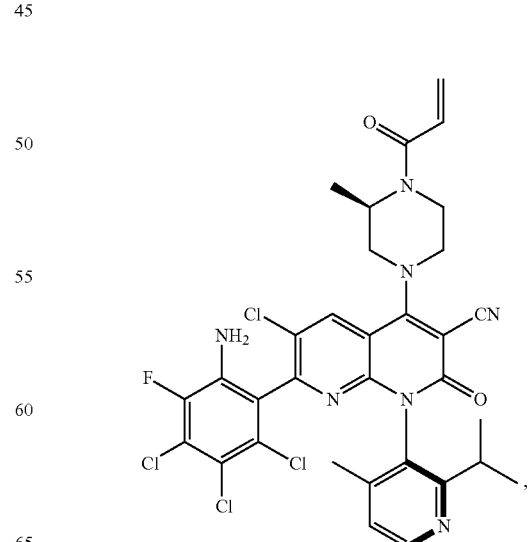

-continued
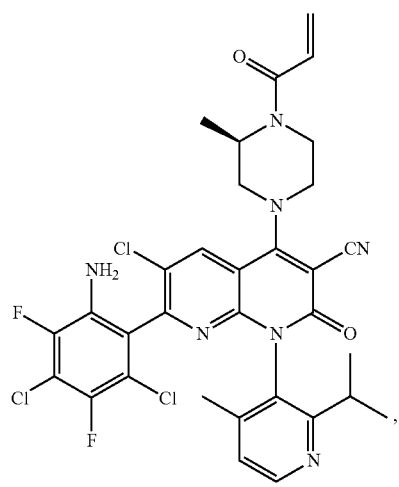
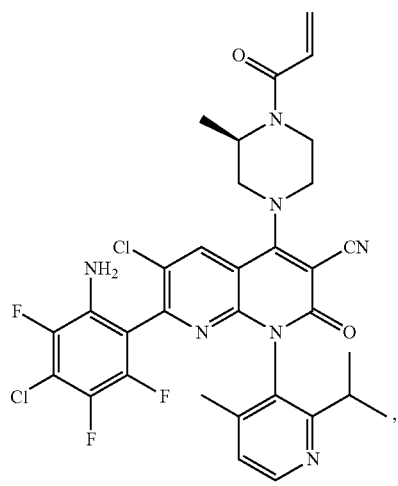
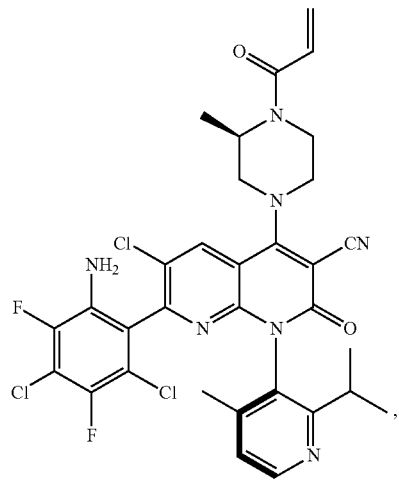
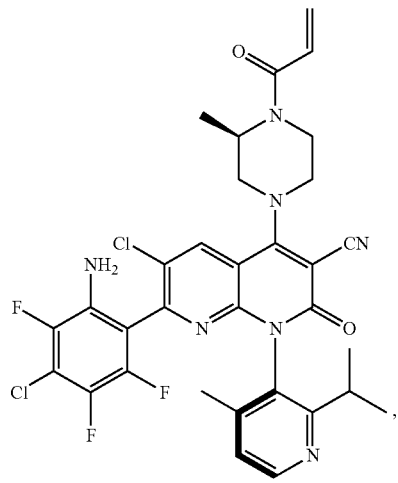
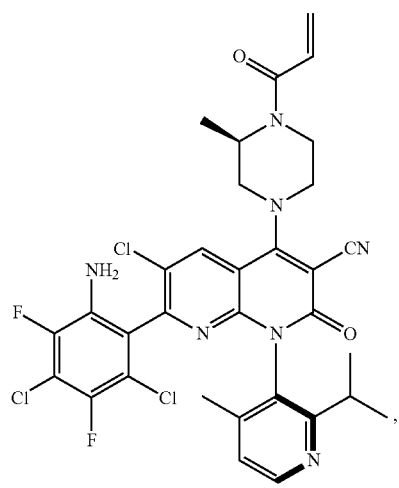
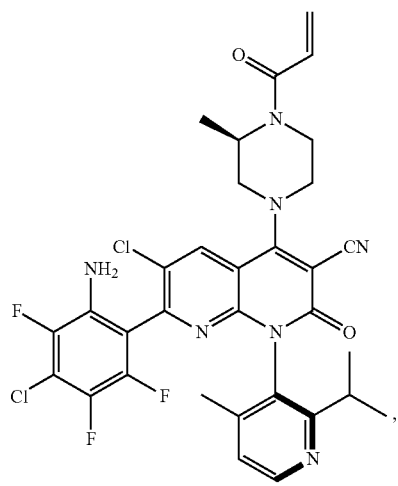

203
-continued
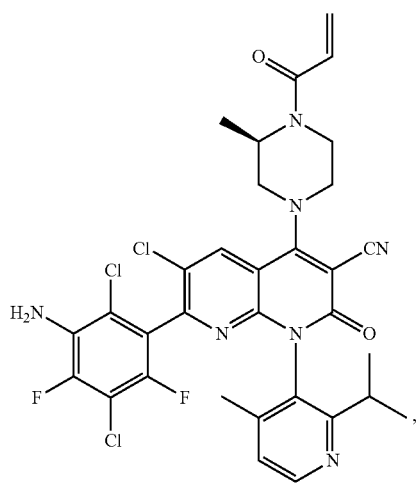
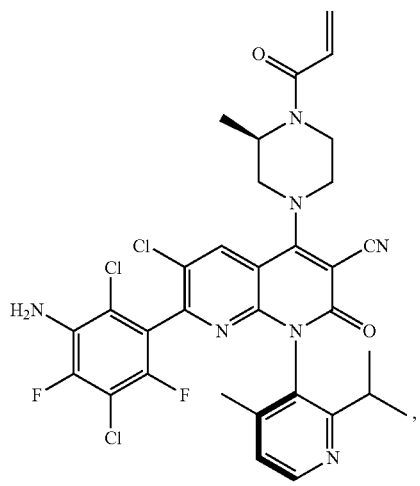
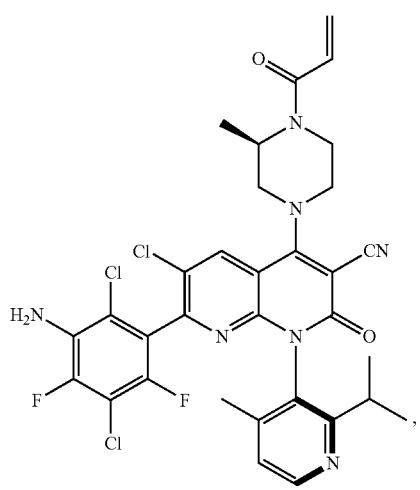
204
-continued
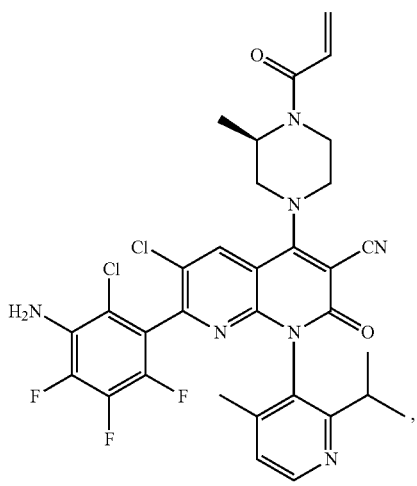
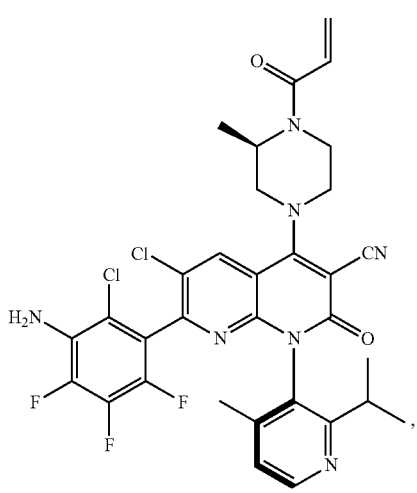
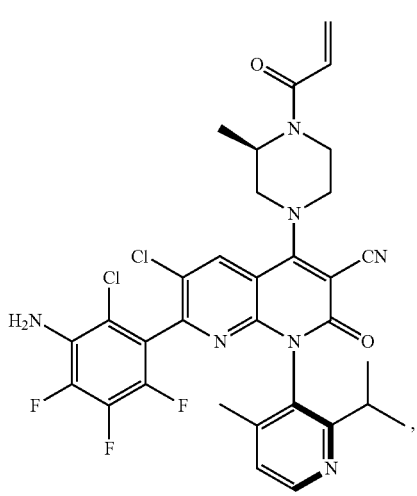

205
-continued
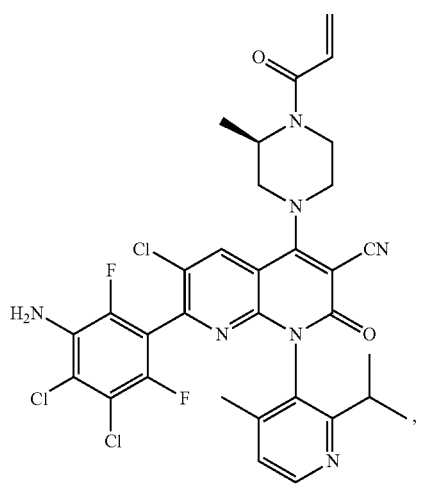
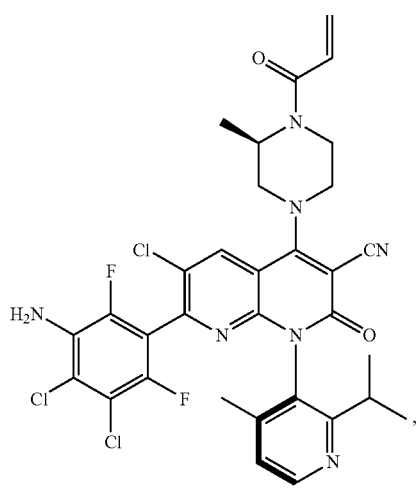
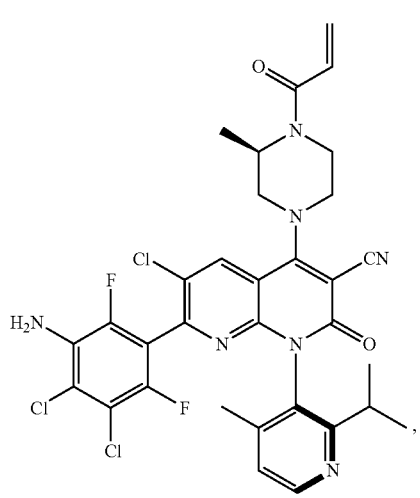
206
-continued
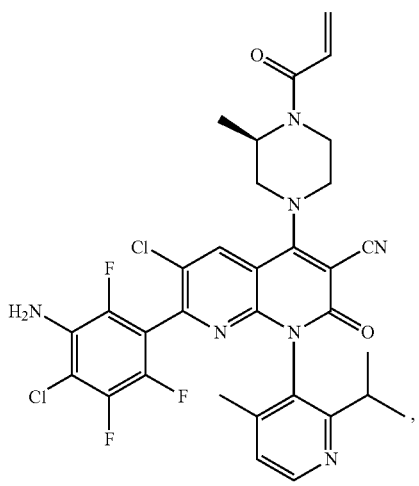
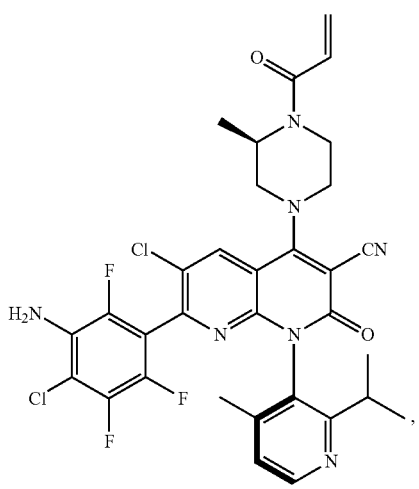
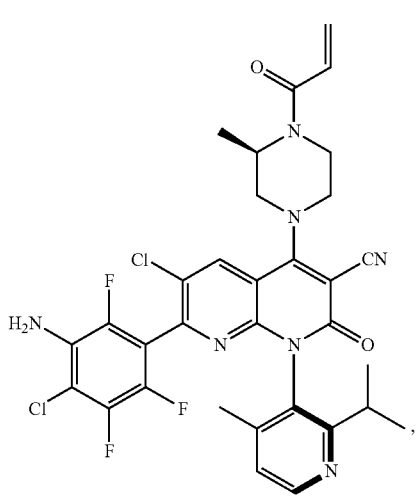

207
-continued
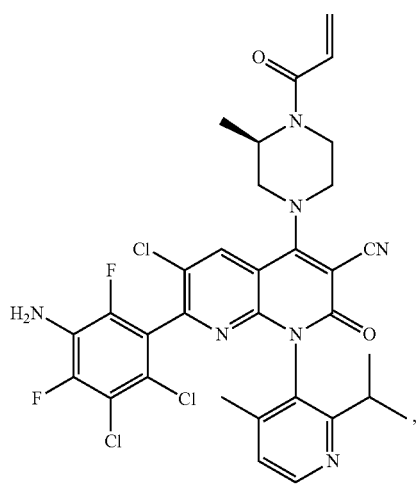
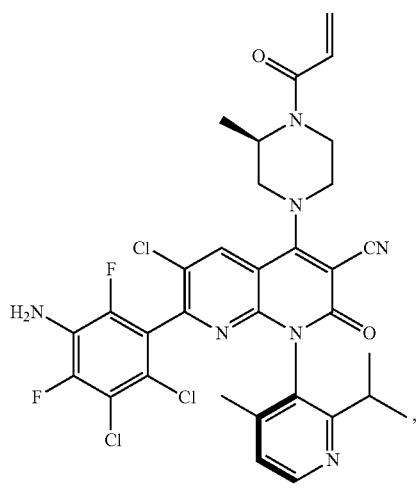
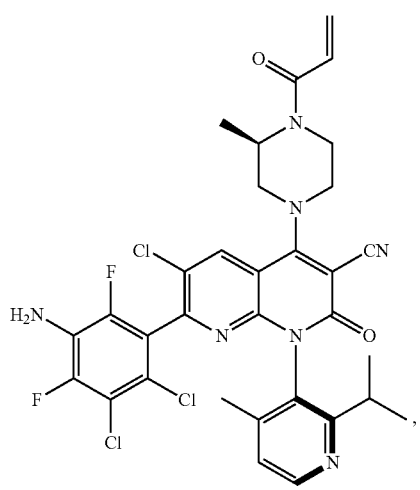
208
-continued
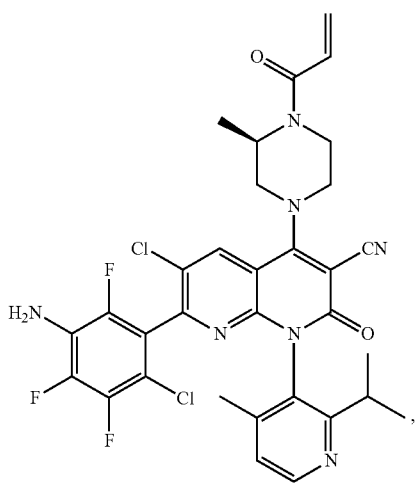
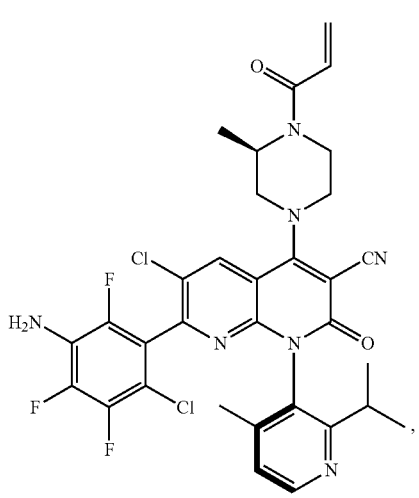
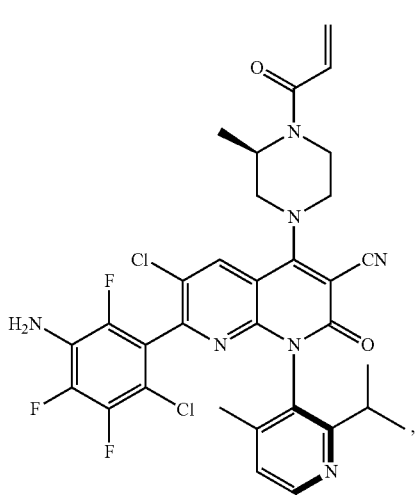

209
-continued
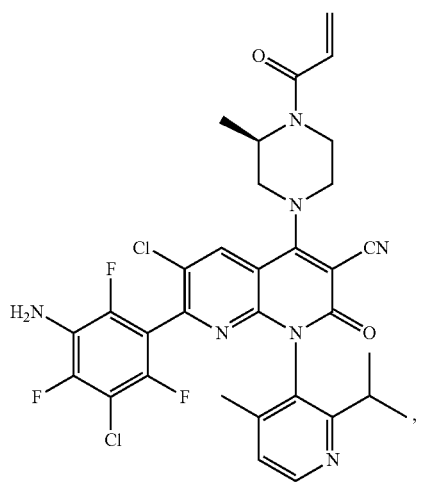
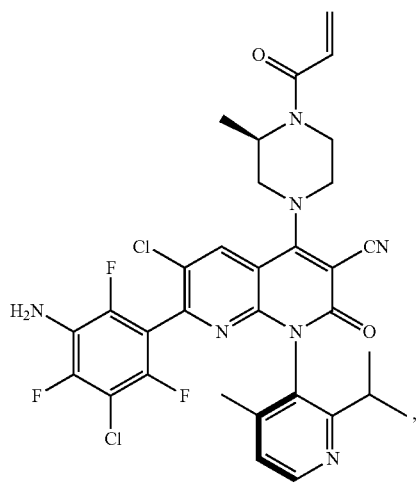
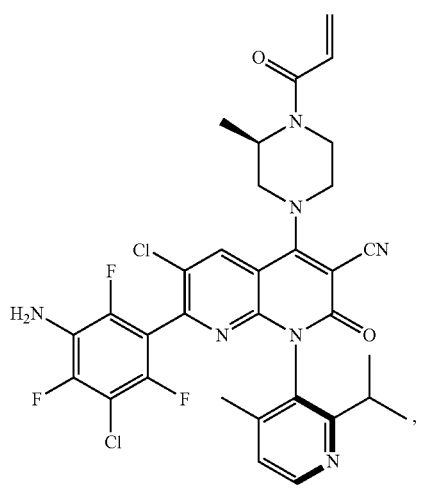
210
-continued
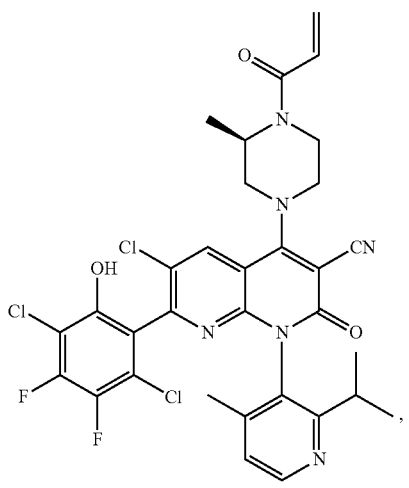
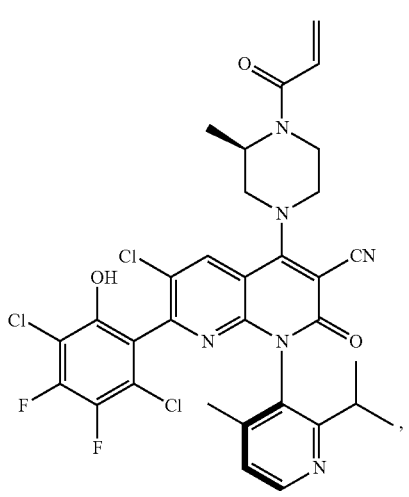
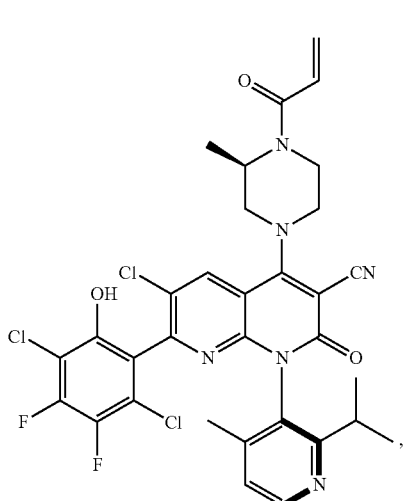

211
-continued
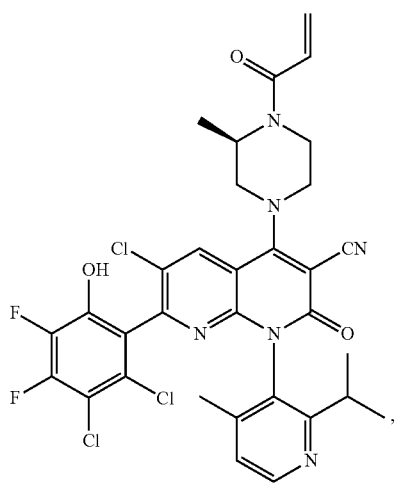
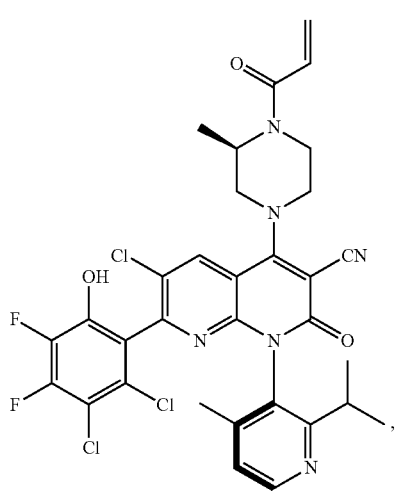
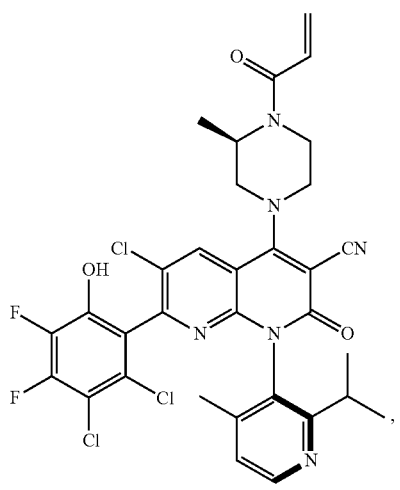
212
-continued
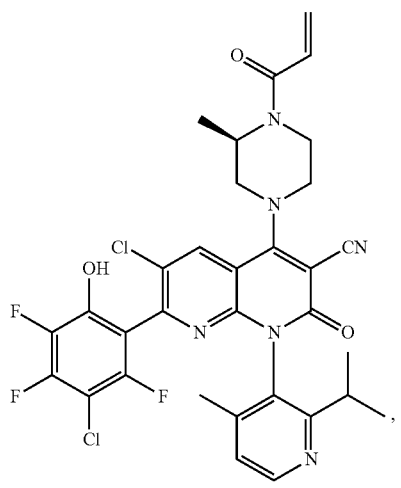
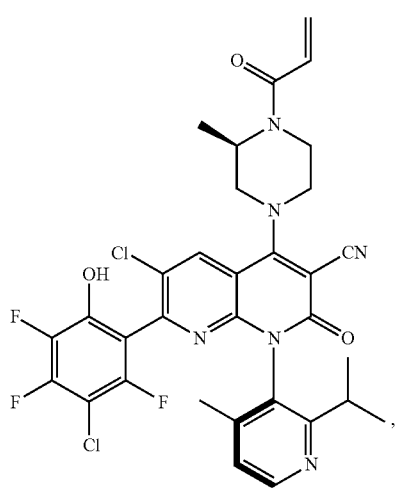
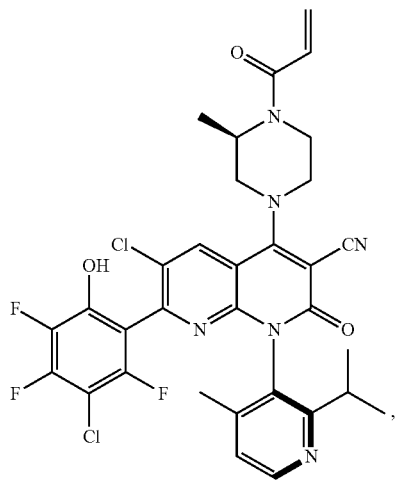

213
-continued
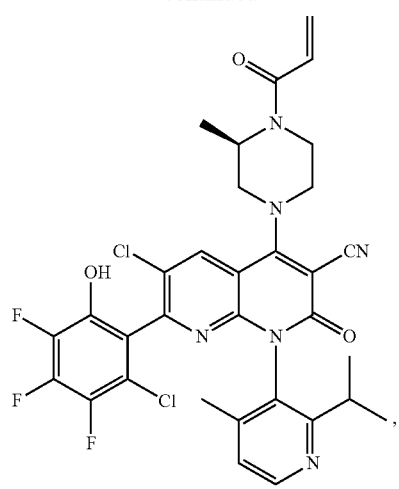
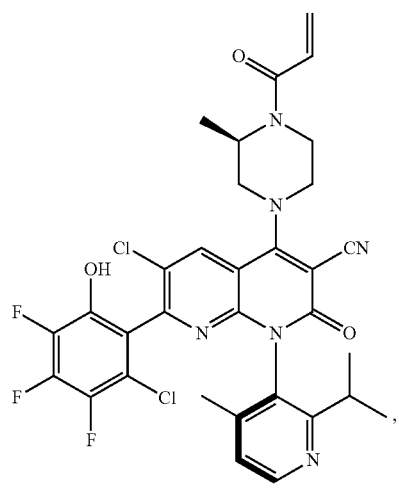
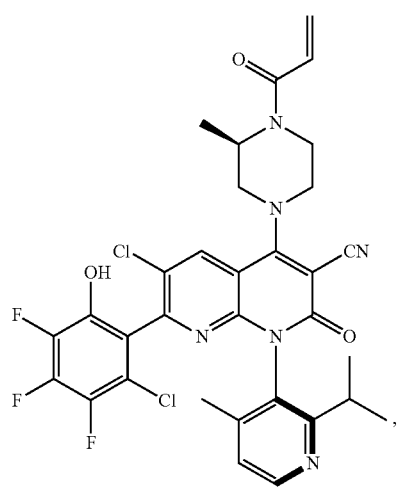
214
-continued
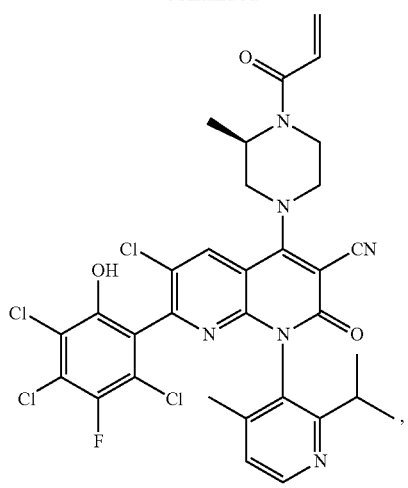
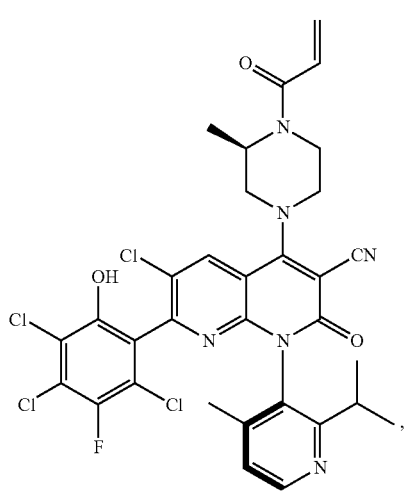
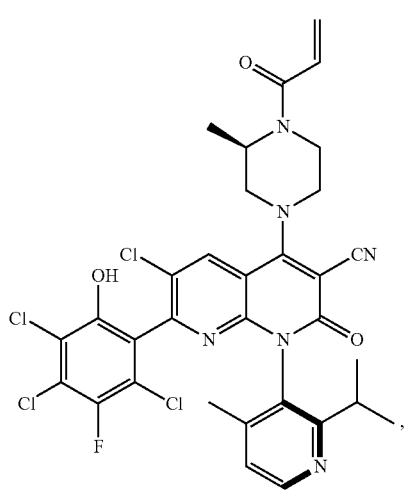

215
-continued
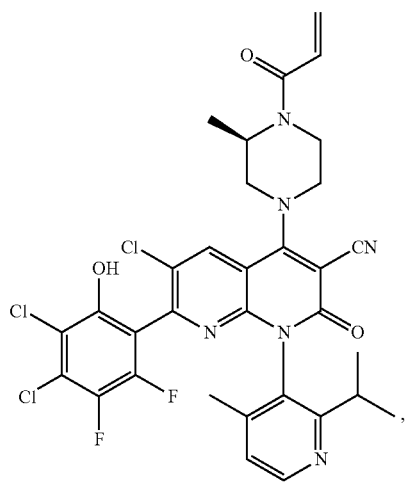
216
-continued
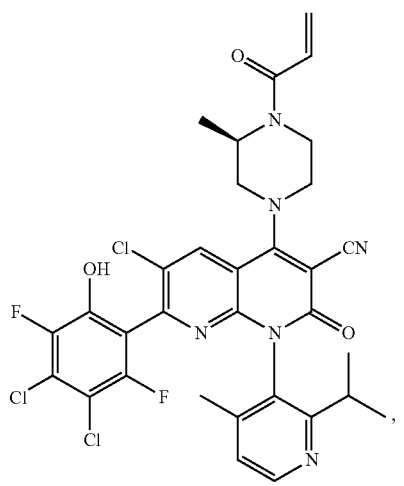
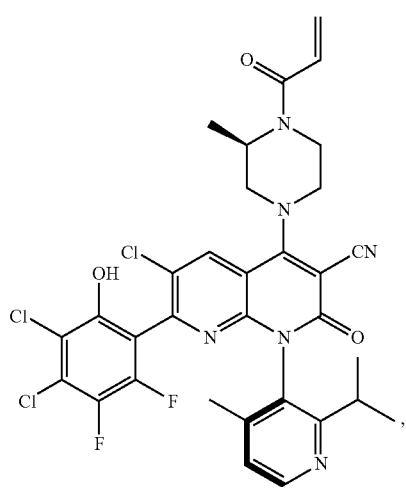
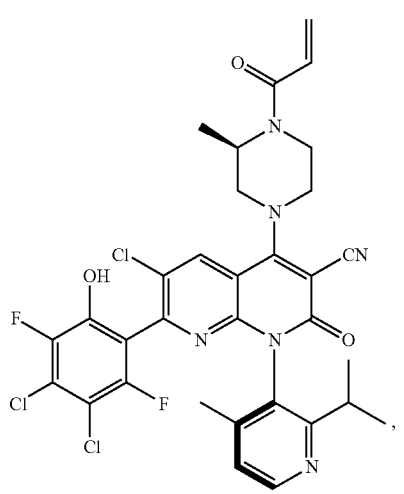
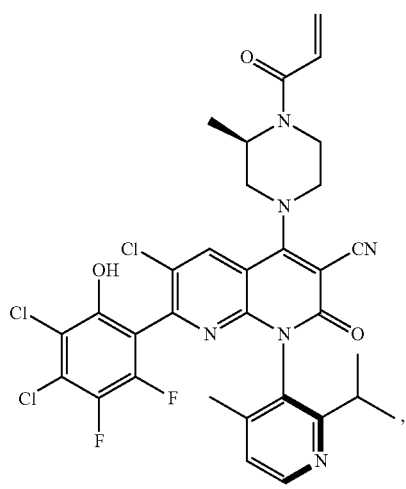
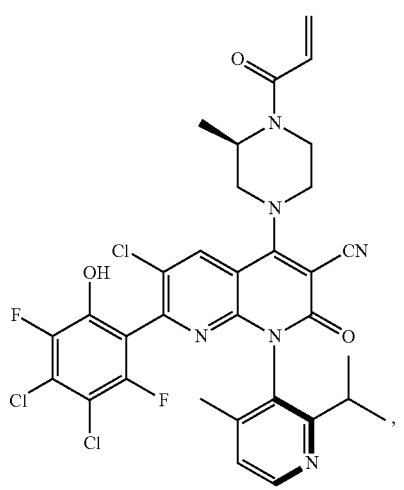

217
-continued
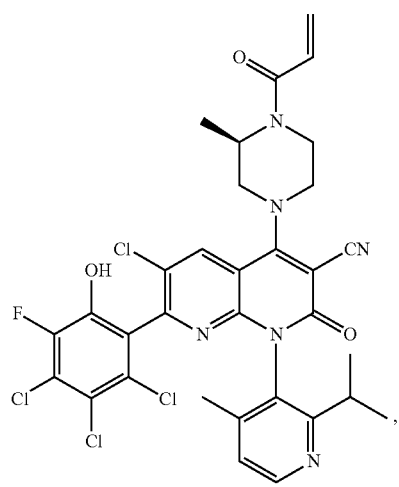
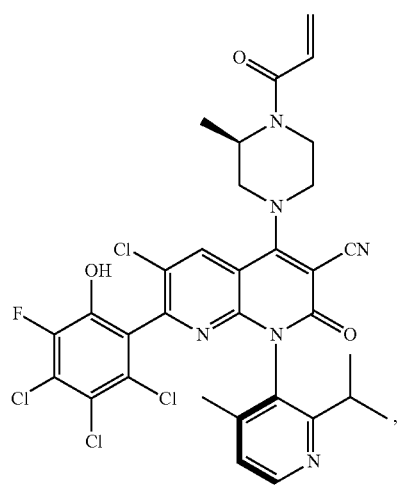
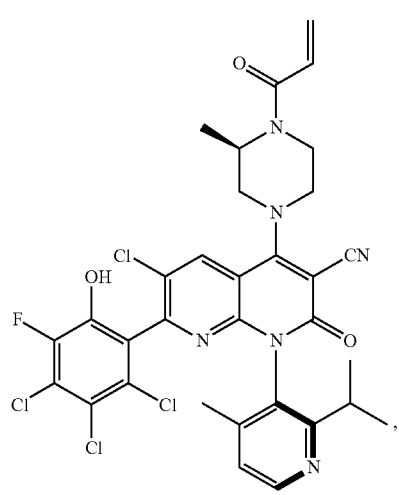
218
-continued
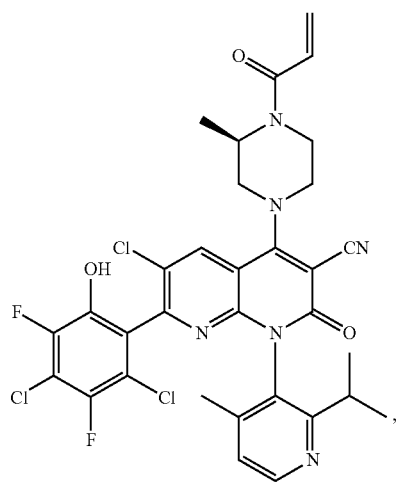
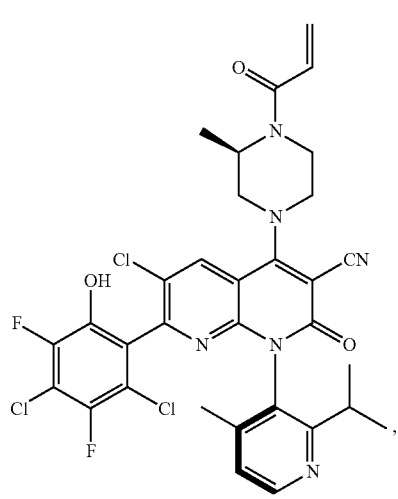
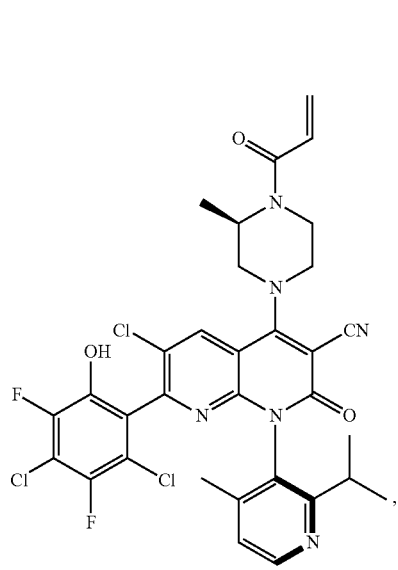

219
-continued
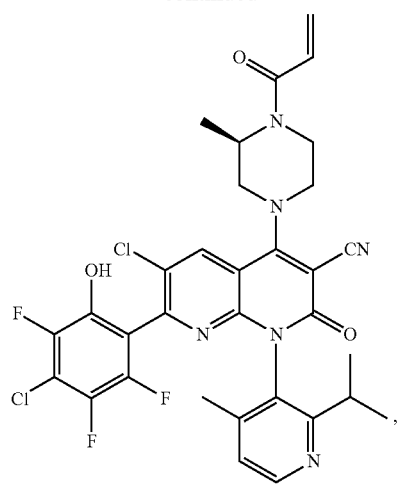
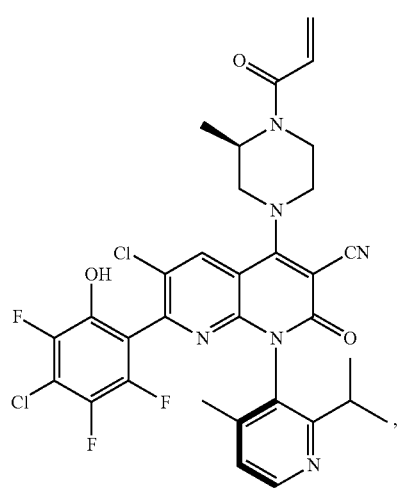
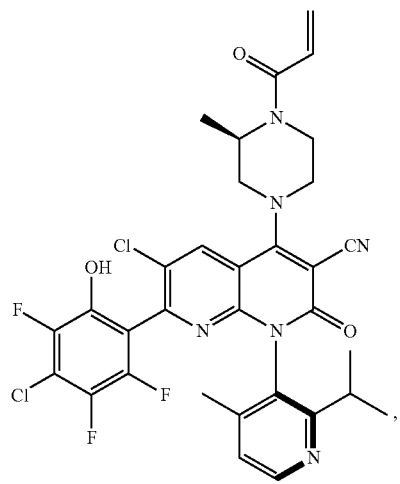
220
-continued
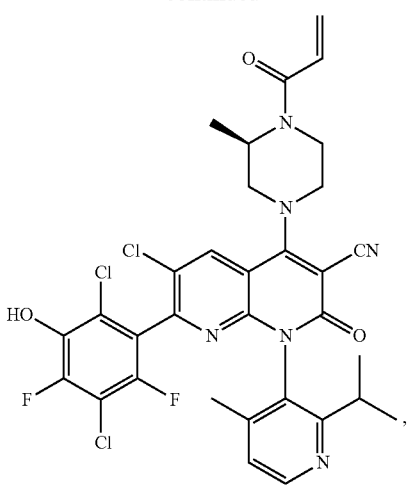
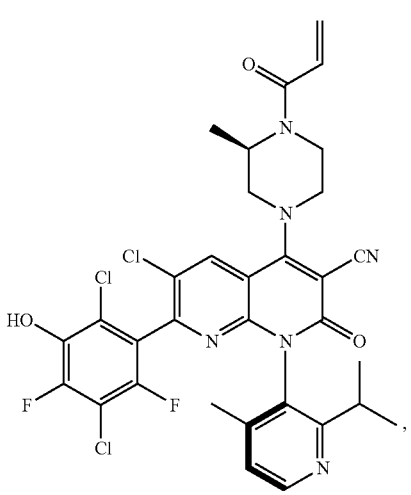
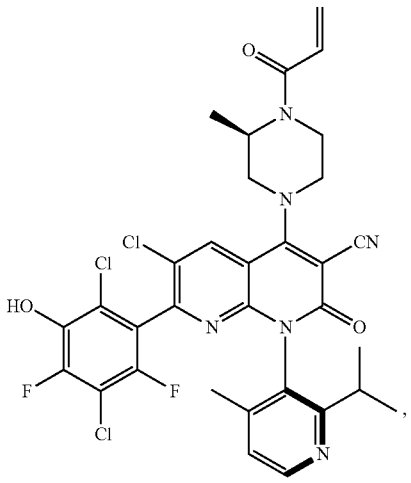

221
-continued
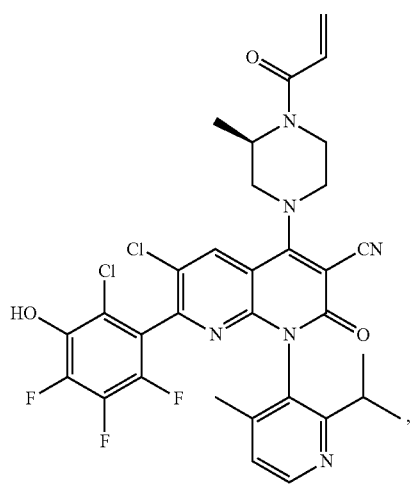
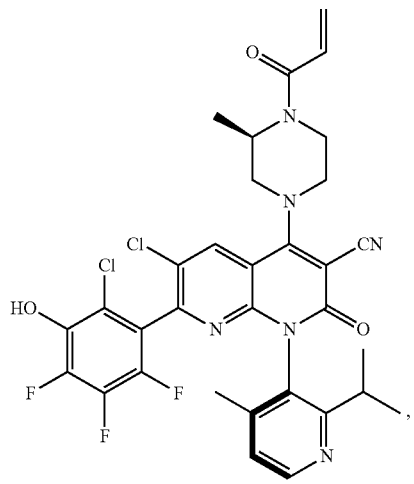
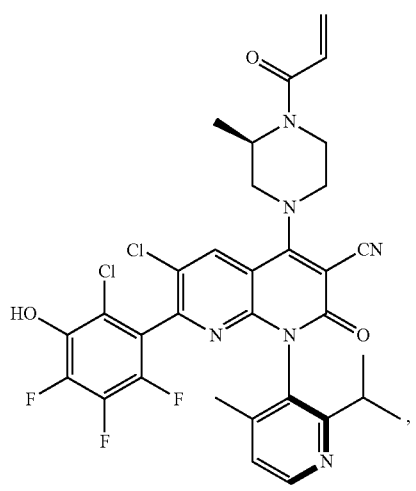
222
-continued
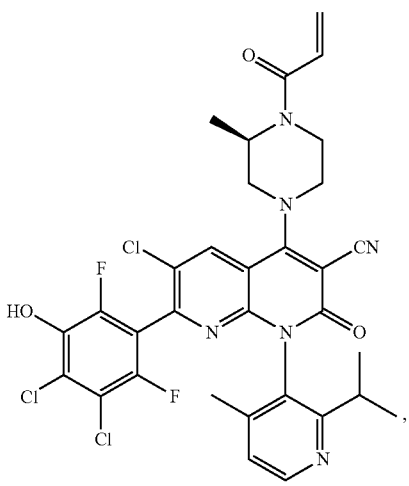
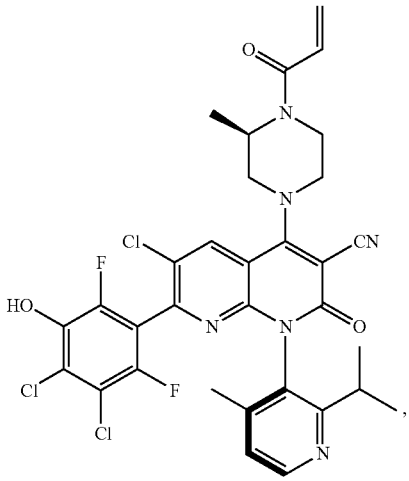
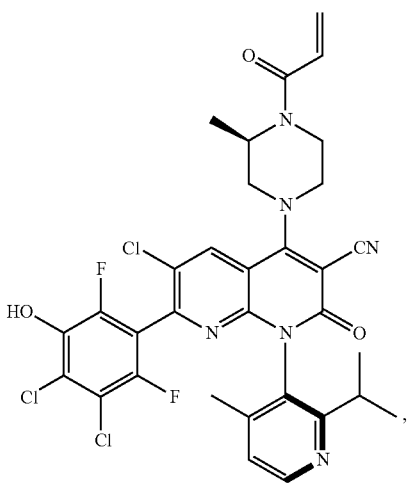

223
-continued
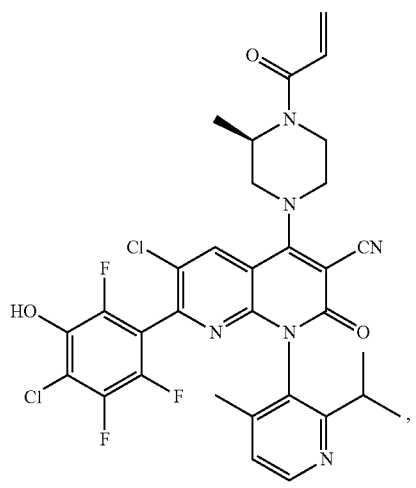
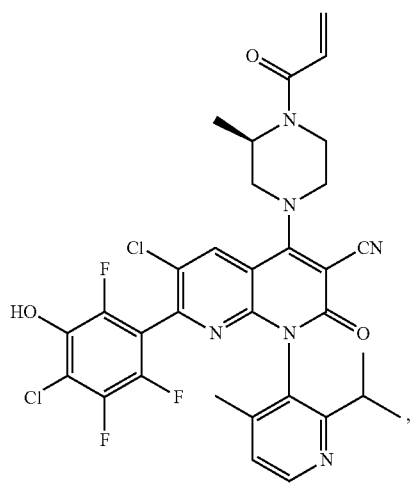
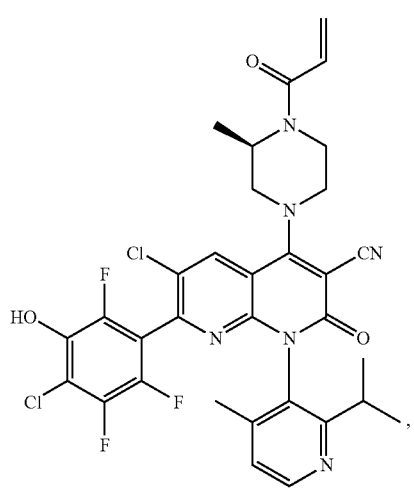
224
-continued
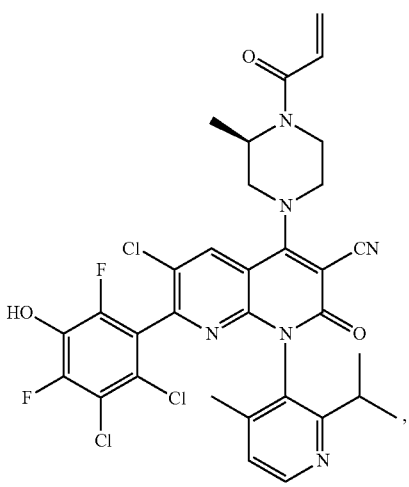
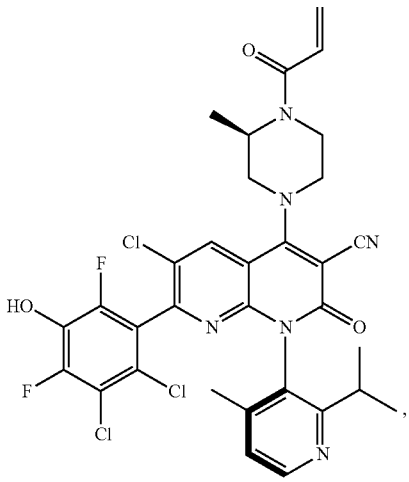
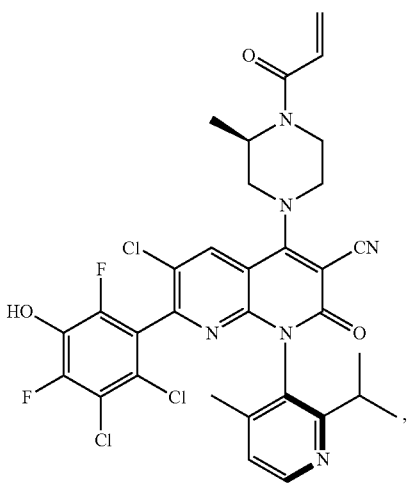

225
-continued
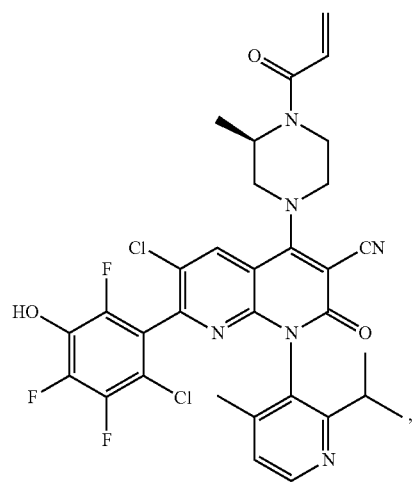
226
-continued
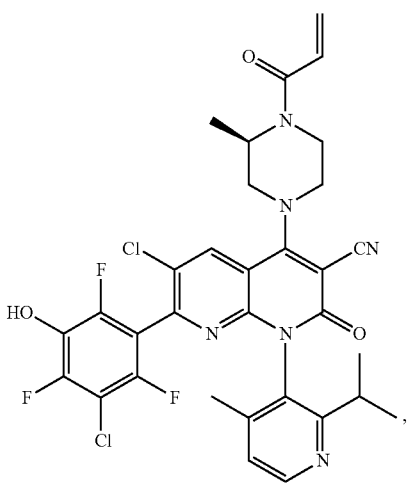
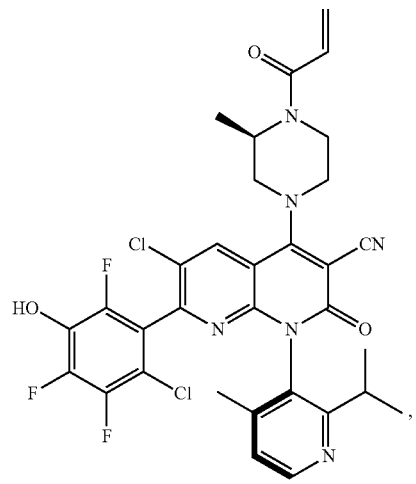
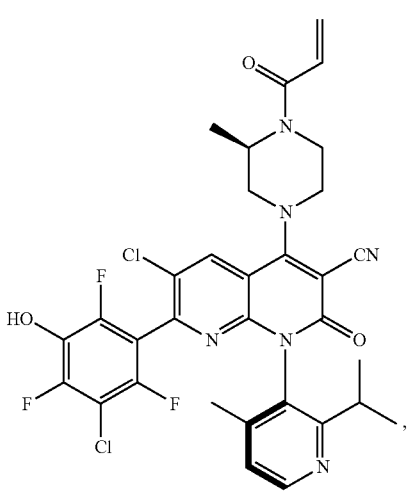
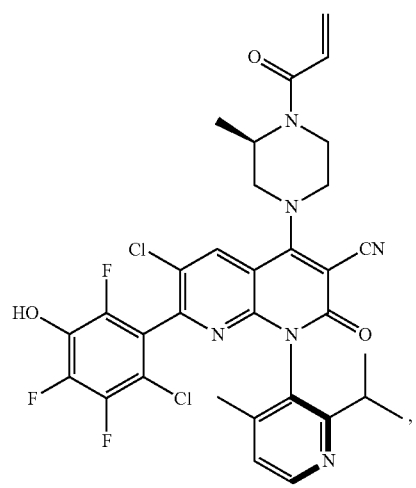
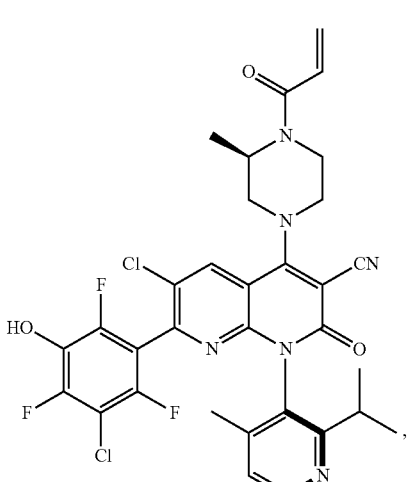

227
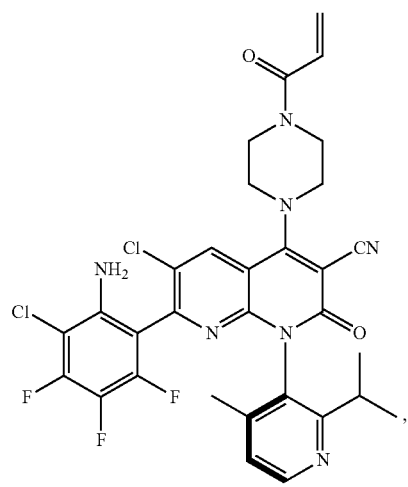
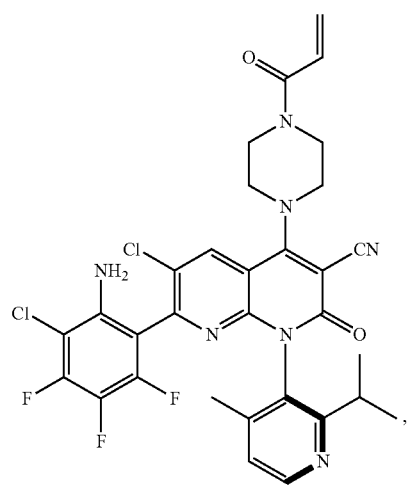
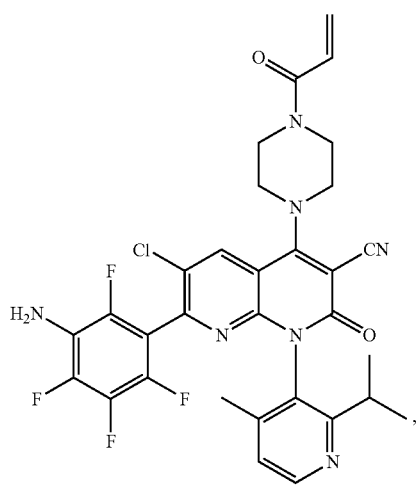
228
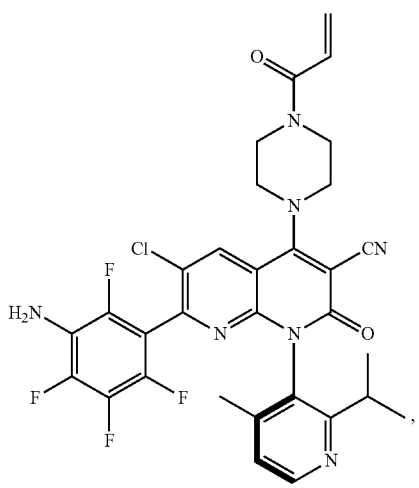
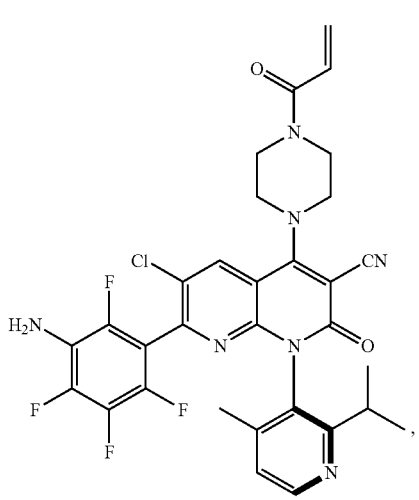
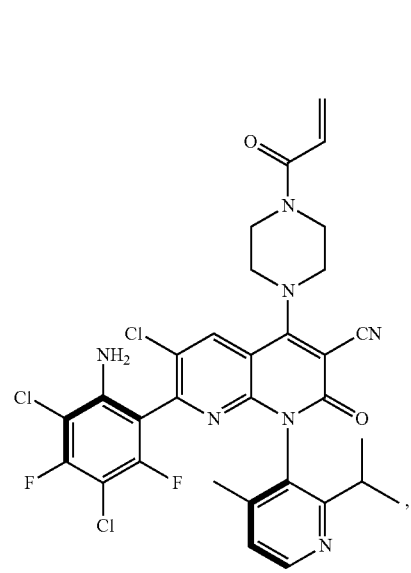

229
-continued
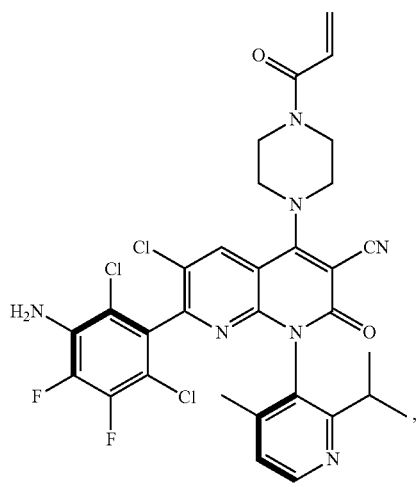
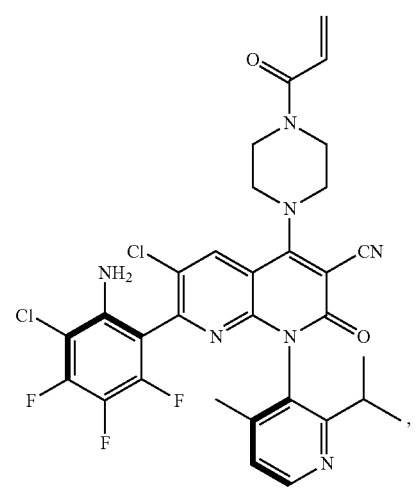
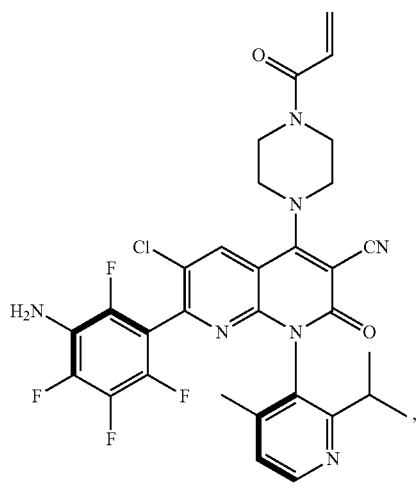
230
-continued
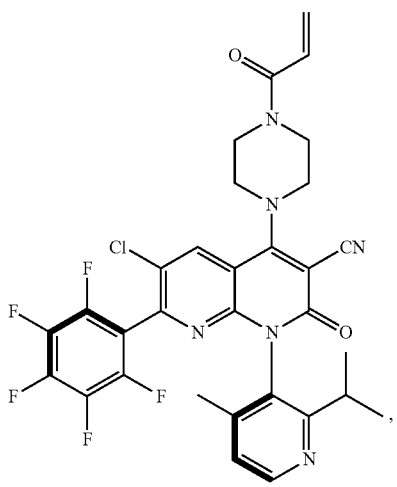
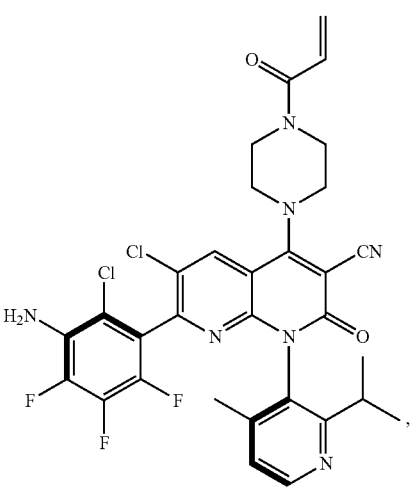
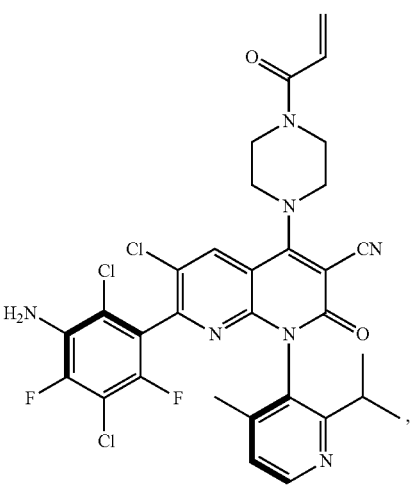

231
-continued
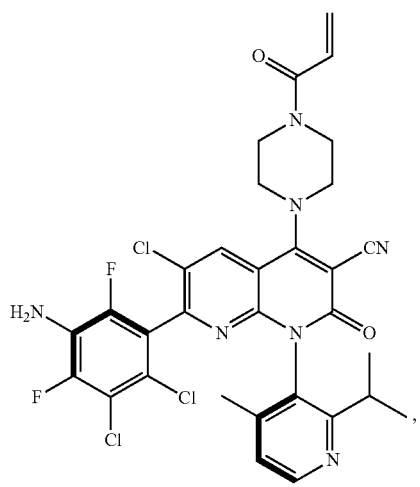
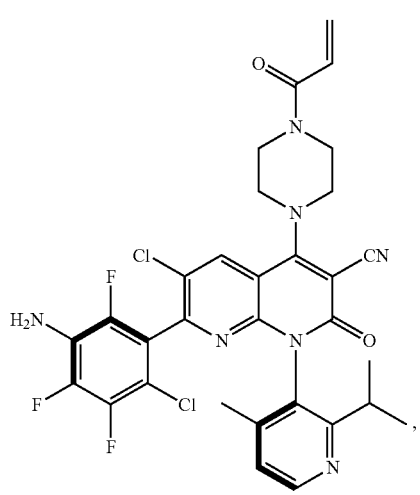
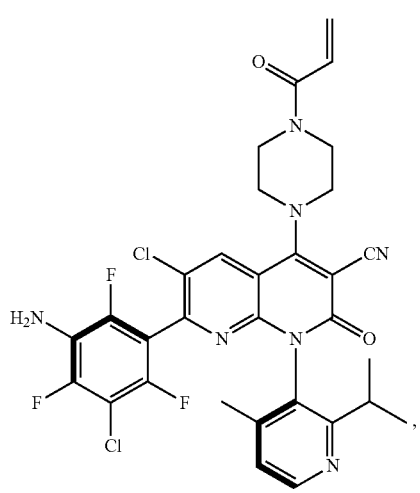
232
-continued
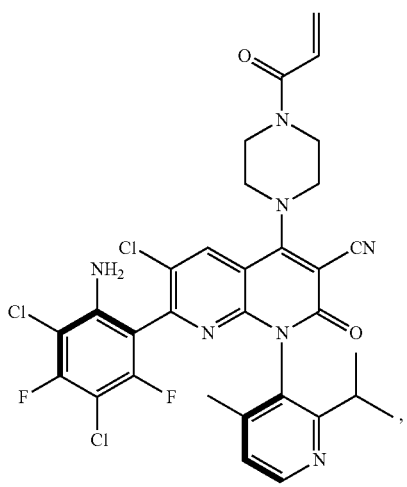
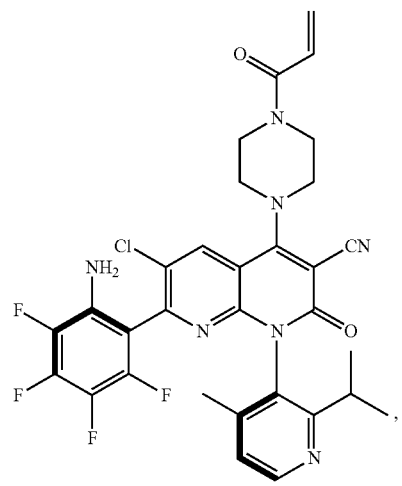
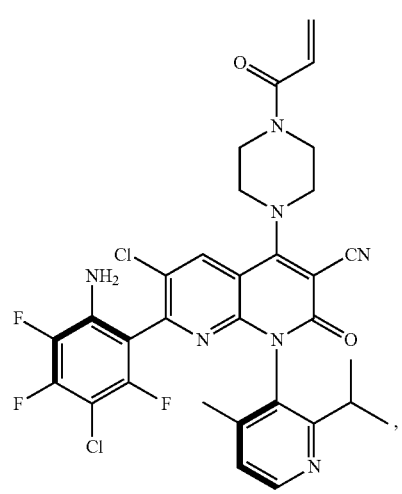

233
-continued
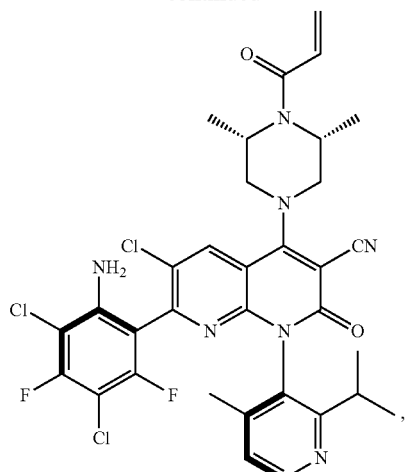
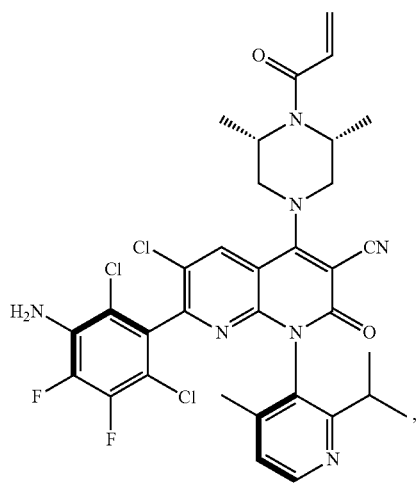
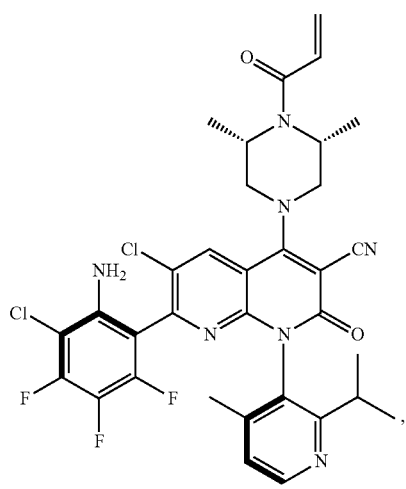
234
-continued
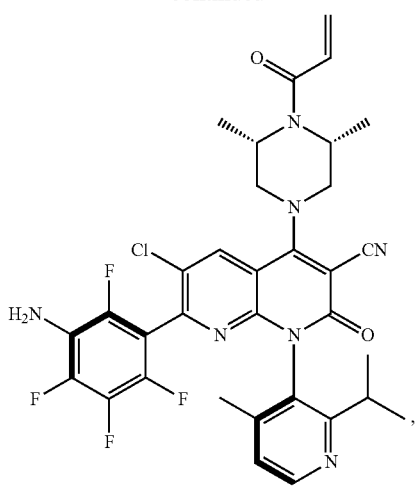
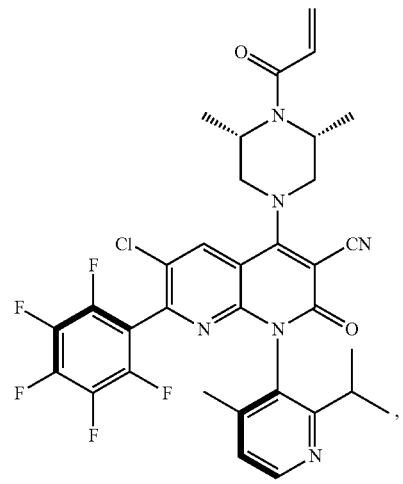
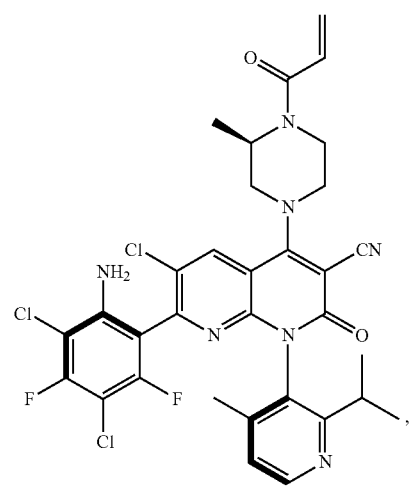

235
-continued
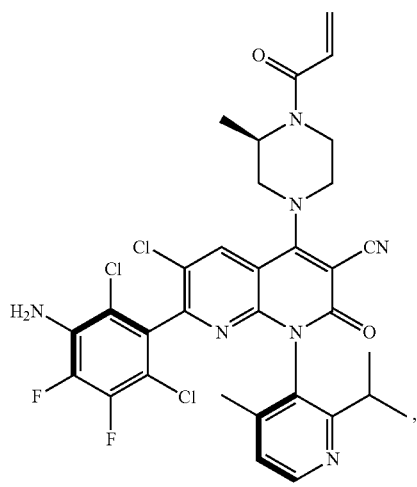
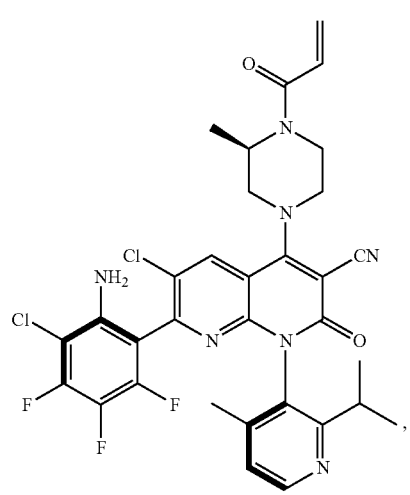
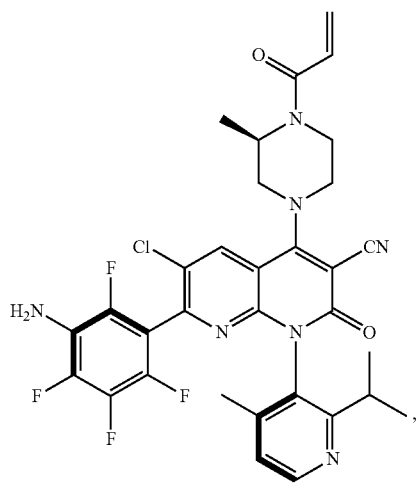
236
-continued
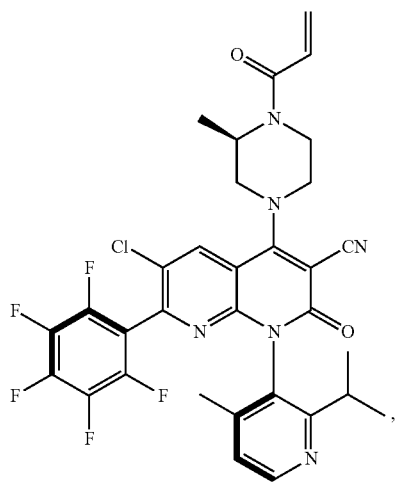
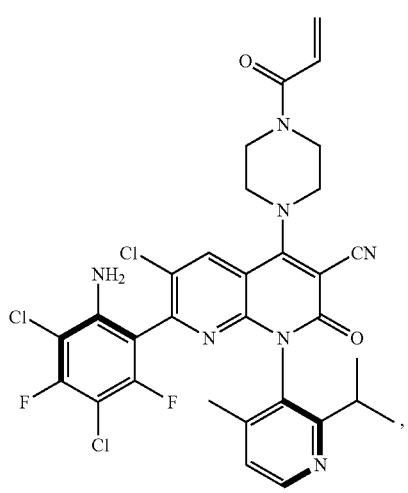
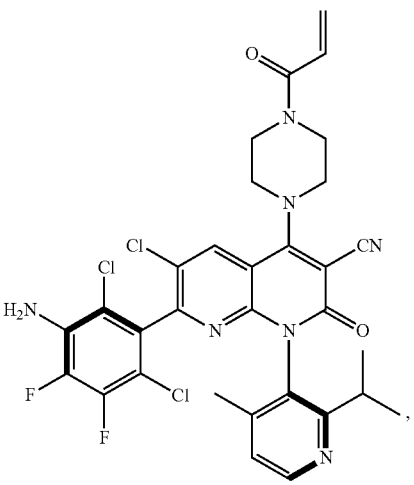

-continued
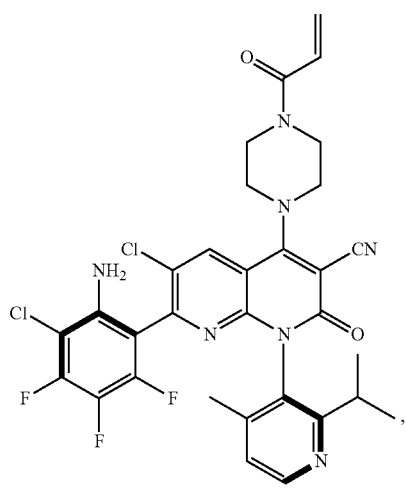
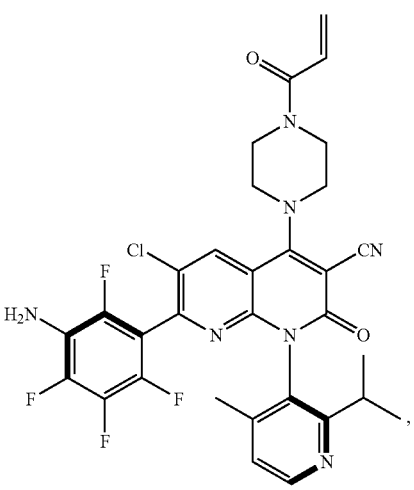
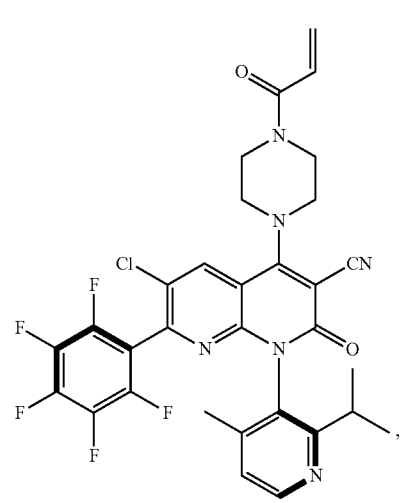
-continued
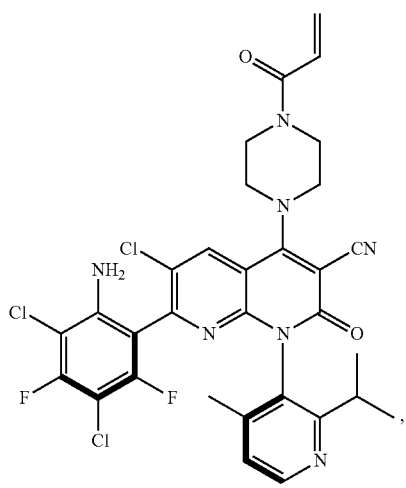
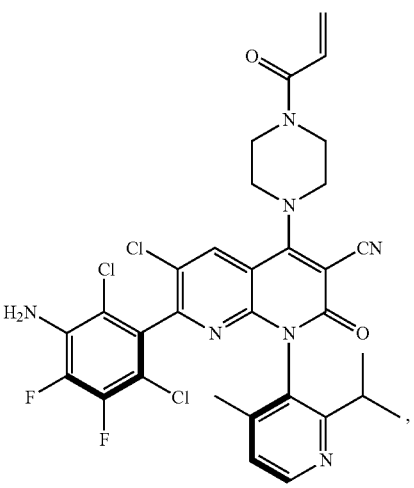
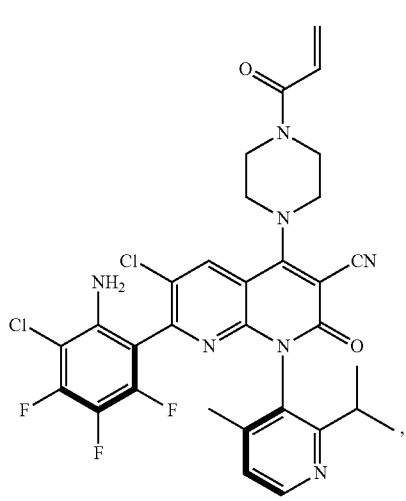

239
-continued
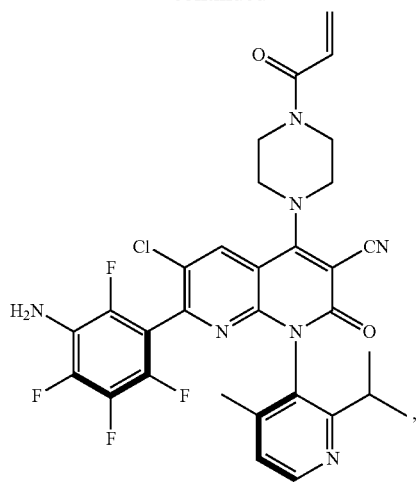
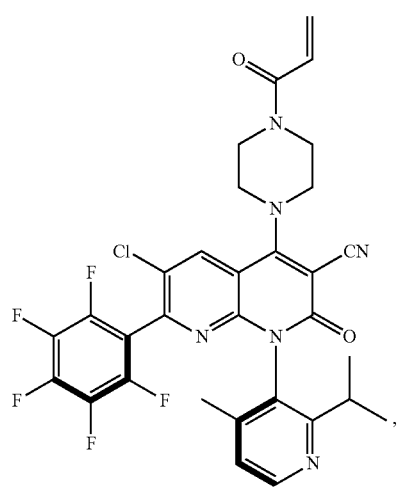
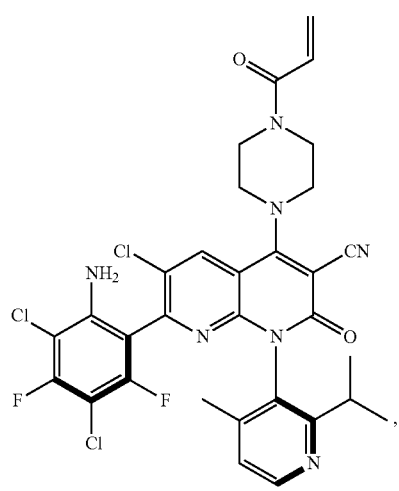
240
-continued
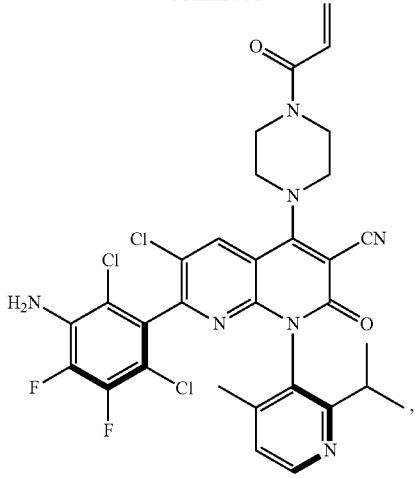
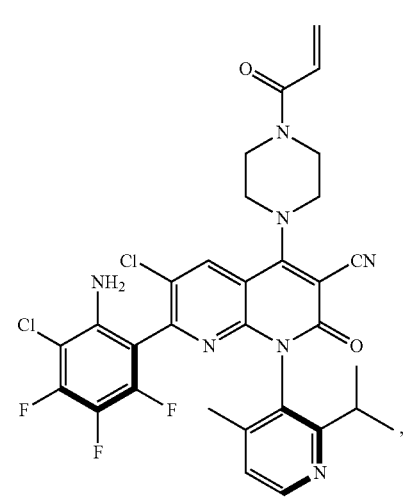
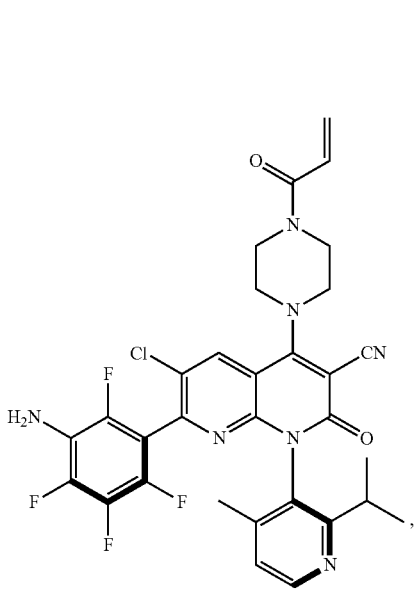

241
-continued
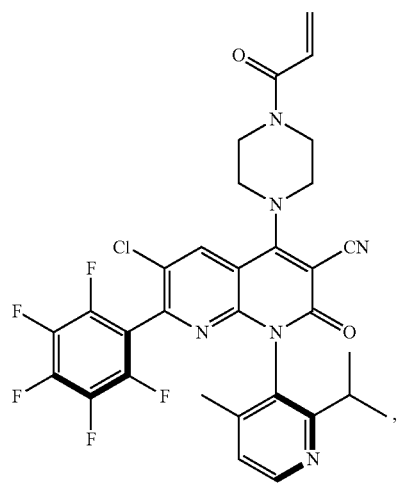
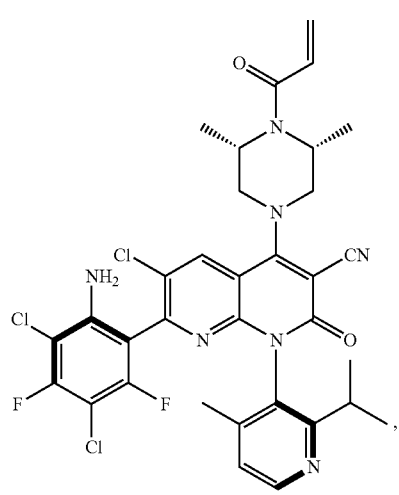
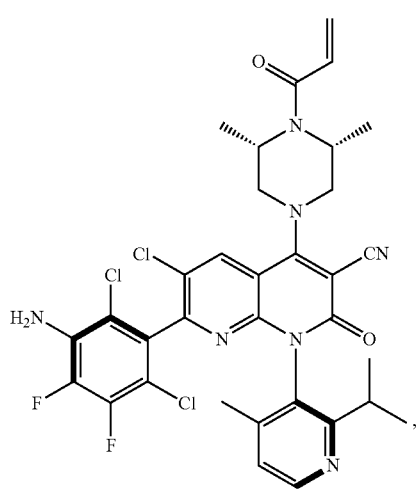
242
-continued
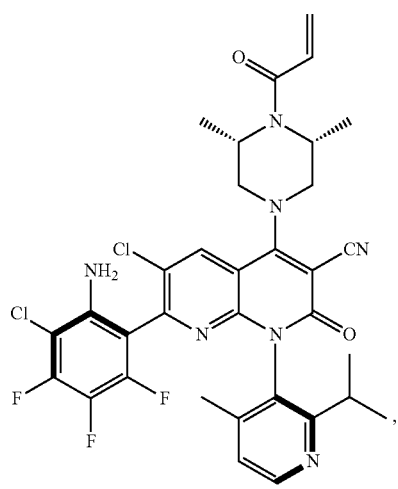
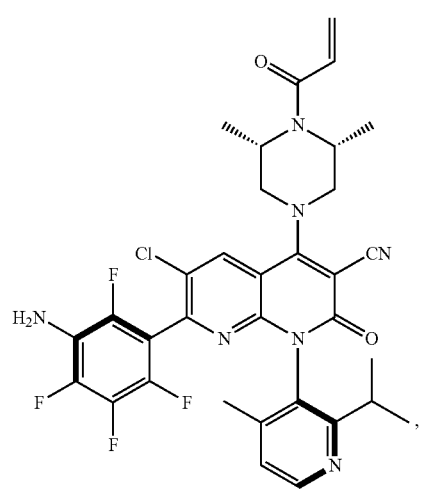
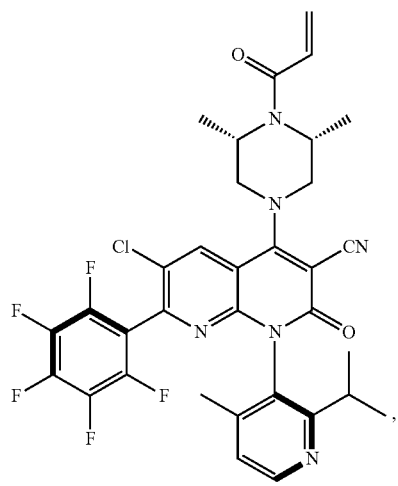

-continued
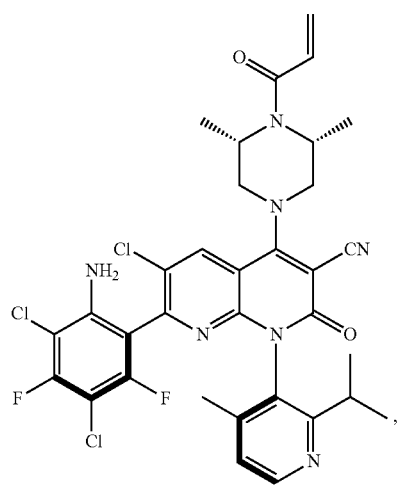
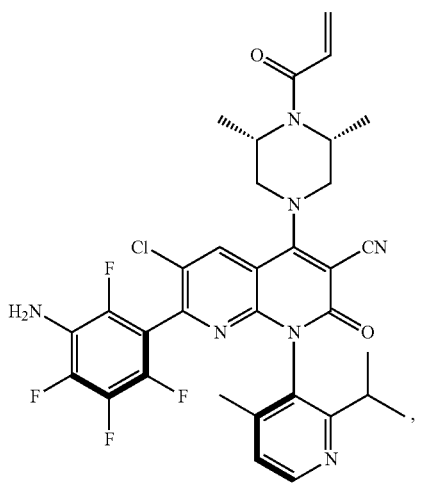
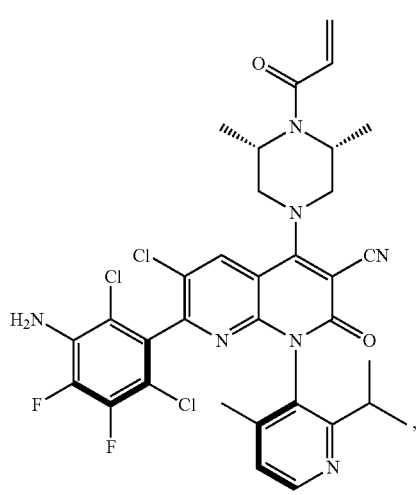
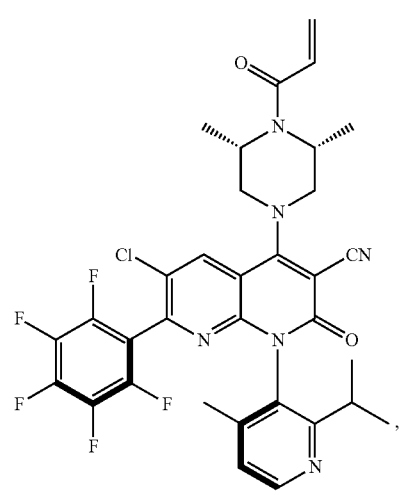
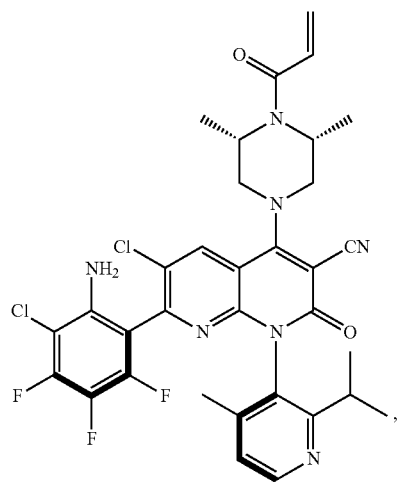
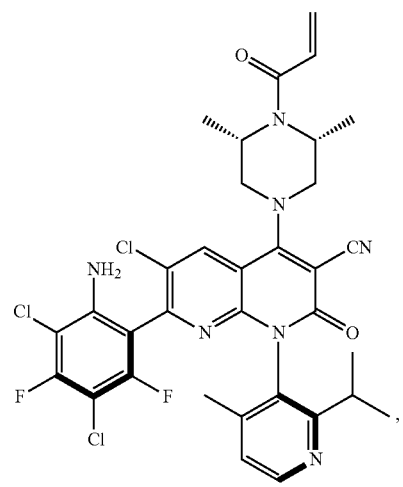

245
-continued
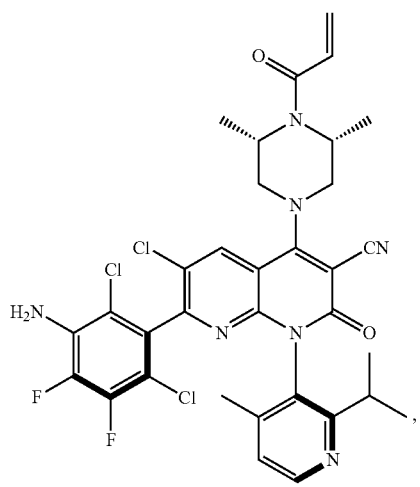
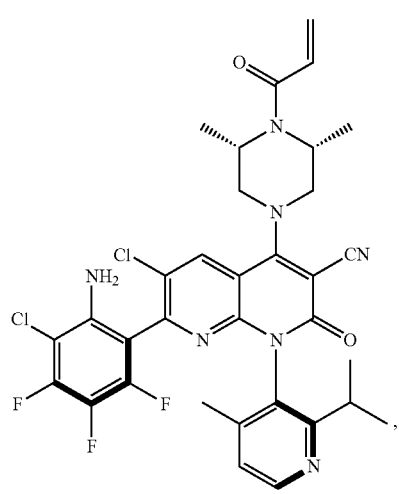
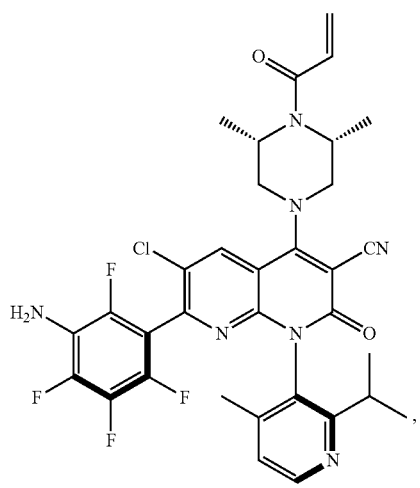
246
-continued
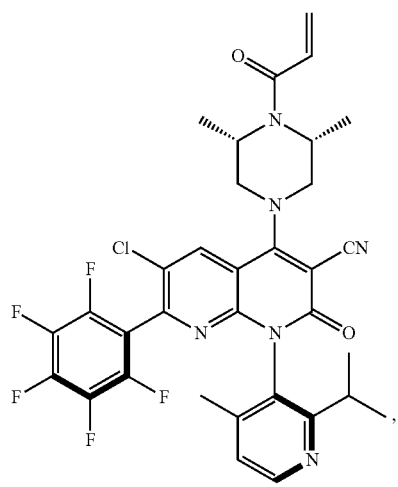
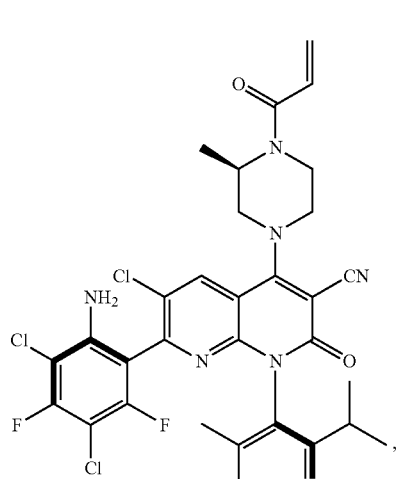
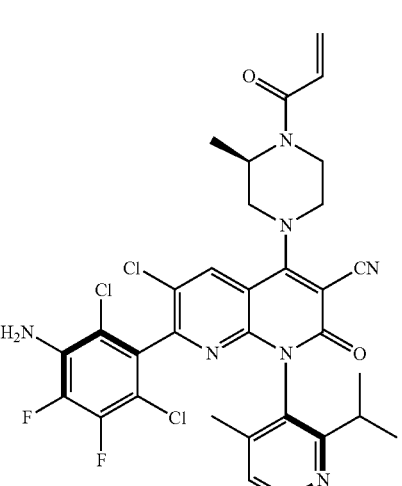

247
-continued
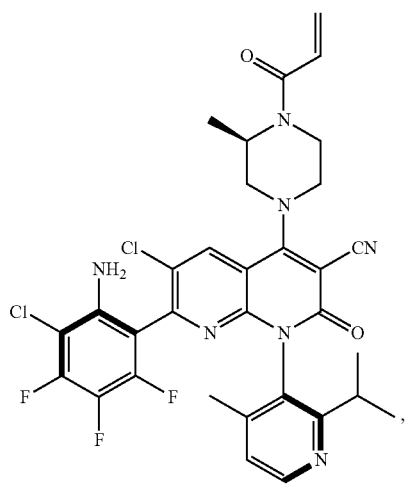
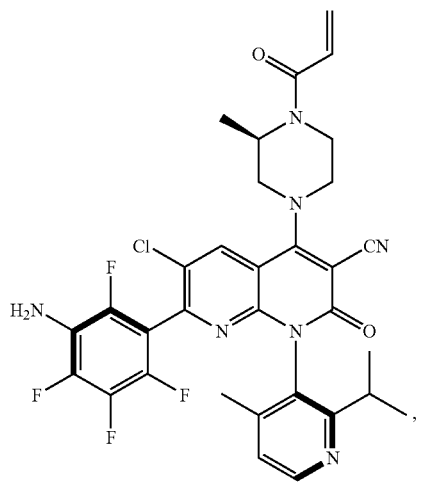
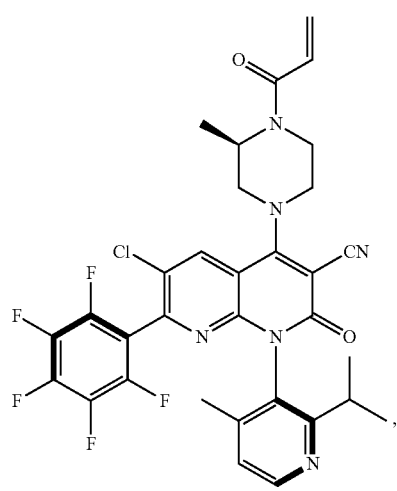
248
-continued
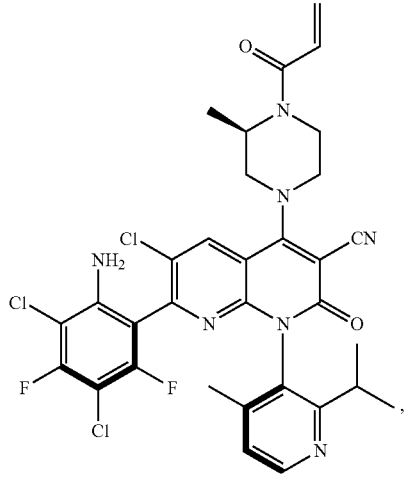
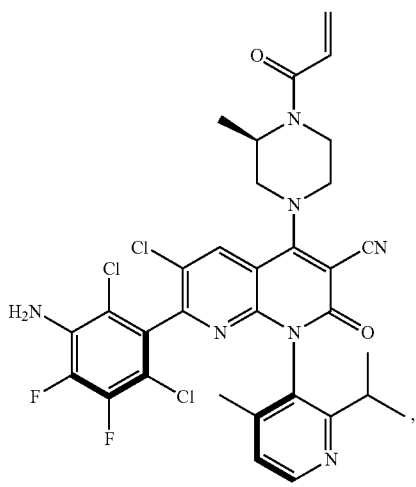
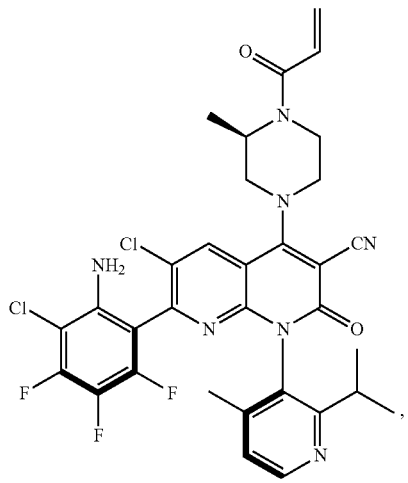

249
-continued
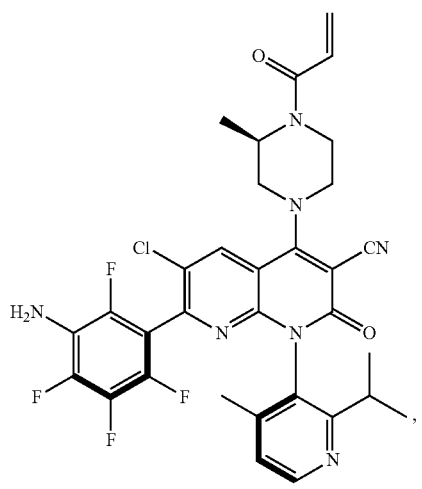
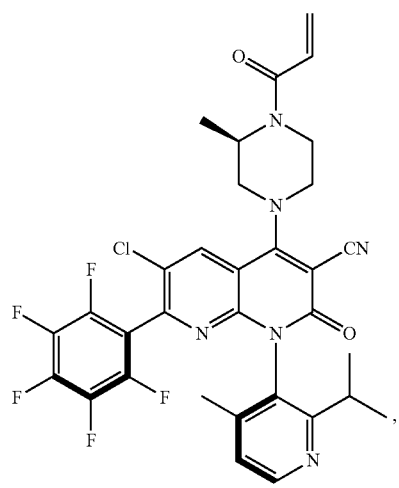
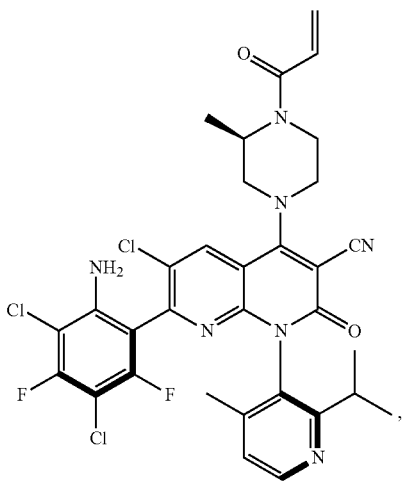
250
-continued
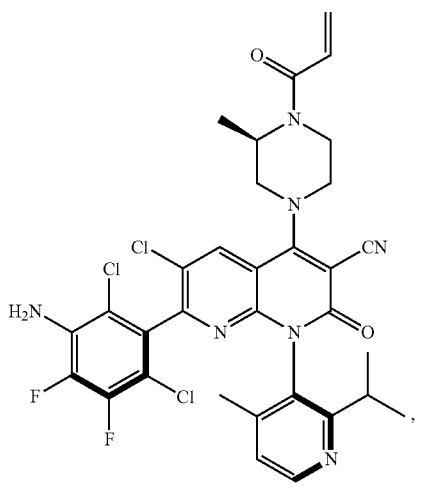
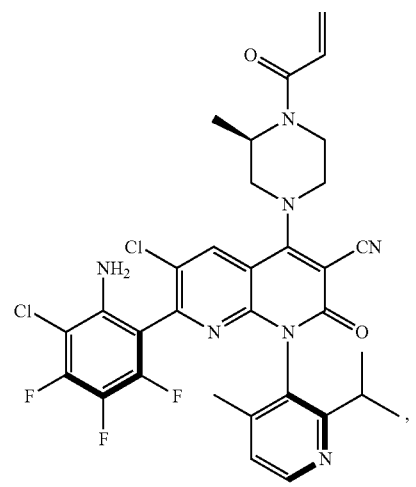
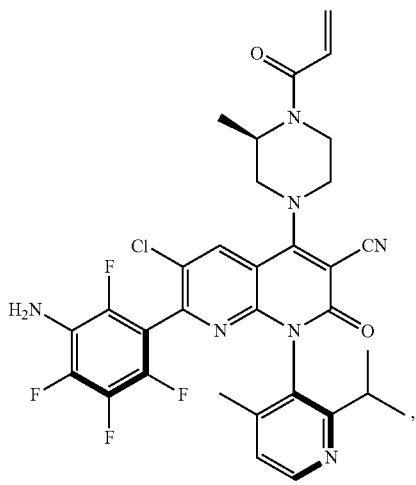

251
-continued
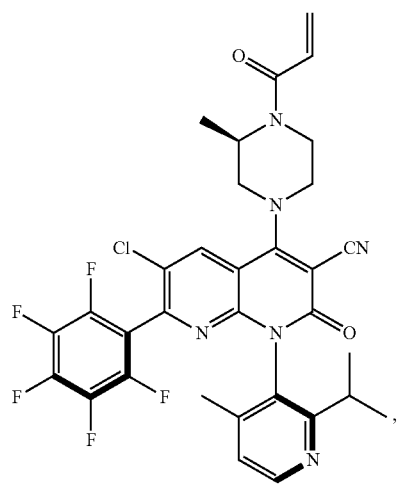
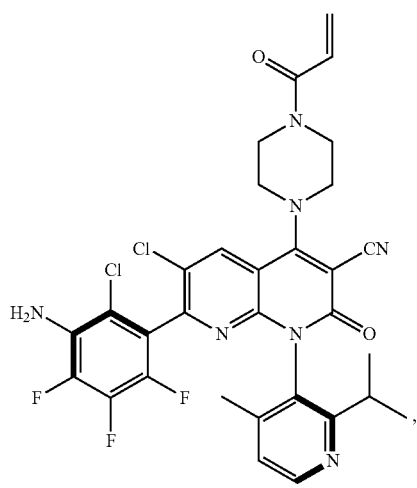
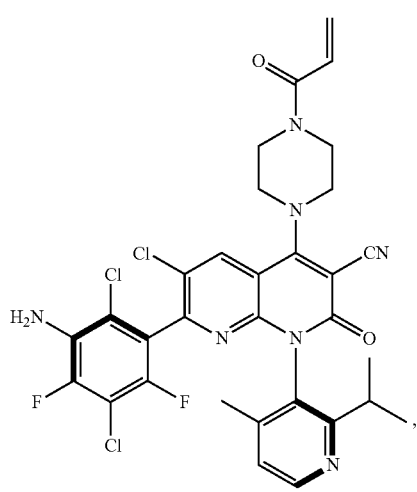
252
-continued
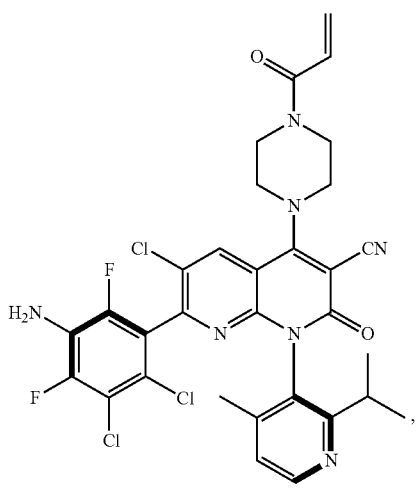
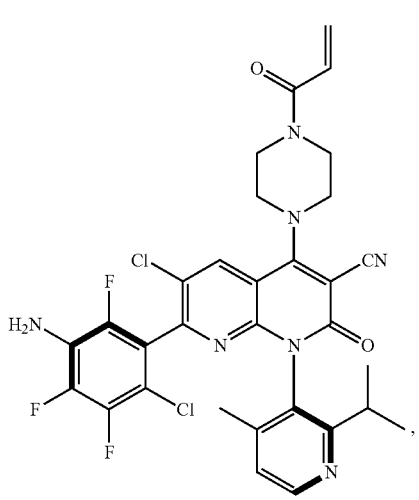
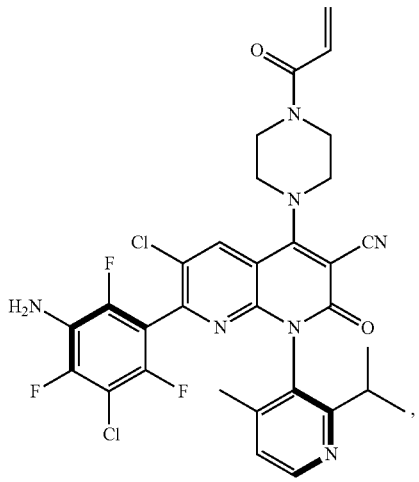

253
-continued
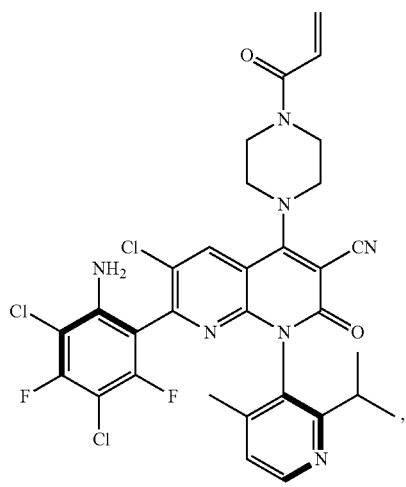
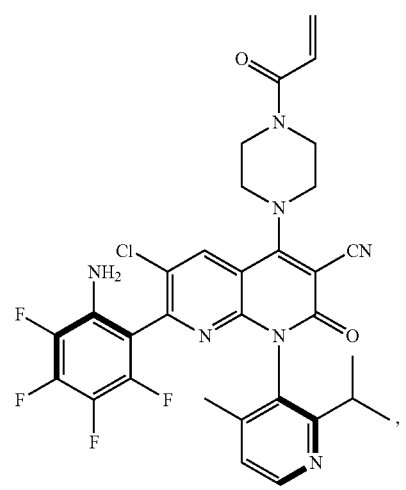
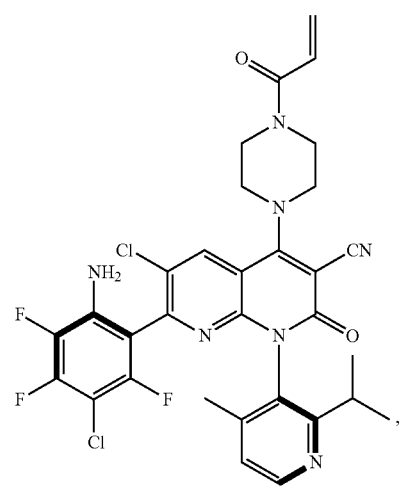
254
-continued
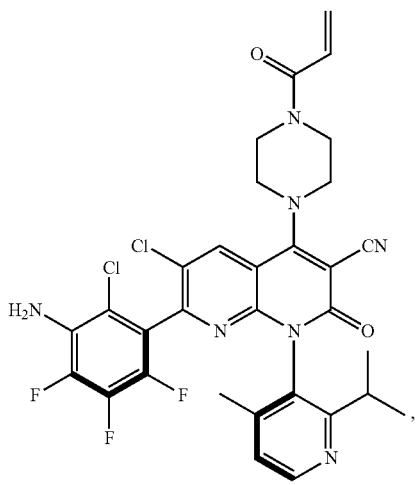
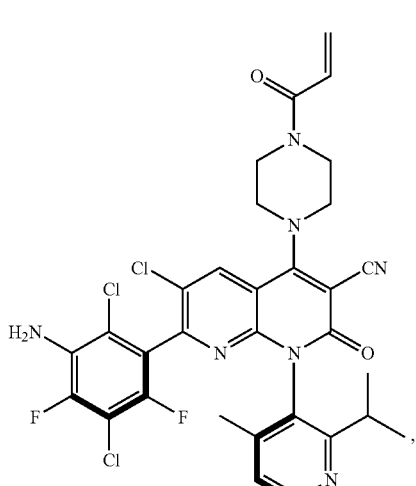
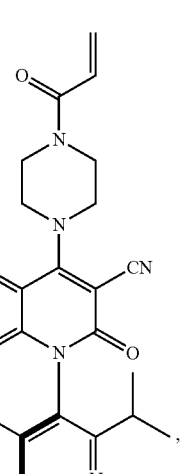

255
-continued
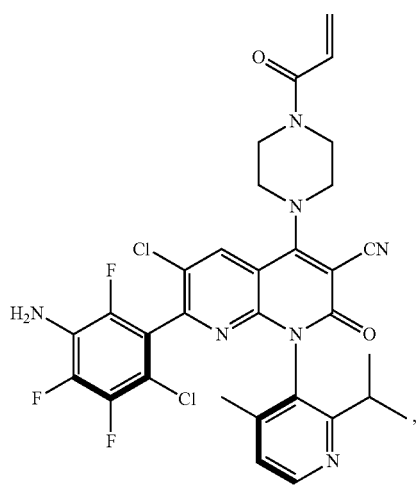
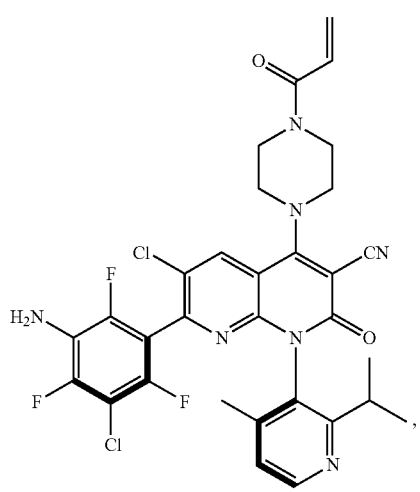
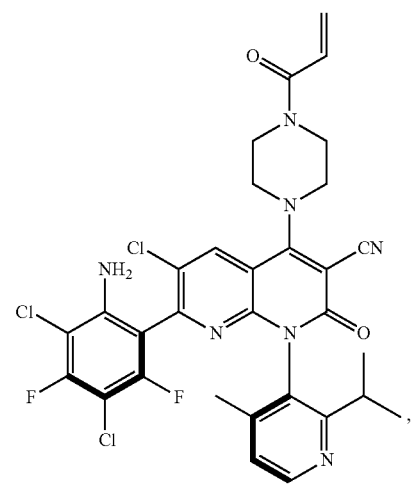
256
-continued
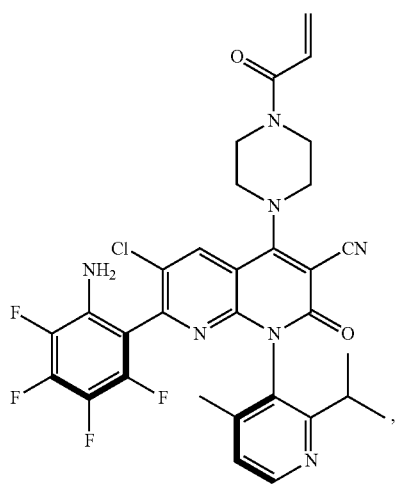
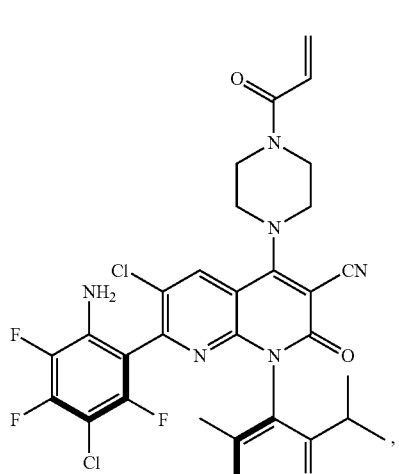
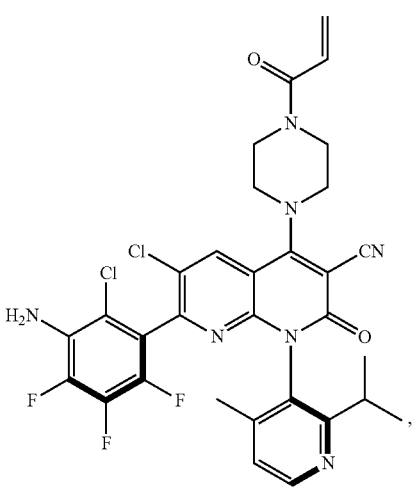

257
-continued
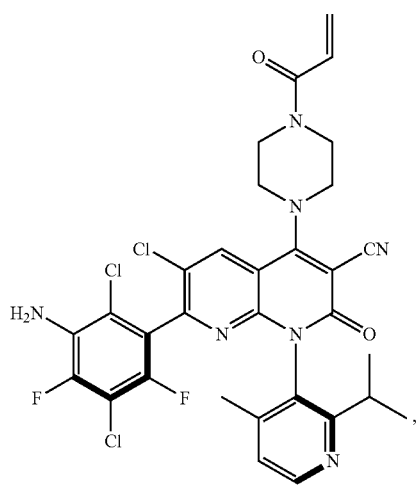
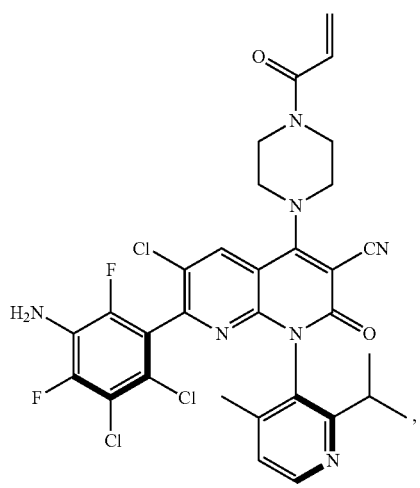
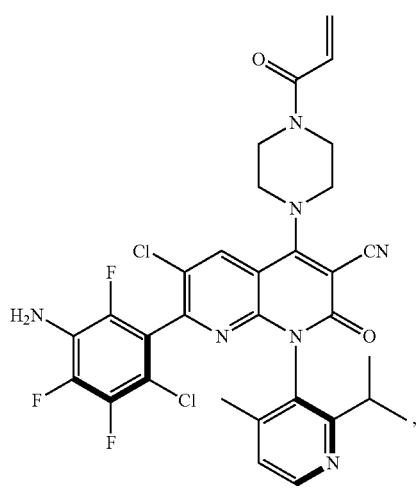
258
-continued
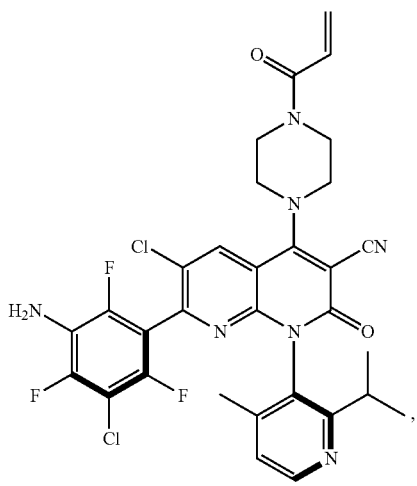
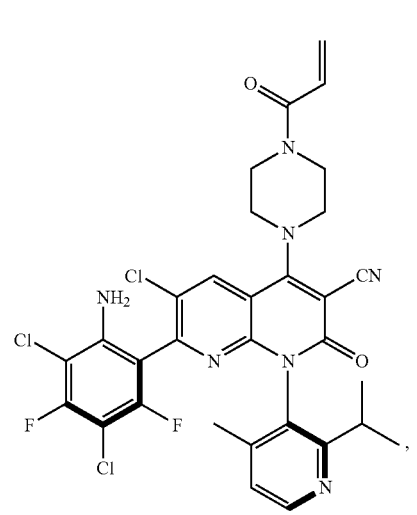
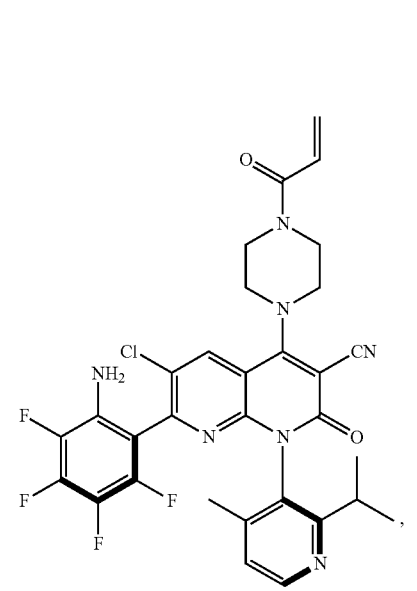

259
-continued
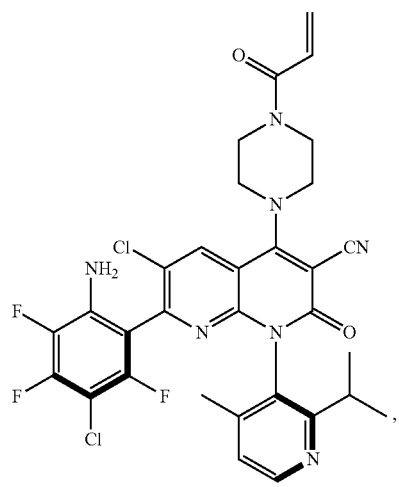
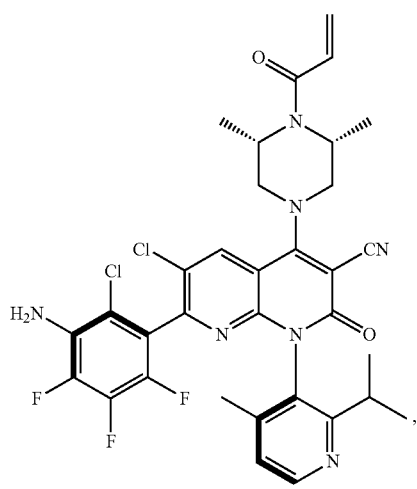
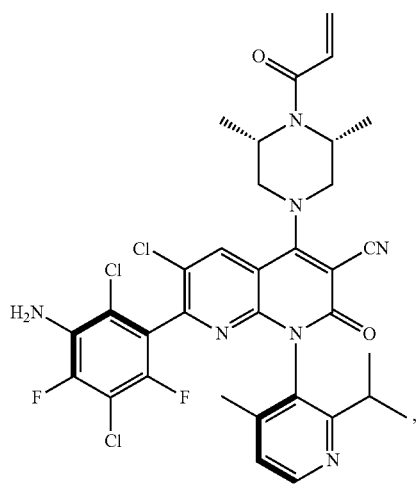
260
-continued
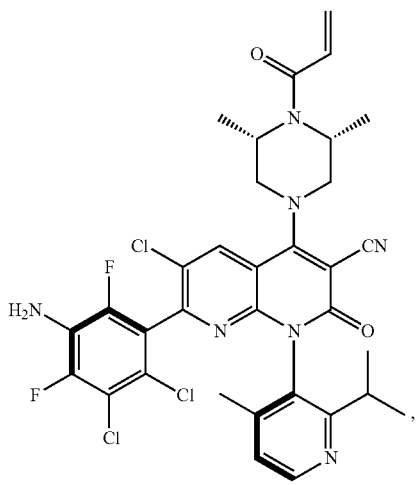
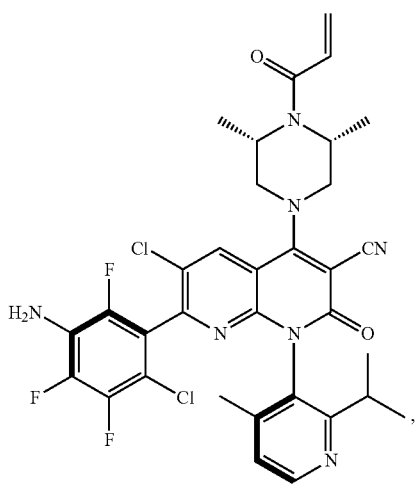
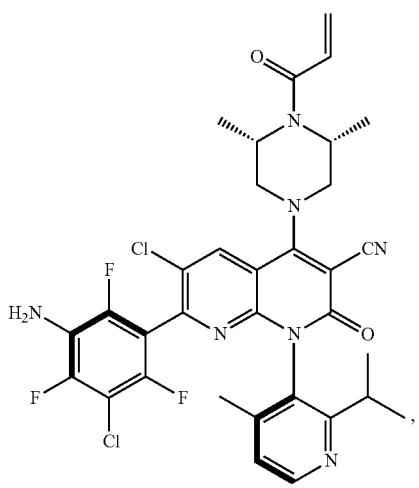

261
-continued
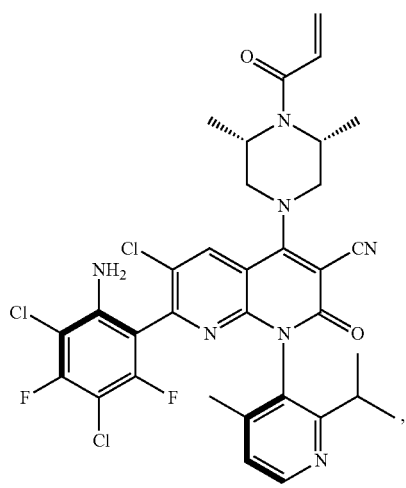
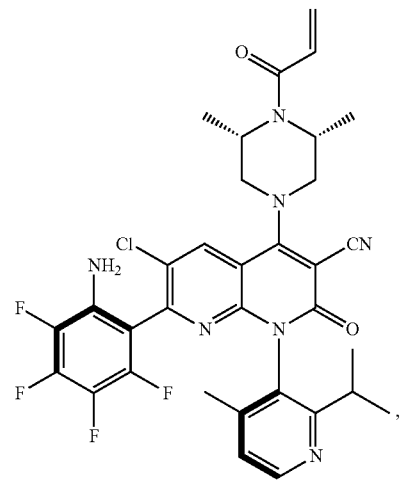
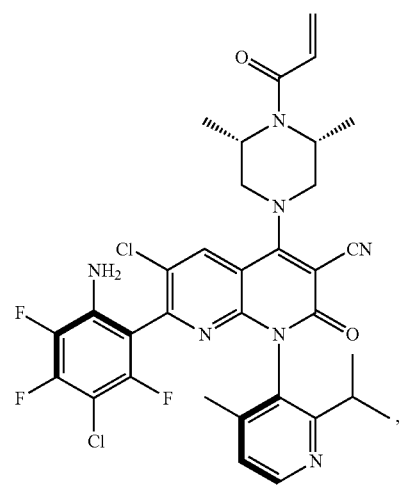
262
-continued
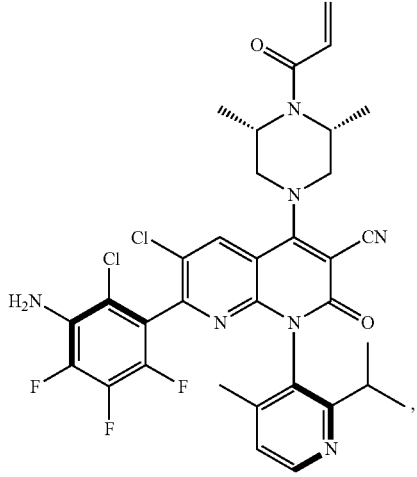
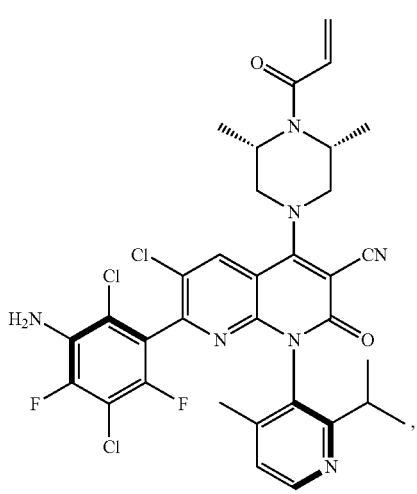
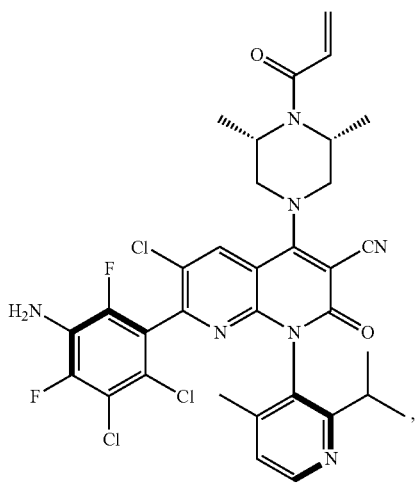

263
-continued
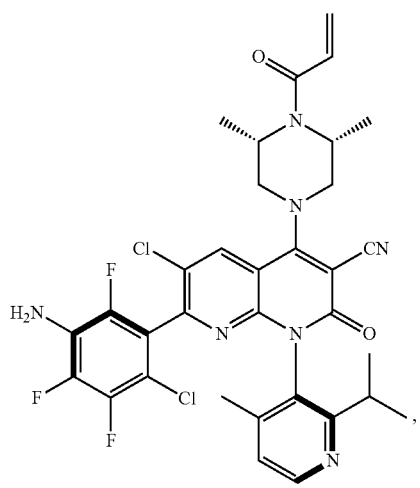
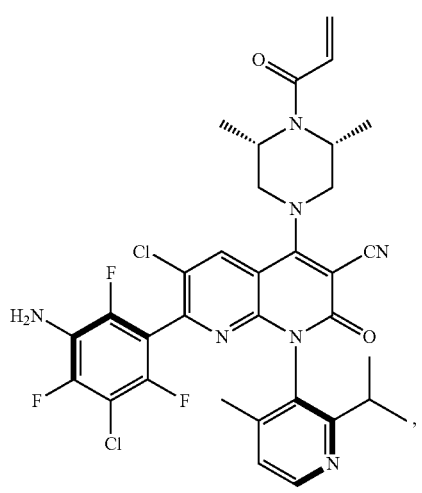
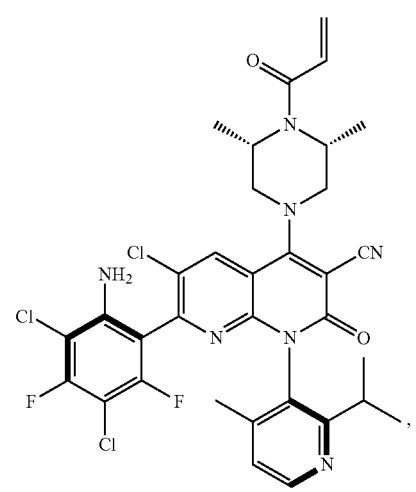
264
-continued
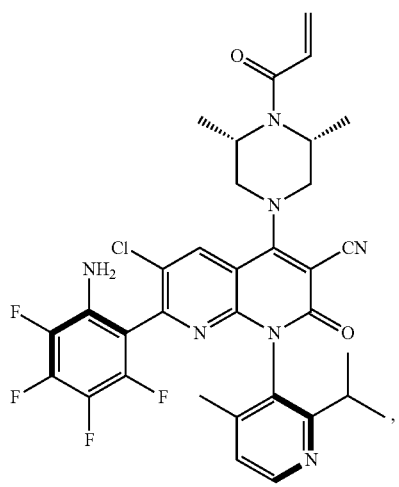
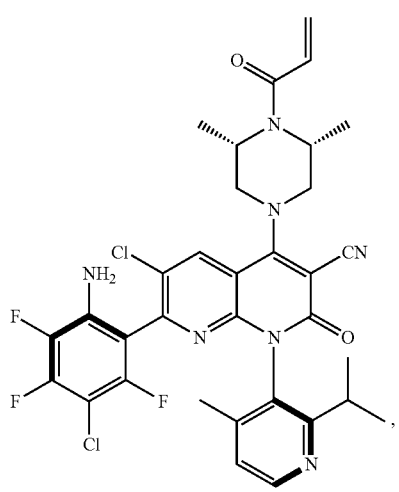
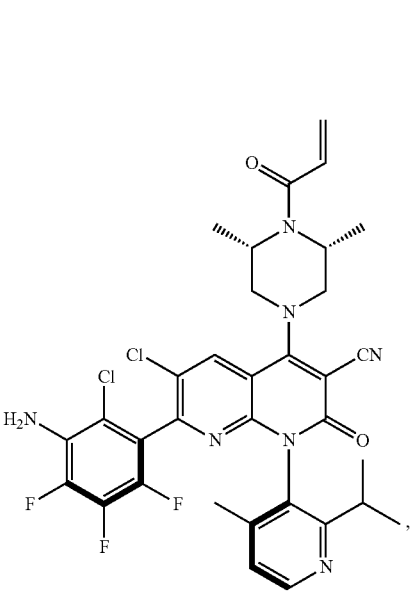

265
-continued
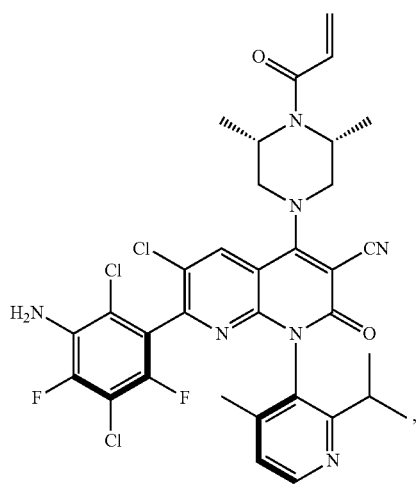
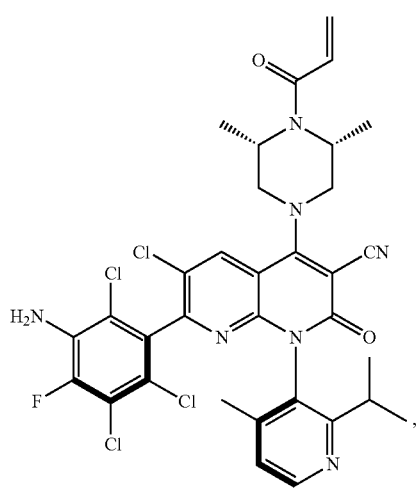
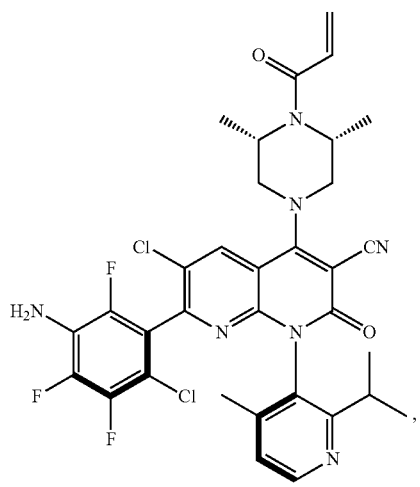
266
-continued
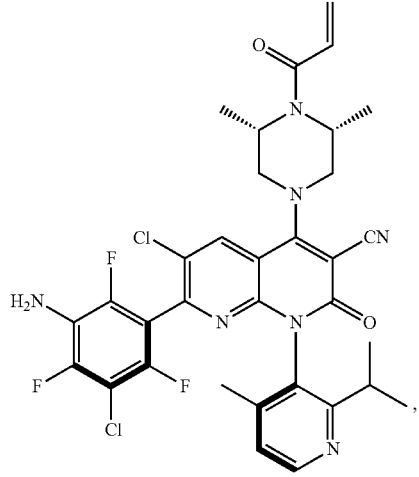
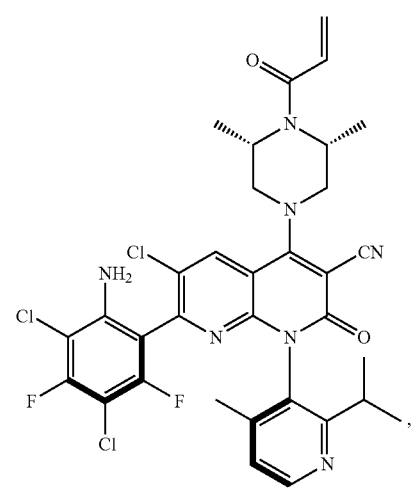
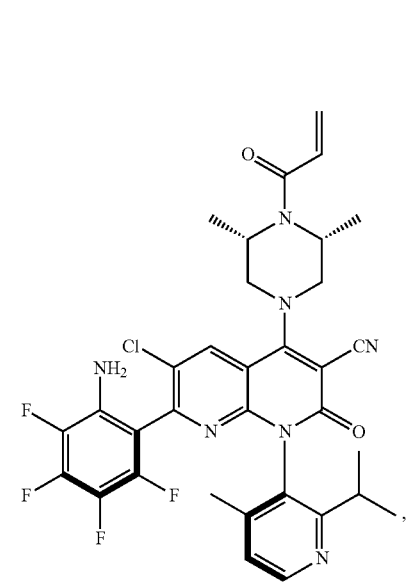

267
-continued
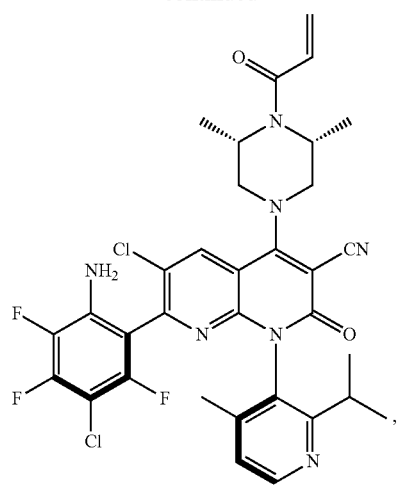
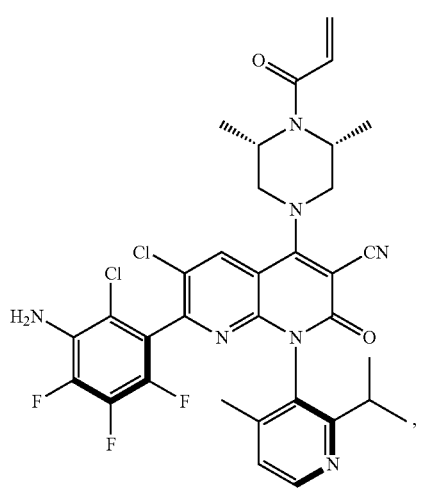
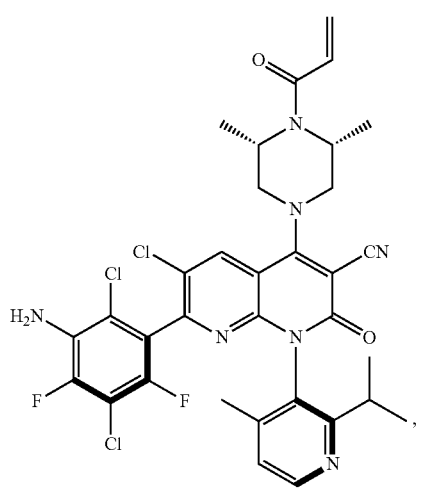
268
-continued
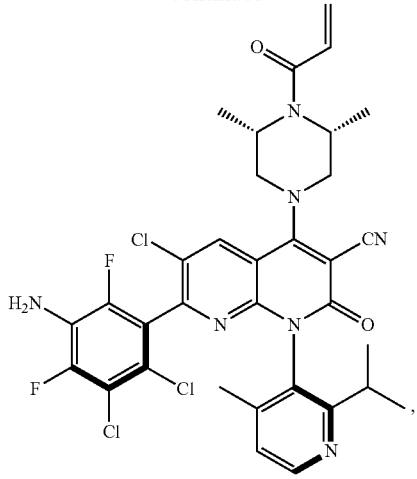
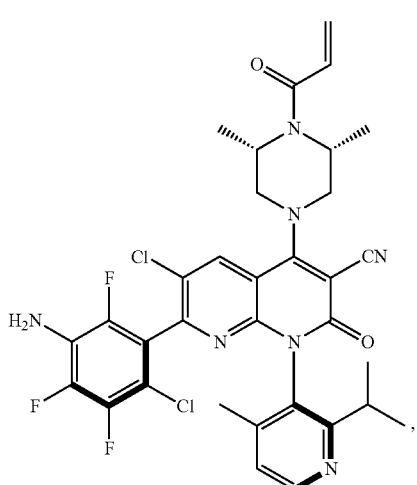
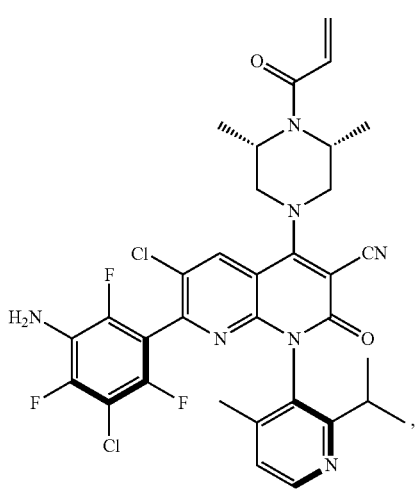

269
-continued
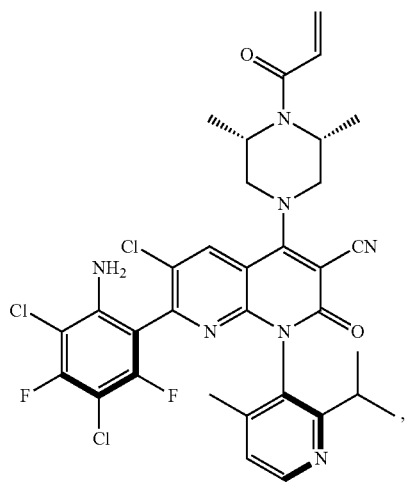
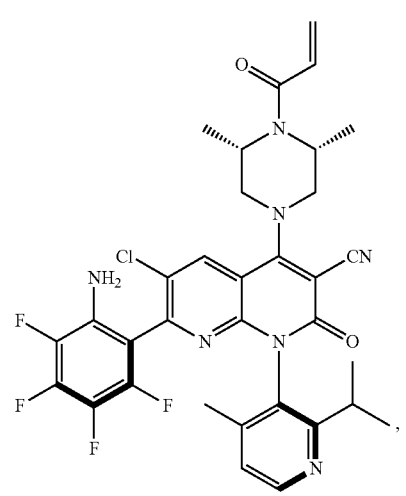
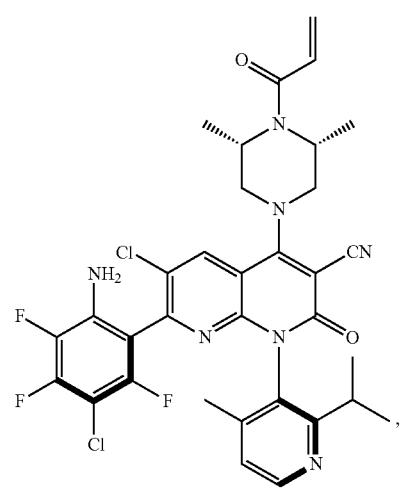
270
-continued
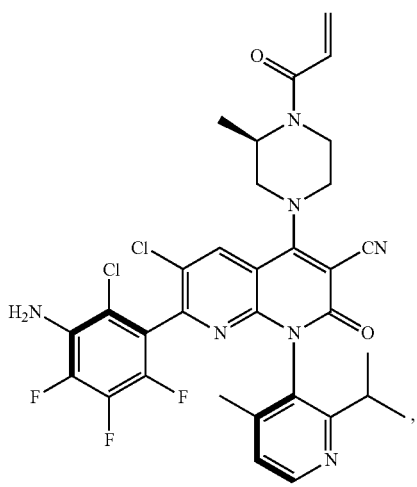
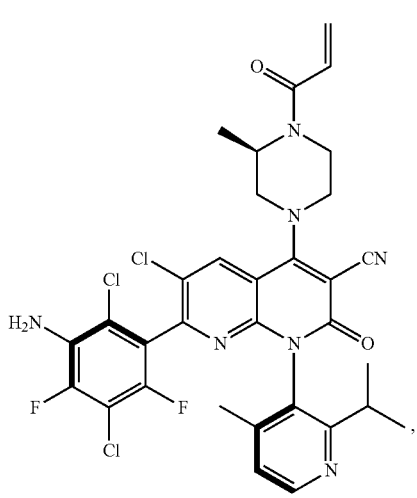
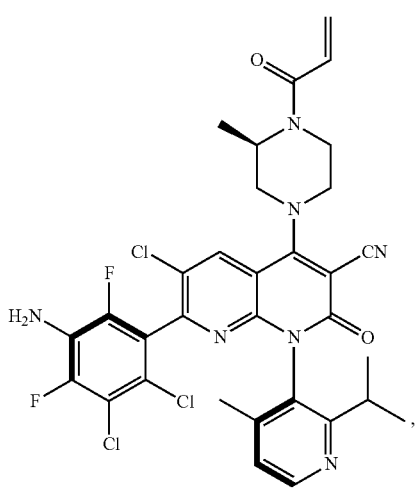

271
-continued
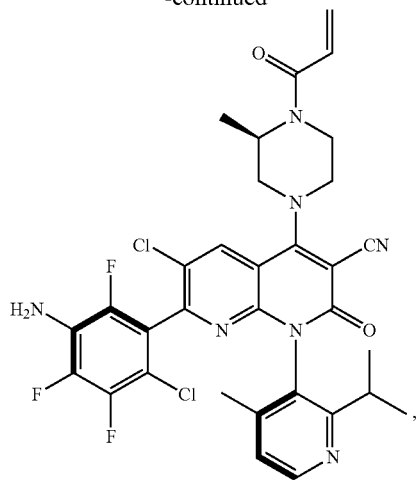
,
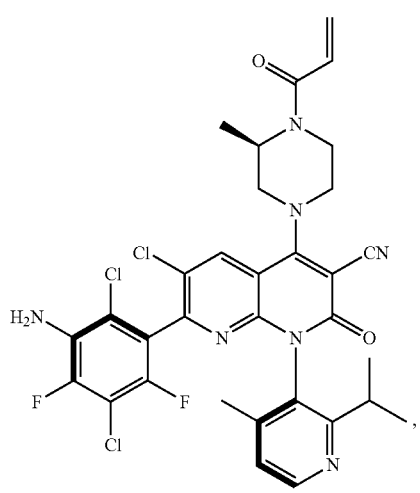
,
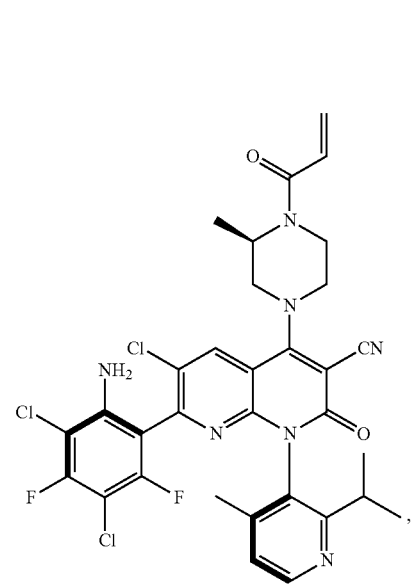
272
-continued
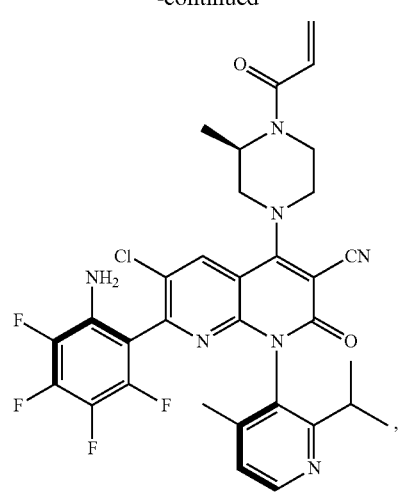
,
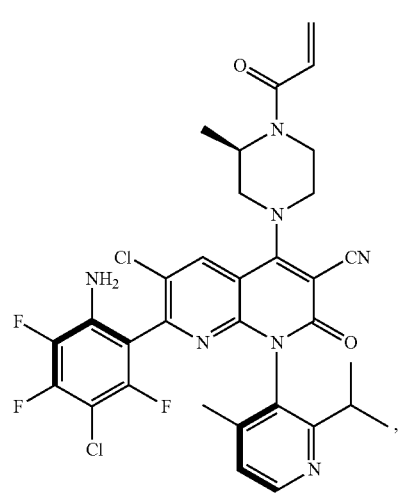
,
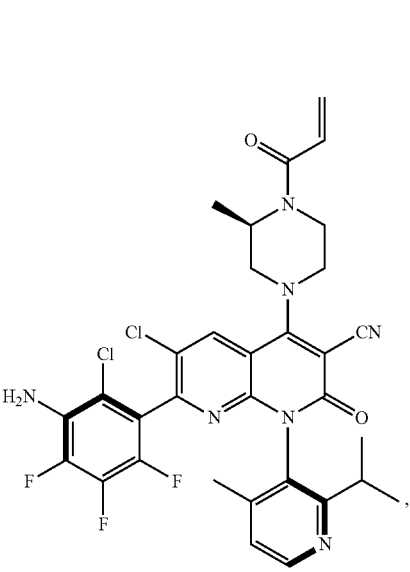

273
-continued
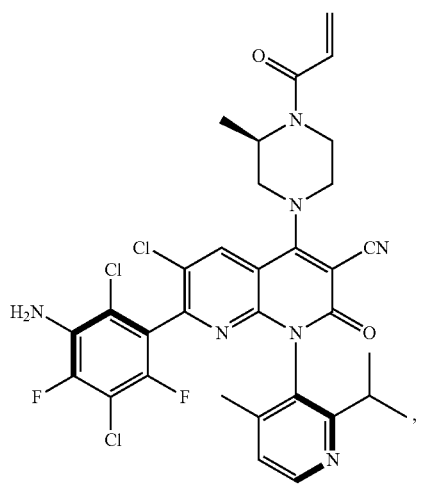
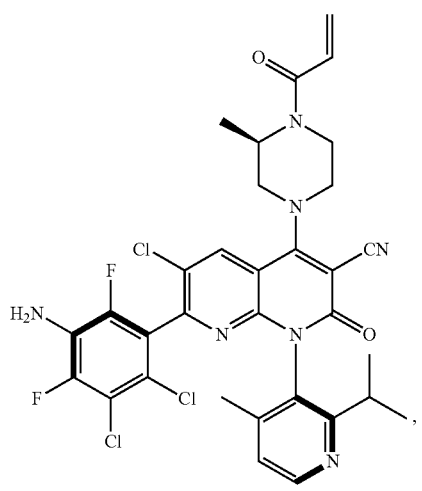
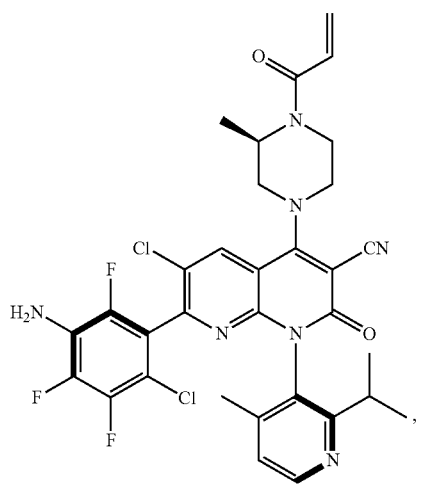
274
-continued
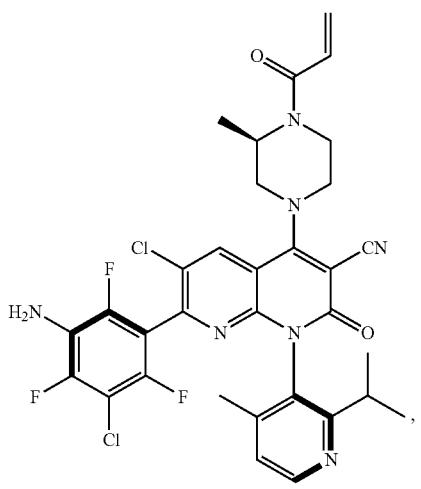
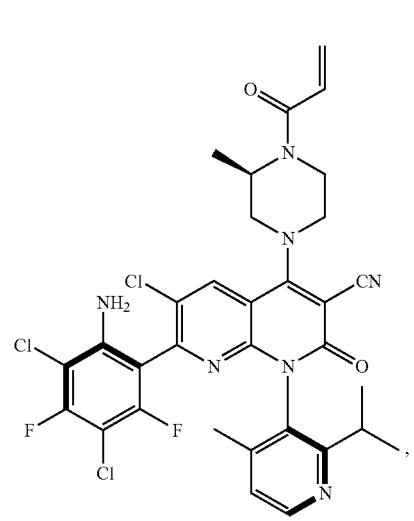
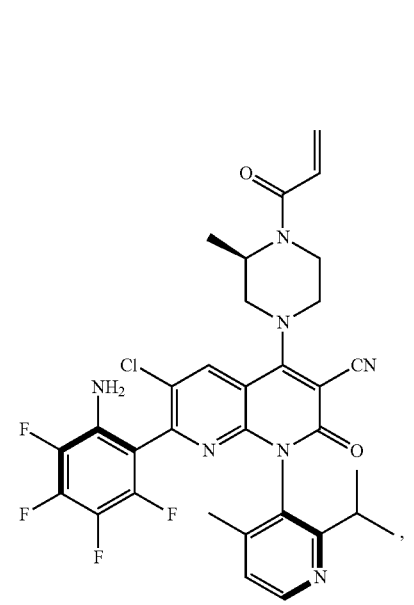

275
-continued
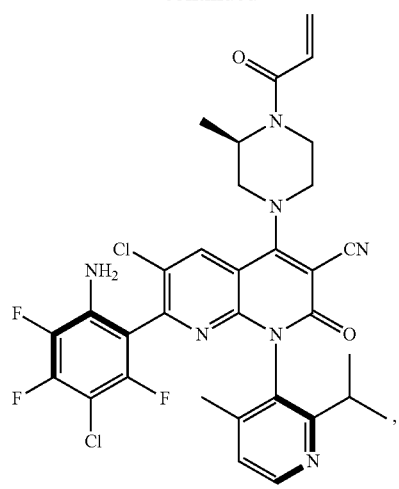
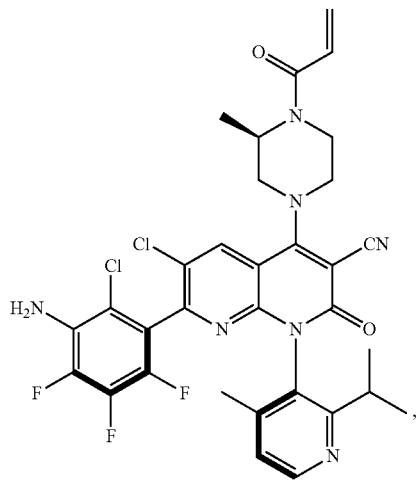
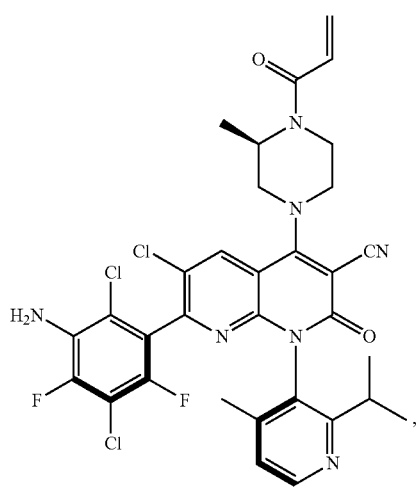
276
-continued
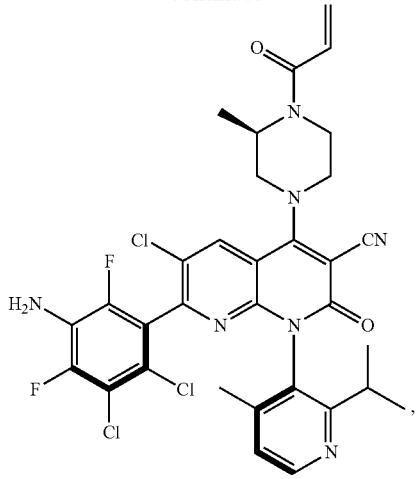
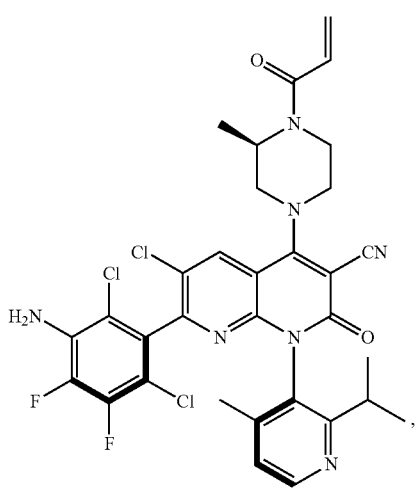
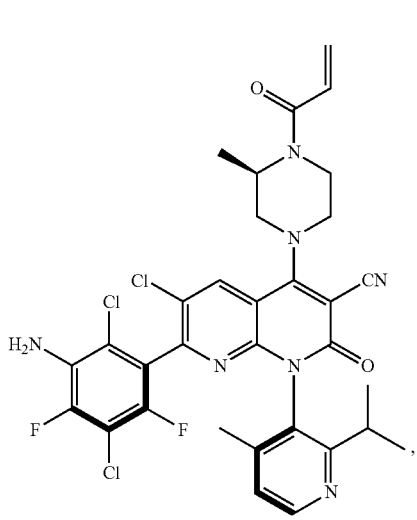

277
-continued
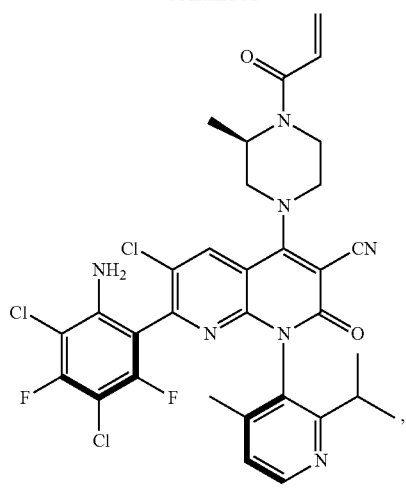
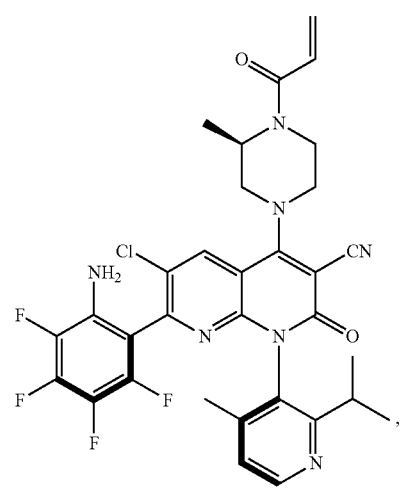
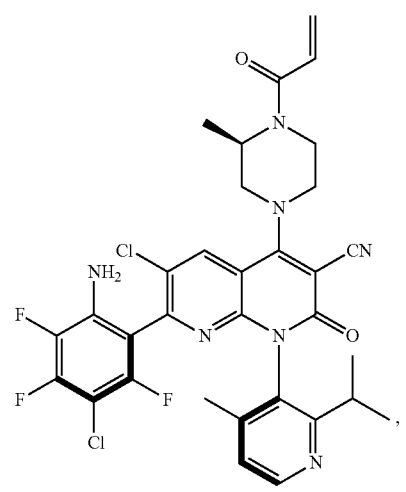
278
-continued
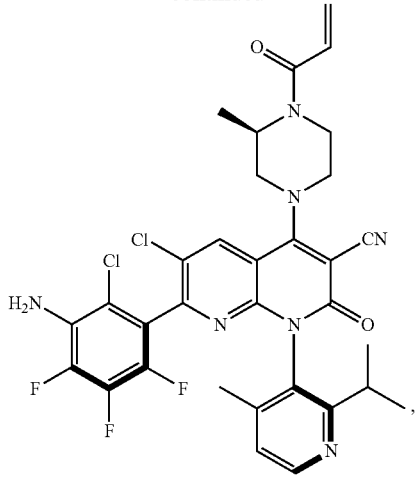
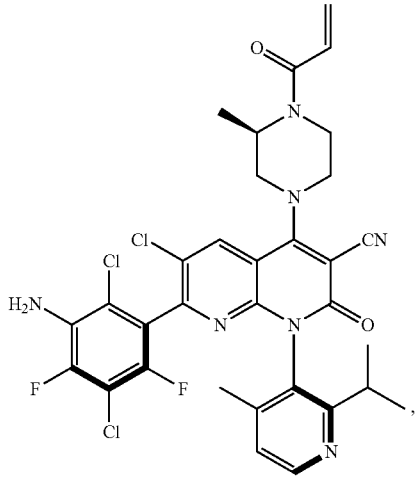
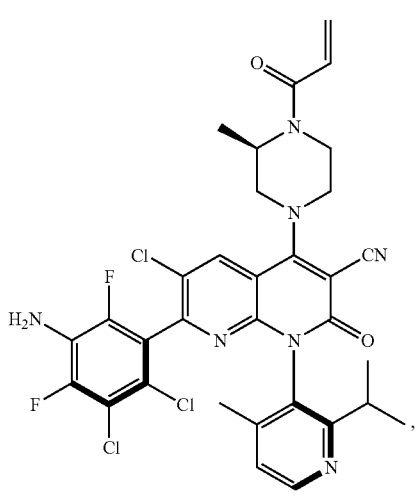

279
-continued
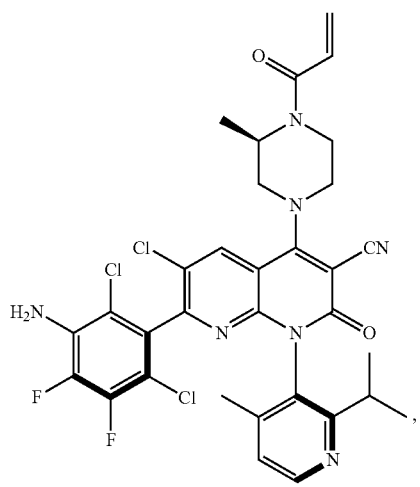
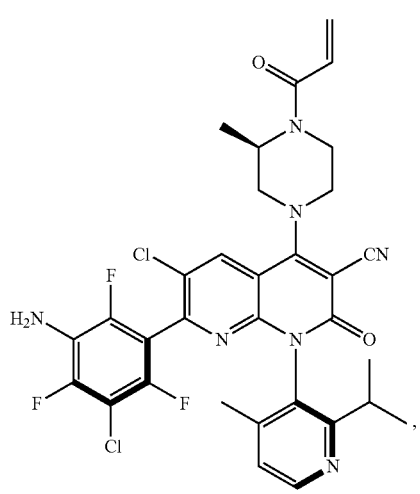
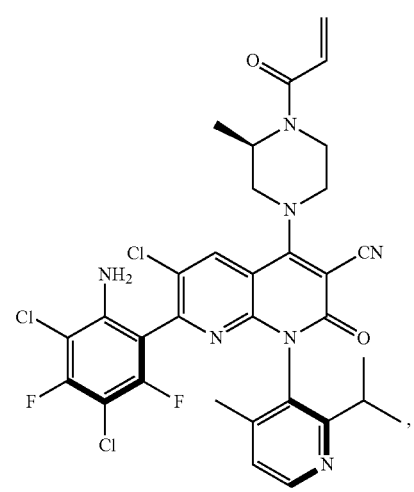
280
-continued
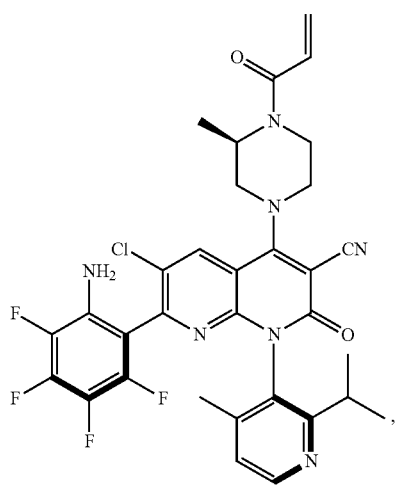
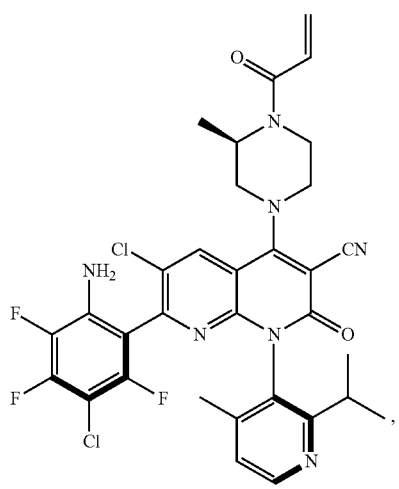
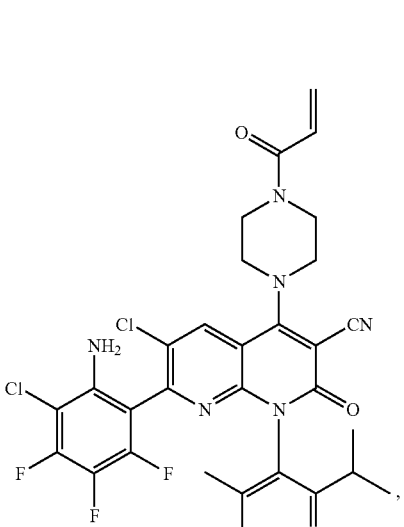

281
-continued
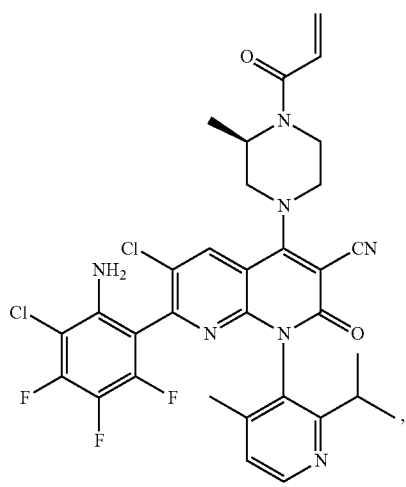
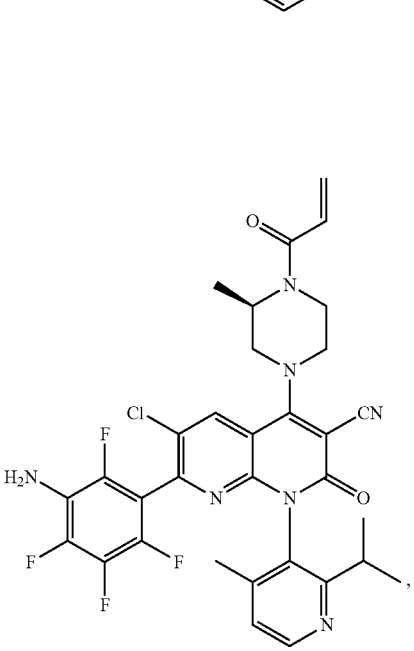
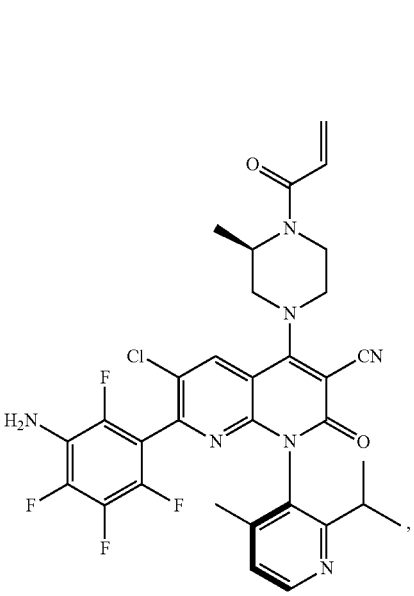
282
-continued
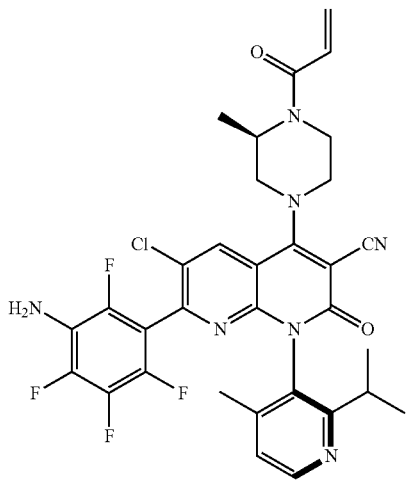
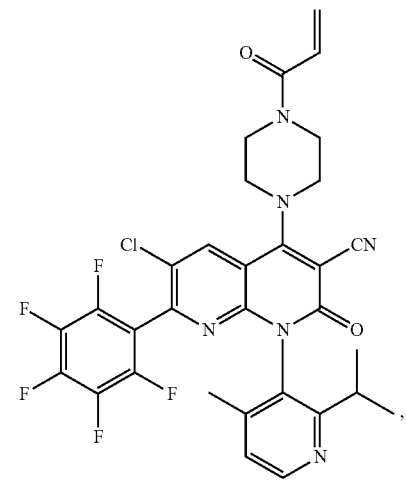
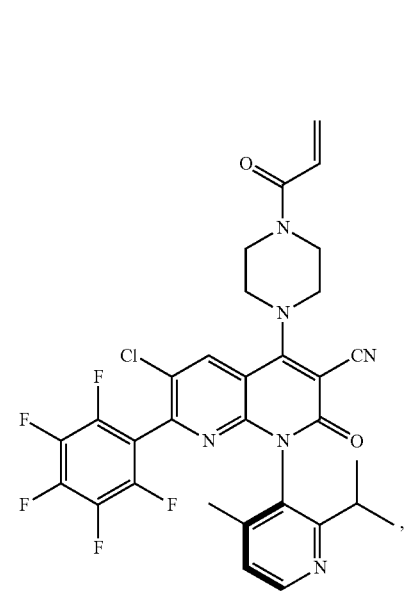

283
-continued


,

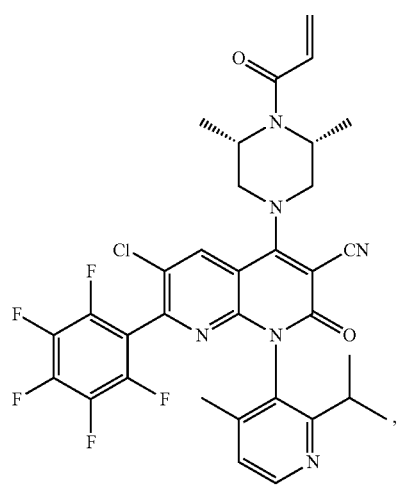

,

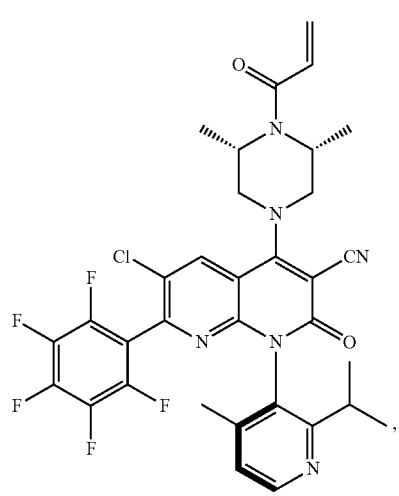

,

284
-continued

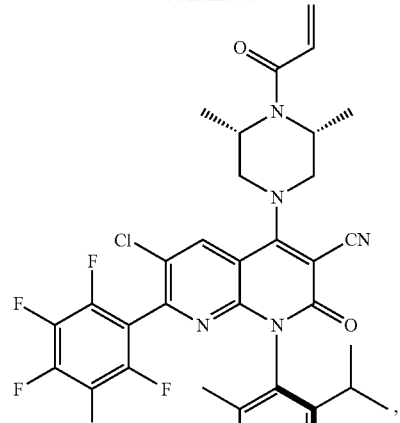

,

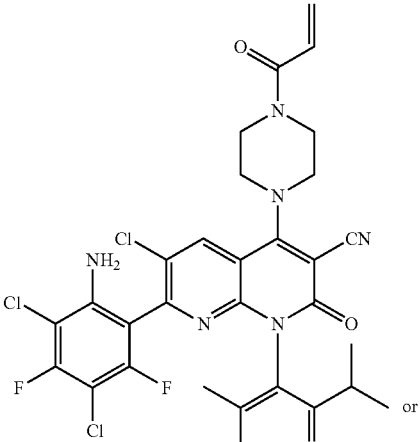

or

.

In another aspect, provided herein is a method for preparing the compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof, the method comprises a coupling reaction between a compound of formula (II) and a compound of formula (III) according to the following reaction Scheme 1 or between a compound of formula (II') and a compound of formula (III') according to the following reaction Scheme 2 catalyzed by a transition metal palladium or nickel reagent:

Scheme 1

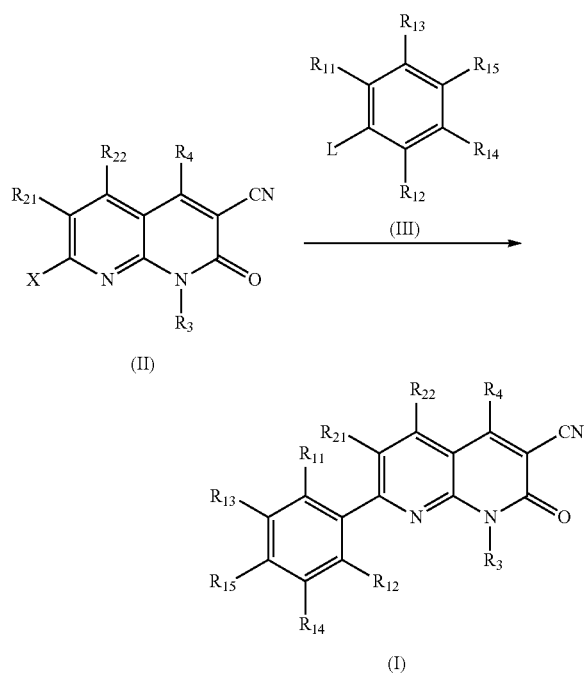

Scheme 2

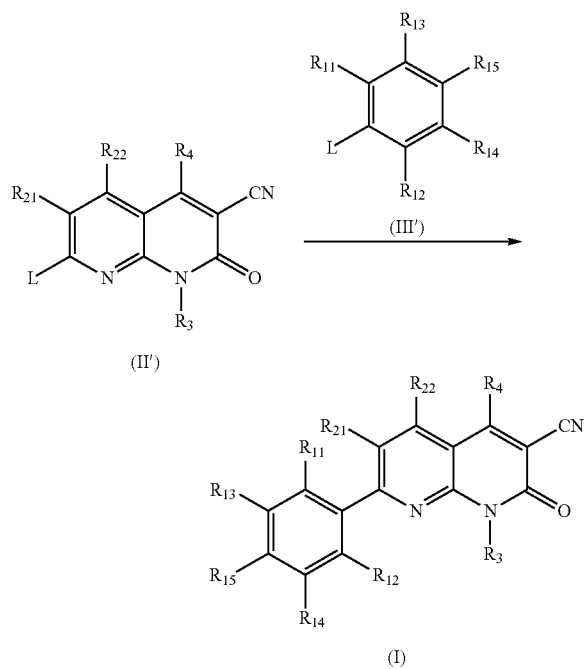

Wherein the L in the compound of formula (III) or formula (II') is a leaving group; preferably, the leaving group is selected from halogen, —OS(O)$_2$CF$_3$ or —OTs; more preferably, the halogen is selected from —F, —Cl, —Br, or —I; more preferably, the leaving group is —Cl or —Br;

the X in the compound of formula (II) or formula (III') is selected from boronic acid, borate ester or organotin; more preferably, the X is selected from

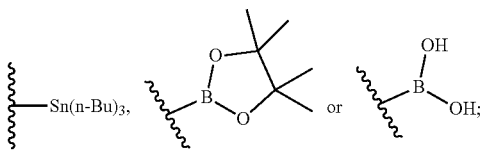

preferably, the coupling reaction is Suzuki coupling reaction or Stille coupling reaction;

preferably, the coupling reaction is catalyzed by the transition metal palladium reagent; more preferably, the transition metal palladium reagent is Pd(PPh$_3$)$_4$.

In another aspect, provided herein is a pharmaceutical composition comprising the compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof of the present invention, and at least one pharmaceutically acceptable excipient. In some embodiments, the said compound in a weight ratio to the said excipient within the range from about 0.0001 to about 10.

In another aspect, provided herein is use of the compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof of the present invention; or the pharmaceutical composition of the present invention for the manufacture of a medicament for the treatment of diseases or conditions related to KRAS mutant protein. In some embodiments, the diseases or conditions related to KRAS mutant protein is the diseases or conditions related to KRAS G12C mutant protein. In some embodiments, the diseases or conditions related to KRAS G12C mutant protein is cancer related to KRAS G12C mutant protein. In some embodiments, the cancer is selected from blood cancer, pancreatic cancer, colon cancer, rectal cancer, colorectal cancer or lung cancer. In some embodiments, the blood cancer is selected from acute myeloid leukemia or acute lymphocytic leukemia; the lung cancer is selected from non-small cell lung cancer or small cell lung cancer.

In another aspect, provided herein is a method of treating a subject having a diseases or conditions related to KRAS mutant protein, said method comprising administering to the subject a therapeutically effective amount of the compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof of the present invention; or the pharmaceutical composition of the present invention. In some embodiments, the diseases or conditions related to KRAS mutant protein is the diseases or conditions related to KRAS G12C mutant protein. In some embodiments, the diseases or conditions related to KRAS G12C mutant protein is cancer related to KRAS G12C mutant protein. In some embodiments, the cancer is selected from blood cancer, pancreatic cancer, colon cancer, rectal cancer, colorectal cancer or lung cancer. In some embodiments, the blood cancer is selected from acute myeloid leukemia or acute lymphocytic leukemia; the lung cancer is selected from non-small cell lung cancer or small cell lung cancer.

Definition

The term "halogen" or "halo", as used herein, unless otherwise indicated, means fluoro, chloro, bromo or iodo. The preferred halogen groups include —F, —Cl and —Br. The preferred halogen groups include —F and —Cl.

The term "alkyl", as used herein, unless otherwise indicated, includes saturated monovalent hydrocarbon radicals having straight or branched. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Similarly, $C_{1-6}$, as in $C_{1-6}$alkyl is defined to identify the group as having 1, 2, 3, 4, 5 or 6 carbon atoms in a linear or branched arrangement.

The term "alkylene" means a difunctional group obtained by removal of a hydrogen atom from an alkyl group that is defined above. For example, methylene (i.e., —CH$_2$—), ethylene (i.e., —CH$_2$—CH$_2$— or —CH(CH$_3$)—) and propylene (i.e., —CH$_2$—CH$_2$—CH$_2$—, —CH(—CH$_2$—CH$_3$)— or —CH$_2$—CH(CH$_3$)—).

The term "alkenyl" means a straight or branch-chained hydrocarbon radical containing one or more double bonds and typically from 2 to 20 carbon atoms in length. For example, "$C_{2-6}$alkenyl" contains from 2 to 6 carbon atoms. Alkenyl group include, but are not limited to, for example, ethenyl, propenyl, butenyl, 2-methyl-2-buten-1-yl, heptenyl, octenyl and the like.

The term "alkynyl" contains a straight or branch-chained hydrocarbon radical containing one or more triple bonds and typically from 2 to 20 carbon atoms in length. For example, "$C_{2-6}$alkynyl" contains from 2 to 6 carbon atoms. Representative alkynyl groups include, but are not limited to, for example, ethynyl, 1-propynyl, 1-butynyl, heptynyl, octynyl and the like.

The term "alkoxy" radicals are oxygen ethers formed from the previously described alkyl groups.

The term "aryl" or "aryl ring", as used herein, unless otherwise indicated, refers to an unsubstituted or substituted mono or polycyclic aromatic ring system only containing carbon ring atoms. The preferred aryls are mono cyclic or bicyclic 6-10 membered aromatic ring systems. Phenyl and naphthyl are preferred aryls.

The term "heterocyclic" or "heterocyclic ring", as used herein, unless otherwise indicated, refers to unsubstituted and substituted mono or polycyclic non-aromatic ring system containing one or more ring heteroatom(s), which comprising moncyclic heterocyclic (ring), bicyclic heterocyclic (ring), bridged heterocyclic (ring), fused heterocyclic (ring) or sipro heterocyclic (ring). Preferred heteroatoms include N, O, and S, including N-oxides, sulfur oxides, and dioxides. Preferably the heterocyclic (ring) is three to ten membered and is either fully saturated or has one or more degrees of unsaturation. Multiple degrees of substitution, preferably one, two or three, are included within the present definition of heterocyclic (ring). Examples of such heterocyclic groups include, but are not limited to azetidinyl, pyrrolidinyl, piperidinyl, piperazinyl, oxopiperazinyl, oxopiperidinyl, oxoazepinyl, azepinyl, tetrahydrofuranyl, dioxolanyl, tetrahydroimidazolyl, tetrahydrothiazolyl, tetrahydrooxazolyl, tetrahydropyranyl, morpholinyl, thiomorpholinyl, thiamorpholinyl sulfoxide, thiamorpholinyl sulfone and oxadiazolyl.

The term "heteroaryl" or "heteroaryl ring", as used herein, unless otherwise indicated, represents an aromatic ring system containing carbon(s) and at least one heteroatom. Heteroaryl or heteroaryl ring may be monocyclic or polycyclic, substituted or unsubstituted. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junction, for example, bycyclic heteroaryl is a polycyclic heteroaryl. Bicyclic heteroaryl rings may contain from 8 to 12 member atoms. Monocyclic heteroaryl rings may contain from 5 to 8 member atoms (cabons and heteroatoms). Examples of heteroaryl groups include, but are not limited to thienyl, furanyl, imidazolyl, isoxazolyl, oxazolyl, pyrazolyl, pyrrolyl, thiazolyl, thiadiazolyl, triazolyl, pyridyl, pyridazinyl, indolyl, azaindolyl, indazolyl, benzimidazolyl, benzofuranyl, benzothienyl, benzisoxazolyl, benzoxazolyl, benzopyrazolyl, benzothiazolyl, benzothiadiazolyl, benzotriazolyl adeninyl, quinolinyl or isoquinolinyl.

The term "carbocyclic" or "carbocyclic ring" refers to a substituted or unsubstituted monocyclic ring, bicyclic ring, bridged ring, fused ring, sipiro ring non-aromatic ring system only containing carbon atoms. The carbocyclic (ring) contain cycloalkyl without substituted degrees and carbocyclic with one or more substituted degrees. Exemplary "cycloalkyl" groups includes but not limited to, cyclopropyl, cyclobutyl, cyclopentyl, cyclohexyl and so on.

The term "oxo" refers to oxygen atom together with the attached carbon atom forms the group

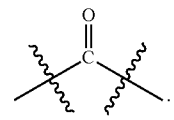 [SMILES: *C(*)=O]

The term "—$C_{1-6}$alkylene-N($C_{1-6}$alkyl)$_2$" refers to the —$C_{1-6}$alkyl as defined above substituted by —N($C_{1-6}$alkyl)$_2$.

The term "—$C_{1-6}$alkylene-CN" refers to the —$C_{1-6}$alkyl as defined above substituted by —CN.

The term "heteroalkyl" refers to the presence of heteroatoms between any two carbon atoms in the alkyl group as defined above, such as N or O atoms. For example, "hetero$C_{2-6}$alkyl" means that there are N atom or O atom between any two carbon atoms in the $C_{2-6}$ alkyl group, including but not limited to —CH$_2$OCH$_3$, —CH$_2$CH$_2$OCH$_3$, —CH$_2$NHCH$_3$, or —CH$_2$N(CH$_3$)$_2$ and the like.

The term "composition", as used herein, is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention.

The compounds of the present invention may also be present in the form of pharmaceutically acceptable salt(s). For use in medicine, the salts of the compounds of this invention refer to non-toxic "pharmaceutically acceptable salt(s)". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid.

The present invention includes within its scope the prodrugs of the compounds of this invention. In general, such prodrugs will be functional derivatives of the compounds that are readily converted in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

The present invention includes compounds described can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof.

The present invention includes all stereoisomers of the compound and pharmaceutically acceptable salts thereof. Further, mixtures of stereoisomers as well as isolated specific stereoisomers are also included. During the course of the synthetic procedures used to prepare such compounds or in using racemization or epimerization procedures known to those skilled in the art, the products of such procedures can be a mixture of stereoisomers.

The term "stereoisomer" as used in the present invention refers to an isomer in which atoms or groups of atoms in the molecule are connected to each other in the same order but differ in spatial arrangement, including conformational isomers and conformational isomers. The configuration isomers include geometric isomers and optical isomers, and optical isomers mainly include enantiomers and diastereomers. The invention includes all possible stereoisomers of the compound.

Certain of the compounds provided herein may exist as atropisomers, which are conformational stereoisomers that occur when rotation about a single bond in the molecule is prevented, or greatly slowed, as a result of steric interactions with other parts of the molecule. The compounds provided herein include all atropisomers, both as pure individual atropisomer preparations, enriched preparations of each, or a non-specific mixture of each. Where the rotational barrier about the single bond is high enough, and interconversion between conformations is slow enough, separation and isolation of the isomeric species may be permitted.

The present invention is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1$H(hydrogen), $^2$H(deuterium) and $^3$H(tritium). They are also commonly denoted as D for deuterium and T for tritium. In the application, $CD_3$ denotes a methyl group wherein all of the hydrogen atoms are deuterium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent.

When a tautomer of the compound exists, the present invention includes any possible tautomers and pharmaceutically acceptable salts thereof, and mixtures thereof, except where specifically stated otherwise.

The pharmaceutical compositions of the present invention comprise the compound (or the stereoisomer, the astropisomer thereof, the pharmaceutically acceptable salt thereof, the pharmaceutically acceptable salt of the stereoisomer, or the pharmaceutically acceptable salt of the astropisomer) as an active ingredient, and a pharmaceutically acceptable carrier and optionally other adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds or a prodrug or a metabolite or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical carrier employed can be, for example, a solid, liquid or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient. For example, a formulation intended for the oral administration to humans may contain from about 0.5 mg to about 5 g of active agent, compounded with an appropriate and convenient amount of carrier material which may vary from about 0.05 to about 95 percent of the total composition. Unit dosage forms will generally contain between from about 0.01 mg to about 2 g of the active ingredient, typically 0.01 mg, 0.02 mg, 1 mg, 2 mg, 3 mg, 4 mg, 5 mg, 6 mg, 7 mg, 8 mg, 9 mg, 10 mg, 25 mg, 50 mg, 100 mg, 200 mg, 300 mg, 400 mg, 500 mg, 600 mg, 800 mg, 1000 mg, 1500 mg or 2000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder or the like. Further, the compositions can be in a form suitable for use in transdermal devices. These formulations may be prepared, utilizing a compound of this invention or a pharmaceutically acceptable salt thereof, via conventional processing methods. As an example, a cream or ointment is prepared by admixing hydrophilic material and water, together with about 0.05 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound or pharmaceutically acceptable salts thereof, may also be prepared in powder or liquid concentrate form.

Generally, dosage levels on the order of from about 0.001 mg/kg to about 150 mg/kg of body weight per day are useful in the treatment of the above-indicated conditions or alternatively about 0.05 mg to about 7 g per patient per day. For example, inflammation, cancer, psoriasis, allergy/asthma, disease and conditions of the immune system, disease and conditions of the central nervous system (CNS), may be effectively treated by the administration of from about 0.001 to 50 mg of the compound per kilogram of body weight per day or alternatively about 0.05 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

METHODS OF PREPARATION

Figure 1:
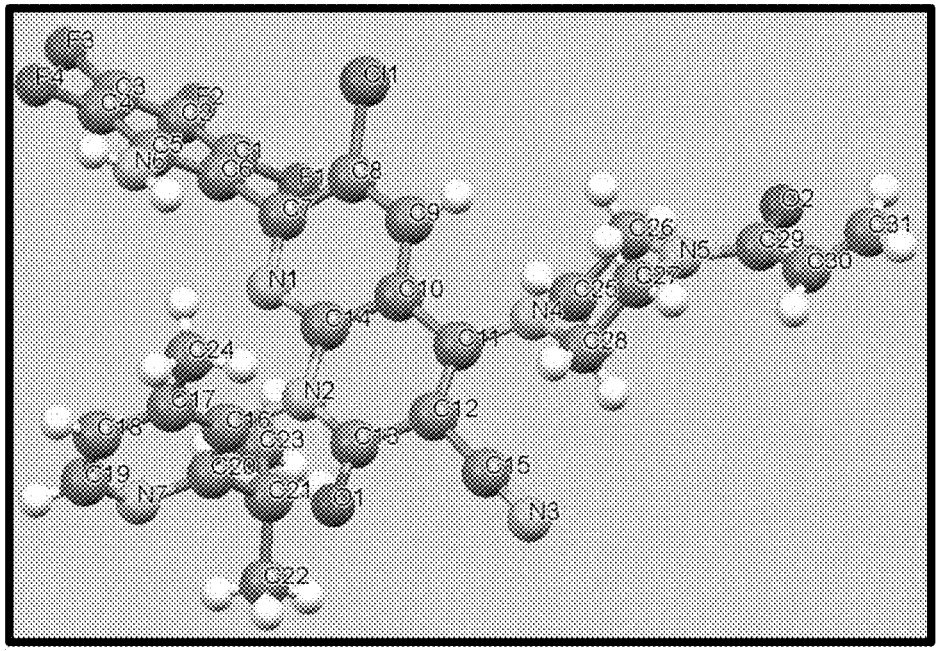
FIG. 1 is the ball and stick model of the absolute configuration of Compound 1-2.

Compounds of the present invention can be synthesized from commercially available reagents using the synthetic methods described herein. The examples which outline specific synthetic route below are meant to provide guidance to the ordinarily skilled synthetic chemist, who will readily appreciate that the solvent, concentration, reagent, protecting group, order of synthetic steps, time, temperature, and the like can be modified as necessary, well within the skill and judgment of the ordinarily skilled artisan.

The following Examples are provided to better illustrate the present invention. All parts and percentages are by weight and all temperatures are degrees Celsius, unless explicitly stated otherwise. The following abbreviations in Table 1 have been used in the examples:

TABLE 1

| | |
|---|---|
| MeOH | Methanol |
| EtOH | Ethanol |
| DCM | Dichloromethane |
| TEA | Triethylamine |
| TFA | Trifluoroacetic acid |
| DMF | N,N-Dimethylformamide |
| DMA | N,N-dimethylacetamide |
| THF | Tetrahydrofuran |
| MeCN/ACN | Acetonitrile |
| HATU | 2-(7-Azabenzotriazol-1-yl)-N,N,N',N'-tetramethyluronium hexafluorophosphate |
| EDCI | 1-Ethyl-3-(3-dimethylaminopropyl)-carbodiimide hydrochloride |
| HOBT | 1-Hydroxybenzotriazole |
| LiHMDS | Lithium Hexamethyldisilazide |
| Hunig's base/DIEA/DIPEA | N,N-Diisopropylethylamine |
| EA | Ethyl acetate |
| min | Minute(s) |
| h | Hour(s) |
| Pre-TLC | Preparative thin layer chromatography |
| prep-HPLC | Preparative High Performance Liquid Chromatography |
| SFC | Supercritical fluid chromatography |
| Pd(dppf)Cl$_2$ | [1,1'-Bis(diphenylphosphino)ferrocene]dichloropalladium(II) |
| R.T./r.t. | Room temperature(20° C.~30° C.) |
| AcOH | Acetic acid |
| Pd(PPh$_3$)$_4$ | Tetrakis(triphenylphosphine)palladium |
| NCS | N-Chlorosuccinimide |
| Hex | n-Hexane |
| PPTS | Pyridinium 4-toluenesulfonate |
| IPA | Isopropanol |
| DHP | 3,4-Dihydro-2H-pyran |
| a.q./aq | Aqueous |
| AcOK/KOAc | Potassium acetate |
| NMP | Methyl-2-pyrrolidinone |

Example 1

4-(4-acryloylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 1"); (P)-4-(4-acryloylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 1-1"); and (M)-4-(4-acryloylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 1-2")

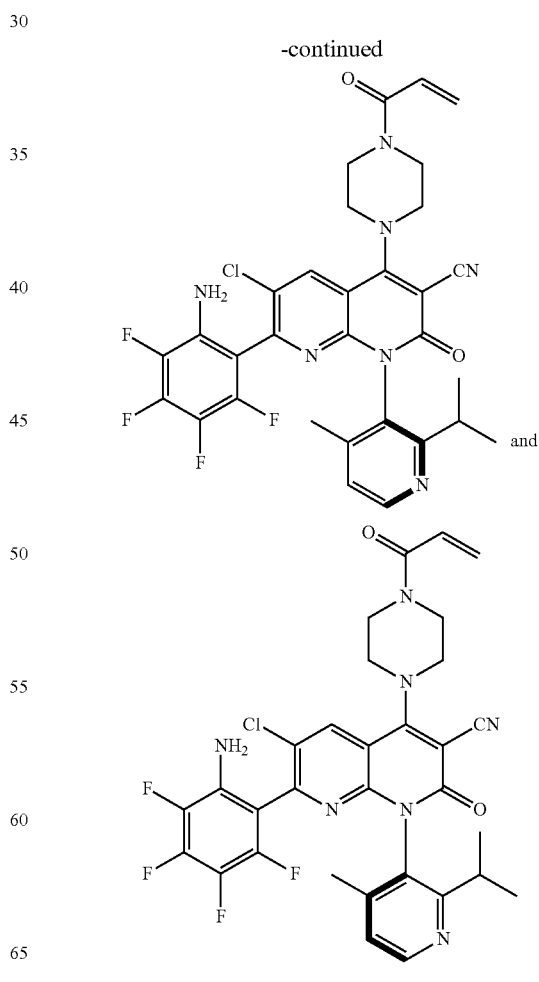

Step 1. 4-methyl-2-(prop-1-en-2-yl)pyridin-3-amine

Into a 350-mL sealed tube purged and maintained with an inert atmosphere of nitrogen, was placed 2-bromo-4-methylpyridin-3-amine (BD, APL099) (15.01 g, 80.25 mmol), 4,4,5,5-tetramethyl-2-(prop-1-en-2-yl)-1,3,2-dioxaborolane (BD, AQA827) (13.62 g, 81.05 mmol), Pd(dppf)Cl$_2$ (5.95 g, 8.03 mmol), K$_2$CO$_3$ (33.52 g, 240 mmol), dioxane (150 mL) and water (20 mL). The reaction mixture was stirred at 100° C. for 8 h. The reaction mixture was filtered and concentrated under vacuum. The residue was applied onto a silica gel column eluted with EA/hexane (v:v=2:3). This resulted in 11.2 g (94%) of 4-methyl-2-(prop-1-en-2-yl)pyridin-3-amine as yellow oil. LCMS: m/z=149 [M+1]$^+$.

Step 2. 2-isopropyl-4-methylpyridin-3-amine (Intermediate A)

Into a 250-mL round-bottom flask purged and maintained with an inert atmosphere of nitrogen, was placed 4-methyl-2-(prop-1-en-2-yl)pyridin-3-amine (11.2 g, 75.67 mmol) and MeOH (100 mL). Palladium on carbon (2.81 g) was added in three portions. The mixture was degassed under vacuum and then purged with H$_2$ (gas) for three cycles. The mixture was stirred for 3 h at 25° C. The resulting mixture was filtered, the filtrate was concentrated under vacuum. This resulted in 11 g (crude) of 2-isopropyl-4-methylpyridin-3-amine which was used directly in the next step. LCMS: m/z=151 [M+1]$^+$.

Step 3. 2-cyano-N-(2-isopropyl-4-methylpyridin-3-yl)acetamide

Into a 100-mL round-bottom flask purged and maintained with an inert atmosphere of nitrogen, was placed 2-cyano-acetic acid (3 g, 35.27 mmol) and DCM (40 mL). Oxalyl chloride (6.2 g, 48.85 mmol) was added in dropwise. After the addition, DMF (0.1 mL) was added. The mixture was stirred for 3 h at 25° C. The resulting solution was concentrated under vacuum. This resulted in 3.10 g (crude) of 2-cyanoacetylchloride which was used directly in the next step.

Into a 100-mL round-bottom flask purged and maintained with an inert atmosphere of nitrogen, was placed 2-isopropyl-4-methylpyridin-3-amine (2.00 g, 13.31 mmol), TEA (5.40 g, 53.36 mmol) and DCM (40 mL) and stirred. The mixture was cooled to 0° C. and then 2-cyanoacetylchloride (3.10 g, crude) was added in dropwise. The resulting solution was stirred for further 2 h at room temperature. The reaction was then quenched by the addition of water (100 mL). The resulting solution was extracted with dichloromethane (3×50 mL), the organic layers were combined and washed with brine (50 mL), dried over anhydrous Na$_2$SO$_4$ and filtered, the filtrate was concentrated under vacuum and applied onto a silica gel column eluted with EA/hexane (v:v=3:2). This resulted in 1.00 g (34%) of 2-cyano-N-(2-isopropyl-4-methyl pyridin-3-yl)acetamide as yellow solid. LCMS: m/z=218 [M+1]$^+$.

Step 4. 2-cyano-N-(2-isopropyl-4-methylpyridin-3-yl)-3-oxo-3-(2,5,6-trichloropyridin-3-yl) propanamide Into a 100-mL round-bottom flask purged and maintained with an inert atmosphere of nitrogen, was placed 2,5,6-trichloronicotinic acid (5.01 g, 22.12 mmol) and SOCl$_2$ (30 mL). The mixture was heated to 80° C. and stirred for 2 h. The solution was concentrated under vacuum. This resulted in 5.10 g (crude) of 2,5,6-trichloronicotinoyl chloride which was used directly in the next step.

Into a 250-mL round-bottom flask, was placed 2-cyano-N-(2-isopropyl-4-methylpyridin-3-yl)acetamide (3.01 g, 13.85 mmol) and THF (40 mL). The mixture was stirred at 0° C. NaH (1.16 g, 28.99 mmol) was added in three batches. The mixture was stirred at 0° C. for further 40 min. Then 2,5,6-trichloronicotinoyl chloride (3.19 g, 13.03 mmol) in THF (10 mL) was added in dropwise. The reaction mixture was stirred at 25° C. for 2 h. The reaction mixture was concentrated under vacuum. The resulting crude product was further purified by C$_{18}$ column eluted with ACN/H$_2$O (v/v=1/3). This resulted in 5.89 g (crude) of 2-cyano-N-(2-isopropyl-4-methylpyridin-3-yl)-3-oxo-3-(2,5,6-trichloropyridin-3-yl)propanamide as yellow solid. LCMS: m/z=425 [M+1]$^+$.

Step 5. 6,7-dichloro-4-hydroxy-1-(2-isopropyl-4-methylpyridin-3-yl)-2-oxo-1,2-dihydro-1,8-naphthyridine-3-carbonitrile (Intermediate B)

Into a 250-mL round-bottom flask purged and maintained with an inert atmosphere of nitrogen, was placed 2-cyano-N-(2-isopropyl-4-methylpyridin-3-yl)-3-oxo-3-(2,5,6-trichloropyridin-3-yl)propanamide (5.89 g, 13.83 mmol) and THF (70 mL) and stirred at room temperature. NaH (2.73 g, 68.25 mmol) was added in batch-wise. The mixture was stirred at 50° C. for 2 h. The reaction mixture was concentrated under vacuum. The residue was dissolved in 100 mL water and adjusted pH to 7 with AcOH. The resulting solid was filtered and dried under vacuum to provide 5.85 g (108% in two steps) of 6,7-dichloro-4-hydroxy-1-(2-isopropyl-4-methylpyridin-3-yl)-2-oxo-1,2-dihydro-1,8-naphthyridine-3-car bonitrile as yellow solid. LCMS: m/z=389 [M+1]$^+$.

$^1$H NMR (400 MHz, DMSO-d$_6$) δ 8.77 (d, J=5.7 Hz, 1H), 8.38 (s, 1H), 7.89 (d, J=5.4 Hz, 1H), 3.01-2.88 (m, 1H), 2.19 (s, 3H), 1.21 (d, J=6.9 Hz, 3H), 1.14 (d, J=6.9 Hz, 3H).

The mixture of 6,7-dichloro-4-hydroxy-1-(2-isopropyl-4-methylpyridin-3-yl)-2-oxo-1,2-dihydro-1,8-naphthyridine-3-carbonitrile atropisomers (10.59 g, "Intermediate B") was purified by Chiral-Prep-HPLC with the following conditions: Column, CHIRALPAK IC, 3.0×100 mm, 3 µm; mobile phase, IPA/ACN=(v/v=1/1); detection wavelength, UV 210 nm. This resulted in 4.99 g (47%) of 6,7-dichloro-4-hydroxy-1-(2-isopropyl-4-methylpyridin-3-yl)-2-oxo-1,2-dihydro-1,8-naphthyridine-3-car bonitrile (the first eluting isomer, "Intermediate B-1", M or P atropisomer) as a brown solid;

$^1$H NMR (400 MHz, CD$_3$OD) δ 8.48 (s, 1H), 8.44 (d, J=5.0 Hz, 1H), 7.33-7.22 (m, 1H), 2.76-2.61 (m, 1H), 2.03 (s, 3H), 1.19 (d, J=6.8 Hz, 3H), 1.06 (d, J=6.8 Hz, 3H).

And 4.60 g (43%) of 6,7-dichloro-4-hydroxy-1-(2-isopropyl-4-methylpyridin-3-yl)-2-oxo-1,2-dihydro-1,8-naphthyridine-3-carbonitrile (the second eluting isomer, "Intermediate B-2", P or M atropisomer) as a brown solid;

$^1$H NMR (400 MHz, CD$_3$OD) δ 8.49 (s, 1H), 8.44 (d, J=5.0 Hz, 1H), 7.28 (d, J=5.0 Hz, 1H), 2.76-2.63 (m, 1H), 2.03 (s, 3H), 1.19 (d, J=6.8 Hz, 3H), 1.08-1.00 (m, 3H).

Step 6. 4,6,7-trichloro-1-(2-isopropyl-4-methylpyridin-3-yl)-2-oxo-1,2-dihydro-1,8-naphthyridine-3-carbonitrile Into a 50-mL round-bottom flask purged and maintained with an inert atmosphere of nitrogen, was placed 6,7- dichloro-4-hydroxy-1-(2-isopropyl-4-methylpyridin-3-yl)-2-oxo-1,2-dihydro-1,8-naphthyridine-3-car bonitrile (Intermediate B, 980 mg, 2.51 mmol), $POCl_3$ (1150 mg, 7.50 mmol), DIEA (1.32 g, 10.21 mmol) and acetonitrile (12 mL). The mixture was stirred at 80° C. for 2 h. The reaction mixture was cooled to room temperature and concentrated under vacuum. This resulted in crude 4,6,7-trichloro-1-(2-isopropyl-4-methyl pyridin-3-yl)-2-oxo-1,2-dihydro-1,8-naphthyridine-3-carbonitrile which was used directly in the next step.

Step 7. tert-butyl 4-(6,7-dichloro-3-cyano-1-(2-isopropyl-4-methylpyridin-3-yl)-2-oxo-1,2-dihydro-1,8-naphthyridin-4-yl)piperazine-1-carboxylate Into a 100-mL round-bottom flask purged and maintained with an inert atmosphere of nitrogen, was placed 4,6,7-trichloro-1-(2-isopropyl-4-methylpyridin-3-yl)-2-oxo-1,2-dihydro-1,8-naphthyridine-3-carbonitrile (1.20 g, crude) and acetonitrile (20 mL). DIEA (660 mg, 5.10 mmol) and tert-butyl piperazine-1-carboxylate (0.57 g, 3.06 mmol) were added. The reaction mixture was stirred for 2 h at room temperature. The reaction was then quenched by the addition of water (50 mL). The resulting solution was extracted with ethyl acetate (3×50 mL), the organic layers were combined and washed with brine (50 mL), dried over anhydrous $Na_2SO_4$, filtered and concentrated under vacuum. The residue was purified by silica gel column eluted with EA/hexane (v/v=30%~70%). This resulted in 0.92 g (65% in two steps) of tert-butyl 4-(6,7-dichloro-3-cyano-1-(2-isopropyl-4-methylpyridin-3-yl)-2-oxo-1,2-dihydro-1,8-naphthyridin-4-yl)piperazine-1-carboxylate as yellow solid. LCMS: m/z=557 $[M+1]^+$.

Step 8. 4-(4-acryloylpiperazin-1-yl)-6,7-dichloro-1-(2-isopropyl-4-methylpyridin-3-yl)-2-oxo-1,2-dihydro-1,8-naphthyridine-3-carbonitrile (Intermediate C)

Into a 20-mL sealed tube purged and maintained with an inert atmosphere of nitrogen, was placed tert-butyl 4-(6,7-dichloro-3-cyano-1-(2-isopropyl-4-methylpyridin-3-yl)-2-oxo-1,2-dihydro-1,8-naphthyridin-4-yl)piperazine-1-carboxylate (920 mg, 1.65 mmol), TFA (4 ml) and DCM (15 mL). The reaction mixture was stirred at room temperature for 2 h. The reaction mixture was concentrated under vacuum. The residue was dissolved by DCM (15 mL) in 50-mL round-bottom flask. DIEA (1.02 g, 10.08 mmol) was added. The reaction mixture was cooled to 0° C. and acryloyl chloride (190 mg, 2.09 mmol) was added. The mixture was stirred at room temperature for 2 h. The reaction was then quenched by the addition of water (30 mL). The resulting solution was extracted with ethyl acetate (3×50 mL), the organic layers were combined and washed with brine (30 mL), dried over anhydrous $Na_2SO_4$, filtered and concentrated under vacuum. The residue was purified by silica gel column eluted with EA/hexane (v/v=40%~80%). This resulted in 0.86 g (crude) of 4-(4-acryloylpiperazin-1-yl)-6,7-dichloro-1-(2-isopropyl-4-methylpyridin-3-yl)-2-oxo-1,2-dihydro-1,8-naphthyridine-3-carbonitrile as yellow solid. LCMS: m/z=511 $[M+1]^+$.

Step 9. 2-bromo-3,4,5,6-tetrafluoroaniline

Into a 50-mL round-bottom flask was placed 2,3,4,5-tetrafluoroaniline (1.99 g, 12.05 mmol), Sodium acetate (1.32 g, 16.09 mmol), iron (0.10 g, 1.79 mmol) and AcOH (7 mL). The reaction mixture was heated to 45° C. This was followed by the added of bromine (3.02 g, 18.90 mmol) in AcOH (7 mL). The reaction mixture was heated to 60° C. and stirred for 1.5 h. The reaction mixture was quenched by the addition of saturated aqueous $Na_2S_2O_3$ (30 mL). The resulting solution was extracted with ethyl acetate (2×50 mL), the organic layers were combined and washed with saturated aqueous $Na_2CO_3$ (50 mL) and brine (50 mL), dried over anhydrous $Na_2SO_4$, filtered and concentrated under vacuum. This resulted in 2.28 g (77%) of 2-bromo-3,4,5,6-tetrafluoroaniline as yellow solid. LCMS: m/z=244,246 $[M+1]^+$.

Step 10. 2,3,4,5-tetrafluoro-6-(4,4,5,5-tetramethyl-1,3,2-dioxaborolan-2-yl)aniline Into a 150-mL sealed tube purged and maintained with an inert atmosphere of nitrogen, was placed 2-bromo-3,4,5,6-tetrafluoroaniline (2.28 g, 9.35 mmol), bis(pinacolato)diboron (3.96 g, 15.59 mmol), $Pd(dppf)Cl_2$ (1.21 g, 1.65 mmol), AcOK (1.84 g, 18.75 mmol) and dioxane (20 mL). The reaction mixture was stirred at 100° C. for 2 h. The reaction mixture was filtered and concentrated under vacuum. The residue was applied onto a silica gel column eluted with EA/hexane (v/v=0%-20%). This resulted in 2.28 g (81% yield) of 2,3,4,5-tetrafluoro-6-(4,4,5,5-tetramethyl-1,3,2-dioxaborolan-2-yl)aniline as white solid. LCMS: m/z=210 $[M+1]^+$.

Step 11. 4-(4-acryloylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 1")

Into a 20-mL sealed tube purged and maintained with an inert atmosphere of nitrogen, was placed 4-(4-acryloylpiperazin-1-yl)-6,7-dichloro-1-(2-isopropyl-4-methylpyridin-3-yl)-2-oxo-1,2-dihydro-1,8-naphthyridine-3-carbonitrile (221 mg, 0.43 mmol), 2,3,4,5-tetrafluoro-6-(4,4,5,5-tetramethyl-1,3,2-dioxaborolan-2-yl)aniline (513 mg, 1.76 mmol), $Pd(PPh_3)_4$ (151 mg, 0.13 mmol), $Na_2CO_3$ (161 mg, 1.52 mmol), dioxane (5 mL) and water (0.5 mL). The reaction mixture was stirred at 80° C. for 1 h. The reaction mixture was filtered and concentrated under vacuum. The resulting crude product was further purified by $C_{18}$ column eluted with $CH_3CN/H_2O$ (v/v=40%~80%). This resulted in 7 mg (2% yield) of 4-(4-acryloylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 1") as yellow solid. LCMS: m/z=640 $[M+1]^+$.

$^1$H NMR (400 MHz, $CD_3OD$) δ 8.55 (s, 1H), 8.43 (d, J=5.0 Hz, 1H), 7.33-7.20 (m, 1H), 6.87 (dd, J=16.7, 10.6 Hz, 1H), 6.31 (d, J=16.9 Hz, 1H), 5.84 (d, J=10.6 Hz, 1H), 3.98 (d, J=23.5 Hz, 8H), 2.73 (d, J=28.0 Hz, 1H), 2.00 (d, J=31.9 Hz, 3H), 1.32-1.10 (m, 3H), 1.00 (dd, J=40.7, 6.8 Hz, 3H).

The mixture of 4-(4-acryloylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile atropisomers (356 mg, several batches) was purified by Chiral-Prep-HPLC with the following conditions: Column, CHIRALPAK IG, 3 cm×25 cm, 5 um; mobile phase, $CO_2$:EtOH=55:45; Detection wavelength, UV 220 nm. This resulted in 175 mg (49.16%) of 4-(4-acryloylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (the first eluting isomer, "Compound 1-1") as a yellow solid. LCMS: m/z=640 [M+1]$^+$.

$^1$H NMR (400 MHz, CD$_3$OD) δ 8.45 (d, J=1.9 Hz, 1H), 8.34 (d, J=5.0 Hz, 1H), 7.17 (d, J=5.0 Hz, 1H), 6.78 (dd, J=16.8, 10.6 Hz, 1H), 6.21 (dd, J=16.8, 2.0 Hz, 1H), 5.74 (dd, J=10.6, 2.0 Hz, 1H), 4.02-3.72 (m, 8H), 2.70-2.58 (m, 1H), 1.97-1.88 (m, 3H), 1.07 (dd, J=8.2, 6.7 Hz, 3H), 0.97-0.88 (m, 3H).

And 184 mg (51.69%) of 4-(4-acryloylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (the second eluting isomer, "Compound 1-2") as a yellow solid. LCMS: m/z=640 [M+1]$^+$.

$^1$H NMR (400 MHz, CD$_3$OD) δ 8.57 (s, 1H), 8.45 (d, J=5.0 Hz, 1H), 7.31 (d, J=4.7 Hz, 1H), 6.88 (dd, J=16.7, 10.7 Hz, 1H), 6.32 (d, J=16.8 Hz, 1H), 5.88 (d, J=10.5 Hz, 1H), 4.08-3.92 (m, 8H), 2.81-2.66 (m, 1H), 2.06-1.98 (m, 3H), 1.18 (t, J=7.4 Hz, 3H), 1.06-0.96 (in, 3H).

About 10 mg Compound 1-2 was taken into a glass vial and dissolved with 0.8 mL ethanol and 0.4 mL n-heptane. The clear solution was evaporated to dryness at room temperature through a small hole to obtain the bulk-like crystals as the sample of the testing of single crystal diffraction using the following instrument and parameters in Table 2:

TABLE 2

Instrument and Parameters

| | |
|---|---|
| Instrument | Single Crystal Diffractometer |
| Model | Bruker SMART APEX II |
| Detector Model | 4K CCD |
| Sources | Enhance Cu radiation |
| Lens | |
| Temperature | 293.44 K |
| Wavelength | 1.54 Å |

The results are shown in Table 3, Table 4, Table 5, Table 6 and Table 7.

Crystallographic Data

TABLE 3

Crystallographic Data and Structure Refinement for Compound 1-2

| Phase Data | |
|---|---|
| Formula | C$_{31}$H$_{26}$ClF$_4$N$_7$O$_2$ |
| Formula Weight | 640.04 |
| Crystal System | Monoclinic |
| Space group | C2 |
| Cell Parameters | a = 20.6796 (7) Å; b = 11.2352 (4) Å; c = 14.0148 (5) Å; α = γ = 90.00°; β = 91.971 (2) |
| Cell Ratio | a/b = 1.8406; b/c = 0.8017; c/a = 0.6777 |
| Z | 4 |
| Cell Volume | 3254.3 (2) Å$^3$ |
| Calc. density | 1.306 g/cm$^3$ |
| Flack | 0.07 (3) |
| R-indices R1 | 0.0962 |
| R-indices WR2 | 0.1665 |
| Goodness-of-Fit, S | 1.015 |
| R$_{sigma}$ | 0.0799 |
| R$_{int}$ | 0.0923 |

Molecular Structure of Compound 1-2

TABLE 4

Molecular Structure of Compound 1-2

Figure 2:
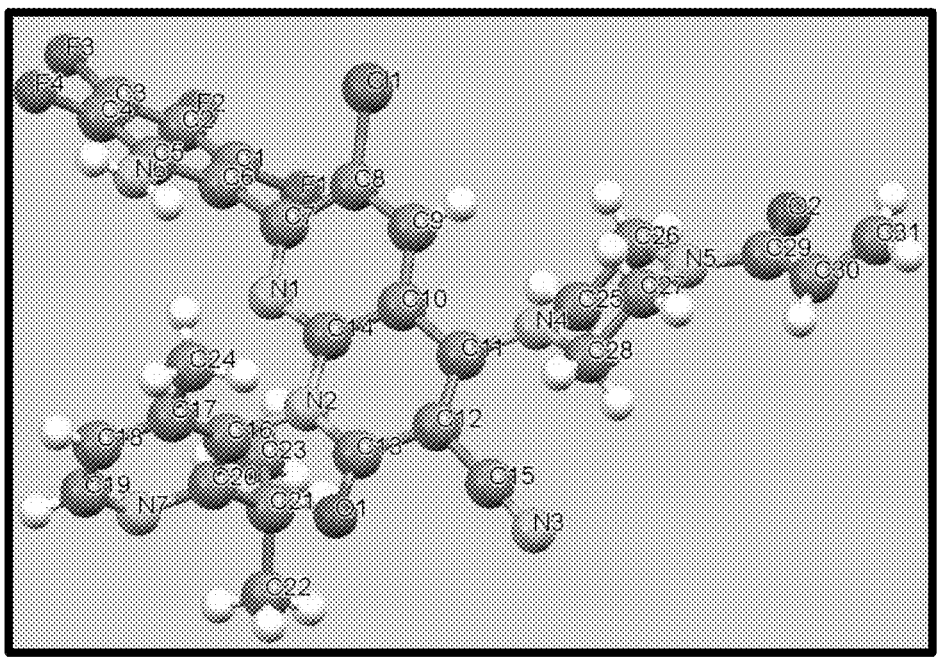
FIG. 2 is the ellipsoid model of the absolute configuration of Compound 1-2.
Figure 3:
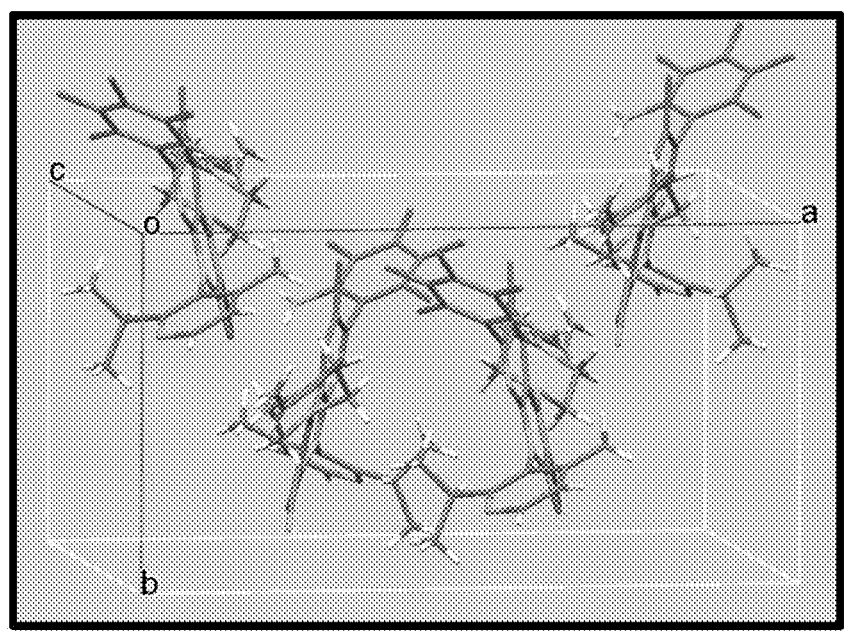
FIG. 3 is the graph of unit cell structure of single crystal diffraction for Compound 1-2.
Figure 4:
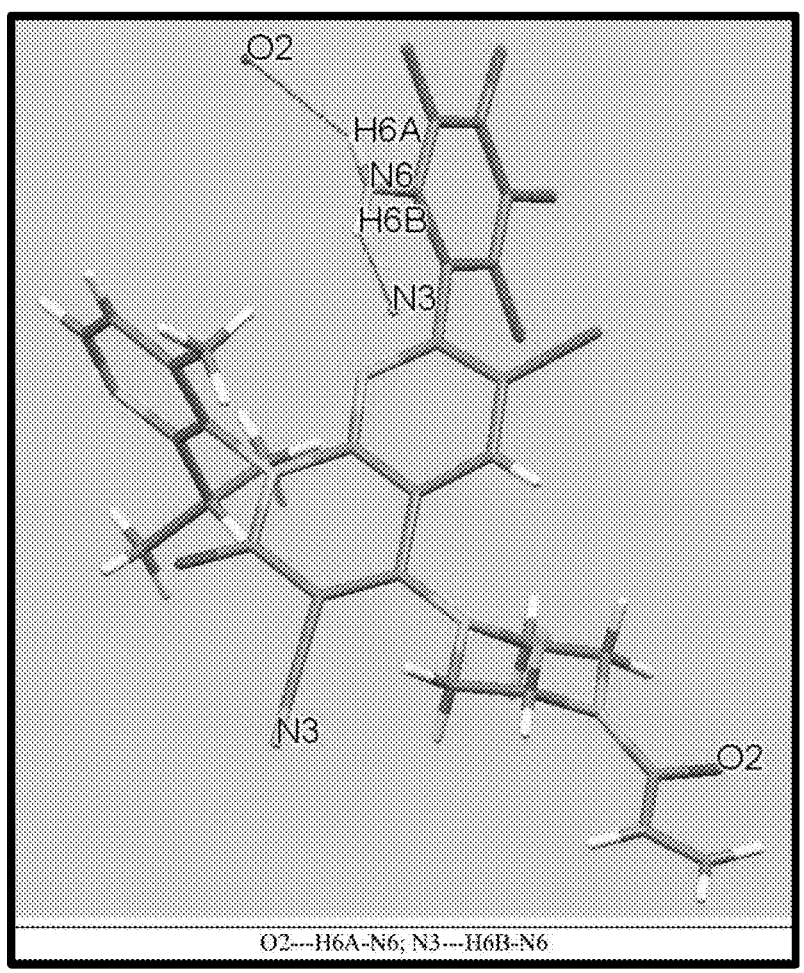
FIG. 4 is the graph of hydrogen bond of single crystal diffraction for Compound 1-2.
Figure 5:
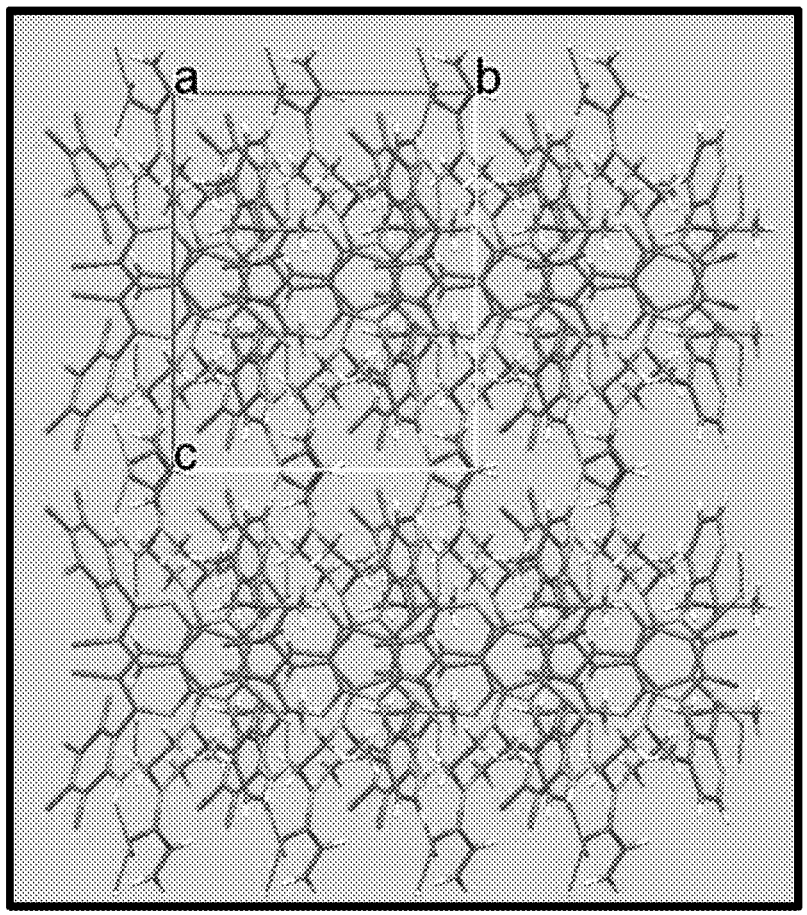
FIG. 5 is the graph of 3D structure-a direction of single crystal diffraction for Compound 1-2.
Figure 6:
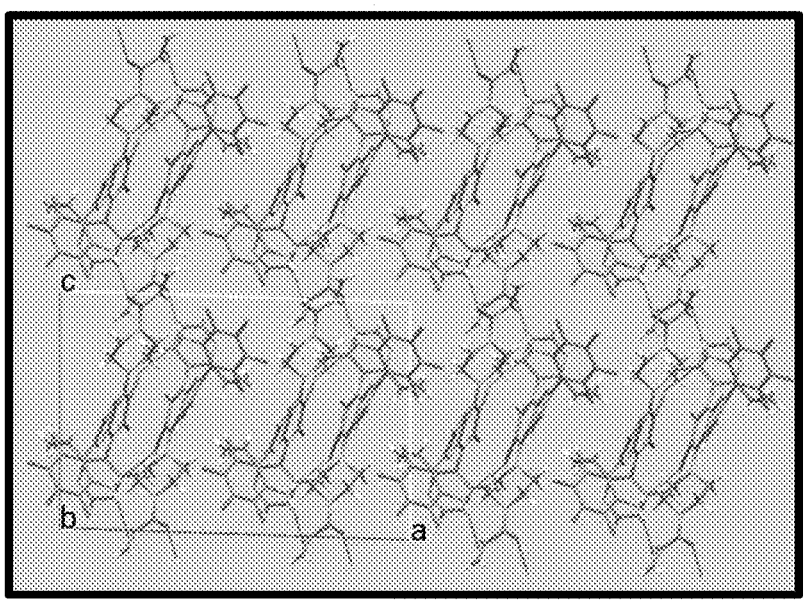
FIG. 6 is the graph of 3D structure-b direction of single crystal diffraction for Compound 1-2.
Figure 7:
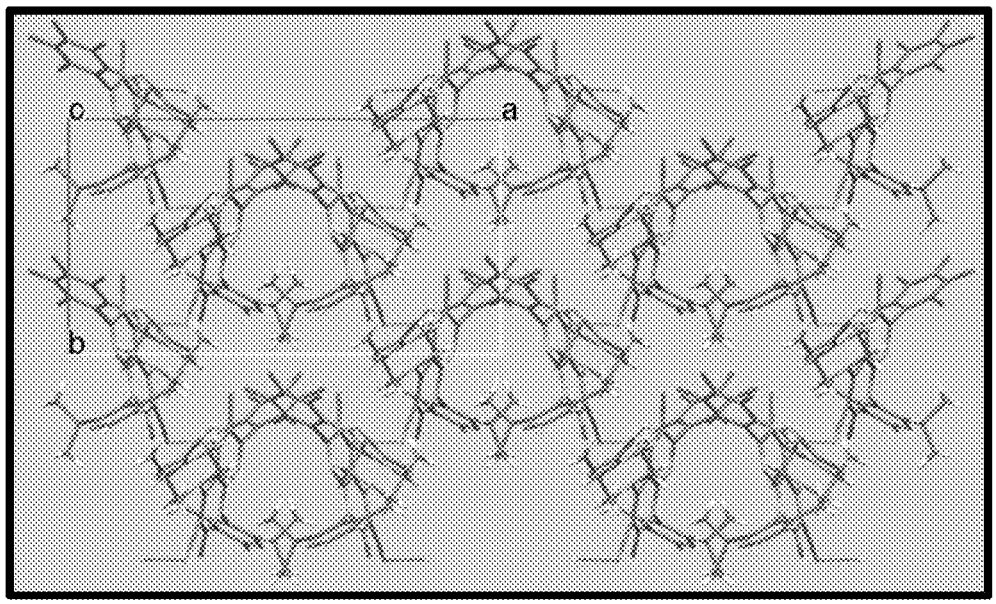
FIG. 7 is the graph of 3D structure-c direction of single crystal diffraction for Compound 1-2.

| | Results |
|---|---|
| Molecular Absolute Configuration in single crystal | Planar chirality (Axis chirality) M |
| Molecular Ball and Stick Model in single crystal | FIG. 1 |
| Molecular Ellipsoid Model in single crystal | FIG. 2 |
| Structure of Absolute Configuration | 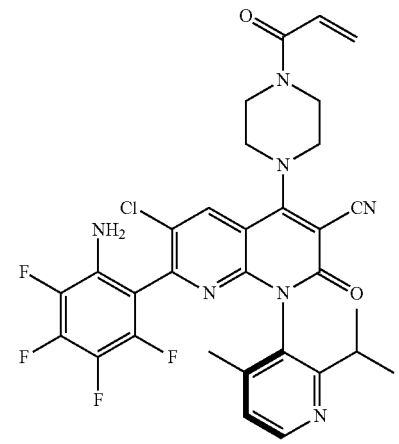 |
| Unit cell Structure | FIG. 3 |
| Main Hydrogen Bond In single crystal | FIG. 4 |
| Proton Transfer in Single crystal | — |
| 3D Structure-a Direction Looking From a Direction | Network FIG. 5 |
| 3D Structure-b Direction Looking From b | Chained and Laminated FIG. 6 |
| 3D Structure-c Direction Looking From c Direction | Chained and Laminated FIG. 7 |

Crystal Structure Solution Data

TABLE 5

Atomic Coordinates (×10$^4$) and Equivalent Isotropic Displacement Parameters (Å$^2$ × 10$^3$) for Compound 1-2. U(eq) is Defined as One Third of the Trace of the Orthogonalized U$^{ij}$ Tensor.

| Atom | x | y | z | U(eq) |
|---|---|---|---|---|
| Cl1 | 6246.0(6) | 1711.4(11) | 4631.9(9) | 90.2(4) |
| F1 | 4785.8(15) | 2906(3) | 3954(3) | 117.0(11) |
| F2 | 4111.9(15) | 1499(4) | 2704(3) | 136.7(14) |
| F3 | 4659(2) | 862(4) | 1040(3) | 148.9(16) |
| F4 | 5807(2) | 1798(5) | 582(2) | 153.1(16) |
| O1 | 6947.1(19) | 8554(3) | 4282(3) | 103.3(12) |
| O2 | 6947(2) | 3659(5) | 9789(3) | 127.4(16) |
| N1 | 6087.9(17) | 4937(3) | 3501(3) | 68.6(9) |
| N2 | 6491.6(17) | 6770(4) | 3932(2) | 72.5(9) |
| N3 | 7296(3) | 8781(6) | 6695(4) | 133(2) |
| N4 | 6971.7(18) | 5546(4) | 6708(3) | 76.7(10) |
| N6 | 6493(2) | 3262(5) | 1777(3) | 105.7(15) |
| N7 | 5536(3) | 8178(6) | 1965(5) | 148(2) |
| C1 | 5043(3) | 2606(5) | 3116(4) | 84.7(13) |
| C2 | 4701(3) | 1929(5) | 2488(5) | 93.3(16) |
| C3 | 4966(3) | 1641(6) | 1637(4) | 100.9(17) |
| C4 | 5555(3) | 2081(5) | 1423(4) | 97.7(17) |
| C5 | 5901(2) | 2829(4) | 2034(3) | 79.3(13) |
| C6 | 5646(2) | 3082(4) | 2919(3) | 71.5(11) |
| C7 | 6001(2) | 3774(4) | 3662(3) | 70.8(12) |

TABLE 5-continued

Atomic Coordinates (×10⁴) and Equivalent Isotropic Displacement Parameters (Å² × 10³) for Compound 1-2. U(eq) is Defined as One Third of the Trace of the Orthogonalized $U^{ij}$ Tensor.

| Atom | x | y | z | U(eq) |
|---|---|---|---|---|
| C8 | 6264(2) | 3232(4) | 4494(3) | 69.3(11) |
| C9 | 6532(2) | 3936(4) | 5196(3) | 70.3(11) |
| C10 | 6571(2) | 5161(4) | 5077(3) | 64.6(10) |
| C11 | 6846(2) | 5977(5) | 5801(3) | 75.2(13) |
| C12 | 6960(2) | 7121(4) | 5505(3) | 73.5(12) |
| C13 | 6820(2) | 7551(5) | 4547(4) | 79.2(13) |
| C14 | 6379(2) | 5597(4) | 4184(3) | 68.9(11) |
| C15 | 7166(3) | 8039(6) | 6156(4) | 94.6(16) |
| C16 | 6309(3) | 7206(4) | 2980(4) | 86.0(15) |
| C17 | 6749(4) | 7054(5) | 2262(4) | 110(2) |
| C18 | 6535(6) | 7460(8) | 1367(5) | 146(3) |
| C19 | 5946(6) | 8011(11) | 1271(7) | 166(4) |
| C20 | 5716(3) | 7763(6) | 2858(4) | 98.4(17) |
| C21 | 5247(3) | 7954(6) | 3613(5) | 114(2) |
| C23 | 4722(4) | 7012(9) | 3532(8) | 173(4) |
| C22 | 4967(6) | 9207(9) | 3602(9) | 199(4) |
| C24 | 7389(4) | 6458(7) | 2421(6) | 142(3) |
| C25 | 6453(5) | 5039(9) | 7253(8) | 79(2) |
| C26 | 6758(4) | 4128(9) | 7917(7) | 85(2) |
| N5 | 7274(4) | 4605(7) | 8506(6) | 85.7(18) |
| C27 | 7753(4) | 5199(8) | 7924(6) | 83.4(19) |
| C28 | 7476(6) | 6148(10) | 7310(8) | 84(2) |
| C25' | 6610(9) | 4538(16) | 7194(14) | 85(3) |
| C26' | 6480(7) | 4955(14) | 8202(9) | 87(2) |
| N5' | 7092(6) | 5244(12) | 8726(9) | 88.7(18) |
| C27' | 7501(7) | 6051(13) | 8300(9) | 88(2) |
| C28' | 7620(9) | 5650(16) | 7238(14) | 87(3) |
| C29 | 7324(3) | 4417(7) | 9488(4) | 109.7(19) |
| C30 | 7861(3) | 4907(7) | 10040(4) | 112(2) |
| C31 | 8076(4) | 4358(8) | 10783(5) | 128(2) |

TABLE 6

Hydrogen Coordinates (×10⁴) and Isotropic Displacement Parameters (Å² × 10³) for Compound 1-2.

| Atom | x | y | z | U(eq) |
|---|---|---|---|---|
| H6A | 6646 | 3067 | 1236 | 127 |
| H6B | 6709 | 3728 | 2156 | 127 |
| H9 | 6691 | 3591 | 5761 | 84 |
| H18 | 6790 | 7358 | 839 | 175 |
| H19 | 5823 | 8293 | 668 | 199 |
| H21 | 5478 | 7841 | 4229 | 137 |
| H23A | 4551 | 6982 | 2887 | 259 |
| H23B | 4381 | 7207 | 3953 | 259 |
| H23C | 4901 | 6250 | 3705 | 259 |
| H22A | 4702 | 9317 | 3034 | 299 |
| H22B | 5314 | 9777 | 3614 | 299 |
| H22C | 4710 | 9319 | 4153 | 299 |
| H24A | 7549 | 6613 | 3059 | 214 |
| H24B | 7689 | 6762 | 1973 | 214 |
| H24C | 7339 | 5615 | 2331 | 214 |
| H25A | 6133 | 4666 | 6828 | 95 |
| H25B | 6242 | 5654 | 7614 | 95 |
| H26A | 6429 | 3808 | 8321 | 102 |
| H26B | 6924 | 3477 | 7542 | 102 |
| H27A | 7955 | 4610 | 7525 | 100 |
| H27B | 8088 | 5538 | 8342 | 100 |
| H28A | 7804 | 6496 | 6919 | 101 |
| H28B | 7288 | 6770 | 7692 | 101 |
| H25C | 6206 | 4369 | 6849 | 102 |
| H25D | 6870 | 3820 | 7212 | 102 |
| H26C | 6205 | 5655 | 8174 | 104 |
| H26D | 6255 | 4335 | 8539 | 104 |
| H27C | 7910 | 6088 | 8659 | 106 |
| H27D | 7307 | 6838 | 8301 | 106 |
| H28C | 7888 | 6231 | 6926 | 104 |
| H28D | 7842 | 4889 | 7236 | 104 |
| H30 | 8050 | 5618 | 9856 | 135 |
| H31A | 7886 | 3647 | 10965 | 153 |
| H31B | 8423 | 4669 | 11143 | 153 |

TABLE 7

Anisotropic Displacement Parameters (Å² × 10³) for Compound 1-2. The Anisotropic Displacement Factor Exponent Takes the Form: $-2\pi^2[h^2 a^{*2}U_{11} + \ldots + 2 h k a^* b^* U_{12}]$

| Atom | $U_{11}$ | $U_{22}$ | $U_{33}$ | $U_{23}$ | $U_{13}$ | $U_{12}$ |
|---|---|---|---|---|---|---|
| Cl1 | 104.2(9) | 71.6(7) | 94.8(9) | 11.9(6) | 4.1(7) | −1.6(7) |
| F1 | 91(2) | 142(3) | 120(3) | −12(2) | 35.8(19) | −15.5(19) |
| F2 | 93(2) | 156(3) | 159(3) | 23(3) | −15(2) | −45(2) |
| F3 | 178(3) | 164(3) | 101(3) | 13(2) | −45(2) | −73(3) |
| F4 | 175(3) | 205(4) | 80(2) | −41(3) | 9(2) | −65(3) |
| O1 | 116(3) | 81(2) | 113(3) | 11(2) | −1(2) | −27(2) |
| O2 | 126(3) | 181(5) | 76(3) | 27(3) | 11(2) | −32(3) |
| N1 | 72(2) | 63(2) | 71(2) | 3.0(17) | 4.7(19) | −2.8(17) |
| N2 | 83(2) | 75(2) | 60(2) | 12.0(19) | 3.0(18) | −11(2) |
| N3 | 137(5) | 136(5) | 125(5) | −46(4) | 7(4) | −27(4) |
| N4 | 75(2) | 96(3) | 59(2) | 2.3(18) | 5.7(19) | −17(2) |
| N6 | 97(3) | 155(4) | 66(3) | −17(3) | 19(2) | −41(3) |
| N7 | 140(5) | 166(6) | 137(5) | 70(5) | −27(4) | −38(4) |
| C1 | 80(3) | 90(3) | 85(4) | 2(3) | 12(3) | −4(3) |
| C2 | 72(3) | 93(4) | 113(4) | 19(3) | −14(3) | −25(3) |
| C3 | 107(4) | 109(4) | 85(4) | 15(3) | −33(3) | −27(4) |
| C4 | 109(4) | 128(5) | 55(3) | −7(3) | −6(3) | −19(3) |
| C5 | 89(3) | 87(3) | 62(3) | 5(2) | 0(3) | −11(3) |
| C6 | 75(3) | 73(3) | 66(3) | −1(2) | 5(2) | −12(2) |
| C7 | 68(3) | 76(3) | 70(3) | 2(2) | 21(2) | 0(2) |
| C8 | 77(3) | 60(3) | 71(3) | 15(2) | 7(2) | −1(2) |
| C9 | 68(3) | 80(3) | 62(3) | 2(2) | 9(2) | −2(2) |
| C10 | 68(3) | 68(3) | 58(2) | 9.1(18) | 5(2) | −3(2) |
| C11 | 64(3) | 98(4) | 64(3) | −4(2) | 11(2) | −12(2) |
| C12 | 68(3) | 84(3) | 70(3) | −9(2) | 9(2) | −18(2) |
| C13 | 73(3) | 83(3) | 82(3) | 3(3) | 6(2) | −15(3) |
| C14 | 69(3) | 65(3) | 73(3) | 2(2) | 20(2) | −10(2) |
| C15 | 95(4) | 102(4) | 88(4) | −12(3) | 15(3) | −10(3) |
| C16 | 111(4) | 78(3) | 69(3) | 15(2) | 1(3) | −22(3) |

TABLE 7-continued

Anisotropic Displacement Parameters (Å² × 10³) for Compound 1-2. The Anisotropic Displacement Factor Exponent Takes the Form: $-2\pi^2[h^2 a^{*2}U_{11} + \ldots + 2 h k a^* b^* U_{12}]$

| Atom | $U_{11}$ | $U_{22}$ | $U_{33}$ | $U_{23}$ | $U_{13}$ | $U_{12}$ |
|---|---|---|---|---|---|---|
| C17 | 155(6) | 101(4) | 76(4) | 20(3) | 29(4) | −26(4) |
| C18 | 219(10) | 138(6) | 82(5) | 28(4) | 21(6) | −29(6) |
| C19 | 186(9) | 200(10) | 111(7) | 70(6) | −19(7) | −54(8) |
| C20 | 95(4) | 110(4) | 90(4) | 35(3) | −6(3) | −22(3) |
| C21 | 85(4) | 111(5) | 145(6) | 29(4) | 2(4) | 1(3) |
| C23 | 101(5) | 180(9) | 239(10) | −11(7) | 35(6) | −29(5) |
| C22 | 213(10) | 132(7) | 252(12) | 30(7) | −6(9) | 37(7) |
| C24 | 162(6) | 114(6) | 156(7) | 6(4) | 67(5) | 10(5) |
| C25 | 72(5) | 94(5) | 71(5) | 14(4) | 9(4) | −14(4) |
| C26 | 79(5) | 95(5) | 81(5) | 13(4) | 7(4) | −16(4) |
| N5 | 92(4) | 91(5) | 74(4) | 12(3) | 8(3) | −7(4) |
| C27 | 88(5) | 97(5) | 65(4) | 0(4) | 0(4) | −16(4) |
| C28 | 87(5) | 97(6) | 67(5) | −2(4) | 0(4) | −15(4) |
| C25' | 90(6) | 93(6) | 72(6) | 7(5) | 12(5) | −12(5) |
| C26' | 92(5) | 95(5) | 74(5) | 7(4) | 11(4) | −8(4) |
| N5' | 97(4) | 95(5) | 75(4) | 8(4) | 7(3) | −9(4) |
| C27' | 97(5) | 93(5) | 75(5) | 8(4) | 5(4) | −12(4) |
| C28' | 95(6) | 91(6) | 75(6) | 7(5) | 3(5) | −16(5) |
| C29 | 107(5) | 150(6) | 72(4) | 10(3) | 11(3) | −23(4) |
| C30 | 138(6) | 131(5) | 68(4) | 3(4) | −1(4) | −18(4) |
| C31 | 129(6) | 164(6) | 90(5) | −6(4) | 9(4) | −4(5) |

The following conclusions were obtained by crystal structure analysis:

The crystal system of Compound 1-2 is monoclinic and has two symmetries and one centering vector, space group is $C_2$.

The single crystal of Compound 1-2 have four molecules in a unit cell.

Compound 1-2 has one planar chirality (axis chirality). Absolute configuration is M.

Unit cell has two kinds of hydrogen bonds, they are respectively O2-H6A-N6, N3-H6B—N6. The three-dimensional structure of the chain, laminate and network is formed through hydrogen bond and van der Waals force in the crystal.

Example 2

4-(4-acryloylpiperazin-1-yl)-7-(3-amino-2,6-dichloro-4,5-difluorophenyl)-6-chloro-1-(2-isopropyl-4-methylpyridin-3-yl)-2-oxo-1,2-dihydro-1,8-naphthyridine-3-carbonitrile ("Compound 2")

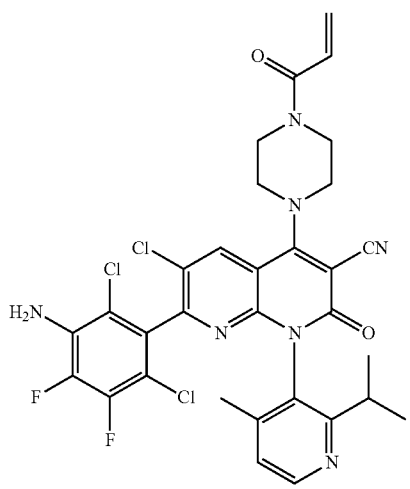 [SMILES: C=CC(=O)N1CCN(c2c(C#N)c(=O)n(-c3c(C)ccnc3C(C)C)c3nc(-c4c(Cl)c(N)c(F)c(F)c4Cl)c(Cl)cc23)CC1]

Step 1. 2-(3,4-difluoro-5-nitrophenyl)-4,4,5,5-tetramethyl-1,3,2-dioxaborolane

Into a 40-mL sealed tube purged and maintained with an inert atmosphere of nitrogen, was placed 5-bromo-1,2-difluoro-3-nitrobenzene (207 mg, 0.38 mmol), bis(pinacolato)diboron (2.16 g, 8.51 mmol), Pd(dppf)Cl₂ (0.322 g, 0.44 mmol), KOAc (1.199 g, 12.22 mmol) and dioxane (10 mL). The reaction mixture was stirred at 100° C. for 2 h. The reaction mixture was filtered and concentrated under vacuum. The residue was applied onto a silica gel column eluted with EA/hexane (v/v=0%-5%). This resulted in 1.528 g (crude) of 2-(3,4-difluoro-5-nitrophenyl)-4,4,5,5-tetramethyl-1,3,2-dioxaborolane as off-white solid.

Step 2. 2,3-difluoro-5-(4,4,5,5-tetramethyl-1,3,2-dioxaborolan-2-yl)aniline

Into a 40-mL round-bottom flask was placed 2-(3,4-difluoro-5-nitrophenyl)-4,4,5,5-tetramethyl-1,3,2-dioxaborolane (1.489 g, 5.22 mmol), iron (1.546 g, 27.68 mmol), NH₄Cl (2.654 g, 49.62 mmol), EtOH (15 mL) and H₂O (5 mL). The reaction mixture was stirred at 80° C. for 1 h. The reaction mixture was filtered and concentrated under vacuum. The residue was washed with DCM (20 mL), filtered and concentrated under vacuum. This resulted in 0.957 g of 2,3-difluoro-5-(4,4,5,5-tetramethyl-1,3,2-dioxaborolan-2-yl)aniline as off-white solid. LCMS: m/z=256 [M+1]⁺.

Step 3. 4-(4-acryloylpiperazin-1-yl)-7-(3-amino-4,5-difluorophenyl)-6-chloro-1-(2-isopropyl-4-methyl pyridin-3-yl)-2-oxo-1,2-dihydro-1,8-naphthyridine-3-carbonitrile Into a 20-mL sealed tube purged and maintained with an inert atmosphere of nitrogen, was placed 4-(4-acryloylpiperazin-1-yl)-6,7-dichloro-1-(2-isopropyl-4-methylpyridin-3-yl)-2-oxo-1,2-dihydro-1,8-naphthyridine-3-carbonitrile (0.21 g, 0.41 mmol), 2,3-difluoro-5-(4,4,5,5-tetramethyl-1,3,2-dioxaborolan-2-yl)aniline (0.279 g, 1.09 mmol), Pd(PPh$_3$)$_4$ (57 mg, 0.05 mmol), Na$_2$CO$_3$ (206 mg, 1.94 mmol), dioxane (5 mL) and water (1 mL). The reaction mixture was stirred at 80° C. for 1 h. The reaction mixture was filtered and concentrated under vacuum. The residue was applied onto a silica gel column eluted with EA/hexane (v/v=50%-100%). This resulted in 125 mg of 4-(4-acryloylpiperazin-1-yl)-7-(3-amino-4,5-difluorophenyl)-6-chloro-1-(2-isopropyl-4-methylpyridin-3-yl)-2-oxo-1,2-dihydro-1,8-naphthyridine-3-carbonitrile as yellow solid. LCMS: m/z=604 [M+1]$^+$.

Step 4. 4-(4-acryloylpiperazin-1-yl)-7-(3-amino-2,6-dichloro-4,5-difluorophenyl)-6-chloro-1-(2-isopropyl-4-methylpyridin-3-yl)-2-oxo-1,2-dihydro-1,8-naphthyridine-3-carbonitrile ("Compound 2")

Into a 50-mL round-bottom flask purged and maintained with an inert atmosphere of nitrogen, was placed 4-(4-acryloylpiperazin-1-yl)-7-(3-amino-4,5-difluorophenyl)-6-chloro-1-(2-isopropyl-4-methylpyridin-3-yl)-2-oxo-1,2-dihydro-1,8-naphthyridine-3-carbonitrile (103 mg, 170.52 μmol), NCS (51 mg, 381.93 μmol) and DMA (1.5 mL). The reaction mixture was stirred for 15 h at room temperature. The reaction was then quenched by the addition of H$_2$O (20 mL). The resulting solution was extracted with ethyl acetate (3×20 mL), the organic layers were combined and concentrated under vacuum. The residues was purified by prep-HPLC eluted with CH$_3$CN/H$_2$O (v/v=7/1). This resulted in 30 mg (26%) of 4-(4-acryloylpiperazin-1-yl)-7-(3-amino-2,6-dichloro-4,5-difluorophenyl)-6-chloro-1-(2-isopropyl-4-methylpyridin-3-yl)-2-oxo-1,2-dihydro-1,8-naphthyridine-3-carbonitrile ("Compound 2"). LCMS: m/z=672 [M+1]$^+$.

$^1$H NMR (400 MHz, CD$_3$OD) δ 8.56 (s, 1H), 8.40 (d, J=5.0 Hz, 1H), 7.29-7.15 (m, 1H), 6.87 (dd, J=16.8, 10.6 Hz, 1H), 6.30 (d, J=16.8 Hz, 1H), 5.83 (d, J=10.7 Hz, 1H), 4.30-3.77 (m, 8H), 2.85-2.66 (m, 1H), 1.99 (s, 3H), 1.18 (d, J=6.7 Hz, 3H), 1.01 (d, J=6.8 Hz, 3H).

Example 3

4-(4-acryloylpiperazin-1-yl)-7-(2-amino-3-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 3")

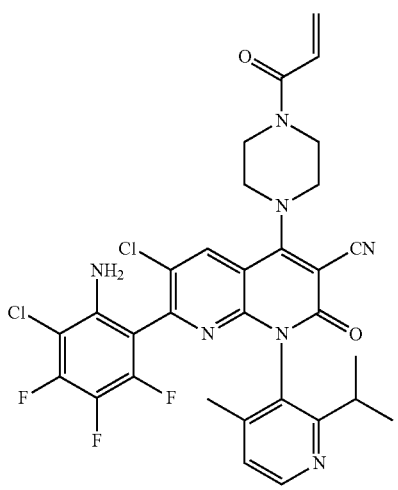 [SMILES: C=CC(=O)N1CCN(c2c(C#N)c(=O)n(-c3c(C)ccnc3C(C)C)c3nc(-c4c(N)c(Cl)c(F)c(F)c4F)c(Cl)cc23)CC1]

Step 1. 2-bromo-3,4,5-trifluoroaniline

Into a 100-mL round-bottom flask was placed 2-bromo-3,4,5-trifluoro-1-nitrobenzene (2.64 g, 10.31 mmol), iron (5.71 g, 102.25 mmol), ammonium chloride (5.67 g, 106.00 mmol), ethanol (25 mL) and water (25 mL). The reaction mixture was heated to 55° C. and stirred for 1.5 h. The reaction mixture was filtered and the filtrate was concentrated under vacuum. The residues was dissolved in ethanol (30 mL) and applied onto a C$_{18}$ column eluted with CH$_3$CN/H$_2$O (v:v=9:1). This resulted in 1.33 g (57%) of 2-bromo-3,4,5-trifluoroaniline. LCMS: m/z=226, 228 [M+1]$^+$.

Step 2. 3,4,5-trifluoro-2-(4,4,5,5-tetramethyl-1,3,2-dioxaborolan-2-yl)aniline

Into a 40-mL sealed tube purged and maintained with an inert atmosphere of nitrogen, was placed 2-bromo-3,4,5-trifluoroaniline (2.99 g, 13.23 mmol), bis(pinacolato)diboron (10.20 g, 40.17 mmol), Pd(dppf)Cl$_2$ (0.98 g, 1.34 mmol), KOAc (4.18 g, 42.59 mmol) and dioxane (40 mL). The reaction mixture was stirred at 100° C. for 5 h. The reaction mixture was concentrated under vacuum. The residue was applied onto a silica gel column eluted with EA/hexane (v/v=0%-10%). This resulted in 5.34 g (crude) of 3,4,5-trifluoro-2-(4,4,5,5-tetramethyl-1,3,2-dioxaborolan-2-yl)aniline.

Step 3. 4-(4-acryloylpiperazin-1-yl)-7-(6-amino-2,3,4-trifluorophenyl)-6-chloro-1-(2-isopropyl-4-methylpyridin-3-yl)-2-oxo-1,2-dihydro-1,8-naphthyridine-3-carbonitrile Into a 20-mL sealed tube purged and maintained with an inert atmosphere of nitrogen, was placed 4-(4-acryloylpiperazin-1-yl)-6,7-dichloro-1-(2-isopropyl-4-methylpyridin-3-yl)-2-oxo-1,2-dihydro-1,8-naphthyridine-3-carbonitrile (0.547 g, 1.08 mmol), 3,4,5-trifluoro-2-(4,4,5,5-tetramethyl-1,3,2-dioxaborolan-2-yl)aniline (0.279 g, 1.09 mmol), Pd(PPh$_3$)$_4$ (1.376 g, 5.04 mmol), Na$_2$CO$_3$ (0.347 g, 3.27 mmol), dioxane (5 mL) and water (1 mL). The reaction mixture was stirred at 80° C. for 4 h. The reaction mixture was filtered and concentrated under vacuum. The residue was applied onto a silica gel column eluted with EA/hexane (v/v=50%-100%). This resulted in 115 mg of 4-(4-acryloylpiperazin-1-yl)-7-(6-amino-2,3,4-trifluorophenyl)-6-chloro-1-(2-isopropyl-4-methylpyridin-3-yl)-2-oxo-1,2-dihydro-1,8-naphthyridine-3-carbonitrile as yellow solid. LCMS: m/z=622 [M+1]$^+$.

Step 4. 4-(4-acryloylpiperazin-1-yl)-7-(2-amino-3-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 3")

Into a 50-mL round-bottom flask purged and maintained with an inert atmosphere of nitrogen, was placed 4-(4-acryloylpiperazin-1-yl)-7-(6-amino-2,3,4-trifluorophenyl)-6-chloro-1-(2-isopropyl-4-methylpyridin-3-yl)-2-oxo-1,2-dihydro-1,8-naphthyridine-3-carbonitrile (100 mg, 160.76 μmol), NCS (0.035 g, 262.11 μmol) and AcOH (1 mL). The reaction mixture was stirred for 7 h at 35° C. and 15 h at room temperature.

The reaction was then quenched by the addition of saturated aqueous NaHCO$_3$ (30 mL). The resulting solution was extracted with ethyl acetate (2×10 mL), the organic layers were combined and concentrated under vacuum. The residues was purified by prep-HPLC eluted with CH$_3$CN/H$_2$O (v/v=6/1). This resulted in 6 mg (5%) of 4-(4-acryloylpiperazin-1-yl)-7-(2-amino-3-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 3") as yellow solid. LCMS: m/z=656 [M+1]$^+$.

$^1$H NMR (400 MHz, CD$_3$OD) δ 8.66-8.51 (m, 1H), 8.43 (d, J=5.1 Hz, 1H), 7.26 (d, J=5.1 Hz, 1H), 6.88 (dd, J=16.8, 10.7 Hz, 1H), 6.31 (d, J=16.7 Hz, 1H), 5.84 (d, J=10.7 Hz, 1H), 4.06-3.92 (m, 8H), 2.84-2.62 (m, 1H), 2.06-1.92 (m, 3H), 1.17 (dd, J=9.6, 7.0 Hz, 3H), 1.06-0.94 (m, 3H).

Example 4

4-(4-acryloylpiperazin-1-yl)-7-(2-amino-3,5-dichloro-4,6-difluorophenyl)-6-chloro-1-(2-isopropyl-4-methylpyridin-3-yl)-2-oxo-1,2-dihydro-1,8-naphthyridine-3-carbonitrile ("Compound 4")

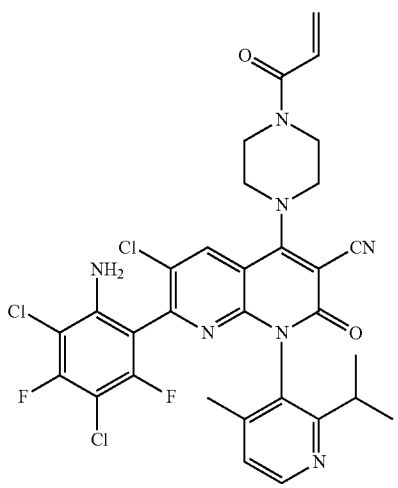 [SMILES: C=CC(=O)N1CCN(c2c(C#N)c(=O)n(-c3c(C)ccnc3C(C)C)c3nc(-c4c(N)c(Cl)c(F)c(Cl)c4F)c(Cl)cc23)CC1]

Step 1. 3,5-difluoro-2-(4,4,5,5-tetramethyl-1,3,2-dioxaborolan-2-yl)aniline

Into a 100-mL sealed tube purged and maintained with an inert atmosphere of nitrogen, was placed 2-bromo-3,5-difluoroaniline (3.01 g, 14.47 mmol), bis(pinacolato)diboron (6.46 g, 25.43 mmol), Pd(dppf)Cl$_2$ (1.03 g, 1.41 mmol), KOAc (4.20 g, 42.83 mmol), dioxane (20 mL). The reaction mixture was stirred at 80° C. for 12 h. The reaction mixture was filtered and concentrated under vacuum. The residue was purified by silica gel column eluted with EA/hexane (v/v=1/19). This resulted in 6.01 g (crude) of 3,5-difluoro-2-(4,4,5,5-tetramethyl-1,3,2-dioxaborolan-2-yl)aniline as yellow oil. LCMS: m/z=256 [M+1]$^+$.

Step 2. tert-butyl 4-(7-(2-amino-4,6-difluorophenyl)-6-chloro-3-cyano-1-(2-isopropyl-4-methylpyridin-3-yl)-2-oxo-1,2-dihydro-1,8-naphthyridin-4-yl)piperazine-1-carboxylate Into a 100-mL sealed tube purged and maintained with an inert atmosphere of nitrogen, was placed 3,5-difluoro-2-(4,4,5,5-tetramethyl-1,3,2-dioxaborolan-2-yl)aniline (5.86 g, 23.00 mmol), tert-butyl 4-(6,7-dichloro-3-cyano-1-(2-isopropyl-4-methylpyridin-3-yl)-2-oxo-1,2-dihydro-1,8-naphthyridin-4-yl)piperazine-1-carboxylate (1.29 g, 2.31 mmol), Pd(PPh$_3$)$_4$ (0.73 g, 0.63 mmol), Na$_2$CO$_3$ (0.84 g, 7.89 mmol), dioxane (15 mL) and water (2 mL). The reaction mixture was stirred at 80° C. for 2 h. The reaction mixture was filtered and concentrated under vacuum. The residue was purified by silica gel column eluted with EA/hexane (v/v=1/1). This resulted in 1.42 g (crude) of tert-butyl 4-(7-(2-amino-4,6-difluorophenyl)-6-chloro-3-cyano-1-(2-isopropyl-4-methylpyridin-3-yl)-2-oxo-1,2-dihydro-1,8-naphthyridin-4-yl)piperazine-1-carboxylate as yellow solid. LCMS: m/z=650 [M+1]$^+$.

Step 3. tert-butyl 4-(7-(2-amino-3,5-dichloro-4,6-difluorophenyl)-6-chloro-3-cyano-1-(2-isopropyl-4-methylpyridin-3-yl)-2-oxo-1,2-dihydro-1,8-naphthyridin-4-yl)piperazine-1-carboxylate Into a 50-mL round-bottom flask purged and maintained with an inert atmosphere of nitrogen, was placed tert-butyl 4-(7-(2-amino-4,6-difluorophenyl)-6-chloro-3-cyano-1-(2-isopropyl-4-methylpyridin-3-yl)-2-oxo-1,2-dihydro-1,8-naphthyridin-4-yl)piperazine-1-carboxylate (1.21 g, 1.87 mmol), NCS (0.49 g, 3.73 mmol) and AcOH (30 mL). The reaction mixture was stirred for 48 h at room temperature. The reaction was then quenched by the addition of water (100 mL). The resulting solution was extracted with ethyl acetate (2×100 mL), the organic layers were combined and washed with brine (10 mL), dried over anhydrous Na$_2$SO$_4$, filtered and concentrated under vacuum. The residue was purified by silica gel column eluted with EA/hexane (v/v=1/1). This resulted in 0.53 g (crude) of tert-butyl 4-(7-(2-amino-3,5-dichloro-4,6-difluorophenyl)-6-chloro-3-cyano-1-(2-isopropyl-4-methylpyridin-3-yl)-2-oxo-1,2-dihydro-1,8-naphthyridin-4-yl)piperazine-1-carboxylate as yellow solid. LCMS: m/z=718[M+1]$^+$.

Step 4. 4-(4-acryloylpiperazin-1-yl)-7-(2-amino-3,5-dichloro-4,6-difluorophenyl)-6-chloro-1-(2-isopropyl-4-methylpyridin-3-yl)-2-oxo-1,2-dihydro-1,8-naphthyridine-3-carbonitrile ("Compound 4")

Into a 20-mL round-bottom flask purged and maintained with an inert atmosphere of nitrogen, was placed tert-butyl 4-(7-(2-amino-3,5-dichloro-4,6-difluorophenyl)-6-chloro-3-cyano-1-(2-isopropyl-4-methyl pyridin-3-yl)-2-oxo-1,2-dihydro-1,8-naphthyridin-4-yl)piperazine-1-carboxylate (0.53 g, 0.73 mmol), TFA (5 ml) and DCM (20 mL). The reaction mixture was stirred at room temperature for 2 h. The reaction mixture was concentrated under vacuum. The residue was dissolved by DCM (10 mL) in 25-mL round-bottom flask. DIEA (1.22 g, 9.48 mmol) was added. The reaction mixture was cooled to 0° C. and acryloyl chloride (0.08 g, 0.88 mmol) was added. The mixture was stirred at room temperature for 0.5 h. The reaction mixture was filtered and concentrated under vacuum. The residue was purified by Prep-HPLC (CH$_3$CN/H$_2$O (v/v=7/3)). This resulted in 239 mg (50% in two steps) of 4-(4-acryloylpiperazin-1-yl)-7-(2-amino-3,5-dichloro-4,6-difluorophenyl)-6-chloro-1-(2-isopropyl-4-methylpyridin-3-yl)-2-oxo-1,2-dihydro-1,8-naphthyridine-3-carbonitrile ("Compound 4") as yellow solid. LCMS: m/z=672 [M+1]$^+$.

$^1$H NMR (400 MHz, CD$_3$OD) δ 8.55 (s, 1H), 8.43 (s, 1H), 7.26 (s, 1H), 6.87 (dd, J=16.1, 11.1 Hz, 1H), 6.31 (d, J=16.3 Hz, 1H), 5.84 (d, J=10.1 Hz, 1H), 4.25-3.75 (m, 8H), 2.85-2.60 (m, 1H), 2.14-1.88 (m, 3H), 1.25-0.87 (m, 6H).

Example 5

4-((3S,5R)-4-acryloyl-3,5-dimethylpiperazin-1-yl)-7-(2-amino-3,5-dichloro-4,6-difluorophenyl)-6-chloro-1-(2-isopropyl-4-methylpyridin-3-yl)-2-oxo-1,2-dihydro-1,8-naphthyridine-3-carbonitrile ("Compound 5")

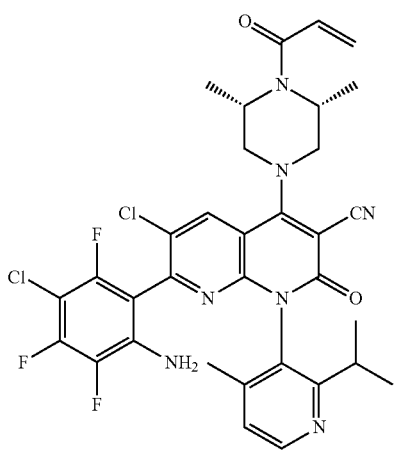 [SMILES: C=CC(=O)N1[C@H](C)CN(c2c(C#N)c(=O)n(-c3c(C)ccnc3C(C)C)c3nc(-c4c(N)c(F)c(F)c(Cl)c4F)c(Cl)cc23)C[C@@H]1C]

Step 1. 4-((3R,5S)-4-acryloyl-3,5-dimethylpiperazin-1-yl)-6,7-dichloro-1-(2-isopropyl-4-methylpyridin-3-yl)-2-oxo-1,2-dihydro-1,8-naphthyridine-3-carbonitrile (Intermediate D)

Into a 500-mL round-bottom flask purged and maintained with an inert atmosphere of nitrogen, was placed 6,7-dichloro-4-hydroxy-1-(2-isopropyl-4-methylpyridin-3-yl)-2-oxo-1,2-dihydro-1,8-naphthyridine-3-carbonitrile (6.21 g, 15.95 mmol), POCl$_3$ (6.88 g, 48.87 mmol), DIEA (6.80 g, 52.61 mmol) and acetonitrile (100 mL). The mixture was stirred for 2 h at 80° C. The reaction was cooled to room temperature and concentrated under vacuum. This resulted in 4,6,7-trichloro-1-(2-isopropyl-4-methylpyridin-3-yl)-2-oxo-1,2-dihydro-1,8-naphthyridine-3-carbonitrile which was used directly in the next step.

Into a 500-mL round-bottom flask purged and maintained with an inert atmosphere of nitrogen, was placed 4,6,7-trichloro-1-(2-isopropyl-4-methylpyridin-3-yl)-2-oxo-1,2-dihydro-1,8-naphthyridine-3-carbonitrile (crude), DIEA (6.80 g, 52.61 mmol) and acetonitrile (100 mL), (2S,6R)-2,6-dimethylpiperazine (2.17 g, 19.00 mmol) was added. The mixture was stirred for 1 h at room temperature. The resulting solution was concentrated under vacuum and applied onto a silica gel column eluted with EA/hexane (v/v=2/1). This resulted in 4.30 g (50% yield) of 4-((3R,5S)-4-acryloyl-3,5-dimethylpiperazin-1-yl)-6,7-dichloro-1-(2-isopropyl-4-methylpyridin-3-yl)-2-oxo-1,2-dihydro-1,8-na phthyridine-3-carbonitrile as yellow solid. LCMS: m/z=539 [M+1]$^+$.

Step 2. 3,5-difluoro-2-(4,4,5,5-tetramethyl-1,3,2-dioxaborolan-2-yl)aniline

Into a 40-mL sealed tube purged and maintained with an inert atmosphere of nitrogen, was placed 2-bromo-3,5-difluoroaniline (2.06 g, 9.91 mmol), bis(pinacolato)diboron (4.95 g, 19.49 mmol), Pd(dppf)Cl$_2$ (809 mg, 1.11 mmol), KOAc (2.23 g, 22.69 mmol), dioxane (20 mL). The reaction mixture was stirred at 100° C. for 19 h. The reaction mixture was concentrated under vacuum. The residue was applied onto a C$_{18}$ column eluted with CH$_3$CN/H$_2$O (v/v=5%-100%). This resulted in 1.19 g of 3,5-difluoro-2-(4,4,5,5-tetramethyl-1,3,2-dioxaborolan-2-yl)aniline as off-white solid. LCMS: m/z=256 [M+1]$^+$.

Step 3. 4-((3S,5R)-4-acryloyl-3,5-dimethylpiperazin-1-yl)-7-(2-amino-4,6-difluorophenyl)-6-chloro-1-(2-isopropyl-4-methylpyridin-3-yl)-2-oxo-1,2-dihydroquinoline-3-carbonitrile Into a 20-mL sealed tube purged and maintained with an inert atmosphere of nitrogen, was placed 4-((3S,5R)-4-acryloyl-3,5-dimethylpiperazin-1-yl)-6,7-dichloro-1-(2-isopropyl-4-methylpyridin-3-yl)-2-oxo-1,2-dihydroquinoline-3-carbonitrile (0.196 g, 0.36 mmol), 3,5-difluoro-2-(4,4,5,5-tetramethyl-1,3,2-dioxaborolan-2-yl)aniline (0.27 g, 1.06 mmol), Pd(PPh$_3$)$_4$ (78 mg, 0.07 mmol), Na$_2$CO$_3$ (207 mg, 1.95 mmol), dioxane (5 mL) and water (1 mL). The reaction mixture was stirred at 80° C. for 1 h. The reaction mixture was filtered and concentrated under vacuum. The residues was applied onto a silica gel column eluted with EA/hexane (v/v=50%-100%). This resulted in 223 mg of 4-((3S,5R)-4-acryloyl-3,5-dimethylpiperazin-1-yl)-7-(2-amino-4,6-difluorophenyl)-6-chloro-1-(2-isopropyl-4-methylpyridin-3-yl)-2-oxo-1,2-dihydroquinoline-3-carbonitrile as yellow solid. LCMS: m/z=632 [M+1]$^+$.

Step 4. 4-((3S,5R)-4-acryloyl-3,5-dimethylpiperazin-1-yl)-7-(2-amino-3,5-dichloro-4,6-difluorophenyl)-6-chl oro-1-(2-isopropyl-4-methylpyridin-3-yl)-2-oxo-1,2-dihydroquinoline-3-carbonitrile ("Compound 5")

Into a 20-mL round-bottom flask was placed 4-((3S,5R)-4-acryloyl-3,5-dimethylpiperazin-1-yl)-7-(2-amino-4,6-difluorophenyl)-6-chloro-1-(2-isopropyl-4-methylpyridin-3-yl)-2-oxo-1,2-dihydroquinoline-3-carbonitrile (223 mg, 0.35 mmol), NCS (98 mg, 0.73 mmol) and HOAc (3 mL). The reaction mixture was stirred at room temperature for 1 day. The reaction was heated to 45° C. and stirred at this temperature for 2 hours. The reaction mixture was concentrated under vacuum. The residues was purified by Prep-HPLC CH$_3$CN/H$_2$O (0.05% NH$_4$HCO$_3$) (v/v=2/1). This resulted in 55 mg (22%) of 4-((3S,5R)-4-acryloyl-3,5-dimethylpiperazin-1-yl)-7-(2-amino-3,5-dichloro-4,6-difluorophenyl)-6-chloro-1-(2-isopropyl-4-methylpyridin-3-yl)-2-oxo-1,2-dihydroquinoline-3-carbonitrile ("Compound 5") as yellow solid. LCMS: m/z=700 [M+1]$^+$.

$^1$H NMR (400 MHz, CD$_3$OD) δ 8.83 (s, 1H), 8.43 (d, J=5.0 Hz, 1H), 7.27 (d, J=5.0 Hz, 1H), 6.95-6.82 (m, 1H), 6.33 (d, J=16.5 Hz, 1H), 5.84 (d, J=10.8 Hz, 1H), 4.77 (s, 2H), 4.13-3.92 (m, 2H), 3.84 (d, J=9.4 Hz, 2H), 2.80-2.60 (m, 1H), 2.08-1.93 (m, 3H), 1.72-1.59 (m, 6H), 1.25-1.10 (m, 3H), 1.10-0.89 (m, 3H).

Example 6

4-(4-acryloylpiperazin-1-yl)-7-(3-amino-2,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 6")

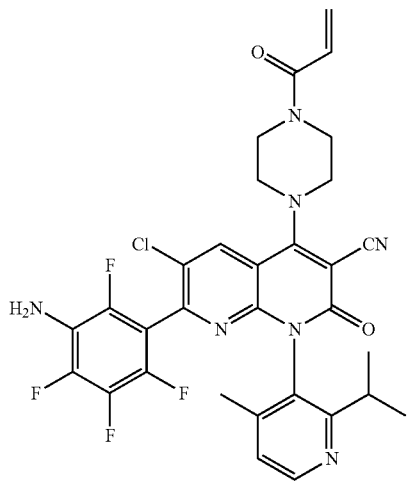 [SMILES: C=CC(=O)N1CCN(c2c(C#N)c(=O)n(-c3c(C)ccnc3C(C)C)c3nc(-c4c(F)c(N)c(F)c(F)c4F)c(Cl)cc23)CC1]

Step 1. 4-(4-acryloylpiperazin-1-yl)-6-chloro-1-(2-isopropyl-4-methylpyridin-3-yl)-2-oxo-7-(tributylstannyl)-1,2-dihydro-1,8-naphthyridine-3-carbonitrile Into a 30-mL sealed tube purged and maintained with an inert atmosphere of nitrogen, was placed 4-(4-acryloylpiperazin-1-yl)-6,7-dichloro-1-(2-isopropyl-4-methylpyridin-3-yl)-2-oxo-1,2-dihydro-1,8-naphthyridine-3-carbonitrile (1.039 g, 2.04 mmol), 1,1,1,2,2,2-Hexabutyl-distannane (4.124 g, 7.11 mmol), Pd(PPh$_3$)$_4$ (0.566 g, 0.49 mmol) and dioxane (10 mL). The reaction mixture was stirred at 100° C. for 1 d. The reaction mixture was filtered and concentrated under vacuum. The residues was purified by silica gel column eluted with EA/hexane (v/v=2/1). This resulted in 273 mg (17%) of 4-(4-acryloylpiperazin-1-yl)-6-chloro-1-(2-isopropyl-4-methylpyridin-3-yl)-2-oxo-7-(tributylstannyl)-1,2-dihydro-1,8-naphthyridine-3-carbonitrile as yellow solid. LCMS: m/z=767 [M+1]$^+$.

Step 2. 4-(4-acryloylpiperazin-1-yl)-7-(3-amino-2,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 6")

Into a 25-mL round-bottom flask purged and maintained with an inert atmosphere of nitrogen, was placed 4-(4-acryloylpiperazin-1-yl)-6-chloro-1-(2-isopropyl-4-methylpyridin-3-yl)-2-oxo-7-(tributylstannyl)-1,2-dihydro-1,8-naphthyridine-3-carbonitrile (0.272 g, 0.36 mmol), 2,3,4,6-tetrafluoro-5-iodoaniline (0.630 g, 2.17 mmol), Pd(PPh$_3$)$_4$ (0.187 g, 0.16 mmol), cuprous iodide (0.294 g, 1.54 mmol), dioxane (10 mL). The reaction mixture was stirred at 100° C. for 1 d. The reaction mixture was filtered and concentrated under vacuum. The residues was purified by prep-HPLC eluted with ACN/H$_2$O (v/v=1/2). This resulted in 6 mg (3%) of 4-(4-acryloylpiperazin-1-yl)-7-(3-amino-2,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 6") as yellow solid. LCMS: m/z=640 [M+1]$^+$.

$^1$H NMR (400 MHz, CD$_3$OD) δ 8.56 (s, 1H), 8.42 (d, J=4.9 Hz, 1H), 7.31-7.20 (m, 1H), 6.87 (dd, J=16.7, 10.6 Hz, 1H), 6.30 (dd, J=16.8, 1.7 Hz, 1H), 5.83 (dd, J=10.6, 1.8 Hz, 1H), 4.08-3.87 (m, 8H), 2.79-2.62 (m, 1H), 2.00 (s, 3H), 1.17 (d, J=6.8 Hz, 3H), 0.98 (d, J=6.7 Hz, 3H).

Example 7

4-((3S,5R)-4-acryloyl-3,5-dimethylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 7")

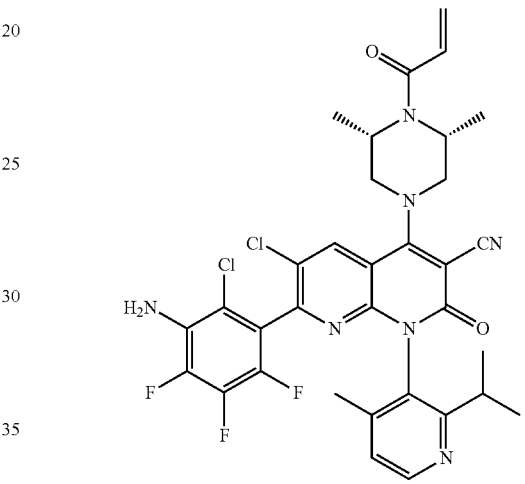

Step 1. 4-((3S,5R)-4-acryloyl-3,5-dimethylpiperazin-1-yl)-7-(5-amino-2,3,4-trifluorophenyl)-6-chloro-1-(2-isopropyl-4-methylpyridin-3-yl)-2-oxo-1,2-dihydro-1,8-naphthyridine-3-carbonitrile Into a 30-mL sealed tube purged and maintained with an inert atmosphere of nitrogen, was placed 4-((3S,5R)-4-acryloyl-3,5-dimethylpiperazin-1-yl)-6,7-dichloro-1-(2-isopropyl-4-methylpyridin-3-yl)-2-oxo-1,2-dihydro-1,8-naphthyridine-3-carbonitrile (0.822 g, 1.52 mmol), (5-amino-2,3,4-trifluorophenyl) boronic acid (0.608 g, 2.23 mmol), Pd(PPh$_3$)$_4$ (0.650 g, 0.56 mmol), Na$_2$CO$_3$ (0.575 g, 5.43 mmol), dioxane (10 mL) and water (2 mL). The reaction mixture was stirred at 80° C. for 1 h. The reaction mixture was filtered and concentrated under vacuum. The residue was purified by silica gel column eluted with EA/hexane (v/v=2/1). This resulted in 1.079 g (91%) of 4-((3S,5R)-4-acryloyl-3,5-dimethylpiperazin-1-yl)-7-(5-amino-2,3,4-trifluorophenyl)-6-chloro-1-(2-isopropyl-4-methylpyridin-3-yl)-2-oxo-1,2-dihydro-1,8-naphthyridine-3-carbonitrile as yellow solid. LCMS: m/z=650 [M+1]$^+$.

Step 2. 4-((3S,5R)-4-acryloyl-3,5-dimethylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 7")

Into a 50-mL round-bottom flask purged and maintained with an inert atmosphere of nitrogen, was placed 4-((3S, 5R)-4-acryloyl-3,5-dimethylpiperazin-1-yl)-7-(5-amino-2,3,4-trifluorophenyl)-6-chloro-1-(2-isopropyl-4-methylpyridin-3-yl)-2-oxo-1,2-dihydro-1,8-naphthyridine-3-carbonitrile (0.622 g, 0.96 mmol), NCS (0.703 g, 5.27 mmol), and AcOH (5 mL). The mixture was stirred at r.t. for 2 d. The reaction was then quenched by the addition of water (10 mL). The resulting solution was extracted with ethyl acetate (3×10 mL), the organic layers were combined and washed with brine (1×50 mL), dried over anhydrous $Na_2SO_4$, filtered and concentrated under vacuum. The residues was purified by Prep-HPLC ($CH_3CN/H_2O$ (v/v=6/4)). This resulted in 35 mg (5%) of 4-((3S,5R)-4-acryloyl-3,5-dimethylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 7") as yellow solid. LCMS: m/z=684 [M+1]$^+$.

$^1$H NMR (400 MHz, $CD_3OD$) δ 8.83 (s, 1H), 8.42 (d, J=5.0 Hz, 1H), 7.22-7.10 (m, 1H), 6.88 (dd, J=16.7, 10.7 Hz, 1H), 6.32 (d, J=16.5 Hz, 1H), 5.74 (dd, J=10.6, 2.0 Hz, 1H), 4.76 (s, 2H), 4.06-3.73 (m, 4H), 2.82-2.69 (m, 1H), 2.10-1.94 (m, 3H), 1.63-1.35 (m, 6H), 1.17 (d, J=6.5 Hz, 3H), 1.06-0.89 (m, 3H).

Example 8

4-((3S,5R)-4-acryloyl-3,5-dimethylpiperazin-1-yl)-7-(3-amino-2,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 8")

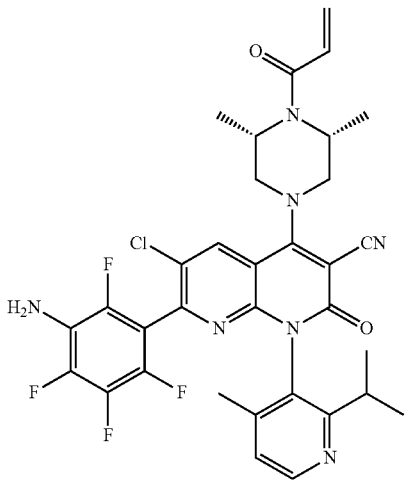 [SMILES: C=CC(=O)N1[C@H](C)CN(c2c(C#N)c(=O)n(-c3c(C)ccnc3C(C)C)c3nc(-c4c(F)c(N)c(F)c(F)c4F)c(Cl)cc23)C[C@@H]1C]

Step 1. 4-((3S,5R)-4-acryloyl-3,5-dimethylpiperazin-1-yl)-6,7-dichloro-1-(2-isopropyl-4-methylpyridin-3-yl)-2-oxo-1,2-dihydro-1,8-naphthyridine-3-carbonitrile Into a 20-mL round-bottom flask purged and maintained with an inert atmosphere of nitrogen, was placed 6,7-dichloro-4-((3S,5R)-3,5-dimethylpiperazin-1-yl)-1-(2-isopropyl-4-methylpyridin-3-yl)-2-oxo-1,2-dihydro-1,8-naphthyridine-3-carbonitrile (6.503 g, 13.39 mmol), DIEA (5.21 g, 40.31 mmol), DCM (6 mL) and acryloyl chloride (1.18 g, 13.04 mmol). The reaction mixture was stirred at room temperature for 0.5 h. The reaction mixture was filtered and concentrated under vacuum. The residue was purified by silica gel column eluted with EA/hexane (v/v=1/1). This resulted in 1.80 g (crude) of 4-((3S,5R)-4-acryloyl-3,5-dimethylpiperazin-1-yl)-6,7-dichloro-1-(2-isopropyl-4-methylpyridin-3-yl)-2-oxo-1,2-dihydro-1,8-naphthyridine-3-carbonitrile as yellow solid. LCMS: m/z=539 [M+1]$^+$.

Step 2. 4-((3S,5R)-4-acryloyl-3,5-dimethylpiperazin-1-yl)-6-chloro-1-(2-isopropyl-4-methylpyridin-3-yl)-2-oxo-7-(tributylstannyl)-1,2-dihydro-1,8-naphthyridine-3-carbonitrile Into a 20-mL sealed tube purged and maintained with an inert atmosphere of nitrogen, was placed 4-((3S,5R)-4-acryloyl-3,5-dimethylpiperazin-1-yl)-6,7-dichloro-1-(2-isopropyl-4-methylpyridin-3-yl)-2-oxo-1,2-dihydro-1,8-naphthyridine-3-carbonitrile (1.77 g, 3.28 mmol), hexabutyldistannane (23.85 g, 6.64 mmol), $Pd(PPh_3)_4$ (0.26 g, 0.23 mmol) and dioxane (20 mL). The reaction mixture was stirred at 110° C. for 18 h. The reaction mixture was filtered and concentrated under vacuum. The residue was purified by silica gel column eluted with EA/hexane (v/v=2/1). This resulted in 0.52 g (crude) of 4-((3S,5R)-4-acryloyl-3,5-dimethylpiperazin-1-yl)-6-chloro-1-(2-isopropyl-4-methylpyridin-3-yl)-2-oxo-7-(tributylstannyl)-1,2-dihydro-1,8-naphthyridine-3-carbonitrile as yellow solid. LCMS: m/z=795 [M+1]$^+$.

Step 3. 4-((3S,5R)-4-acryloyl-3,5-dimethylpiperazin-1-yl)-7-(3-amino-2,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 8")

Into a 20-mL round-bottom flask purged and maintained with an inert atmosphere of nitrogen, was placed 4-((3S,5R)-4-acryloyl-3,5-dimethylpiperazin-1-yl)-6-chloro-1-(2-isopropyl-4-methylpyridin-3-yl)-2-oxo-7-(tributylstannyl)-1,2-dihydro-1,8-naphthyridine-3-carbonitrile (0.40 g, 0.51 mmol), 2,3,4,6-tetrafluoro-5-iodoaniline (0.27 g, 0.93 mmol), $Pd(PPh_3)_4$ (0.27 g, 0.23 mmol), CuI (0.40 g, 2.11 mmol), DMA (15 mL). The reaction mixture was stirred at 90° C. for 18 h. The reaction mixture was filtered and concentrated under vacuum. The residue was purified by Prep-HPLC ($CH_3CN/H_2O$ (v/v=7/3)). This resulted in 8 mg (2.3% in two steps) of 4-((3S,5R)-4-acryloyl-3,5-dimethylpiperazin-1-yl)-7-(3-amino-2,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 8") as yellow solid. LCMS: m/z=668 [M+1]$^+$.

$^1$H NMR (400 MHz, $CD_3OD$) δ 8.73 (s, 1H), 8.34 (d, J=5.0 Hz, 1H), 7.23-7.15 (m, 1H), 6.79 (dd, J=16.7, 10.7 Hz, 1H), 6.23 (dd, J=16.7, 2.0 Hz, 1H), 5.74 (dd, J=10.6, 2.0 Hz, 1H), 4.73-4.58 (m, 2H), 3.95-3.70 (m, 4H), 2.66-2.57 (m, 1H), 1.93 (d, J=8.4 Hz, 3H), 1.55-1.57 (m, 6H), 1.07 (d, J=6.8 Hz, 3H), 0.89 (d, J=5.7 Hz, 3H).

Example 9

(P)-4-((R)-4-acryloyl-3-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile; or (M)-4-((R)-4-acryloyl-3-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile; ("Compound 9")

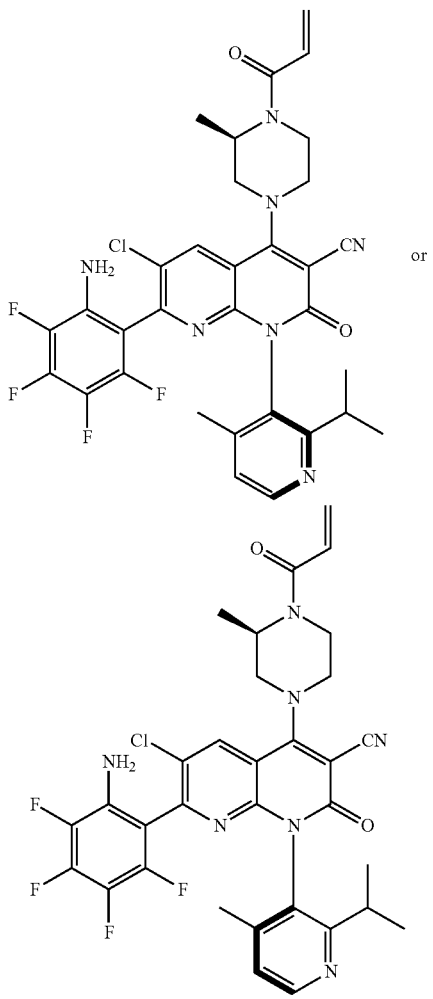

Step 1. 6,7-dichloro-4-hydroxy-1-(2-isopropyl-4-methylpyridin-3-yl)-2-oxo-1,2-dihydro-1,8-naphthyridine-3-carbonitrile Into a 250-mL round-bottom flask purged and maintained with an inert atmosphere of nitrogen, was placed 2-cyano-N-(2-isopropyl-4-methylpyridin-3-yl)-3-oxo-3-(2,5,6-trichloropyridin-3-yl)propanamide (5.89 g, 13.83 mmol) and THF (70 mL), the mixture was stirred at room temperature. This was followed by the addition of NaH (2.73 g, 68.25 mmol) in batch-wise. The mixture was stirred at 50° C. for 2 h. The reaction mixture was concentrated under vacuum. The residue was dissolved in 100 mL water and adjusted pH to 7 with AcOH. The resulting solid was filtered and dried under vacuum to provide 5.85 g (108% in two steps) of 6,7-dichloro-4-hydroxy-1-(2-isopropyl-4-methylpyridin-3-yl)-2-oxo-1,2-dihydro-1,8-naphthyridine-3-carbonitrile as yellow solid. LCMS: m/z=389 [M+1]$^+$.

$^1$H NMR (400 MHz, DMSO-$d_6$) δ 8.77 (d, J=5.7 Hz, 1H), 8.38 (s, 1H), 7.89 (d, J=5.4 Hz, 1H), 3.01-2.88 (m, 1H), 2.19 (s, 3H), 1.21 (d, J=6.9 Hz, 3H), 1.14 (d, J=6.9 Hz, 3H).

The mixture of 6,7-dichloro-4-hydroxy-1-(2-isopropyl-4-methylpyridin-3-yl)-2-oxo-1,2-dihydro-1,8-naphthyridine-3-carbonitrile atropisomers (10.59 g, "Intermediate B", several batches) was purified by Chiral-Prep-HPLC with the following conditions: Column, CHIRALPAK IC, 3.0×100 mm, 3 μm; mobile phase, IPA/ACN=1/1(V/V); Detection wavelength, UV 210 nm. This resulted in 4.99 g (47%) of 6,7-dichloro-4-hydroxy-1-(2-isopropyl-4-methylpyridin-3-yl)-2-oxo-1,2-dihydro-1,8-naphthyridine-3-carbonitrile (the first eluting isomer, "Intermediate B-1", M or P atropisomer) as a brown solid;

$^1$H NMR (400 MHz, CD$_3$OD) δ 8.48 (s, 1H), 8.44 (d, J=5.0 Hz, 1H), 7.33-7.22 (m, 1H), 2.76-2.61 (m, 1H), 2.03 (s, 3H), 1.19 (d, J=6.8 Hz, 3H), 1.06 (d, J=6.8 Hz, 3H).

And 4.60 g (43%) of 6,7-dichloro-4-hydroxy-1-(2-isopropyl-4-methylpyridin-3-yl)-2-oxo-1,2-dihydro-1,8-naphthyridine-3-carbonitrile (the second eluting isomer, "Intermediate B-2", P or M atropisomer) as a brown solid;

$^1$H NMR (400 MHz, CD$_3$OD) δ 8.49 (s, 1H), 8.44 (d, J=5.0 Hz, 1H), 7.28 (d, J=5.0 Hz, 1H), 2.76-2.63 (m, 1H), 2.03 (s, 3H), 1.19 (d, J=6.8 Hz, 3H), 1.079-1.00 (m, 3H).

Step 2. tert-butyl (R)-4-(6,7-dichloro-3-cyano-1-(2-isopropyl-4-methylpyridin-3-yl)-2-oxo-1,2-dihydro-1,8-naphthyridin-4-yl)-2-methylpiperazine-1-carboxylate (single isomer)

Into a 50-mL round-bottom flask purged and maintained with an inert atmosphere of nitrogen, was placed 6,7-dichloro-4-hydroxy-1-(2-isopropyl-4-methylpyridin-3-yl)-2-oxo-1,2-dihydro-1,8-naphthyridine-3-carbonitrile (the first eluting isomer in step 1) (1.05 g, 2.71 mmol), POCl$_3$ (2.04 g, 13.27 mmol), DIEA (3.09 g, 23.93 mmol) and acetonitrile (20 mL). The mixture was stirred at 80° C. for 2 h. The reaction was cooled to room temperature and concentrated under vacuum. This resulted in 4,6,7-trichloro-1-(2-isopropyl-4-methylpyridin-3-yl)-2-oxo-1,2-dihydro-1,8-naphthyridine-3-carbonitrile which was used directly in the next step.

Into a 100-mL round-bottom flask purged and maintained with an inert atmosphere of nitrogen, was placed 4,6,7-trichloro-1-(2-isopropyl-4-methylpyridin-3-yl)-2-oxo-1,2-dihydro-1,8-naphthyridine-3-carbonitrile (crude) and acetonitrile (10 mL), DIEA (3.09 g, 23.93 mmol) and tert-butyl (R)-2-methylpiperazine-1-carboxylate (507 mg, 2.53 mmol) were added. The reaction mixture was stirred for 2 h at room temperature. The reaction was then quenched by the addition of water (50 mL). The resulting solution was extracted with ethyl acetate (3×50 mL), the organic layers were combined and washed with brine (50 mL), dried over anhydrous Na$_2$SO$_4$, filtered and concentrated under vacuum. The residue was purified by silica gel column eluted with EA/hexane (v/v=5/4). This resulted in 0.95 g (65% in two steps) of tert-butyl (R)-4-(6,7-dichloro-3-cyano-1-(2-isopropyl-4-methylpyridin-3-yl)-2-oxo-1,2-dihydro-1,8-naphthyridin-4-yl)-2-methylpiperazine-1-carboxylate (single isomer, P or M) as red solid. LCMS: m/z=571 [M+1]$^+$.

Step 3. (R)-4-(4-acryloyl-3-methylpiperazin-1-yl)-6,7-dichloro-1-(2-isopropyl-4-methylpyridin-3-yl)-2-oxo-1,2-dihydro-1,8-naphthyridine-3-carbonitrile Into a 50-mL round-bottom flask purged and maintained with an inert atmosphere of nitrogen, was placed tert-butyl (R)-4-(6,7-dichloro-3-cyano-1-(2-isopropyl-4-methylpyridin-3-yl)-2-oxo-1,2-dihydro-1,8-naphthyridin-4-yl)-2-methylpiperazine-1-carboxylate (P or M isomer, 1.01 g, 1.767 mmol), DCM (8 mL) and TFA (4.605 g, 40.386 mmol). The reaction mixture was stirred at room temperature for 1 h. The reaction mixture was concentrated under vacuum. The residue was dissolved by DCM (10 mL) into a 50 mL round-bottom flask, triethylamine (1.30 g, 12.85 mmol) was added. The reaction mixture was cooled to 0° C. and acryloyl chloride (0.23 g, 2.541 mmol) was added. The mixture stirred at room temperature for 0.5 h. The reaction was then quenched by the addition of water (20 mL). The resulting solution was extracted with ethyl acetate (3×20 mL), the organic layers were combined and washed with brine (20 mL), dried over anhydrous $Na_2SO_4$, filtered and concentrated under vacuum. The residues was purified by Prep-HPLC $CH_3CN/H_2O$ (v/v=3/2). This resulted in 1.46 g (crude) of (R)-4-(4-acryloyl-3-methylpiperazin-1-yl)-6,7-dichloro-1-(2-isopropyl-4-methylpyridin-3-yl)-2-oxo-1,2-dihydro-1,8-naphthyridine-3-carbonitrile (P or M isomer) as yellow solid. LCMS: m/z=525 [M+1]$^+$.

Step 4. 4-((R)-4-acryloyl-3-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (P or M isomer, "Compound 9")

Into a 100 mL round bottom flask purged and maintained with an inert atmosphere of nitrogen was placed (R)-4-(4-acryloyl-3-methylpiperazin-1-yl)-6,7-dichloro-1-(2-isopropyl-4-methylpyridin-3-yl)-2-oxo-1,2-dihydro-1,8-naphthyridine-3-carbonitrile (P or M isomer, 1.64 g, 3.11 mmol), (2-amino-3,4,5,6-tetrafluorophenyl)boronic acid (1.37 g, 6.57 mmol), $Pd(PPh_3)_4$ (0.37 g, 315.86 mol), $Na_2CO_3$ (1.11 g, 10.49 mmol), 1,4-Dioxane (15 mL) and Water (2 mL). The resulting mixture was stirred at 80° C. for 30 min. Three batches of (2-amino-3,4,5,6-tetrafluorophenyl)boronic acid (2.84 g, 13.59 mmol) was added in 3 h. After the reaction was completed, the reaction was evaporated under vacuum and applied onto a silica gel column eluted with EA/Hexane (v/v=7/3), the crude was purified by HPLC eluted with $CH_3CN/H_2O$ (v/v=3/2), this resulted in (784 mg, 38.50%) of 7-(2-amino-3,4,5,6-tetrafluoro-phenyl)-6-chloro-1-(2-isopropyl-4-methyl-3-pyridyl)-4-[(3R)-3-methyl-4-prop-2-enoyl-piperazin-1-yl]-2-oxo-1,8-naphthyridine-3-carbonitrile (P or M isomer, "Compound 9") as light yellow solid. LCMS: m/z=654 [M+1]$^+$.

$^1$H NMR (400 MHz, $CD_3OD$) δ 8.48 (s, 1H), 8.42-8.31 (m, 1H), 7.23 (d, J=5.0 Hz, 1H), 6.76 (dd, J=16.7, 10.7 Hz, 1H), 6.20 (dd, J=16.7, 1.8 Hz, 1H), 5.73 (dd, J=10.6, 1.9 Hz, 1H), 4.40 (s, 1H), 4.18-4.10 (m, 2H), 3.94-3.83 (m, 2H), 3.65-3.54 (m, 2H), 2.64-2.51 (m, 1H), 2.06-1.92 (m, 3H), 1.44-1.30 (m, 3H), 1.10-1.03 (m, 3H), 0.96-0.81 (m, 3H).

Example 10

4-((R)-4-acryloyl-3-methylpiperazin-1-yl)-7-(2-amino-6-chloro-3,4,5-trifluorophenyl)-6-chloro-1-(2-isopropyl-4-methylpyridin-3-yl)-2-oxo-1,2-dihydro-1,8-naphthyridine-3-carbonitrile ("Compound 10"); (P)-4-((R)-4-acryloyl-3-methylpiperazin-1-yl)-7-(2-amino-6-chloro-3,4,5-trifluorophenyl)-6-chloro-1-(2-isopropyl-4-methylpyridin-3-yl)-2-oxo-1,2-dihydro-1,8-naphthyridine-3-carbonitrile; and (M)-4-((R)-4-acryloyl-3-methylpiperazin-1-yl)-7-(2-amino-6-chloro-3,4,5-trifluorophenyl)-6-chloro-1-(2-isopropyl-4-methylpyridin-3-yl)-2-oxo-1,2-dihydro-1,8-naphthyridine-3-carbonitrile

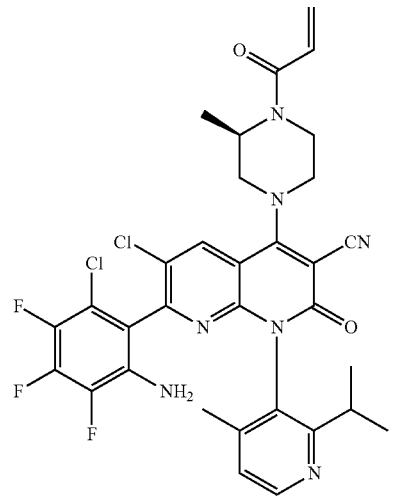

and

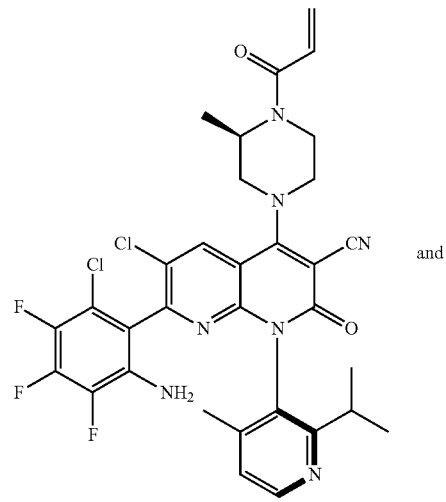

-continued

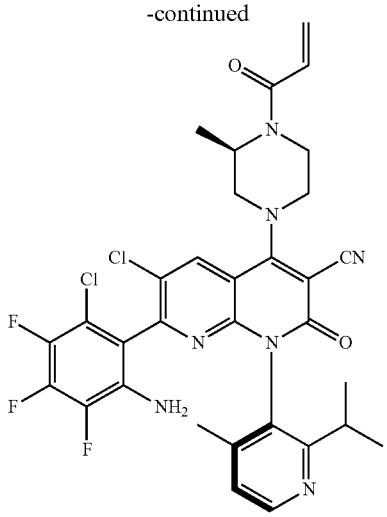

Step 1. (R)-4-(4-acryloyl-3-methylpiperazin-1-yl)-7-(2-amino-3,4,5-trifluorophenyl)-6-chloro-1-(2-isopropyl-4-methylpyridin-3-yl)-2-oxo-1,2-dihydro-1,8-naphthyridine-3-carbonitrile Into a 20-mL round-bottom flask was placed (R)-4-(4-acryloyl-3-methylpiperazin-1-yl)-6,7-dichloro-1-(2-isopropyl-4-methylpyridin-3-yl)-2-oxo-1,2-dihydro-1,8-naphthyridine-3-carbonitrile (1.114 g, 2.12 mmol), (2-amino-3,4,5-trifluorophenyl)boronic acid (0.787 g, 4.12 mmol), Pd(PPh₃)₄ (0.527 g, 0.45 mmol), Na₂CO₃ (0.652 g, 6.15 mmol), dioxane (15 mL) and water (3 mL). The reaction mixture was stirred at 80° C. for 1 h. The reaction mixture was filtered and concentrated under vacuum. The residue was purified by Prep-HPLC CH₃CN/H₂O (0.05% NH₄HCO₃) (v/v=2/1). This resulted in 1.941 g (69%) of (R)-4-(4-acryloyl-3-methylpiperazin-1-yl)-7-(2-amino-3,4,5-trifluorophenyl)-6-chloro-1-(2-isopropyl-4-methylpyridin-3-yl)-2-oxo-1,2-dihydro-1,8-naphthyridine-3-carbonitrile as yellow solid. LCMS: m/z=636 [M+1]⁺.

Step 2. 4-((R)-4-acryloyl-3-methylpiperazin-1-yl)-7-(2-amino-6-chloro-3,4,5-trifluorophenyl)-6-chloro-1-(2-isopropyl-4-methylpyridin-3-yl)-2-oxo-1,2-dihydro-1,8-naphthyridine-3-carbonitrile ("Compound 10")

Into a 50-mL round-bottom flask purged and maintained with an inert atmosphere of nitrogen, was placed (R)-4-(4-acryloyl-3-methylpiperazin-1-yl)-7-(2-amino-3,4,5-trifluorophenyl)-6-chloro-1-(2-isopropyl-4-methylpyridin-3-yl)-2-oxo-1,2-dihydro-1,8-naphthyridine-3-carbonitrile (1.904 g, 3.00 mmol), NCS (0.946 g, 6.17 mmol) and AcOH (5 mL). The mixture was stirred at r.t. for 1 d. The residue was purified by Prep-HPLC (CH₃CN/H₂O)(v/v=6/4). This resulted in 0.497 g (25%) of 4-((R)-4-acryloyl-3-methylpiperazin-1-yl)-7-(2-amino-6-chloro-3,4,5-trifluorophenyl)-6-chloro-1-(2-isopropyl-4-methylpyridin-3-yl)-2-oxo-1,2-dihydro-1,8-naphthyridine-3-carbonitrile ("Compound 10") as yellow solid. LCMS: m/z=670 [M+1]⁺.

Step 3. 4-((R)-4-acryloyl-3-methylpiperazin-1-yl)-7-(2-amino-6-chloro-3,4,5-trifluorophenyl)-6-chloro-1-(2-isopropyl-4-methylpyridin-3-yl)-2-oxo-1,2-dihydro-1,8-naphthyridine-3-carbonitrile (first eluting isomer, "Compound 10-1") & 4-((R)-4-acryloyl-3-methylpiperazin-1-yl)-7-(2-amino-6-chloro-3,4,5-trifluorophenyl)-6-chloro-1-(2-isopropyl-4-methylpyridin-3-yl)-2-oxo-1,2-dihydro-1,8-naphthyridine-3-carbonitrile (second eluting isomer, "Compound 10-2")

The mixture of 4-((R)-4-acryloyl-3-methylpiperazin-1-yl)-7-(2-amino-6-chloro-3,4,5-trifluorophenyl)-6-chloro-1-(2-isopropyl-4-methylpyridin-3-yl)-2-oxo-1,2-dihydro-1,8-naphthyridine-3-carbonitrile atropisomers (495 mg) was purified by Chiral-Prep-HPLC with the following conditions: Column, CHIRAL ART Cellulose-SB, 3 cm×25 cm, 5 um; mobile phase, (Hex:DCM=3:1):EtOH (v/v=90:10); Detection wavelength, UV 220 nm. This resulted in 204 mg (41.21%) of 4-((R)-4-acryloyl-3-methylpiperazin-1-yl)-7-(2-amino-6-chloro-3,4,5-trifluorophenyl)-6-chloro-1-(2-isopropyl-4-methylpyridin-3-yl)-2-oxo-1,2-dihydro-1,8-naphthyridine-3-carbonitrile (the first eluting isomer, "Compound 10-1") as a yellow solid. LCMS: m/z=670 [M+1]⁺.

¹H NMR (400 MHz, CD₃OD) δ 8.58 (s, 1H), 8.41 (dd, J=5.0, 1.4 Hz, 1H), 7.23 (dd, J=8.4, 3.2 Hz, 1H), 6.85 (dd, J=16.7, 10.7 Hz, 1H), 6.29 (dd, J=16.8, 1.8 Hz, 1H), 5.82 (dd, J=10.6, 1.9 Hz, 1H), 4.88 (s, 2H), 4.60 (s, 1H), 4.29-4.22 (m, 1H), 4.09-3.90 (m, 2H), 3.62 (s, 1H), 2.89-2.70 (m, 1H), 1.95 (d, J=12.6 Hz, 3H), 1.45 (d, J=6.5 Hz, 3H), 1.18 (t, J=8.0 Hz, 3H), 1.00 (dd, J=12.5, 6.8 Hz, 3H).

And 170 mg (28.34%) of 4-((R)-4-acryloyl-3-methylpiperazin-1-yl)-7-(2-amino-6-chloro-3,4,5-trifluorophenyl)-6-chloro-1-(2-isopropyl-4-methylpyridin-3-yl)-2-oxo-1,2-dihydro-1,8-naphthyridine-3-carbonitrile (the second eluting isomer, "Compound 10-2") as a yellow solid. LCMS: m/z=670 [M+1]⁺.

¹H NMR (400 MHz, CD₃OD) δ 8.59 (s, 1H), 8.41 (d, J=5.0 Hz, 1H), 7.34-7.17 (m, 1H), 6.85 (dd, J=16.7, 10.7 Hz, 1H), 6.29 (dd, J=16.8, 1.8 Hz, 1H), 5.82 (dd, J=10.6, 1.9 Hz, 1H), 4.88 (s, 2H), 4.60 (s, 1H), 4.27-4.18 (m, 1H), 4.00 (s, 2H), 3.73-3.56 (m, 1H), 2.77-2.49 (m, 1H), 2.05 (d, J=10.4 Hz, 3H), 1.46 (d, J=6.5 Hz, 3H), 1.16 (dd, J=6.8, 1.3 Hz, 3H), 1.06-0.84 (m, 3H).

Example 11

4-((S)-4-acryloyl-2-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 11"); (P)-4-((S)-4-acryloyl-2-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile; and (M)-4-((S)-4-acryloyl-2-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile

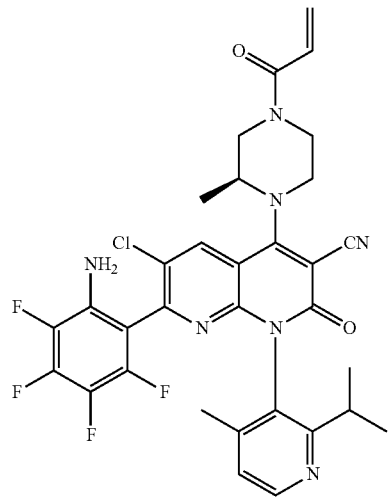

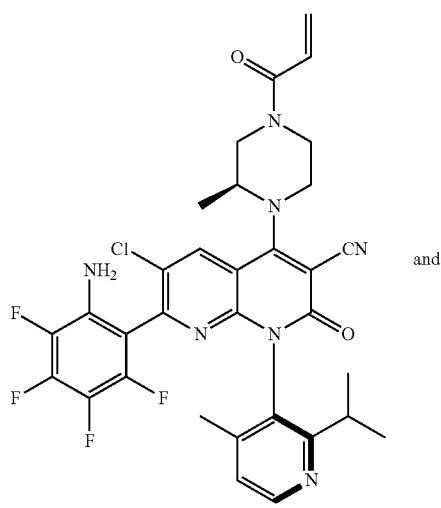

and

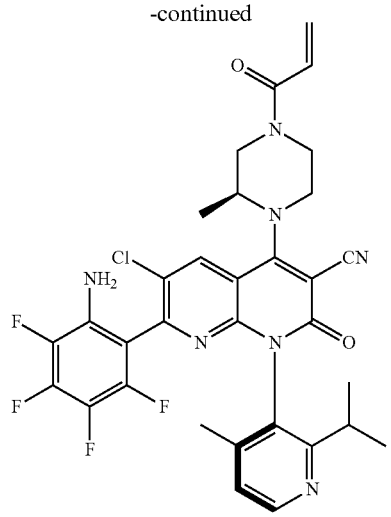

Step 1. 4-((S)-4-acryloyl-2-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 11")

Into a 20-mL round-bottom flask was placed (S)-4-(4-acryloyl-2-methylpiperazin-1-yl)-6,7-dichloro-1-(2-isopropyl-4-methylpyridin-3-yl)-2-oxo-1,2-dihydro-1,8-naphthyridine-3-carbonitrile (0.311 g, 0.59 mmol), (2-amino-3,4,5,6-tetrafluorophenyl)boronic acid (0.512 g, 1.49 mmol), Pd(PPh$_3$)$_4$ (0.085 g, 0.073 mmol), Na$_2$CO$_3$ (0.126 g, 1.19 mmol), dioxane (8 mL) and water (2 mL). The reaction mixture was stirred at 80° C. for 1 h. The reaction mixture was filtered and concentrated under vacuum. The residue was purified by Prep-HPLC CH$_3$CN/H$_2$O (0.05% NH$_4$HCO$_3$)(v/v=2/1). This resulted in 135 mg (35%) of 4-((S)-4-acryloyl-2-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile as yellow solid ("Compound 11"). LCMS: m/z=654 [M+1]$^+$.

Step 2. 4-((S)-4-acryloyl-2-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (first eluting isomer, "Compound 11-1") & 4-((S)-4-acryloyl-2-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (second eluting isomer, "Compound 11-2")

The mixture of 4-((S)-4-acryloyl-2-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile atropisomers (135 mg) was purified by Chiral-Prep-HPLC with the following conditions: Column, CHIRALPAK IF, 2 cm×25 cm, 5 um mobile phase, ((Hex:DCM=3:1):IPA=80:20; Detection wavelength, UV 220 nm. This resulted in 67 mg (49%) of 4-((S)-4-acryloyl-2-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (the first eluting isomer, "Compound 11-1") as a yellow solid. LCMS: m/z=654 [M+1]$^+$.

$^1$H NMR (400 MHz, CD$_3$OD) δ 8.52 (s, 1H), 8.43-8.44 (m, 1H), 7.26 (t, J=5.5 Hz, 1H), 7.02-6.77 (m, 1H), 6.33 (d, J=16.2 Hz, 1H), 5.85 (d, J=10.5 Hz, 1H), 4.67-4.39 (m, 2H), 4.17-4.18 (m, 3H), 3.78-3.56 (m, 2H), 2.81-2.83 (m, 1H), 1.93-1.94 (m, 3H), 1.38-1.40 (m, 3H), 1.18-1.19 (m, 3H), 1.01-1.04 (m, 3H).

And 61 mg (45%) of 4-((S)-4-acryloyl-2-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (the second eluting isomer, "Compound 11-2") as a yellow solid. LCMS: m/z=654 [M+1]$^+$.

$^1$H NMR (400 MHz, CD$_3$OD) δ 8.53 (s, 1H), 8.43-8.44 (m, 1H), 7.29-7.25 (m, 1H), 6.85-6.86 (m, 1H), 6.33 (d, J=15.3 Hz, 1H), 5.85 (d, J=10.7 Hz, 1H), 4.53-4.54 (m, 2H), 4.16-4.17 (m, 3H), 3.65-3.67 (m, 2H), 2.58-2.59 (m, 1H), 2.16-2.02 (m, 3H), 1.38-1.40 (m, 3H), 1.19-1.11 (m, 3H), 0.98-0.99 (m, 3H).

Example 12

4-(4-acryloylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 12"); (P)-4-(4-acryloylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile; and (M)-4-(4-acryloylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile

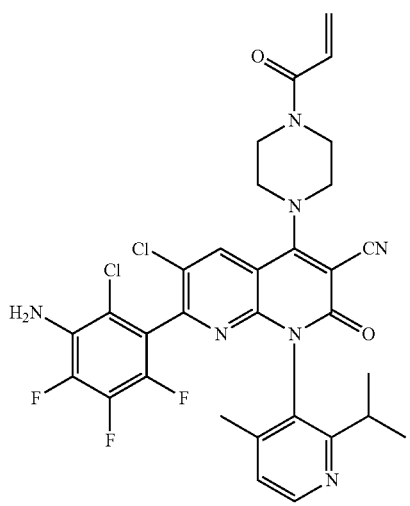

-continued

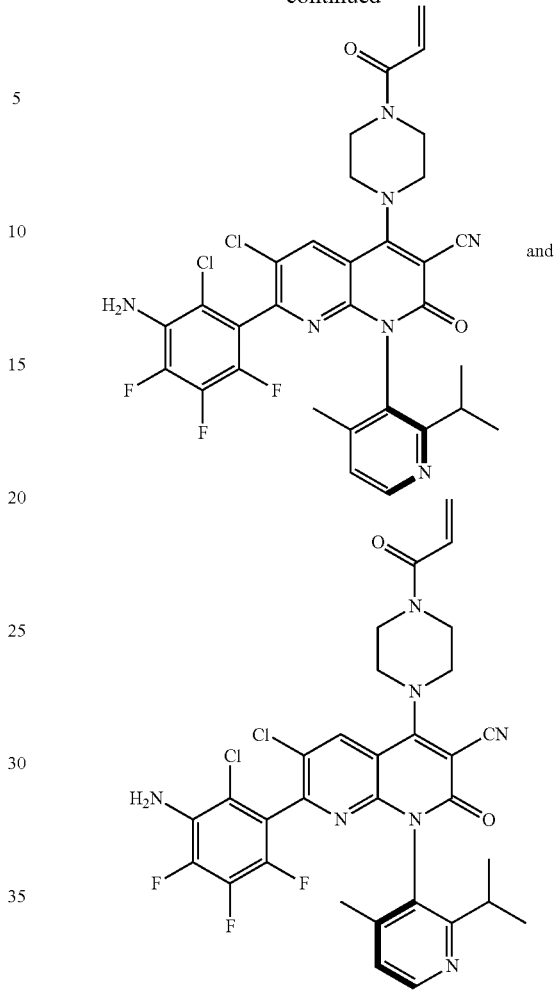

Step 1. 2,3,4-trifluoro-1-iodo-5-nitrobenzene

Into a 250-mL three-neck bottom flask purged and maintained with an inert atmosphere of nitrogen, was placed 1,2,3-trifluoro-4-nitrobenzene (4.98 g, 28.12 mmol), N-iodosuccinimide (15.99 g, 71.07 mmol), trifluoromethanesulfonic acid (25 mL) and stirred. The resulting solution was stirred overnight at room temperature. The reaction was then quenched by the addition of water (200 mL) slowly. The resulting solution was extracted with EA (2×100 mL), the organic layers were combined, washed with water (100 mL) and brine (100 mL), dried over anhydrous Na$_2$SO$_4$, the residue was concentrated under vacuum. The resulting crude product was further purified by C$_{18}$ column eluted with ACN/H$_2$O (v/v=0%~100%). This resulted in 4.66 g (54.69% yield) of 2,3,4-trifluoro-1-iodo-5-nitrobenzene.

Step 2. 2,3,4-trifluoro-5-iodoaniline

Into a 250-mL round-bottom flask purged and maintained with an inert atmosphere of nitrogen, was placed 2,3,4-trifluoro-1-iodo-5-nitrobenzene (4.66 g, 15.38 mmol), Fe iron (5.02 g, 89.93 mmol), ammonium chloride (8.57 g, 160.25 mmol), EtOH (30 mL) and water (30 mL). The reaction mixture was stirred at 55° C. for 1 h. The reaction was filtered and the filter cake was washed with EA (2×20 mL). The organic layers were combined and washed with brine (100 mL), dried over anhydrous $Na_2SO_4$. The resulting solution was concentrated under vacuum and applied onto a silica gel column eluted with EA/hexane (v/v=1/1). This resulted in 3.69 g (87% yield) of 2,3,4-trifluoro-5-iodoaniline as yellow oil. LCMS: m/z=274 [M+1]$^+$.

Step 3. (5-amino-2,3,4-trifluorophenyl)boronic acid

Into a 250-mL sealed tube purged and maintained with an inert atmosphere of nitrogen, was placed 2,3,4-trifluoro-5-iodoaniline (2.09 g, 7.67 mmol), Bis(pinacolato)diboron (9.46 g, 37.25 mmol), Pd(dppf)Cl$_2$ (1.06 g, 1.45 mmol), KOAc (5.10 g, 52.00 mmol) and NMP (80 mL). The reaction mixture was stirred at 95° C. for 2 h. The reaction was then quenched by the addition of saturated sodium carbonate aqueous solution (100 mL). The reaction mixture was stirred at room temperature for 2 h. The resulting solution was extracted with EA (3×100 mL), the organic layers were combined, then washed with brine (100 mL), dried over anhydrous $Na_2SO_4$, the residue was concentrated under vacuum. The resulting crude was further purified by C$_{18}$ column eluted with ACN/H$_2$O (v/v=30%~50%). This resulted in 1.48 g (106% yield) of (5-amino-2,3,4-trifluorophenyl)boronic acid as yellow oil. LCMS: m/z=192 [M+1]$^+$.

Step 4. 4-(4-acryloylpiperazin-1-yl)-7-(5-amino-2,3,4-trifluorophenyl)-6-chloro-1-(2-isopropyl-4-methylpyridin-3-yl)-2-oxo-1,2-dihydro-1,8-naphthyridine-3-carbonitrile Into a 40-mL sealed tube purged and maintained with an inert atmosphere of nitrogen, was placed 4-(4-acryloylpiperazin-1-yl)-6,7-dichloro-1-(2-isopropyl-4-methylpyridin-3-yl)-2-oxo-1,2-dihydro-1,8-naphthyridine-3-carbonitrile (0.68 g, 1.34 mmol), (5-amino-2,3,4-trifluorophenyl)boronic acid (0.51 g, 2.67 mmol), Pd(PPh$_3$)$_4$ (0.31 g, 0.27 mmol), Na$_2$CO$_3$ (0.41 g, 3.86 mmol), dioxane (20 mL) and water (4 mL). The reaction mixture was stirred at 80° C. for 2 h. The reaction was then quenched by the addition of water (50 mL) and ethyl acetate (20 mL). The resulting solution was extracted with ethyl acetate (1×50 mL), the organic layers were combined and dried over anhydrous Na$_2$SO$_4$, filtered and concentrated under vacuum. The resulting crude product was further purified by C$_{18}$ column eluted with ACN/H$_2$O (v/v=0%~60%). This resulted in 0.15 g (18% yield) of 4-(4-acryloylpiperazin-1-yl)-7-(5-amino-2,3,4-trifluorophenyl)-6-chloro-1-(2-isopropyl-4-methylpyridin-3-yl)-2-oxo-1,2-dihydro-1,8-naphthyridine-3-carbonitrile as yellow solid. LCMS: m/z=622 [M+1]$^+$.

Step 5. 4-(4-acryloylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 12")

Into a 8-mL sealed tube purged and maintained with an inert atmosphere of nitrogen, was placed 4-(4-acryloylpiperazin-1-yl)-7-(5-amino-2,3,4-trifluorophenyl)-6-chloro-1-(2-isopropyl-4-methylpyridin-3-yl)-2-oxo-1,2-dihydro-1,8-naphthyridine-3-carbonitrile (0.15 g, 0.25 mmol), NCS (0.10 g, 0.77 mmol) and AcOH (4 mL). The mixture was stirred for overnight at room temperature. The reaction was then quenched by the addition of water (50 mL). The resulting solution was extracted with ethyl acetate (2×50 mL), the organic layers were combined and washed with saturated sodium bicarbonate aqueous solution (2×50 mL), dried over anhydrous Na$_2$SO$_4$, filtered and concentrated under vacuum. The resulting crude product was further purified by C$_{18}$ column eluted with ACN/H$_2$O (0.15% NH$_4$HCO$_3$) (v/v=30%~80%). This resulted in 21 mg (13% yield) of 4-(4-acryloylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 12") as yellow solid. LCMS: m/z=656 [M+1]$^+$.

$^1$H NMR (400 MHz, DMSO-d$_6$) δ 8.57 (s, 1H), 8.44 (d, J=4.7 Hz, 1H), 7.23 (t, J=4.6 Hz, 1H), 6.92 (dd, J=16.7, 10.5 Hz, 1H), 6.20 (dd, J=16.6, 2.3 Hz, 1H), 5.86 (s, 2H), 5.77 (dd, J=10.4, 2.2 Hz, 1H), 4.29-3.50 (m, 8H), 3.72-3.66 (m, 1H), 1.89 (d, J=10.7 Hz, 3H), 1.08 (dd, J=6.6, 2.4 Hz, 3H), 0.97-0.77 (m, 3H).

Step 6. 4-(4-acryloylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile (first eluting isomer, "Compound 12-1") & 4-(4-acryloylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile (second eluting isomer, "Compound 12-2")

The mixture of 4-(4-acryloylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile atropisomers (110 mg, several batches) was purified by Chiral-Prep-HPLC with the following conditions: Column, CHIRAL ART Cellulose-SB, 3 cm×25 cm, 5 um; mobile phase, (Hex:DCM=3:1):EtOH (v/v=95:5); Detection wavelength, UV 220 nm. This resulted in 53 mg (48.18%) of 4-(4-acryloylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile (the first eluting isomer, "Compound 12-1") as a yellow solid. LCMS: m/z=656 [M+1]$^+$.

$^1$H NMR (400 MHz, DMSO-d$_6$) δ 8.57 (s, 1H), 8.44 (dd, J=4.9, 1.5 Hz, 1H), 7.24 (t, J=4.8 Hz, 1H), 6.92 (dd, J=16.7, 10.4 Hz, 1H), 6.21 (dd, J=16.6, 2.4 Hz, 1H), 5.88 (s, 2H), 5.77 (dd, J=10.4, 2.4 Hz, 1H), 4.25-2.64 (d, J=27.7 Hz, 8H), 2.78-2.60 (m, 1H), 1.89 (d, J=10.4 Hz, 3H), 1.12-1.01 (m, 3H), 0.97-0.83 (m, 3H).

And 51 mg (46.36%) of 4-(4-acryloylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile (the second eluting isomer, "Compound 12-2") as a yellow solid. LCMS: m/z=656 [M+1]$^+$.

$^1$H NMR (400 MHz, DMSO-d$_6$) δ 8.57 (s, 1H), 8.44 (d, J=4.9 Hz, 1H), 7.24 (t, J=4.7 Hz, 1H), 6.92 (dd, J=16.6, 10.4 Hz, 1H), 6.21 (dd, J=16.6, 2.5 Hz, 1H), 5.88 (s, 2H), 5.77 (dd, J=10.3, 2.4 Hz, 1H), 3.89 (d, J=25.8 Hz, 8H), 2.73-2.64 (m, 1H), 1.89 (d, J=10.5 Hz, 3H), 1.08 (dd, J=6.8, 2.6 Hz, 3H), 0.90 (dd, J=19.2, 6.7 Hz, 3H).

Example 13

4-((3S,5R)-4-acryloyl-3,5-dimethylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 13"); (P)-4-((3S,5R)-4-acryloyl-3,5-dimethylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile; and (M)-4-((3S,5R)-4-acryloyl-3,5-dimethylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile

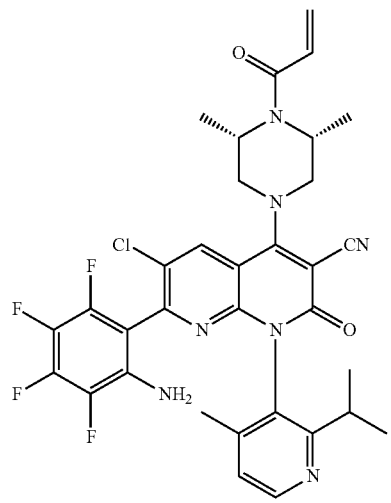

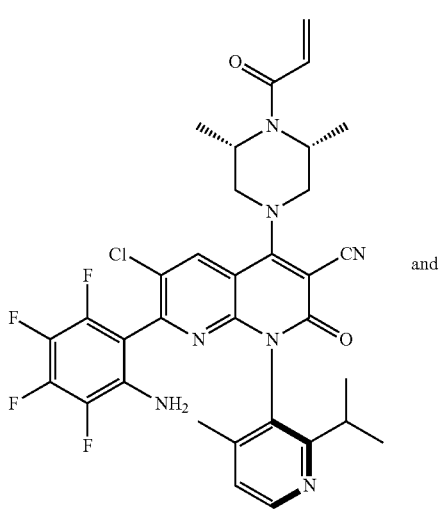

and

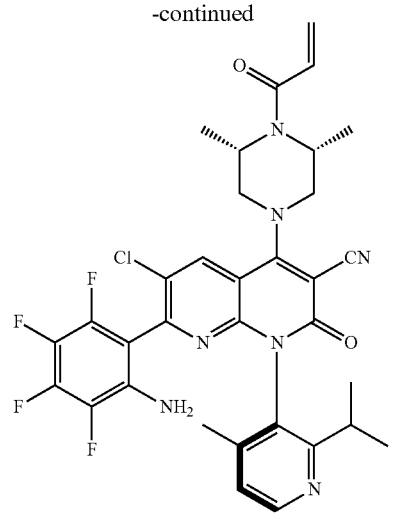

Step 1. 4-((3S,5R)-4-acryloyl-3,5-dimethylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 13")

Into a 20-mL round-bottom flask was placed 4-((3S,5R)-4-acryloyl-3,5-dimethylpiperazin-1-yl)-6,7-dichloro-1-(2-isopropyl-4-methylpyridin-3-yl)-2-oxo-1,2-dihydro-1,8-naphthyridine-3-carbonitrile (0.312 g, 0.58 mmol), 2,3,4,5-tetrafluoro-6-(4,4,5,5-tetramethyl-1,3,2-dioxaborolan-2-yl)aniline (0.601 g, 2.07 mmol), Pd(pph$_3$)$_4$ (0.125 g, 0.11 mmol), Na$_2$CO$_3$ (0.189 g, 1.78 mmol), dioxane (8 mL) and water (2 mL).

The reaction mixture was stirred at 80° C. for 1 h. The reaction mixture was filtered and concentrated under vacuum. The residue was purified by Prep-HPLC CH$_3$CN/H$_2$O (0.05% NH$_4$HCO$_3$)(v/v=2/1). This resulted in 0.132 g (34%) of 4-((3S,5R)-4-acryloyl-3,5-dimethylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 13") as yellow solid. LCMS: m/z=668 [M+1]$^+$.

$^1$H NMR (400 MHz, CD$_3$OD) δ 8.85 (s, 1H), 8.67 (d, J=5.8 Hz, 1H), 7.85 (d, J=5.9 Hz, 1H), 6.94-6.81 (m, 1H), 6.33 (d, J=16.6 Hz, 1H), 5.84 (d, J=10.8 Hz, 1H), 4.78 (s, 2H), 4.09-3.95 (m, 2H), 3.95-3.81 (m, 2H), 3.13-2.99 (m, 1H), 2.33-2.18 (m, 3H), 1.68-1.59 (m, 6H), 1.36-1.24 (m, 3H), 1.23-1.09 (m, 3H).

Step 2. 4-((3S,5R)-4-acryloyl-3,5-dimethylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (first eluting isomer, "Compound 13-1") & 4-((3S,5R)-4-acryloyl-3,5-dimethylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (second eluting isomer, "Compound 13-2")

The mixture of 4-((3S,5R)-4-acryloyl-3,5-dimethylpiperazin-1-yl)-7-(2-amino-3,4,5,6-tetrafluoro phenyl)-6-chloro-1-(2-isopropyl-4-methylpyridin-3-yl)-2-oxo-1,2-dihydro-1,8-naphthyridine-3-carbonitrile atropisomers (930 mg, several batches) was purified by Chiral-Prep-HPLC with the following conditions: Column, CHIRALPAK IA, 3 cm×25 cm, 5 um; mobile phase, Hex:EtOH=80:20; Detection wavelength, UV 220 nm. This resulted in 424 mg (45.59%) of 4-((3S,5R)-4-acryloyl-3,5-dimethylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (the first eluting isomer, "Compound 13-1") as a yellow solid. LCMS: m/z=668 [M+1]$^+$.

$^1$H NMR (400 MHz, CD$_3$OD) δ 8.83 (s, 1H), 8.52 (d, J=5.3 Hz, 1H), 7.47 (d, J=5.2 Hz, 1H), 6.88 (dd, J=16.7, 10.6 Hz, 1H), 6.33 (dd, J=16.7, 1.9 Hz, 1H), 5.84 (dd, J=10.6, 1.9 Hz, 1H), 4.77 (s, 2H), 4.10-3.94 (m, 2H), 3.91-3.79 (m, 2H), 2.81-2.83 (m, 1H), 2.08-2.10 (m, 3H), 1.65 (t, J=6.0 Hz, 6H), 1.26-1.19 (m, 3H), 1.01-1.02 (m, 3H).

And 372 mg (40.00%) of 4-((3S,5R)-4-acryloyl-3,5-dimethylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile (the second eluting isomer, "Compound 13-2") as a yellow solid. LCMS: m/z=668 [M+1]$^+$.

$^1$H NMR (400 MHz, CD$_3$OD) δ 8.83 (s, 1H), 8.52 (d, J=5.3 Hz, 1H), 7.47 (d, J=5.2 Hz, 1H), 6.88 (dd, J=16.7, 10.6 Hz, 1H), 6.33 (dd, J=16.7, 1.9 Hz, 1H), 5.84 (dd, J=10.6, 1.9 Hz, 1H), 4.77 (s, 2H), 4.10-3.94 (m, 2H), 3.91-3.79 (m, 2H), 2.82-2.83 (m, 1H), 2.09-2.11 (m, 3H), 1.65 (t, J=6.0 Hz, 6H), 1.26-1.19 (m, 3H), 1.04-1.06 (m, 3H).

Example 14

4-((R)-4-acryloyl-3-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 14")

3-carbonitrile (353 mg, 0.67 mmol), 2,3,4,5-tetrafluoro-6-(4,4,5,5-tetramethyl-1,3,2-dioxaborolan-2-yl)aniline (604 mg, 2.08 mmol), Pd(PPh$_3$)$_4$ (185 mg, 0.16 mmol), Na$_2$CO$_3$ (235 mg, 2.22 mmol), dioxane (7 mL) and water (0.7 mL). The reaction mixture was stirred at 80° C. for 1 h. The reaction mixture was filtered and concentrated under vacuum. The reaction mixture was concentrated under vacuum. The residue was purified by Prep-HPLC (CH$_3$CN/H$_2$O (v/v=7/3)). This resulted in 29 mg (7% yield) of 4-((R)-4-acryloyl-3-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 14") as yellow solid. LCMS: m/z=654 [M+1]$^+$.

$^1$H NMR (400 MHz, CD$_3$OD) δ 8.50 (d, J=52.4 Hz, 2H), 7.27 (s, 1H), 6.96-6.66 (m, 1H), 6.29 (d, J=16.2 Hz, 1H), 5.83 (d, J=9.6 Hz, 1H), 4.70-4.43 (m, 1H), 4.18-4.08 (m, 4H), 3.70-3.60 (m, 2H), 2.82-2.48 (m, 1H), 2.03 (s, 3H), 1.48-1.40 (m, 3H), 1.24-0.84 (m, 6H).

Example 15

4-((S)-4-acryloyl-2-methylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 15"); (P)-4-((S)-4-acryloyl-2-methylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile; and (M)-4-((S)-4-acryloyl-2-methylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile

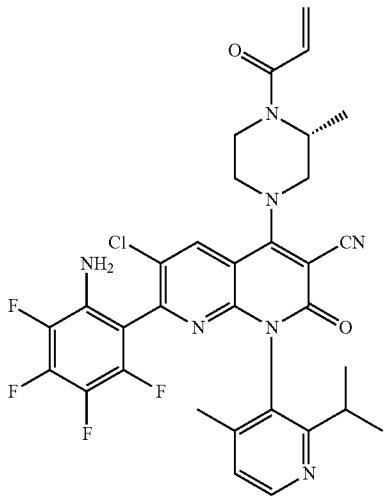 [SMILES: C=CC(=O)N1CCN(c2c(C#N)c(=O)n(-c3c(C)ccnc3C(C)C)c3nc(-c4c(N)c(F)c(F)c(F)c4F)c(Cl)cc23)C[C@H]1C]

Step 1. 4-((R)-4-acryloyl-3-methylpiperazin-1-yl)-7-(2-amino-3,4,5,6-tetrafluorophenyl)-6-chloro-1-(2-isopropyl-4-methylpyridin-3-yl)-2-oxo-1,2-dihydro-1,8-naphthyridine-3-carbonitrile ("Compound 14")

Into a 20-mL sealed tube purged and maintained with an inert atmosphere of nitrogen, was placed (R)-4-(4-acryloyl-3-methylpiperazin-1-yl)-6,7-dichloro-1-(2-isopropyl-4-methylpyridin-3-yl)-2-oxo-1,2-dihydro-1,8-naphthyridine-

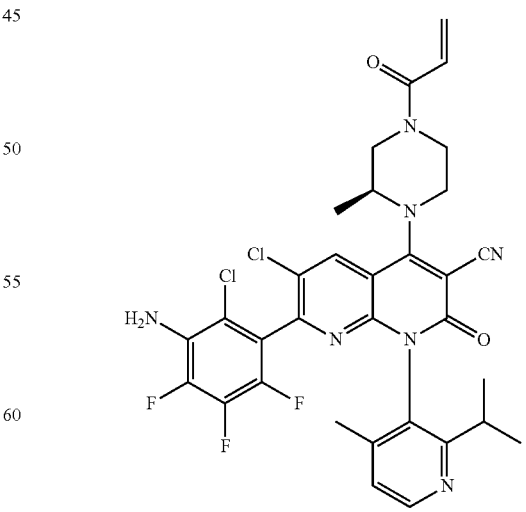

-continued

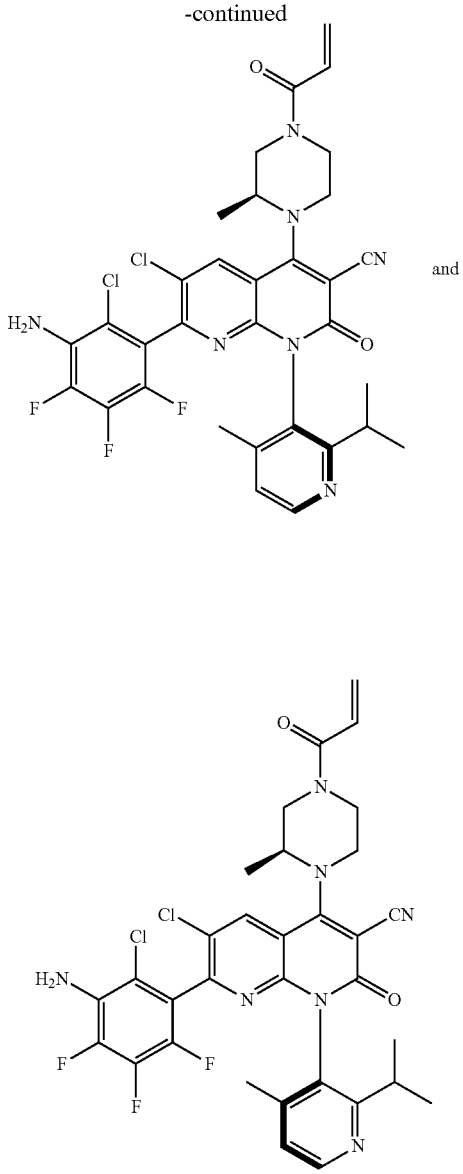

Step 1. (S)-4-(4-acryloyl-2-methylpiperazin-1-yl)-7-(5-amino-2,3,4-trifluorophenyl)-6-chloro-1-(2-isopropyl-4-methylpyridin-3-yl)-2-oxo-1,2-dihydro-1,8-naphthyridine-3-carbonitrile Into a 20-mL round-bottom flask purged and maintained with an inert atmosphere of nitrogen was placed (S)-4-(4-acryloyl-2-methylpiperazin-1-yl)-6,7-dichloro-1-(2-isopropyl-4-methylpyridin-3-yl)-2-oxo-1,2-dihydro-1,8-naphthyridine-3-carbonitrile (0.310 g, 0.59 mmol), (5-amino-2,3,4-trifluorophenyl)boronic acid (0.285 g, 1.49 mmol), Pd(PPh$_3$)$_4$ (0.085 g, 0.073 mmol), Na$_2$CO$_3$ (0.126 g, 1.19 mmol), dioxane (8 mL) and water (2 mL). The reaction mixture was stirred at 80° C. for 1 h. The reaction mixture was filtered and concentrated under vacuum. The residue was purified by Prep-HPLC CH$_3$CN/H$_2$O (0.05% NH$_4$HCO$_3$)(v/v=2/1). This resulted in 135 mg (35%) of (S)-4-(4-acryloyl-2-methylpiperazin-1-yl)-7-(5-amino-2,3,4-trifluorophenyl)-6-chloro-1-(2-isopropyl-4-m ethylpyridin-3-yl)-2-oxo-1,2-dihydro-1,8-naphthyridine-3-carbonitrile as yellow solid. LCMS: m/z=636 [M+1]$^+$.

Step 2. 4-((S)-4-acryloyl-2-methylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 15")

Into a 8-mL sealed tube purged and maintained with an inert atmosphere of nitrogen, was placed (S)-4-(4-acryloyl-2-methylpiperazin-1-yl)-7-(5-amino-2,3,4-trifluorophenyl)-6-chloro-1-(2-isopropyl-4-m ethylpyridin-3-yl)-2-oxo-1,2-dihydro-1,8-naphthyridine-3-carbonitrile (0.123 g, 193.376 μmol), NCS (0.053 g, 396.906 mol) and AcOH (2 mL). The mixture was stirred for overnight at room temperature. The reaction was then quenched by the addition of saturated sodium bicarbonate aqueous solution (100 mL). The resulting solution was extracted with ethyl acetate (3×100 mL), the organic layers were combined and concentrated under vacuum. The resulting crude product was further purified by C$_{18}$ column eluted with ACN/H$_2$O (0.15% NH$_4$HCO$_3$) (v/v=30%~80%). This resulted in 55 mg (42% yield) of 4-((S)-4-acryloyl-2-methylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile ("Compound 15") as yellow solid. LCMS: m/z=670 [M+1]$^+$.

$^1$H NMR (400 MHz, CD$_3$OD) δ 8.54 (s, 1H), 8.41 (d, J=4.8 Hz, 1H), 7.24 (dd, J=11.5, 5.9 Hz, 1H), 6.98-6.74 (m, 1H), 6.33 (d, J=16.3 Hz, 1H), 5.84 (d, J=10.5 Hz, 1H), 4.69-3.97 (m, 5H), 3.78-3.52 (m, 2H), 2.86-2.56 (m, 1H), 2.12-1.88 (m, 3H), 1.47-1.30 (m, 3H), 1.25-1.10 (m, 3H), 1.07-0.88 (m, 3H).

Step 2. 4-((S)-4-acryloyl-2-methylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile (first eluting isomer, "Compound 15-1") & 4-((S)-4-acryloyl-2-methylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile (second eluting isomer, "Compound 15-2")

The mixture of 4-((S)-4-acryloyl-2-methylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile atropisomers (53 mg) was purified by Chiral-Prep-HPLC with the following conditions: Column, CHIRALPAK IF, 2 cm×25 cm, 5 um mobile phase, (Hex:DCM=3:1):EtOH (v/v=9:1); Detection wavelength, UV 220 nm. This resulted in 20 mg (49%) of 4-((S)-4-acryloyl-2-methylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile (the first eluting isomer. "Compound 15-1") as a yellow solid. LCMS: m/z=670 [M+1]$^+$.

$^1$H NMR (400 MHz, CD$_3$OD) δ 8.56 (s, 1H), 8.43 (d, J=5.0 Hz, 1H), 7.28 (t, J=4.9 Hz, 1H), 6.99-6.79 (m, 1H), 6.35 (d, J=18.0 Hz, 1H), 5.87 (d, J=10.7 Hz, 1H), 4.68-4.06 (m, 5H), 3.78-3.56 (m, 2H), 2.69-2.56 (m, 1H), 2.09 (d, J=9.8 Hz, 3H), 1.42 (s, 3H), 1.17 (d, J=6.8 Hz, 3H), 0.98 (dd, J=18.6, 6.8 Hz, 3H).

And 17 mg (45%) of 4-((S)-4-acryloyl-2-methylpiperazin-1-yl)-7-(3-amino-2-chloro-4,5,6-trifluorophenyl)-6-chloro-1-(2-isopropyl-4-methylpyridin-3-yl)-2-oxo-1,2-dihydro-1,8-naphthyridine-3-carbonitrile (the second eluting isomer, "Compound 15-2") as a yellow solid. LCMS: m/z=670 [M+1]⁺.
¹H NMR (400 MHz, CD₃OD) δ 8.56 (s, 1H), 8.44 (d, J=5.0 Hz, 1H), 7.26 (t, J=5.4 Hz, 1H), 6.87 (d, J=27.5 Hz, 1H), 6.97-6.80 (m, 1H), 5.87 (d, J=11.5 Hz, 1H), 4.65-4.05 (m, 5H), 3.78-3.57 (m, 2H), 2.88-2.78 (m, 1H), 1.95 (d, J=12.5 Hz, 3H), 1.44-1.34 (m, 3H), 1.22 (d, J=6.7 Hz, 3H), 1.03 (dd, J=11.9, 6.8 Hz, 3H).
The following compounds can be synthesized following the similar methods as described in the above-mentioned examples:
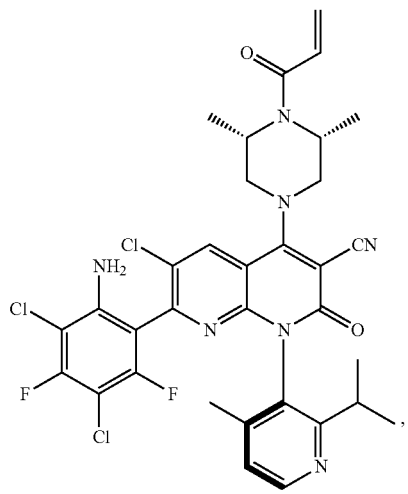
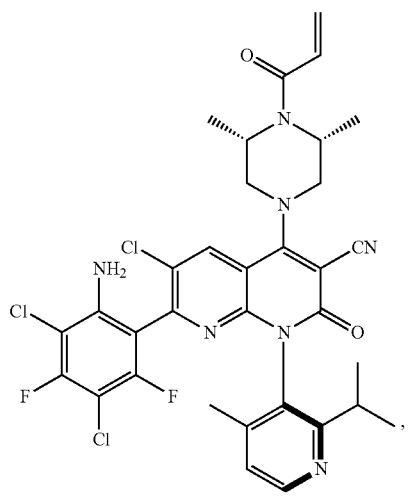
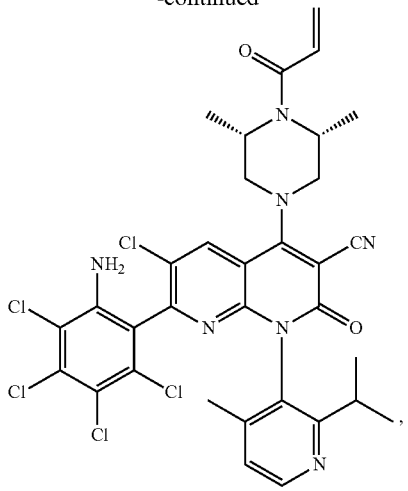
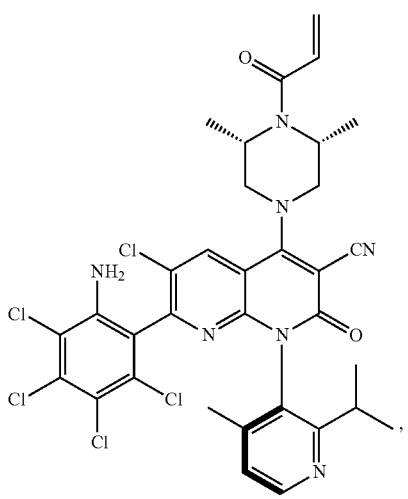
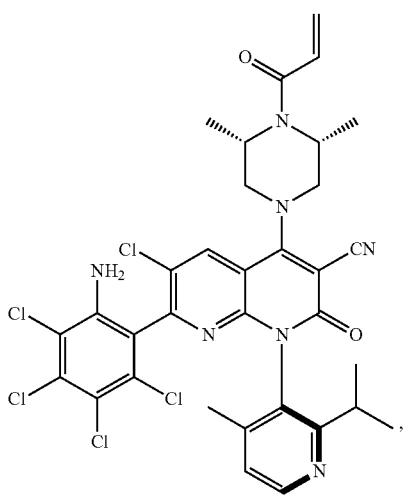

335
-continued
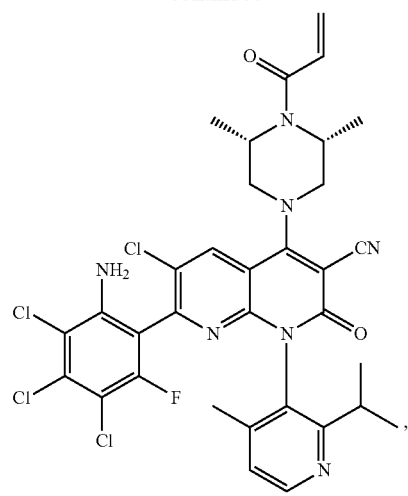
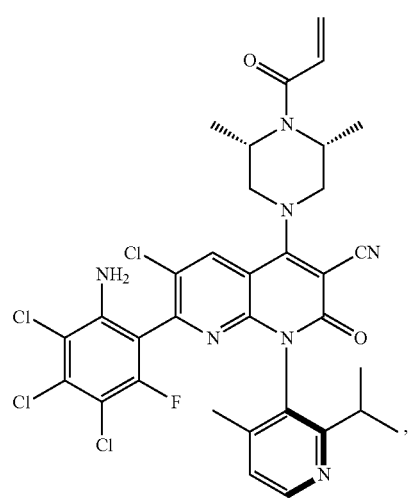
336
-continued
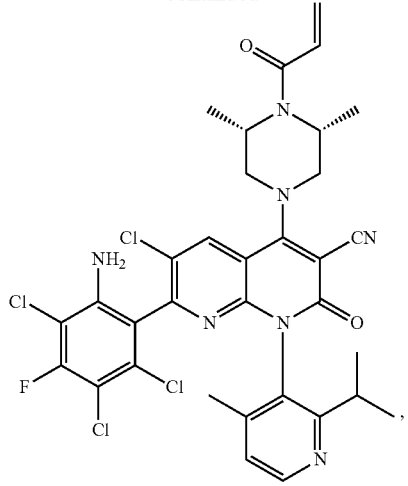
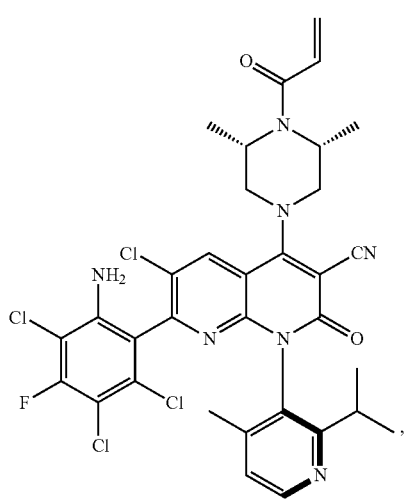

337
-continued
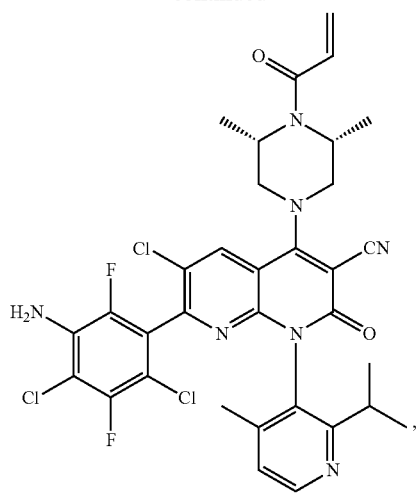
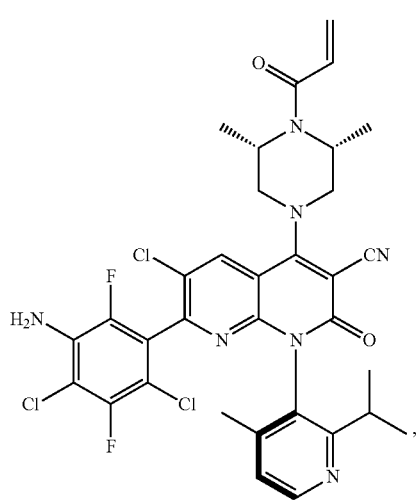
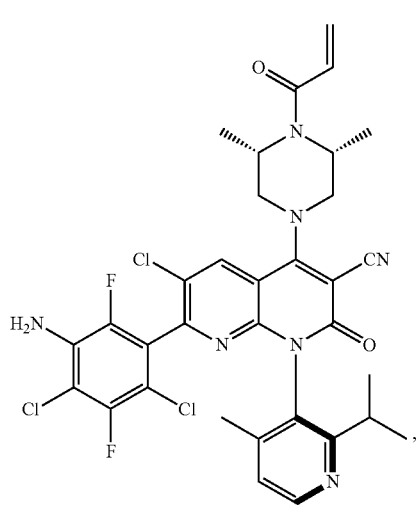
338
-continued
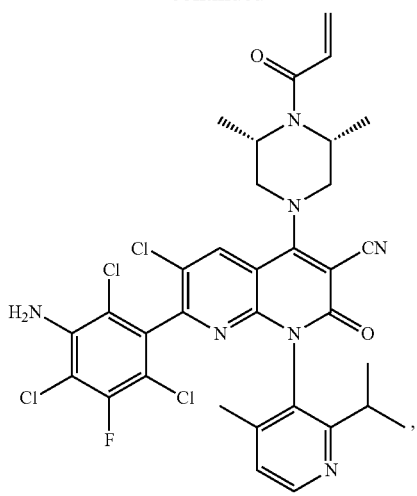

339
-continued
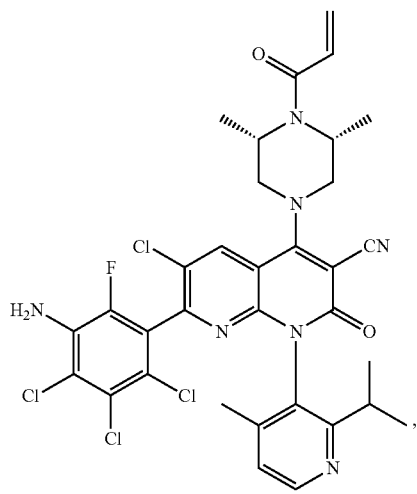
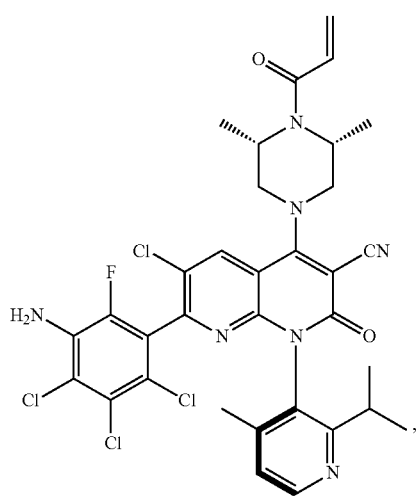
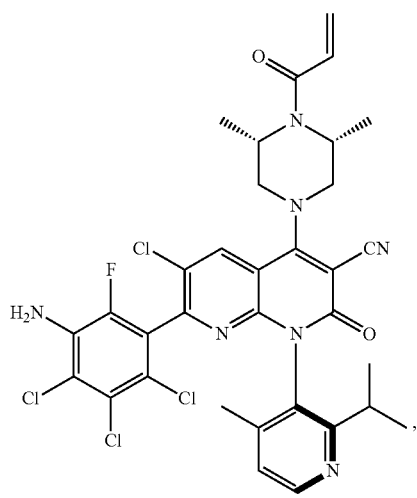
340
-continued
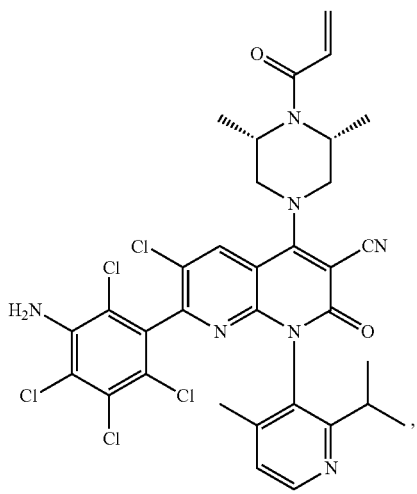
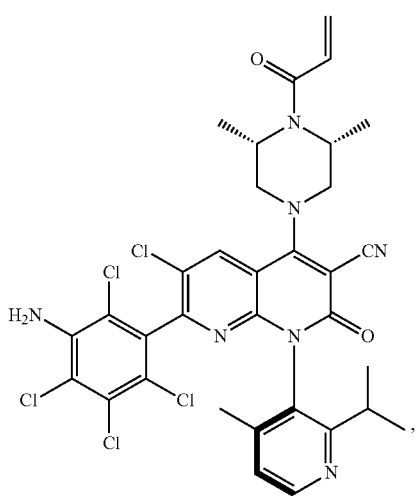
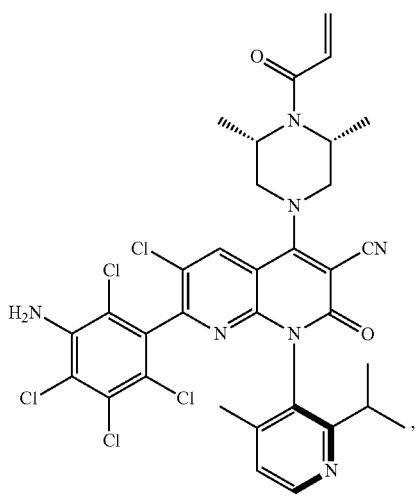

341
-continued
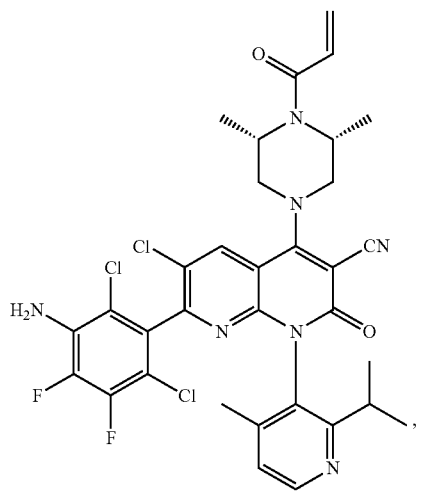
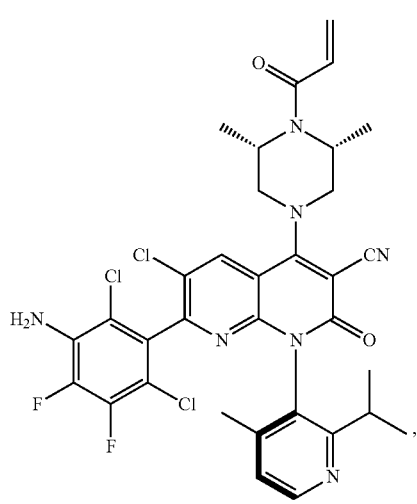
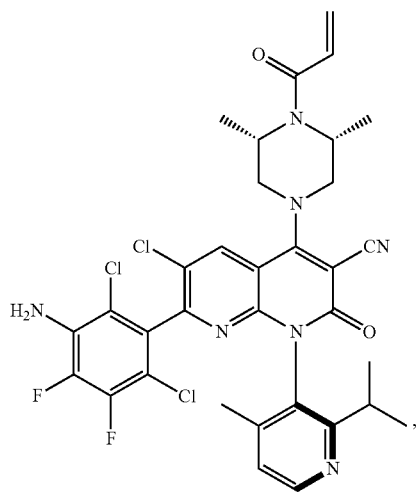
342
-continued
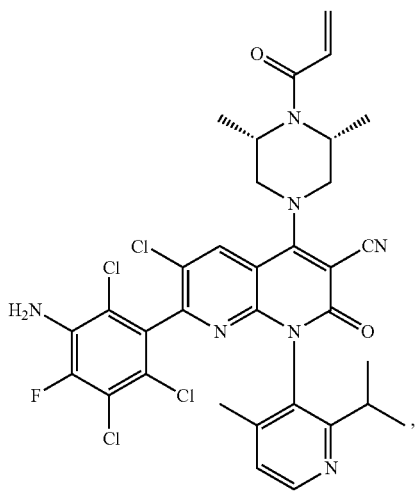
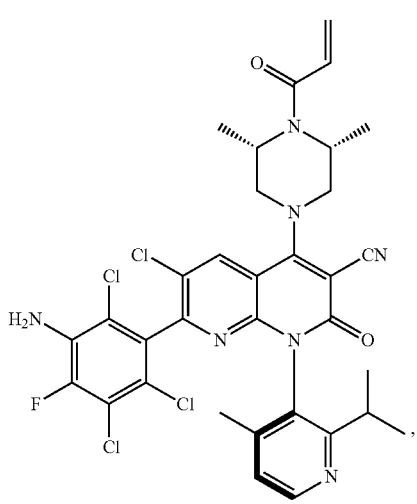
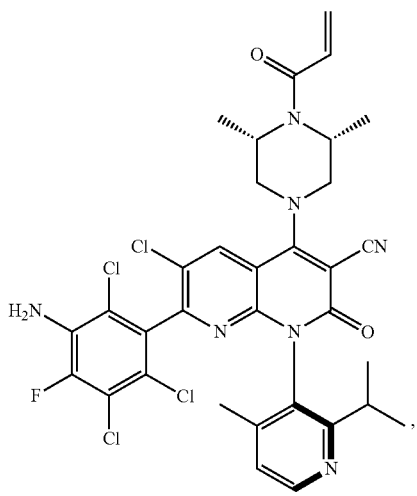

343
-continued
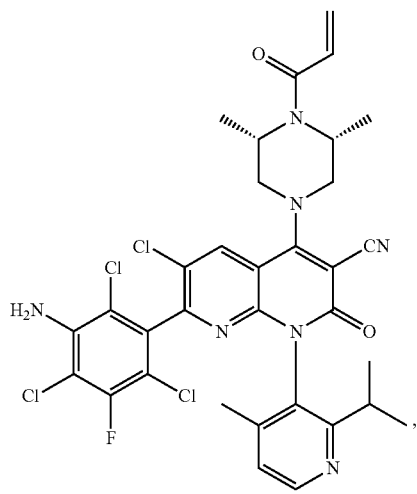
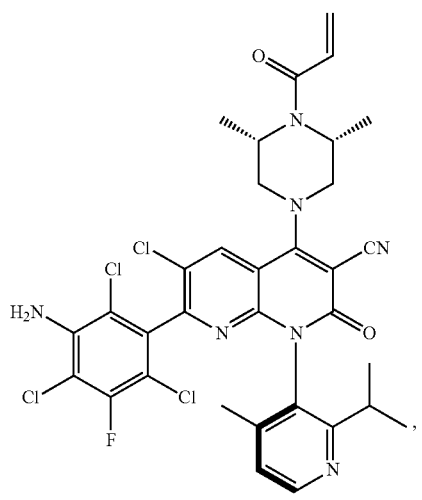
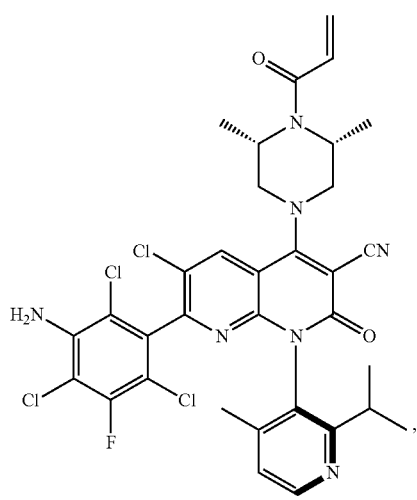
344
-continued
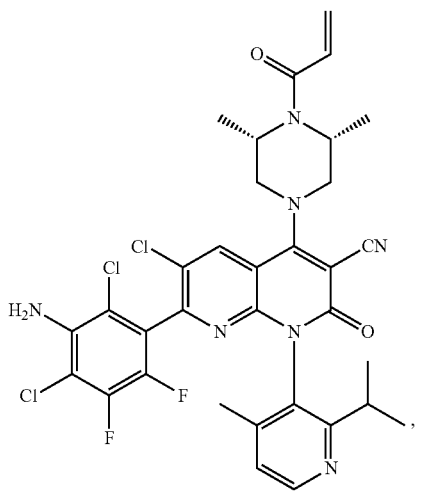
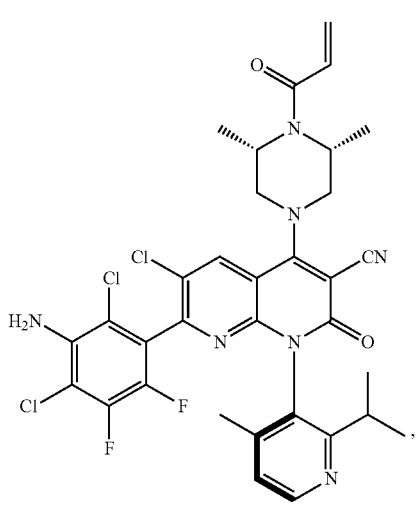
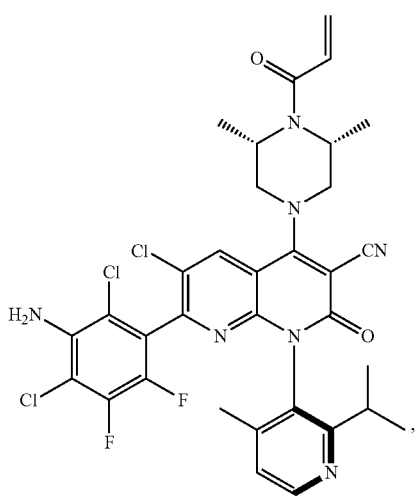

345
-continued
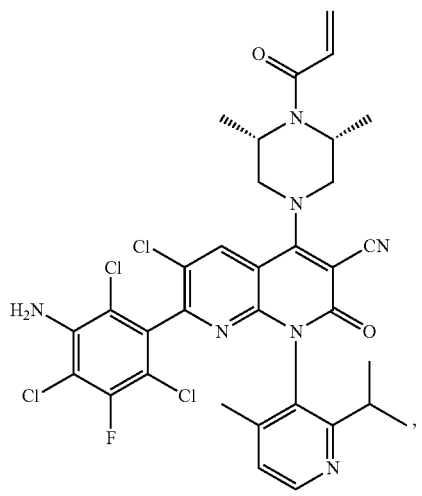
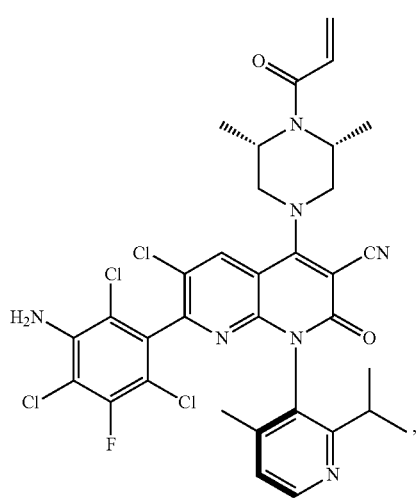
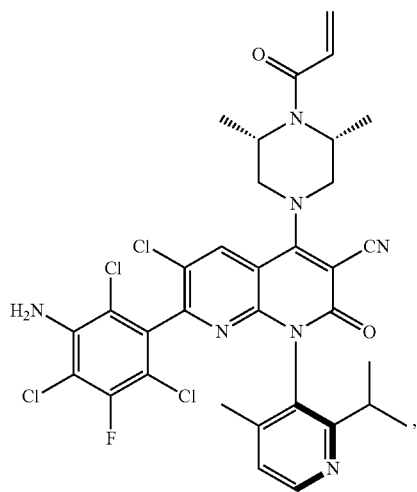
346
-continued
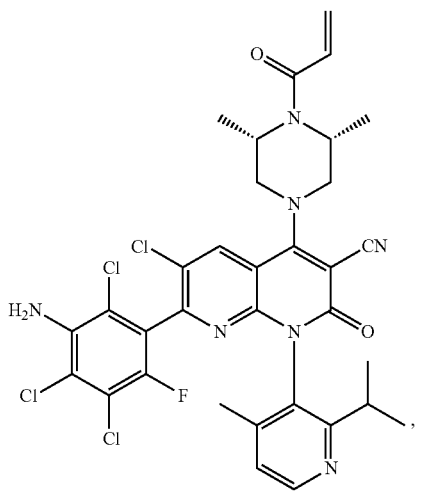
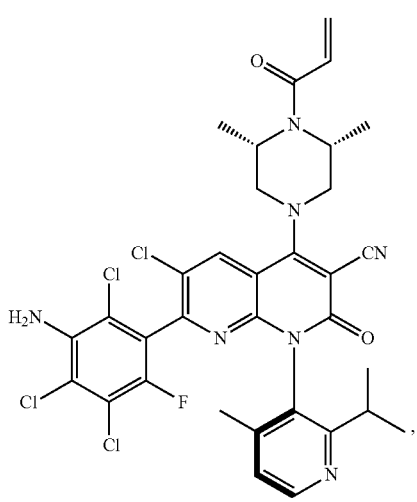
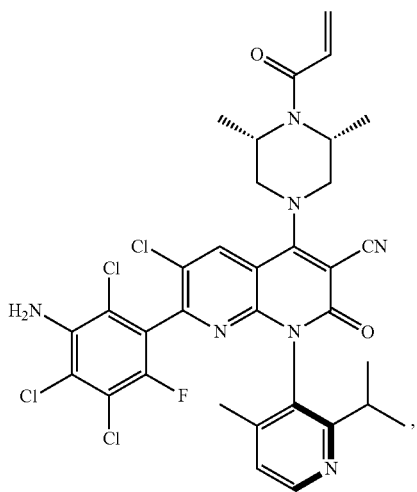

347
-continued
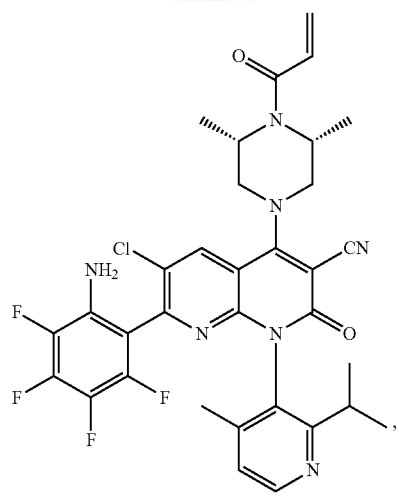
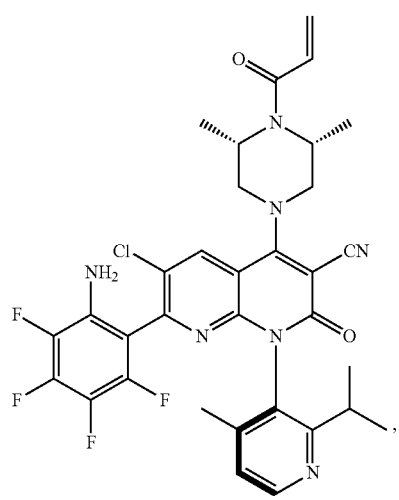
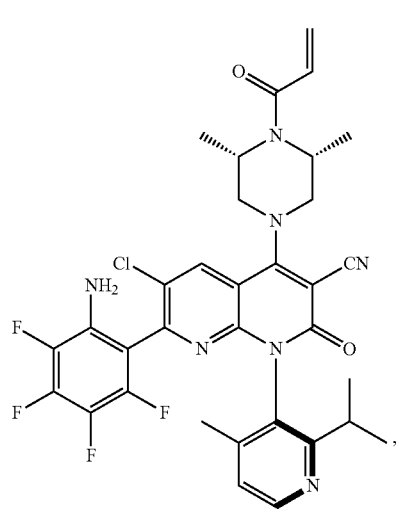
348
-continued
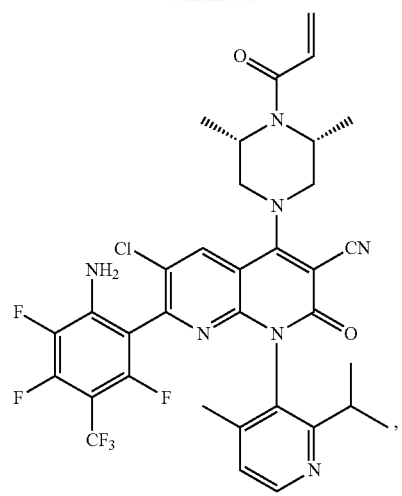
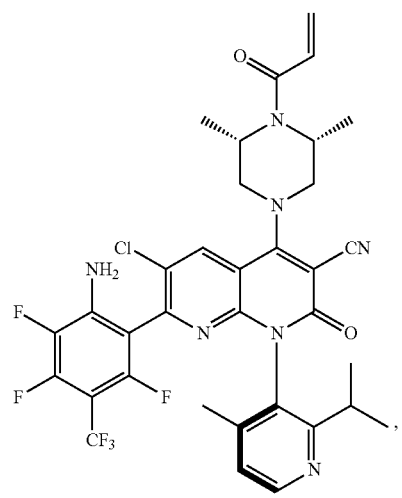
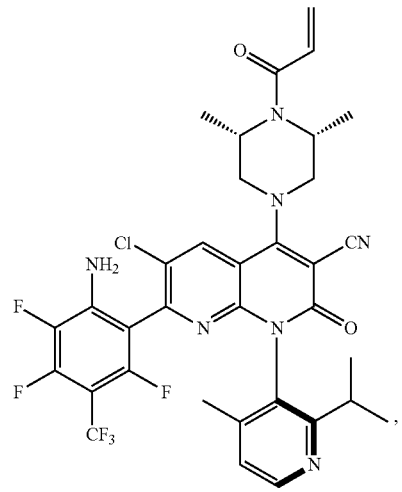

349
-continued
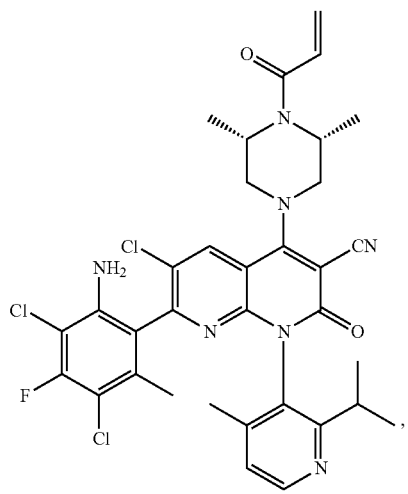
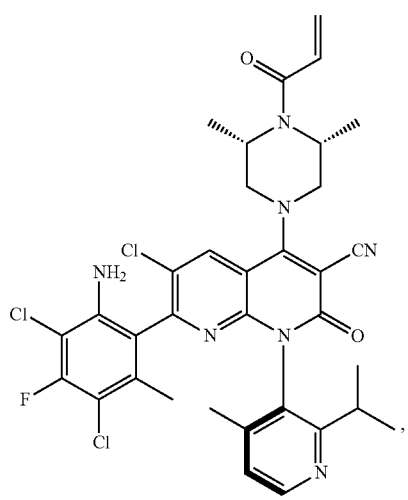
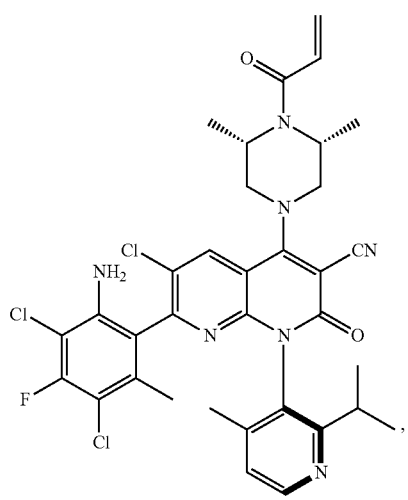
350
-continued
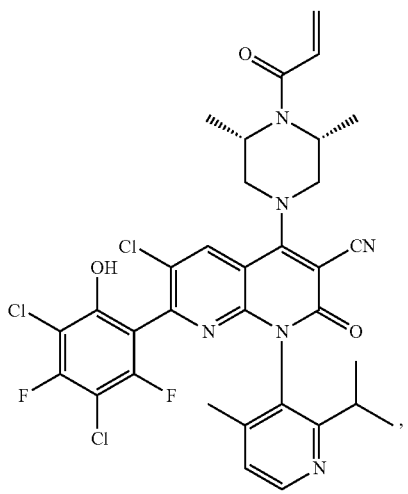
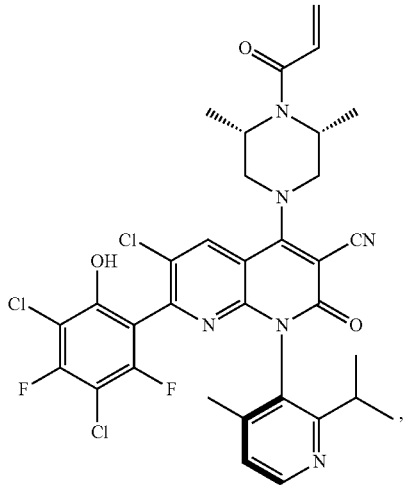
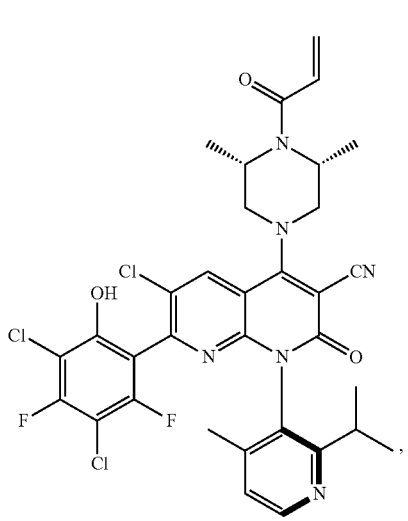

351
-continued
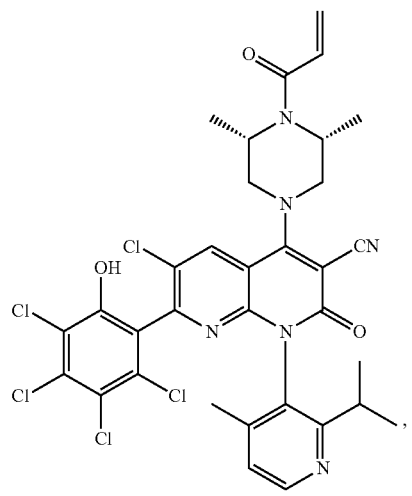
352
-continued
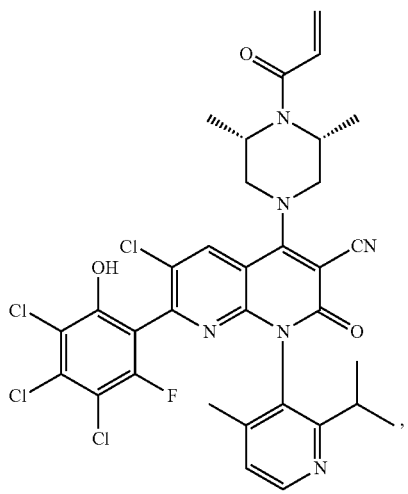
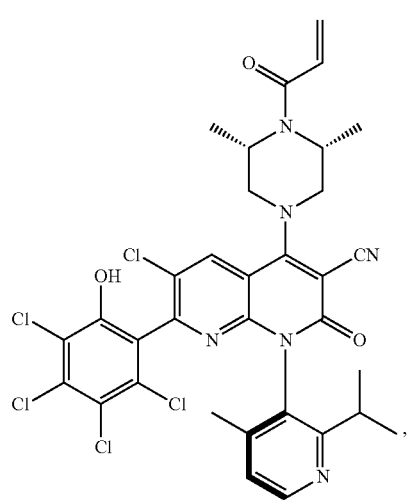
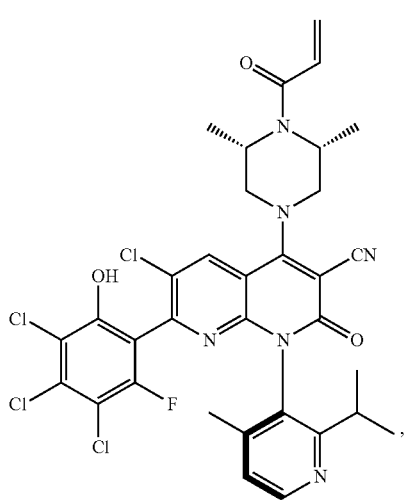
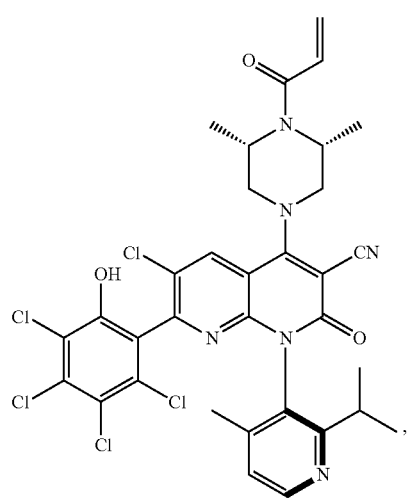
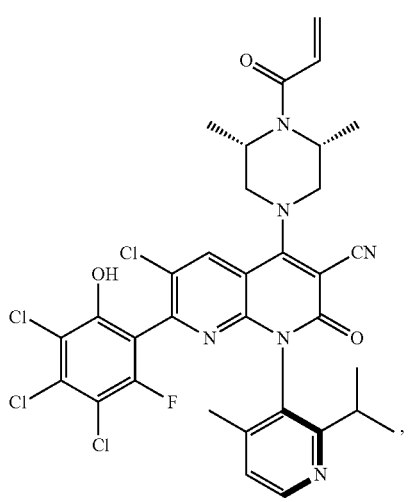

353
-continued
354
-continued
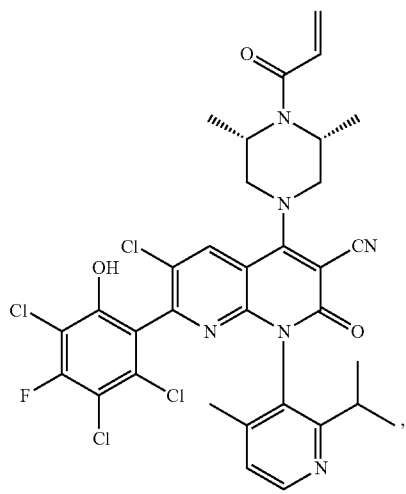
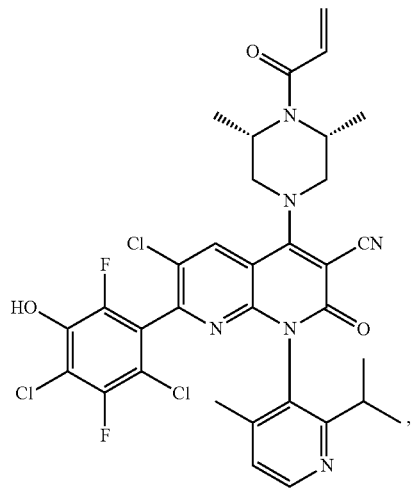
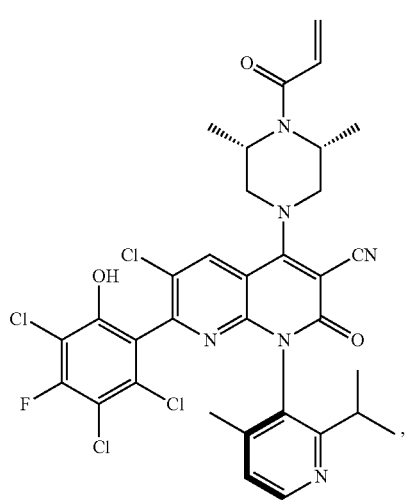
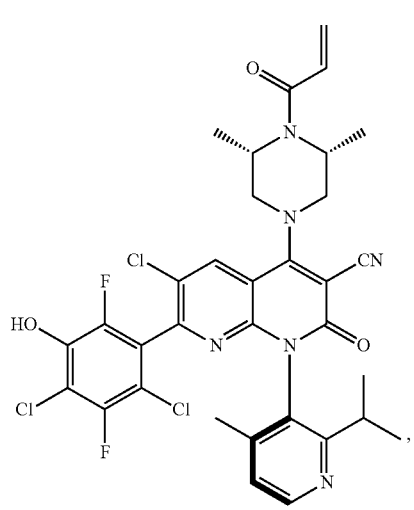
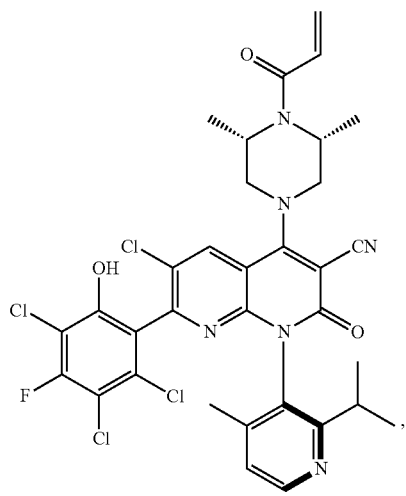
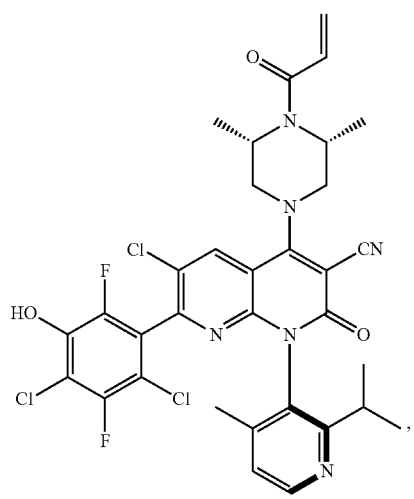

355
-continued
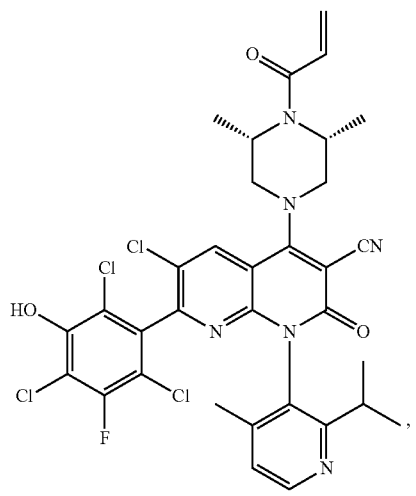
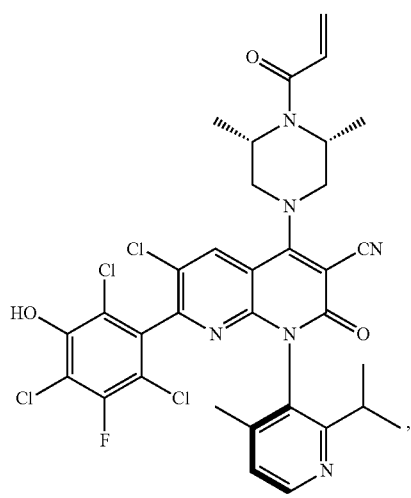
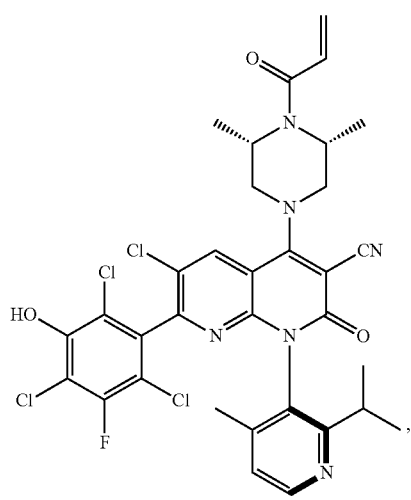
356
-continued
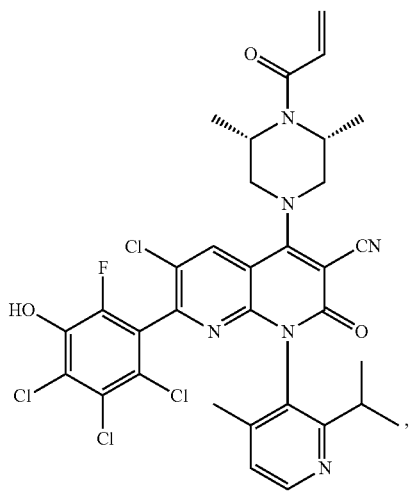
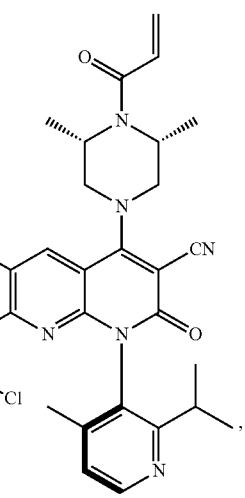
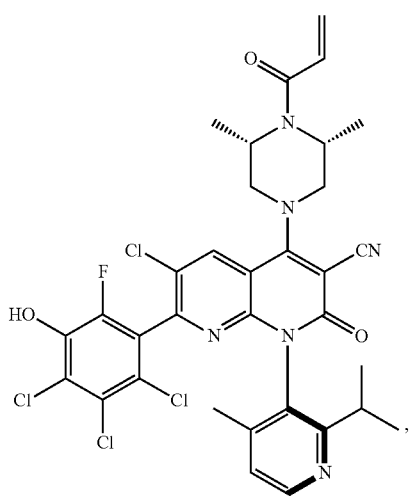

357
-continued
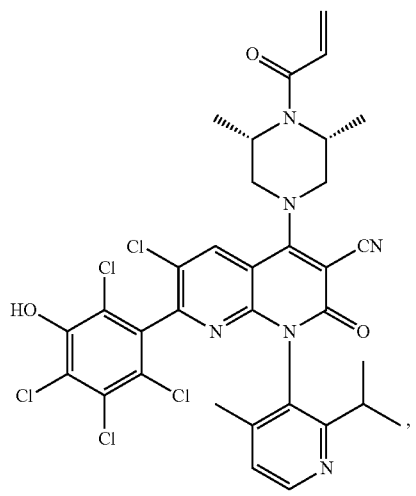
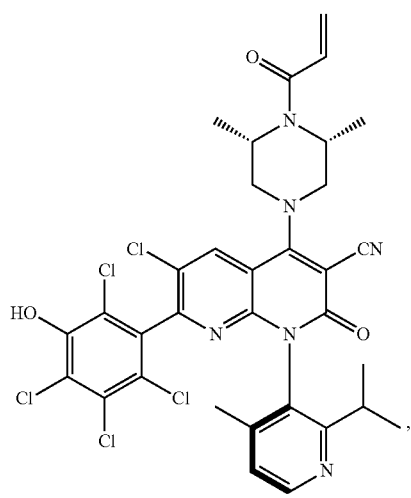
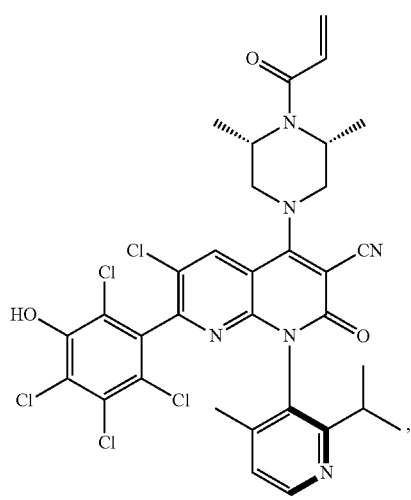
358
-continued
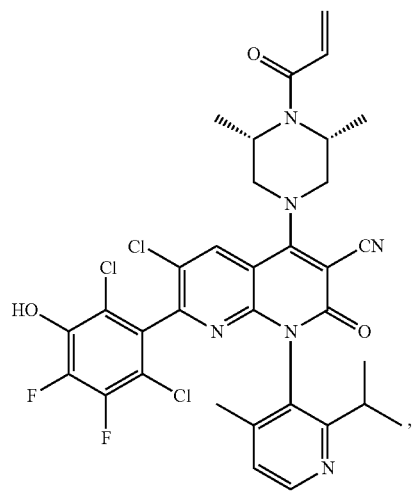
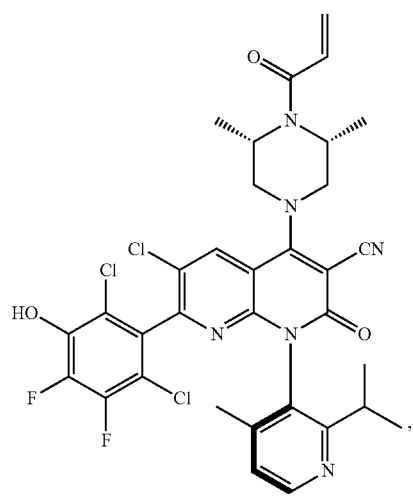
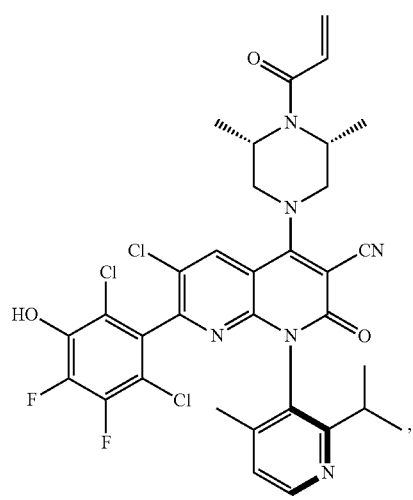

359
-continued
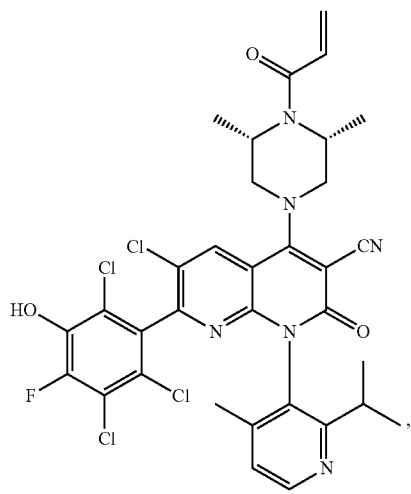
360
-continued
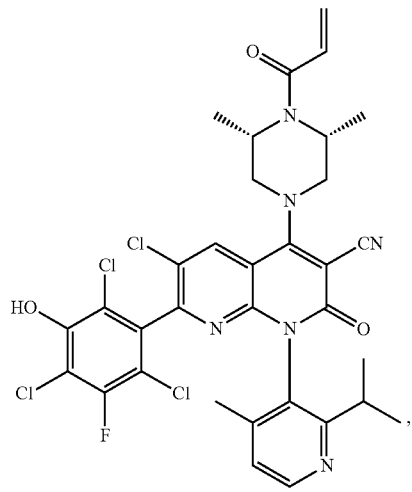
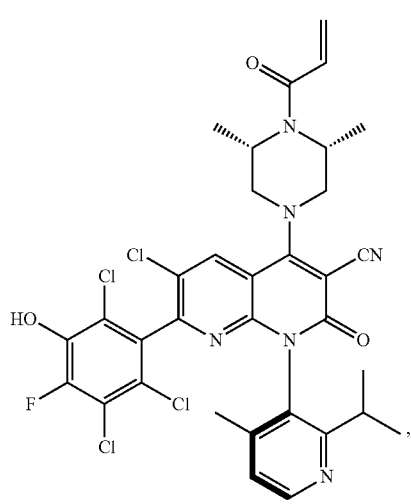
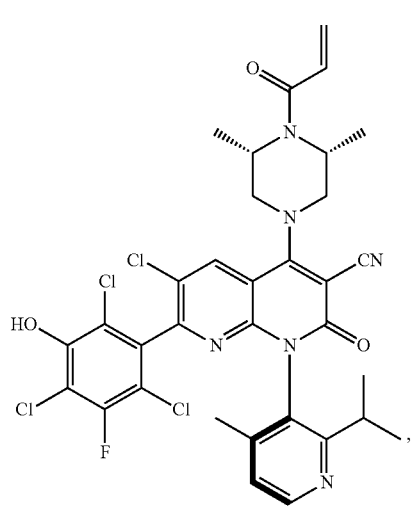
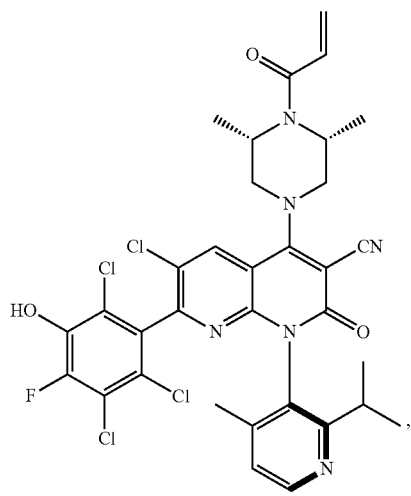
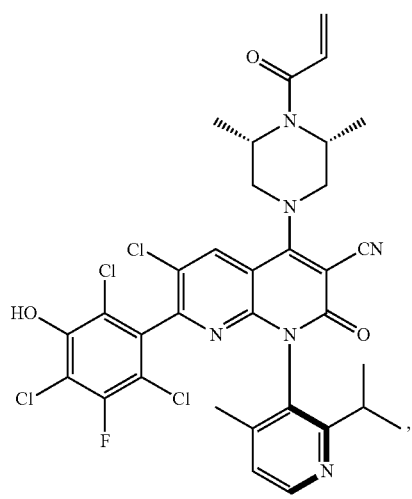

361
-continued
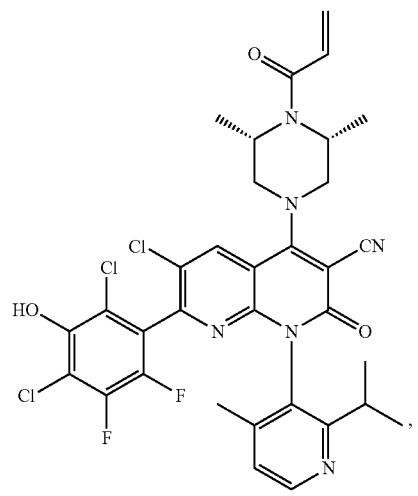
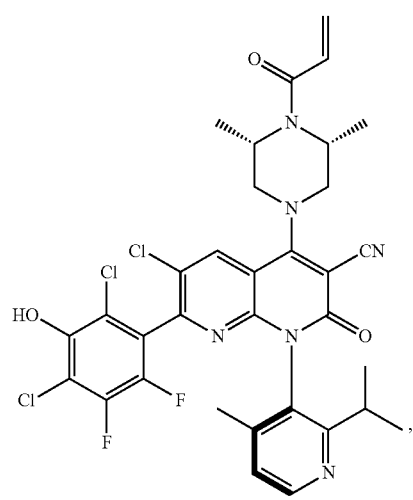
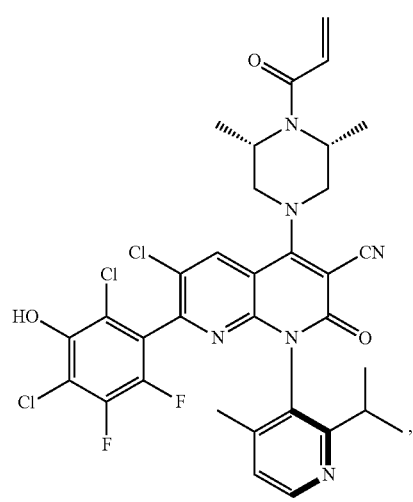
362
-continued
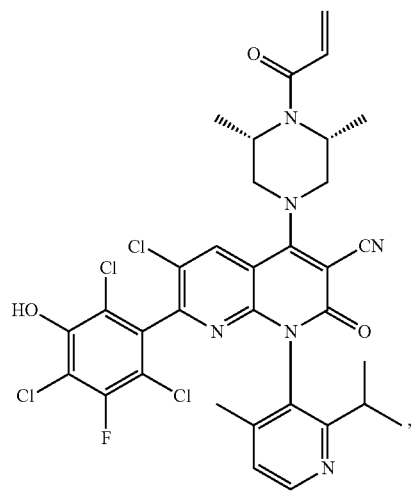
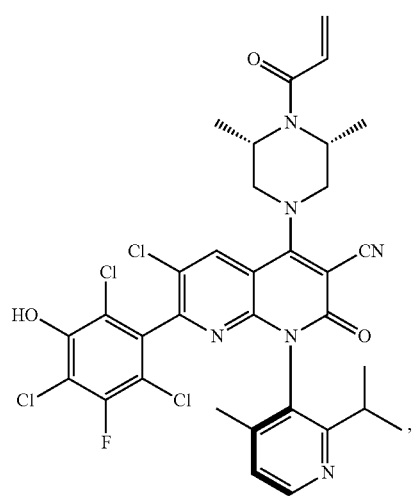
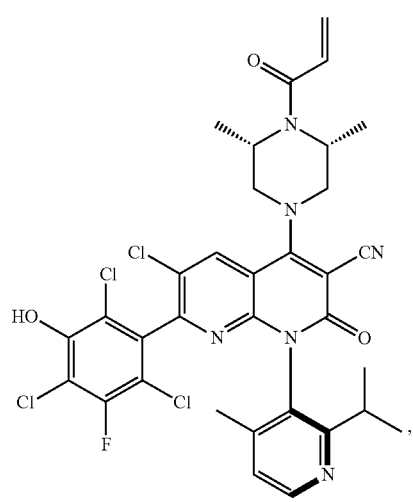

363
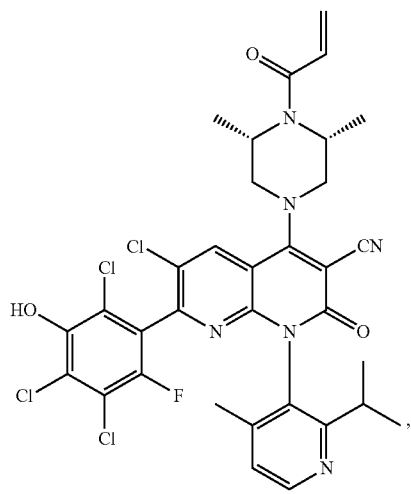
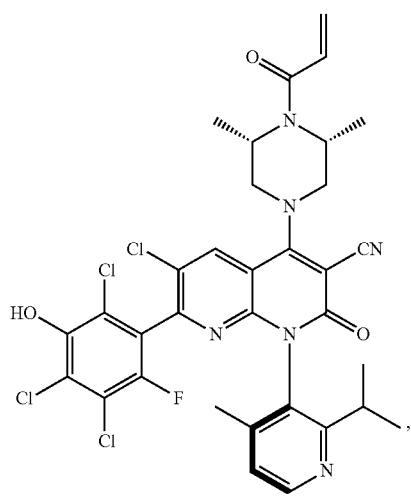
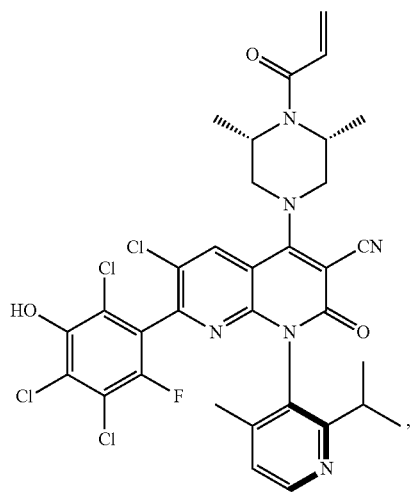
364
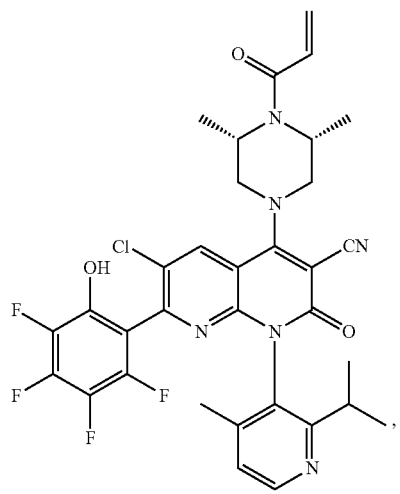
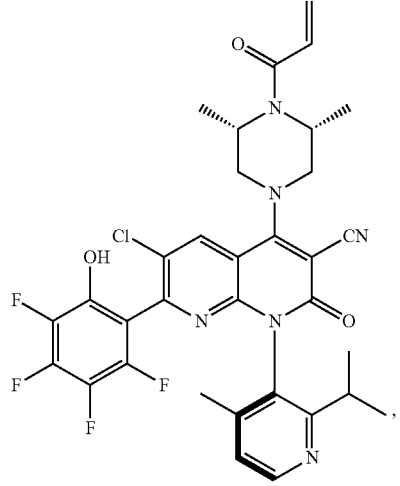
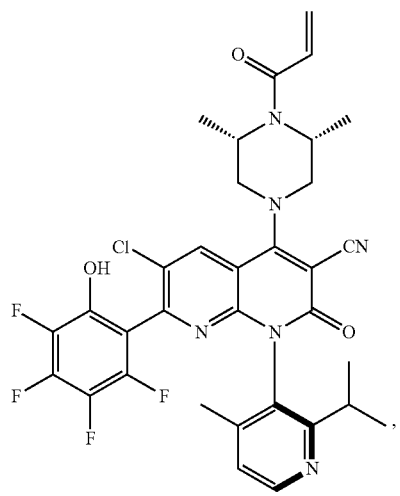

365
-continued
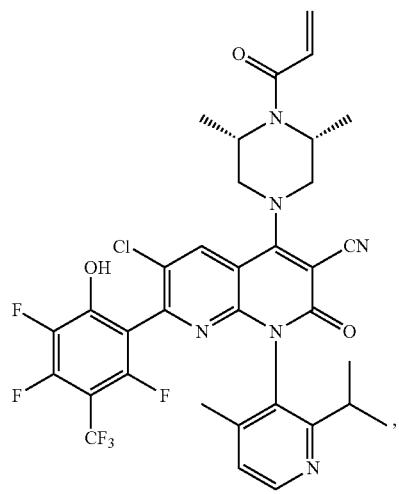
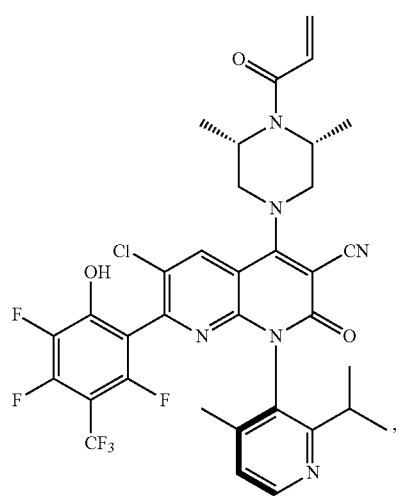
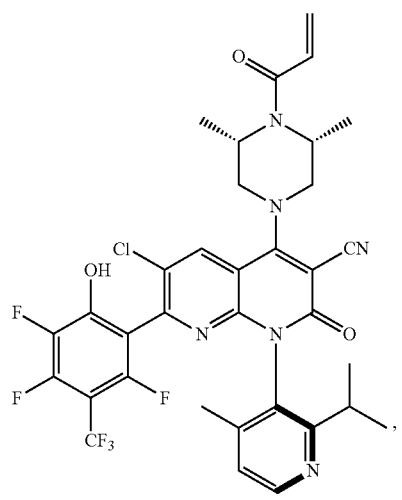
366
-continued
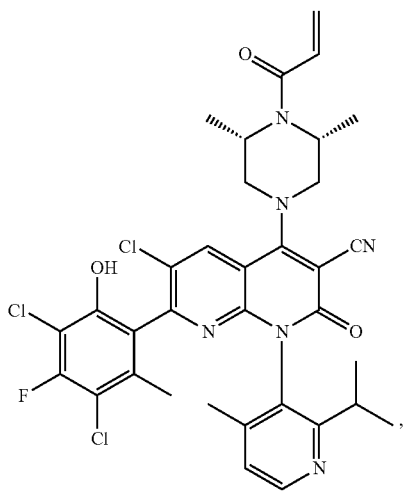
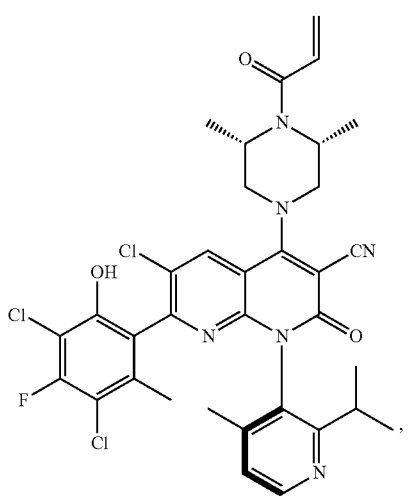
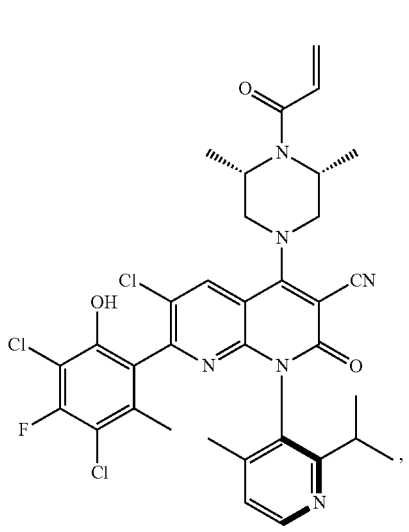

367
-continued
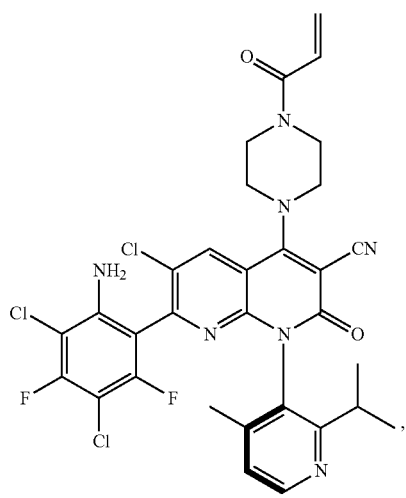
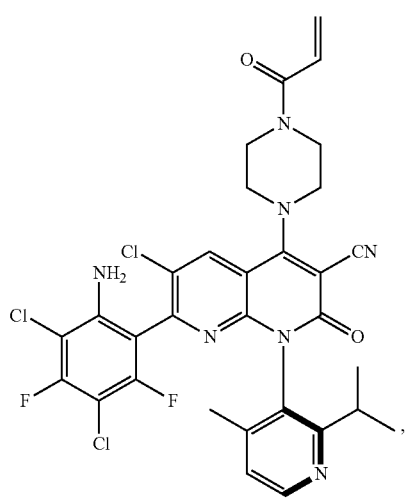
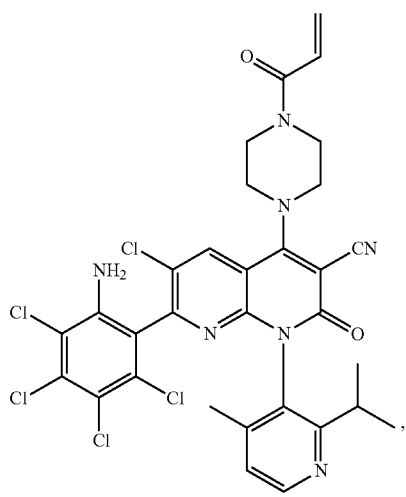
368
-continued
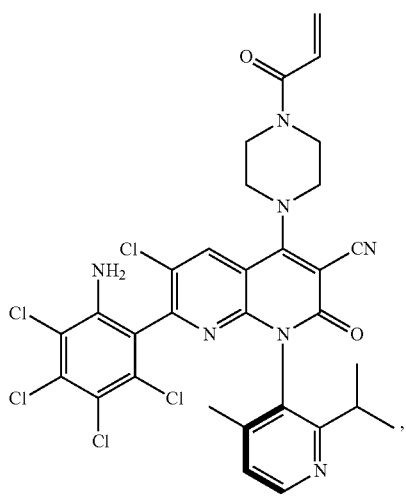
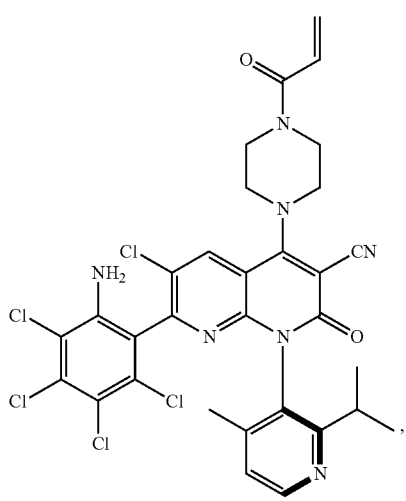
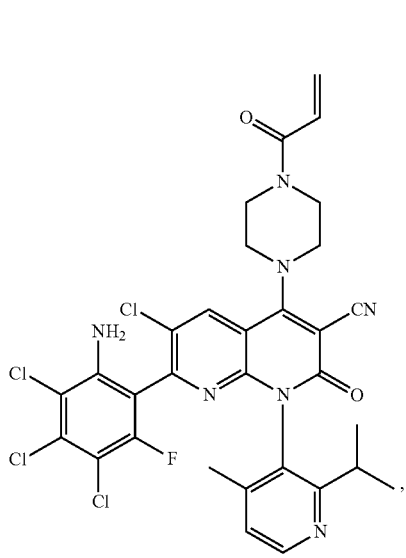

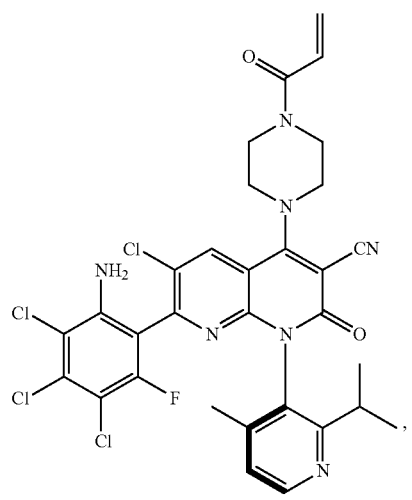
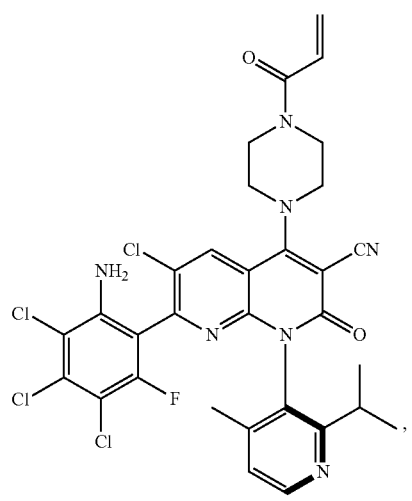
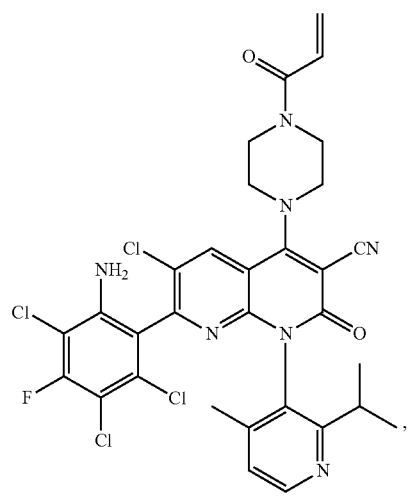
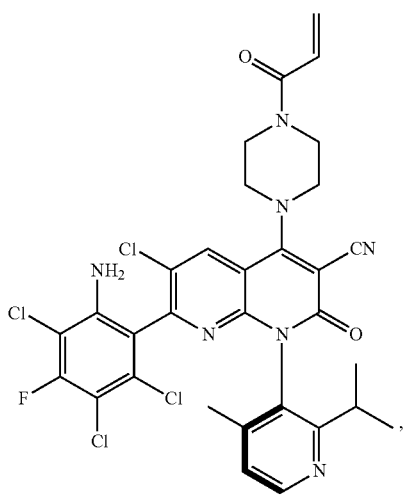
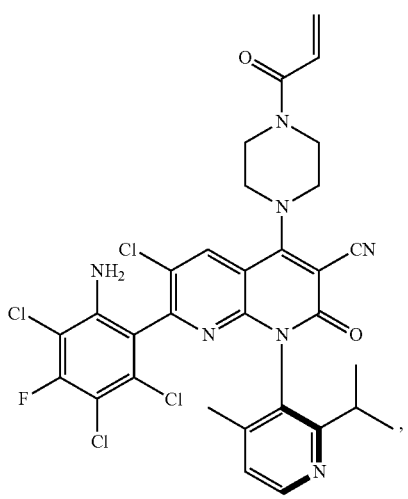
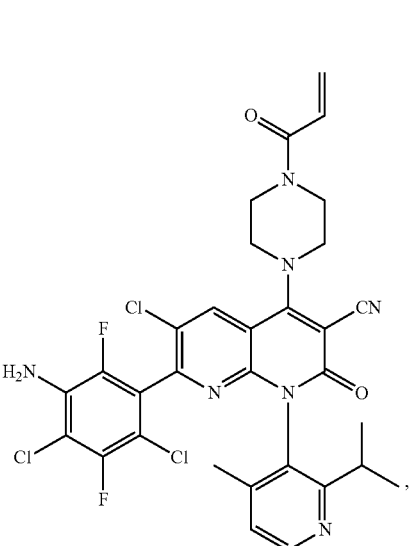

371
-continued
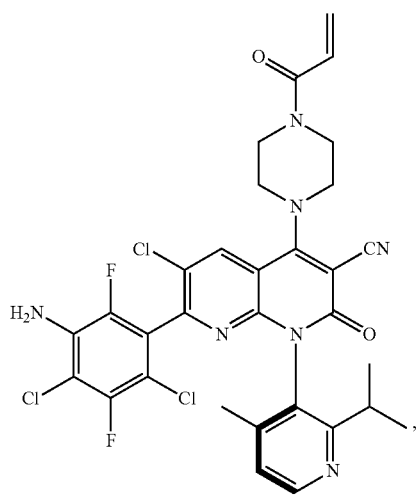
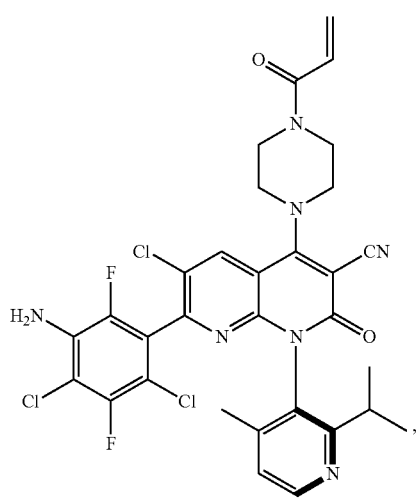
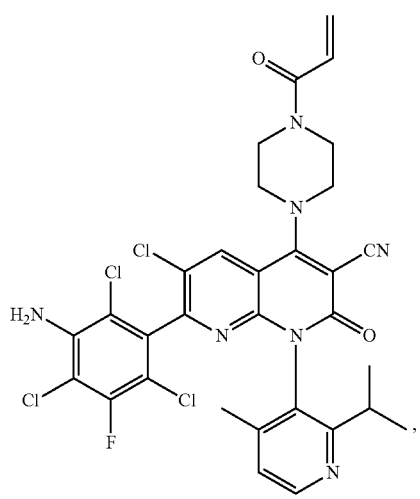
372
-continued
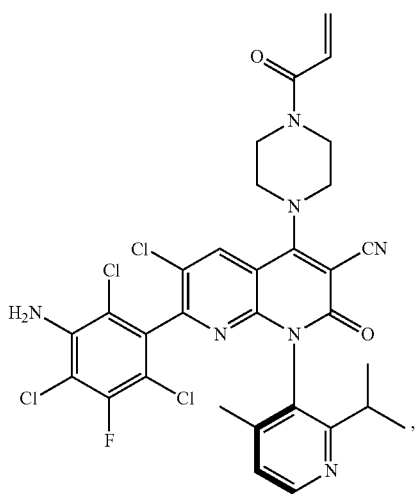
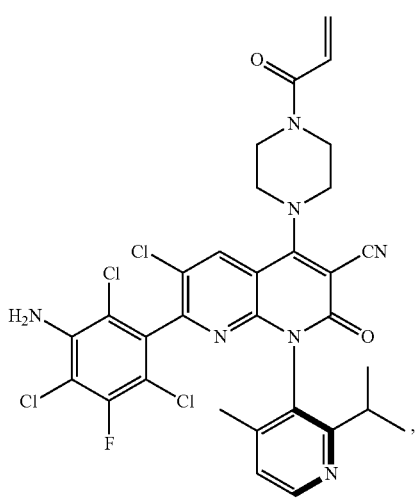
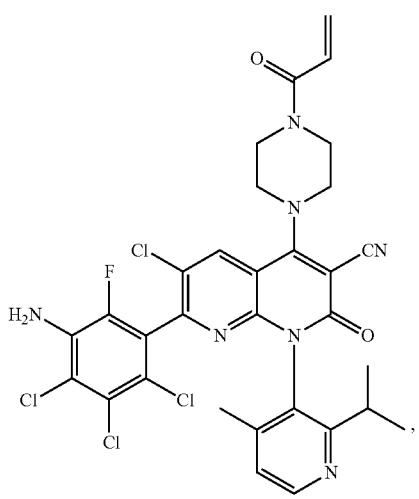

373
-continued
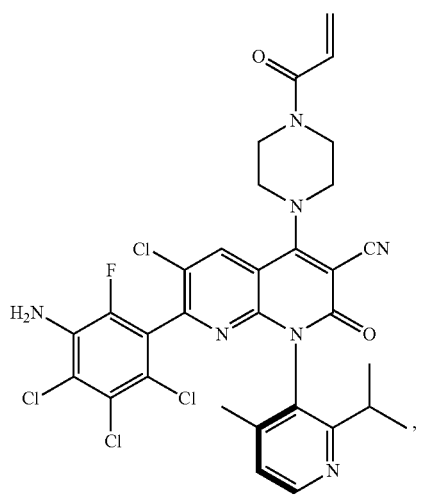
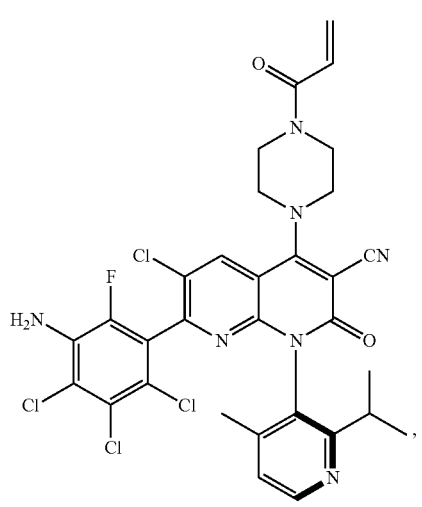
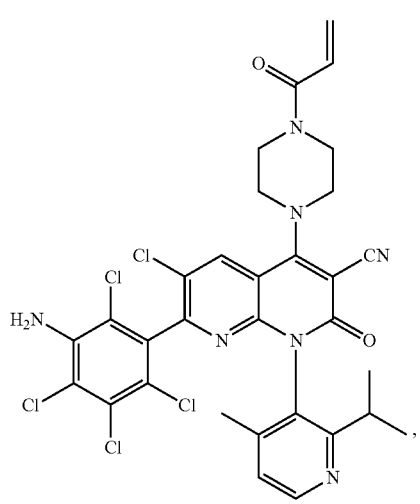
374
-continued
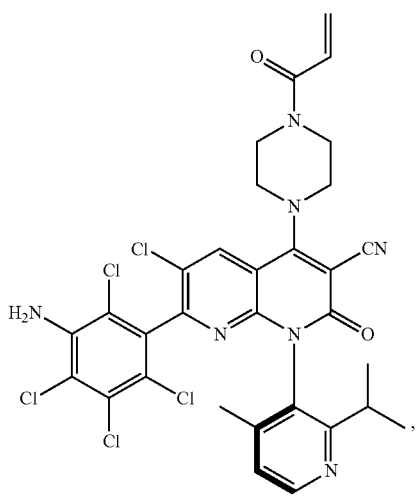
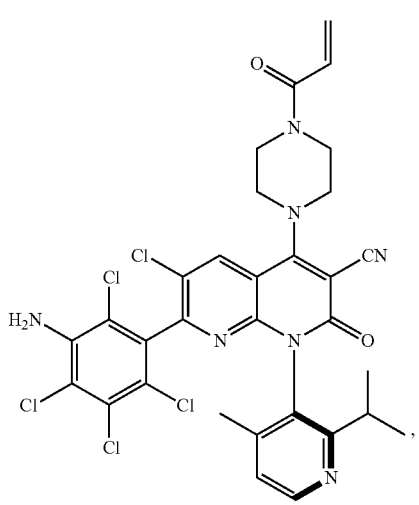
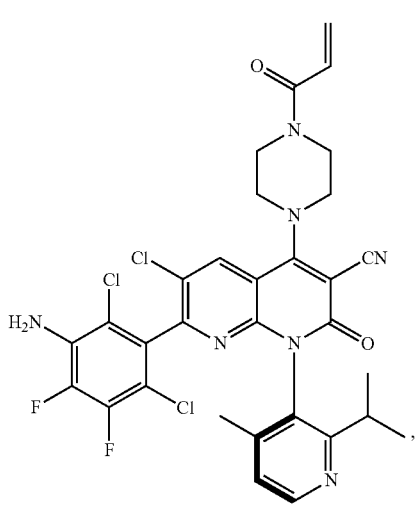

375
-continued
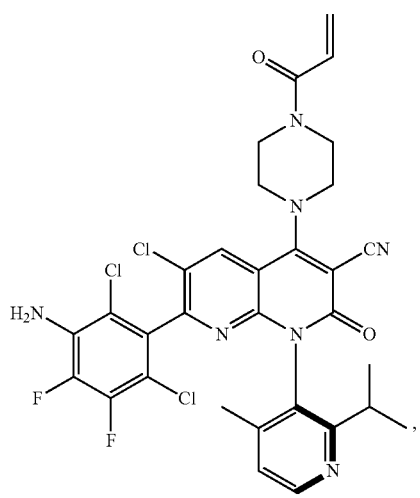
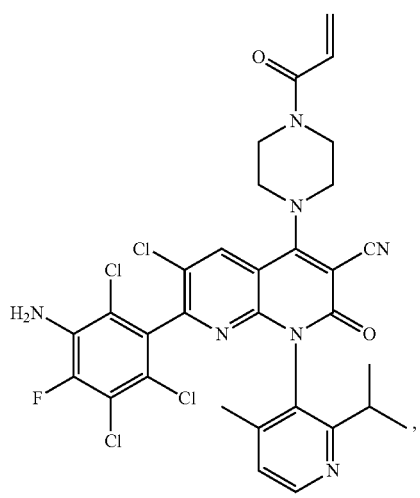
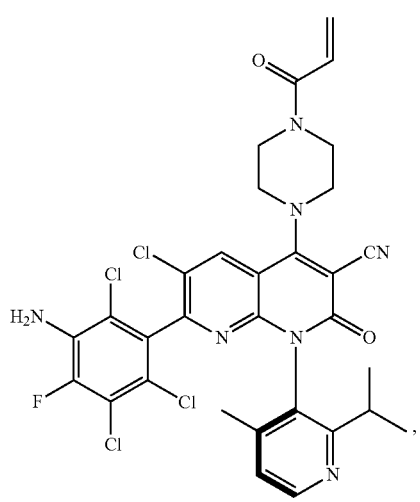
376
-continued
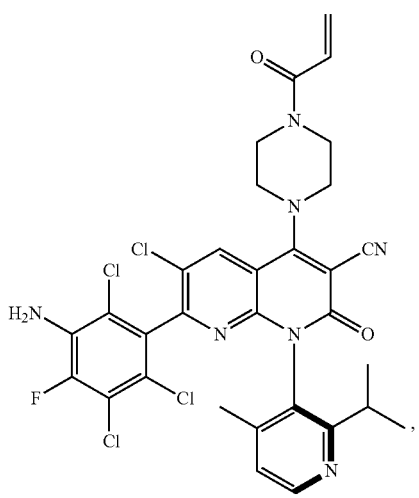
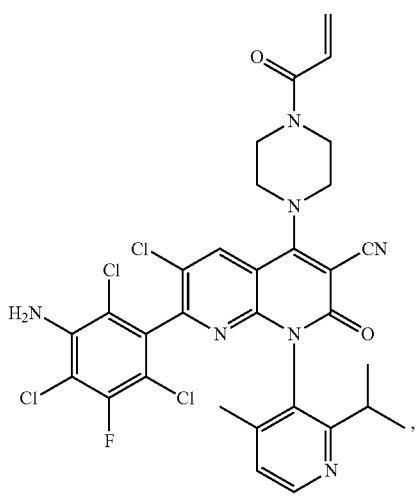
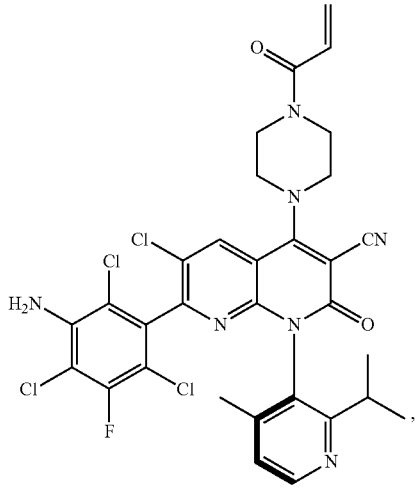

377
-continued
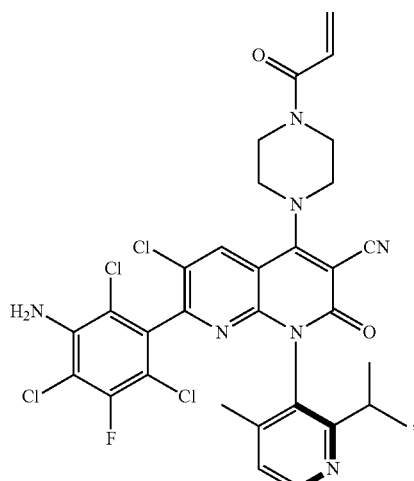
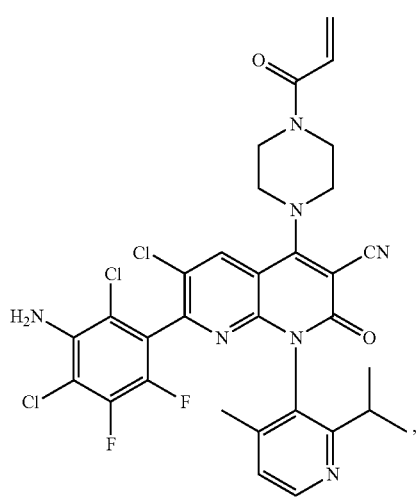
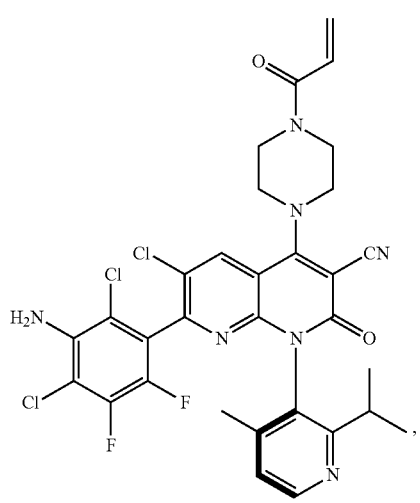
378
-continued
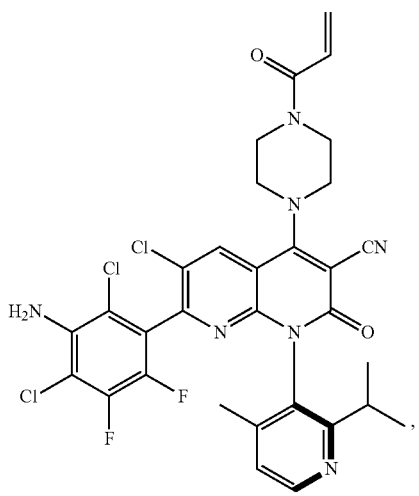
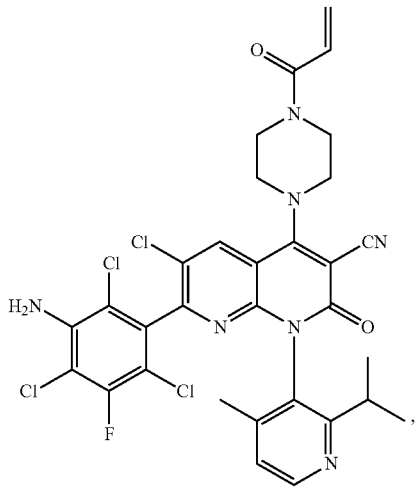
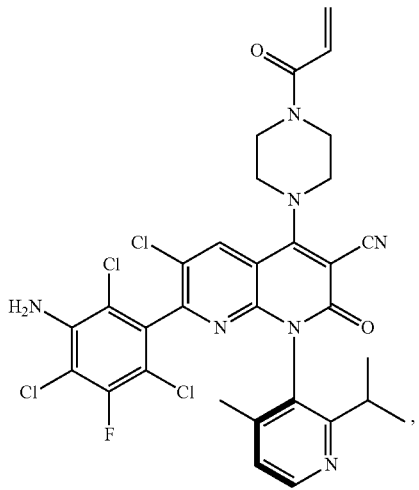

379
-continued
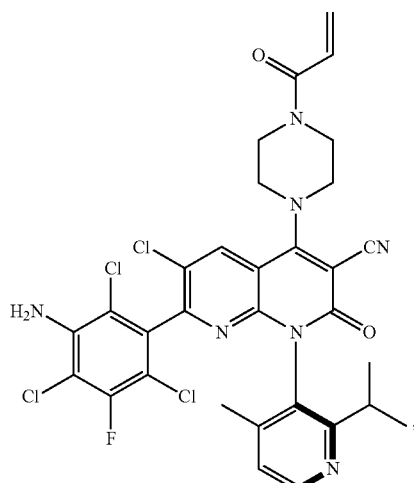
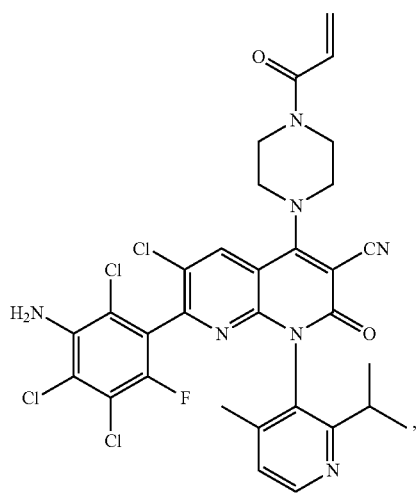
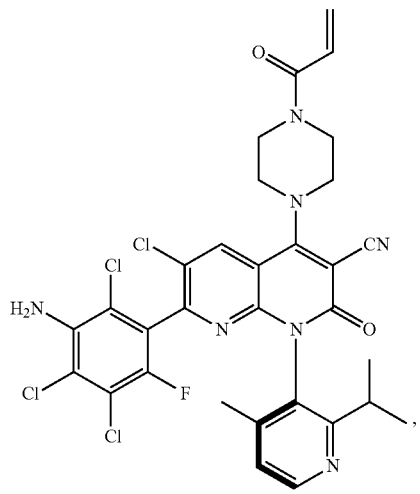
380
-continued
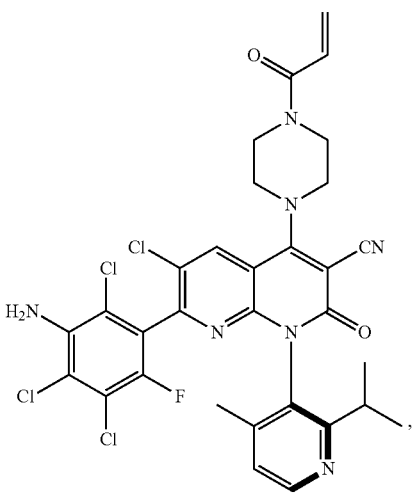
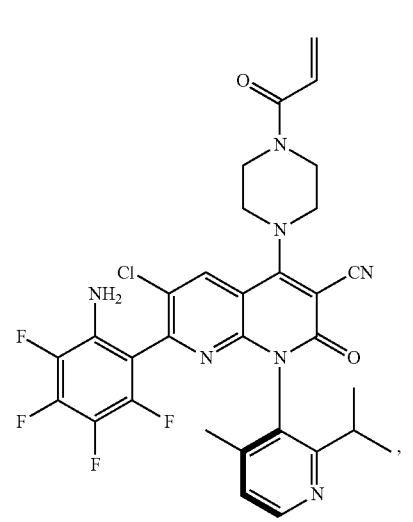
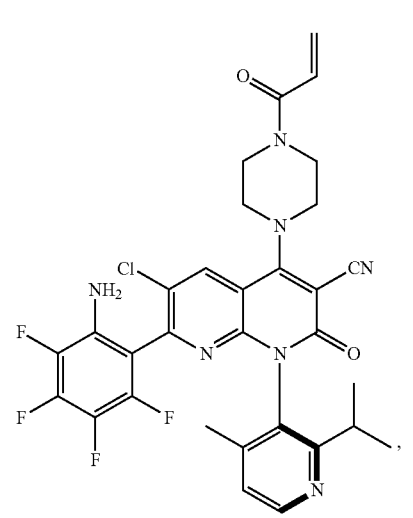

381
-continued
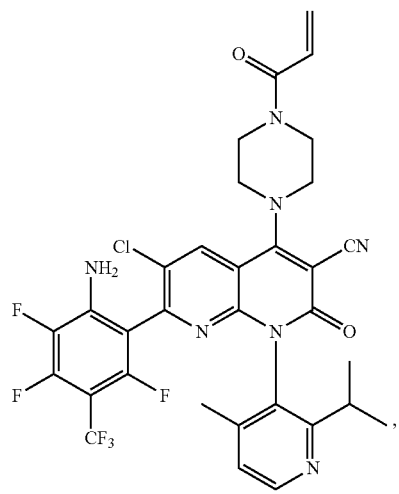
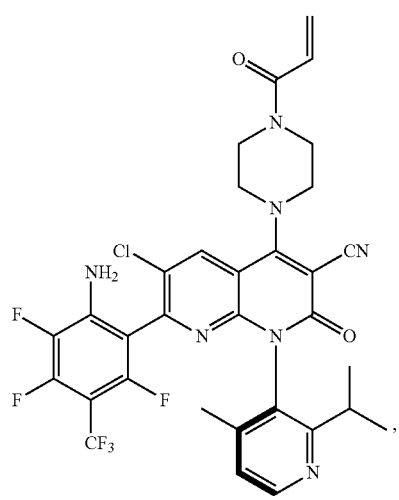
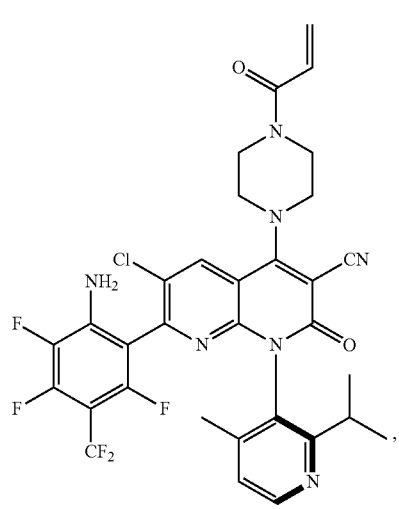
382
-continued
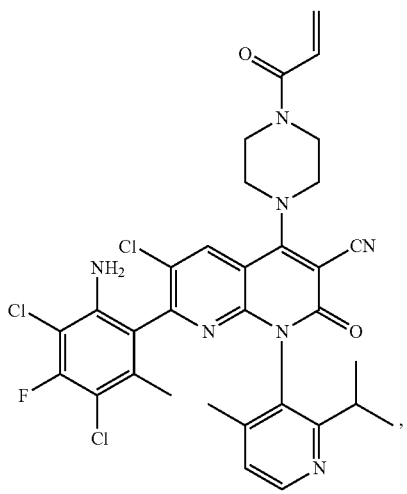
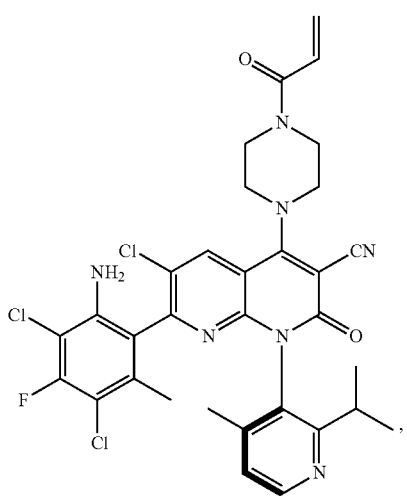
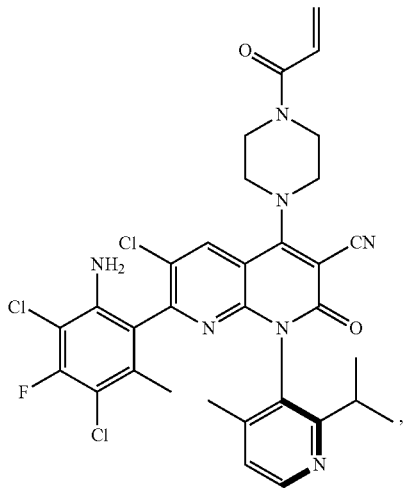

383
-continued
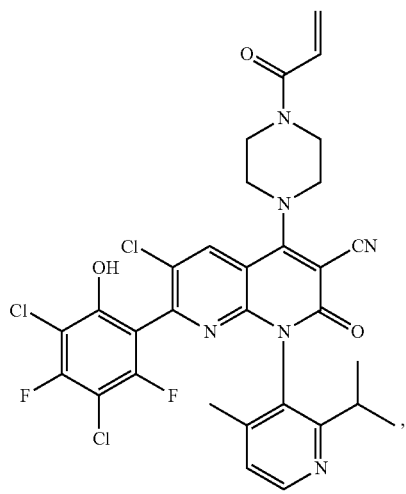
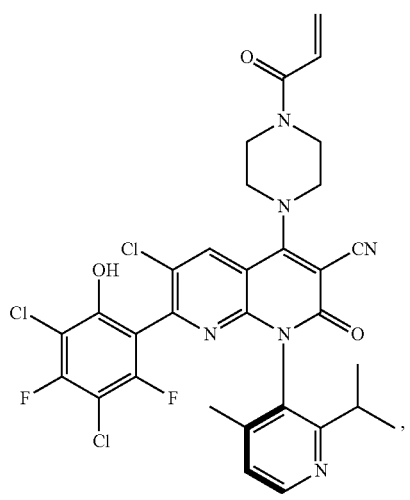
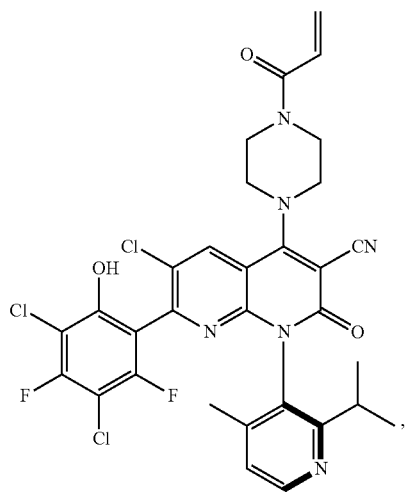
384
-continued
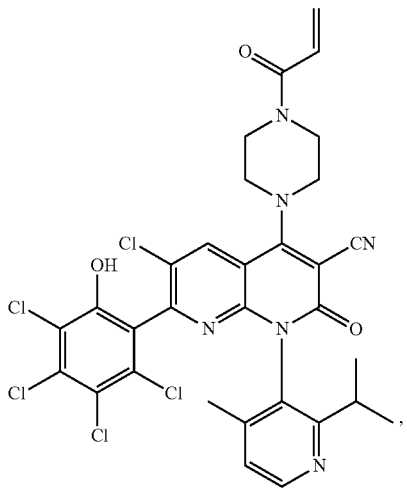
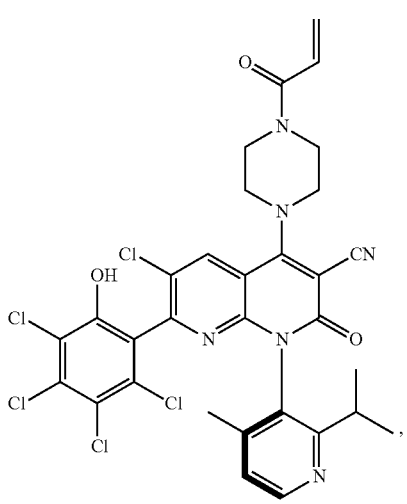
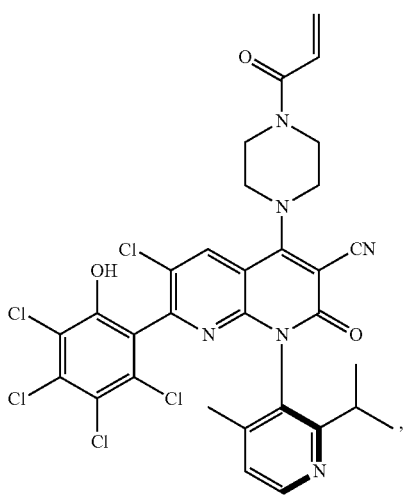

385
-continued
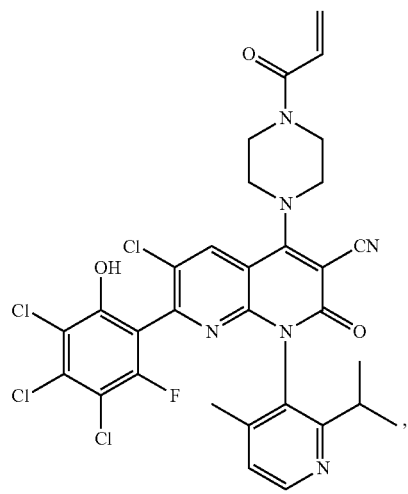
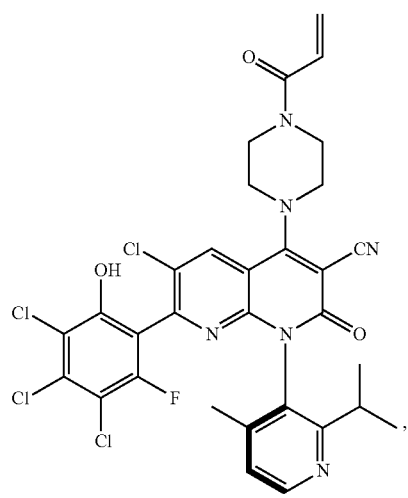
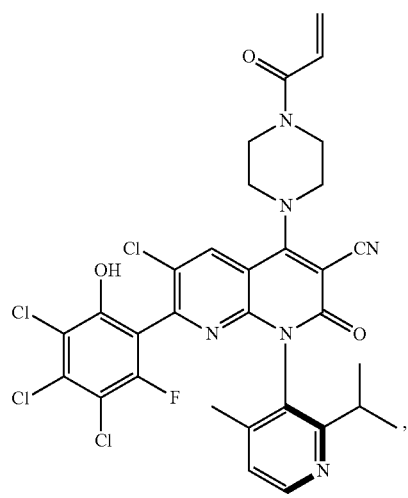
386
-continued
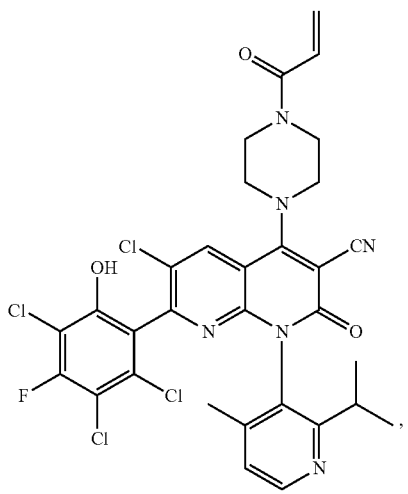
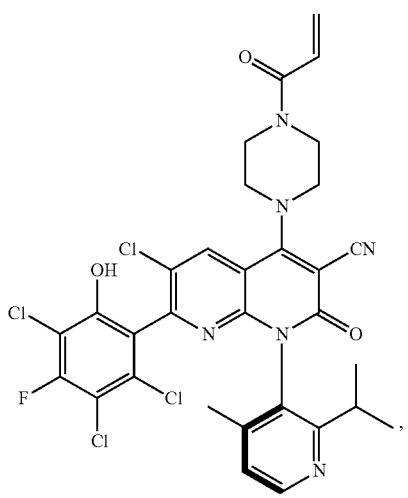
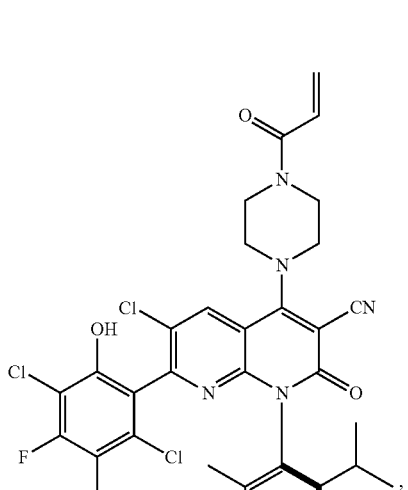

387
-continued
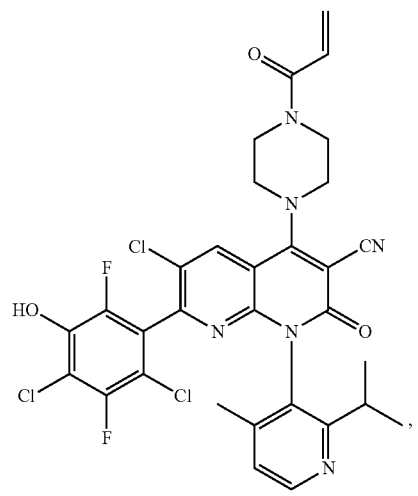
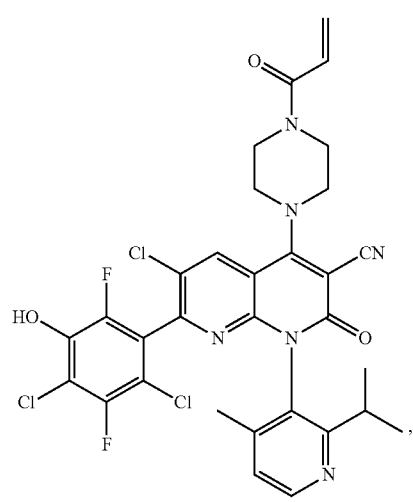
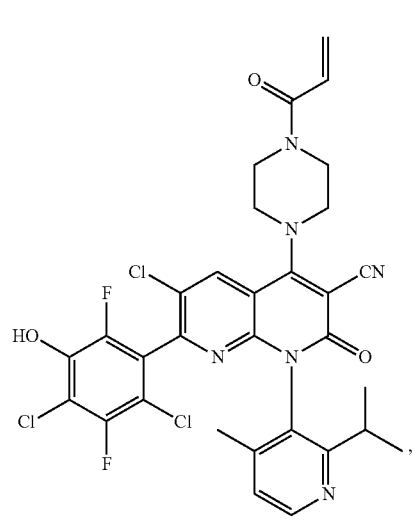
388
-continued
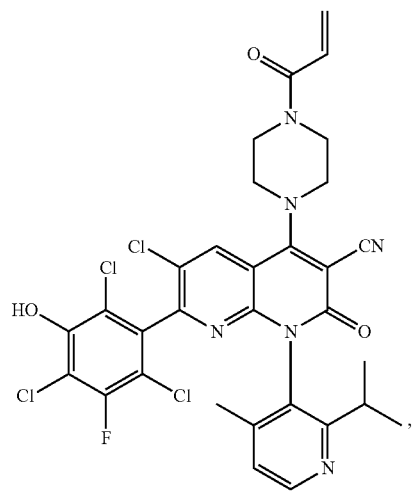
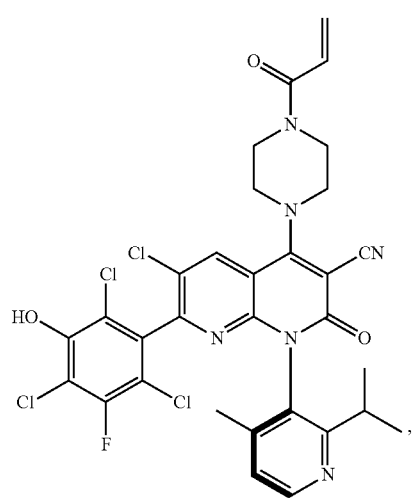
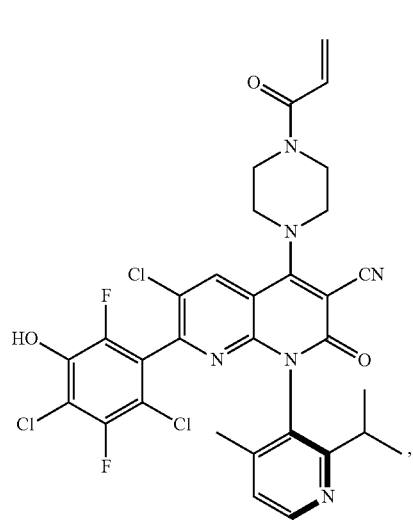

389
-continued
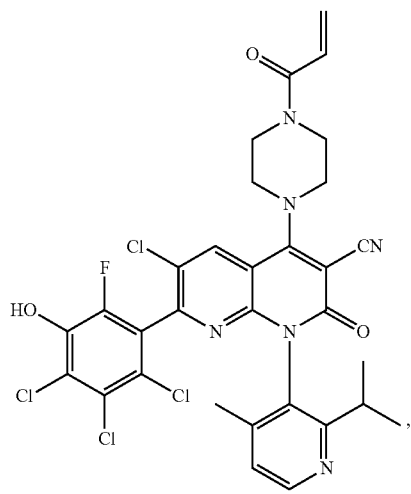
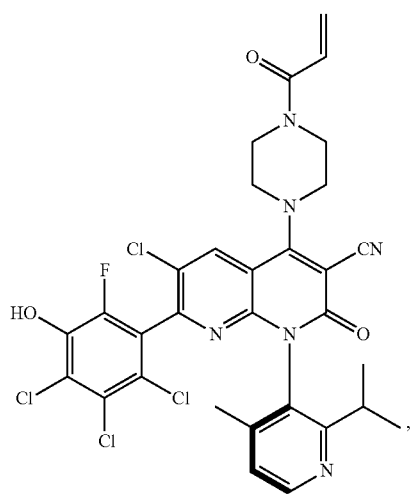
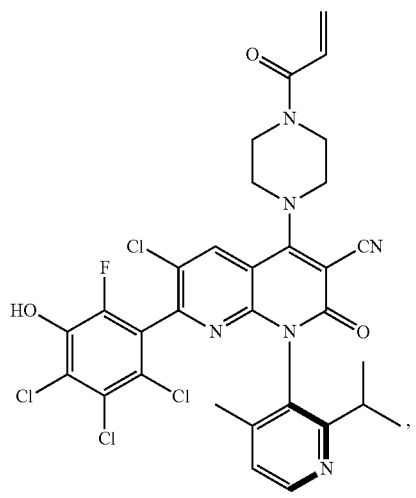
390
-continued
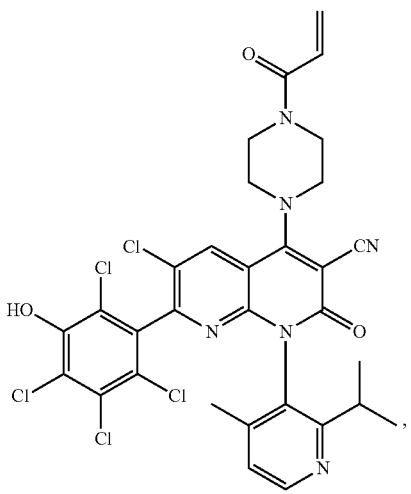
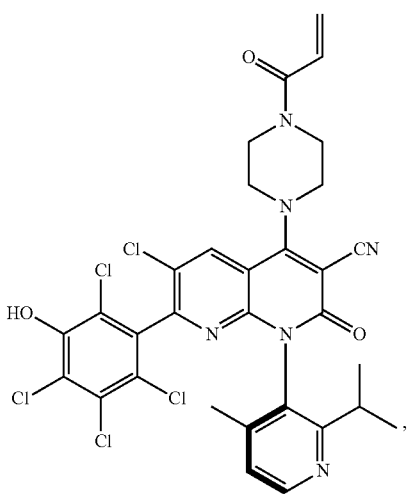
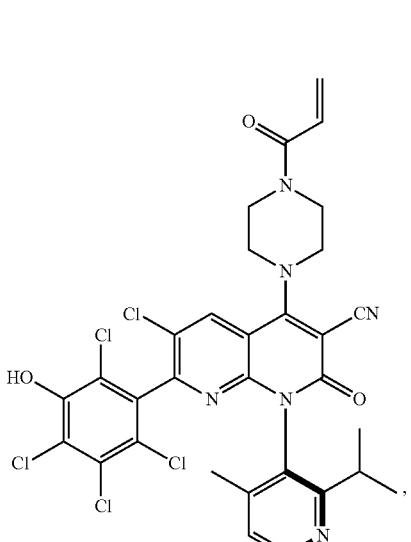

391
-continued
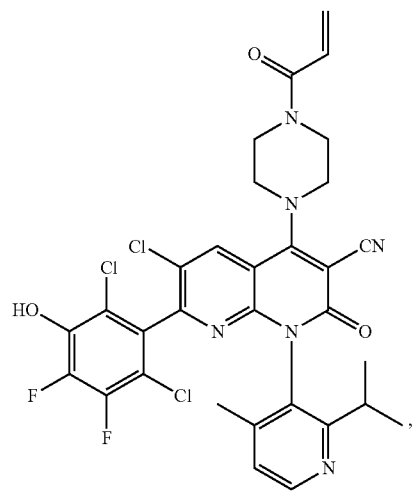
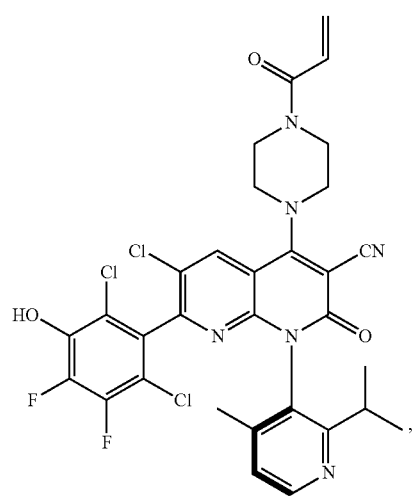
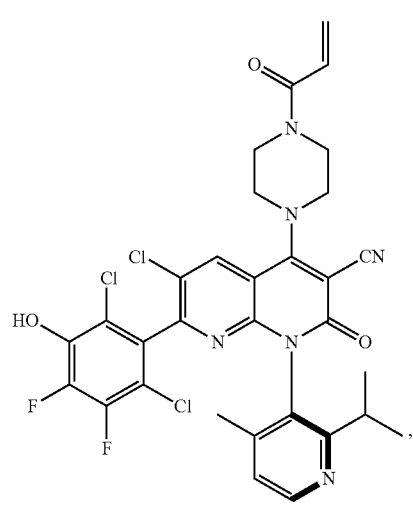
392
-continued
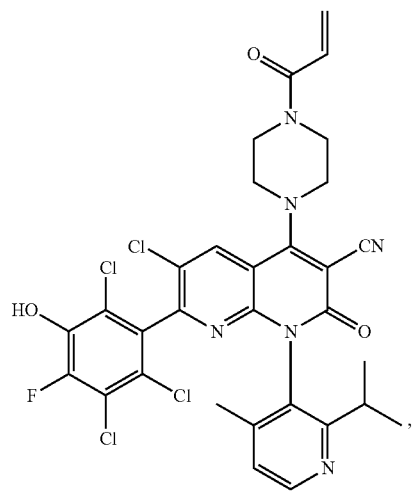
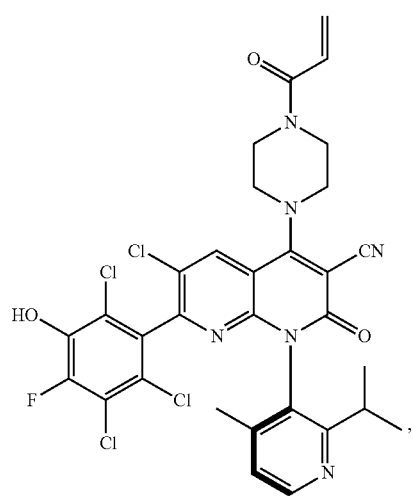
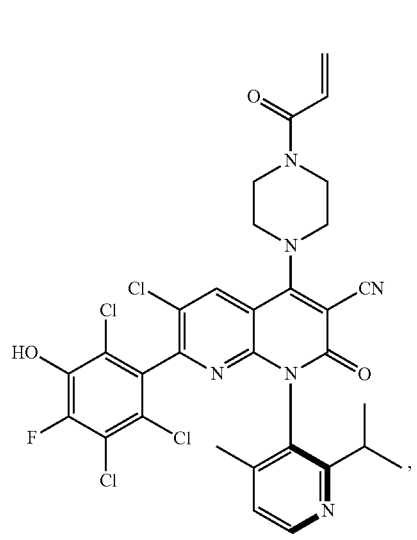

393
-continued
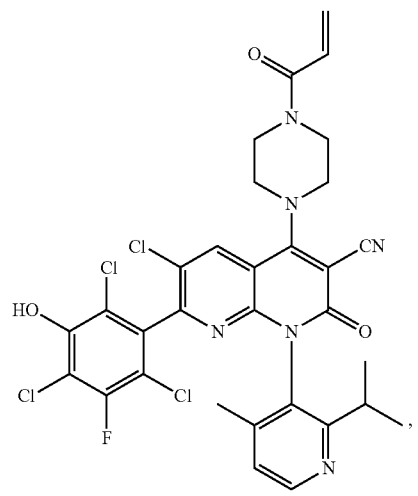
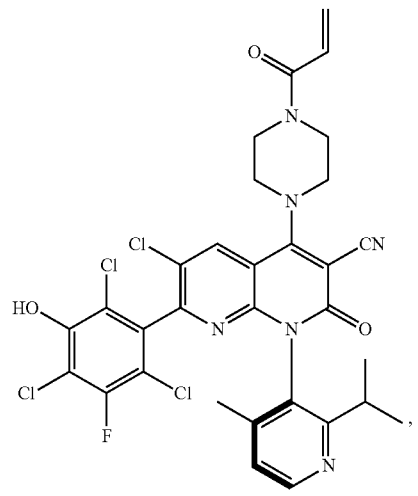
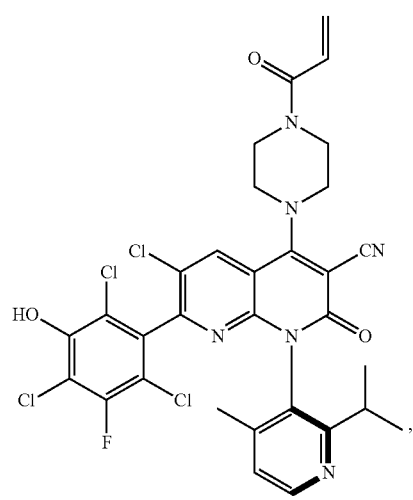
394
-continued
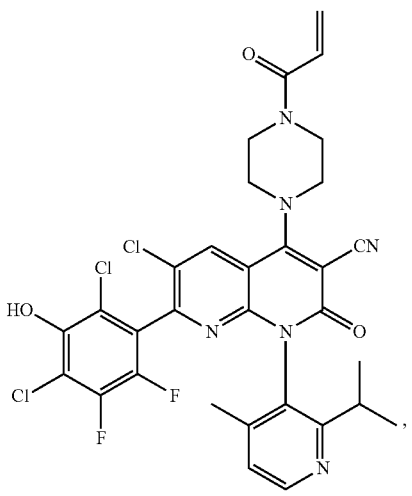
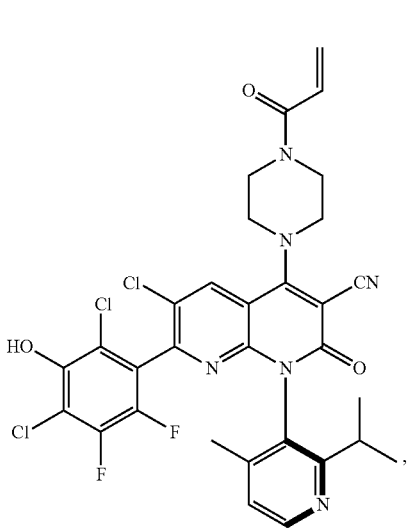

395
-continued
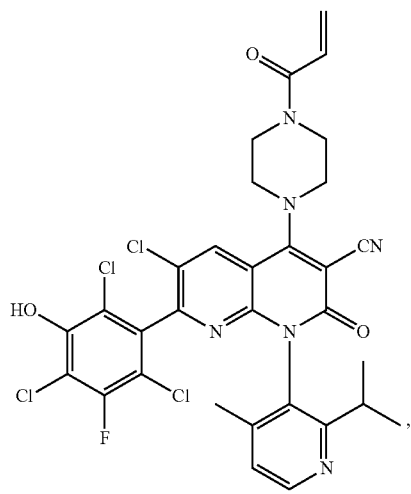
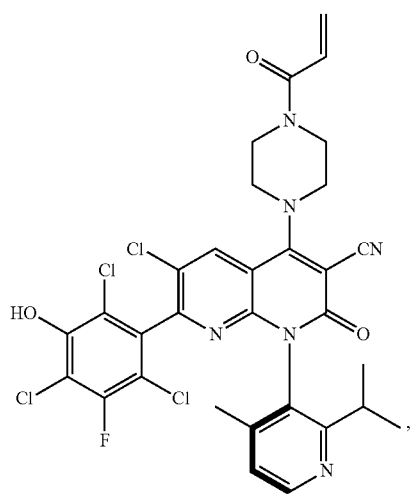
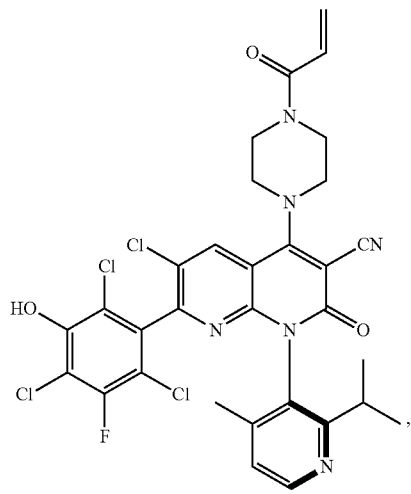
396
-continued
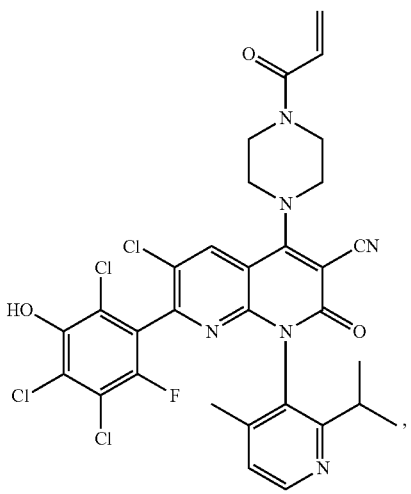
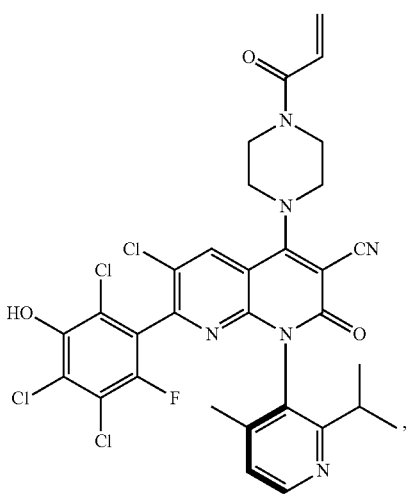
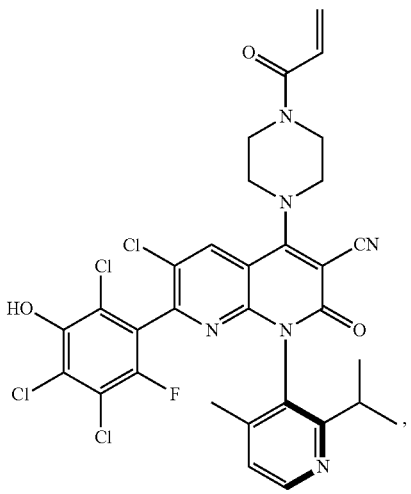

397
-continued
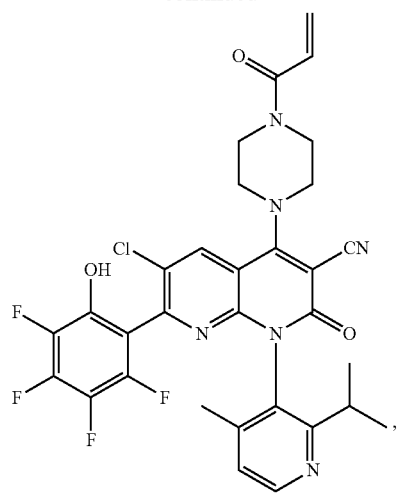
398
-continued
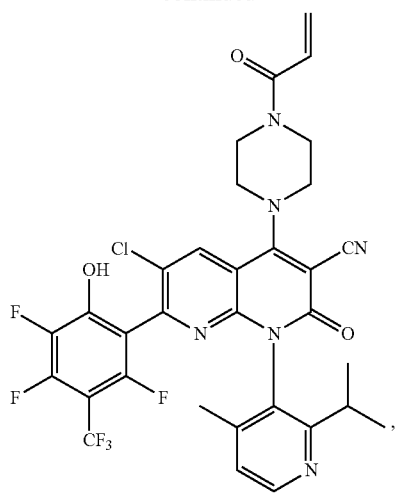

399
-continued
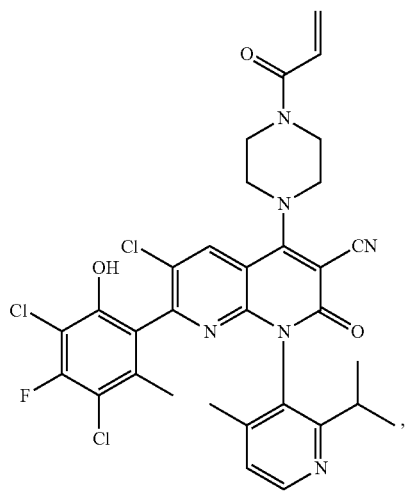
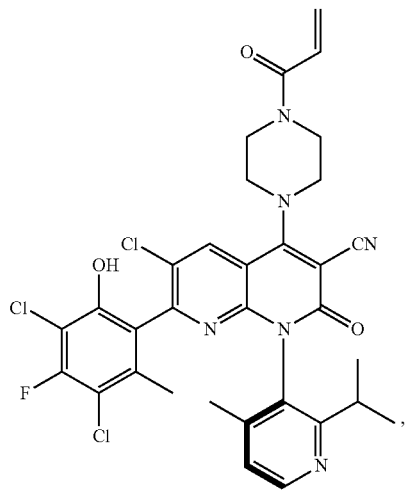
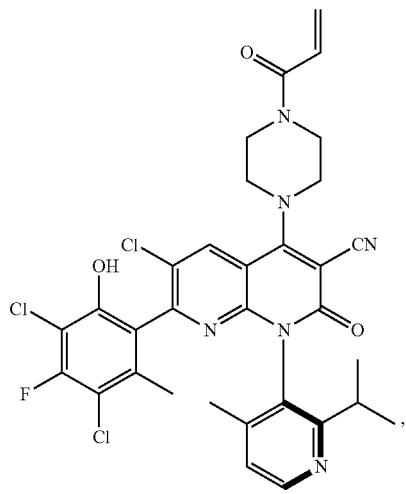
400
-continued
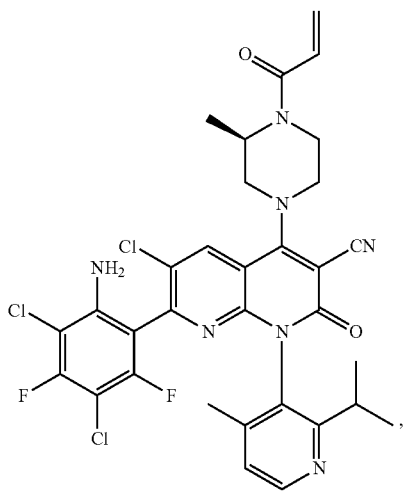
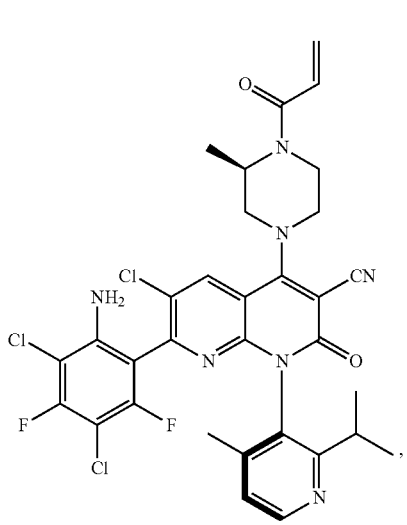
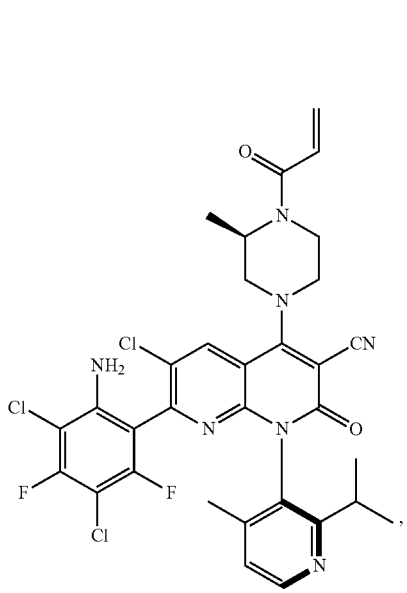

401
-continued
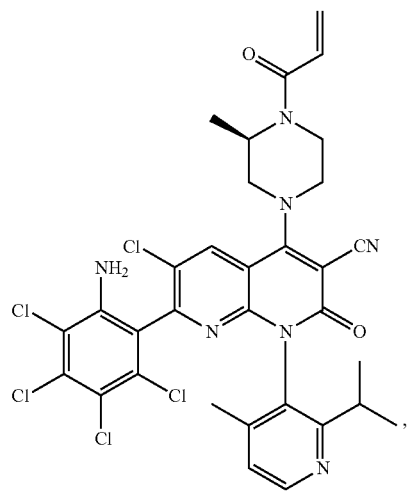
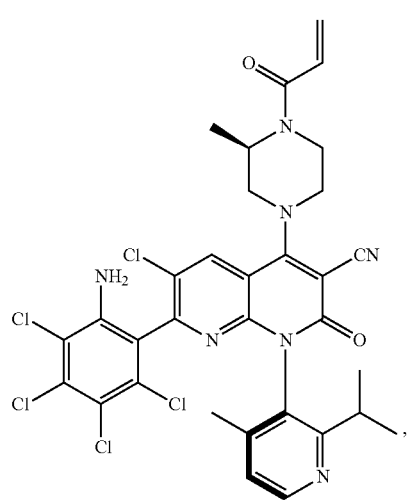
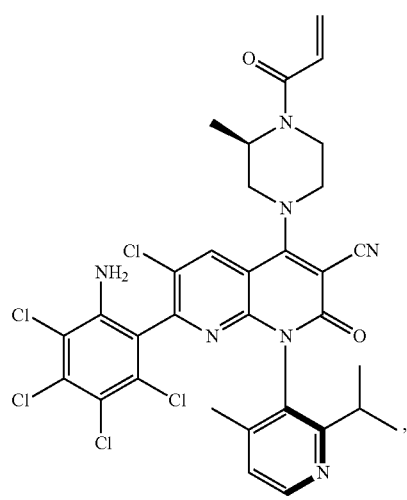
402
-continued
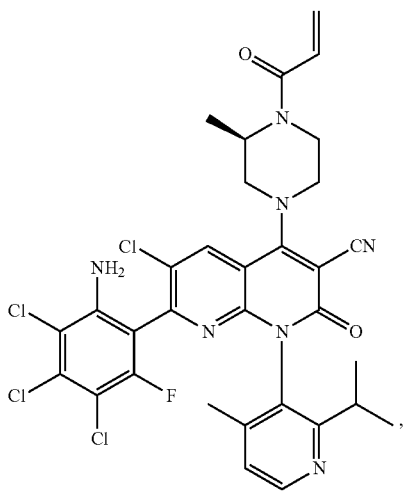
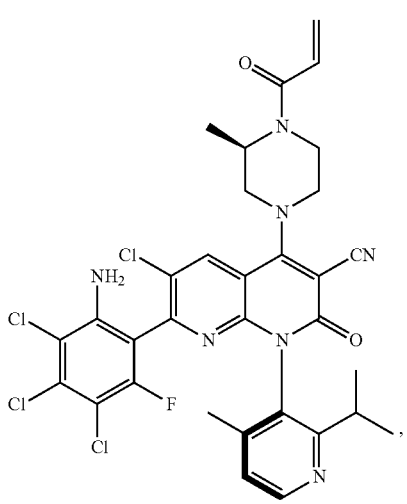
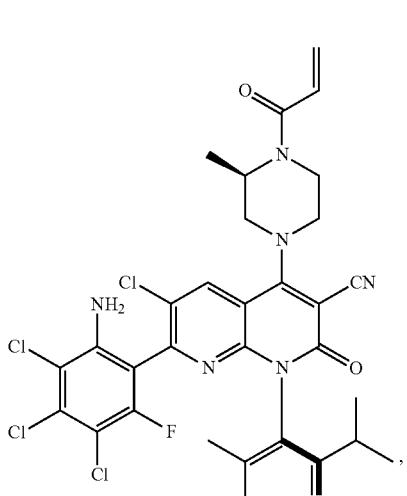

403
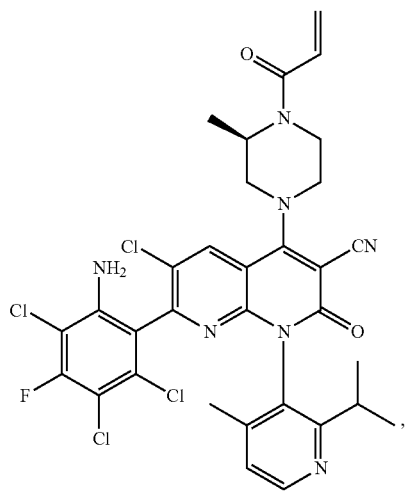
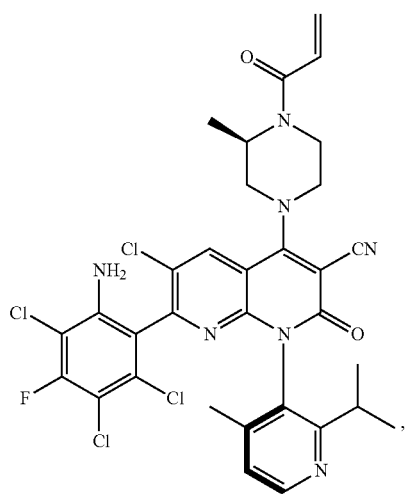
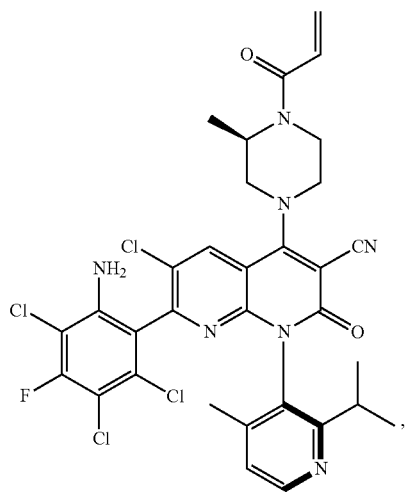
404
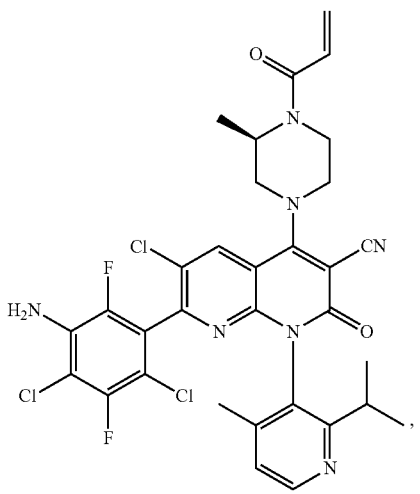
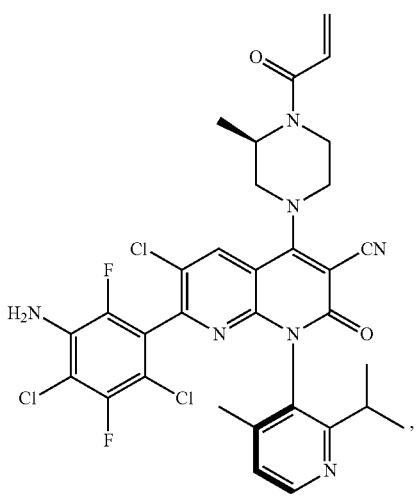
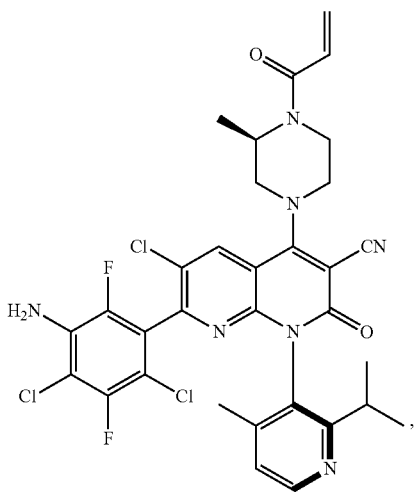

405
-continued
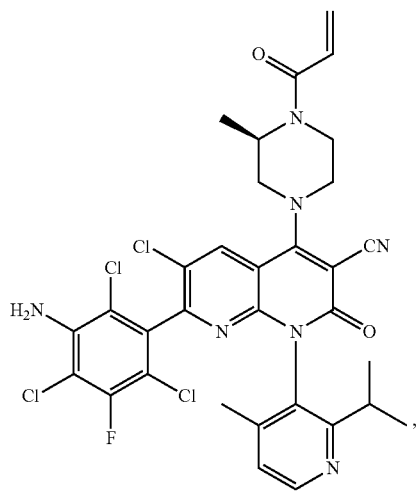
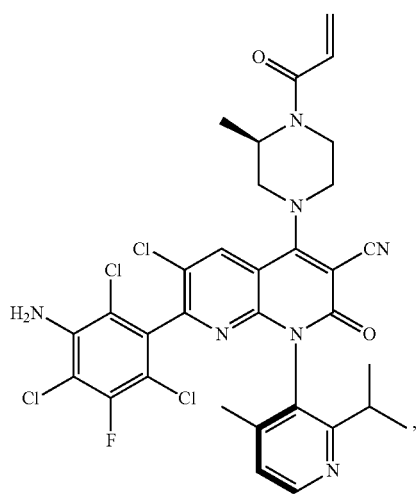
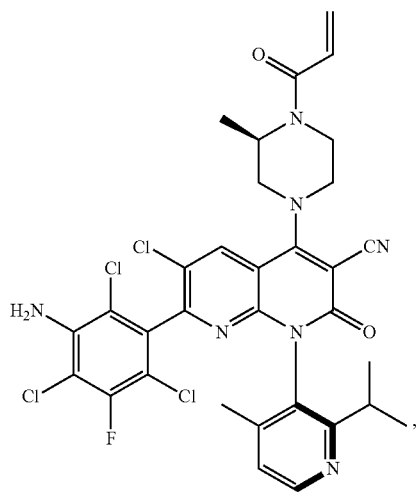
406
-continued
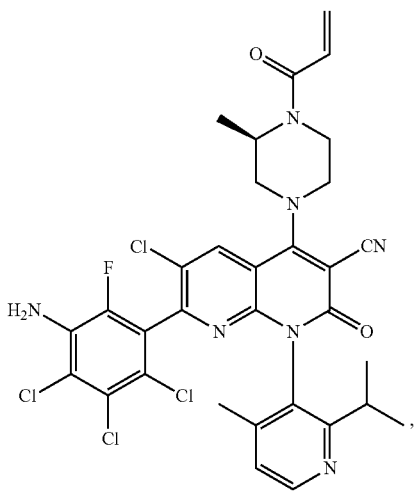
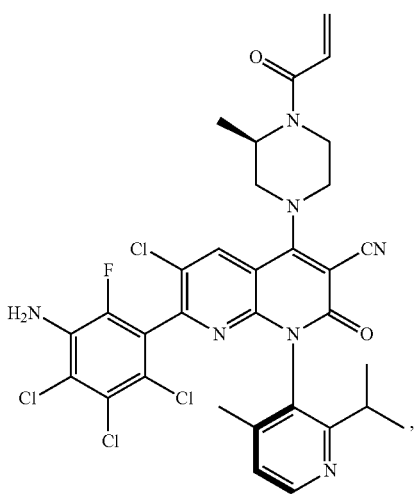
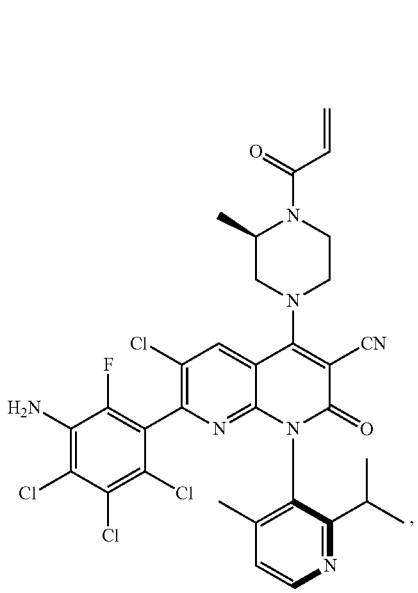

407
-continued
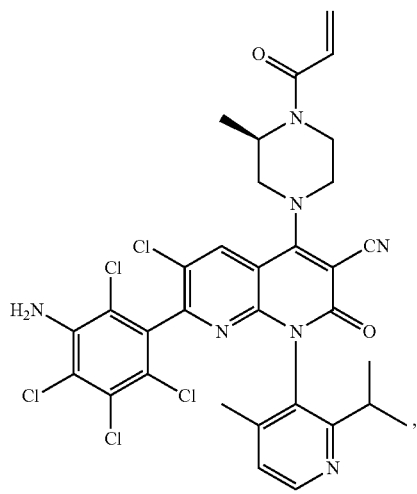
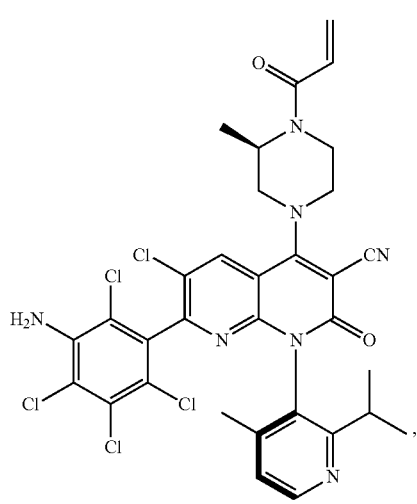
408
-continued
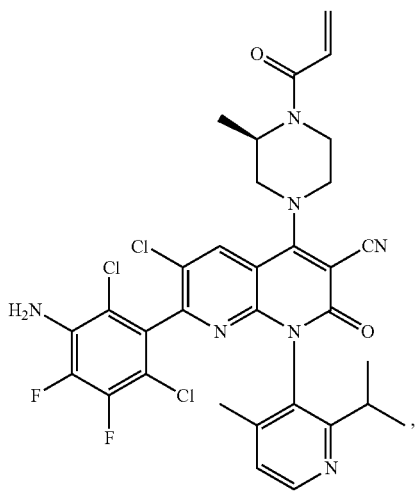
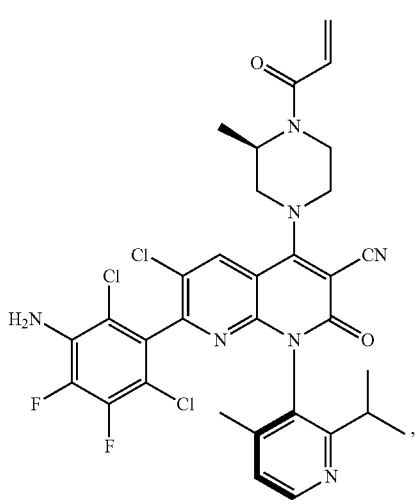

409
-continued
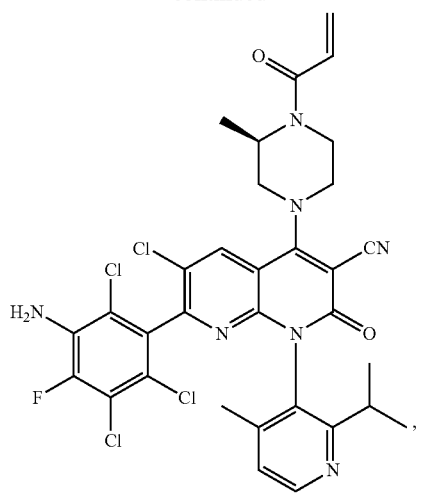
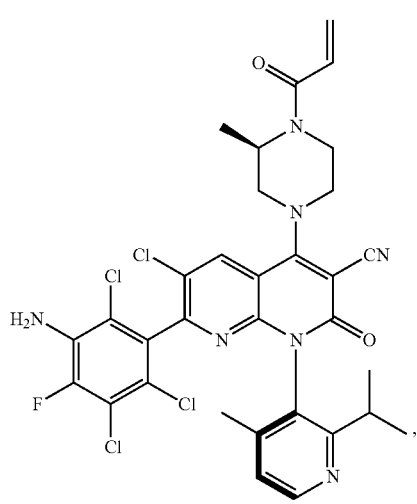
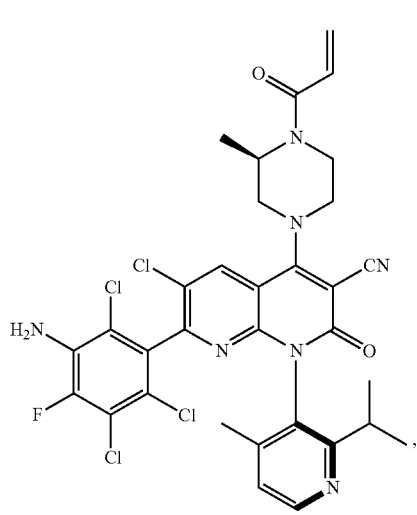
410
-continued
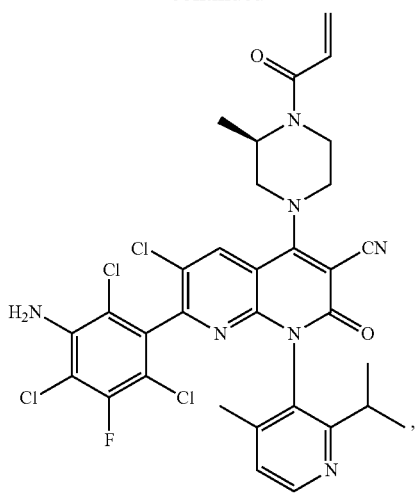
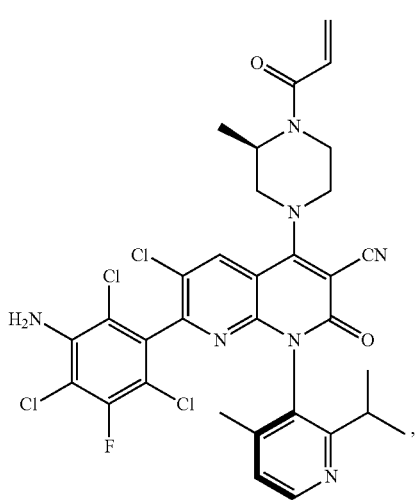
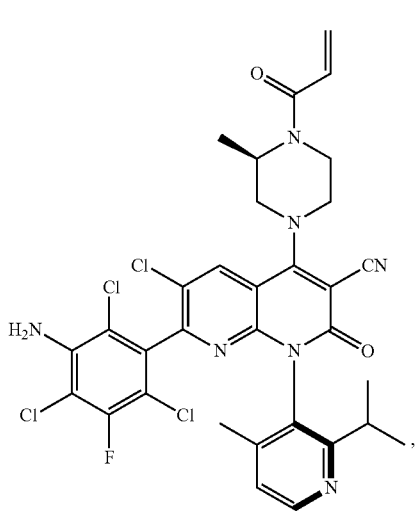

411
-continued
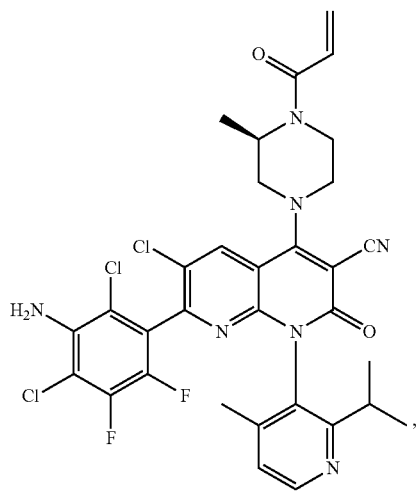
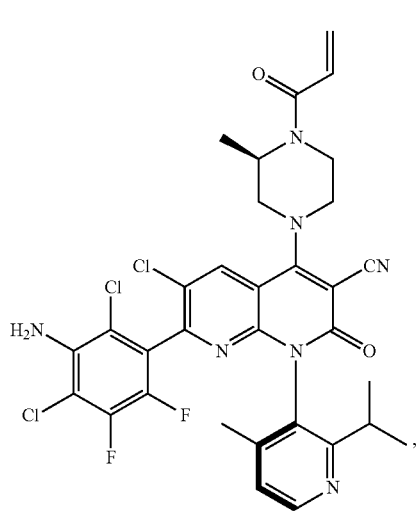
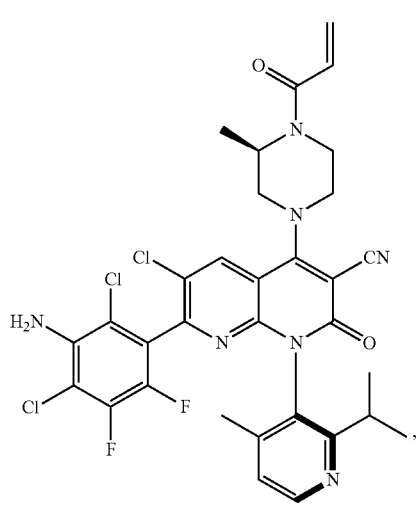
412
-continued
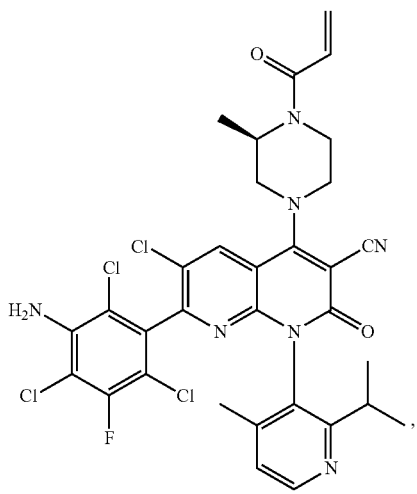
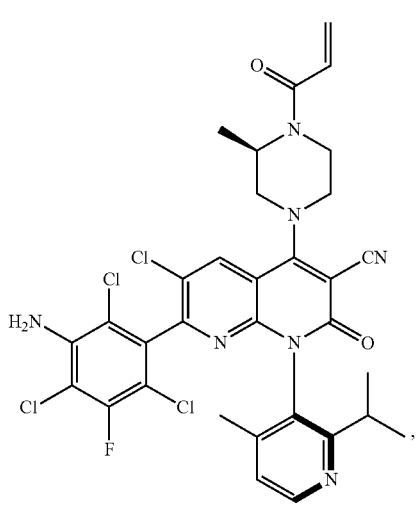

413
-continued
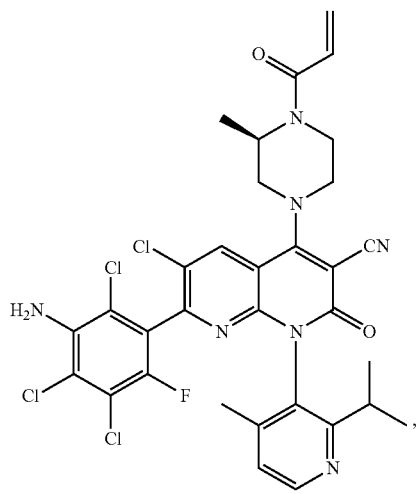
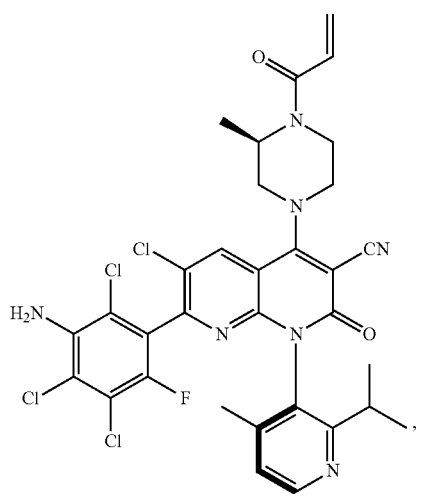
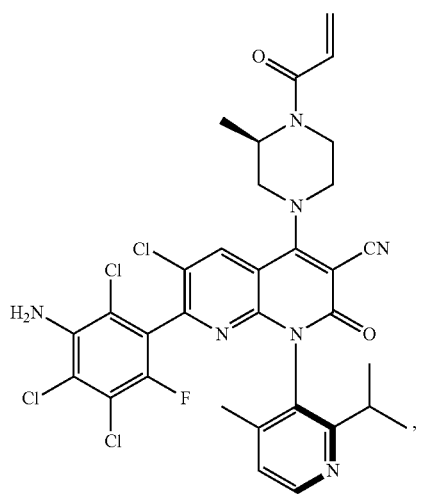
414
-continued
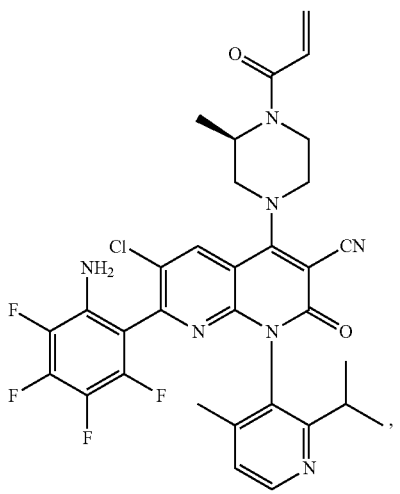
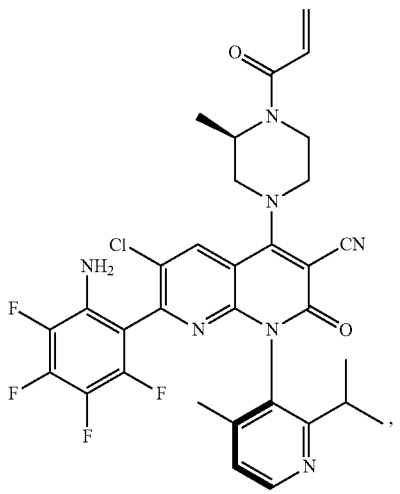
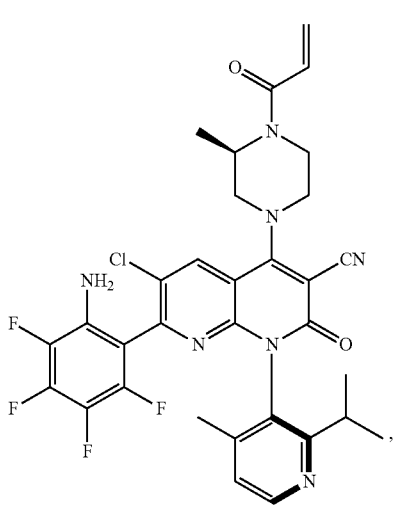

415
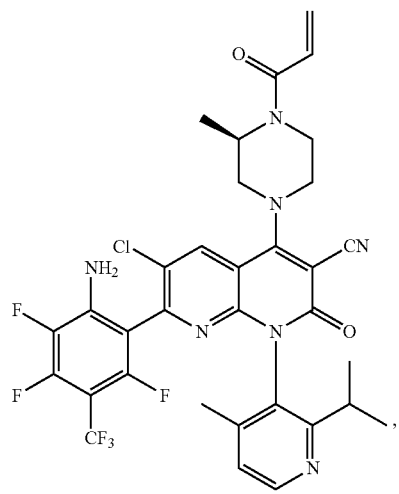
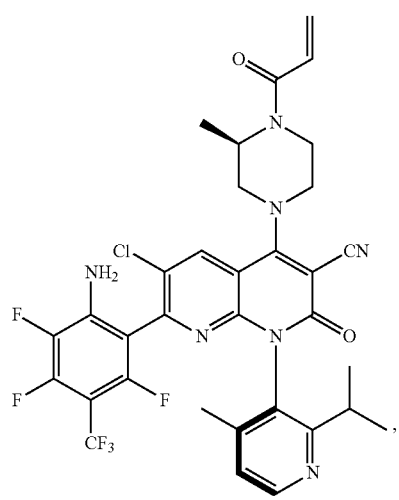
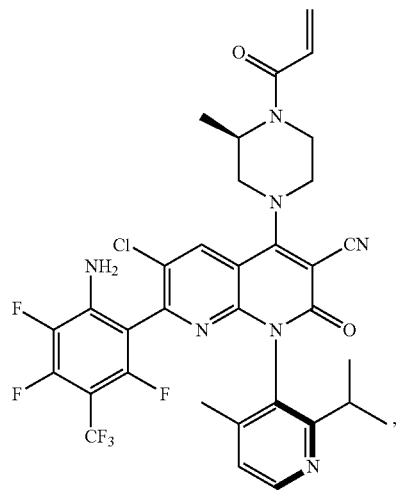
416
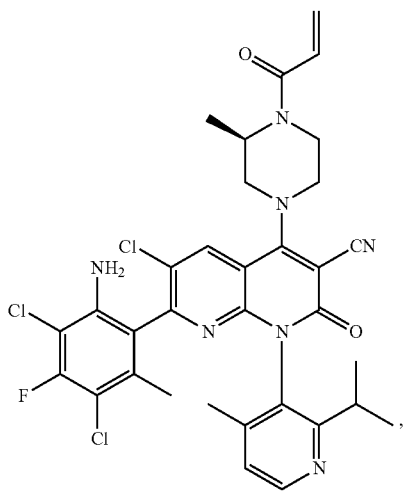
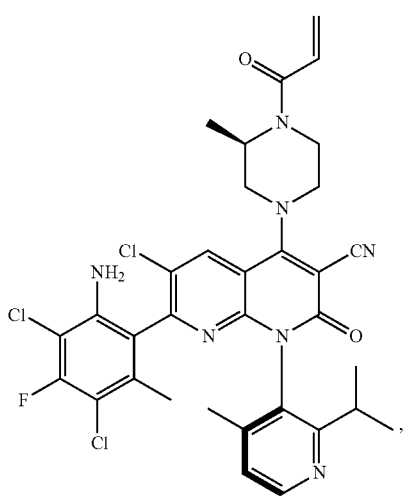
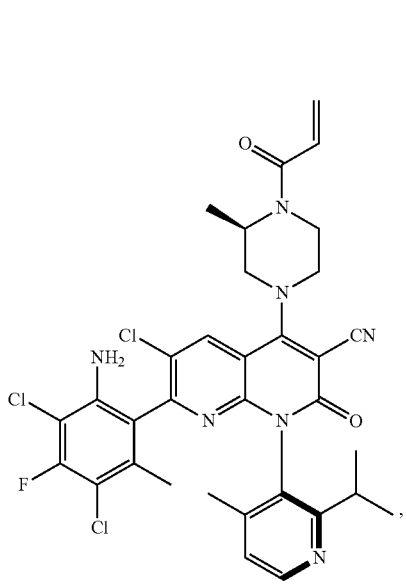

417
-continued
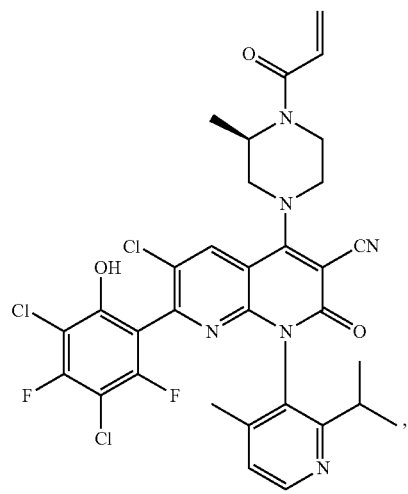
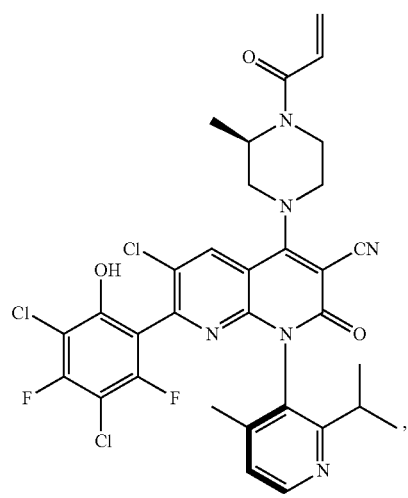
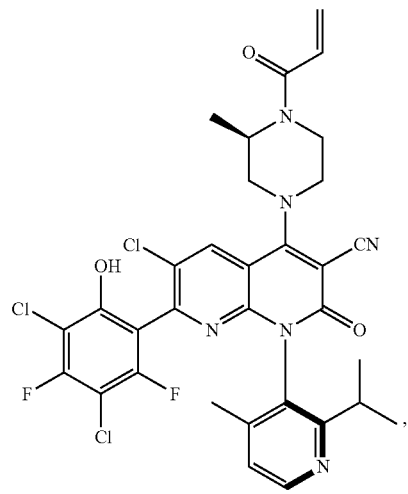
418
-continued
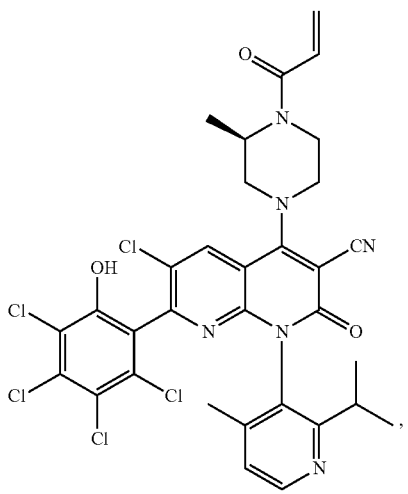
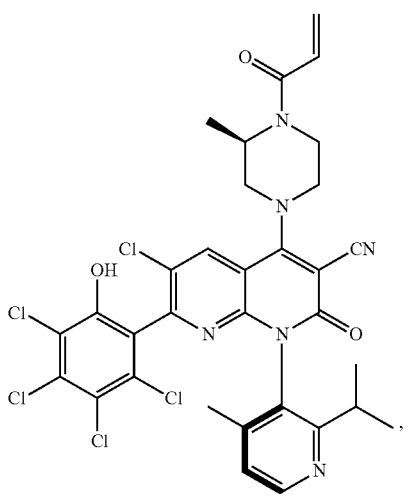
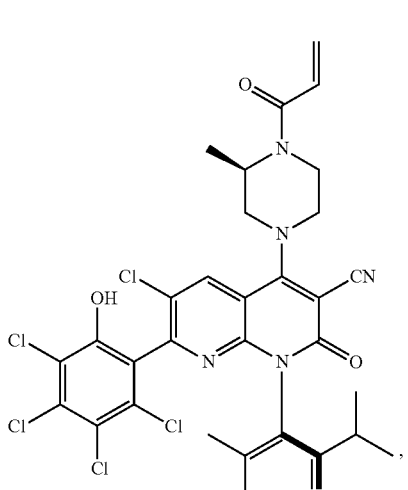

419
-continued
420
-continued
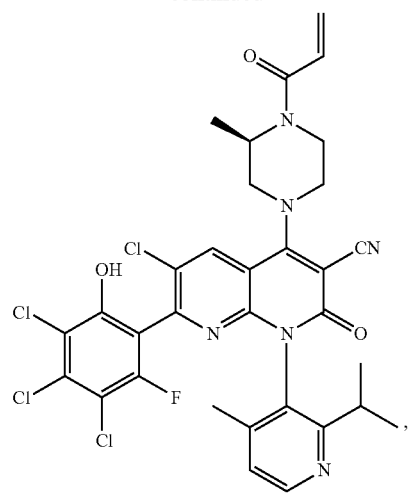
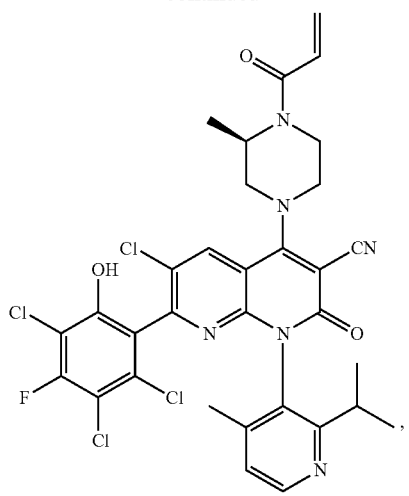
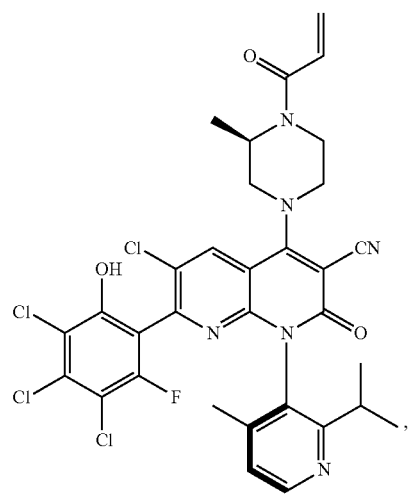
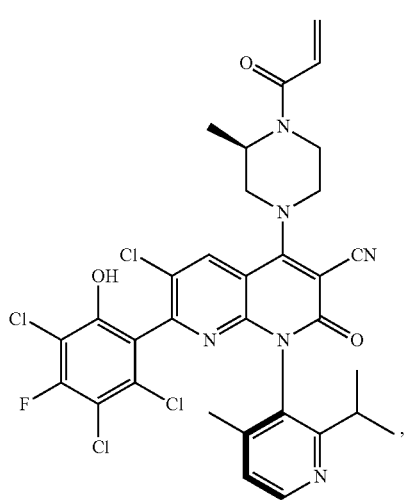
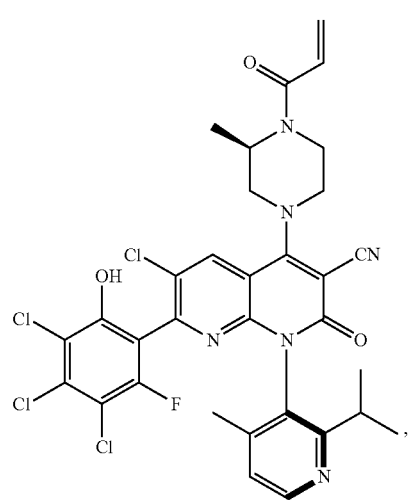
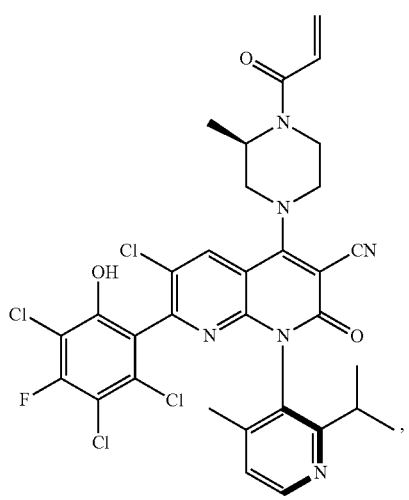

421
-continued
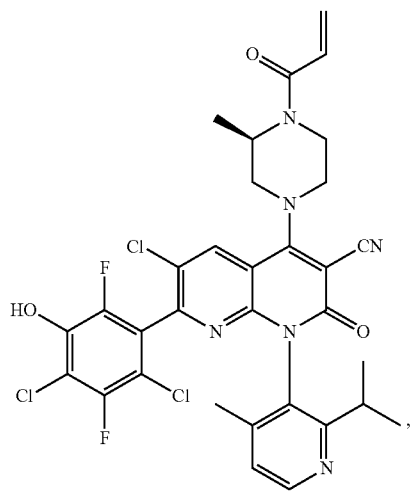
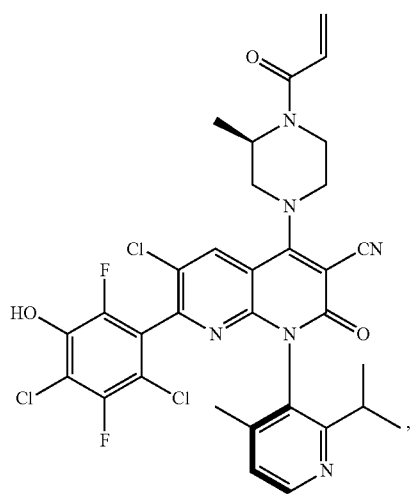
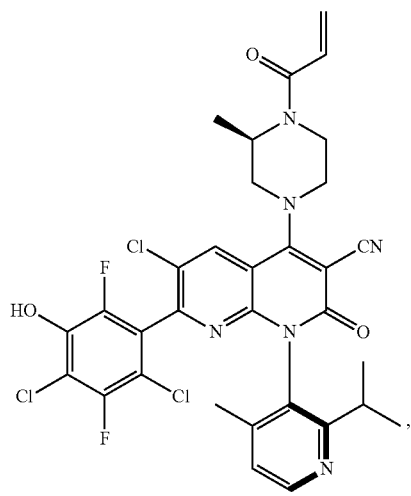
422
-continued
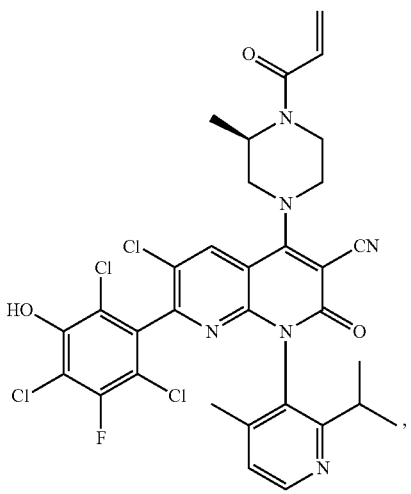
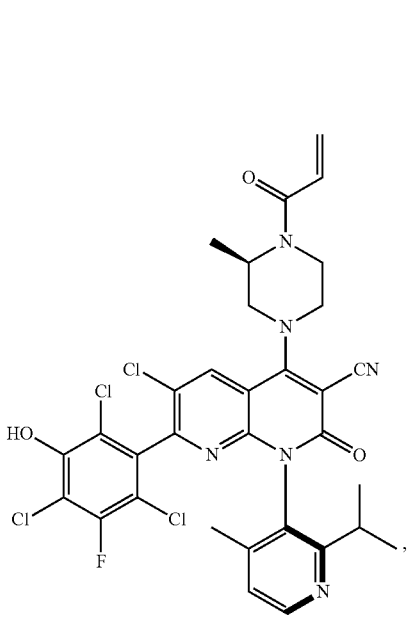

423
-continued
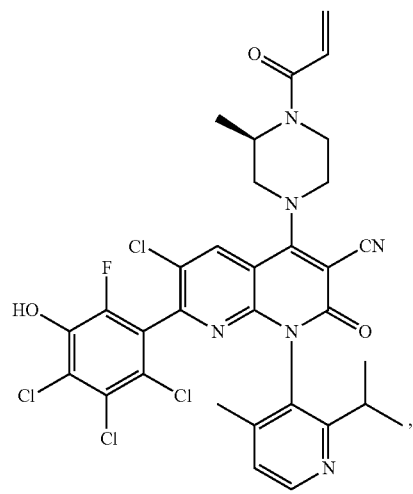
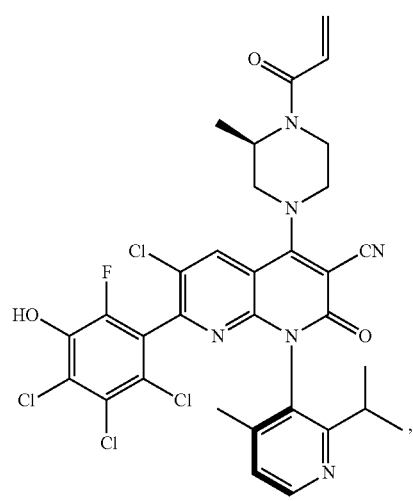
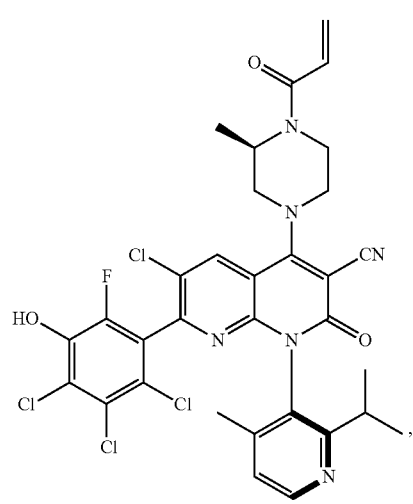
424
-continued
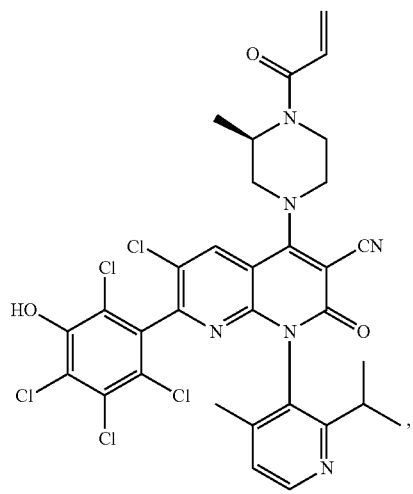
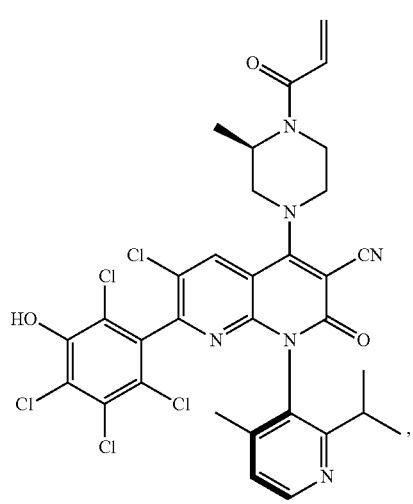
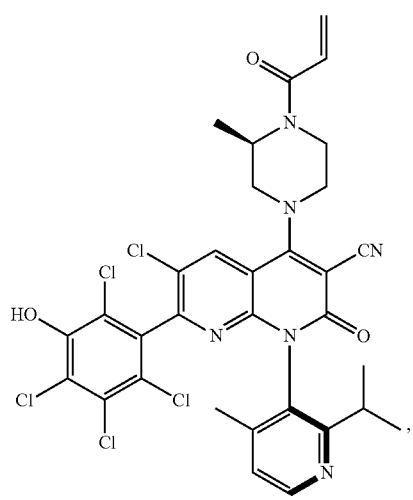

425
-continued
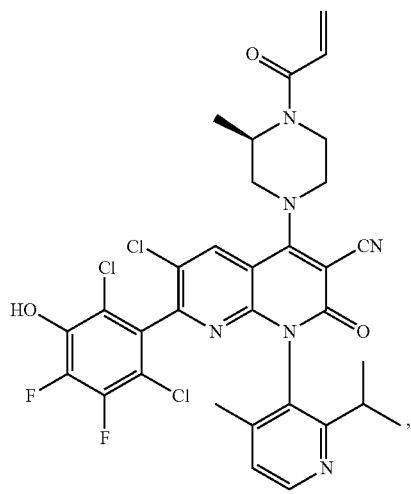
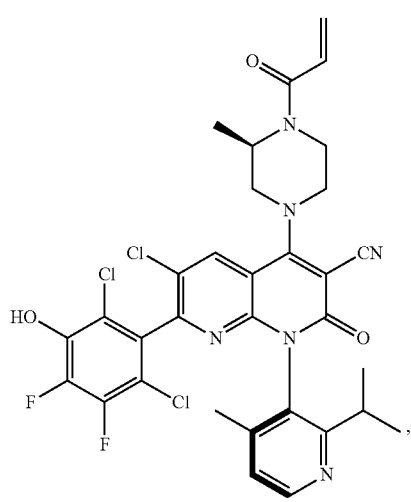
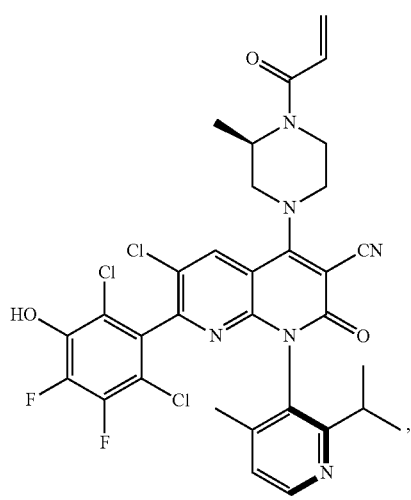
426
-continued
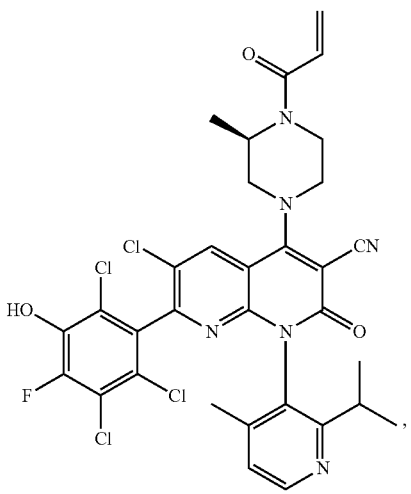
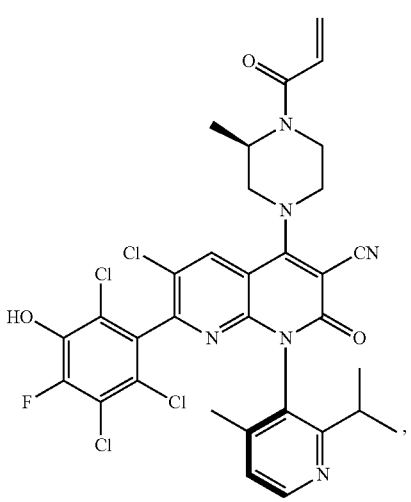
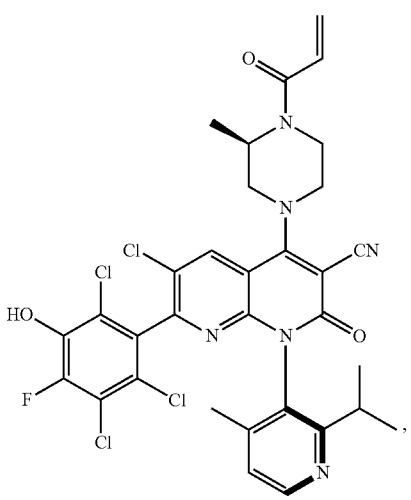

427
-continued
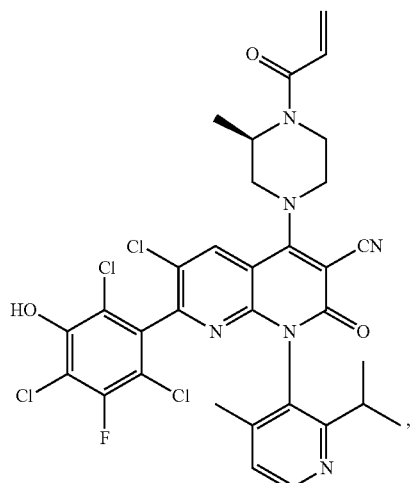
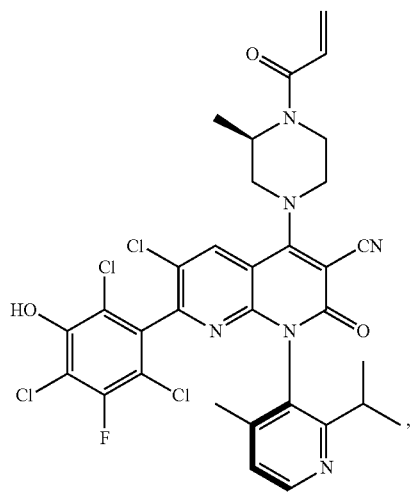
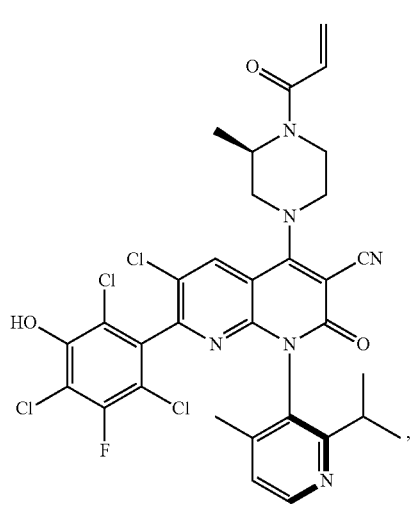
428
-continued
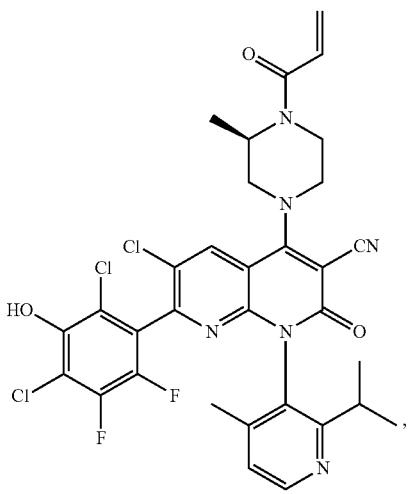
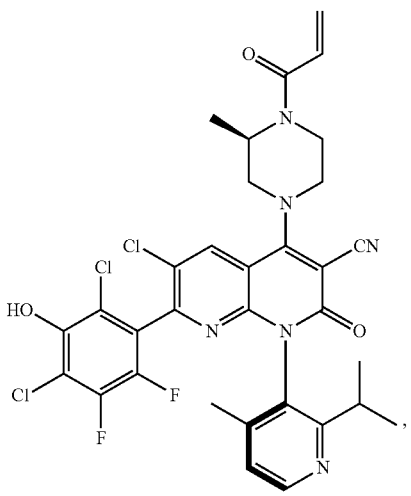
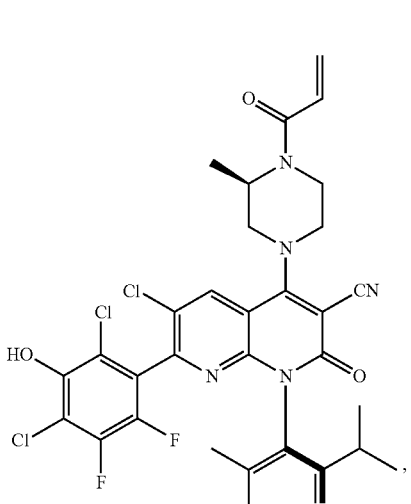

429
-continued
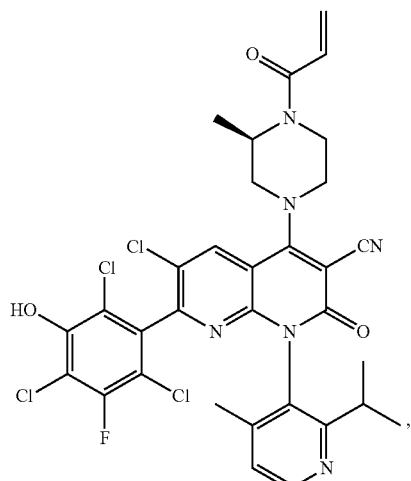
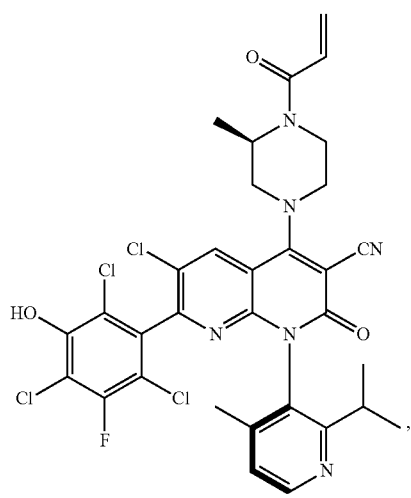
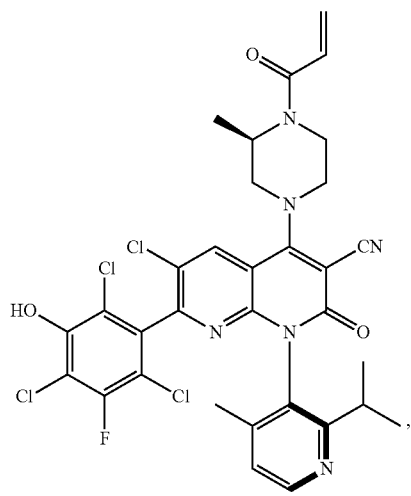
430
-continued
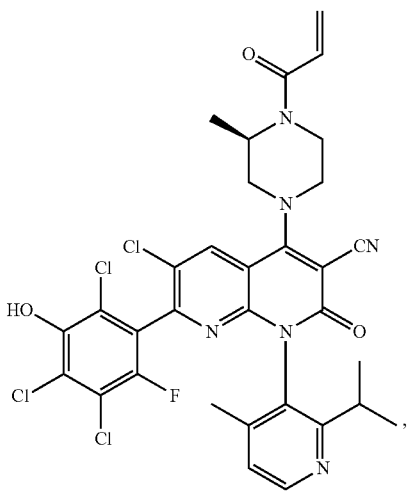
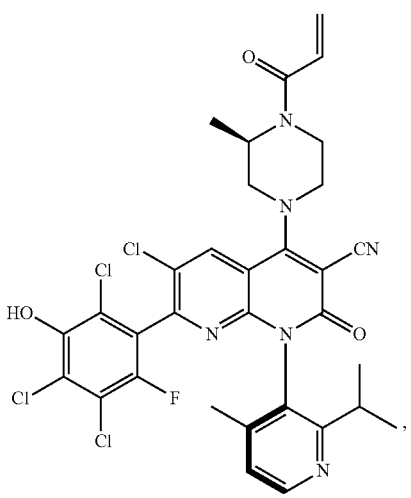
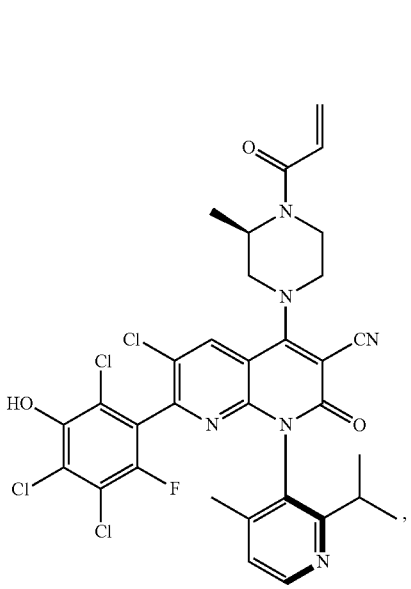

431
-continued
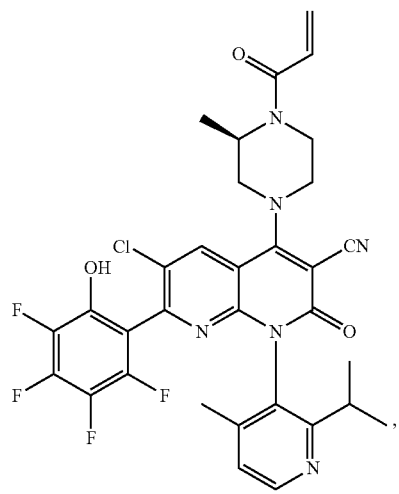
432
-continued
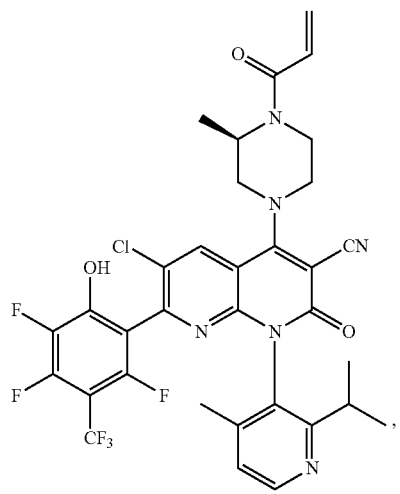
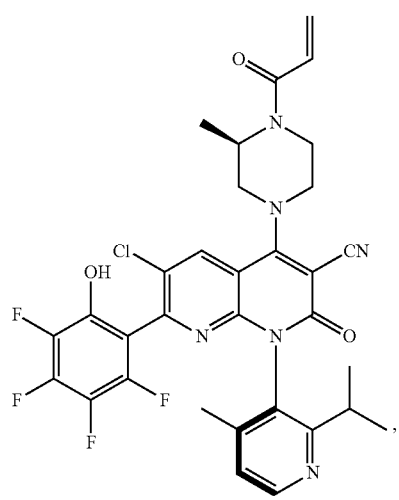
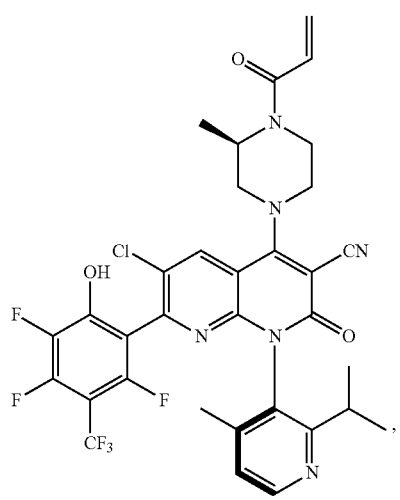
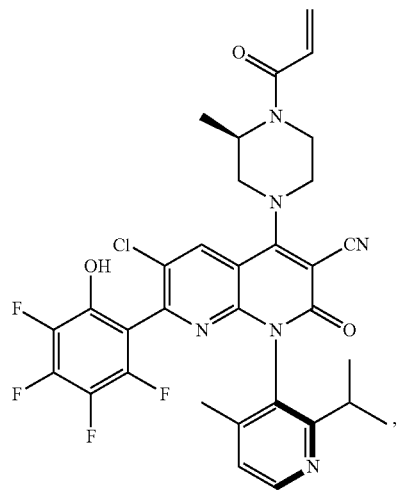
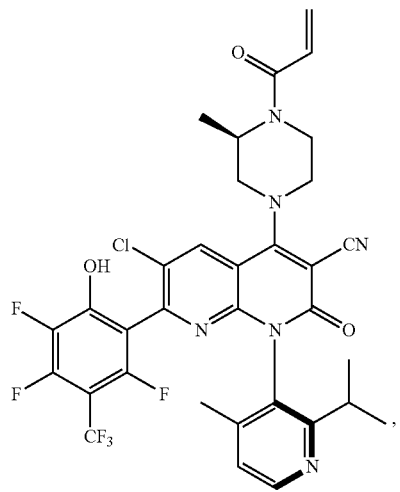

433
-continued
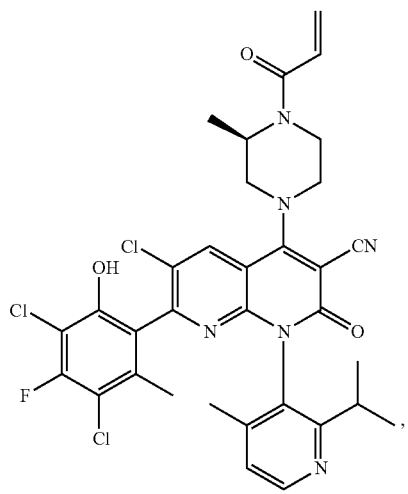
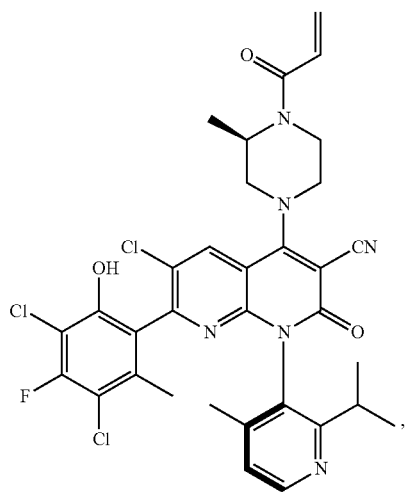
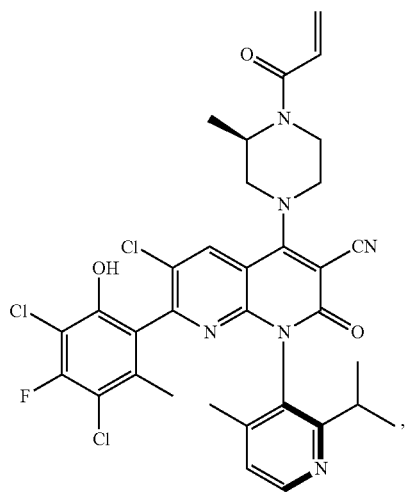
434
-continued
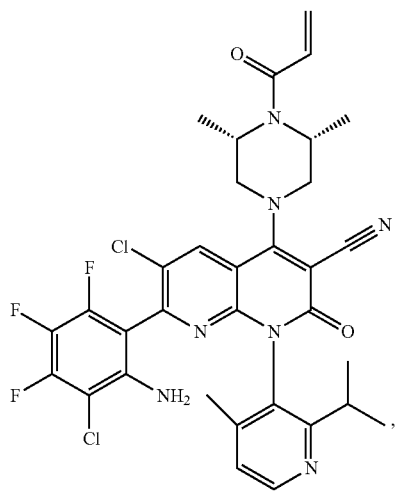
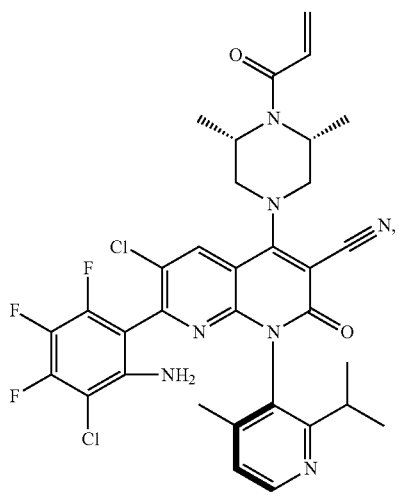
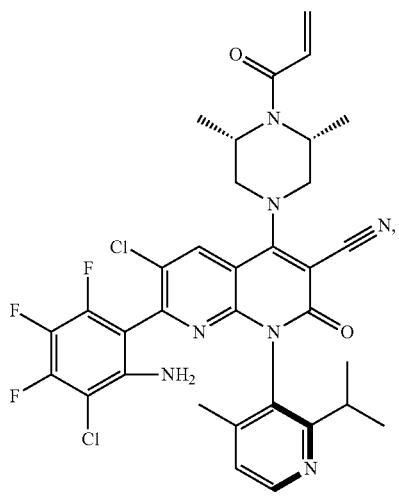

435
-continued
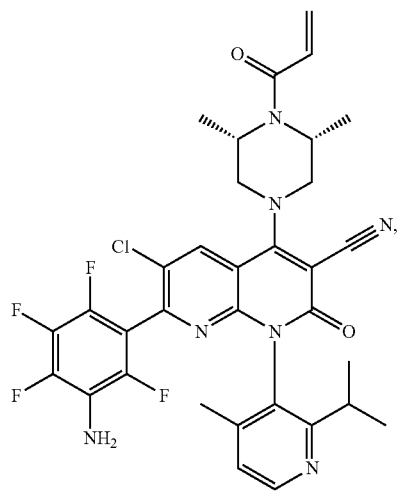
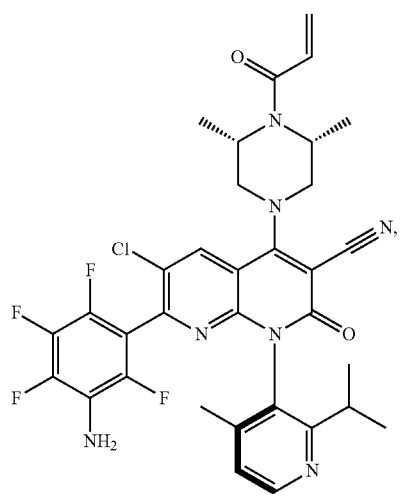
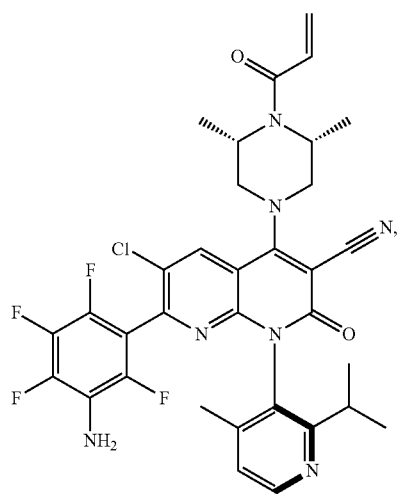
436
-continued
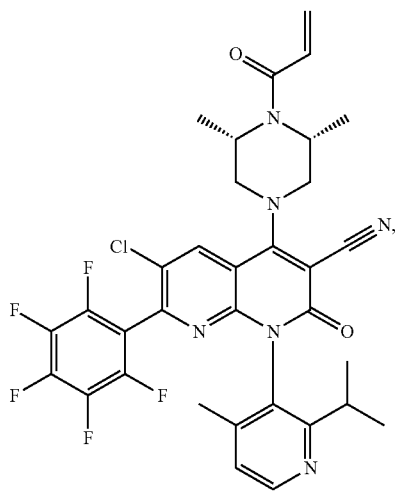
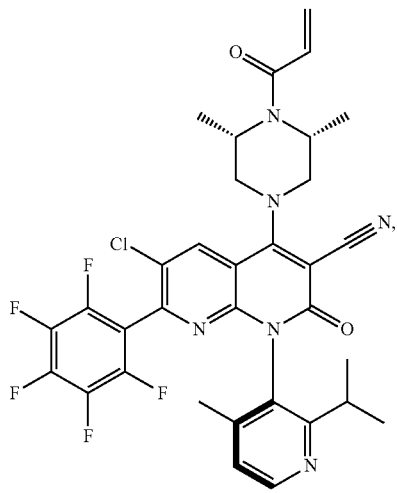
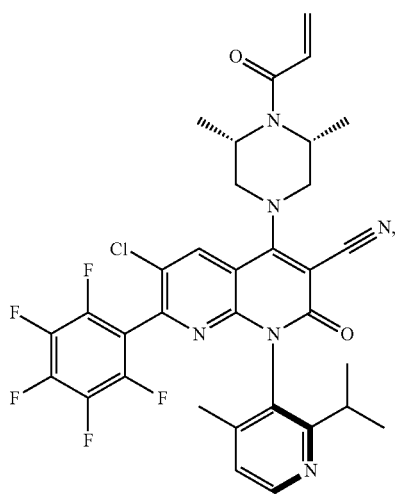

437
-continued
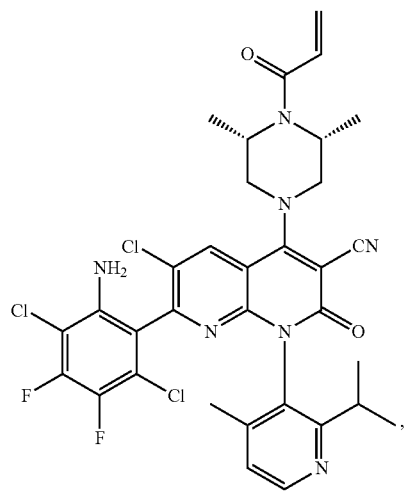
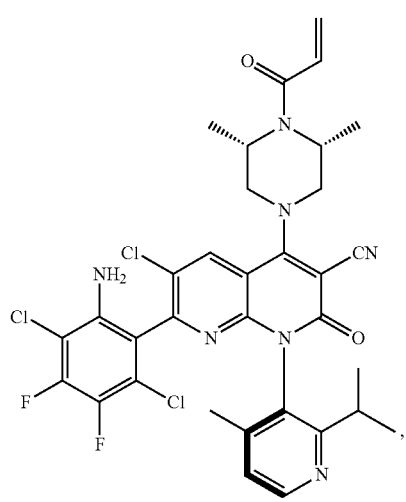
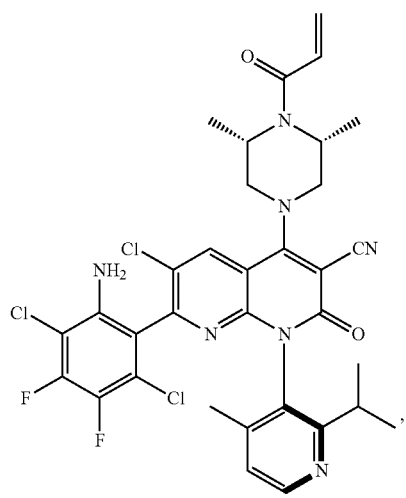
438
-continued
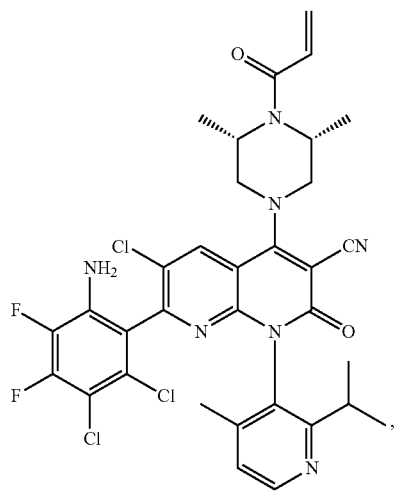
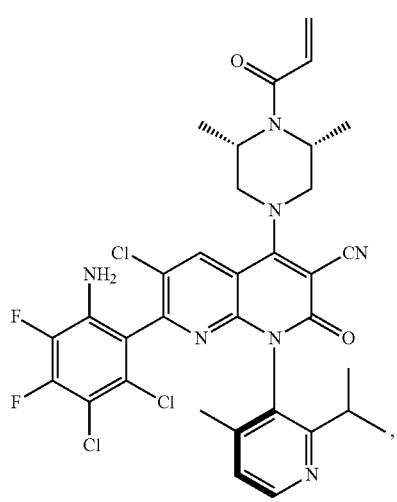
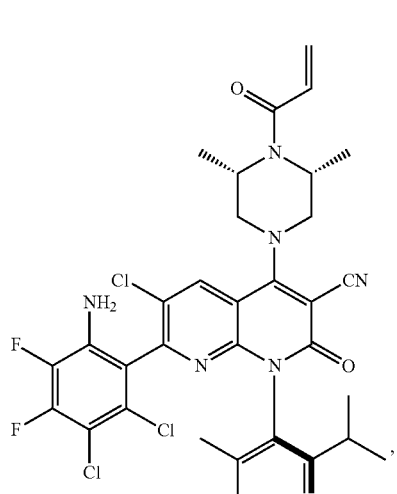

439
-continued
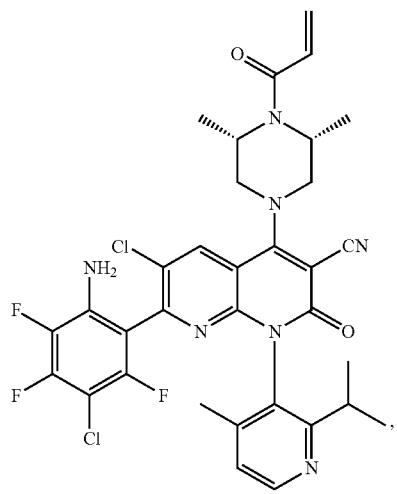
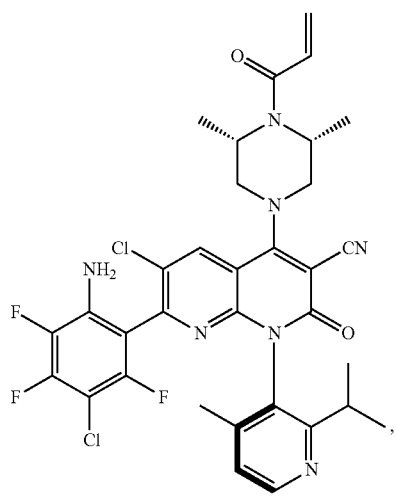
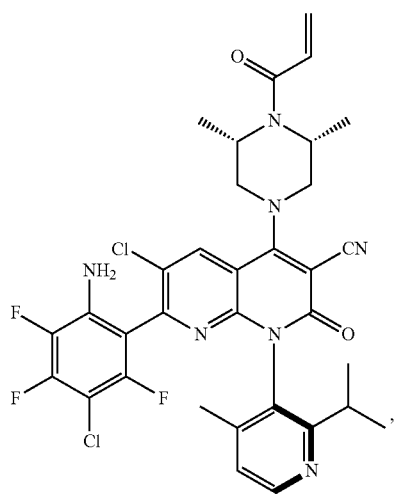
440
-continued
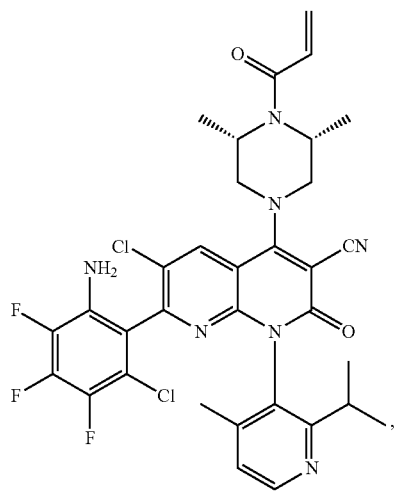
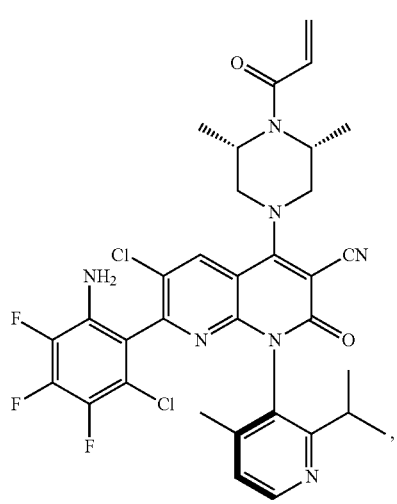
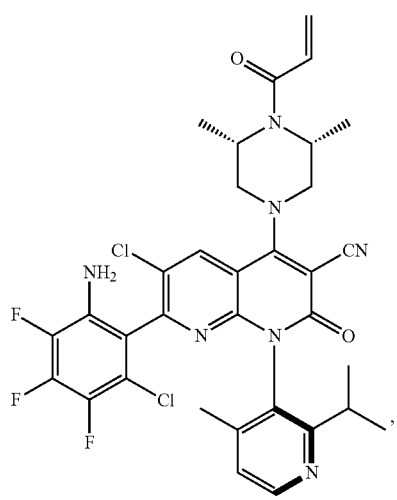

441
-continued
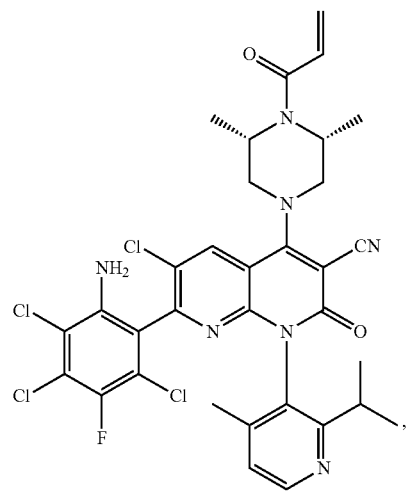
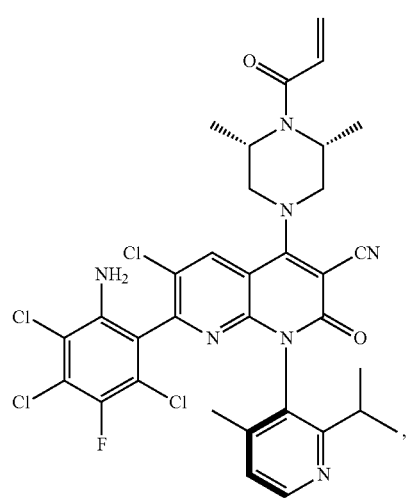
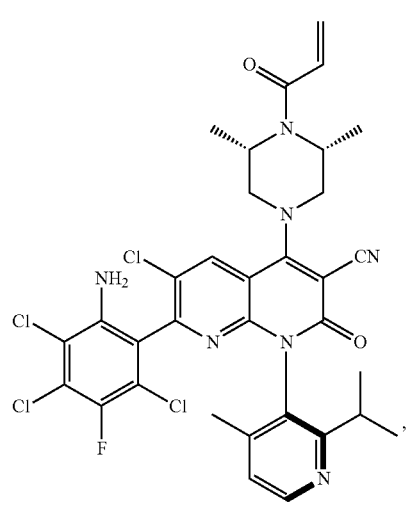
442
-continued
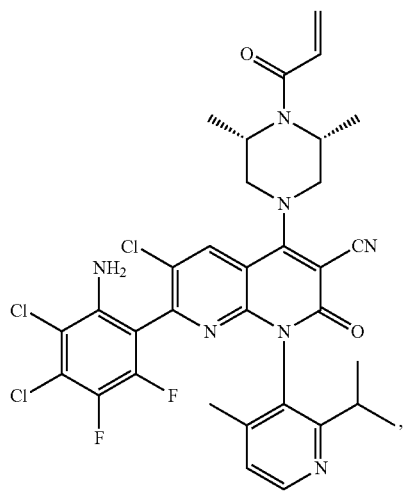
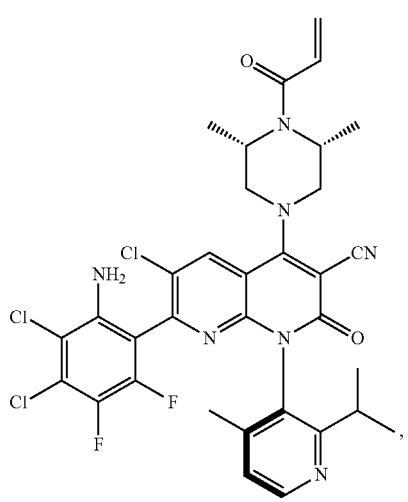
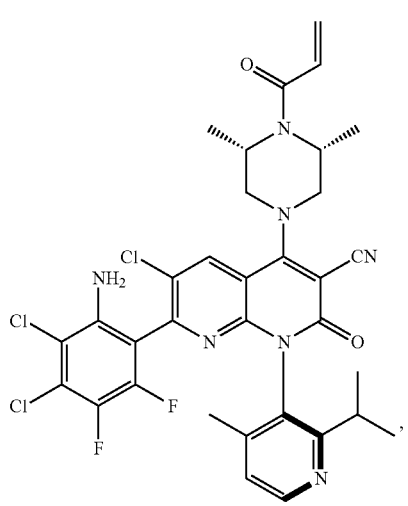

443
-continued
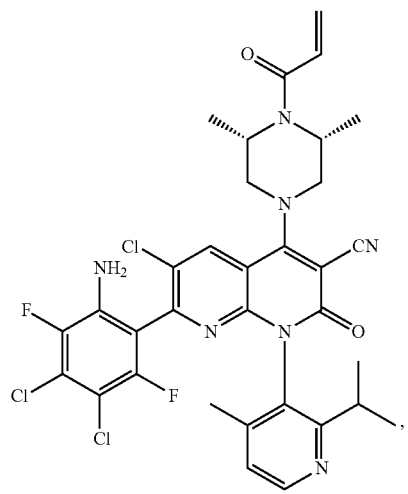
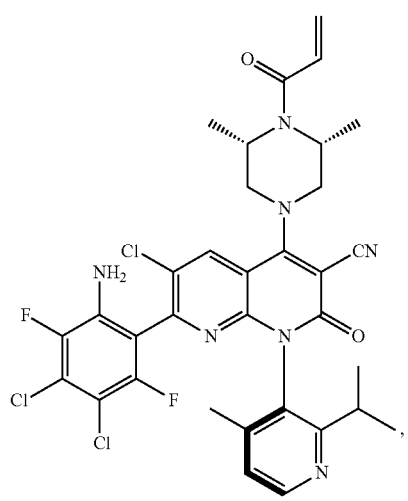
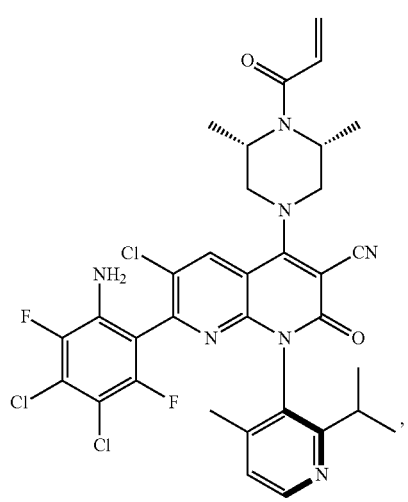
444
-continued
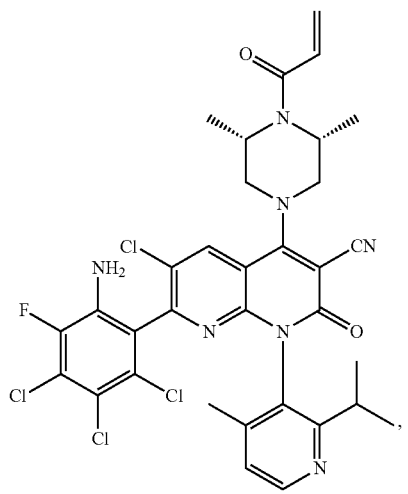
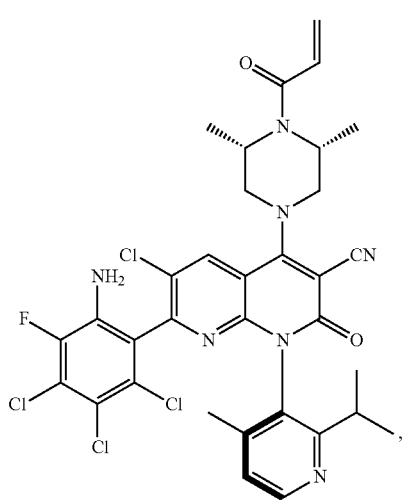
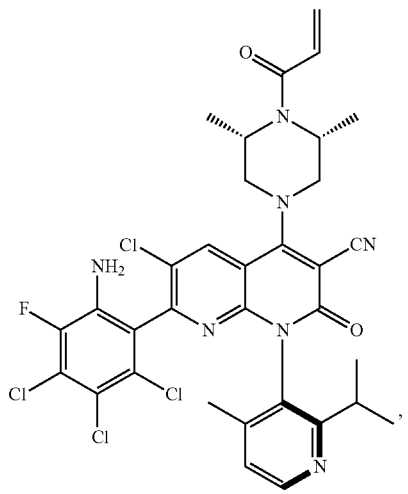

445
-continued
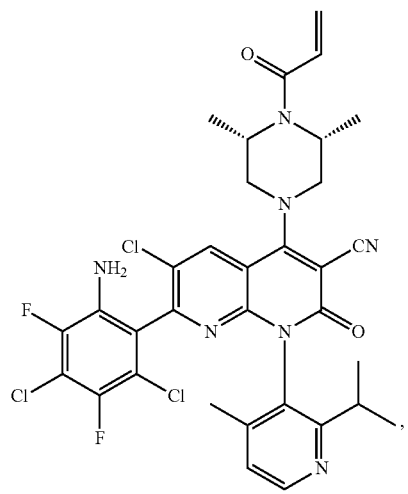
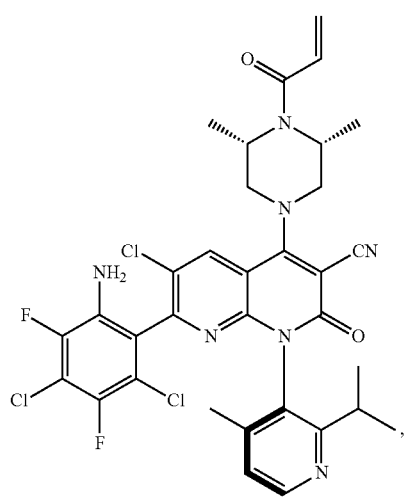
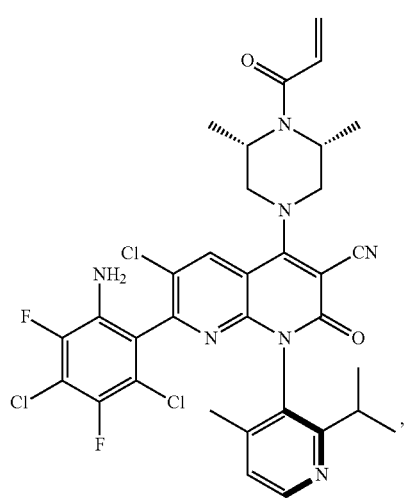
446
-continued
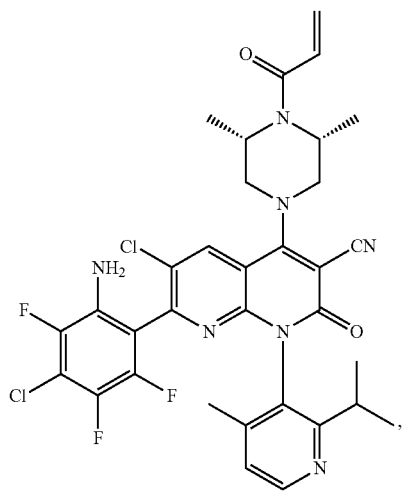
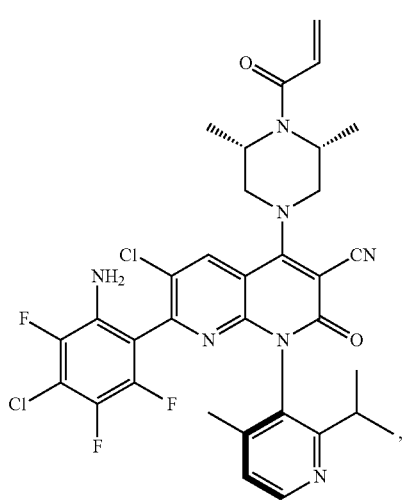
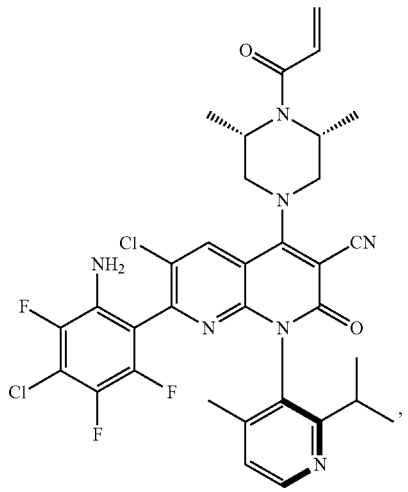

447
-continued
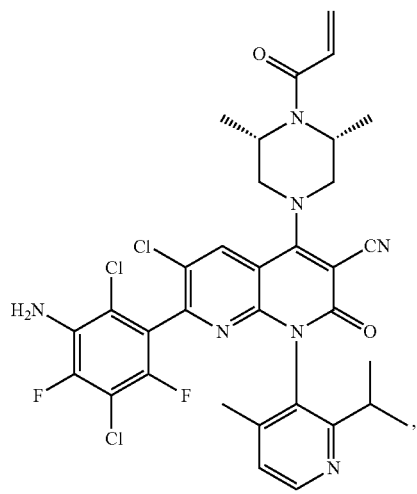
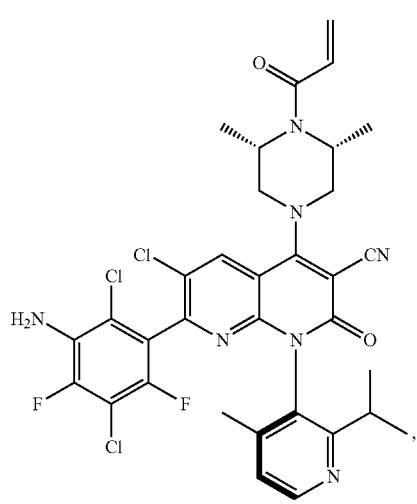
448
-continued
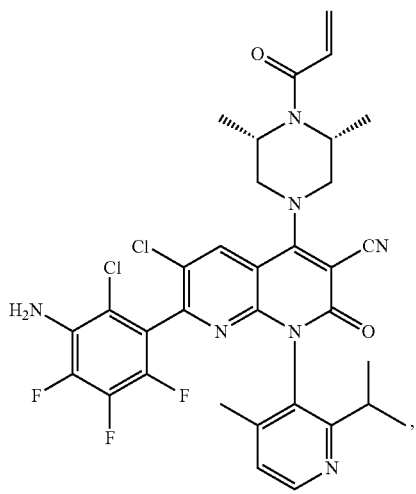
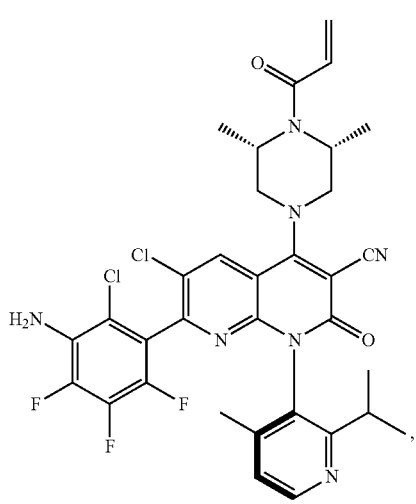

449
-continued
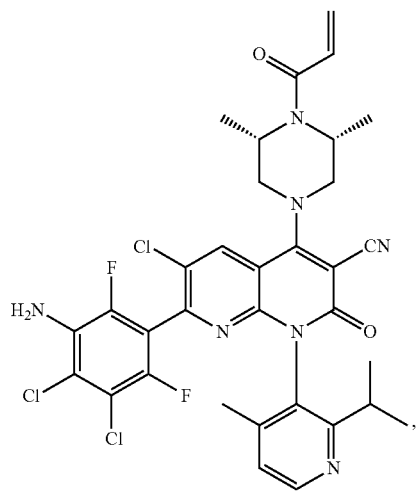
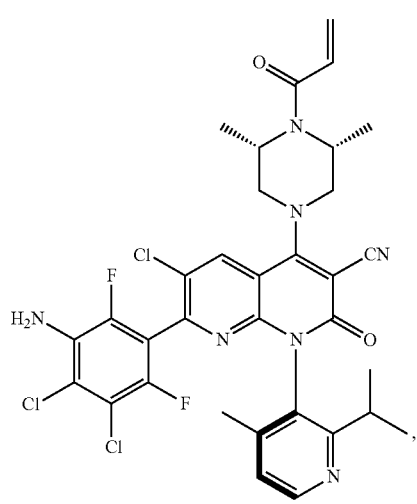
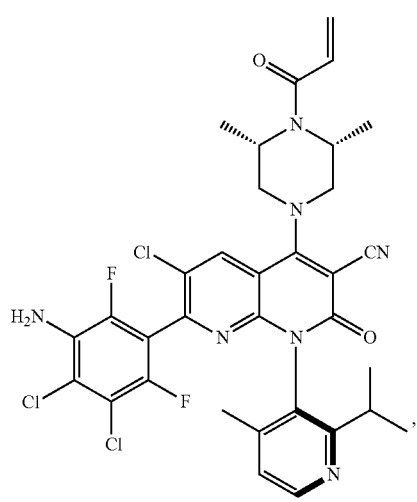
450
-continued
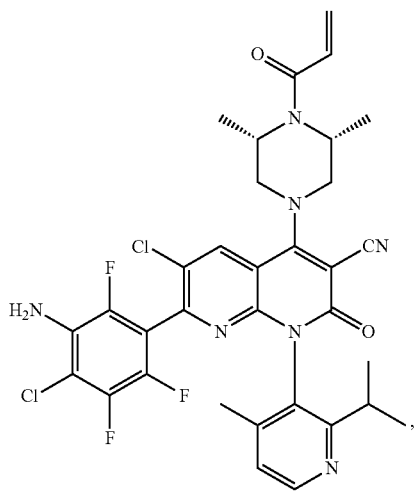
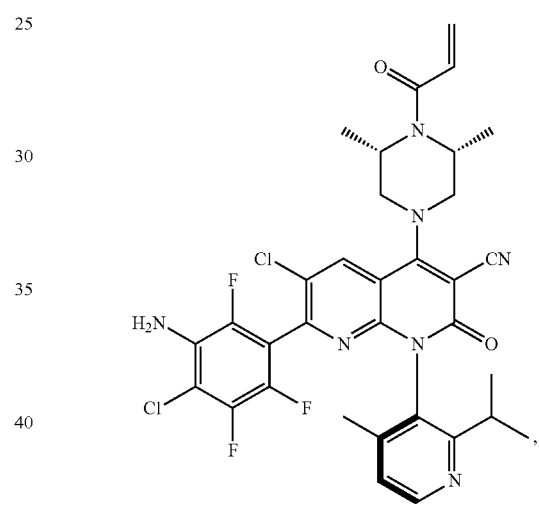
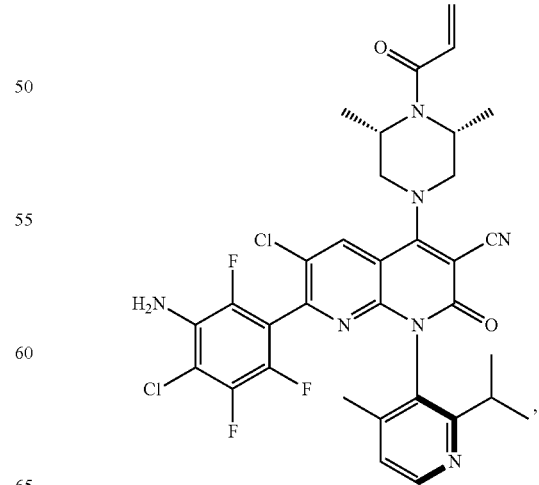

451
-continued
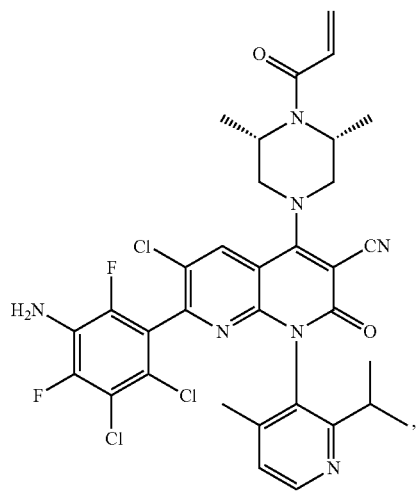
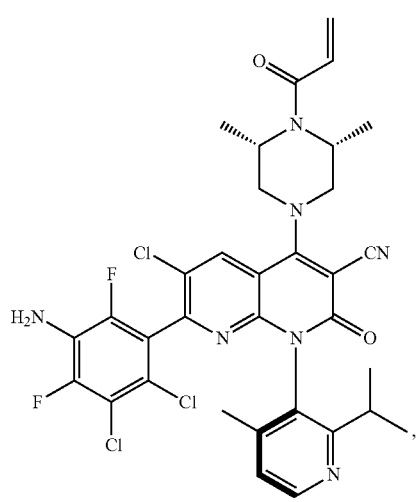
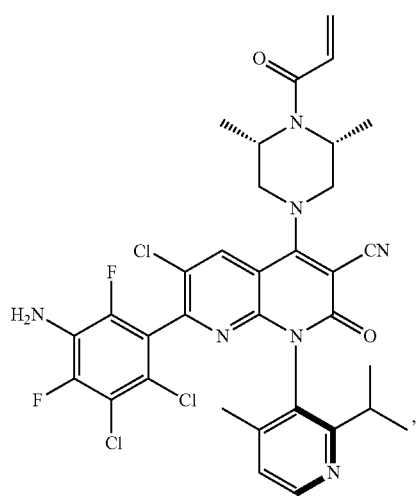
452
-continued
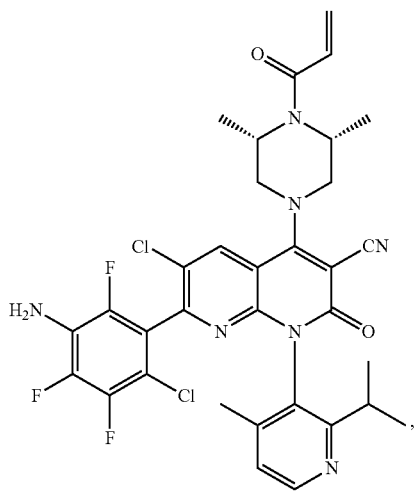
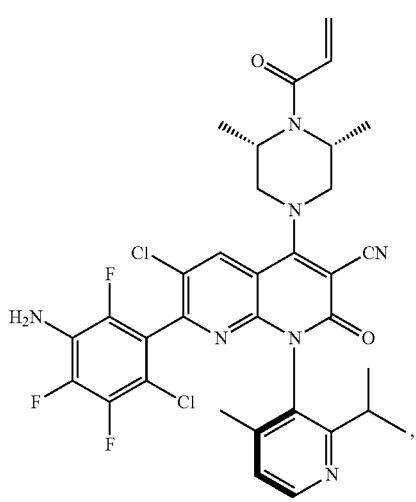
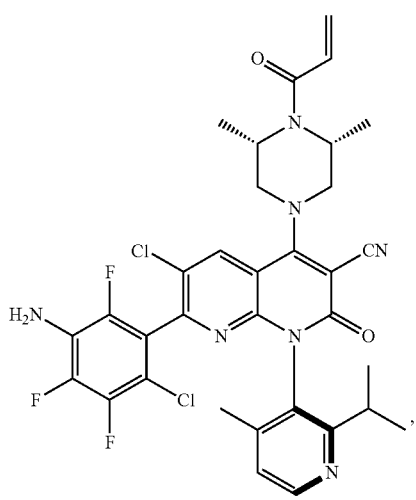

453
-continued
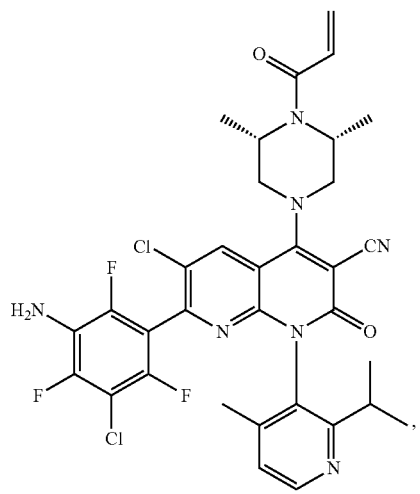
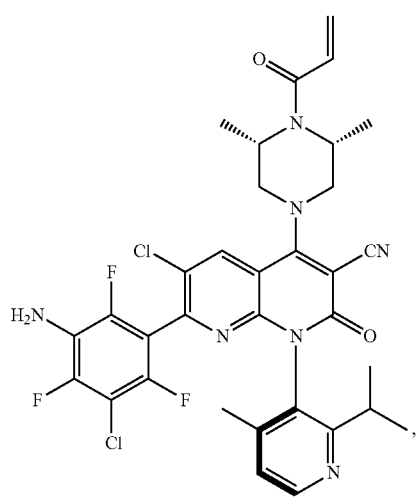
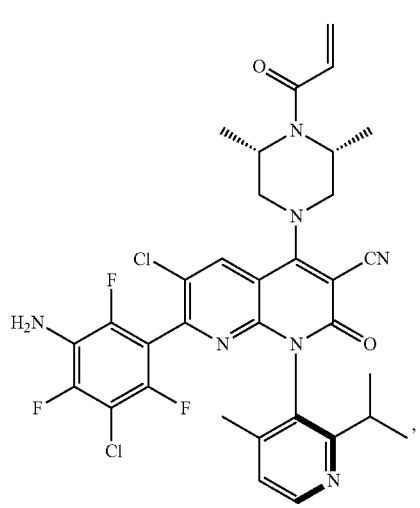
454
-continued
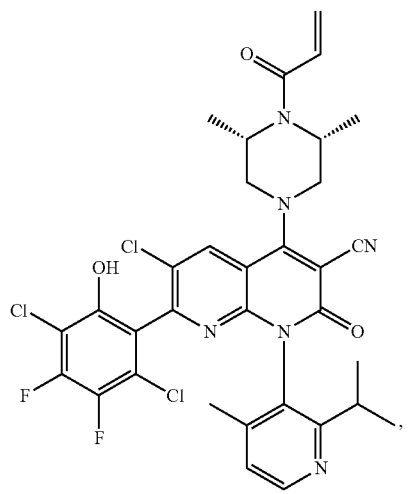
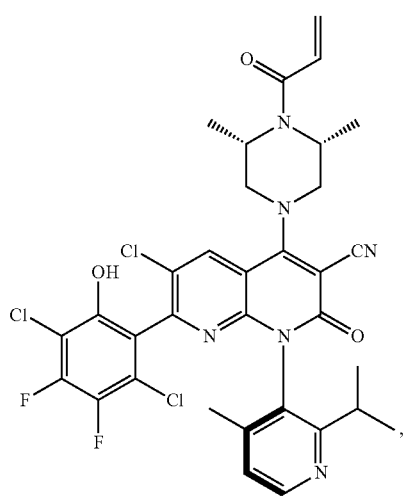
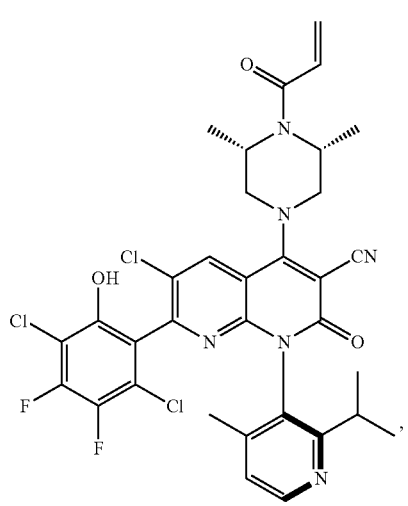

455
-continued
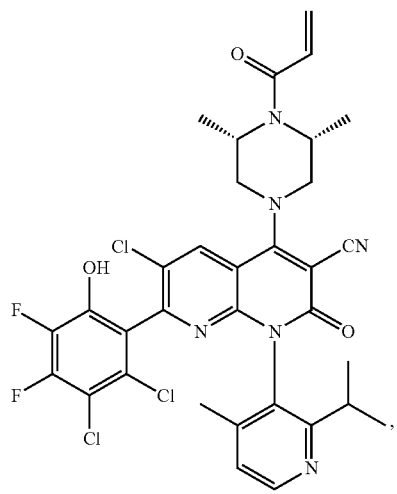
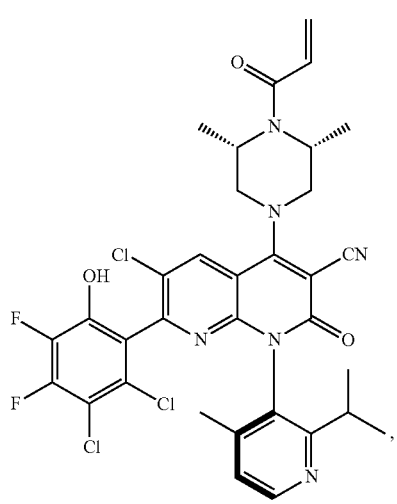
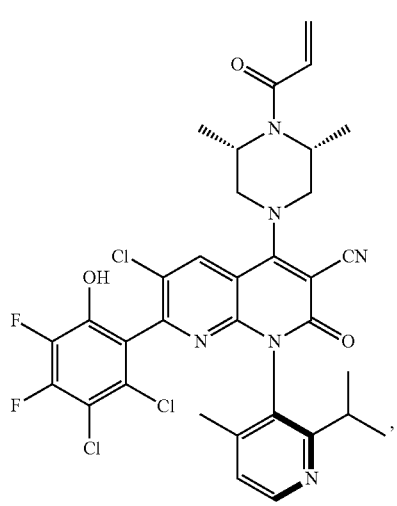
456
-continued
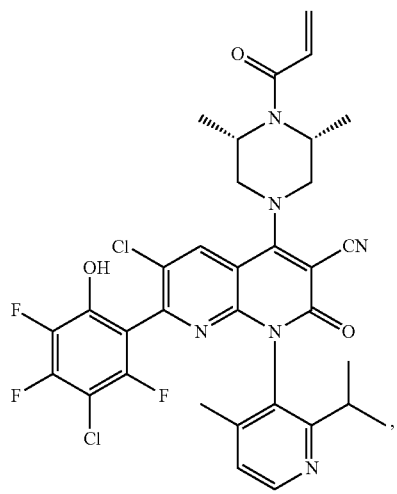
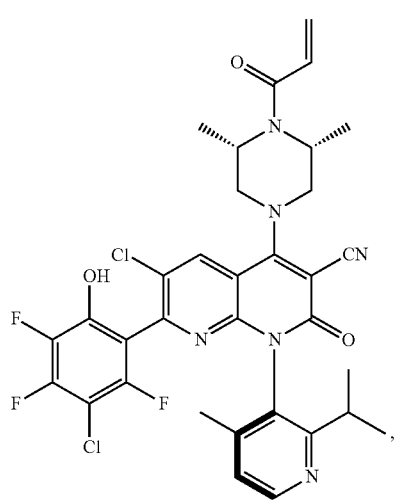
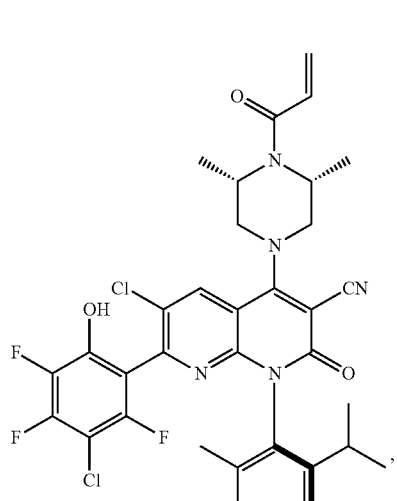

457
-continued
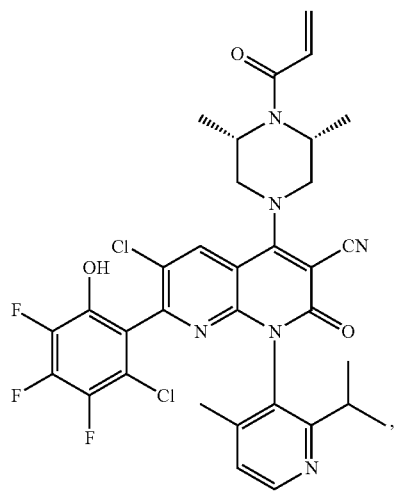
458
-continued
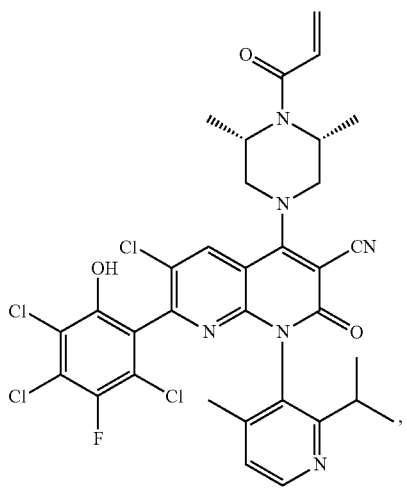
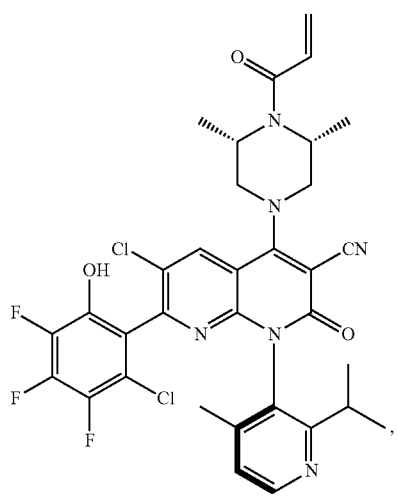
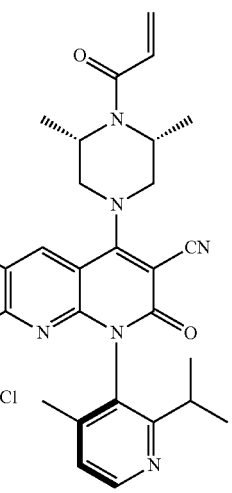
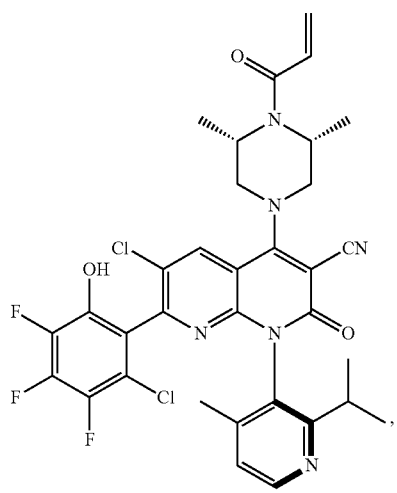
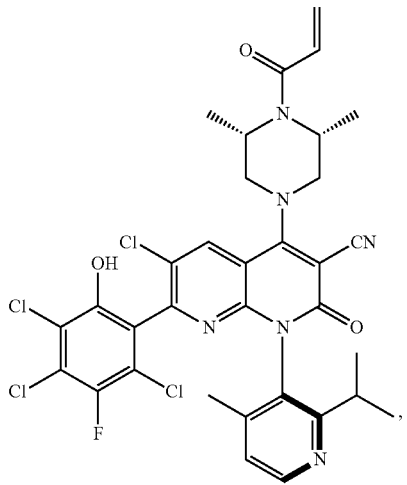

459
-continued
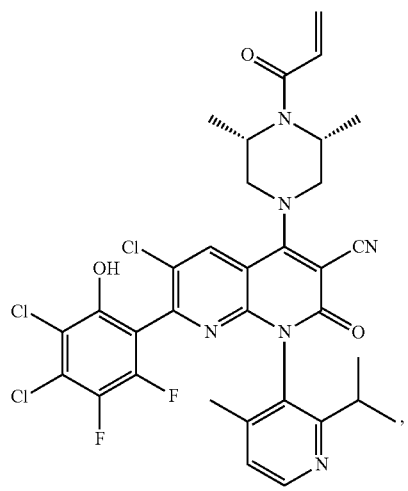
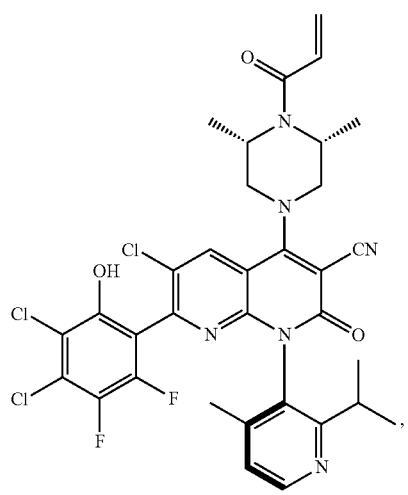
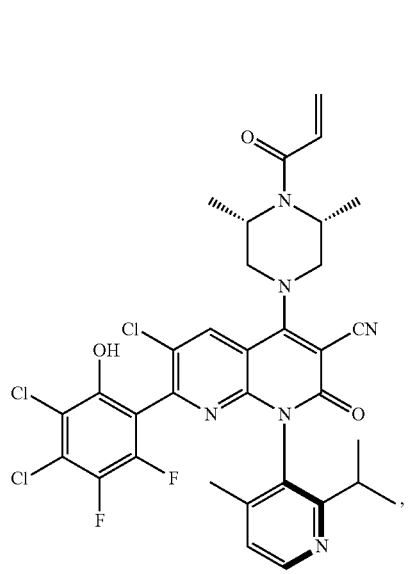
460
-continued
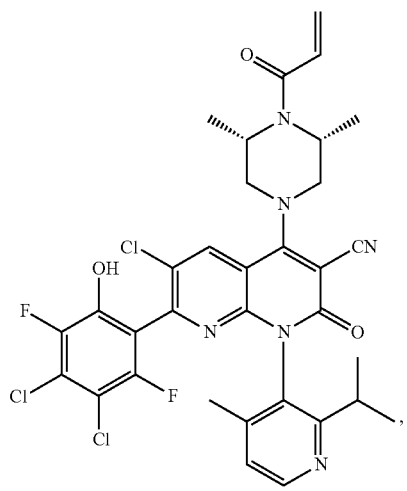
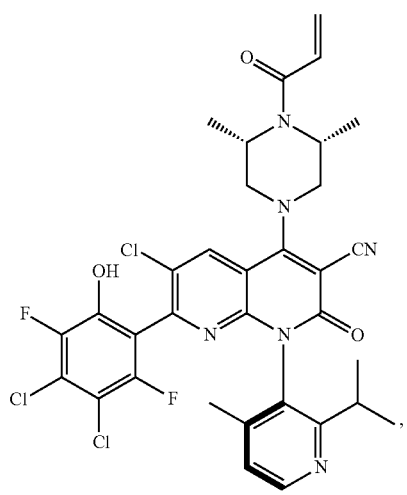
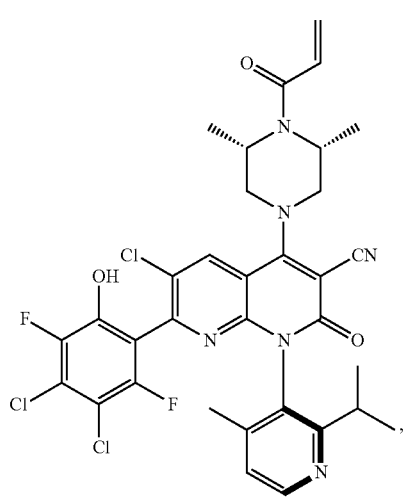

461
-continued
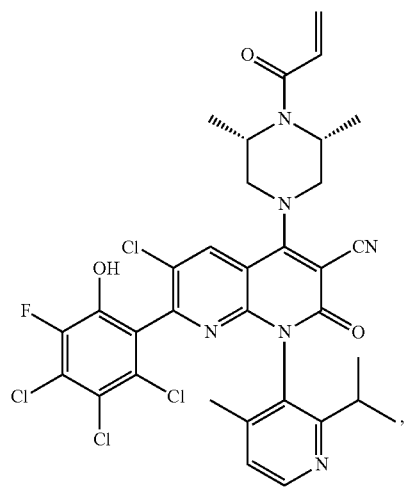
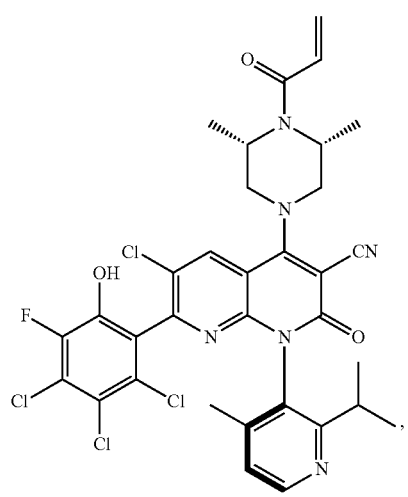
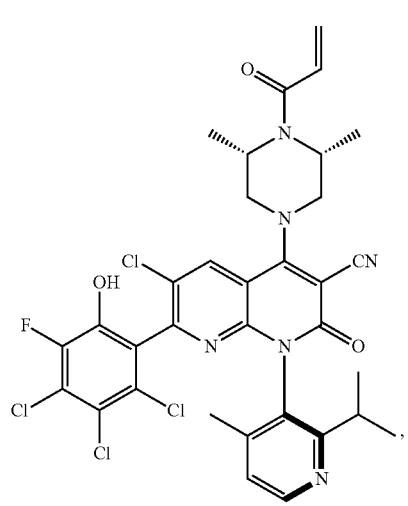
462
-continued
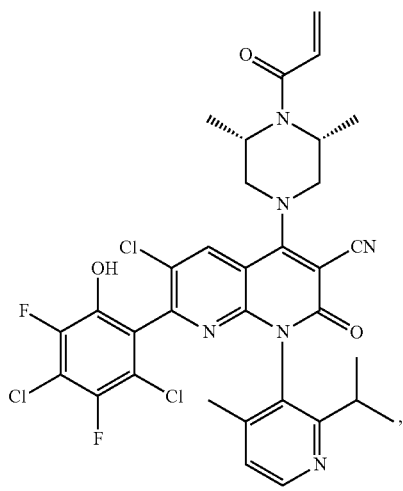
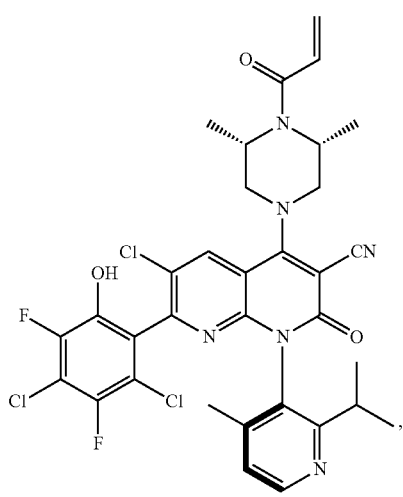
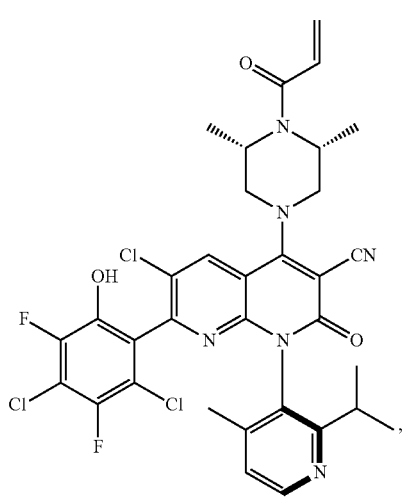

463
-continued
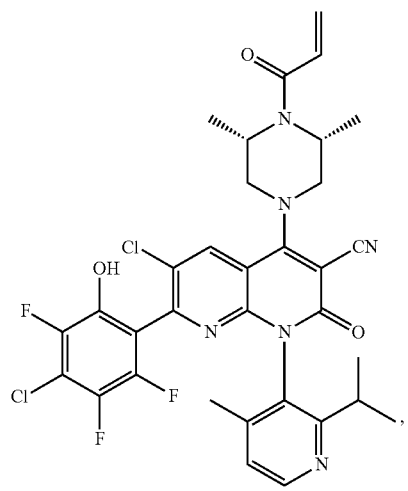
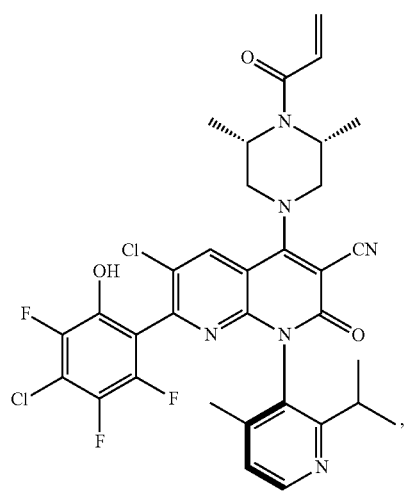
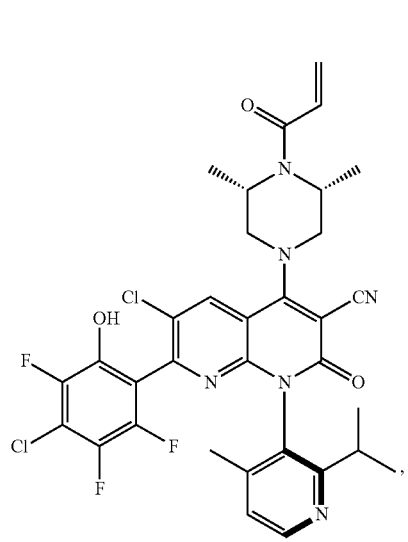
464
-continued
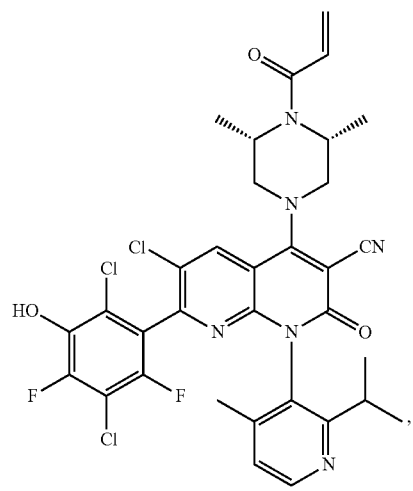
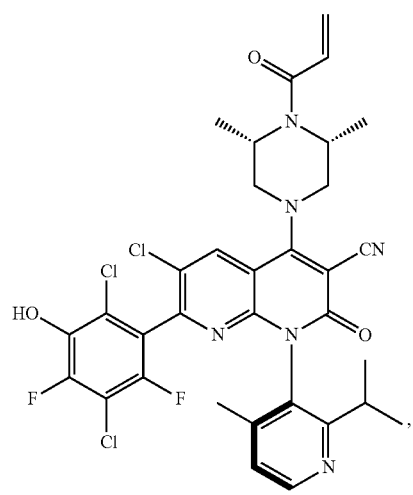
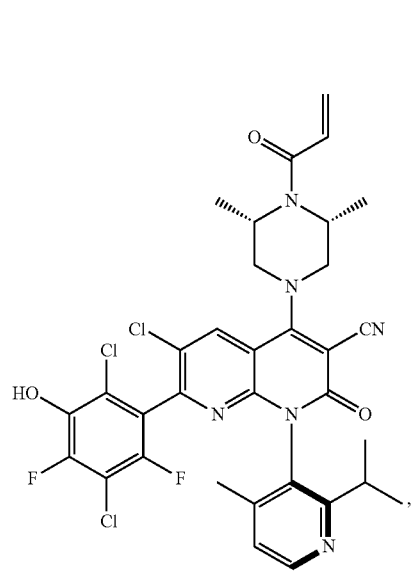

465
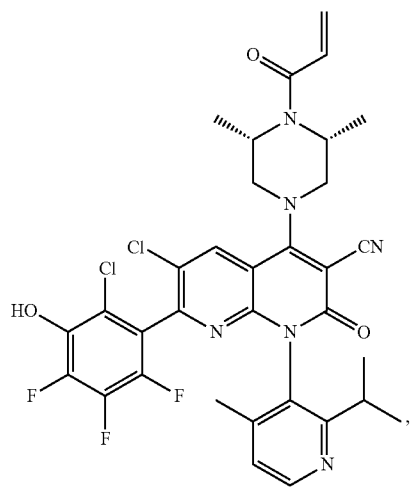
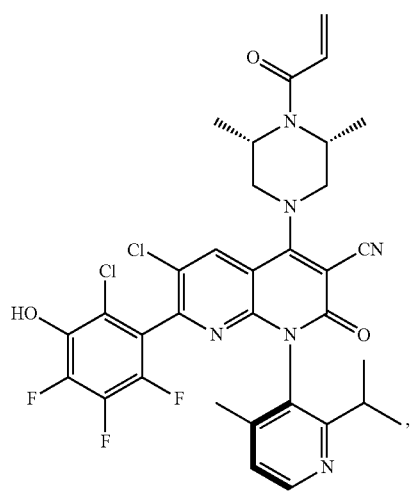
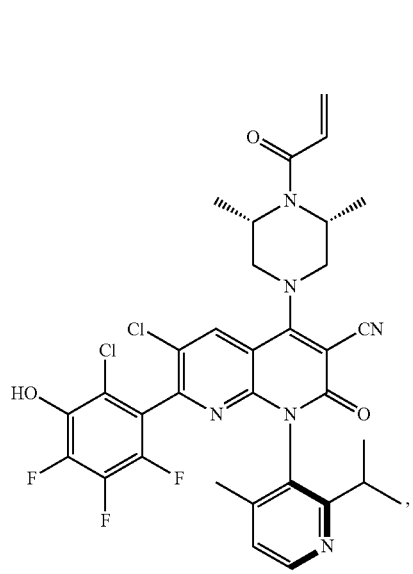
466
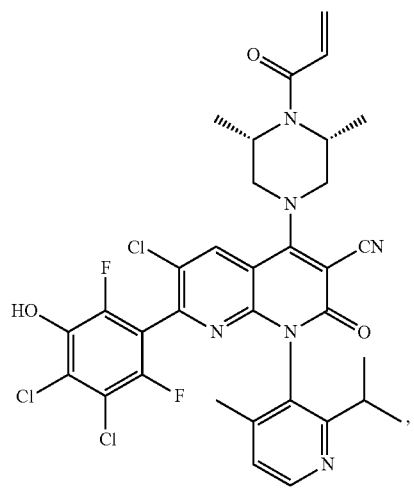
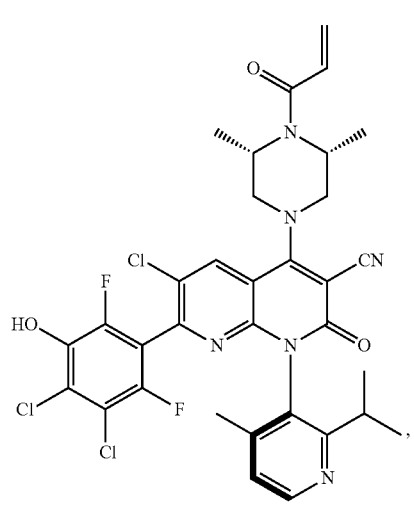
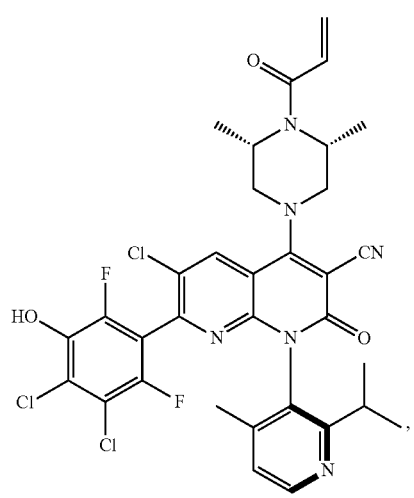

467
-continued
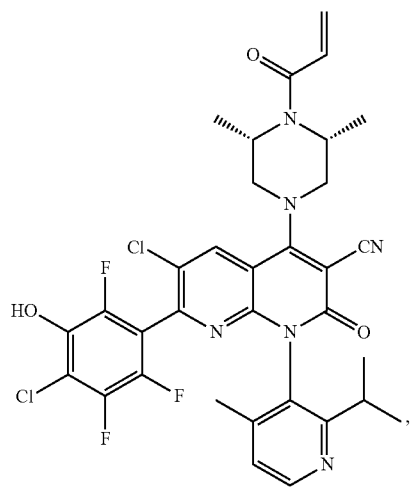
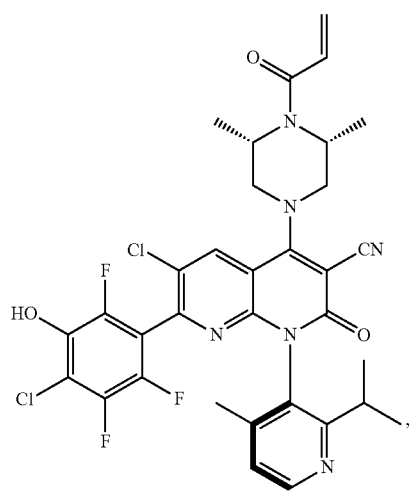
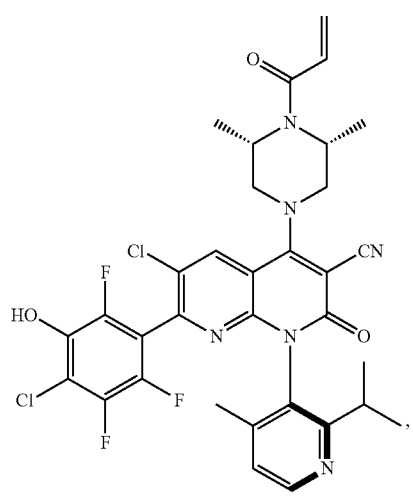
468
-continued
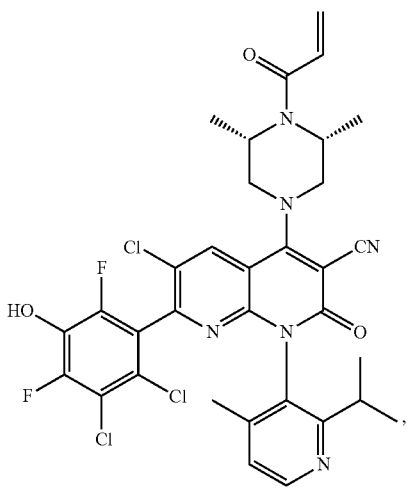
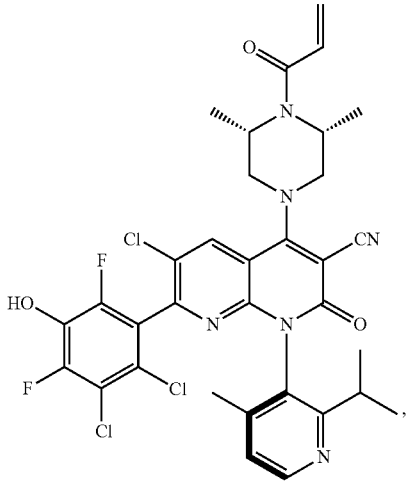
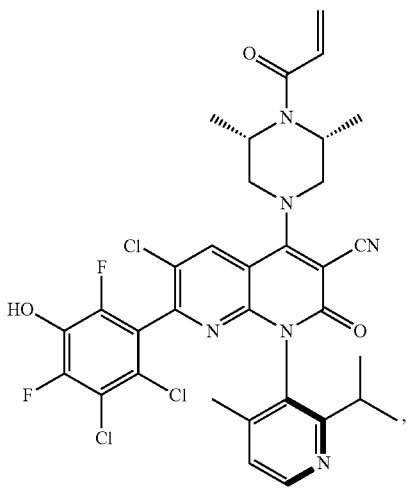

469
-continued
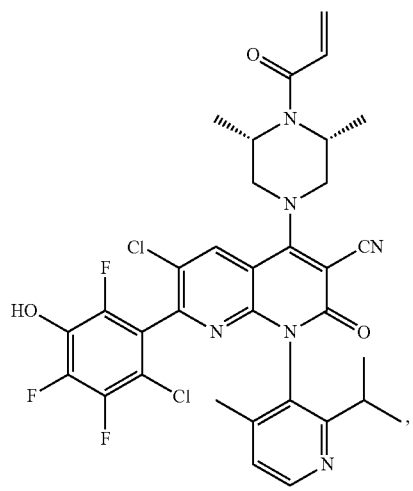
470
-continued
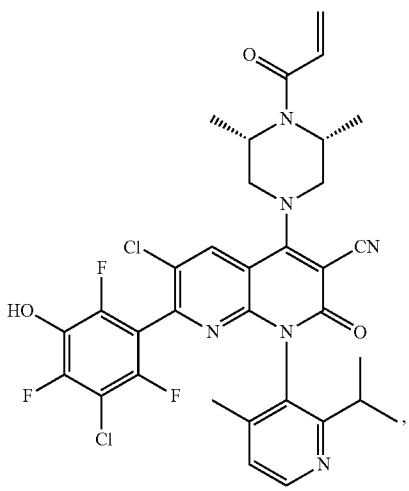
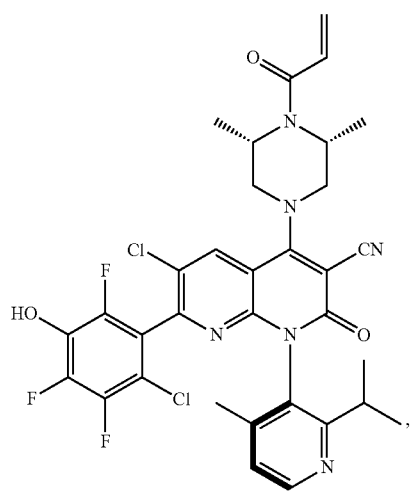
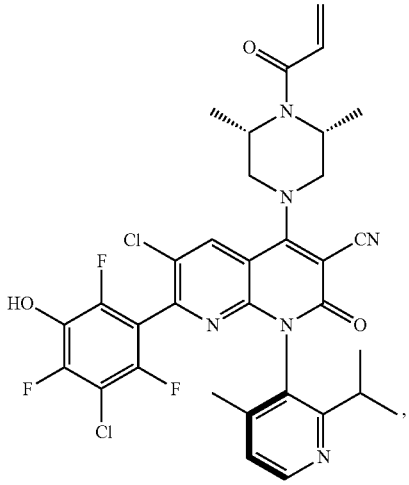
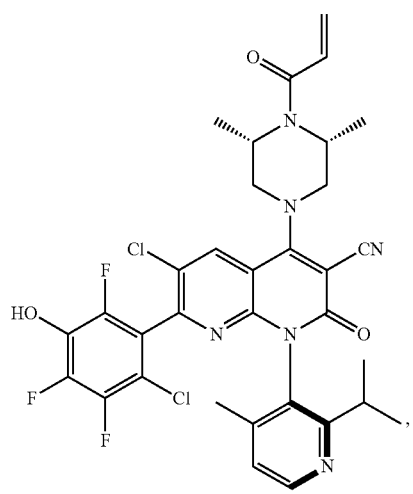
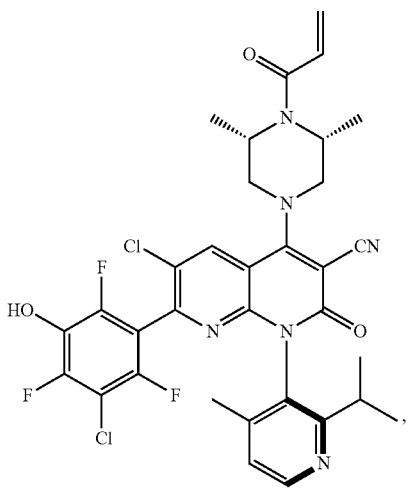

471
-continued
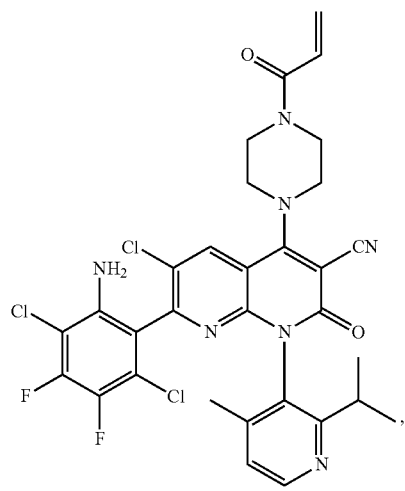
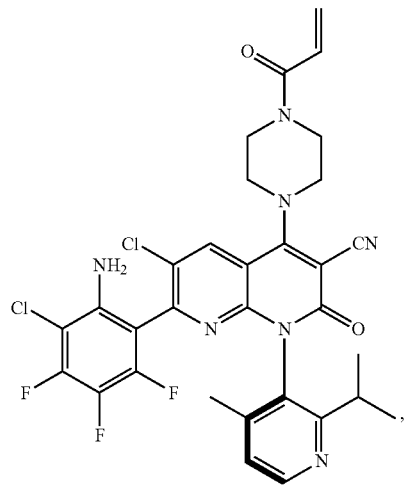
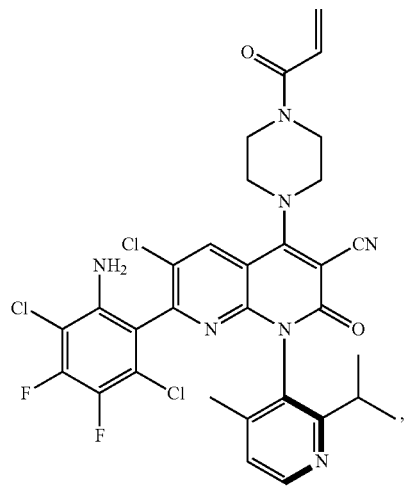
472
-continued
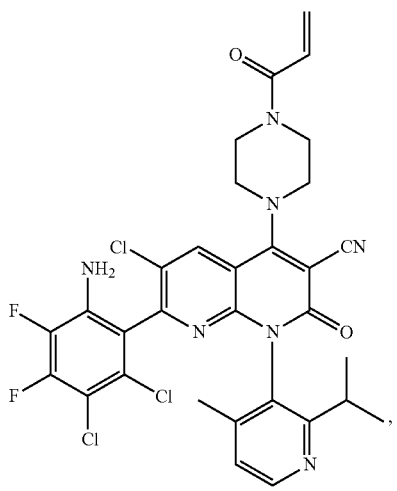
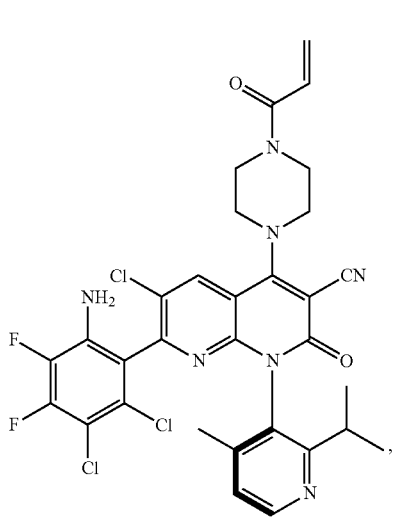
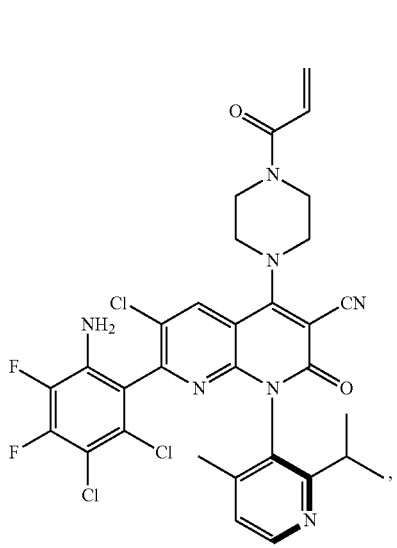

-continued
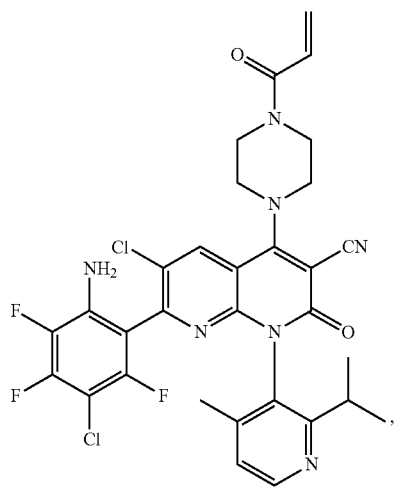
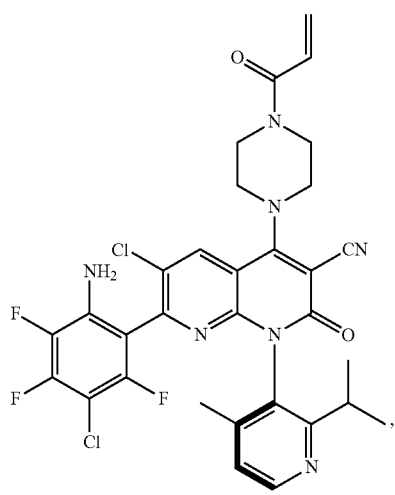
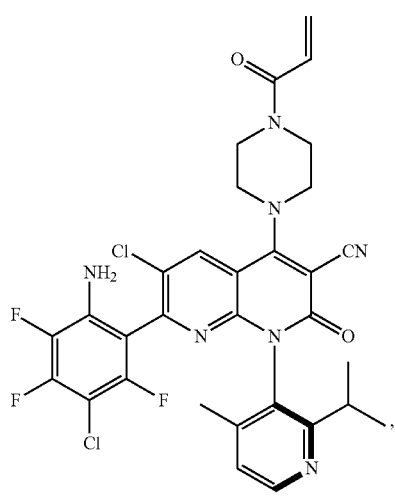
-continued
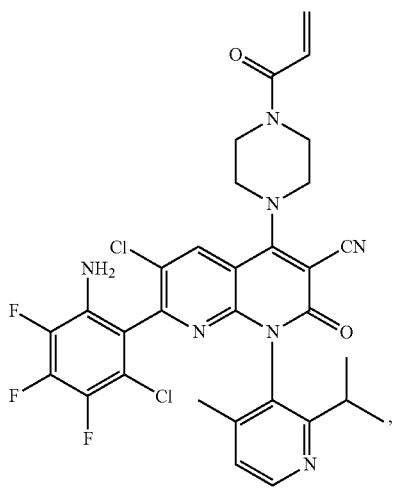
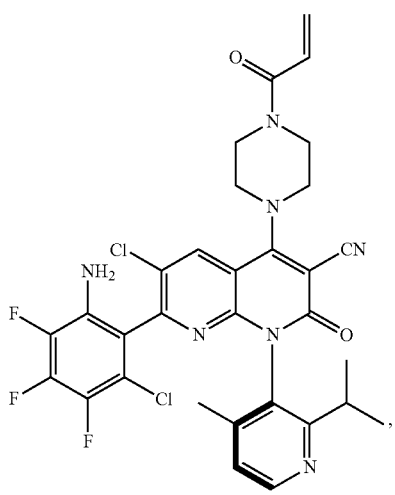
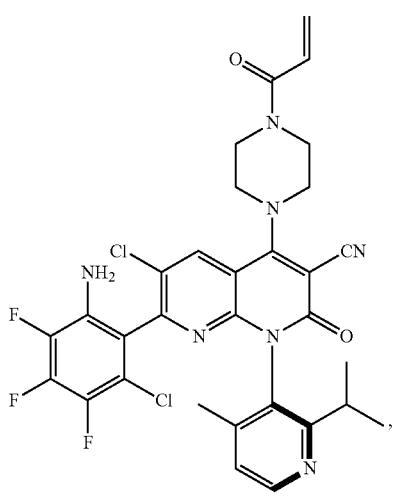

475
-continued
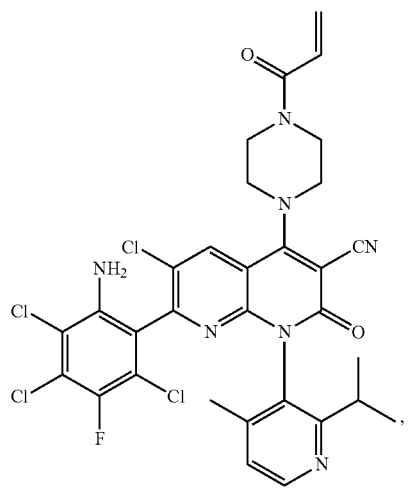
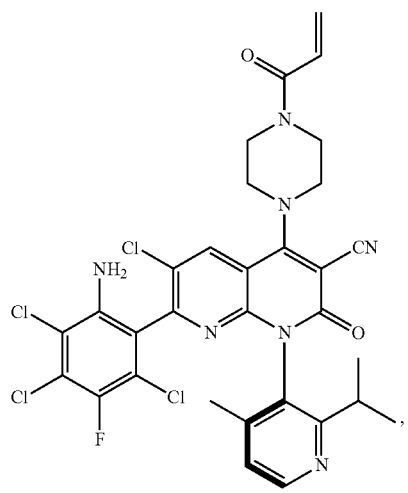
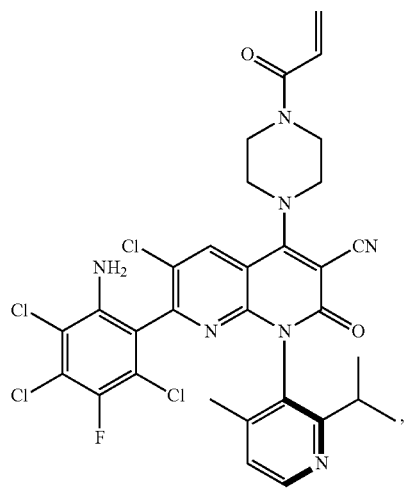
476
-continued
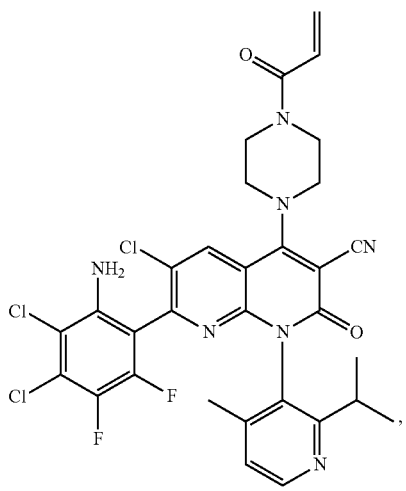
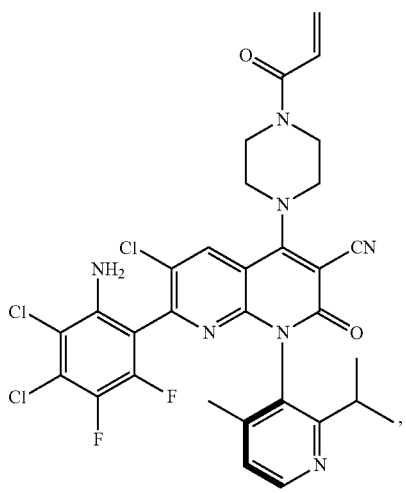
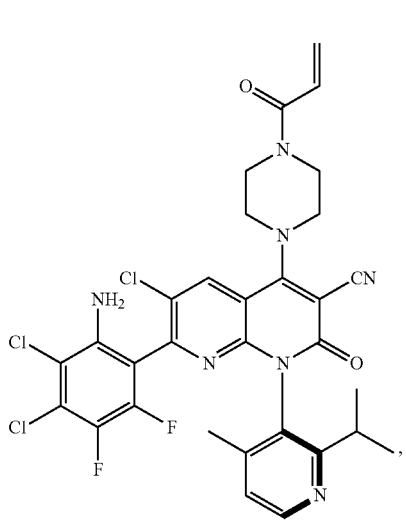

477
-continued
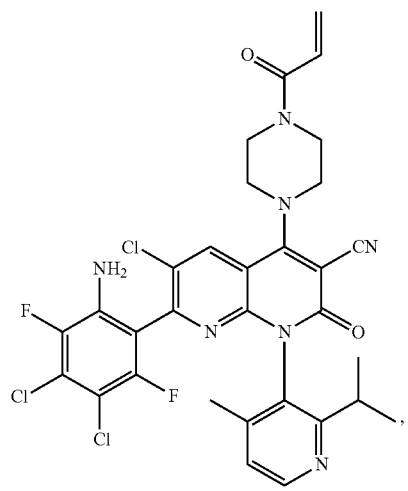
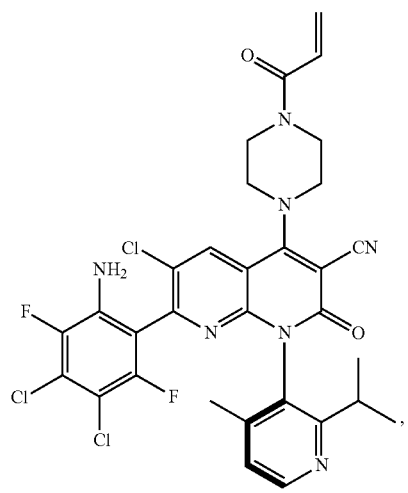
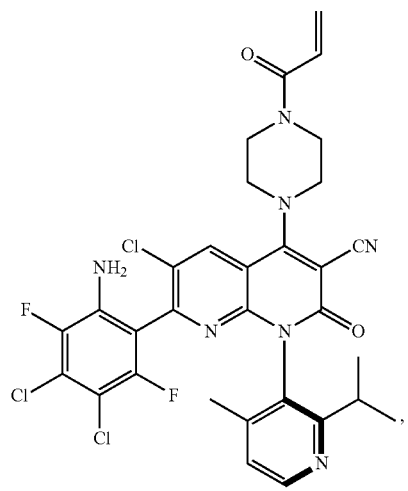
478
-continued
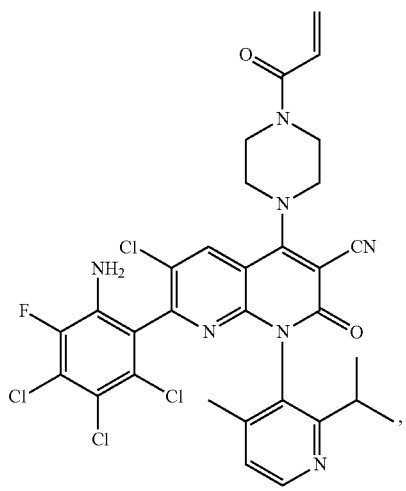
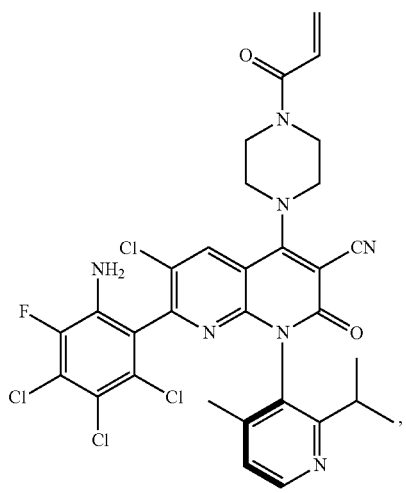
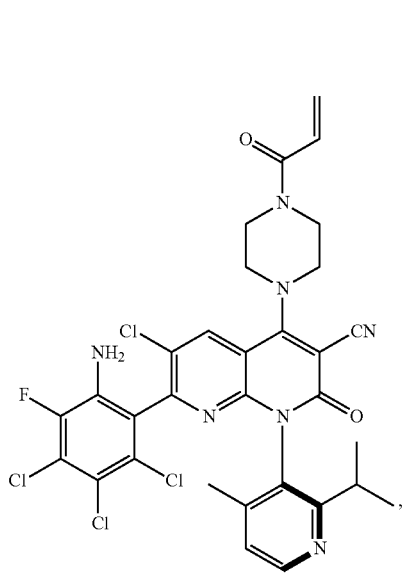

479
-continued
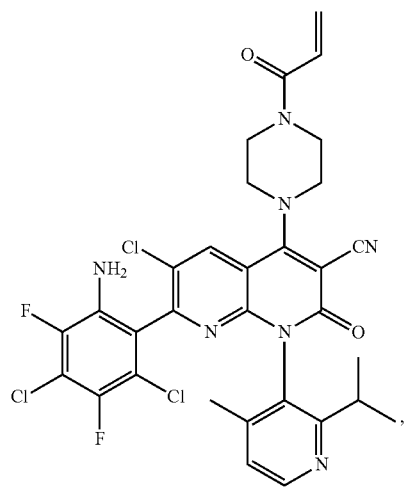
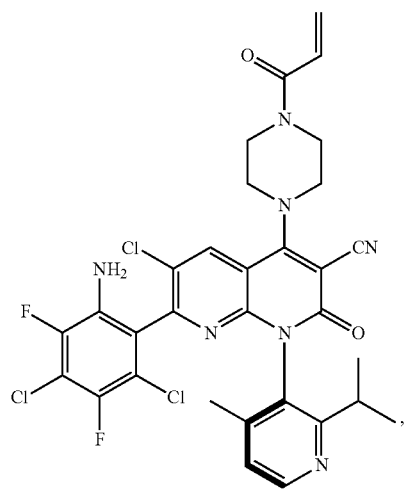
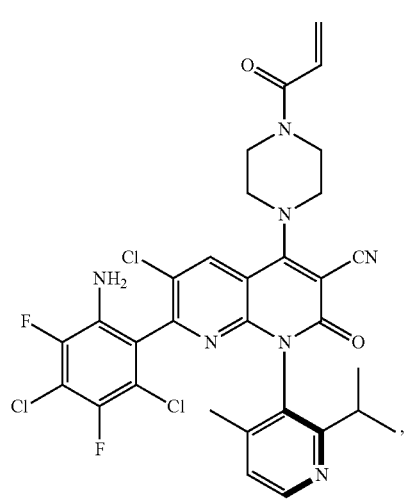
480
-continued
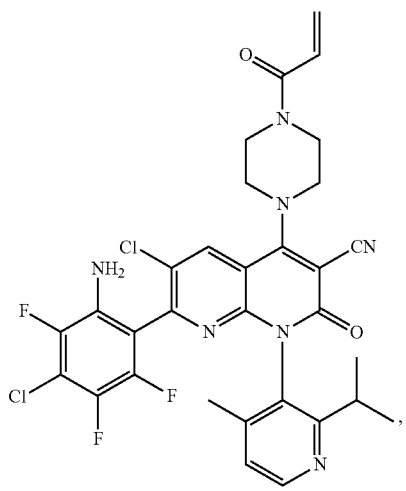
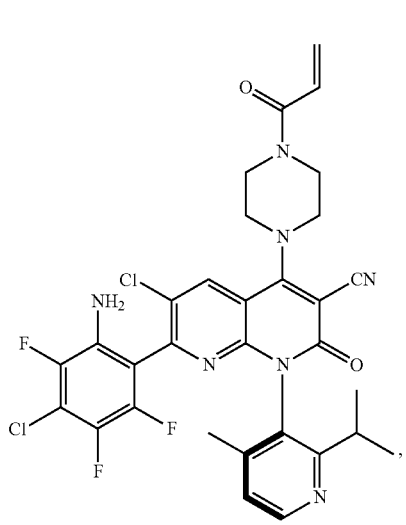
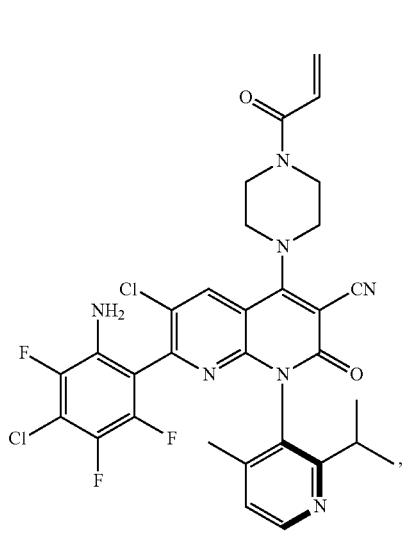

481
-continued
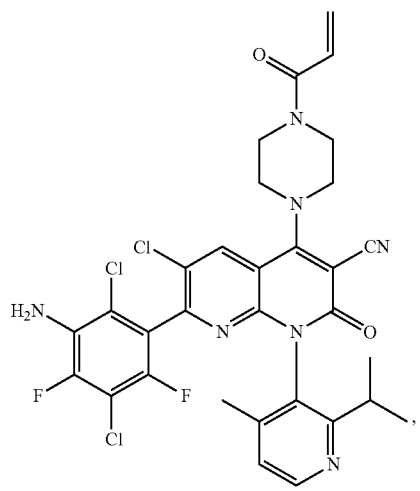
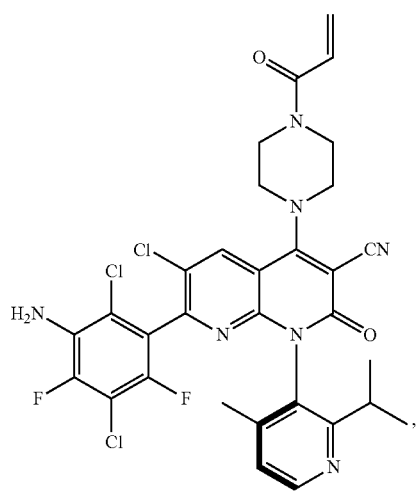
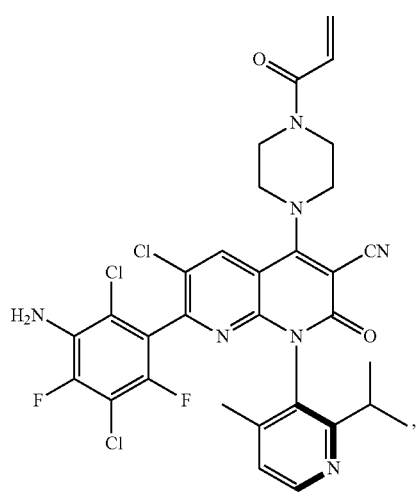
482
-continued
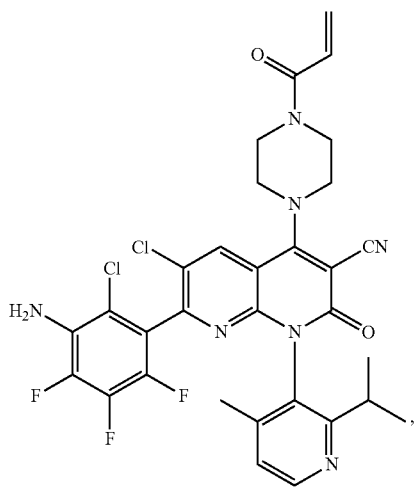
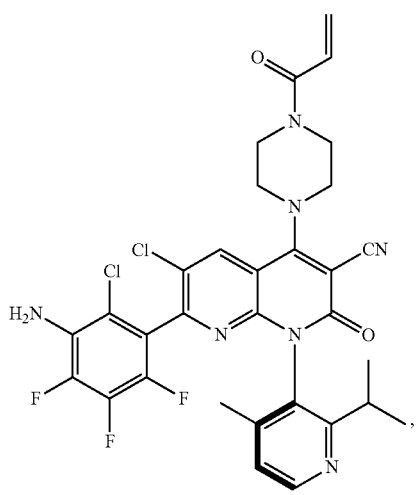
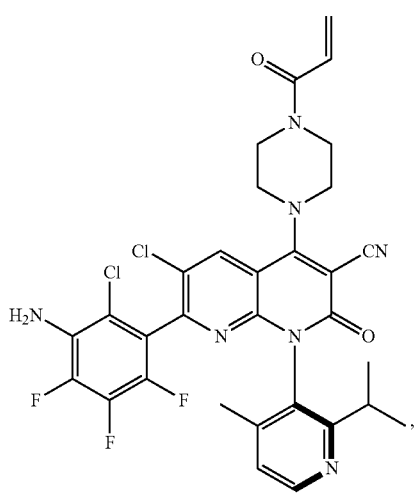

483
-continued
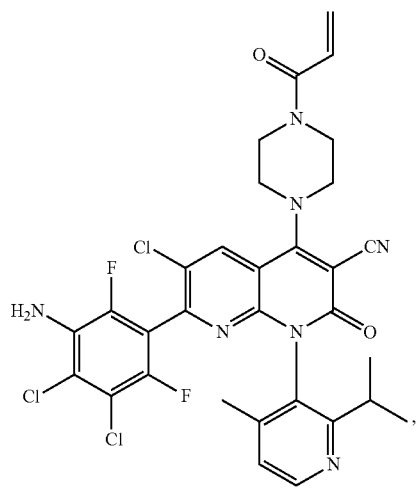
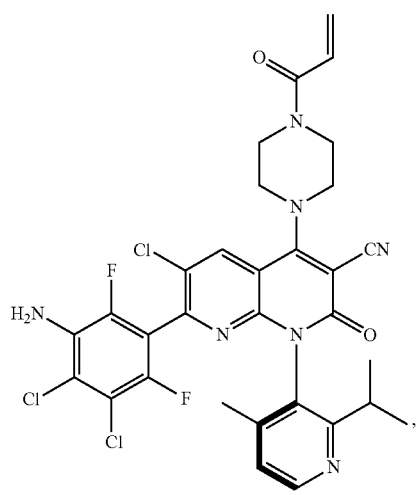
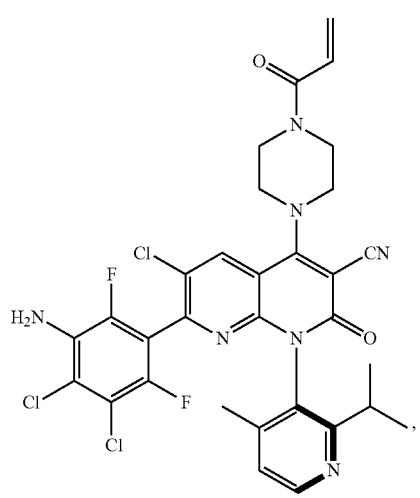
484
-continued
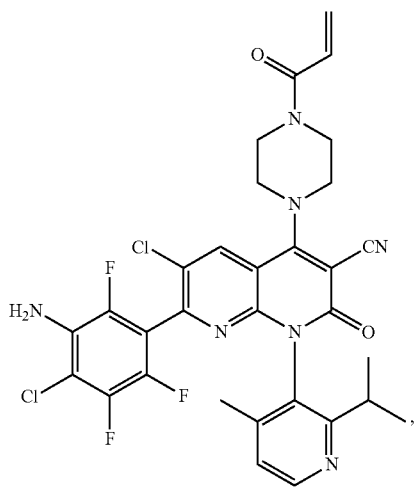
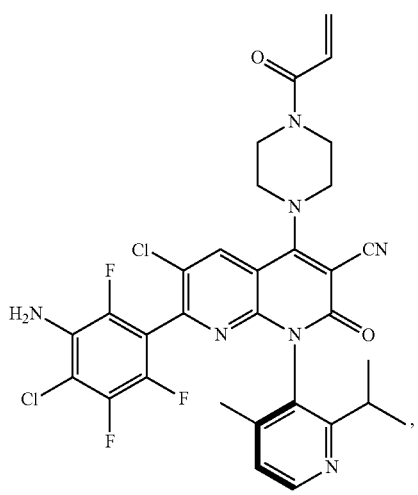
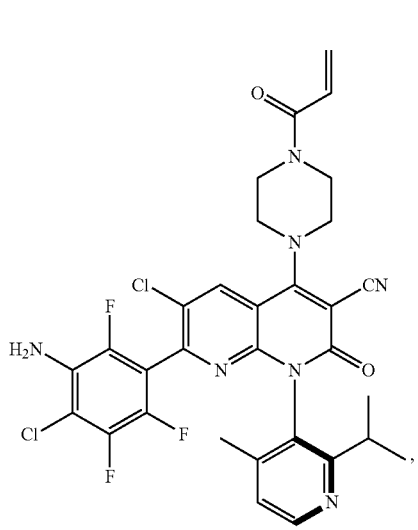

485
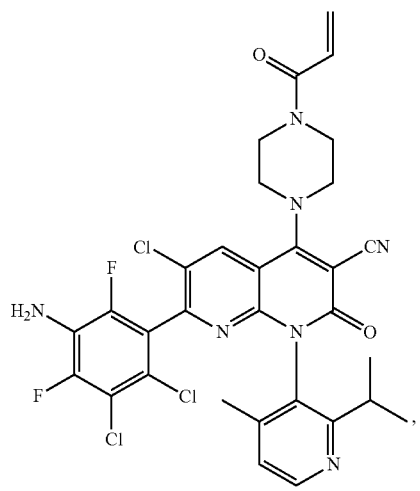
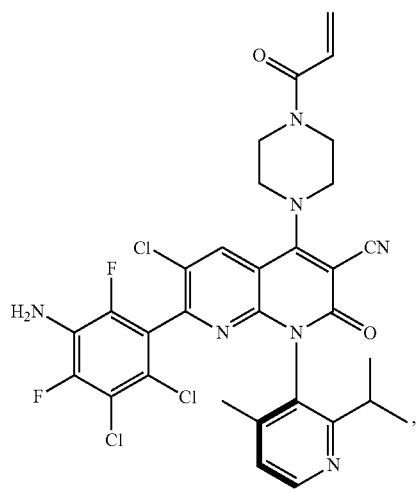
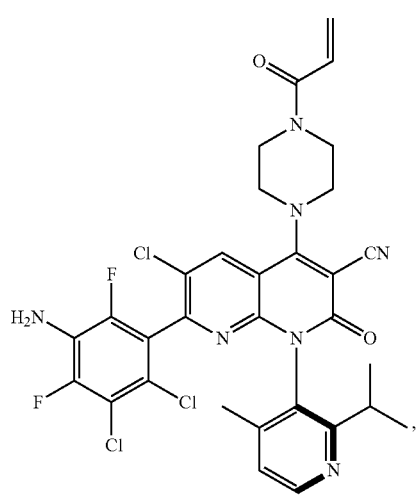
486
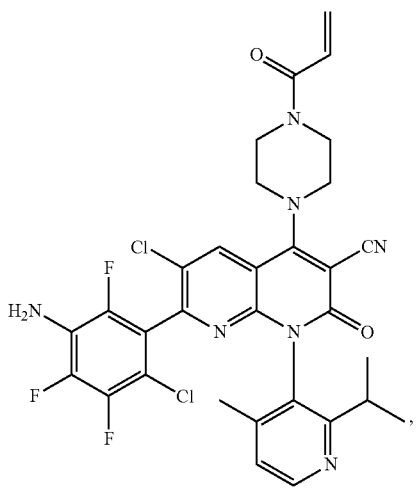
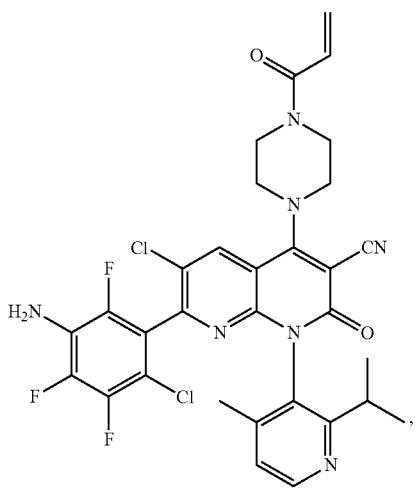
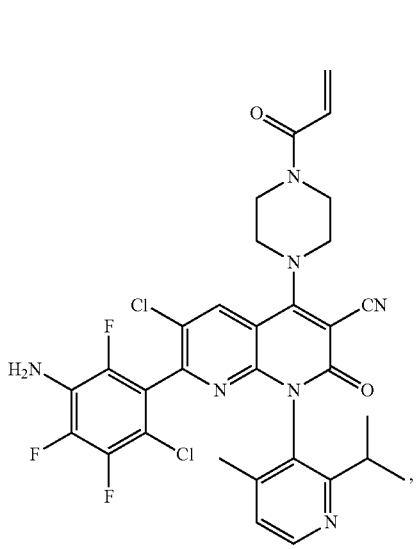

487
-continued
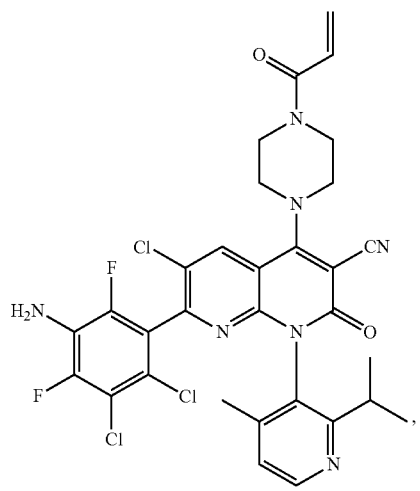
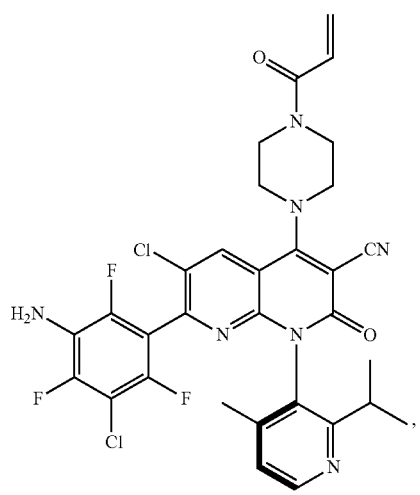
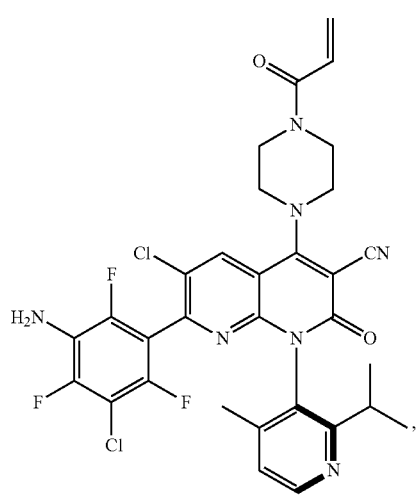
488
-continued
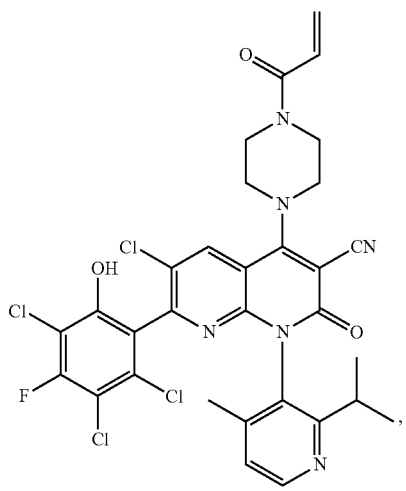
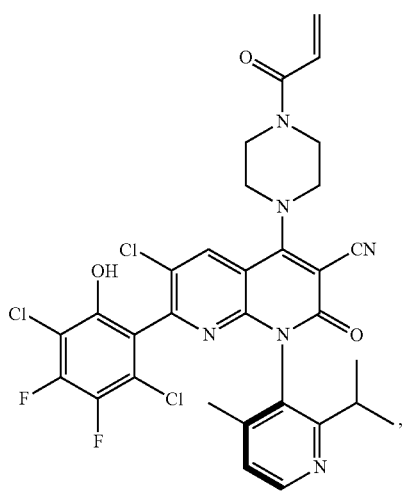
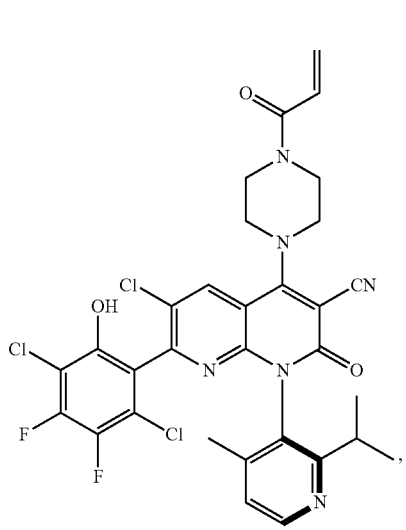

489
-continued
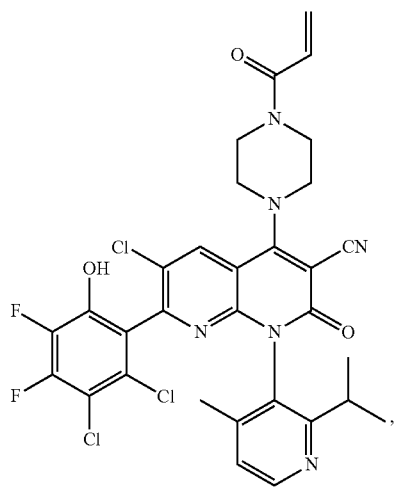
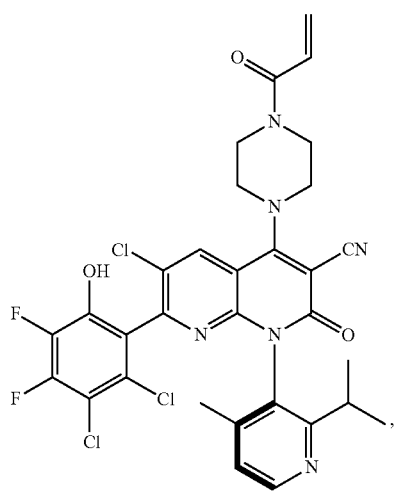
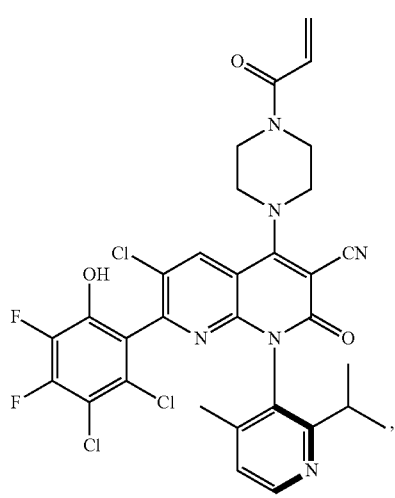
490
-continued
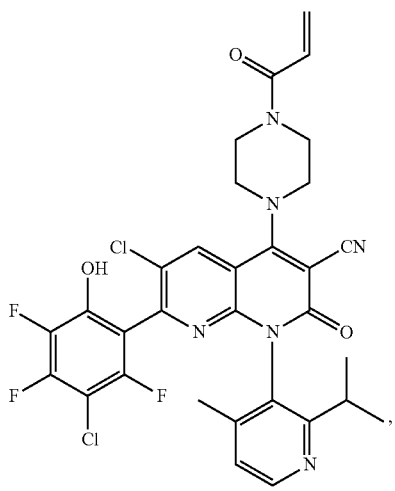
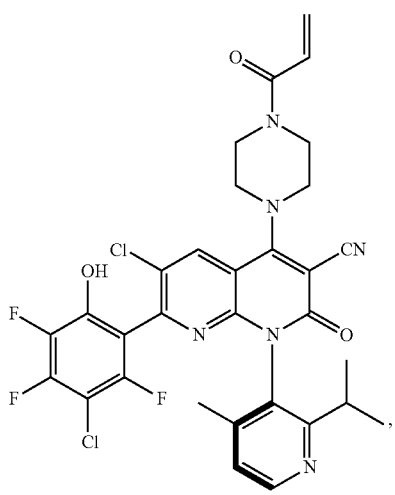
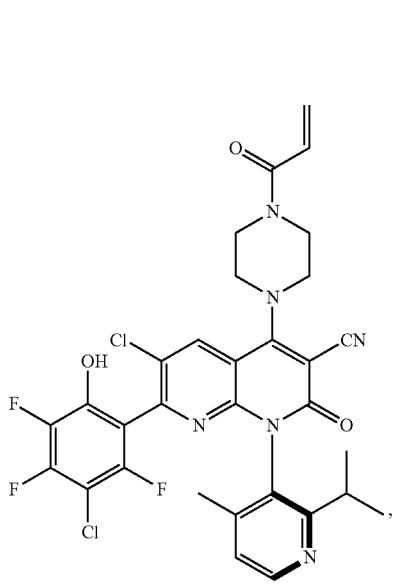

491
-continued
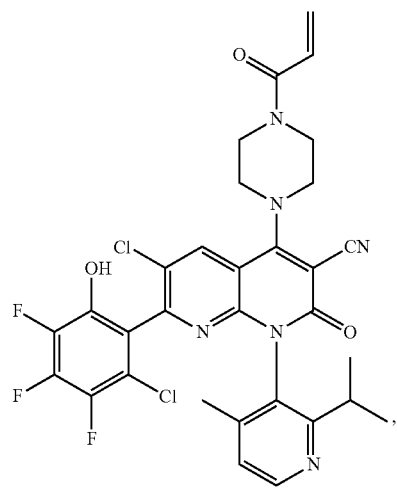
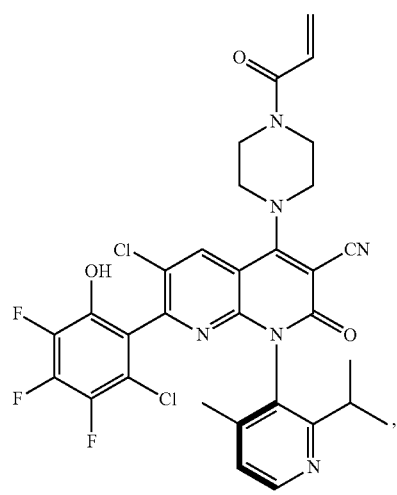
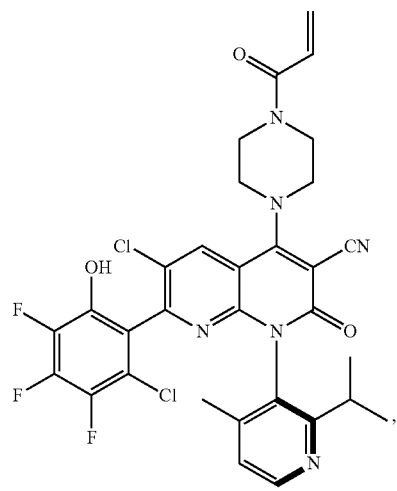
492
-continued
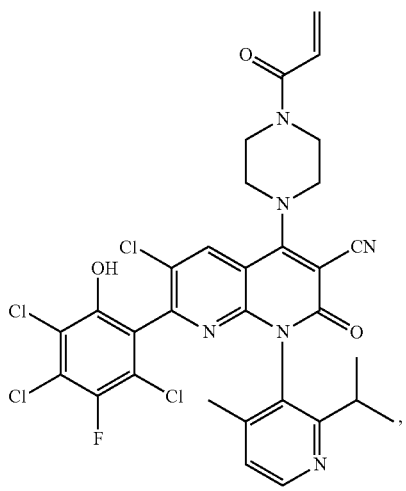
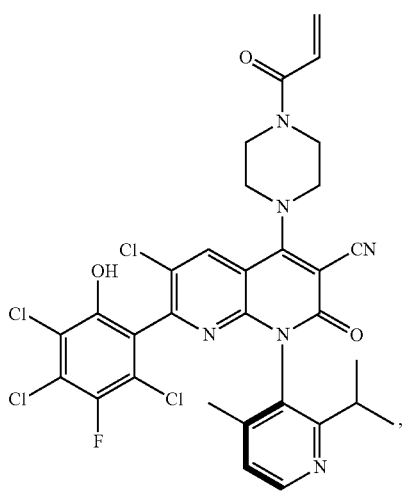
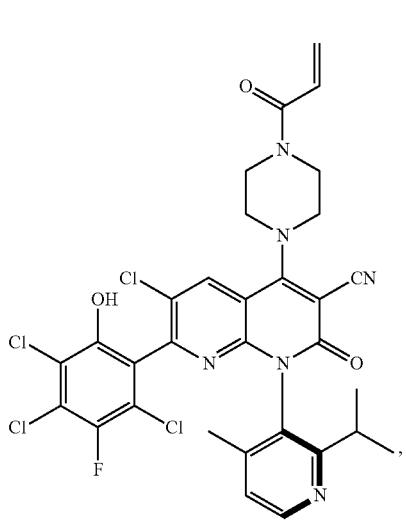

493
-continued
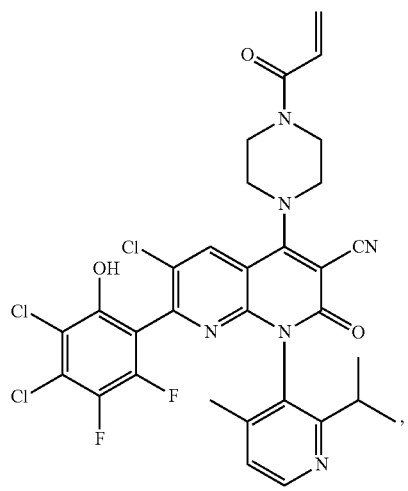
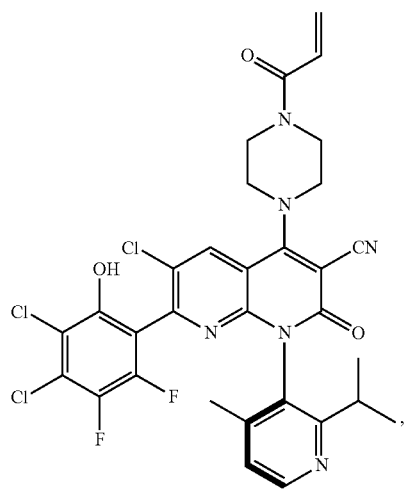
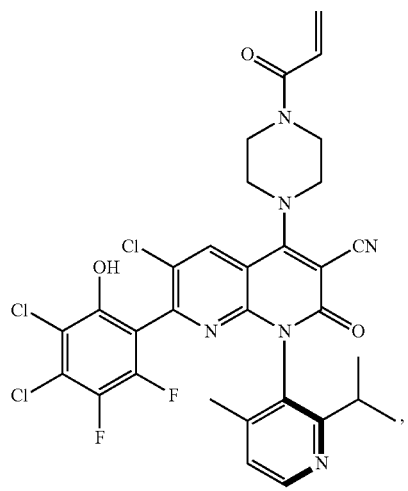
494
-continued
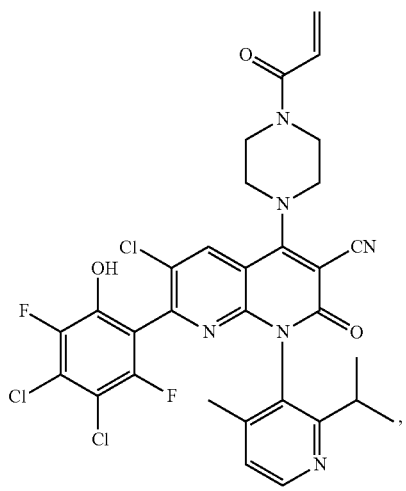
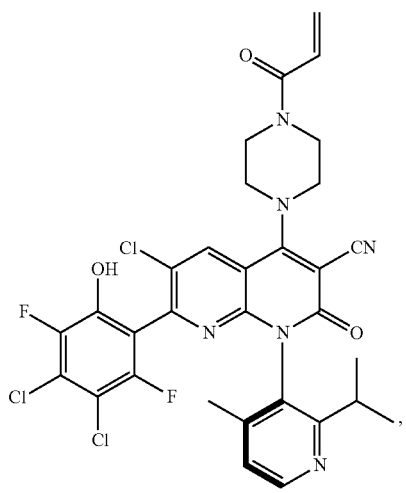
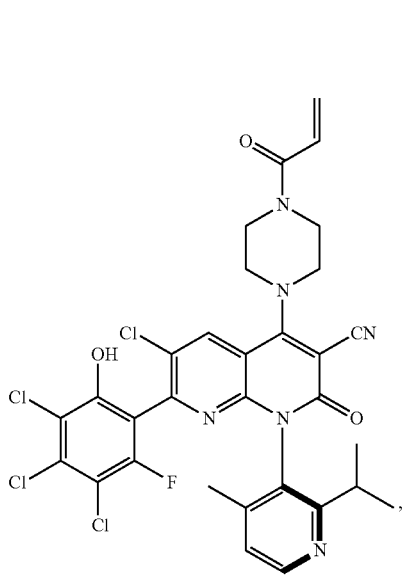

495
-continued
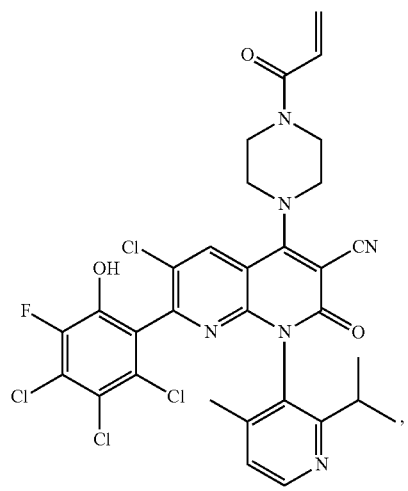
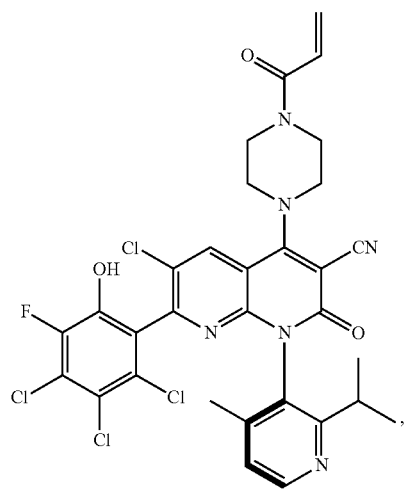
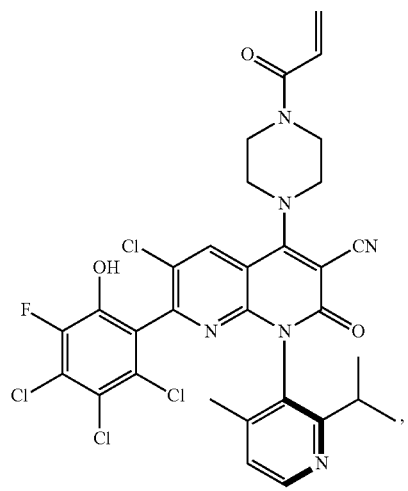
496
-continued
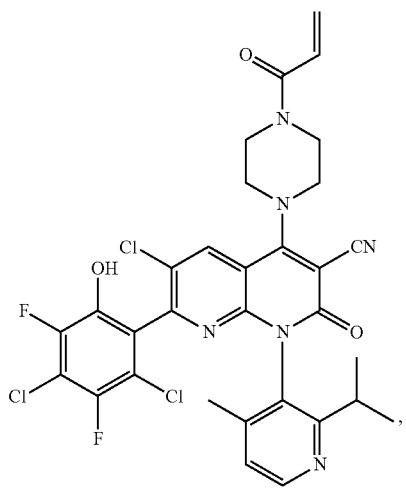
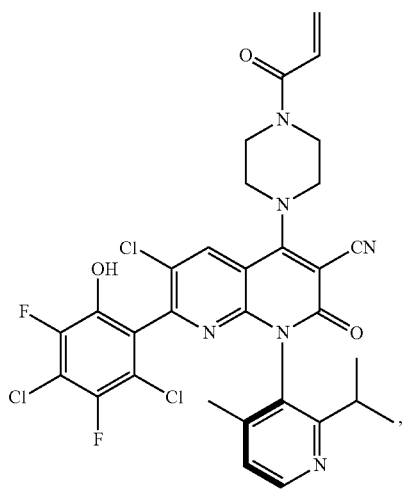
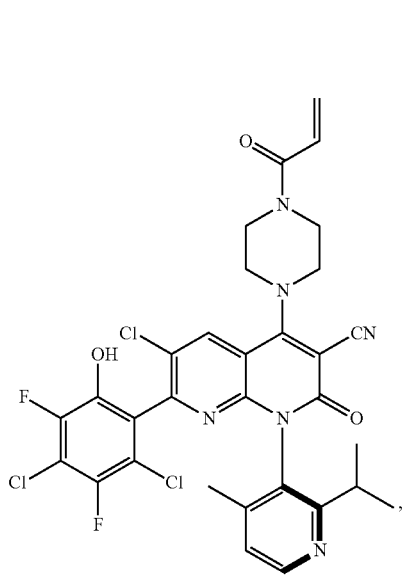

497
-continued
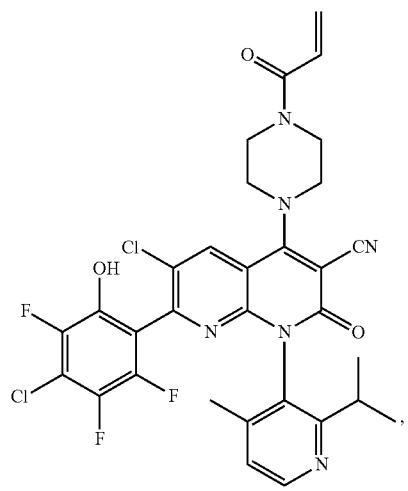
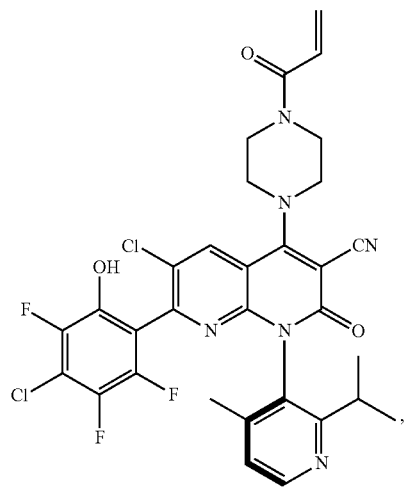
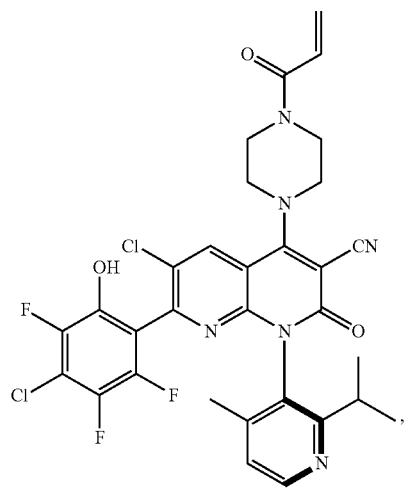
498
-continued
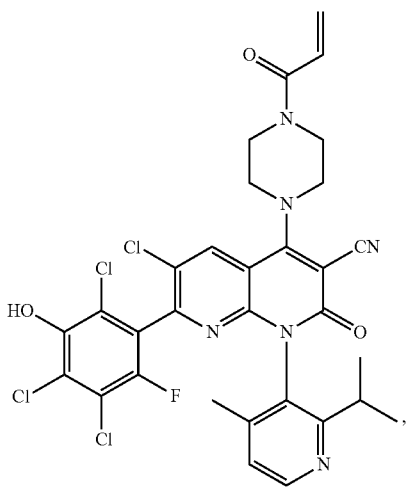
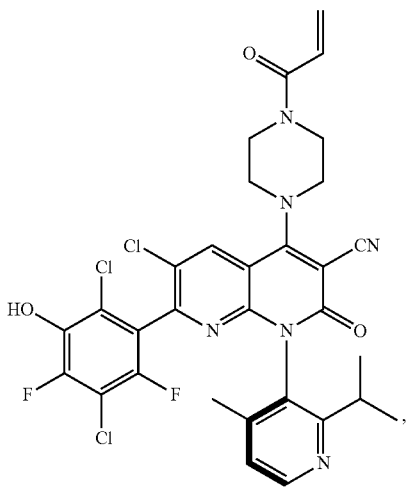
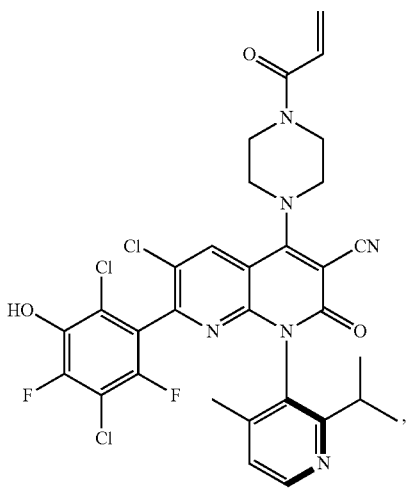

499
-continued
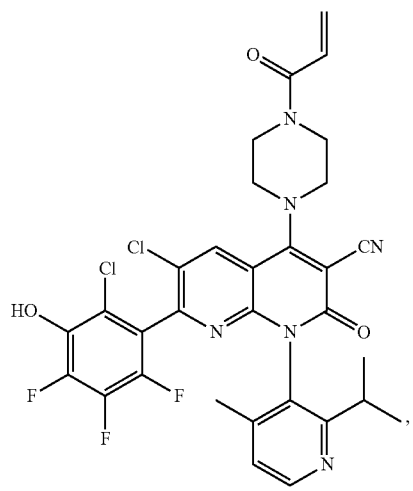
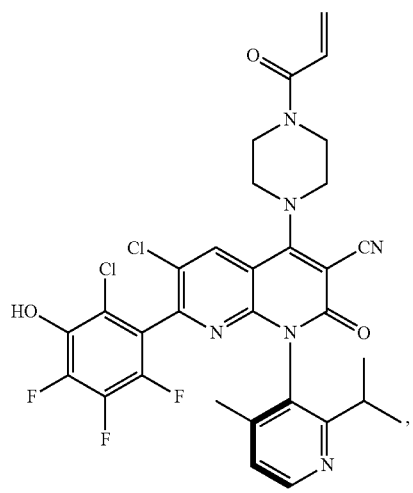
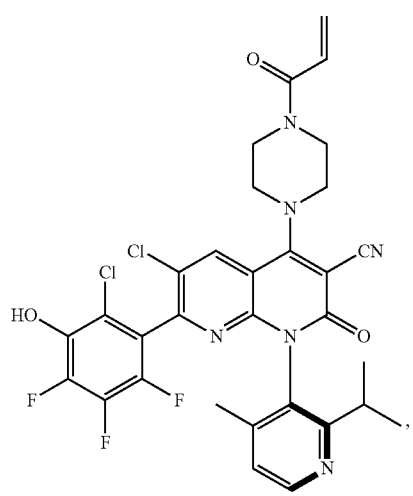
500
-continued
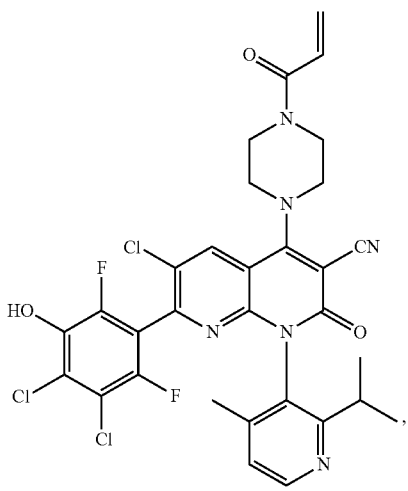
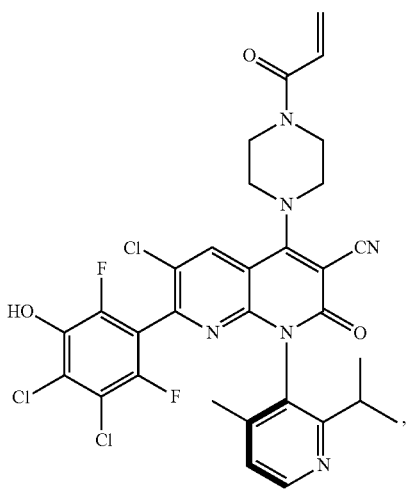
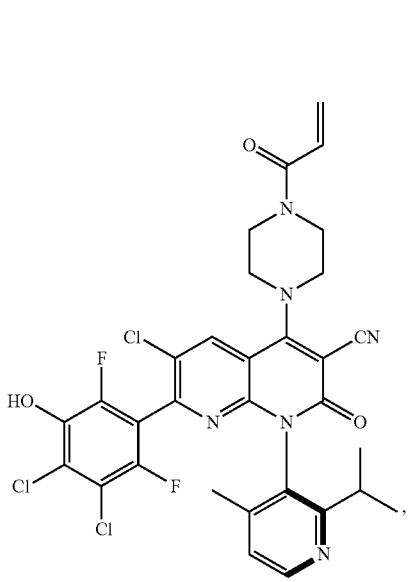

501
-continued
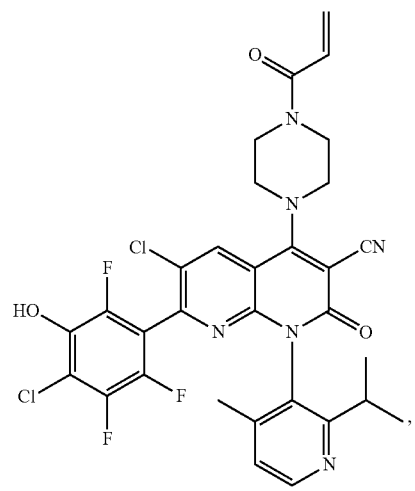
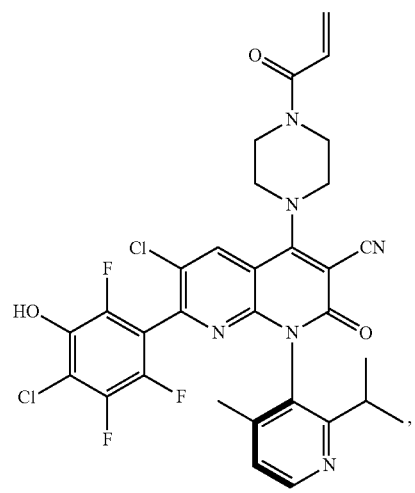
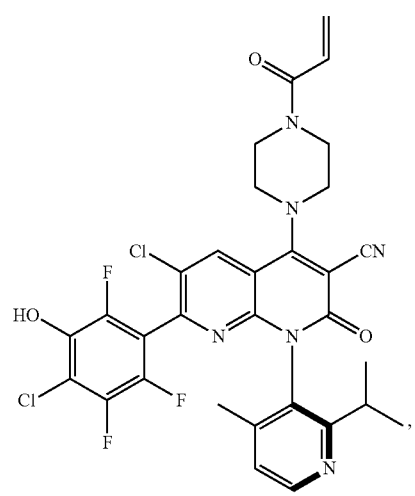
502
-continued
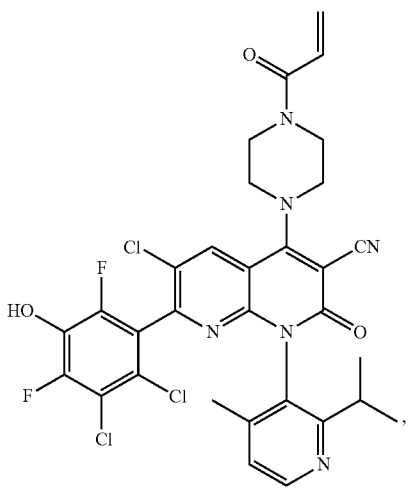
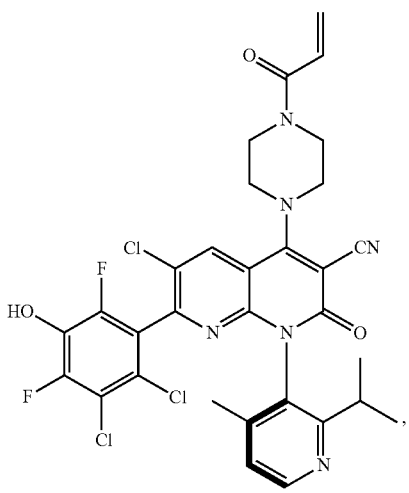
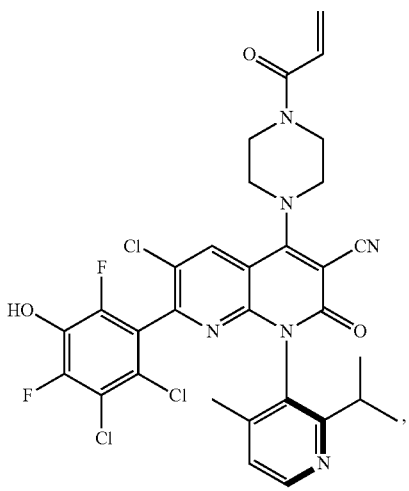

503
-continued
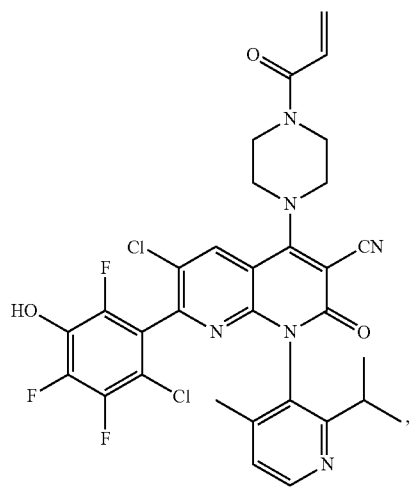
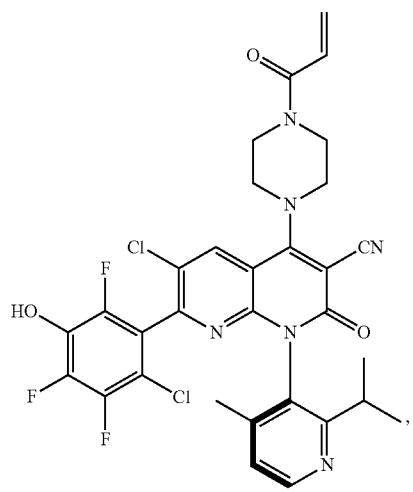
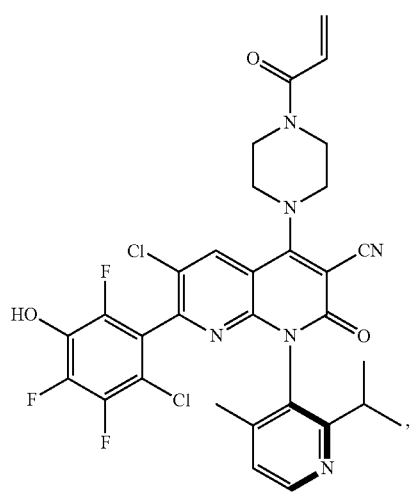
504
-continued
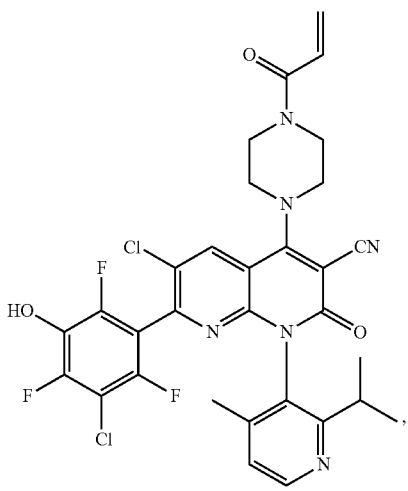
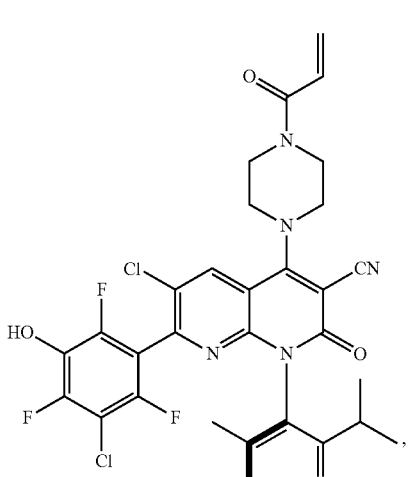
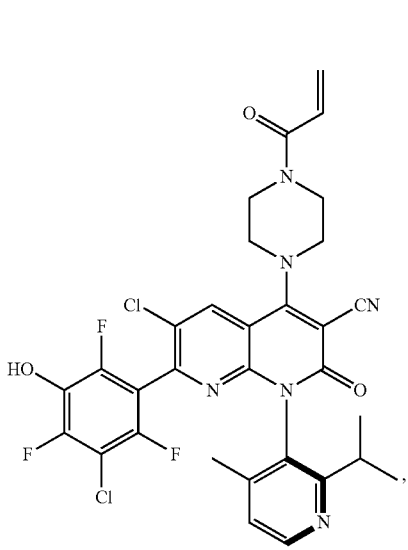

505
-continued
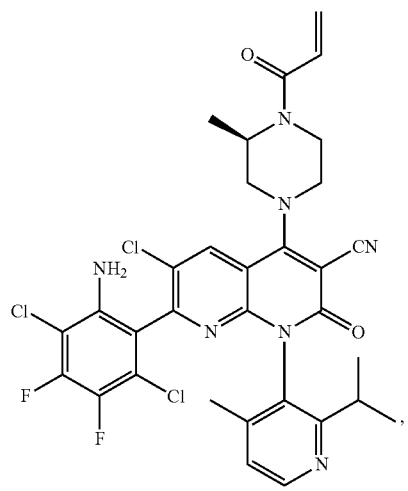
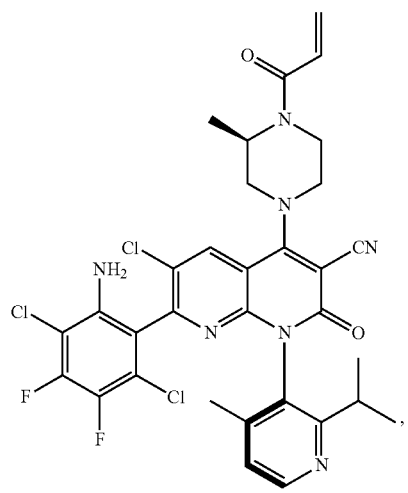
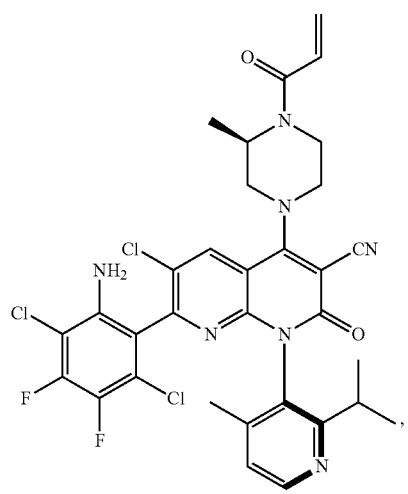
506
-continued
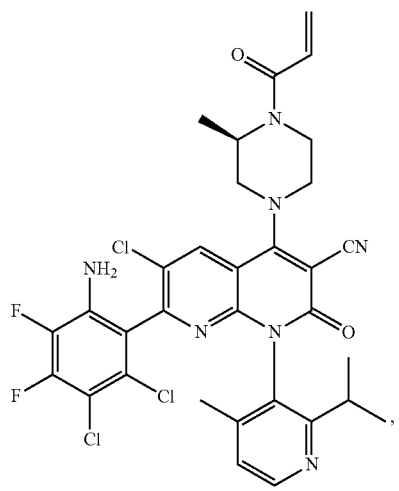
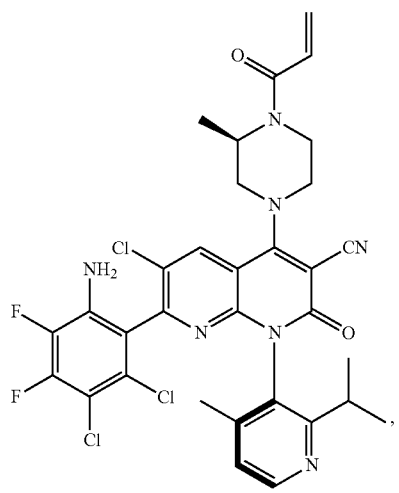
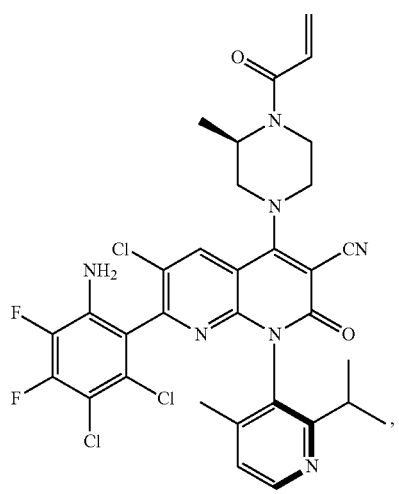

507
-continued
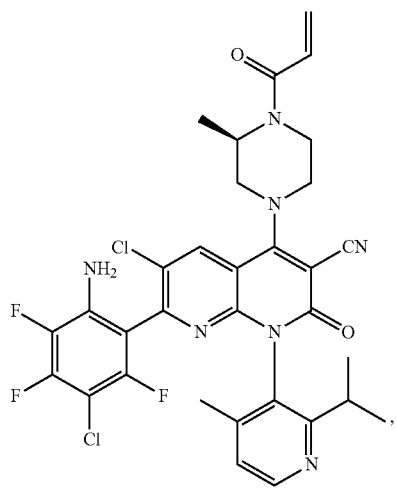
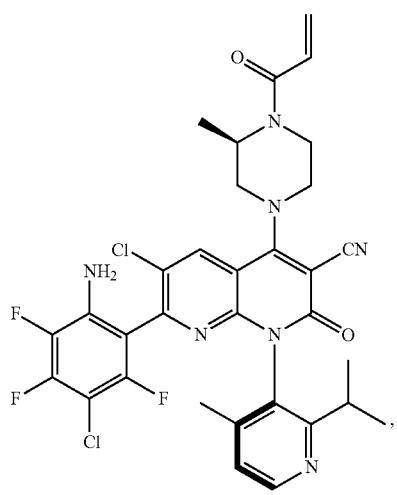
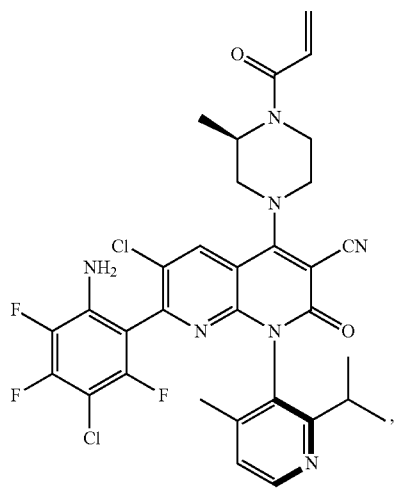
508
-continued
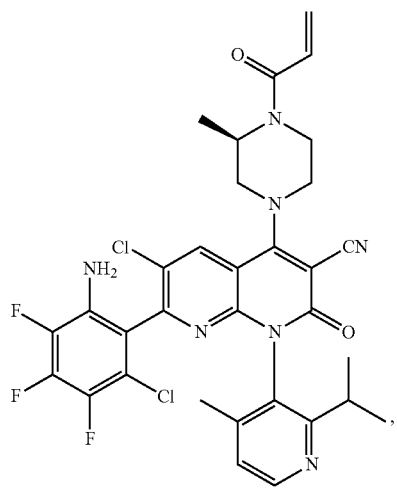
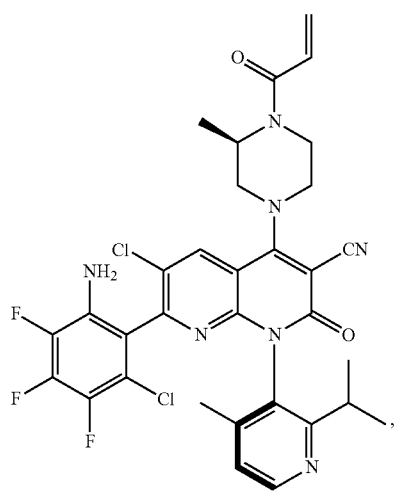
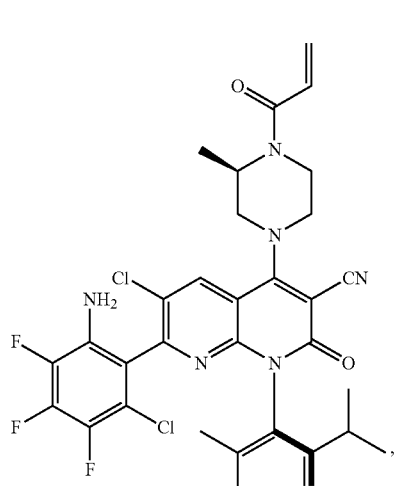

509
-continued
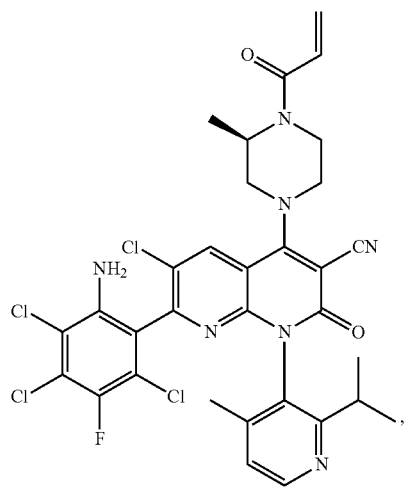
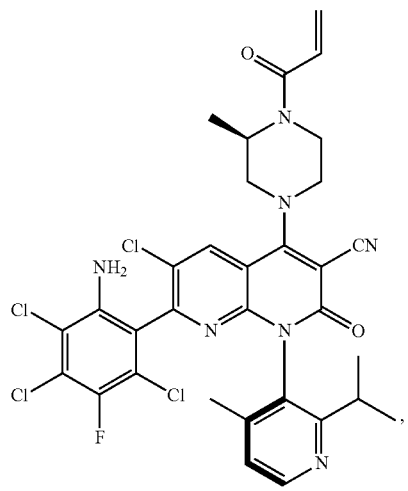
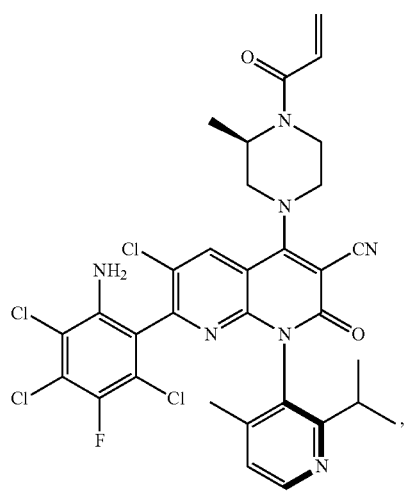
510
-continued
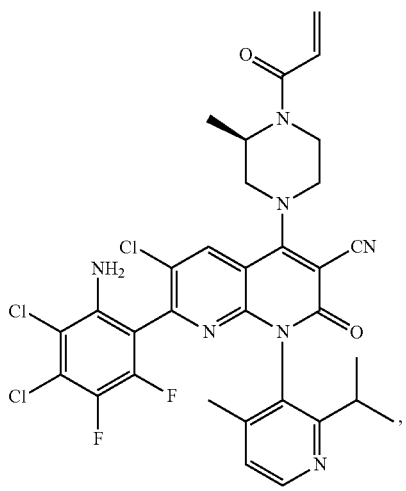
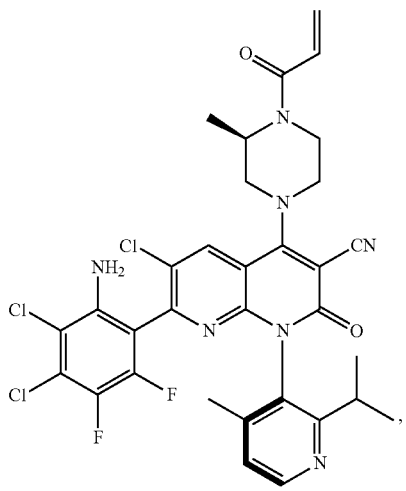
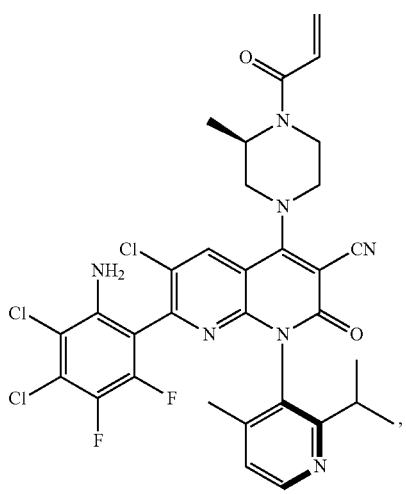

511
-continued
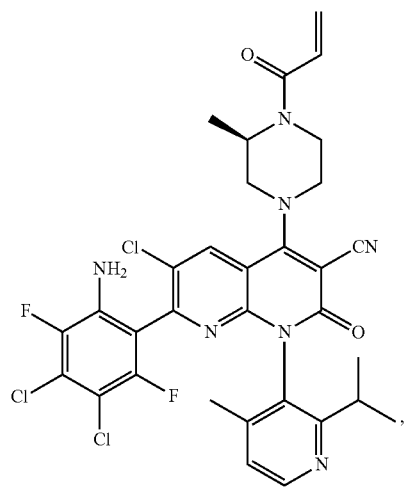
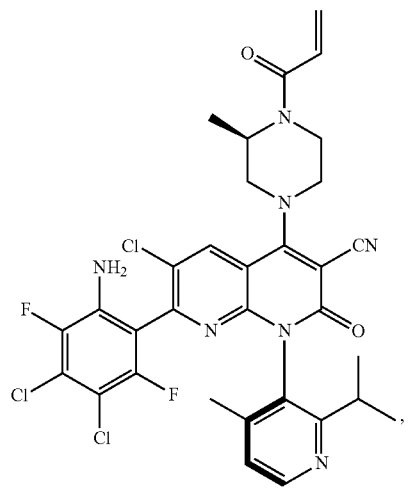
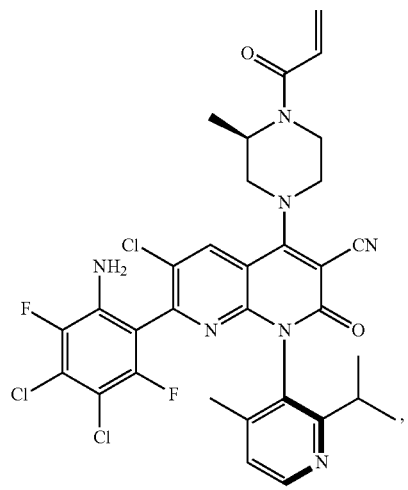
512
-continued
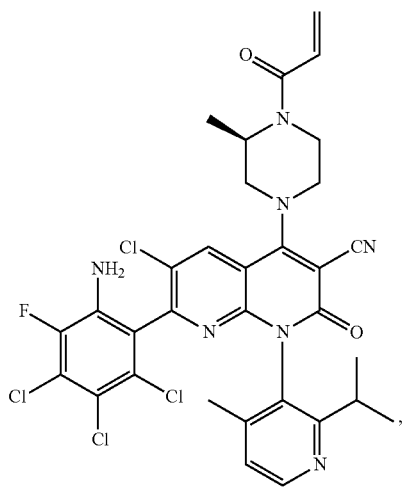
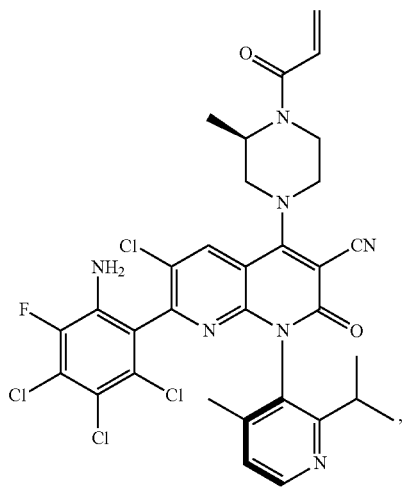
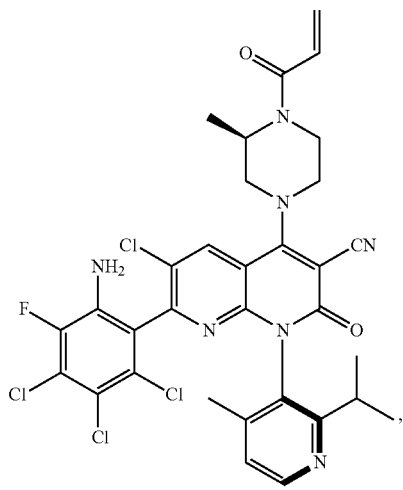

513
-continued
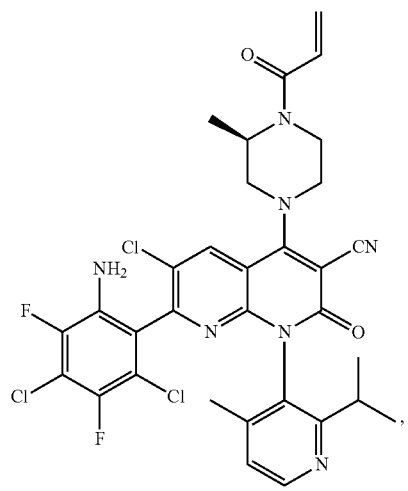
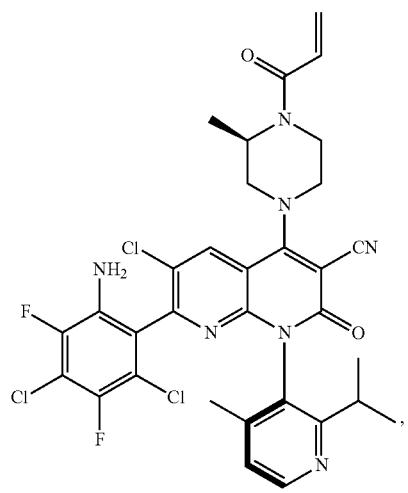
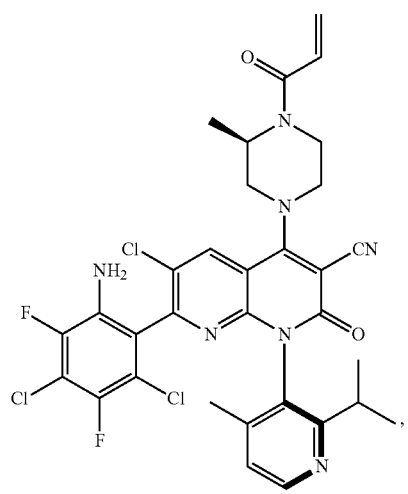
514
-continued
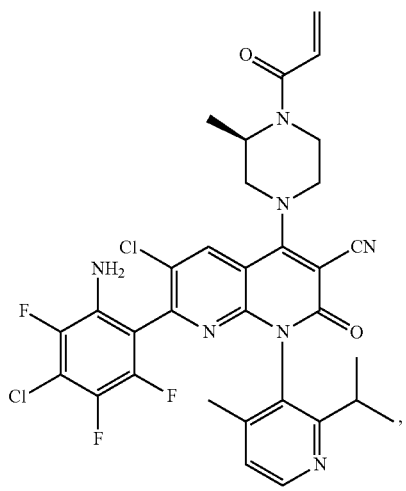
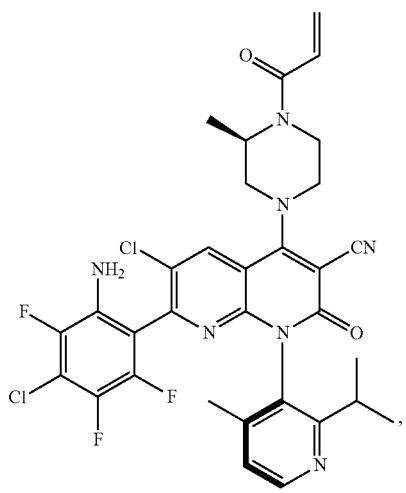
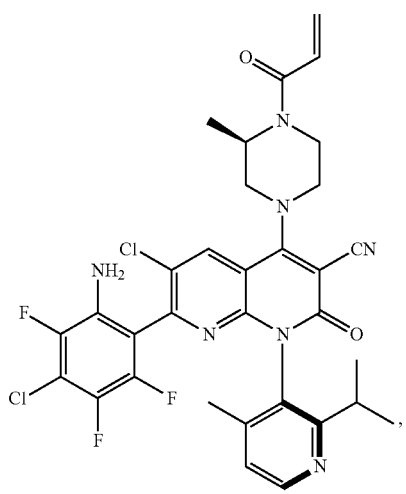

515
-continued
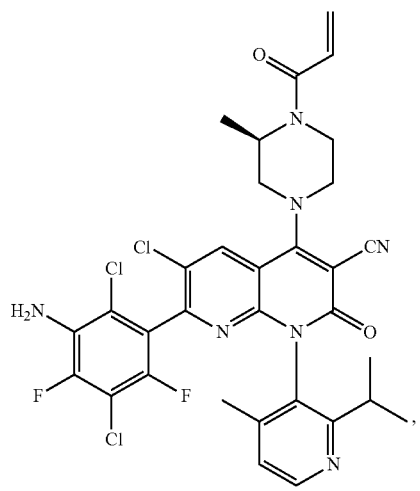
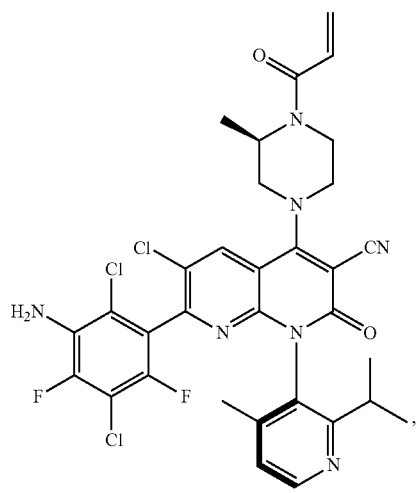
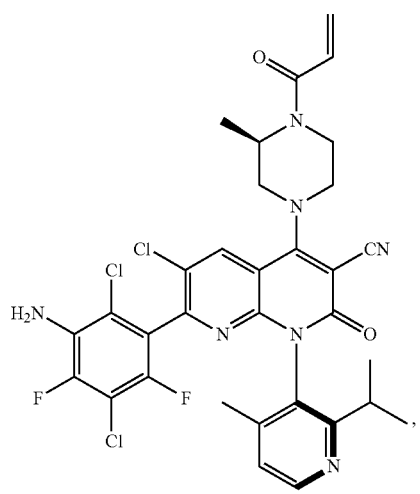
516
-continued
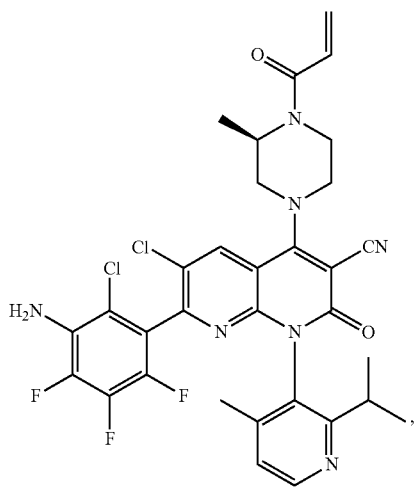
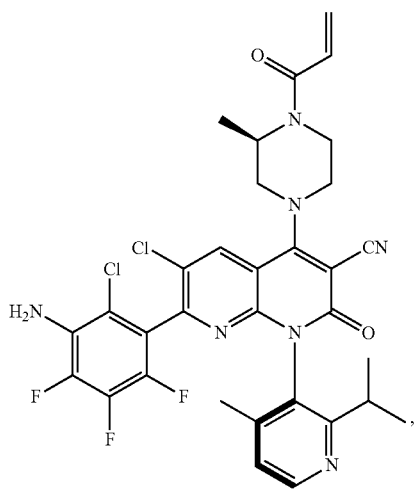
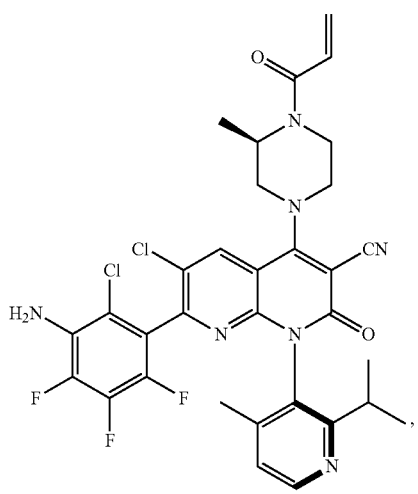

517
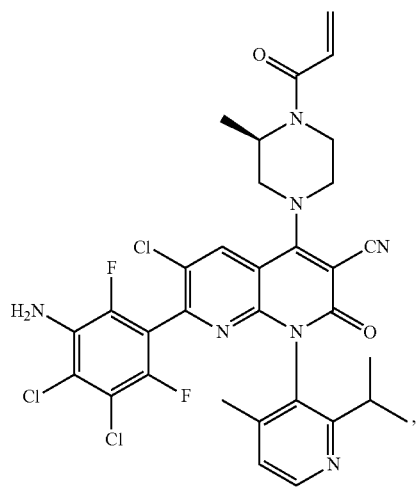
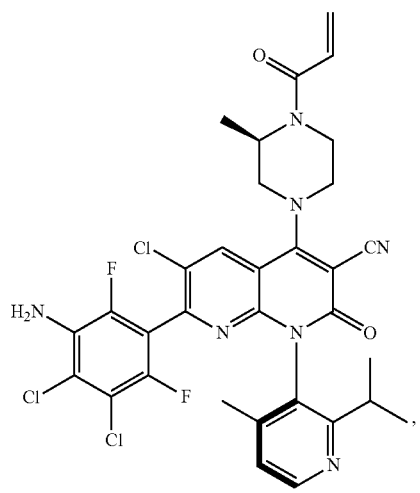
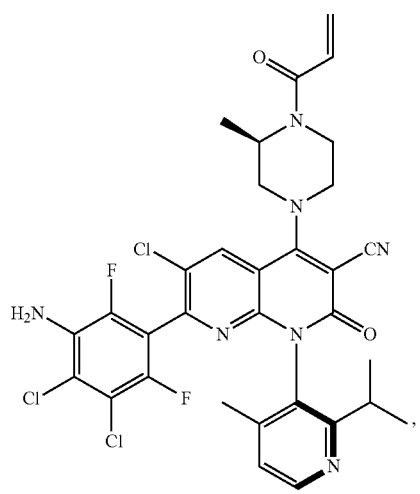
518
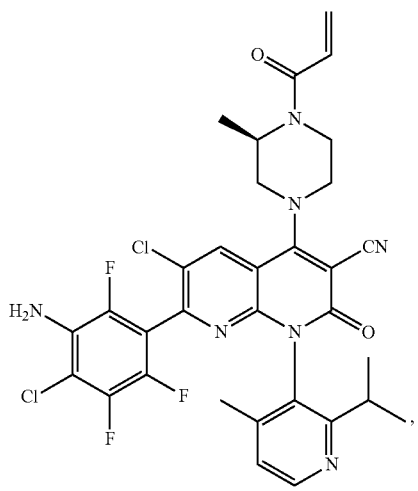
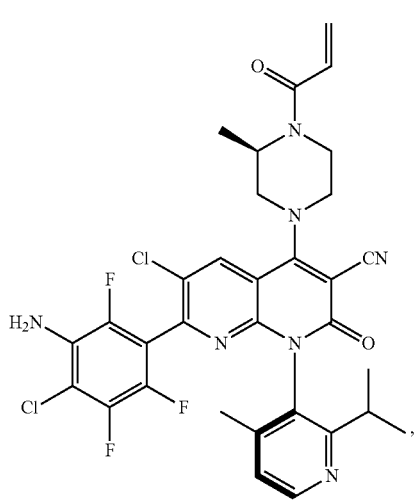
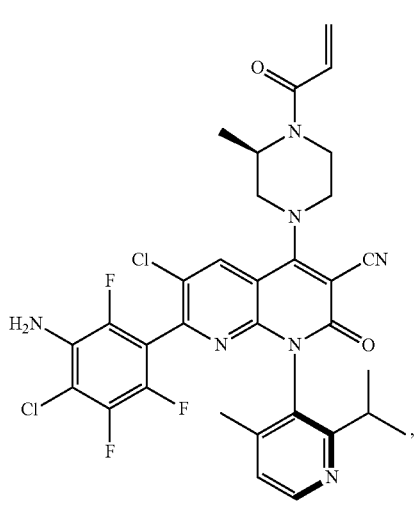

519
-continued
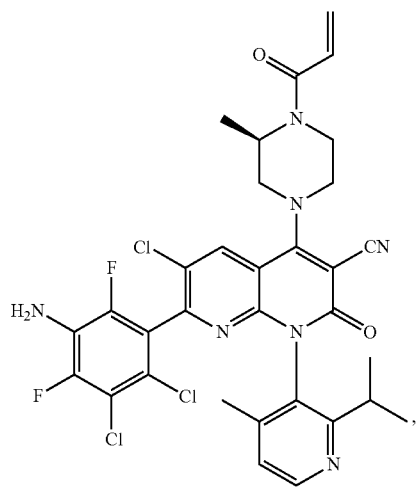
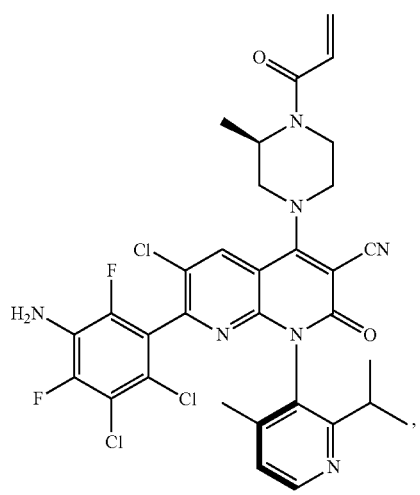
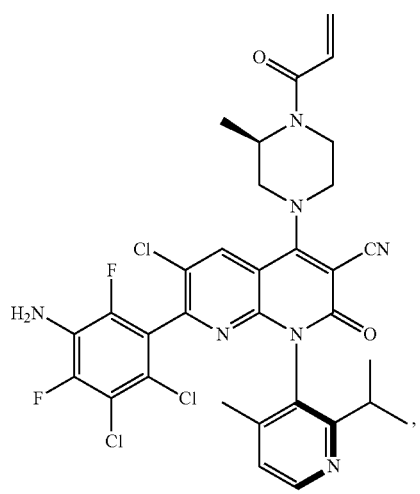
520
-continued
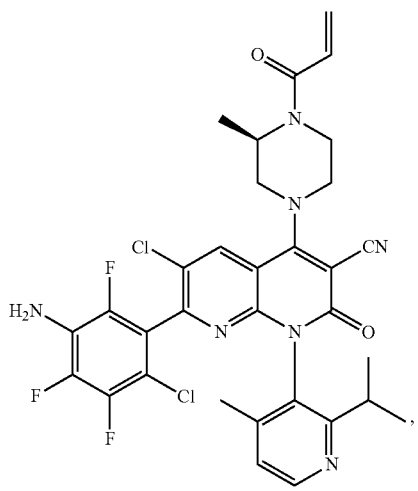
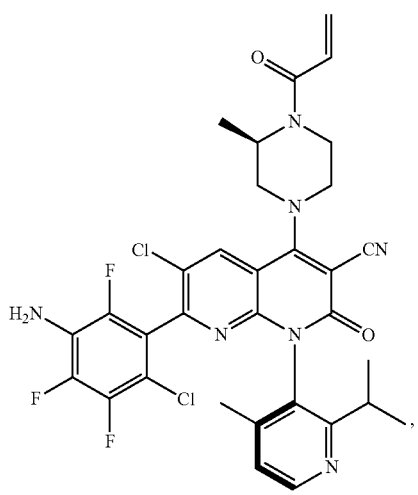
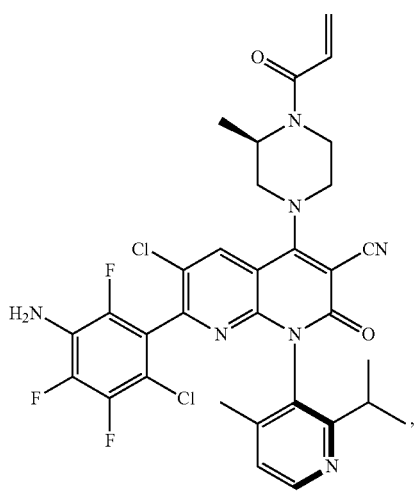

521
-continued
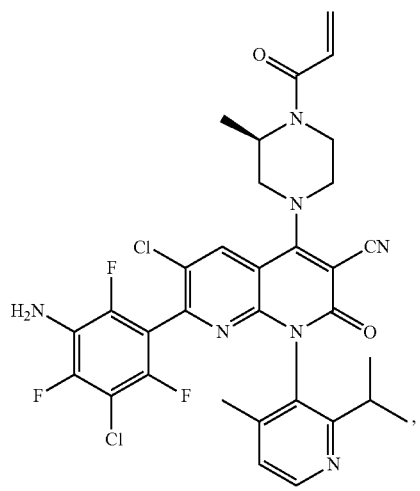
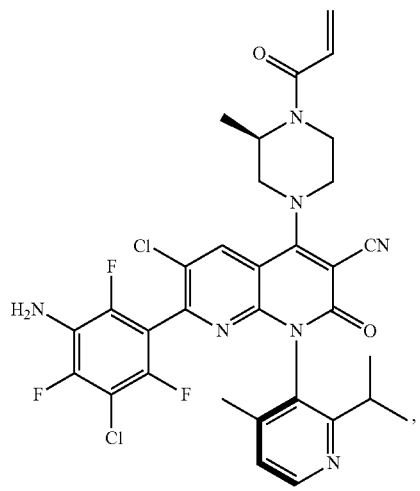
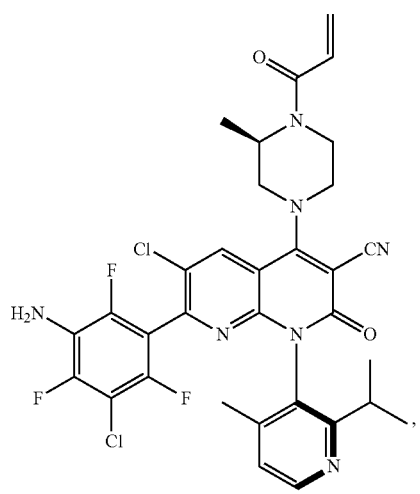
522
-continued
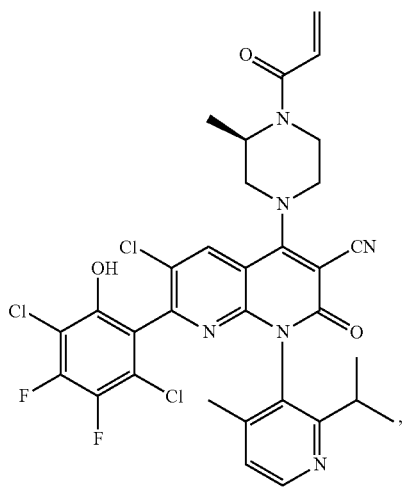
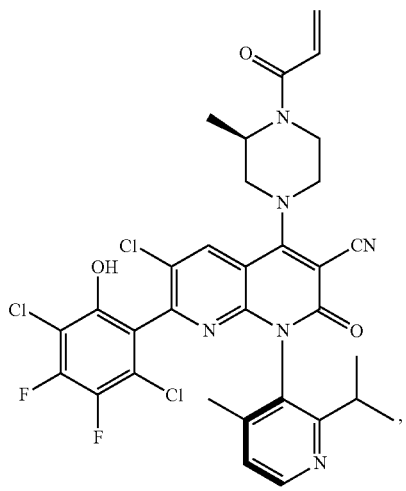
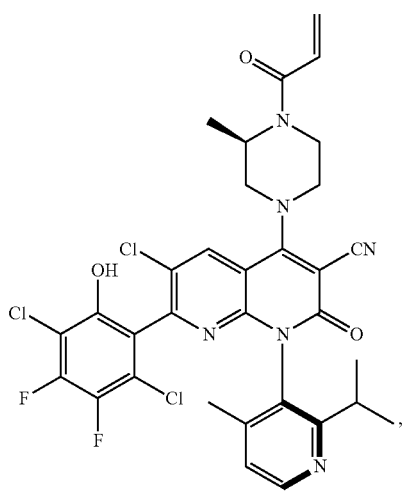

523
-continued
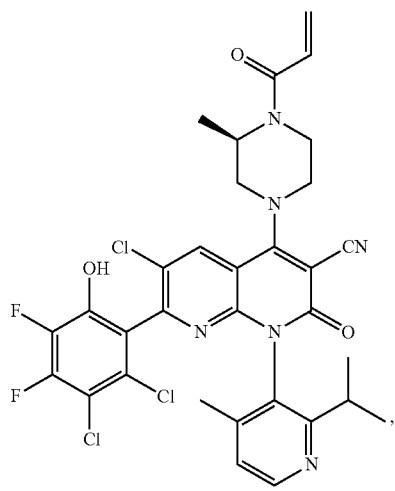
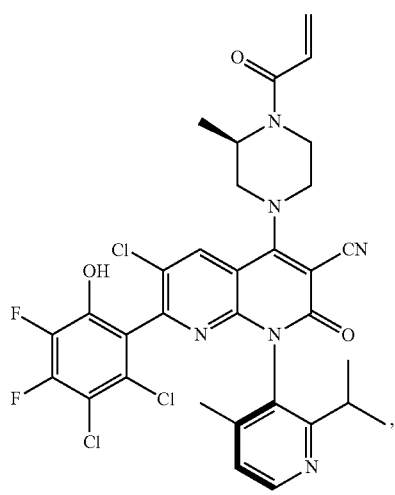
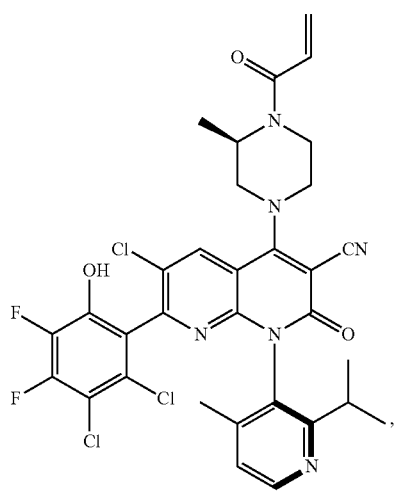
524
-continued
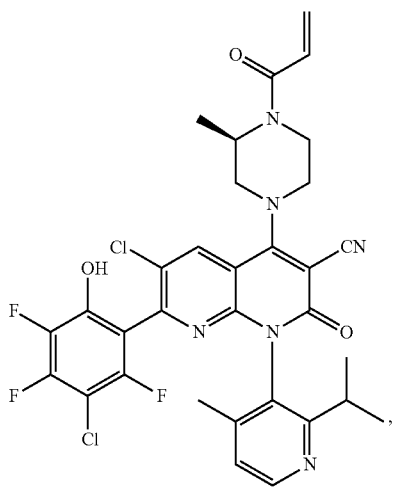
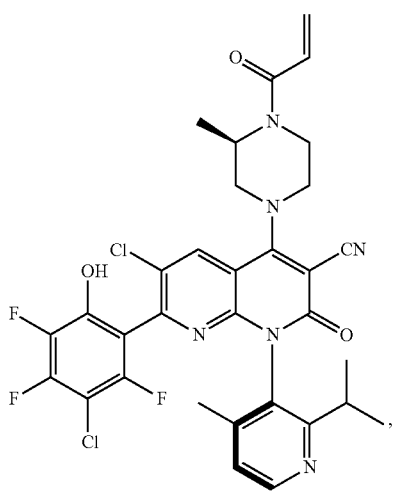
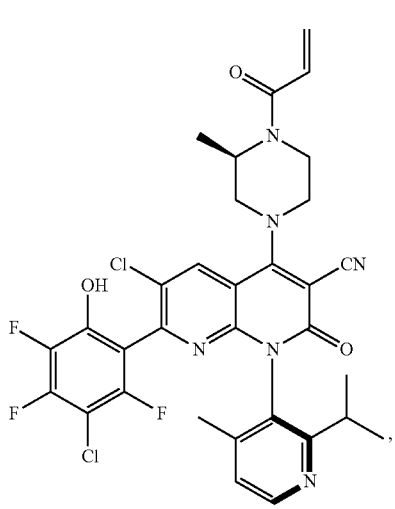

525
-continued
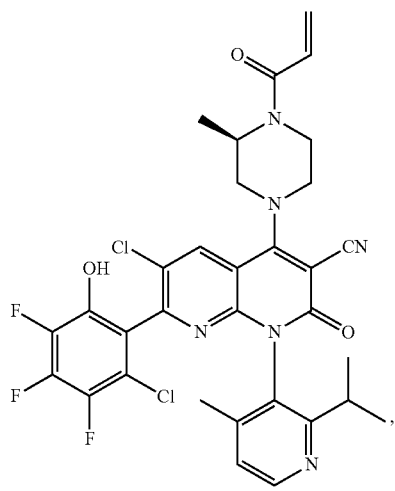
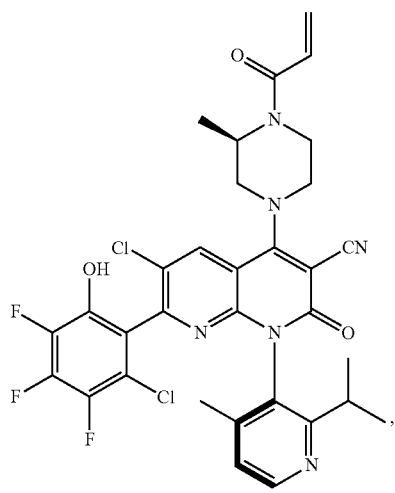
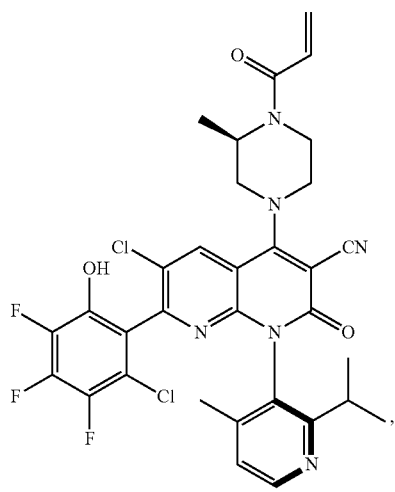
526
-continued
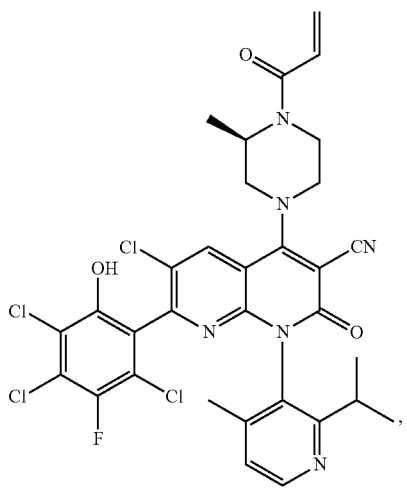
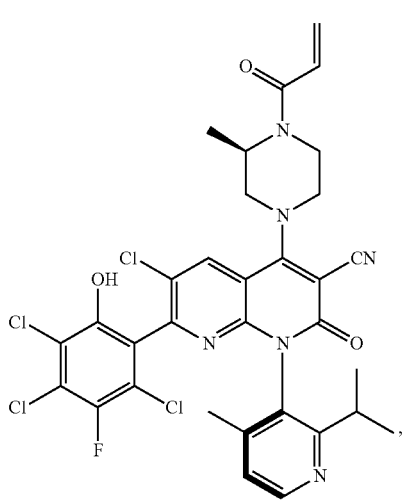
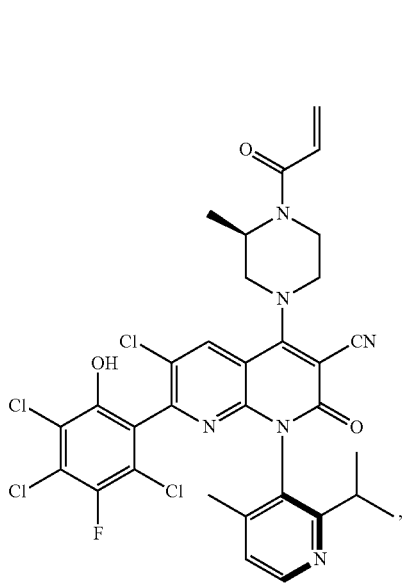

527
-continued
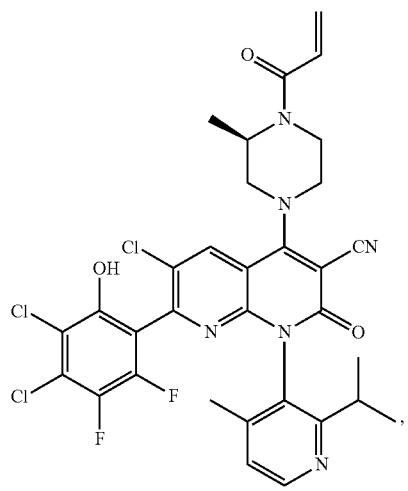
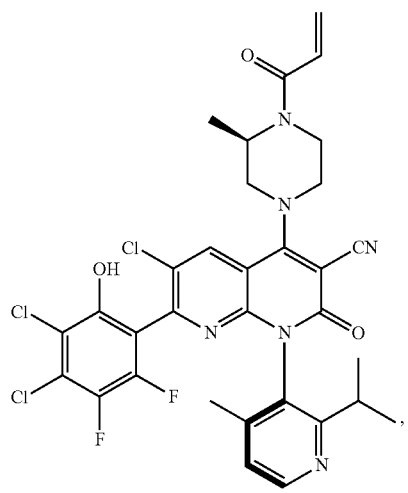
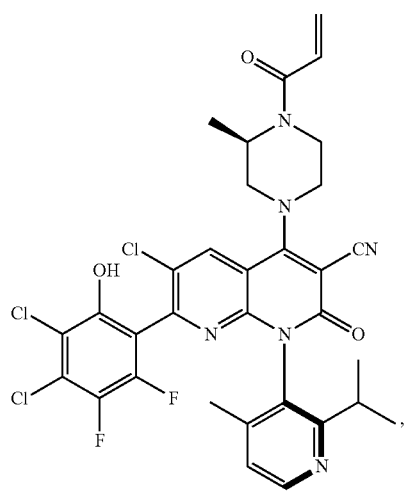
528
-continued
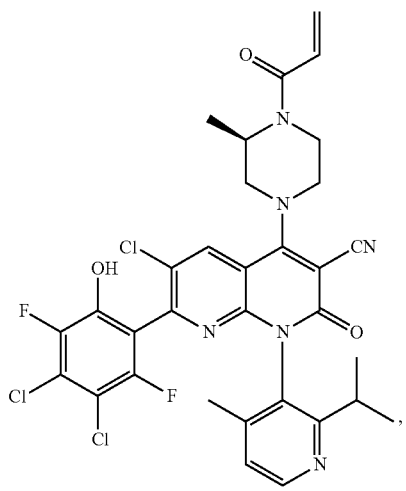
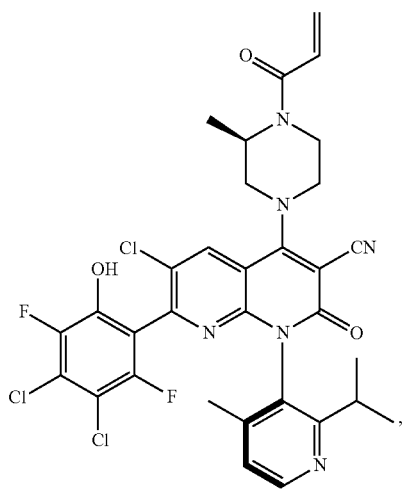
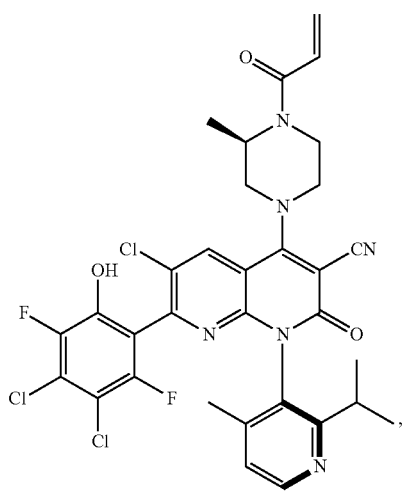

529
-continued
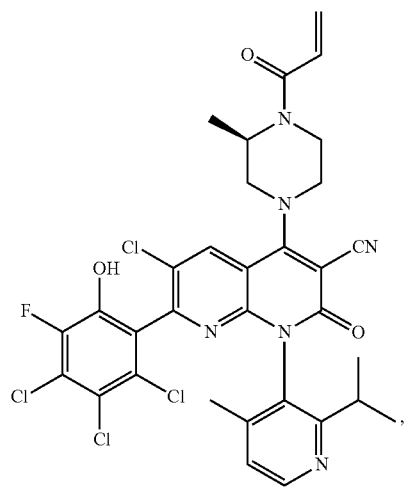
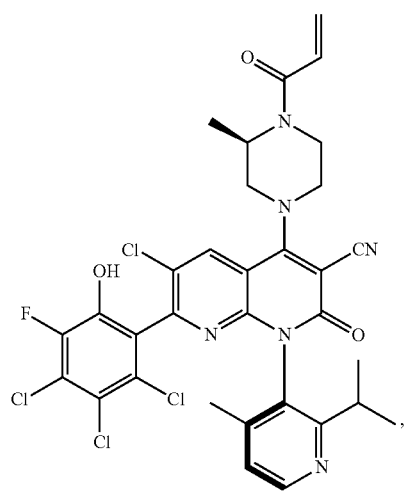
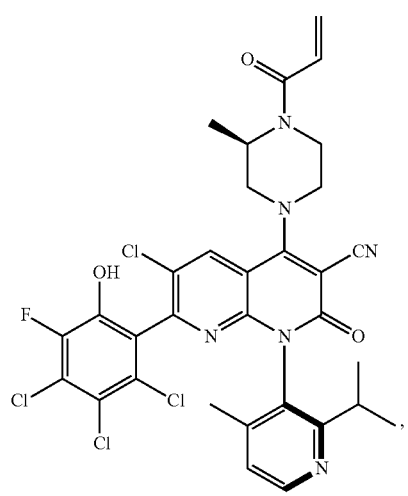
530
-continued
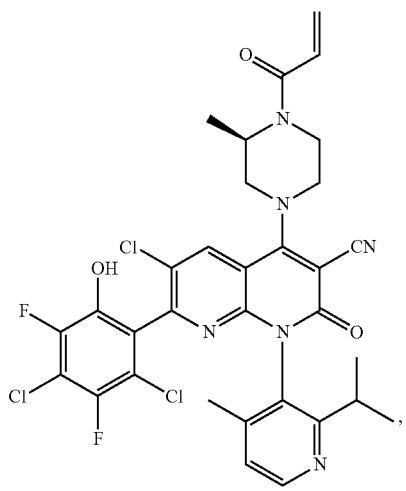
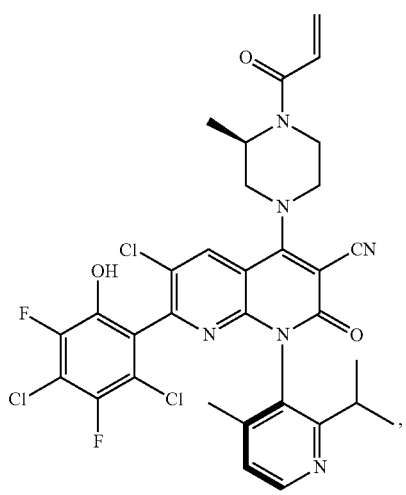
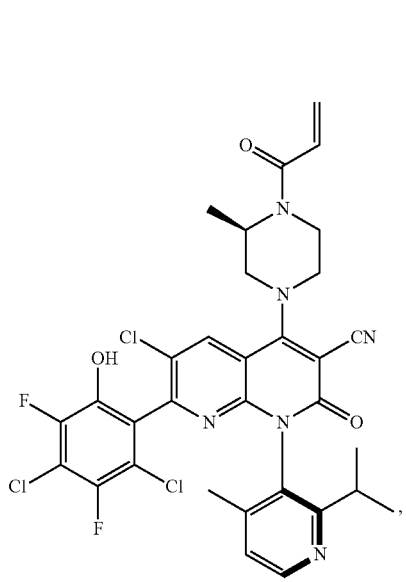

531
-continued
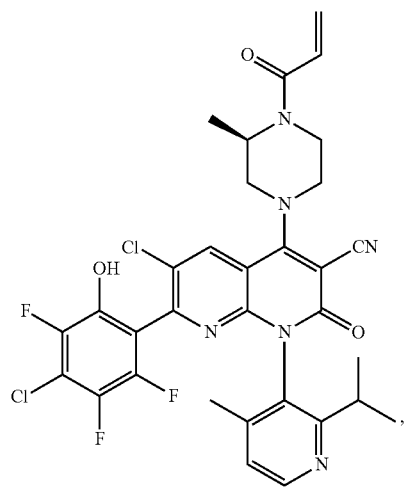
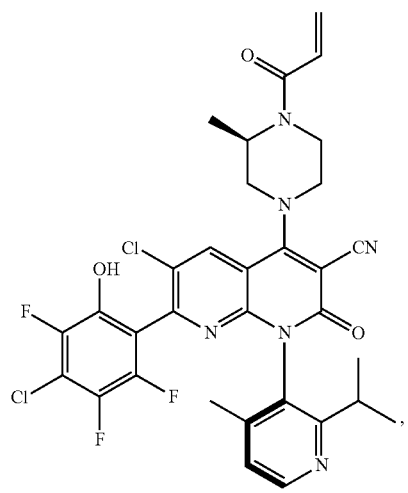
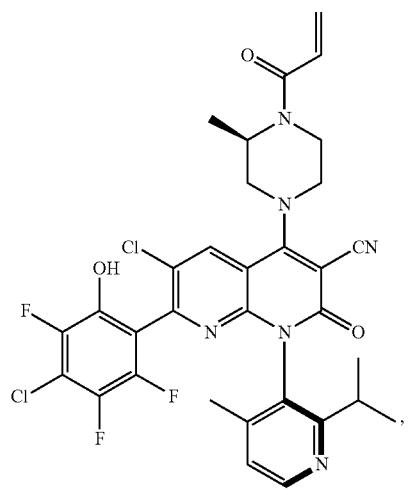
532
-continued
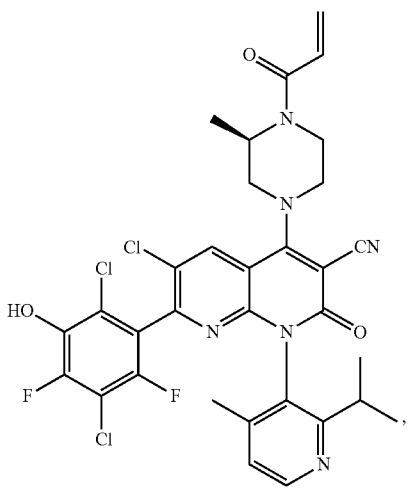
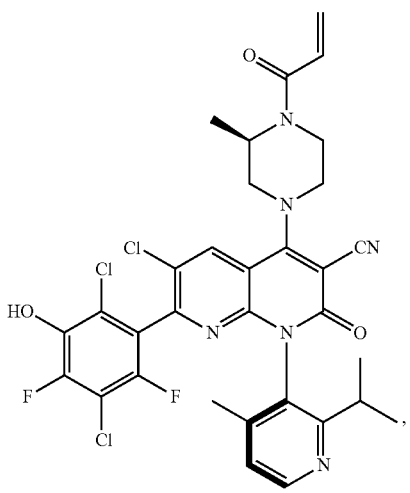
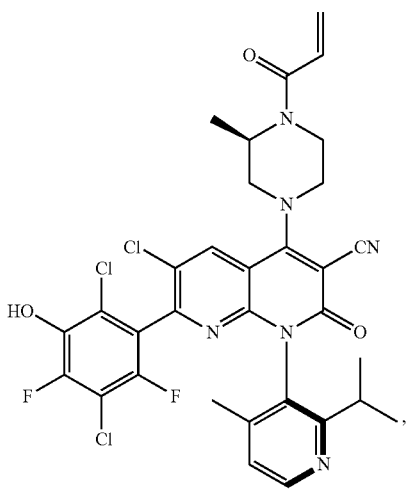

533
-continued
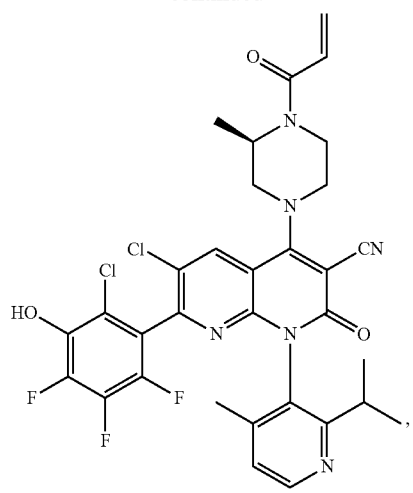
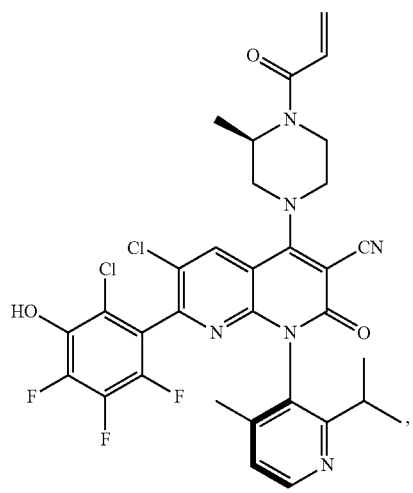
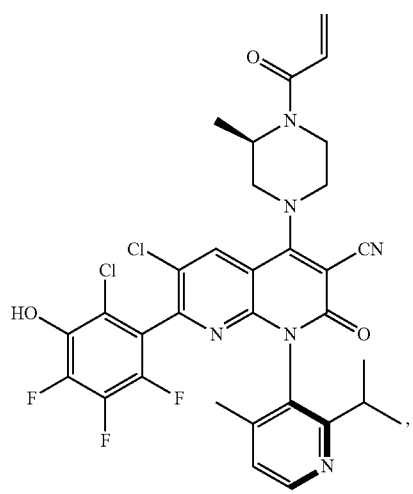
534
-continued
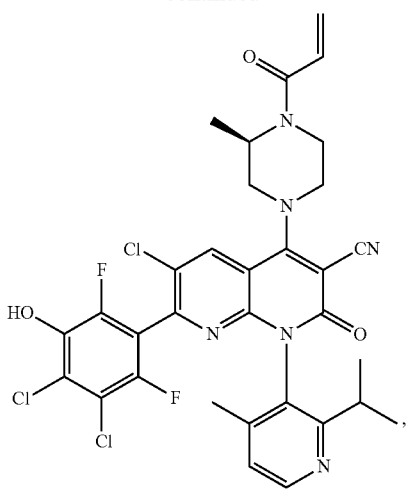
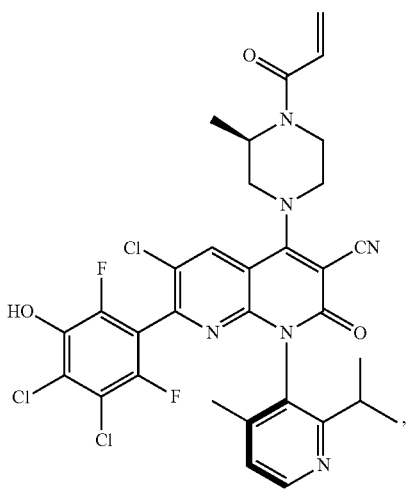
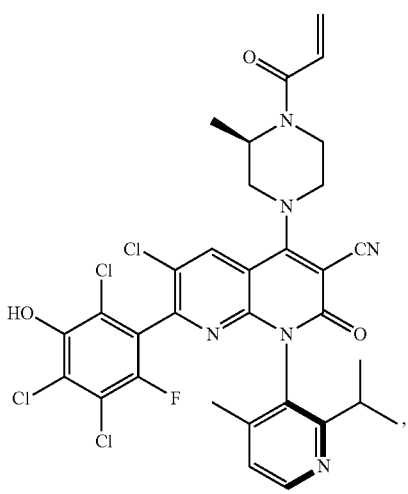

535
-continued
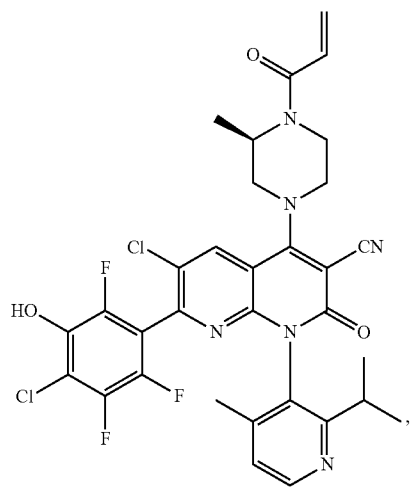
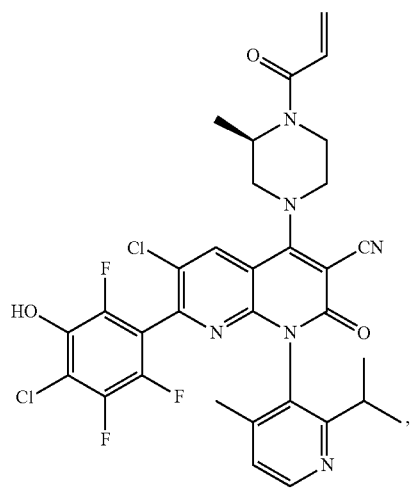
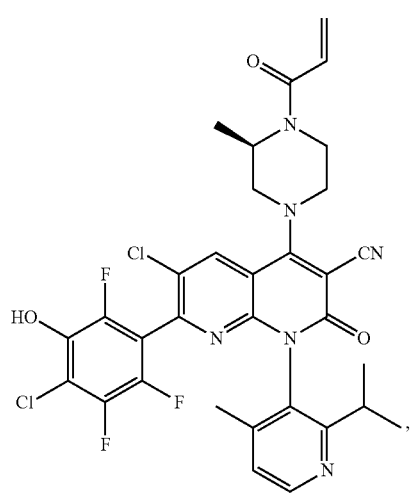
536
-continued
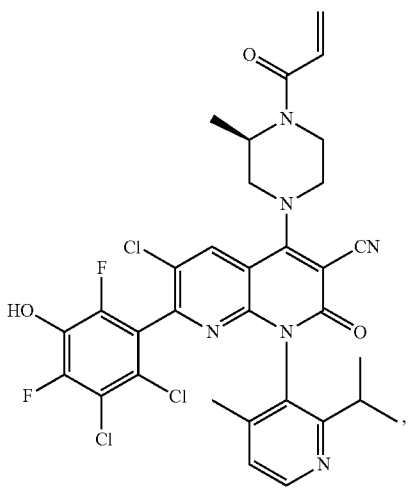
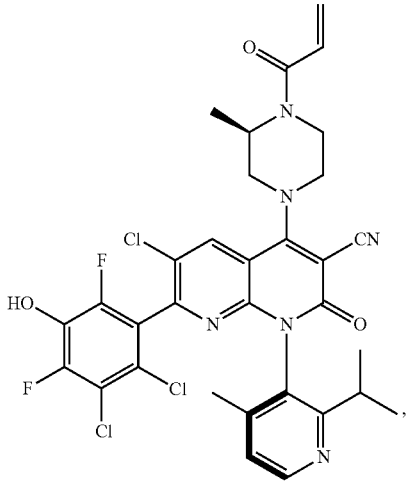
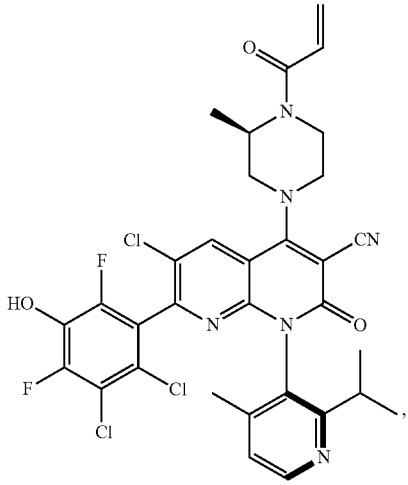

537
-continued
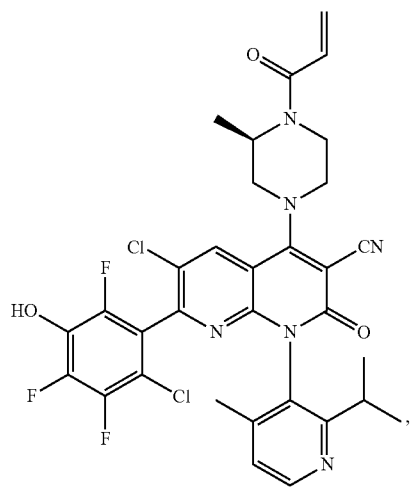
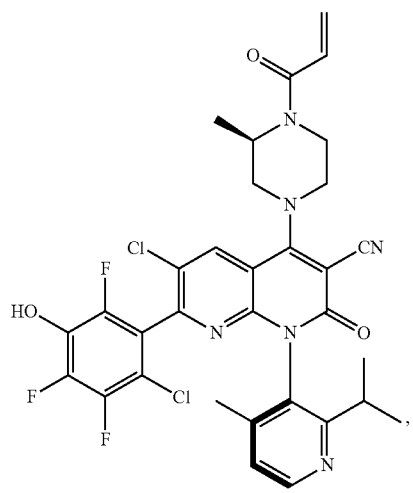
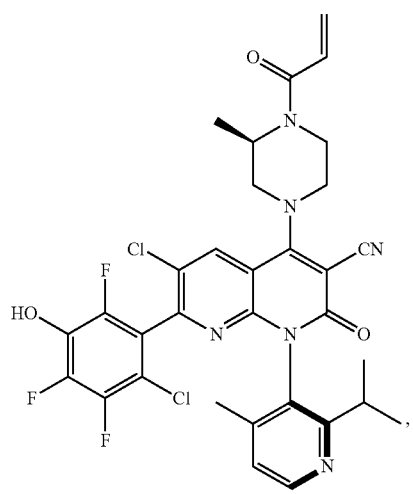
538
-continued
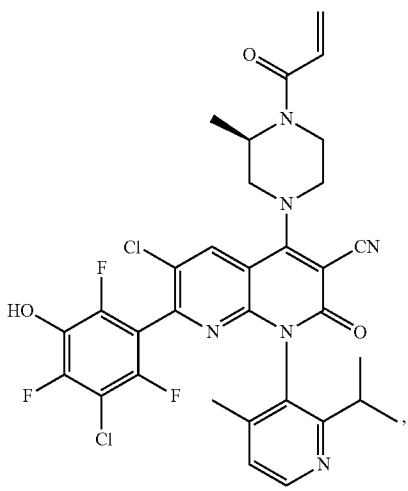
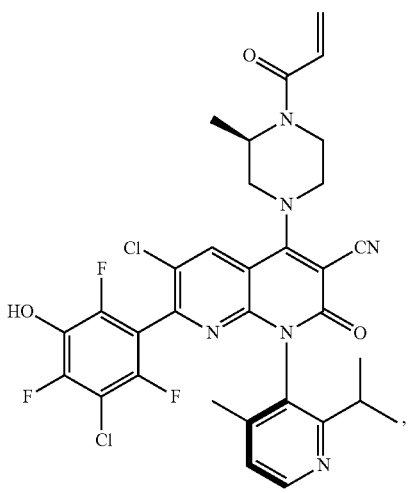
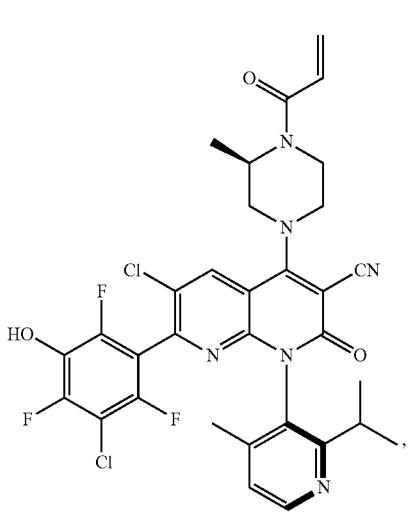

539
-continued
540
-continued
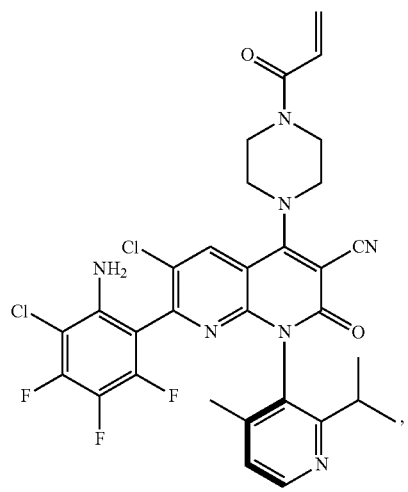
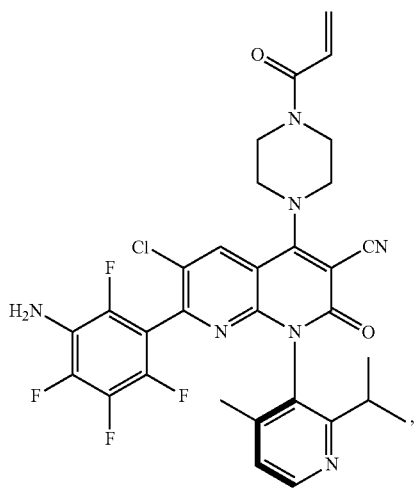
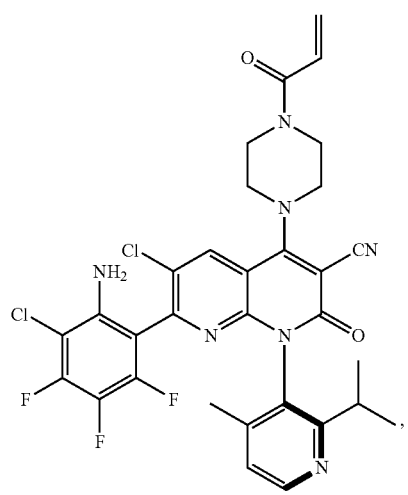
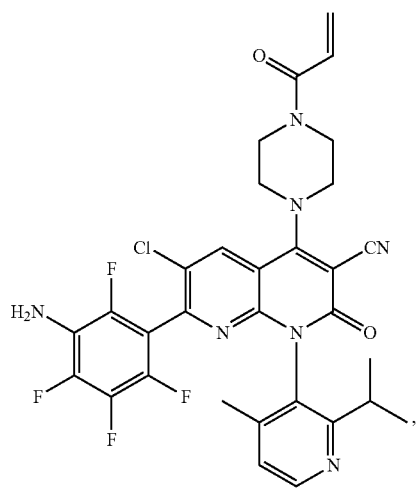

541
-continued
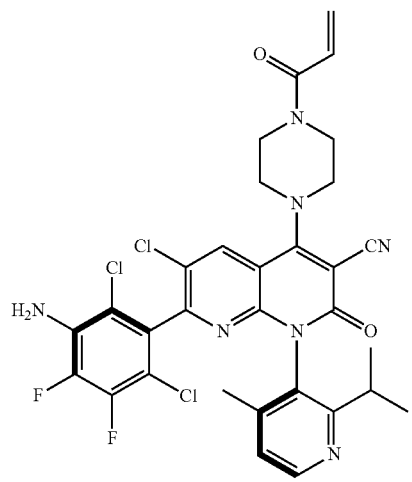
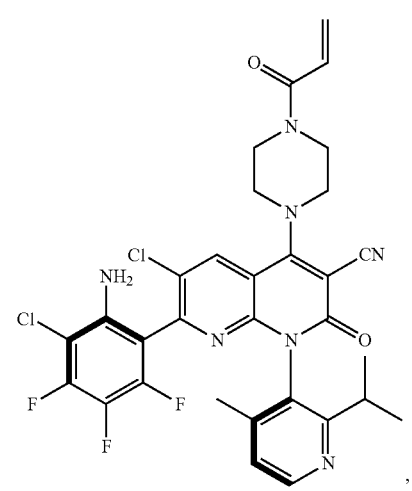
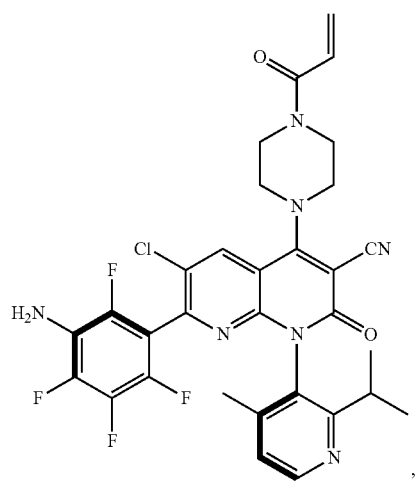
542
-continued
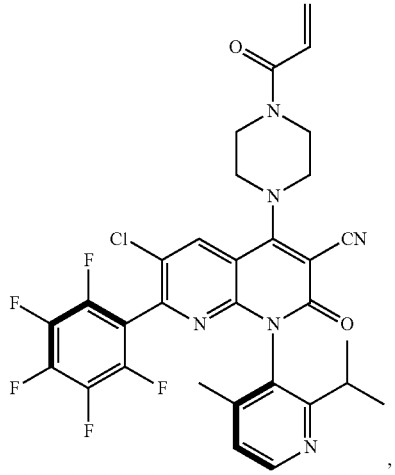
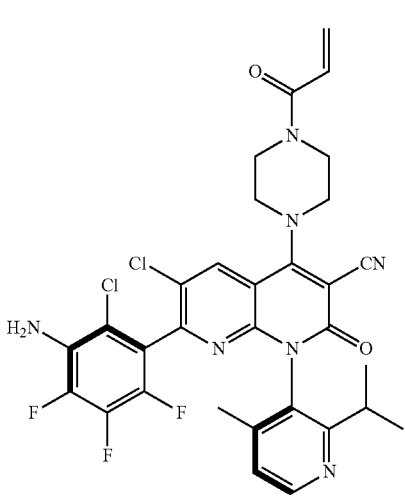
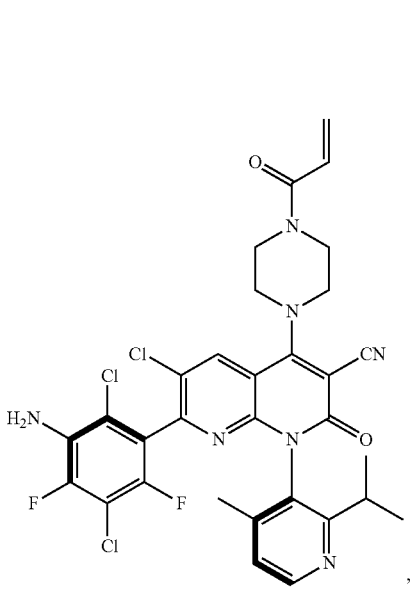

543
-continued
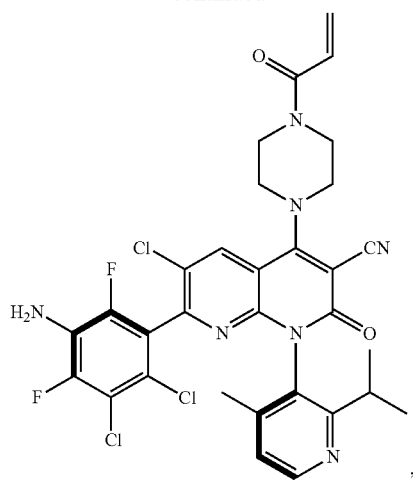
,
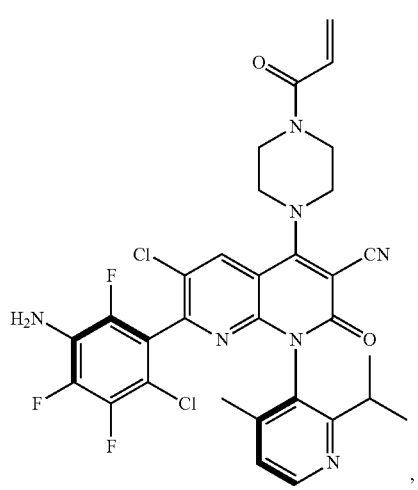
,
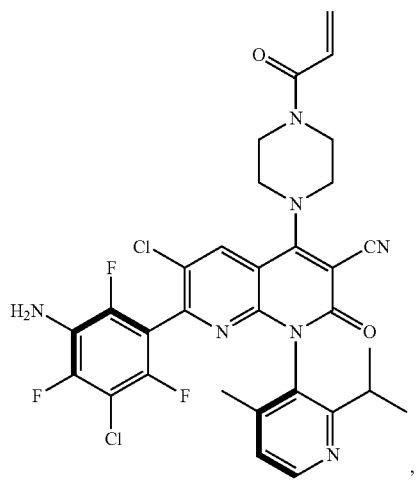
,
544
-continued
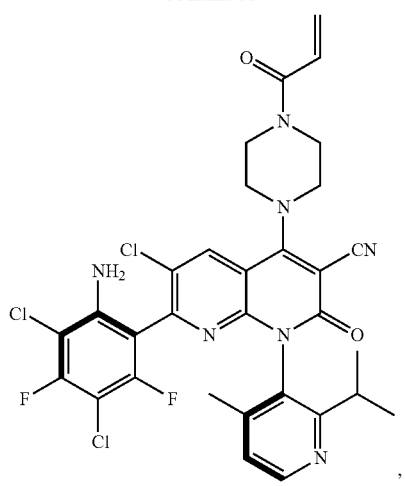
,

545
-continued
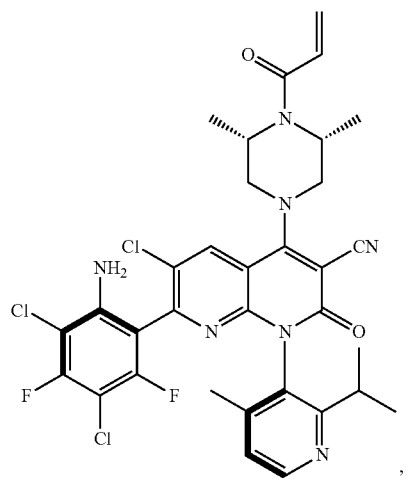
,
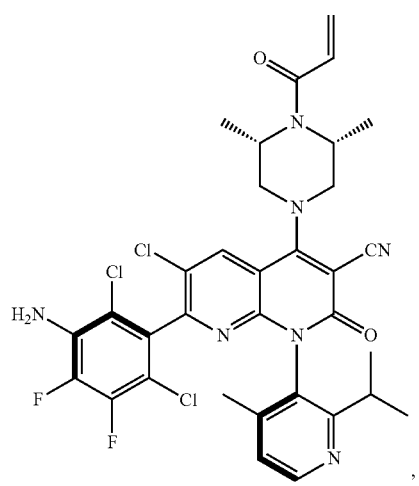
,
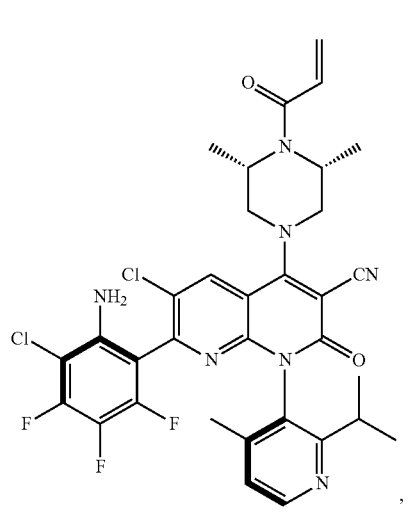
,
546
-continued
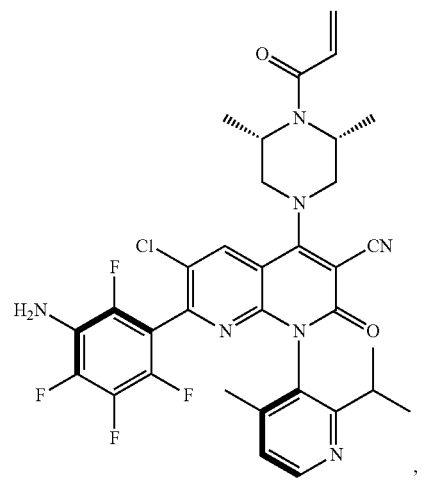
,
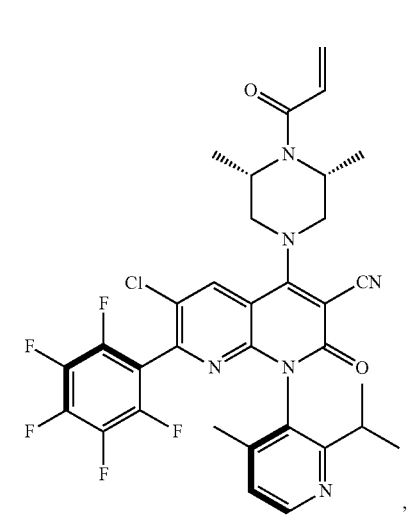
,
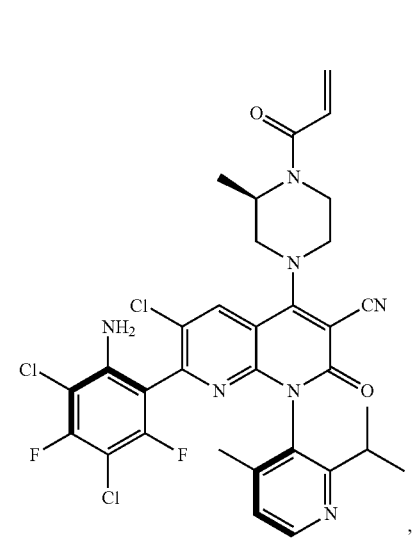
,

547
-continued
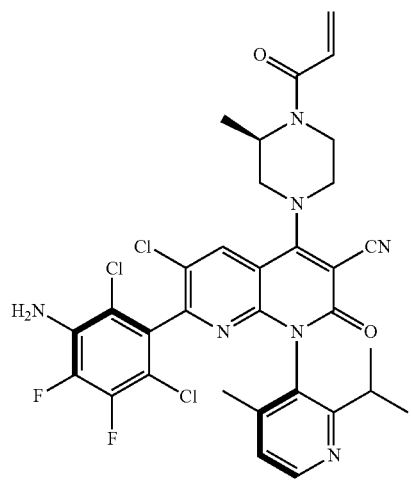
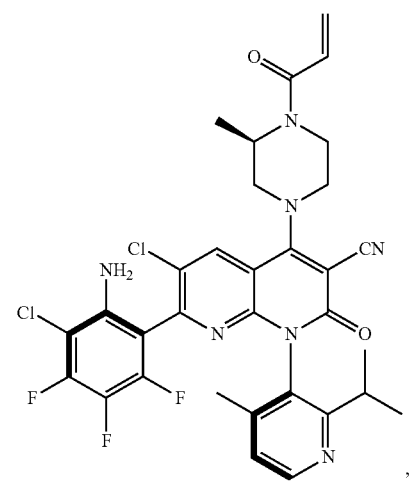
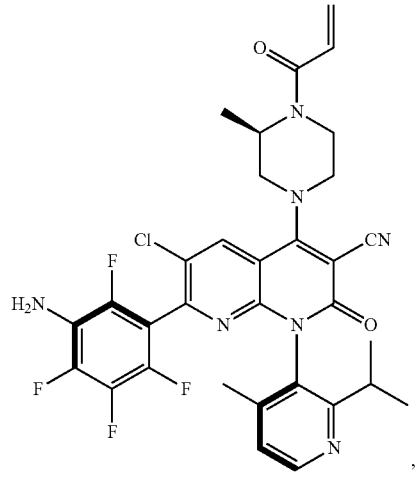
548
-continued
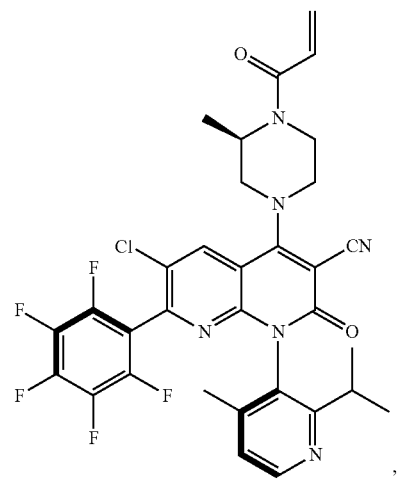
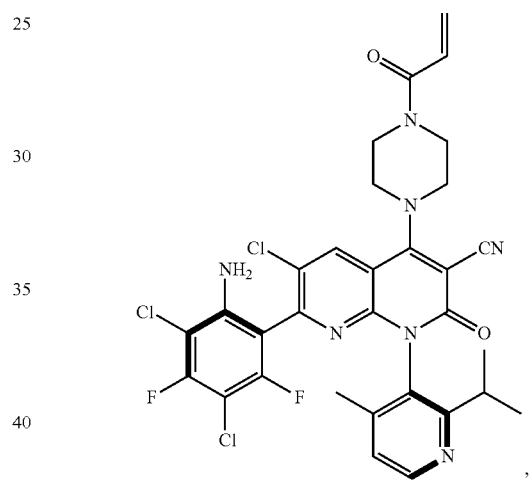
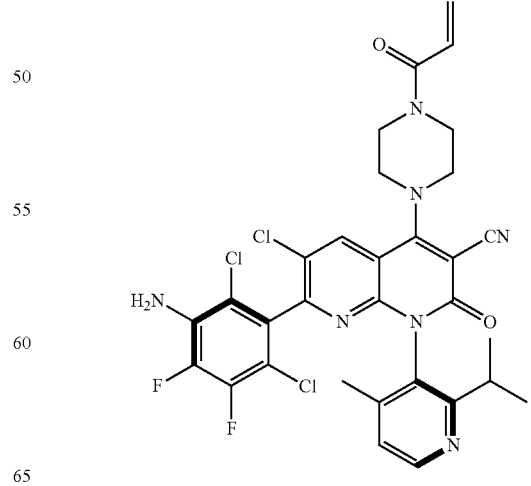

549
-continued
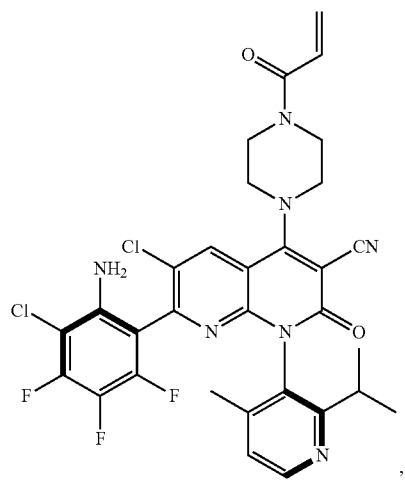
,
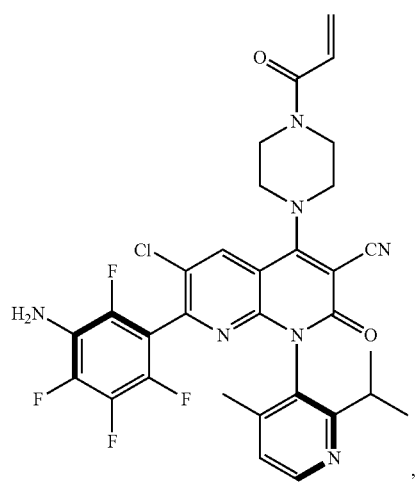
,
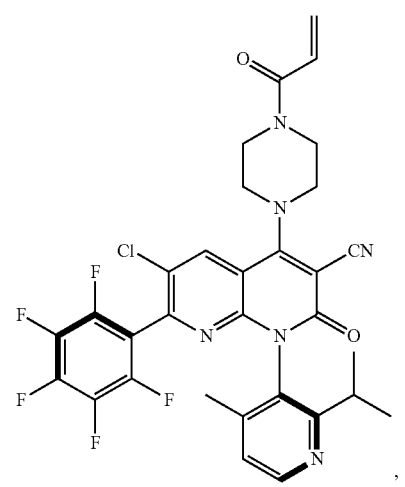
,
550
-continued
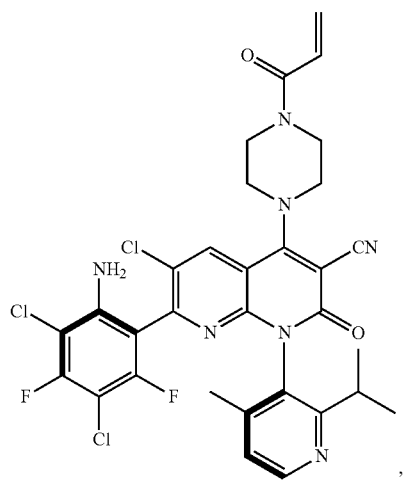
,
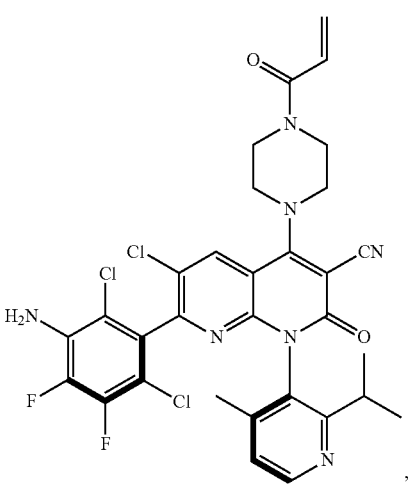
,
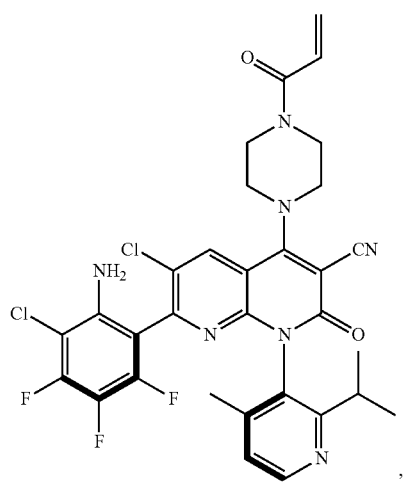
, 551
-continued
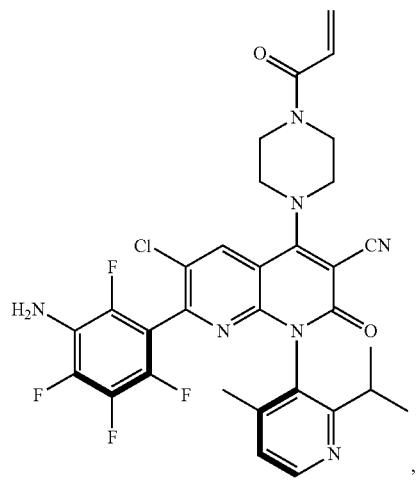
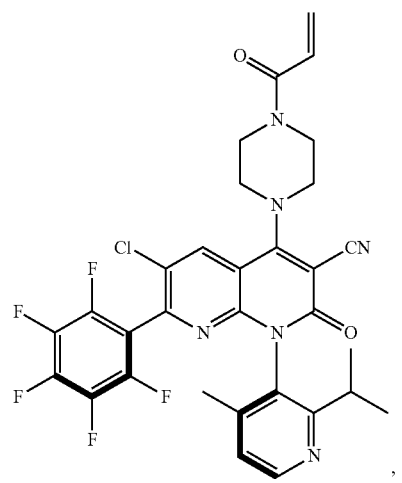
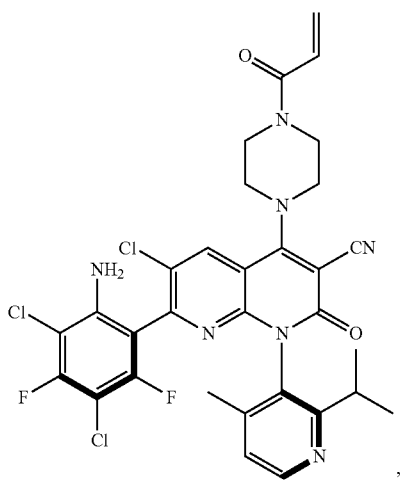
552
-continued
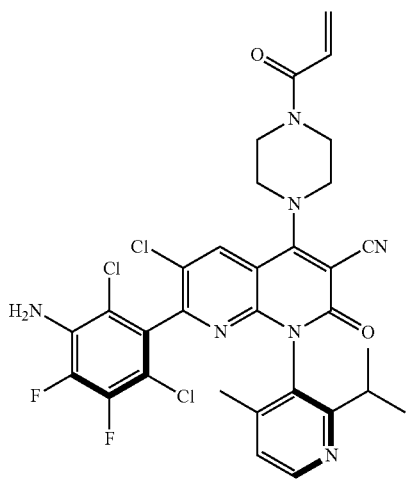
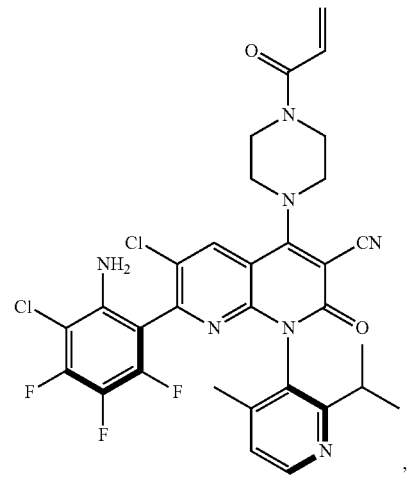
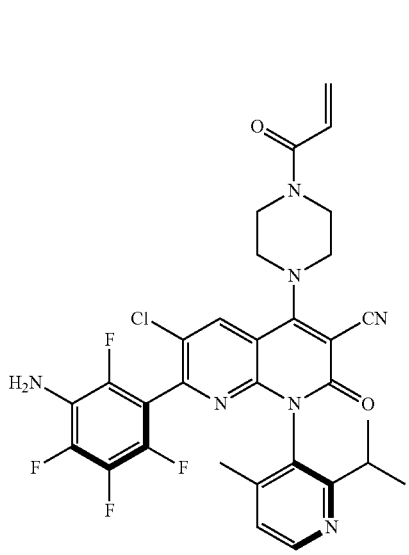

553
-continued
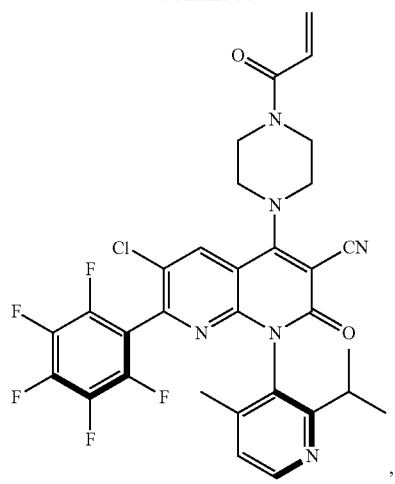
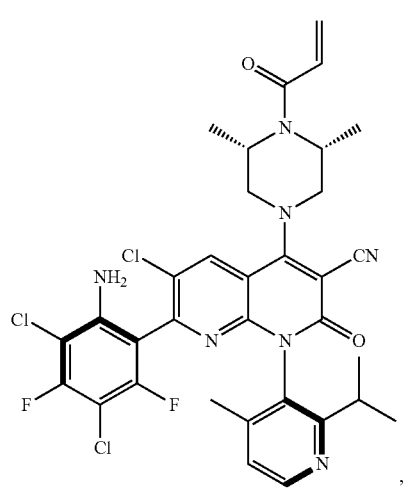
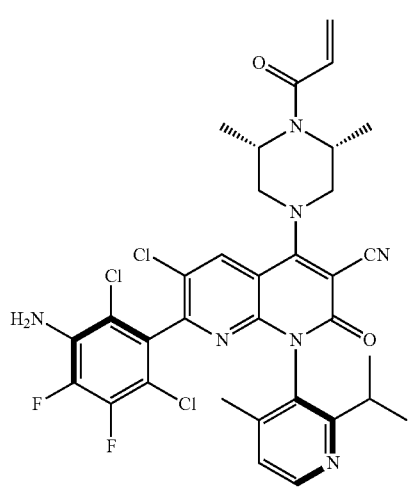
554
-continued
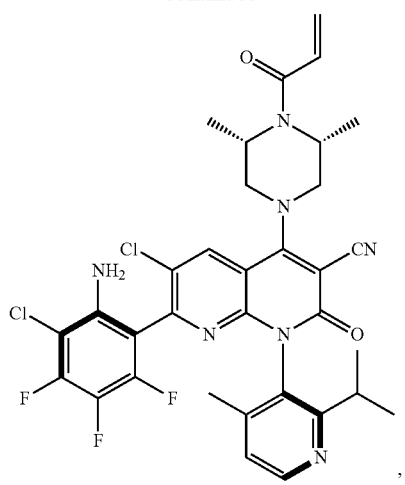
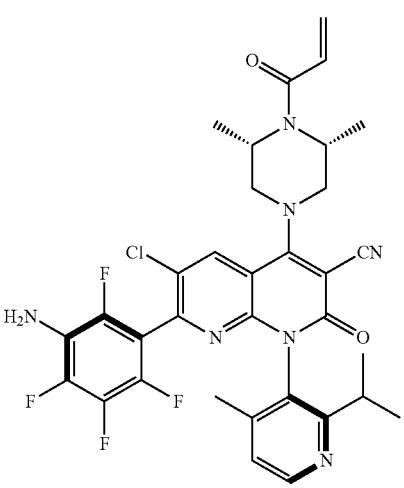
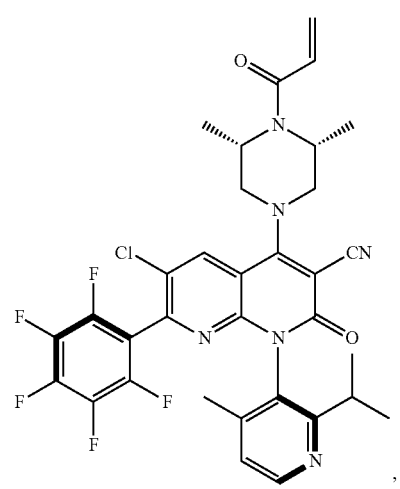

555
-continued
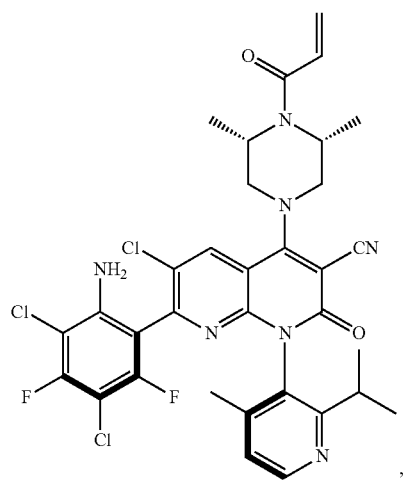
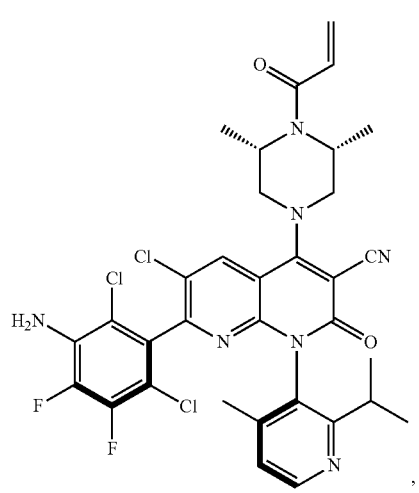
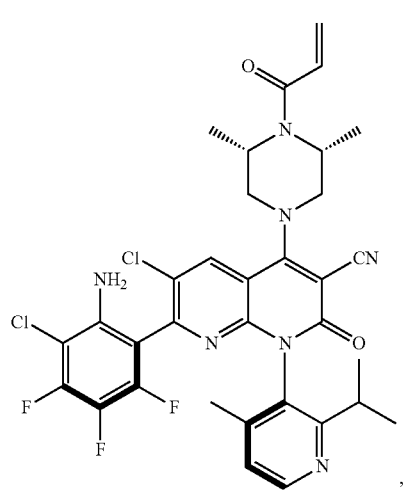
556
-continued
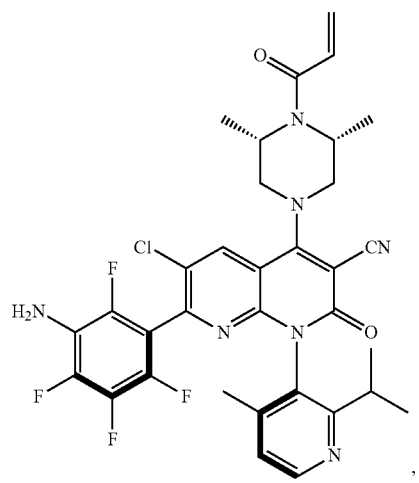
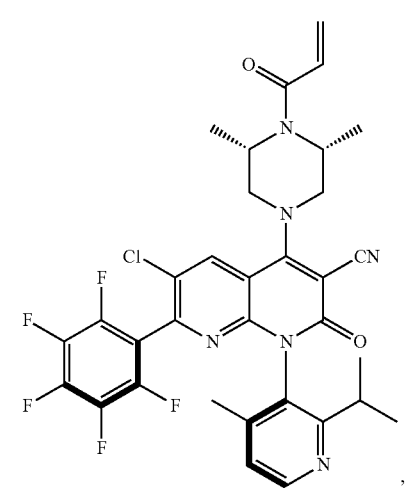
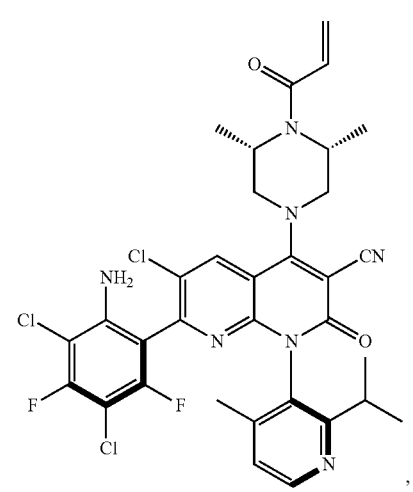

557
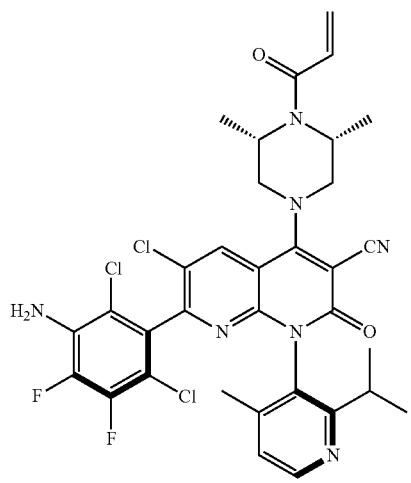
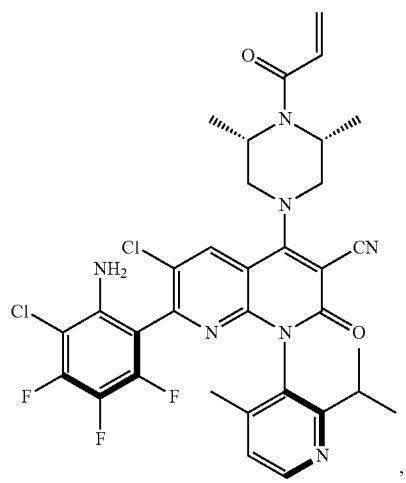
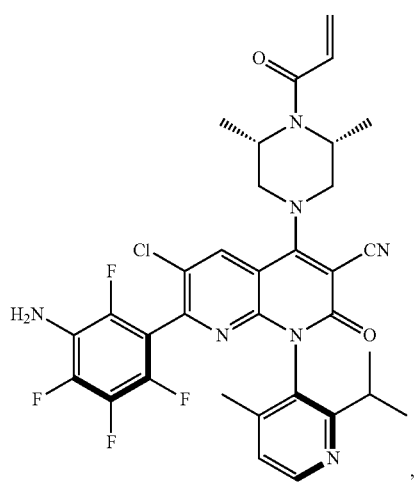
558
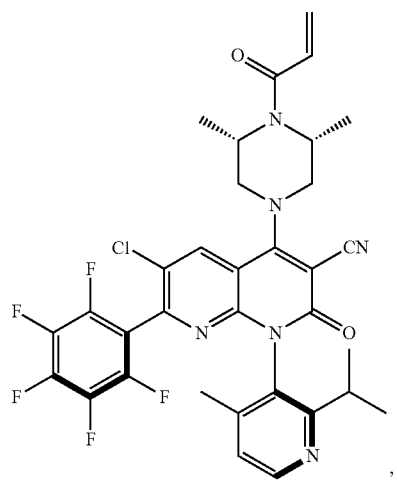
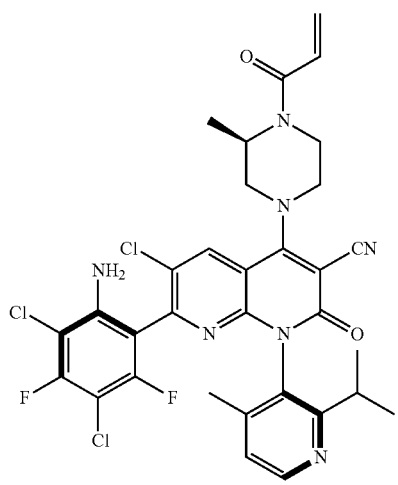
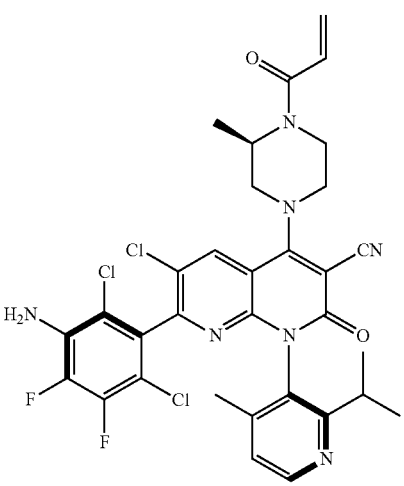

559
-continued
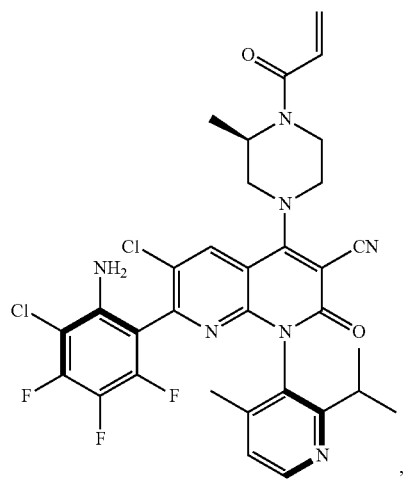
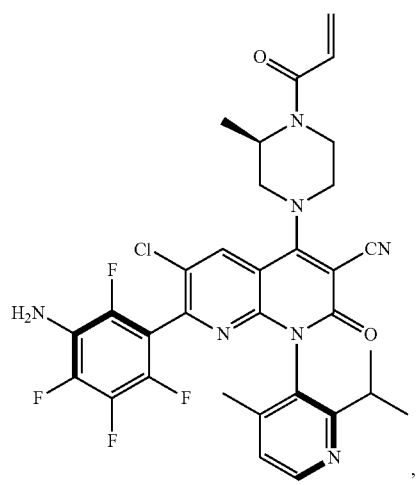
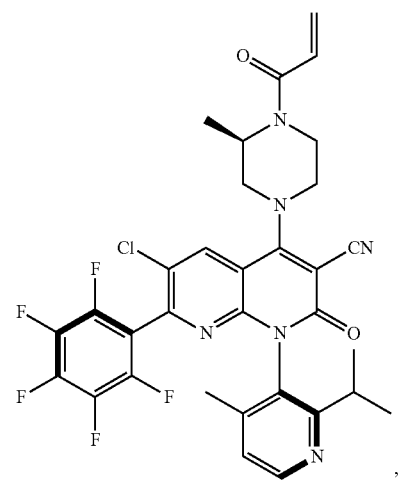
560
-continued
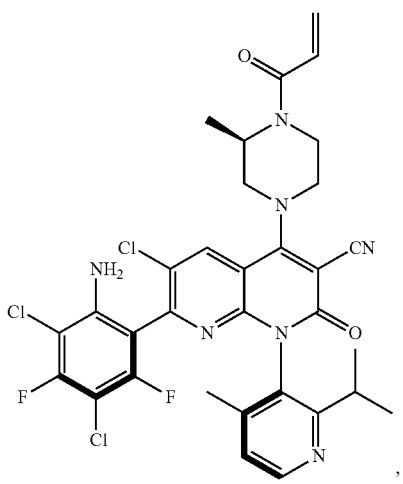
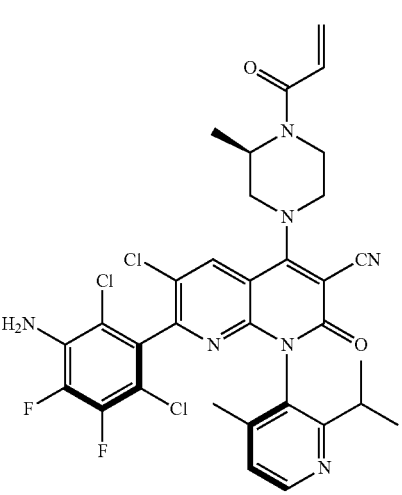
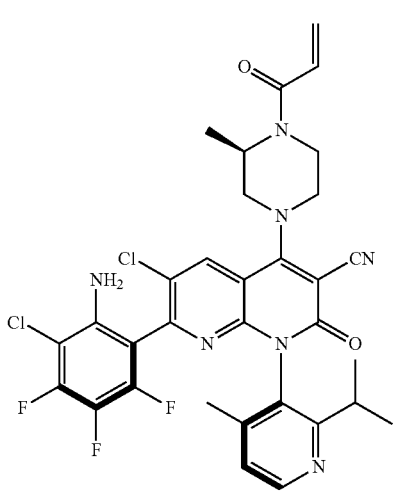

561
-continued
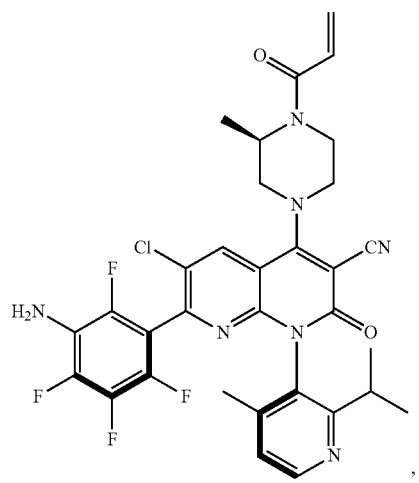
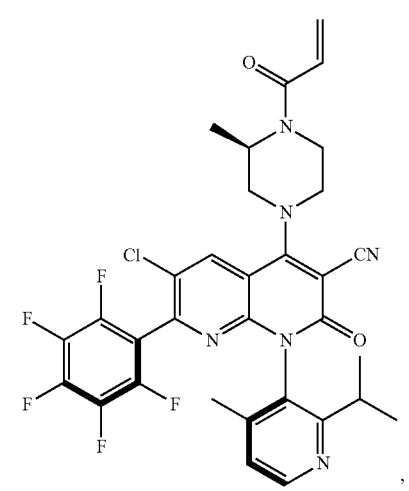
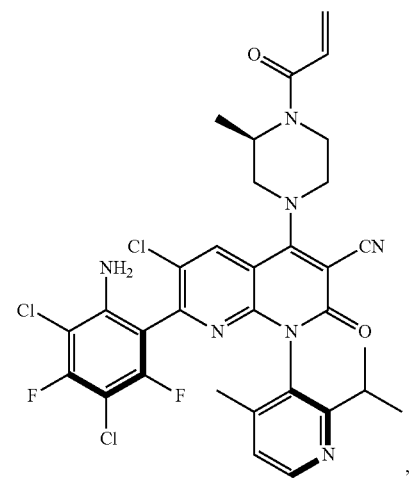
562
-continued
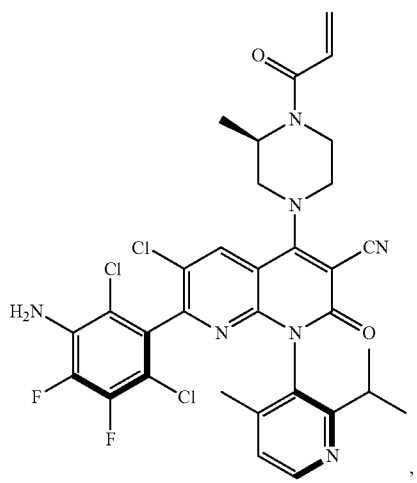
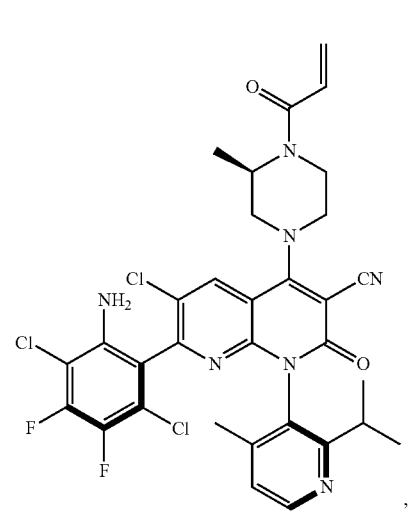
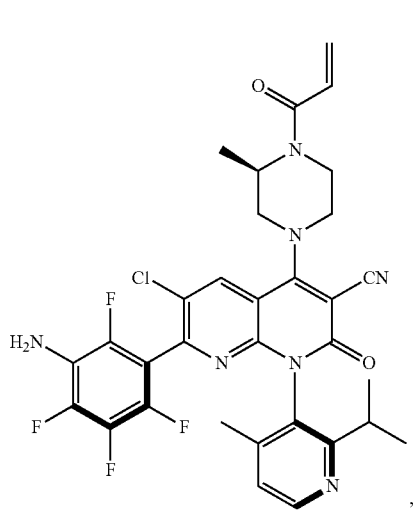

563
-continued
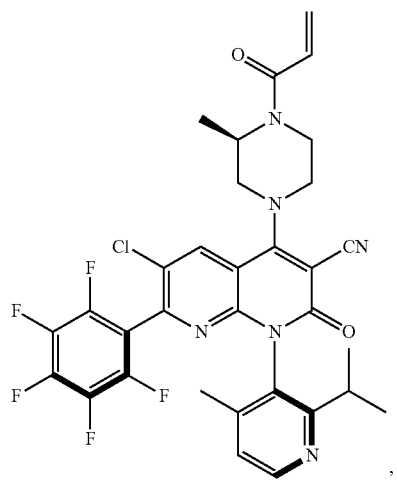
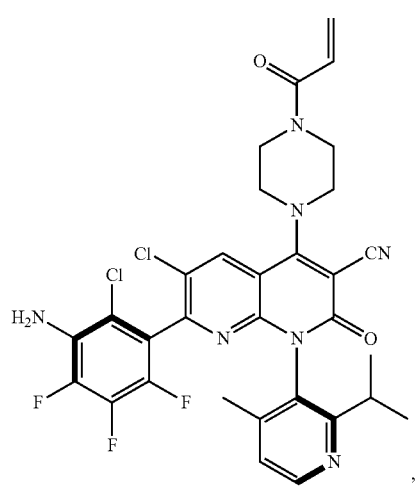
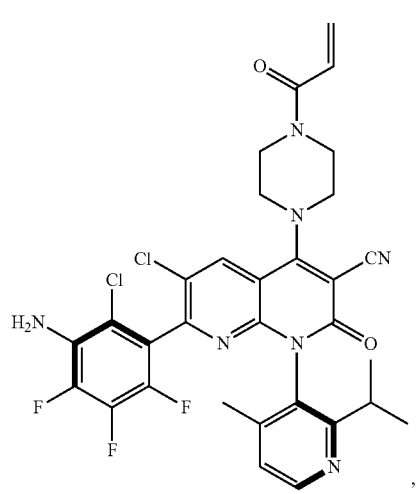
564
-continued
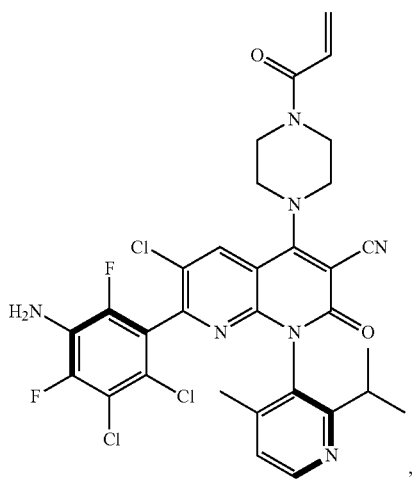
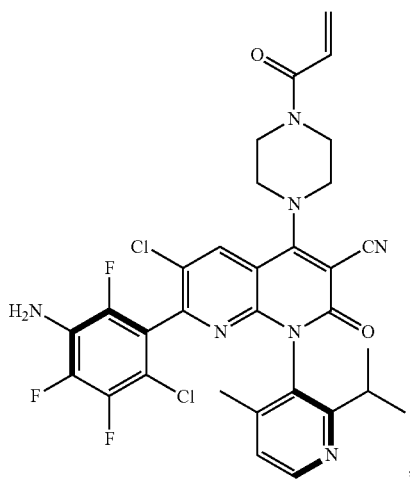
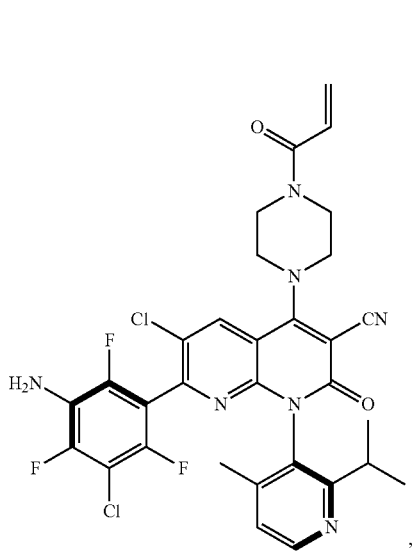

565
-continued
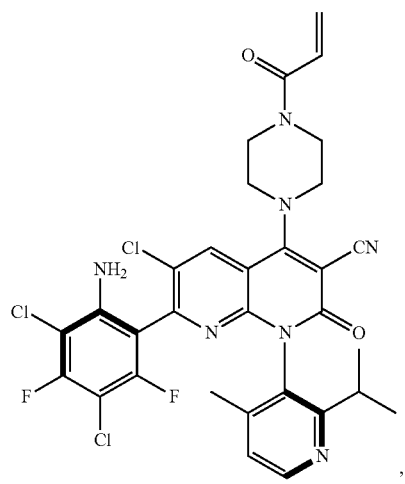
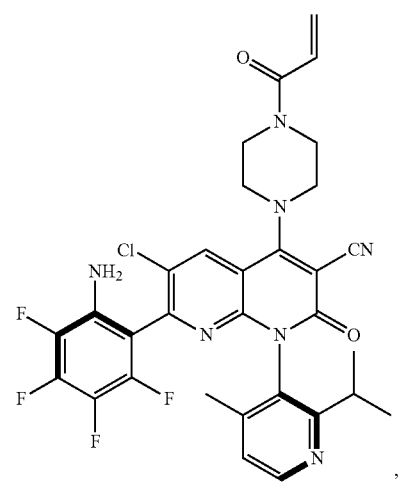
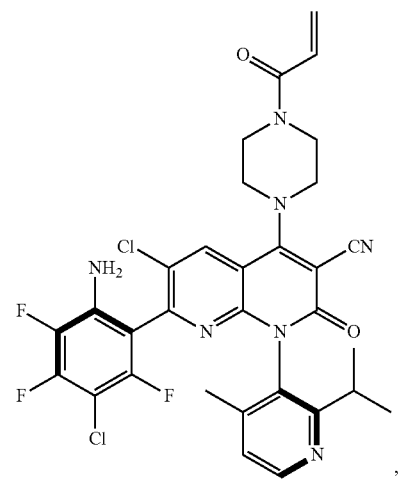
566
-continued
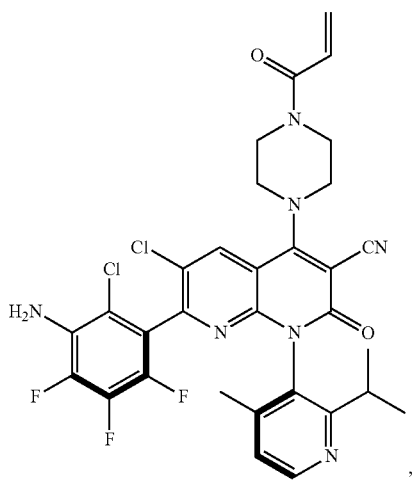
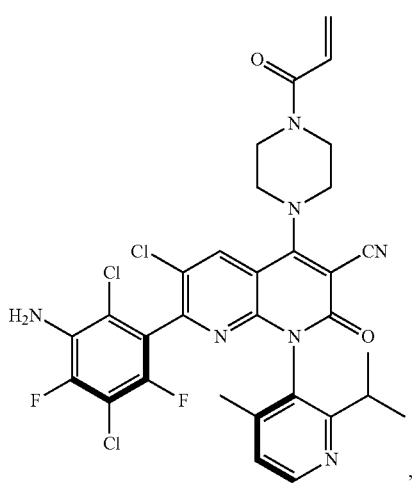
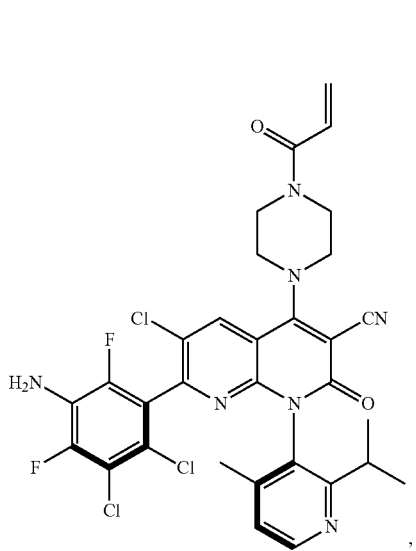

567
-continued
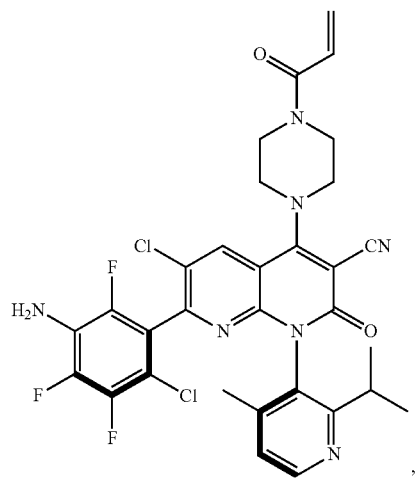
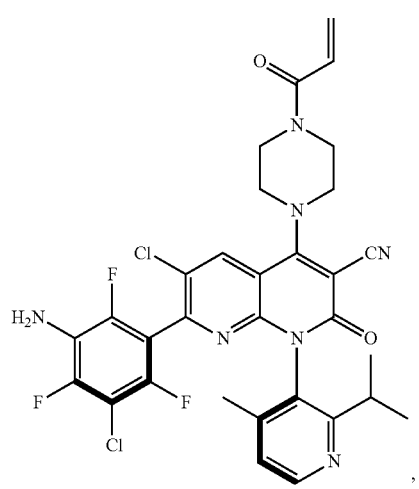
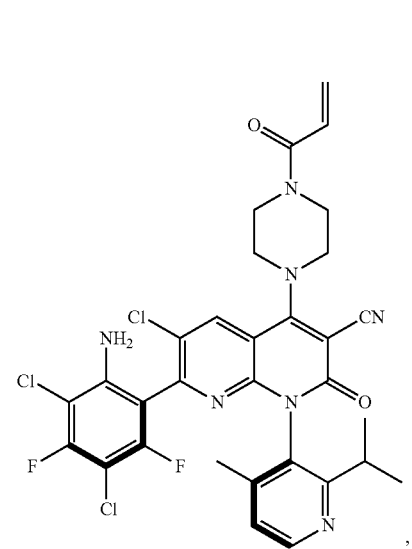
568
-continued
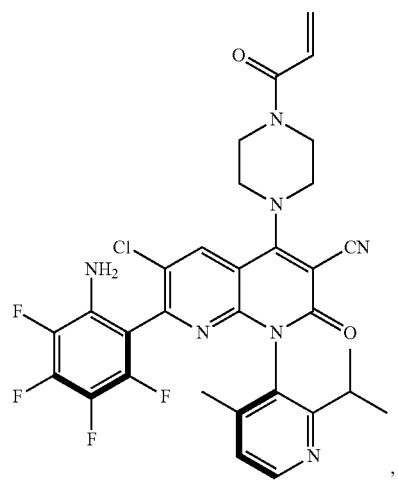
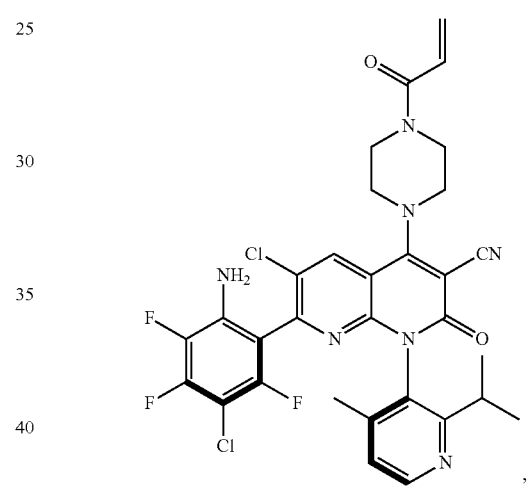
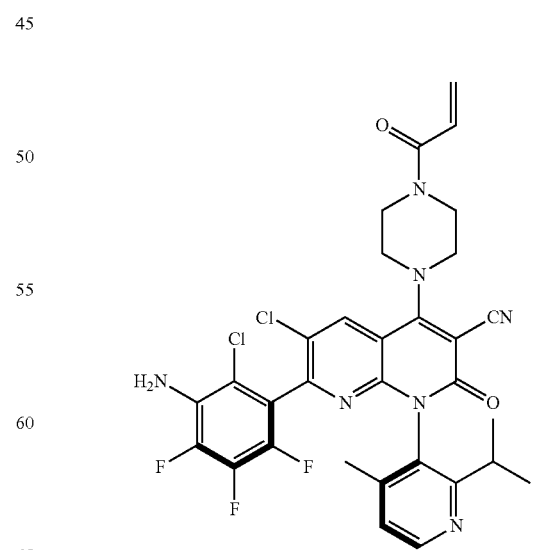

569
-continued
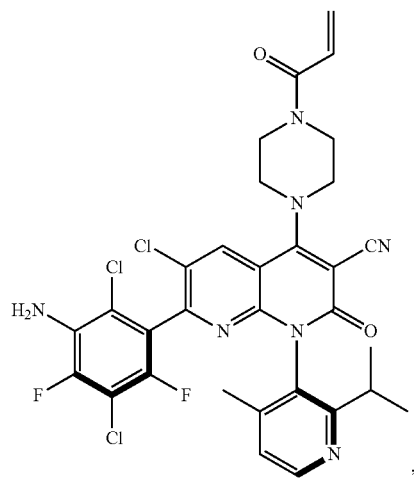
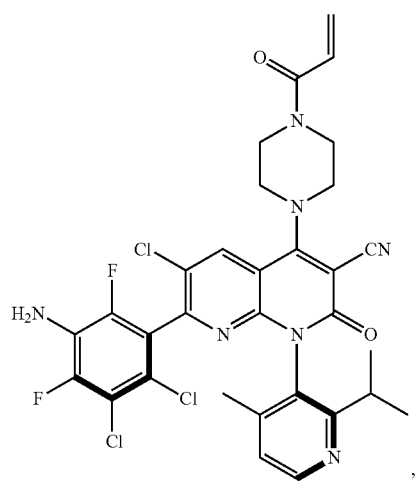
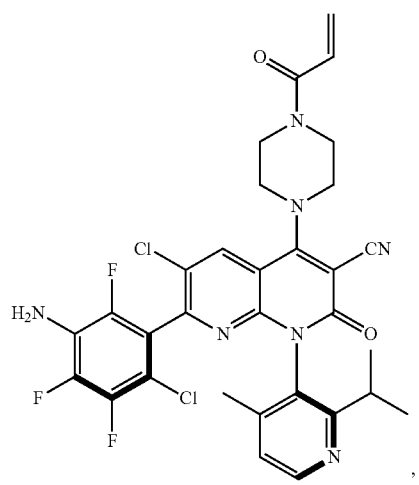
570
-continued
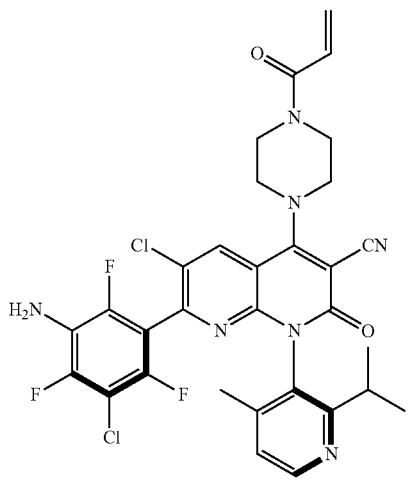
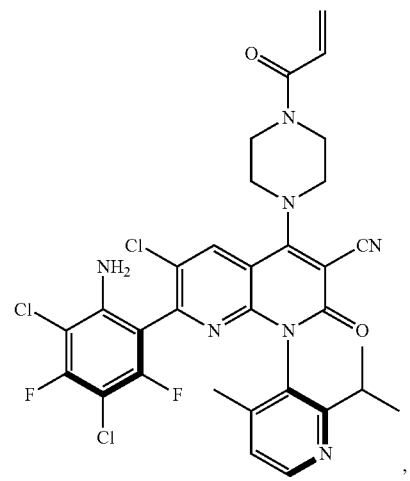
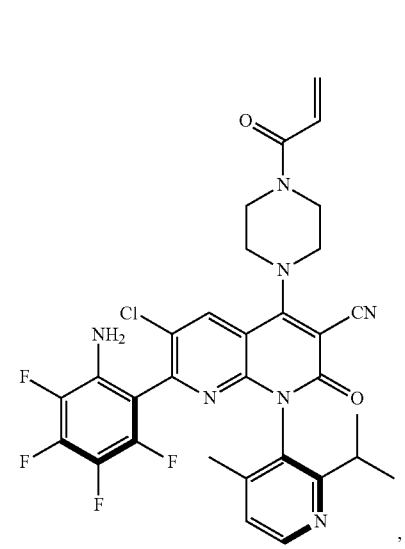

571
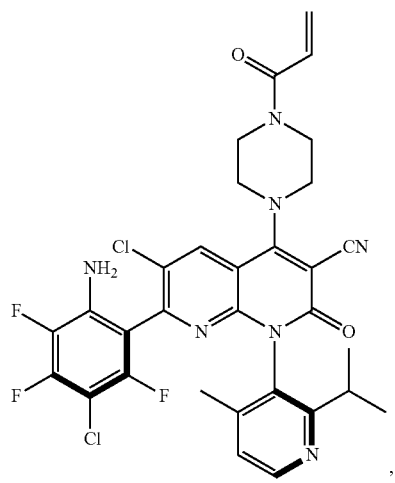
,
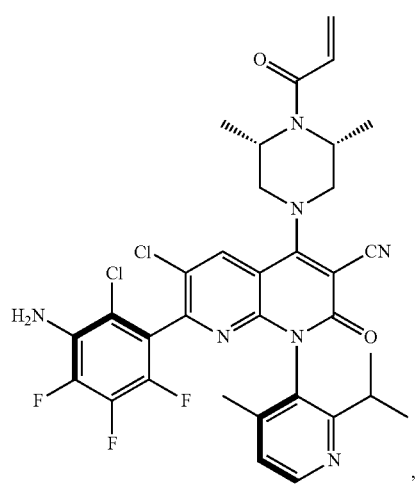
,
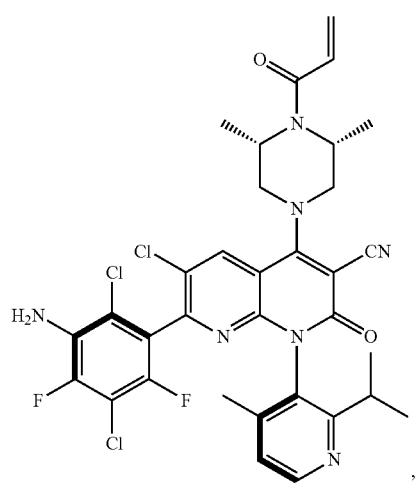
,
572
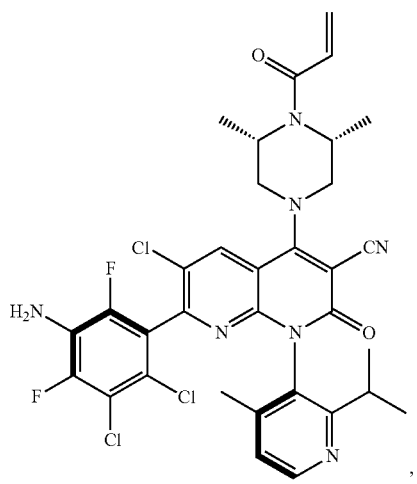
,
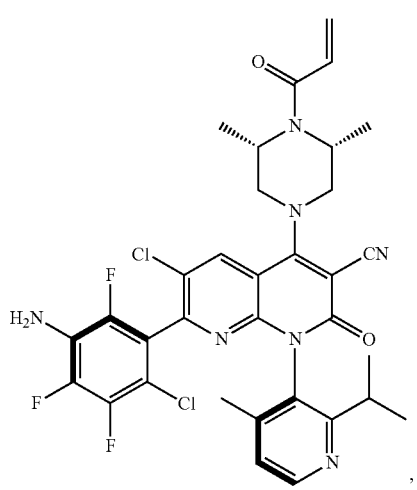
,
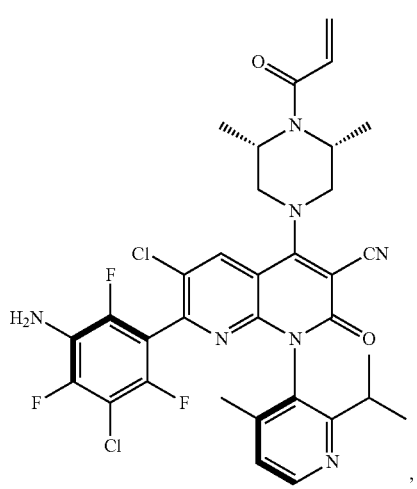
, 573
-continued
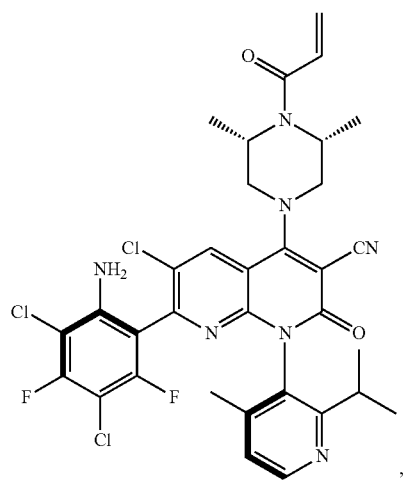
,
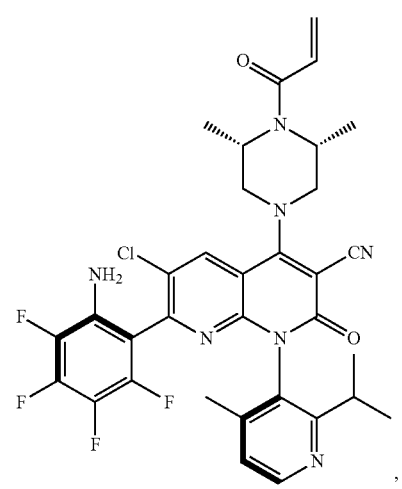
,
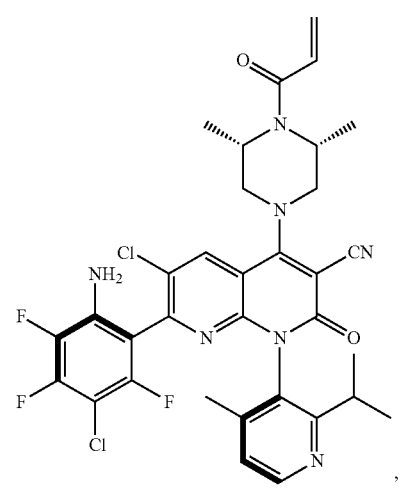
,
574
-continued
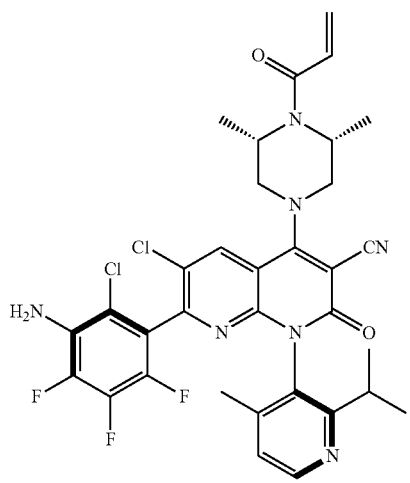
,
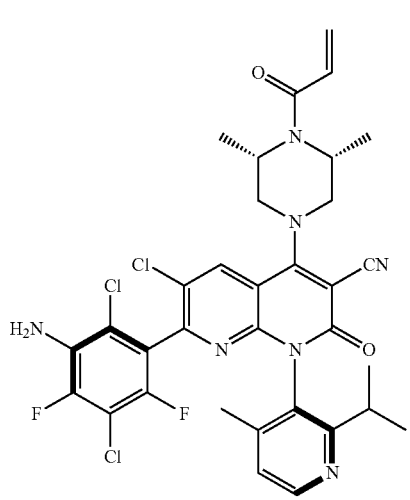
,
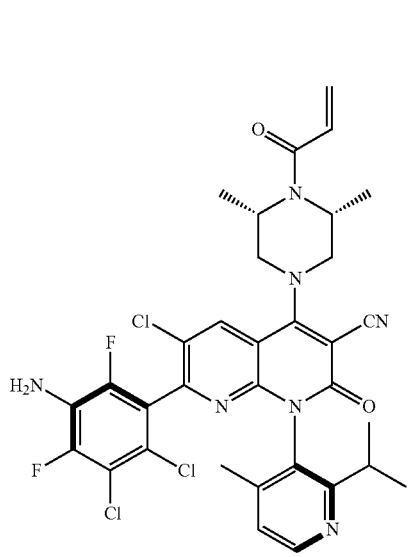
, 575
-continued
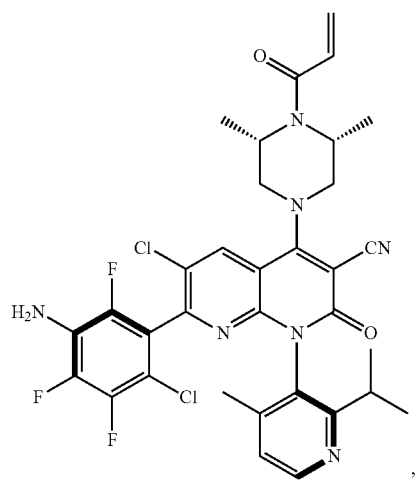
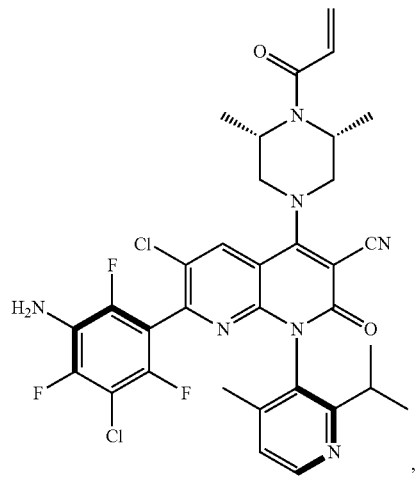
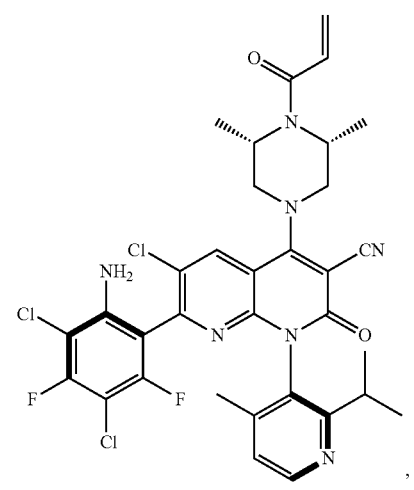
576
-continued
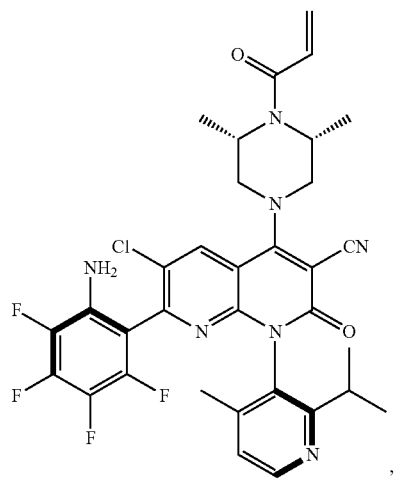

577
-continued
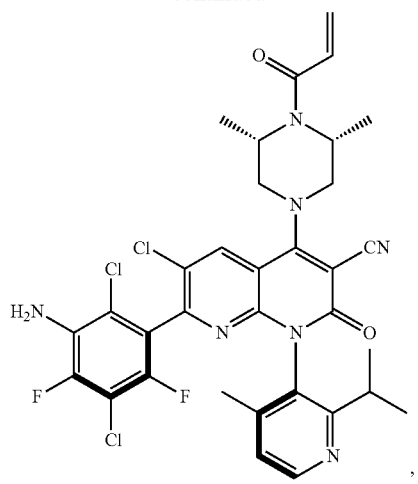
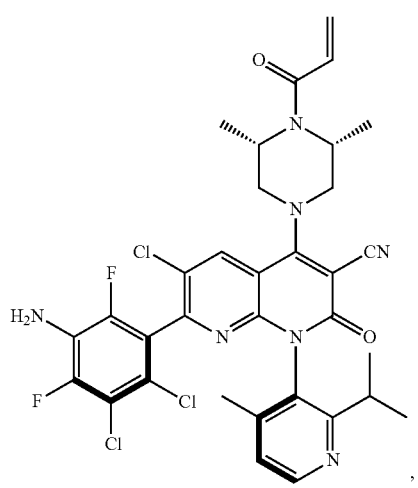
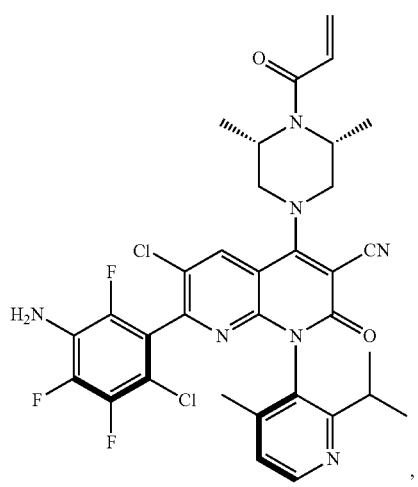
578
-continued
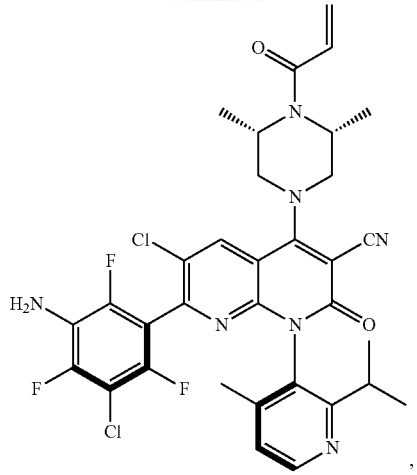
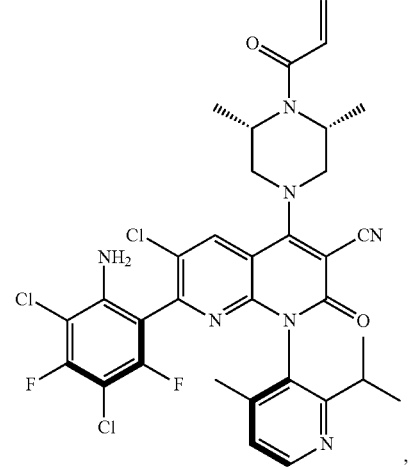
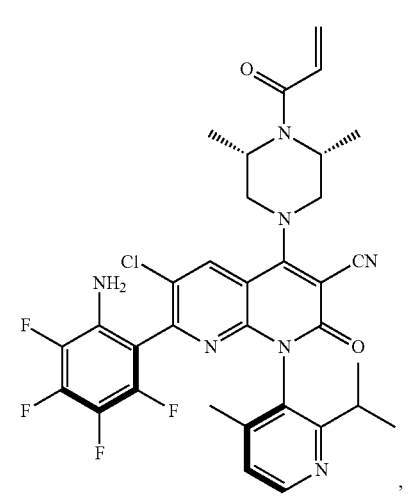

579
-continued
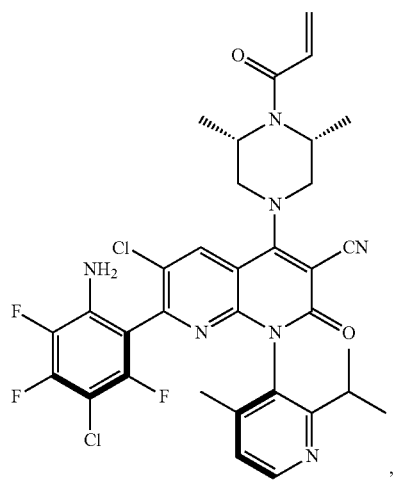
,
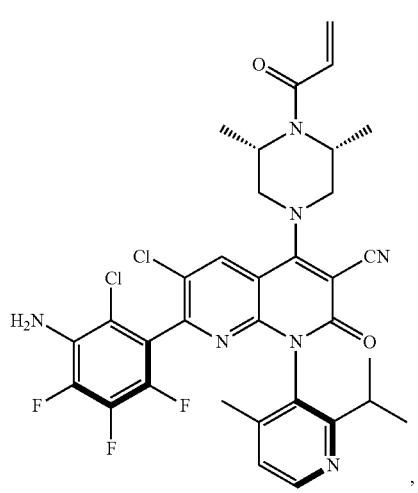
,
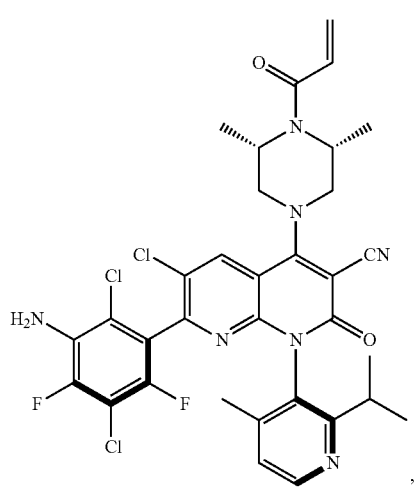
,
580
-continued
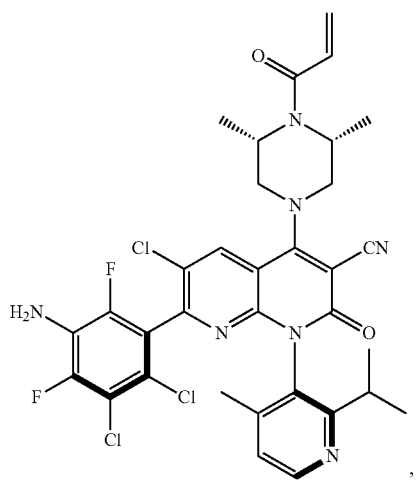
,
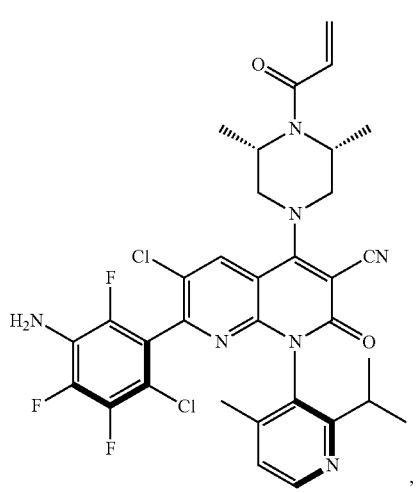
,
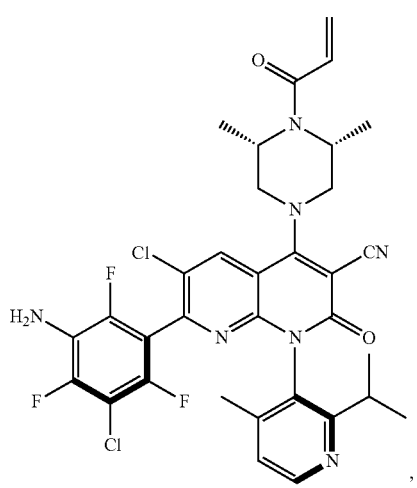
, 581
-continued
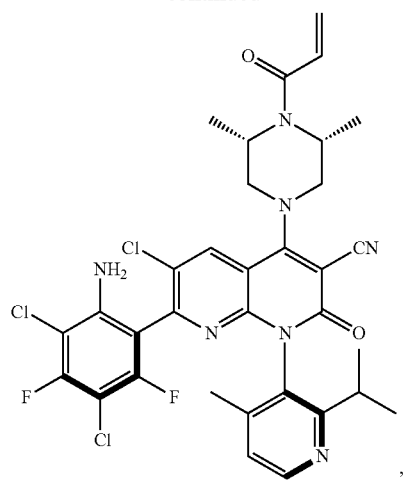
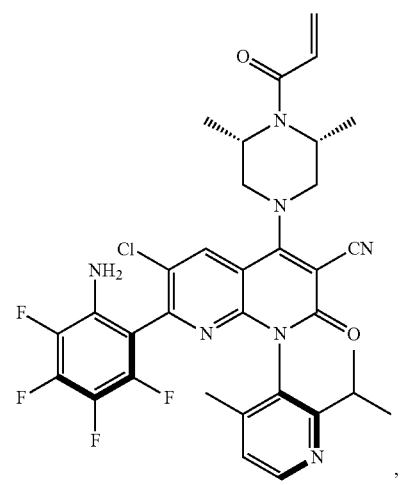
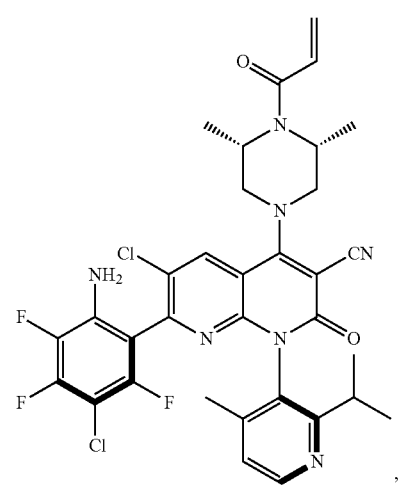
582
-continued
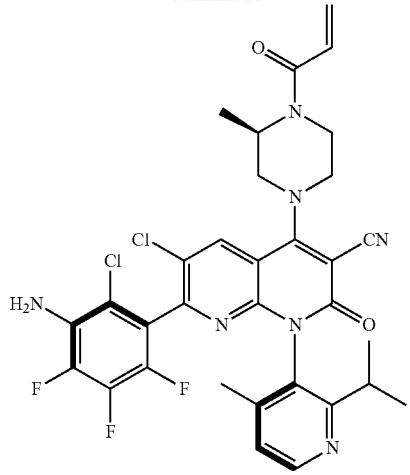
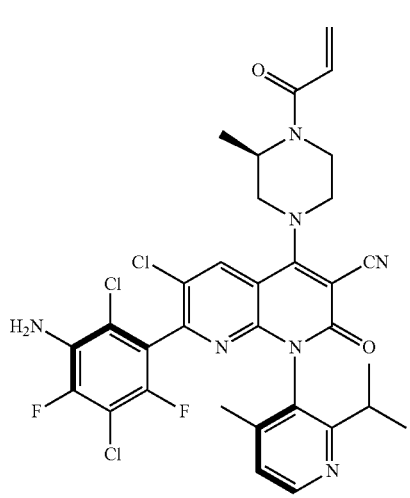

583
-continued
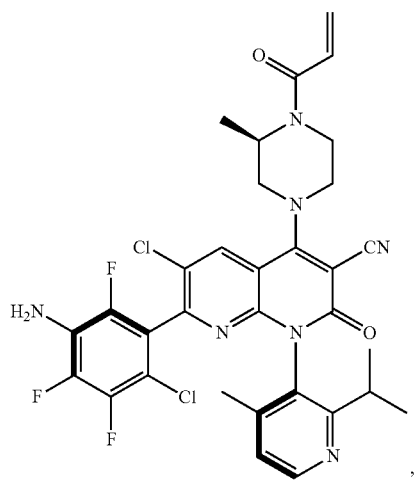
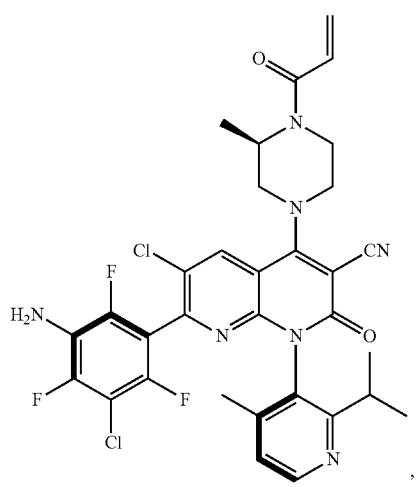
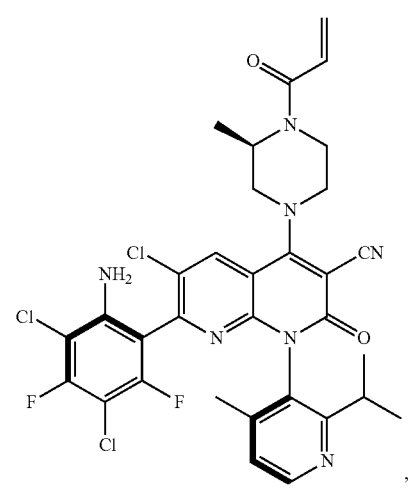
584
-continued
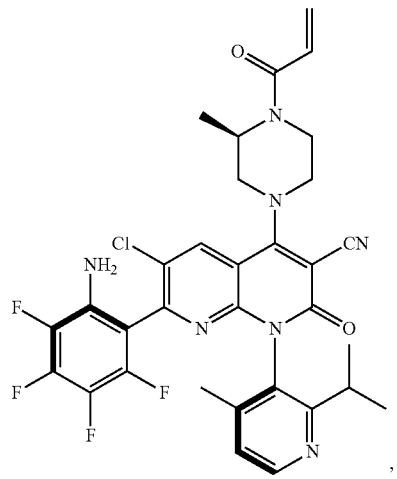
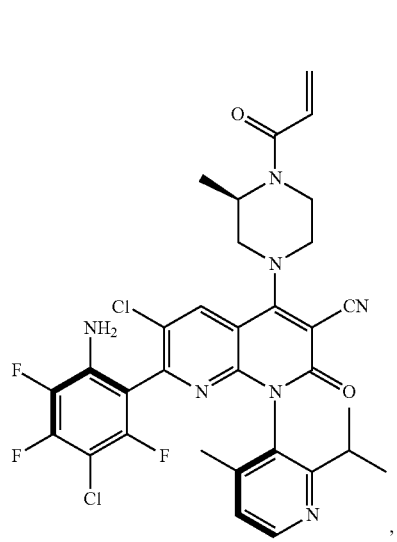
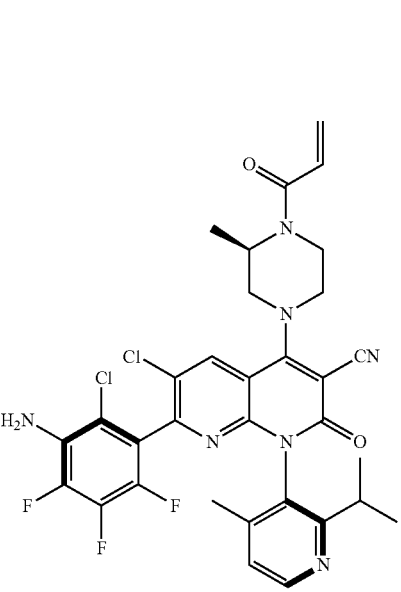

585
-continued
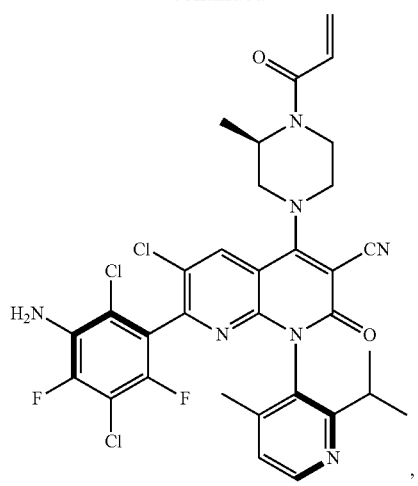
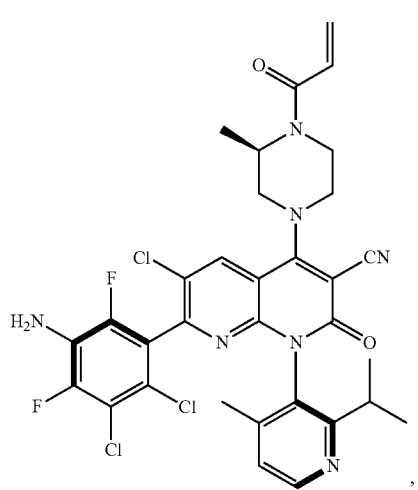
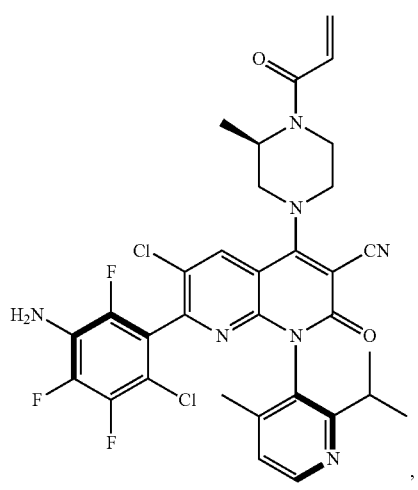
586
-continued
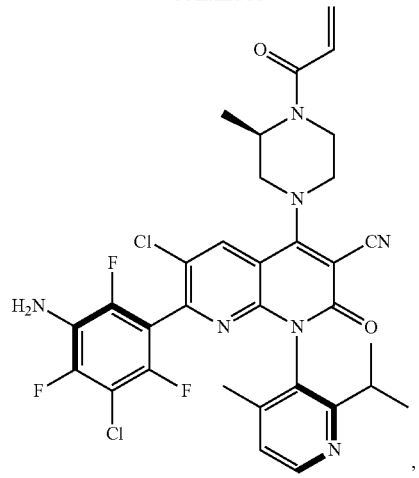
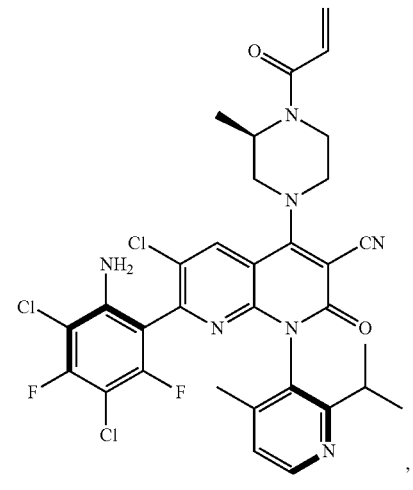
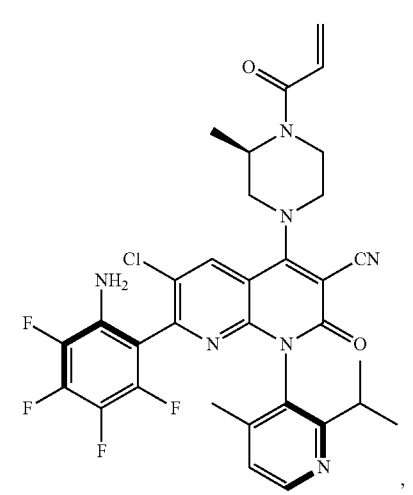

587
-continued
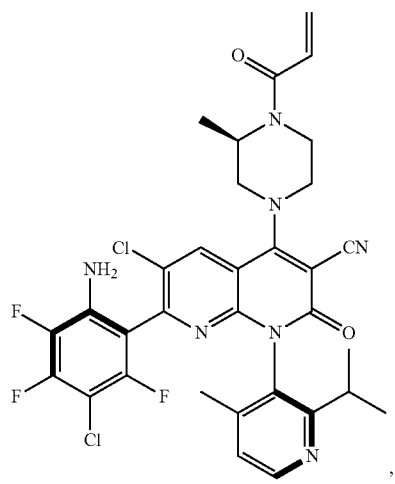
,
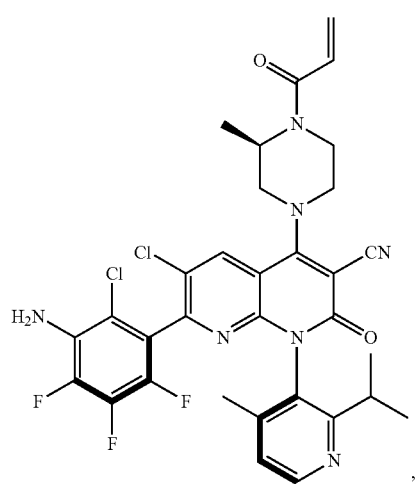
,
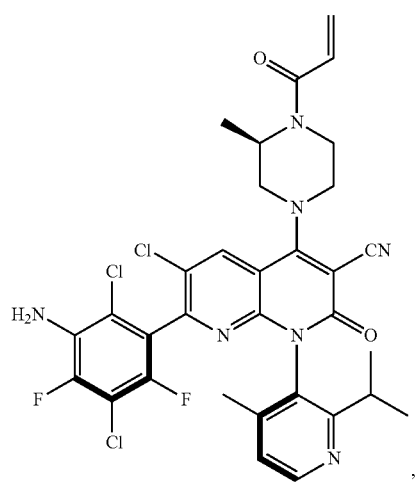
,
588
-continued
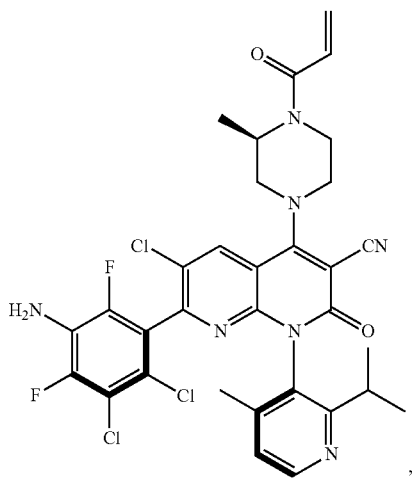
,
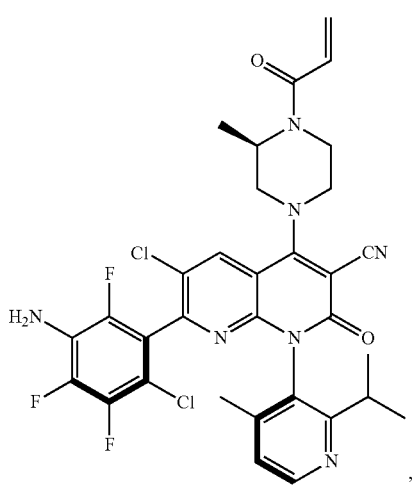
,
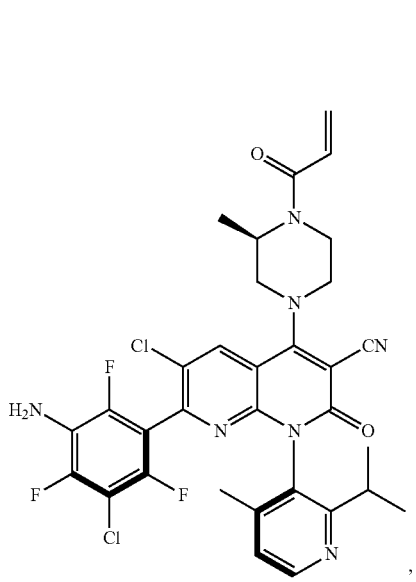
, 589
-continued
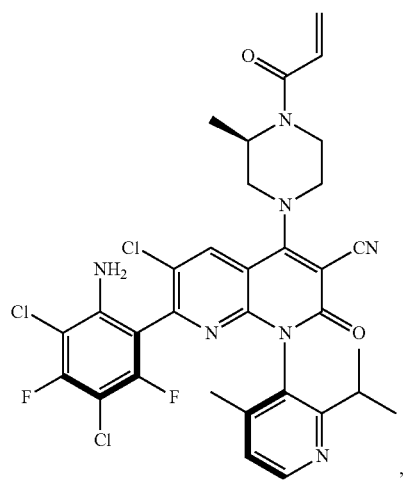
,
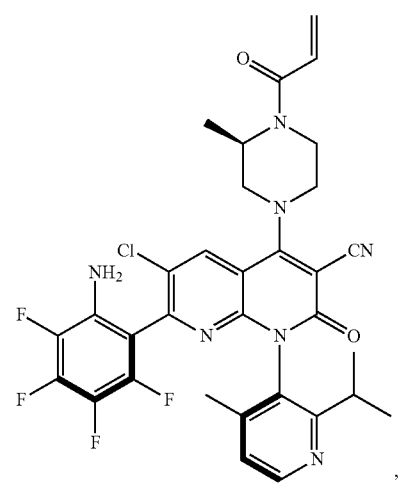
,
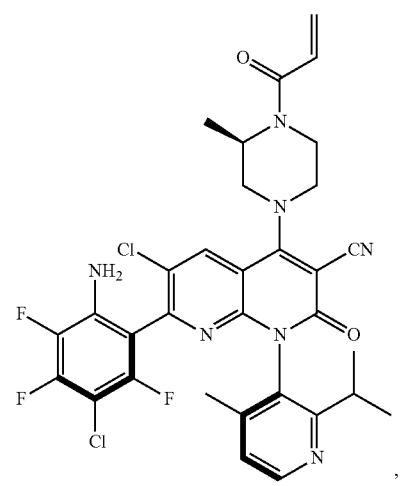
,
590
-continued
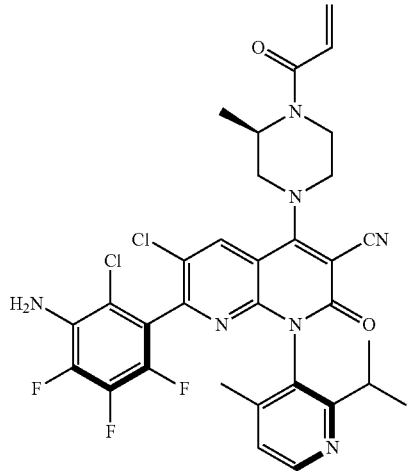
,
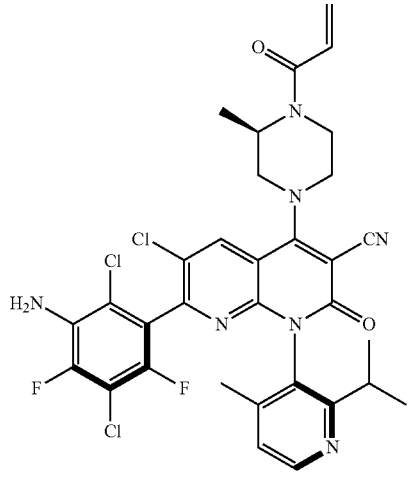
,
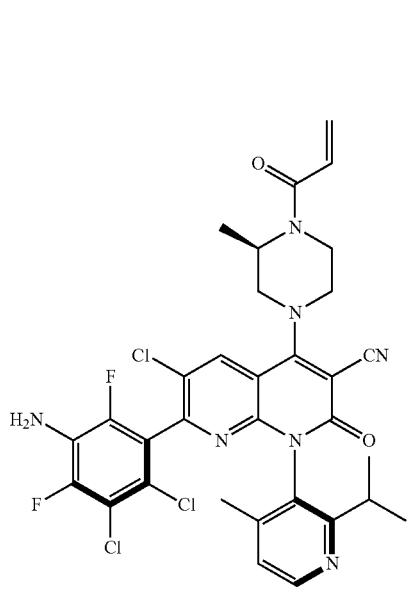
, 591
-continued
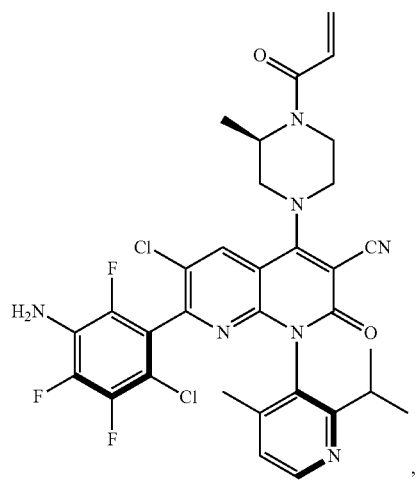
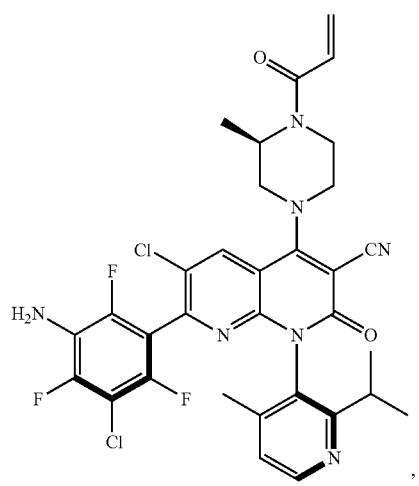
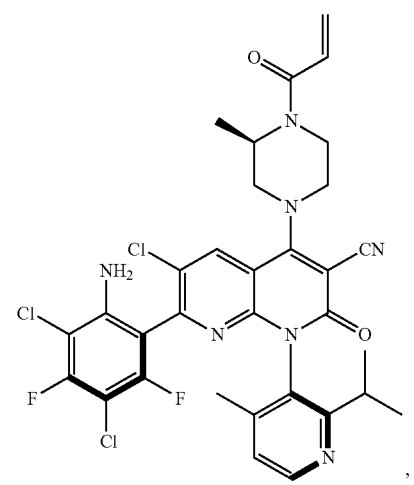
592
-continued
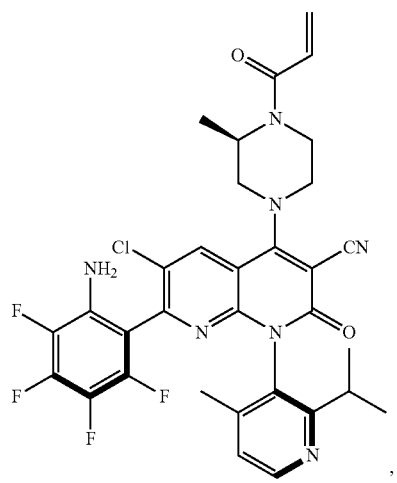
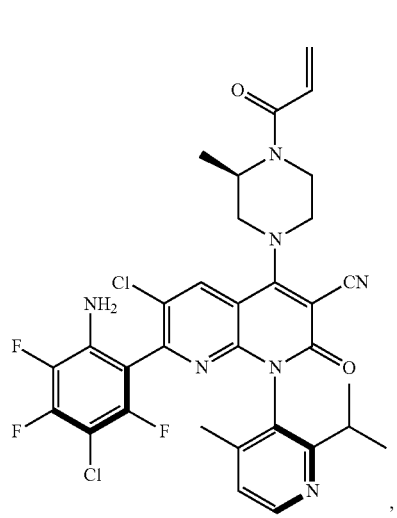
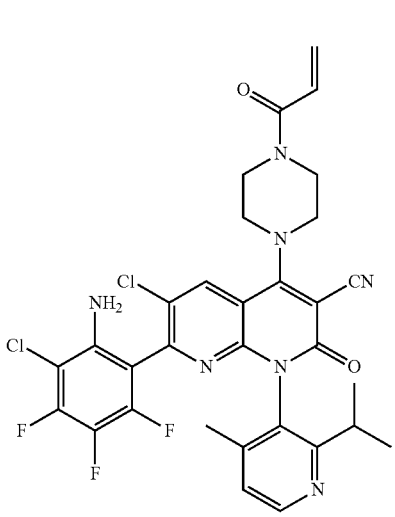

593
-continued
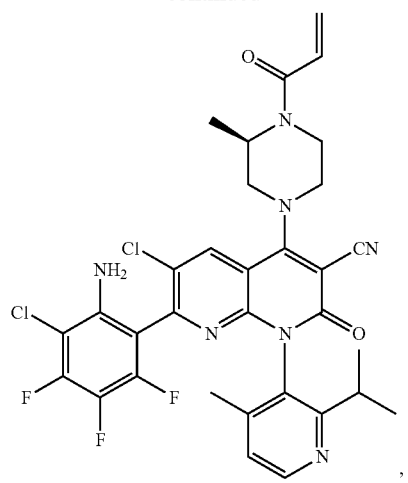
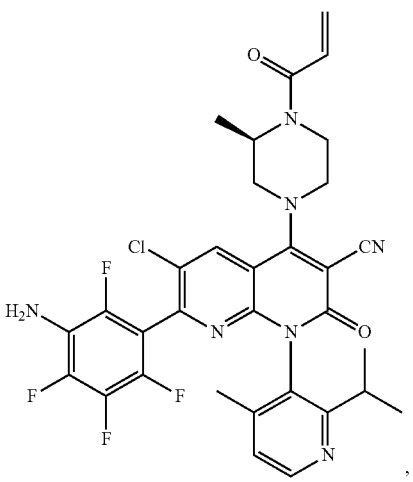
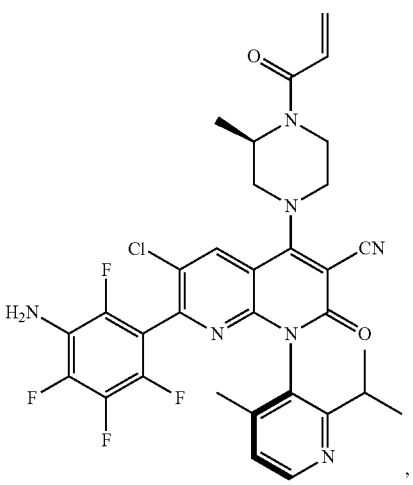
594
-continued
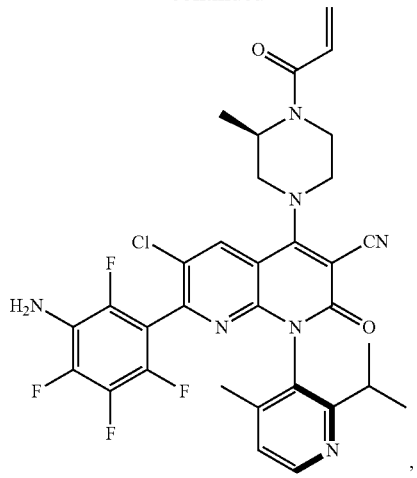
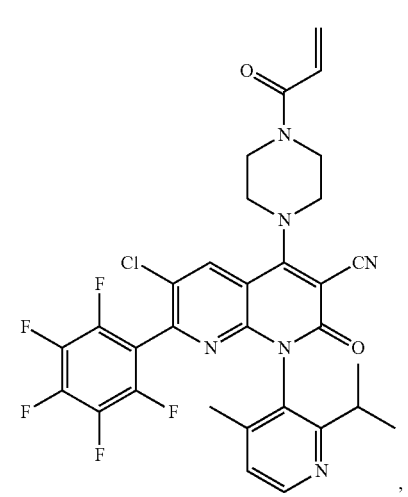
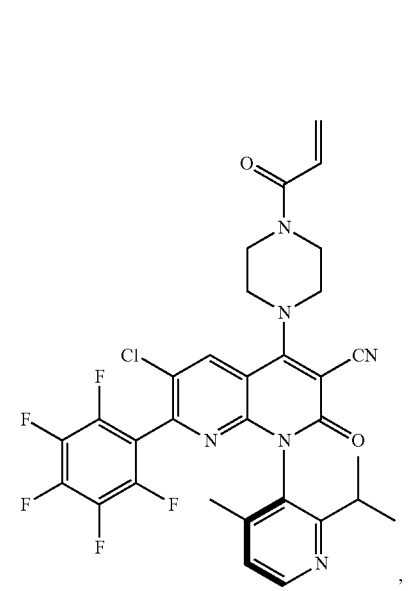

595
-continued
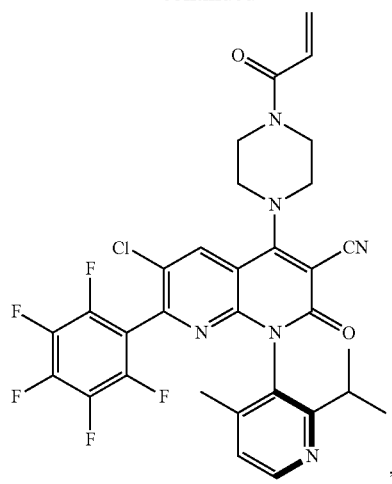
,
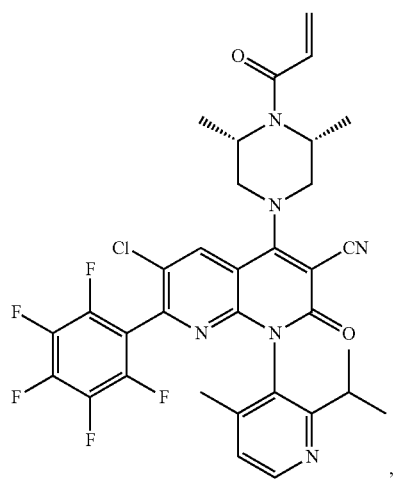
,
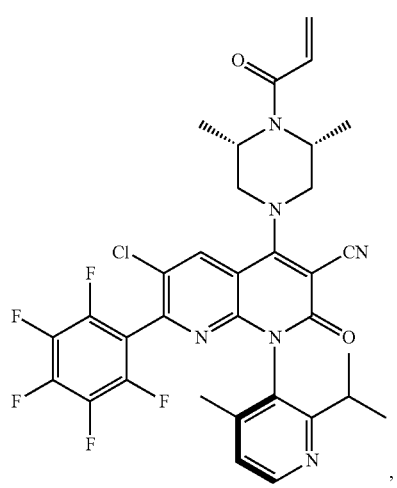
,
596
-continued
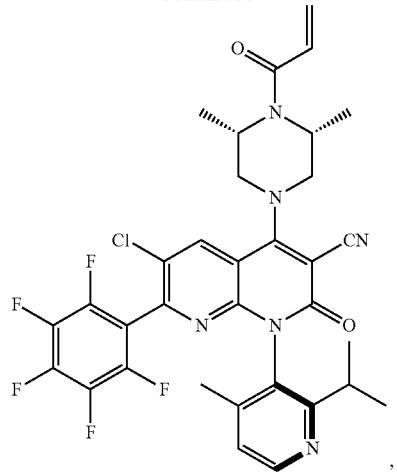
,
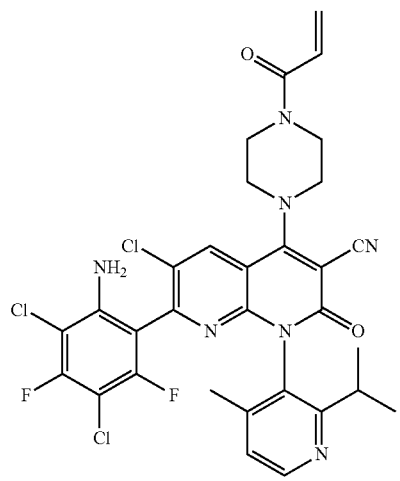
and
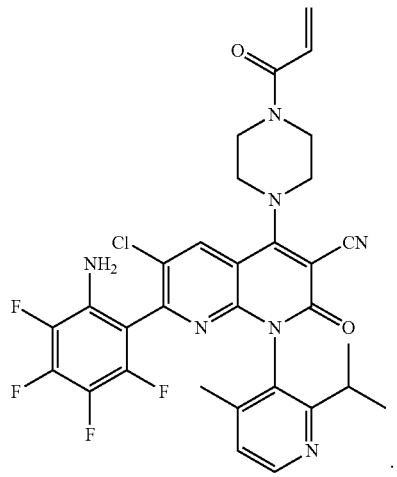
.

EXAMPLE A 4-(4-acryloylpiperazin-1-yl)-7-(2-amino-6-fluorophenyl)-6-chloro-1-(2-isopropyl-4-methylpyridin-3-yl)-2-oxo-1,2-dihydro-1,8-naphthyridine-3-carbonitrile ("Compound A")

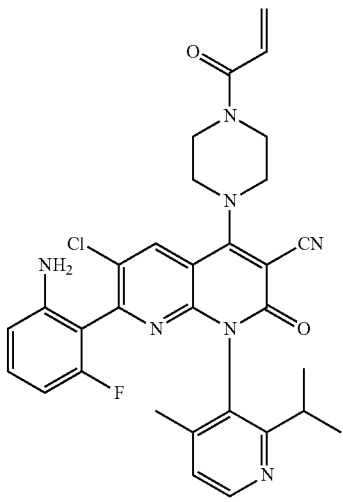

Compound A

Step 1. 4,6,7-trichloro-1-(2-isopropyl-4-methylpyridin-3-yl)-2-oxo-1,2-dihydro-1,8-naphthyridine-3-carbonitrile Into a 50-mL round-bottom flask purged and maintained with an inert atmosphere of nitrogen, was placed 6,7-dichloro-4-hydroxy-1-(2-isopropyl-4-methylpyridin-3-yl)-2-oxo-1,2-dihydro-1,8-naphthyridine-3-carbonitrile (980 mg, 2.51 mmol), $POCl_3$ (1150 mg, 7.50 mmol), DIEA (1.32 g, 10.21 mmol) and acetonitrile (12 mL). The mixture was stirred at 80° C. for 2 h. The reaction was cooled to room temperature and concentrated under vacuum. This resulted in 4,6,7-trichloro-1-(2-isopropyl-4-methylpyridin-3-yl)-2-oxo-1,2-dihydro-1,8-naphthyridine-3-carbonitrile which was used directly in the next step.

Step 2. tert-butyl 4-(6,7-dichloro-3-cyano-1-(2-isopropyl-4-methylpyridin-3-yl)-2-oxo-1,2-dihydro-1,8-naphthyridin-4-yl)piperazine-1-carboxylate Into a 100-mL round-bottom flask purged and maintained with an inert atmosphere of nitrogen, was placed 4,6,7-trichloro-1-(2-isopropyl-4-methylpyridin-3-yl)-2-oxo-1,2-dihydro-1,8-naphthyridine-3-carbonitrile (1.20 g, crude), acetonitrile (20 mL), DIEA (660 mg, 5.10 mmol) and tert-butyl piperazine-1-carboxylate (0.57 g, 3.06 mmol). The reaction mixture was stirred for 2 h at room temperature. The reaction was then quenched by the addition of water (50 mL). The resulting solution was extracted with ethyl acetate (3×50 mL), the organic layers were combined and washed with brine (50 mL), dried over anhydrous $Na_2SO_4$, filtered and concentrated under vacuum. The residues was purified by silica gel column eluted with EA/hexane (v/v=30%~70%). This resulted in 0.92 g (65% in two steps) of tert-butyl 4-(6,7-dichloro-3-cyano-1-(2-isopropyl-4-methylpyridin-3-yl)-2-oxo-1,2-dihydro-1,8-naphthyridin-4-yl)piperazine-1-carboxylate as yellow solid. LCMS: m/z=557 [M+1]$^+$.

Step 3. 4-(4-acryloylpiperazin-1-yl)-6,7-dichloro-1-(2-isopropyl-4-methylpyridin-3-yl)-2-oxo-1,2-dihydro-1,8-naphthyridine-3-carbonitrile Into a 50-mL sealed tube purged and maintained with an inert atmosphere of nitrogen, was placed tert-butyl 4-(6,7-dichloro-3-cyano-1-(2-isopropyl-4-methylpyridin-3-yl)-2-oxo-1,2-dihydro-1,8-naphthyridin-4-yl)piperazine-1-carboxylate (920 mg, 1.65 mmol), TFA (4 ml) and DCM (15 mL). The reaction mixture was stirred at room temperature for 2 h. The reaction mixture was concentrated under vacuum. The residue was dissolved by DCM (15 mL) in 50-mL round-bottom flask, which was followed by the added of DIEA (1.02 g, 10.08 mmol). The reaction mixture was cooled to 0° C. and acryloyl chloride (190 mg, 2.09 mmol) was added. The mixture stirred at room temperature for 2 h. The reaction was then quenched by the addition of water (30 mL). The resulting solution was extracted with ethyl acetate (3×50 mL), the organic layers were combined and washed with brine (30 mL), dried over anhydrous $Na_2SO_4$, filtered and concentrated under vacuum. The residue was purified by silica gel column eluted with EA/hexane (V/V=40%~80%). This resulted in 0.86 g (crude) of 4-(4-acryloylpiperazin-1-yl)-6,7-dichloro-1-(2-isopropyl-4-methylpyridin-3-yl)-2-oxo-1,2-dihydro-1,8-naphthyridine-3-carbonitrile as yellow solid. LCMS: m/z=511 [M+1]$^+$.

Step 4. 4-(4-acryloylpiperazin-1-yl)-7-(2-amino-6-fluorophenyl)-6-chloro-1-(2-isopropyl-4-methylpyridin-3-yl)-2-oxo-1,2-dihydro-1,8-naphthyridine-3-carbonitrile ("Compound A")

Into a 20-mL sealed tube purged and maintained with an inert atmosphere of nitrogen, was placed 4-(4-acryloylpiperazin-1-yl)-6,7-dichloro-1-(2-isopropyl-4-methylpyridin-3-yl)-2-oxo-1,2-dihydro-1,8-naphthyridine-3-carbonitrile (99 mg, 0.19 mmol), 3-fluoro-2-(4,4,5,5-tetramethyl-1,3,2-dioxaborolan-2-yl)aniline (78 mg, 0.33 mmol), $Pd(PPh_3)_4$ (44 mg, 0.03 mmol), $Na_2CO_3$ (65 mg, 0.61 mmol), dioxane (4 mL) and water (1 mL). The reaction mixture was stirred at 90° C. for 2 h. The reaction mixture was filtered and concentrated under vacuum. The residue was purified by Prep-HPLC $CH_3CN/H_2O$ (v:v=1/1)). This resulted in 12 mg (10%) of 4-(4-acryloylpiperazin-1-yl)-7-(2-amino-6-fluorophenyl)-6-chloro-1-(2-isopropyl-4-methylpyridin-3-yl)-2-oxo-1,2-dihydro-1,8-naphthyridine-3-carbonitrile ("Compound A") as yellow solid. LCMS: m/z=586 [M+1]$^+$.

$^1$H NMR (400 MHz, $CD_3OD$) δ 8.52 (s, 1H), 8.46 (d, J=5.0 Hz, 1H), 7.29 (d, J=4.7 Hz, 1H), 7.11 (d, J=6.6 Hz, 1H), 6.89 (dd, J=16.7, 10.6 Hz, 1H), 6.56-6.49 (m, 1H), 6.38-6.30 (m, 2H), 5.90-5.81 (m, 1H), 4.18-3.84 (m, 8H), 2.82-2.70 (m, 1H), 2.08-1.98 (m, 3H), 1.19 (t, J=7.1 Hz, 3H), 1.10-0.93 (m, 3H).

Amgen 6

4-(4-acryloylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile ("Amgen 6")

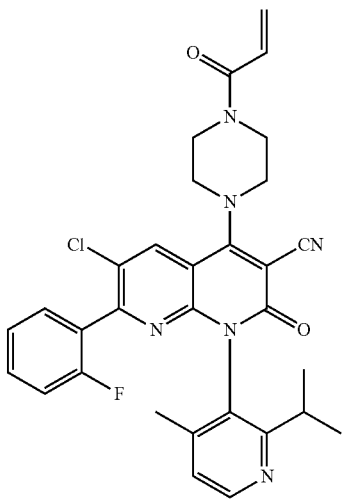

Amgen 6

Step 1. 4-(4-acryloylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile Into a 8-mL sealed tube purged and maintained with an inert atmosphere of nitrogen, was placed 4-(4-acryloylpiperazin-1-yl)-6,7-dichloro-1-(2-isopropyl-4-methylpyridin-3-yl)-2-oxo-1,2-dihydro-1,8-na phthyridine-3-carbonitrile (75 mg, 0.15 mmol), (2-fluorophenyl)boronic acid (56 mg, 0.40 mmol), Pd(dppf)Cl$_2$ (25 mg, 34.17 umol), Na$_2$CO$_3$ (69 mg, 0.65 mmol), dioxane (1 mL) and water (0.2 mL). The reaction mixture was stirred at 90° C. for 2 h. The reaction mixture was filtered and concentrated under vacuum. The residue was purified by silica gel column eluted with EA/hexane (v/v=7/3). The collecting fluid concentrated under vacuum. The residue was purified by Prep-HPLC CH$_3$CN/H$_2$O (v/v=3/2). This resulted in 22 mg of 4-(4-acryloylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile ("Amgen 6") as yellow solid. LCMS: m/z=571 [M+1]$^+$.

$^1$H NMR (400 MHz, CD$_3$OD) δ 8.52 (s, 1H), 8.43 (d, J=5.0 Hz, 1H), 7.54-7.46 (m, 1H), 7.32-7.13 (m, 4H), 6.89 (dd, J=16.7, 10.6 Hz, 1H), 6.33 (d, J=16.7 Hz, 1H), 5.86 (d, J=10.6 Hz, 1H), 4.15-3.90 (m, 8H), 2.79-2.65 (m, 1H), 2.04 (s, 3H), 1.19 (d, J=6.8 Hz, 3H), 1.00 (d, J=6.7 Hz, 3H).

The mixture of 4-(4-acryloylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile atropisomers (1.59 g) was purified by Chiral-Prep-HPLC with the following conditions: Column, CHIRAL Cellulose-SB, 3 cm×25 cm, 5 um; mobile phase, CO$_2$, IPA:ACN=1:1; Detector, UV 254 nm. This resulted in 739 mg (46%) of 4-(4-acryloylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile (the first eluting isomer, "Amgen 6-1") as a yellow solid; LCMS: m/z=571 [M+1]$^+$.

And 709 mg (45%) of 4-(4-acryloylpiperazin-1-yl)-6-chloro-7-(2-fluorophenyl)-1-(2-isopropyl-4-methyl pyridin-3-yl)-2-oxo-1,2-dihydro-1,8-naphthyridine-3-carbonitrile (the second eluting isomer, "Amgen 6-2") as a yellow solid; LCMS: m/z=571 [M+1]$^+$.

$^1$H NMR (400 MHz, CD$_3$OD) δ 8.50 (s, 1H), 8.41 (d, J=5.0 Hz, 1H), 7.52-7.37 (m, 1H), 7.30-7.08 (m, 4H), 6.87 (dd, J=16.8, 10.6 Hz, 1H), 6.38-6.24 (m, 1H), 5.83 (dd, J=10.6, 1.8 Hz, 1H), 4.09-3.82 (m, 8H), 2.78-2.63 (m, 1H), 2.02 (s, 3H), 1.16 (d, J=6.8 Hz, 3H), 0.98 (d, J=6.8 Hz, 3H).

Amgen 6.3

4-(4-acryloylpiperazin-1-yl)-7-(2-amino-6-fluorophenyl)-6-chloro-1-(4,6-diisopropylpyrimidin-5-yl)-2-oxo-1,2-dihydro-1,8-naphthyridine-3-carbonitrile ("Amgen 6.3")

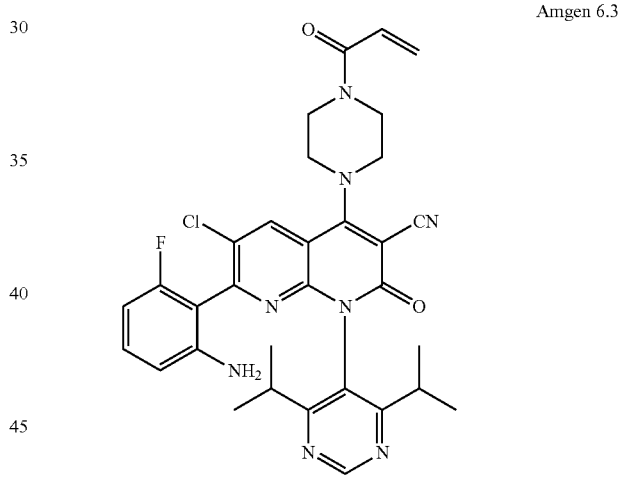

Amgen 6.3

4-(4-acryloylpiperazin-1-yl)-7-(2-amino-6-fluorophenyl)-6-chloro-1-(4,6-diisopropylpyrimidin-5-yl)-2-oxo-1,2-dihydro-1,8-naphthyridine-3-carbonitrile ("Amgen 6.3") were prepared according to prior method as yellow solid. LCMS: m/z=615 [M+1]$^+$.

$^1$H NMR (400 MHz, DMSO-d$_6$) δ 9.09 (s, 1H), 8.48 (s, 1H), 7.05 (q, J=7.8 Hz, 1H), 6.93 (dd, J=16.6, 10.4 Hz, 1H), 6.44 (d, J=8.3 Hz, 1H), 6.31 (t, J=8.9 Hz, 1H), 6.21 (dd, J=16.7, 2.4 Hz, 1H), 5.77 (dd, J=10.4, 2.4 Hz, 1H), 5.08 (s, 2H), 3.90 (m, 8H), 2.90-2.74 (m, 1H), 2.70-2.55 (m, 1H), 1.07 (dd, J=12.2, 6.7 Hz, 6H), 1.00 (d, J=6.6 Hz, 3H), 0.86 (d, J=6.7 Hz, 3H).

Amgen 7.3

4-((3S,5R)-4-acryloyl-3,5-dimethylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile ("Amgen 7.3")

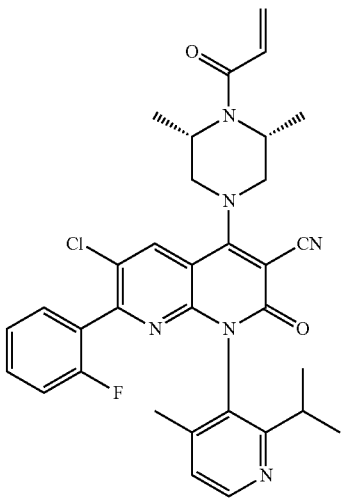

Amgen 7.3

Step 1. 4-((3S,5R)-4-acryloyl-3,5-dimethylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile Into a 20-mL sealed tube purged and maintained with an inert atmosphere of nitrogen, was placed 4-((3S,5R)-4-acryloyl-3,5-dimethylpiperazin-1-yl)-6,7-dichloro-1-(2-isopropyl-4-methylpyridin-3-yl)-2-oxo-1,2-dihydro-1,8-naphthyridine-3-carbonitrile (109 mg, 0.20 mmol), ((2-fluorophenyl)boronic acid (110 mg, 0.79 mmol), Pd(PPh$_3$)$_4$ (85 mg, 0.073 mmol), Na$_2$CO$_3$ (69 mg, 0.65 mmol), dioxane (6 mL) and water (2 mL). The reaction mixture was stirred at 80° C. for 4 h. The reaction was then quenched by the addition of water (100 mL). The resulting solution was extracted with ethyl acetate (3×100 mL), the organic layers were combined and washed with brine (100 mL), dried over anhydrous Na$_2$SO$_4$, filtered and concentrated under vacuum. The residue was purified by Prep-HPLC (CH$_3$CN/H$_2$O (v/v=1/1). This resulted in 31 mg (26% in two steps) of 4-((3S,5R)-4-acryloyl-3,5-dimethylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile ("Amgen 7.3") as yellow solid. LCMS: m/z=599 [M+1]$^+$.

$^1$H NMR (400 MHz, CD$_3$OD) δ 8.80 (s, 1H), 8.44 (d, J=5.0 Hz, 1H), 7.48 (dd, J=8.4, 4.6 Hz, 1H), 7.40-7.22 (m, 4H), 6.98-6.85 (m, 1H), 6.35 (d, J=16.5 Hz, 1H), 5.86 (d, J=10.6 Hz, 1H), 4.79 (s, 2H), 4.14-3.79 (m, 4H), 2.80-2.74 (m, 1H), 2.05 (s, 3H), 1.68 (d, J=7.0 Hz, 6H), 1.19 (d, J=6.8 Hz, 3H), 1.01 (d, J=6.7 Hz, 3H).

The mixture of 4-((3S,5R)-4-acryloyl-3,5-dimethylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile atropisomers (1.48 g) was purified by Chiral-Prep-HPLC with the following conditions: Column, CHIRAL Cellulose-SB, 3 cm×25 cm, 5 um; mobile phase, Hex/EtOH=(v/v=50/50); Detection wavelength, UV 254 nm. This resulted in 625 mg (42%) of 4-((3S,5R)-4-acryloyl-3,5-dimethylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile (the first eluting isomer, "Amgen 7.3-1") as a yellow solid; LCMS: m/z=599 [M+1]$^+$.

$^1$H NMR (400 MHz, CD$_3$OD) δ 8.68 (s, 1H), 8.32 (d, J=5.0 Hz, 1H), 7.42-7.30 (m, 1H), 7.23-7.01 (m, 4H), 6.78 (dd, J=16.7, 10.6 Hz, 1H), 6.22 (dd, J=16.7, 1.9 Hz, 1H), 5.73 (dd, J=10.6, 1.9 Hz, 1H), 4.66 (s, 2H), 3.99-3.83 (m, 2H), 3.74-3.72 (m, 2H), 2.63-2.61 (m, 1H), 1.93 (s, 3H), 1.55 (d, J=7.0 Hz, 6H), 1.10-1.08 (m, 3H), 0.90-0.89 (m, 3H).

And 669 mg (45%) of 4-((3S,5R)-4-acryloyl-3,5-dimethylpiperazin-1-yl)-6-chloro-7-(2-fluorophenyl)-1-(2-isopropyl-4-methylpyridin-3-yl)-2-oxo-1,2-dihydro-1,8-naphthyridine-3-carbonitrile (the second eluting isomer, "Amgen 7.3-2") as a yellow solid; LCMS: m/z=599 [M+1]$^+$.

$^1$H NMR (400 MHz, CD$_3$OD) δ 8.80 (s, 1H), 8.43 (d, J=5.0 Hz, 1H), 7.57-7.41 (m, 1H), 7.37-7.07 (m, 4H), 6.90 (dd, J=16.7, 10.6 Hz, 1H), 6.34 (dd, J=16.7, 1.9 Hz, 1H), 5.85 (dd, J=10.6, 1.9 Hz, 1H), 4.78 (s, 2H), 4.07-3.98 (m, 2H), 3.86-3.84 (m, 2H), 2.76-2.74 (m, 1H), 2.05 (s, 3H), 1.68-1.66 (m, 6H), 1.12-1.10 (m, 3H), 0.91-0.89 (m, 3H).

Pharmacological Testing

1. SOS1 Catalyzed Nucleotide Exchange Assay

HIS-KRAS (G12C, aa 2-185, Sino biological) was diluted to 5 μM in EDTA buffer (20 mM HEPES, pH 7.4, 50 mM NaCl, 10 mM EDTA, 0.01% (v/v) Tween-20) and incubated for 30 min at 25° C. The EDTA pretreated HIS-KRAS (G12C) was diluted to 12 nM in assay buffer (25 mM HEPES, pH 7.4, 120 mM NaCl, 5 mM MgCl$_2$, 1 mM DTT, 0.01% (v/v) Tween 20, 0.1% (w/v) BSA) containing 120 nM GDP (Sigma) and MAb Anti 6HIS-Tb cryptate Gold (Cisbio) and incubated for 1 hour at 25° C. to prepare GDP-loaded HIS-KRAS (G12C). The GDP-loaded HIS-KRAS (G12C) was pre-incubation with diluted compounds in a 384-well plate (Greiner) for 1 hour, then purified SOS1 ExD (Flag tag, aa 564-1049) and BODIPY™ FL GTP (Invitrogen) were added to the assay wells (Final concentration: 3 nM HIS-KRAS (G12C), 2 μM SOS1 ExD, 80 nM BODIPY™ FL GTP, 21 ng/mL MAb Anti 6HIS-Tb cryptate Gold) and incubated for 4 hours at 25° C. TR-FRET signals were then read on Tecan Spark multimode microplate reader. The parameters were F486: Excitation 340 nm, Emission 486 nm, Lag time 100 μs, Integration time 200 μs; F515: Excitation 340 nm, Emission 515 nm, Lag time 100 μs, Integration time 200 μs. TR-FRET ratios for each individual wells were calculated by equation: TR-FRET ratio=(Signal F515/Signal F486)*10000. Then the data were analyzed using a 4-parameter logistic model to calculate IC$_{50}$ values. The results of the SOS1 catalyzed nucleotide exchange assay are in the following Table 8:

TABLE 8

| Compound | SOS1 catalyzed nucleotide exchange IC$_{50}$ (nM) |
| --- | --- |
| Compound 1 | 3.06 |
| Compound 1-1 | 14.1 |
| Compound 1-2 | 1.41 |
| Compound 2 | 6.66 |
| Compound 3 | 3.67 |
| Compound 4 | 3.48 |
| Compound 5 | 5.97 |
| Compound 6 | 1.51 |

TABLE 8-continued

| Compound | SOS1 catalyzed nucleotide exchange IC$_{50}$ (nM) |
| --- | --- |
| Compound 7 | 14.9 |
| Compound 8 | 6.68 |
| Compound 9 | 2.30 |
| Compound 10-1 | 43.9 |
| Compound 10-2 | 4.16 |
| Compound 11-1 | 29.6 |
| Compound 11-2 | 2.11 |
| Compound 12 | 3.85 |
| Compound 12-1 | 16.0 |
| Compound 12-2 | 2.01 |
| Compound 13 | 6.63 |
| Compound 13-1 | 2.73 |
| Compound 13-2 | 11.5 |
| Compound 14 | 3.56 |
| Compound 15-1 | 6.87 |
| Compound 15-2 | 83.9 |
| Compound A | 1.69 |
| Amgen 6 | 4.40 |
| Amgen 6.3 | 2.77 |
| Amgen 7.3 | 10.5 |

From the Table 8, it can be seen that the representative compounds in the present invention have better activity to inhibit the SOS1 catalyzed nucleotide exchange.

2. Phospho-ERK1/2(THR202/TYR204) HTRF Assay

NCI-H358 cells expressing KRAS G12C were cultured in RPMI 1640 medium (Gibco) containing 10% fetal bovine serum (Gibco). The NCI-H358 cells in culture medium were seeded in 96-well plates at a concentration of 40,000 cells/well and then put in a 37° C./5% $CO_2$ cell incubator to incubate overnight. The next day, culture medium was removed and the compound diluted in assay medium (RPMI 1640, 0.1% FBS) was added in each well. After 2 hours incubation in a 37° C./5% $CO_2$ cell incubator, the assay medium in 96-well plates was removed, then 50 μL of 1× blocking reagent-supplemented lysis buffer (Cisbio) was added and the plates were incubated at 25° C. for 45 min with shaking. 10 μL of cell lysates from the 96-well plates were transferred to a 384-well plate (Greiner) containing 2.5 μL/well HTRF® pre-mixed antibodies (Cisbio 64AER-PEH). Incubate 4 hours at 25° C. and then read HTRF signals on Tecan Spark multimode microplate reader. The data were analyzed using a 4-parameter logistic model to calculate IC$_{50}$ values. The results of the Phospho-ERK1/2 (THR202/TYR204) HTRF assay are in the following Table 9:

TABLE 9

| Compound | p-ERK IC$_{50}$ (nM) |
| --- | --- |
| Compound 1 | 16.4 |
| Compound 1-1 | 176 |
| Compound 1-2 | 10.2 |
| Compound 2 | 33.6 |
| Compound 3 | 21.4 |
| Compound 4 | 40.1 |
| Compound 5 | 141 |
| Compound 6 | 25.1 |
| Compound 8 | 48.0 |
| Compound 9 | 26.3 |
| Compound 10-1 | 217 |
| Compound 10-2 | 22.0 |
| Compound 11-1 | 258 |
| Compound 11-2 | 23.6 |
| Compound 12 | 39.7 |
| Compound 12-1 | 117 |
| Compound 12-2 | 12.3 |
| Compound 13 | 87.0 |
| Compound 13-1 | 21.8 |
| Compound 13-2 | 138 |
| Compound 14 | 37.6 |
| Compound 15-1 | 44.0 |
| Compound 15-2 | 327 |
| Compound A | 14.2 |
| Amgen 6 | 29.9 |
| Amgen 6.3 | 20.1 |
| Amgen 7.3 | 44.5 |

From Table 9, it can be seen that representative compounds in the present invention have better activity to inhibit the phosphorylation of ERK1/2 the NCI-H358 cells.

3. Mouse Pharmacokinetic Study

The purpose of this study was to evaluate the pharmacokinetic properties of compounds in Balb/c mouse (♀) following single dose administration. The day before administration, mice were fasted overnight and free access to water. Six mice were needed for each compound and the six mice were divided into two groups (n=3/group), group A and group B. Mice in group A were treated with a single 3 mg/kg dose of compound (iv). Mice in group B were treated with a single 10 mg/kg dose of compound (po). For each mouse in group A, blood samples were collected at pre-dose, and at the time point of 0.083, 0.25, 0.5, 1, 2, 4, 6, 8 and 24 h post-dose. For each mouse in group B, blood samples were collected at pre-dose, and at the time point of 0.25, 0.5, 1, 2, 3, 4, 6, 8 and 24 h post-dose. Blood samples were placed on ice until centrifugation to obtain plasma samples. The plasma samples were stored at −80° C. until analysis. The concentration of compound in plasma samples were determined using a LC-MS/MS method. The results are in the following Table 10:

TABLE 10

| | 3 mg/kg, iv | | 10 mg/kg, po | | |
| --- | --- | --- | --- | --- | --- |
| Compound | CL (mL/min/kg) | Vss (L/kg) | C$_{max}$ (ng/mL) | AUC$_{0-24\,h}$ (ng · h/mL) | Oral BA (F %) |
| Compound 1 | 21.4 | 1.87 | 1397 | 4025 | 51.3 |
| Compound 11 | 7.2 | 1.0 | 3340 | 9587 | 38 |
| Compound 13 | 9.8 | 1.4 | 3013 | 12763 | 74 |
| Compound 14 | 10 | 0.9 | 4023 | 10498 | 63 |
| Compound A | 65.2 | 1.13 | 241 | 207 | 8.05 |
| Amgen 6 | 72 | 2.6 | 901 | 1032 | 44 |
| Amgen 6.3 | 32 | 1.4 | 1587 | 1658 | 32 |

From Table 10, it can be seen that Compound 1, Compound 11, Compound 13 and Compound 14 have excellent pharmacokinetic properties (such as the higher C$_{max}$ and AUC) in mouse model comparative with the Compound A, Amgen 6 and Amgen 6.3, which make them more suitable for treating cancers with KRAS G12C mutation as an orally therapeutic active ingredient in clinic.

4. Dog Pharmacokinetic Study

The purpose of this study was to evaluate the pharmacokinetic properties of compounds in beagle dog following single dose administration. The day before administration, dogs were fasted overnight and free access to water. Four beagle dogs were needed for each compound and the four dogs were divided into two groups (one male (♂) and one female (♀) in each group). Dogs in group A were treated with a single 1 mg/kg dose of compound (iv). Dogs in group B were treated with a single 10 mg/kg dose of compound (po). For dogs in group A, blood samples were collected at pre-dose, and at the time point of 0.083, 0.25, 0.5, 1, 2, 4, 6, 8 and 24 h. For dogs in group B, blood samples were collected at pre-dose, and at the time point of 0.25, 0.5, 1, 2, 4, 6, 8 and 24 h post-dose. Blood samples were placed on ice until centrifugation to obtain plasma samples. The plasma samples were stored at −80° C. until analysis. The concentration of compound in plasma samples were determined using a LC-MS/MS method. The results are in following Table 11:

TABLE 11

| Compound | Sex | 1 mg/kg, iv | | 10 mg/kg, po | | |
|---|---|---|---|---|---|---|
| | | CL (mL/min/kg) | $V_{SS}$ (L/kg) | $C_{max}$ (ng/mL) | $AUC_{0-24\,h}$ (ng·h/mL) | Oral BA (F %) |
| Compound 1-2 | ♂ | 15.9 | 0.9 | 3420 | 6724 | 64.3 |
| | ♀ | 18.1 | 1.1 | 2980 | 5953 | 65.1 |
| Compound 9 | ♂ | 17.7 | 1.37 | 2490 | 7788 | 83.2 |
| | ♀ | 20.5 | 1.72 | 2260 | 6323 | 78.5 |
| Amgen 6 | ♂ | 11.8 | 0.412 | 3690 | 2944 | 20.9 |
| | ♀ | 15.5 | 0.543 | 2580 | 1326 | 12.4 |
| Amgen 6.3 | ♂ | 239 | 2.3 | 8.0 | 5.1 | 0.7 |
| | ♀ | 329 | 3.1 | — | — | — |

From Table 11, it can be seen that Compound 1-2 and Compound 9 have excellent pharmacokinetic properties (such as the higher $C_{max}$ and AUC) in beagle dog model comparative with the Amgen 6 and 6.3, which make them more suitable for treating cancers with KRAS G12C mutation as an orally therapeutic active ingredient in clinic.

5. Cynomolgus Monkey Pharmacokinetic Study

The purpose of this study was to evaluate the pharmacokinetic properties of compounds in Cynomolgus monkey following single dose administration. The day before administration, monkeys were fasted overnight and free access to water. Four monkeys are needed for each compound and the four monkeys were divided into two groups (one male(♂) and one female (♀) in each group), group A and group B. Monkeys in group A were treated with a single 1 mg/kg dose of compound (iv). Monkeys in group B were treated with a single 3 mg/kg dose of compound (po). For monkeys in group A, blood samples were collected at pre-dose, and at the time point of 0.083, 0.25, 0.5, 1, 2, 4, 6, 8 and 24 h. For monkeys in group B, blood samples were collected at pre-dose, and at the time point of 0.25, 0.5, 1, 2, 4, 6, 8 and 24 h post-dose. Blood samples were placed on ice until centrifugation to obtain plasma samples. The plasma samples were stored at −80° C. until analysis. The concentration of compound in plasma samples were determined using a LC-MS/MS method. The results are in following Table 12:

TABLE 12

| Compound | Sex | 1 mg/kg, iv | | 3 mg/kg, po | | |
|---|---|---|---|---|---|---|
| | | CL (mL/min/kg) | $V_{SS}$ (L/kg) | $C_{max}$ (ng/mL) | $AUC_{0-24\,h}$ (ng·h/mL) | Oral BA (F %) |
| Compound 1-2 | ♂ | 5.25 | 0.61 | 2030 | 7938 | 83.5 |
| | ♀ | 7.19 | 0.86 | 2680 | 6854 | 98.9 |
| Compound 9 | ♂ | 6.06 | 0.66 | 2130 | 9697 | 120 |
| | ♀ | 5.73 | 0.77 | 1060 | 3741 | 44.4 |

From Table 12, it can be seen that Compound 1-2 and Compound 9 have excellent pharmacokinetic properties (such as the higher $C_{max}$ and AUC) in monkey model, which make them more suitable for treating cancers with KRAS G12C mutation as an orally therapeutic active ingredient in clinic.

6. The Efficacy in NCI-H1373 Xenograft Model

NCI-H1373 cells (5.0E+06 cells) were injected subcutaneously into the right flank of female BALB/c nude mice (6-8 weeks) in a mixture with PBS and Matrigel (Corning) (PBS/Matrigel=1:1 (v/v)). Mice were monitored daily and caliper measurements began when tumors became visible. Tumor volume was calculated by measuring two perpendicular diameters using the formula: $(L*W^2)/2$ in which L and W refer to the length and width tumor diameter, respectively. When the average tumor volume reached 150-200 mm³, mice were grouped randomly (n=6/group) and treated with compounds. Tumor volume and mice weight was measured twice a week during treatment (~ 3 weeks). Tumor growth inhibition rates were calculated by TGI %=(1−(Vt−Vt$_0$)/(Vc−Vc$_0$))*100%, wherein Vc and Vt are the mean tumor volume of control and treated groups at the end of the study respectively, and Vc$_0$ and Vt$_0$ are the mean tumor volume of control and treated groups at the start respectively. The results are in the following Table 13 and FIG. 8:

TABLE 13

| Groups | Tumor volume at the start, mm³ | Tumor volume at the end (Day 21), mm³ | TGI % |
|---|---|---|---|
| Vehicle | 193 | 1879 | — |
| Compound 1-2, 10 mg/kg, QD | 193 | 144 | 103 |
| Compound 12-2, 10 mg/kg, QD | 193 | 63 | 108 |

Figure 8:
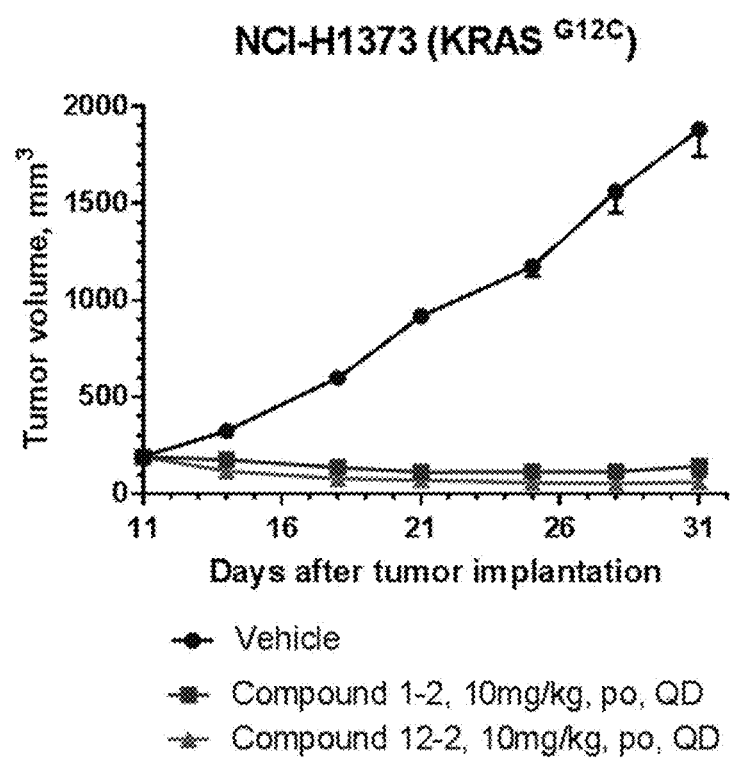
FIG. 8 shows the efficacy of Compound 1-2 and Compound 12-2 in NCI-H1373 xenograft model.

From Table 13 and FIG. 8, it can be seen that Compound 1-2 and Compound 12-2 have excellent efficacy in vivo.

7. Safety Exploration in MIA PaCa-2 xenograft Model

MIA PaCa-2 cells (1.0E+07 cells) were injected subcutaneously into the right flank of female BALB/c nude mice (6-8 weeks) in a mixture with PBS and Matrigel (Corning) (PBS/Matrigel=1:1 (v/v)). Mice were monitored daily and caliper measurements began when tumors became visible.-

Figure 9:
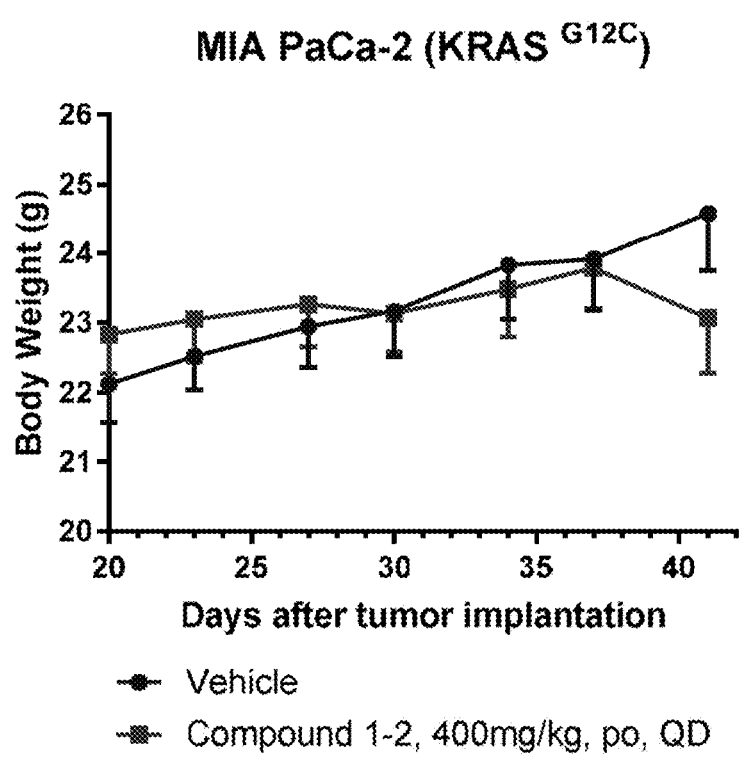
FIG. 9 shows the safety of Compound 1-2 in MIA-PaCa-2 model.

Tumor volume was calculated by measuring two perpendicular diameters using the following formula: $(L*W^2)/2$ in which L and W refer to the length and width tumor diameter, respectively. After mice were grouped to study the efficacy, the remaining mice (n=6) were used to explore the safety. The mice were treated with 400 mg/kg compound 1-2 (po, QD) for 22 days, and mice body weight was measured twice a week during treatment. The weight of mice varies with the number of days after cell inoculation is shown in FIG. 9. From FIG. 9, it can be seen that the Compound 1-2 have good safety.

It is to be understood that, if any prior art publication is referred to herein; such reference does not constitute an admission that the publication forms a part of the common general knowledge in the art in any country. Although the foregoing invention has been described in some detail by way of illustration and example for purposes of clarity of understanding, it is apparent to those skilled in the art that certain minor changes and modifications will be practiced. Therefore, the description and Examples should not be construed as limiting the scope of the invention.

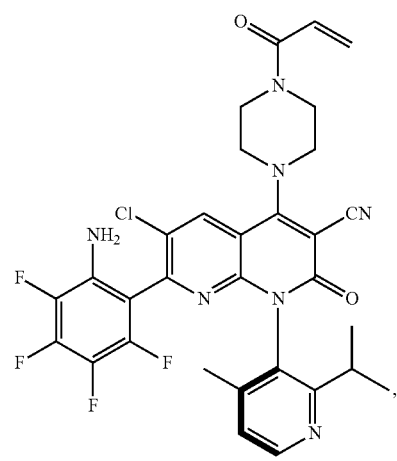

and wherein the method comprises a coupling reaction between a compound of
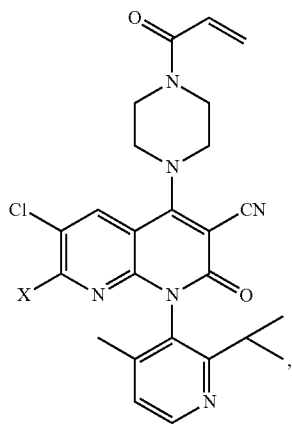
and a compound of
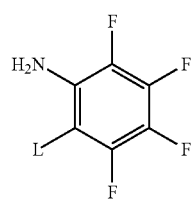
according to the following reaction Scheme 3 or between a compound of
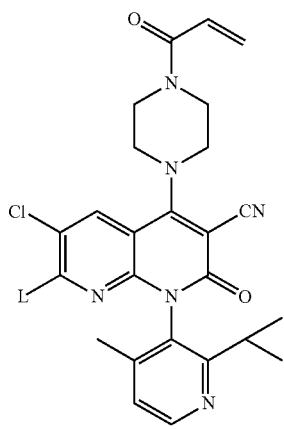
and a compound of
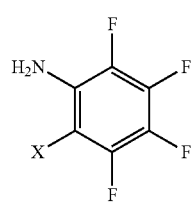
according to the following reaction Scheme 4 catalyzed by a transition metal palladium or nickel reagent,
Scheme 3
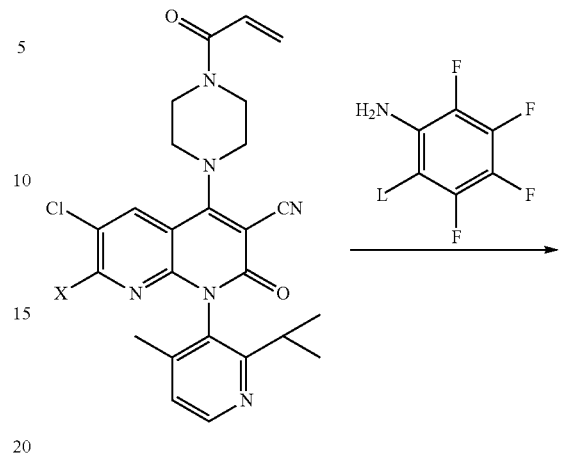
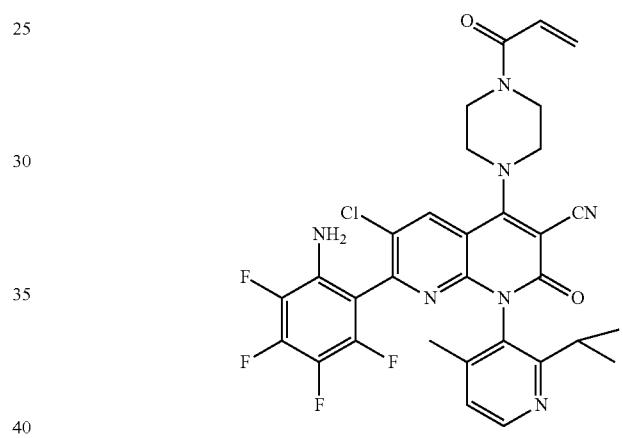
Scheme 4
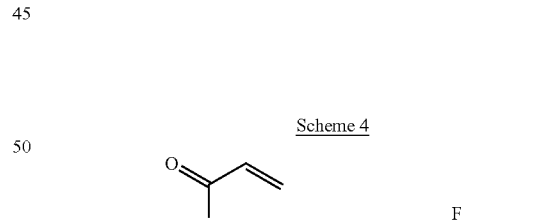

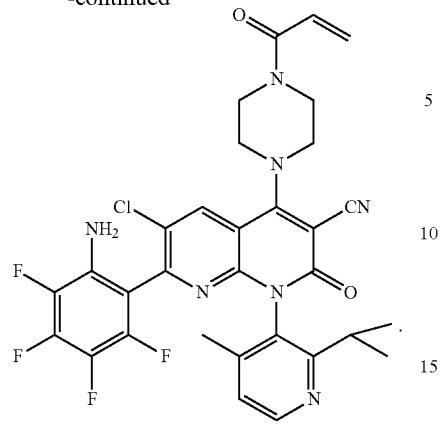

What is claimed is:

1. An intermediate of the following formula:

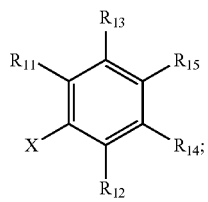

wherein, the moiety of

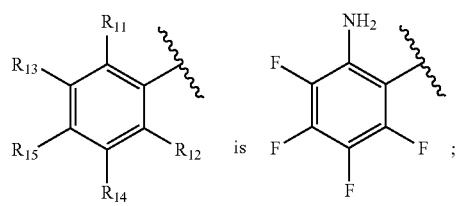

X is selected from

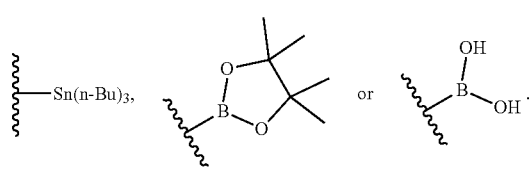

2. The intermediate of claim 1, wherein the intermediate is

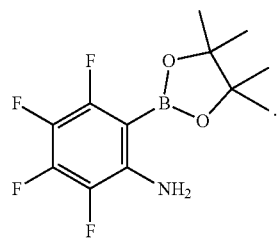 [SMILES: CC1(C)OB(c2c(N)c(F)c(F)c(F)c2F)OC1(C)C]

3. A method for preparing the compound of formula (I), a stereoisomer thereof, an atropisomer thereof, a pharmaceutically acceptable salt thereof, a pharmaceutically acceptable salt of the stereoisomer thereof or a pharmaceutically acceptable salt of the atropisomer thereof, wherein the method comprises a coupling reaction between a compound of formula (II) and a compound of formula (III) according to the following reaction Scheme 1 or between a compound of formula (II') and a compound of formula (III') according to the following reaction Scheme 2 catalyzed by a transition metal palladium or nickel reagent:

Scheme 1

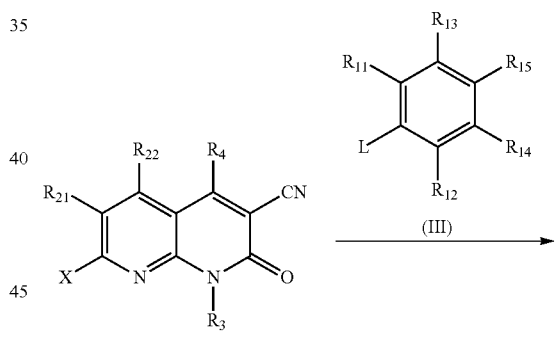

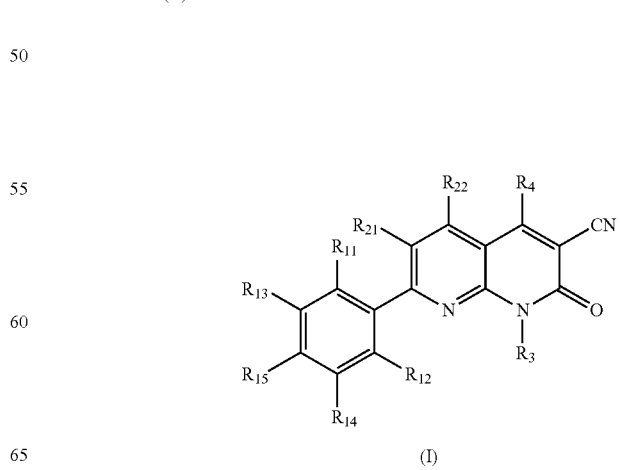

Scheme 2
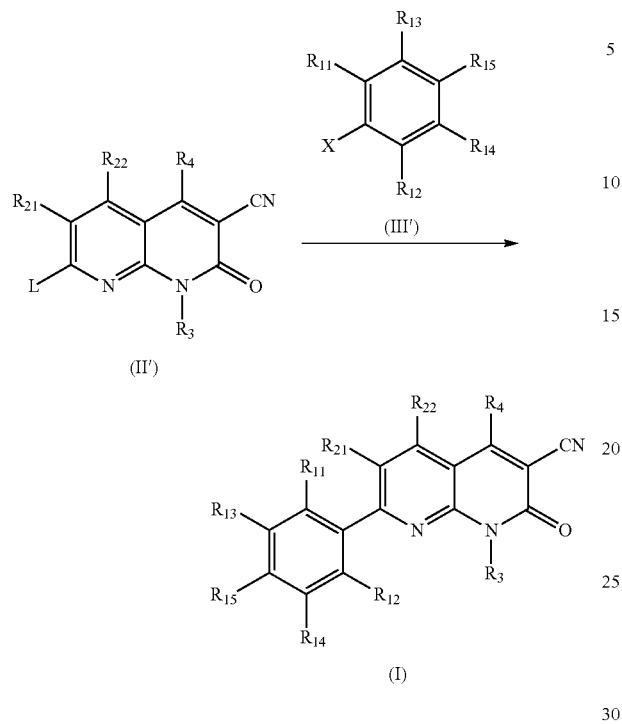
wherein
the L in the compound of formula (III) or formula (II′) is a leaving group;
the X in the compound of formula (II) or formula (III′) is selected from boronic acid, borate ester or organotin;
the moiety of
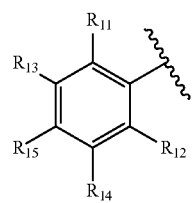
is selected from:
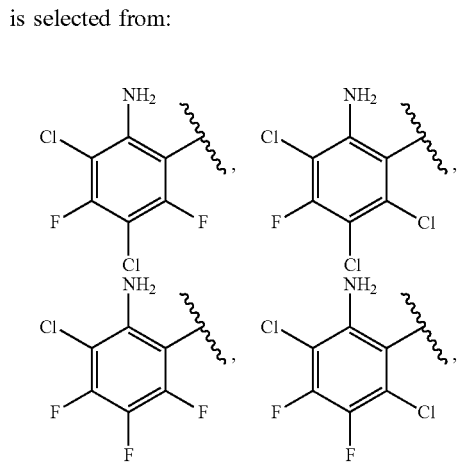
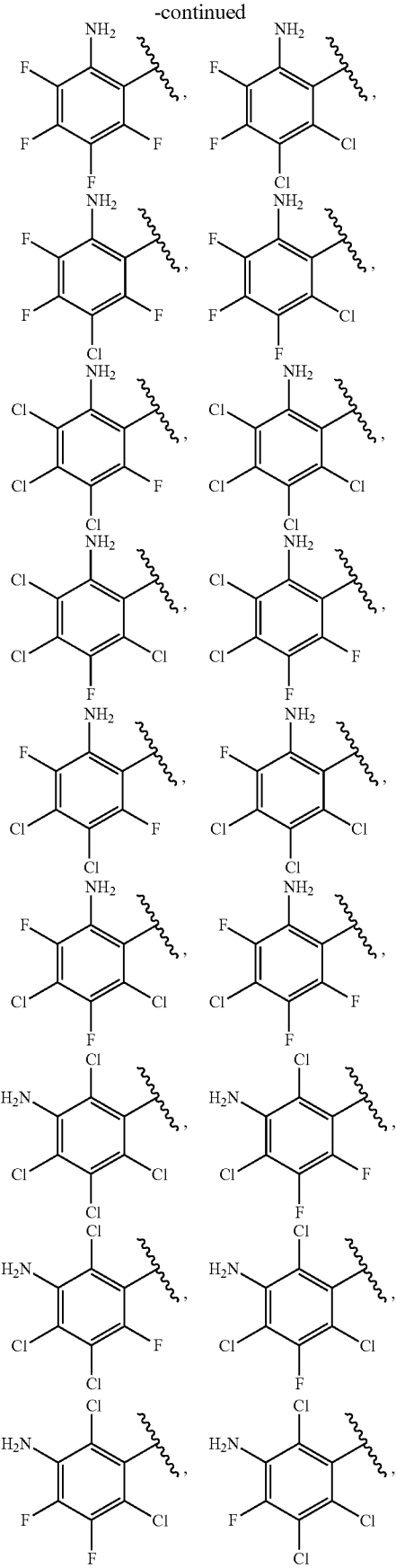

-continued

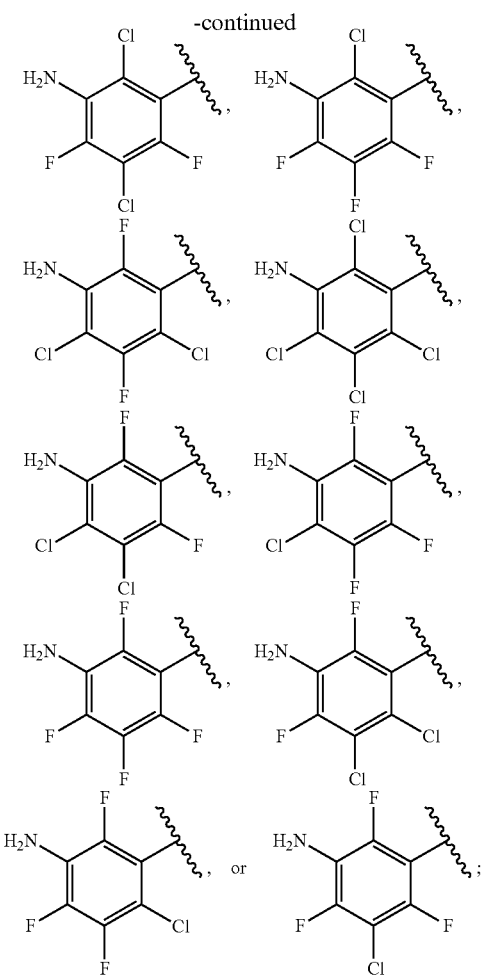

$R_{21}$ is selected from halogen;
$R_{22}$ is selected from hydrogen;
$R_3$ is selected from

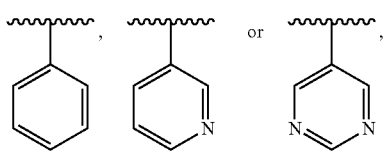

each hydrogen in the $R_3$ at each occurrence is independently optionally substituted by 1 $R_{31}$ or 2 $R_{31}$;
each $R_{31}$ at each occurrence is independently selected from $-C_{1-6}$alkyl;
$R_4$ is selected from

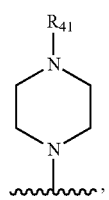

each hydrogen in the

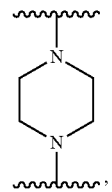

is independently optionally substituted with 1 $R_{42}$ or 2 $R_{42}$;
$R_{41}$ is selected from

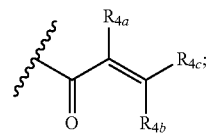

$R_{4a}$, $R_{4b}$ or $R_{4c}$ is independently selected from hydrogen or halogen; and
each $R_{42}$ at each occurrence is independently selected from $-C_{1-6}$alkyl or $-C_{1-6}$alkylene-CN.

4. The method of claim 3, wherein the leaving group is selected from halogen, $-OS(O)_2CF_3$ or $-OTs$.

5. The method of claim 4, wherein the leaving group is $-Cl$ or $-Br$.

6. The method of claim 3, wherein X is selected from

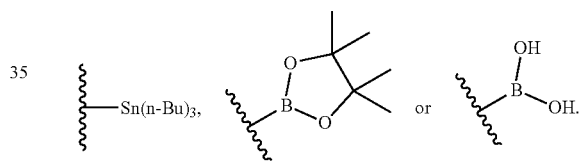

7. The method of claim 3, wherein the coupling reaction is Suzuki coupling reaction or Stille coupling reaction.

8. The method of claim 7, wherein the coupling reaction is catalyzed by the transition metal palladium reagent.

9. The method of claim 8, wherein the transition metal palladium reagent is $Pd(PPh_3)_4$.

10. The method of claim 3, wherein the compound of formula (I) is